(12) United States Patent
Wesselhoeft et al.

(10) Patent No.: US 11,802,144 B2
(45) Date of Patent: Oct. 31, 2023

(54) CIRCULAR RNA COMPOSITIONS AND METHODS

(71) Applicants: Massachusetts Institute of Technology, Cambridge, MA (US); Orna Therapeutics, Inc., Cambridge, MA (US)

(72) Inventors: Robert Alexander Wesselhoeft, Cambridge, MA (US); Daniel G. Anderson, Cambridge, MA (US); Shinichiro Fuse, Cambridge, MA (US); Brian Goodman, Cambridge, MA (US); Allen T. Horhota, Cambridge, MA (US); Raffaella Squilloni, Cambridge, MA (US)

(73) Assignee: Orna Therapeutics, Inc., Cambridge, MA (US)

( * ) Notice: Subject to any disclaimer, the term of this patent is extended or adjusted under 35 U.S.C. 154(b) by 0 days.

(21) Appl. No.: 17/384,460

(22) Filed: Jul. 23, 2021

(65) Prior Publication Data
US 2021/0371494 A1 Dec. 2, 2021

Related U.S. Application Data

(63) Continuation of application No. PCT/US2020/034418, filed on May 22, 2020.

(60) Provisional application No. 62/972,194, filed on Feb. 10, 2020, provisional application No. 62/943,779, filed on Dec. 4, 2019, provisional application No. 62/943,796, filed on Dec. 4, 2019, provisional application No. 62/857,121, filed on Jun. 4, 2019, provisional application No. 62/851,548, filed on May 22, 2019.

(30) Foreign Application Priority Data

Jun. 5, 2019 (WO) ................ PCT/US2019/035531

(51) Int. Cl.
| | | |
|---|---|---|
| A61K 48/00 | (2006.01) | |
| C07K 14/725 | (2006.01) | |
| A61K 9/51 | (2006.01) | |
| A61K 35/17 | (2015.01) | |
| C07K 16/28 | (2006.01) | |
| A61K 38/00 | (2006.01) | |
| A61K 39/00 | (2006.01) | |

(52) U.S. Cl.
CPC ............ *C07K 14/7051* (2013.01); *A61K 9/51* (2013.01); *A61K 35/17* (2013.01); *C07K 16/28* (2013.01); *A61K 38/00* (2013.01); *A61K 2039/505* (2013.01); *C07K 2319/30* (2013.01); *C12N 2310/532* (2013.01); *C12N 2840/203* (2013.01); *C12N 2840/60* (2013.01)

(58) Field of Classification Search
None
See application file for complete search history.

(56) References Cited

U.S. PATENT DOCUMENTS

| | | |
|---|---|---|
| 4,323,689 A | 4/1982 | Vogel et al. |
| 4,661,450 A | 4/1987 | Kempe et al. |
| 5,434,261 A | 7/1995 | Schoen et al. |
| 5,580,859 A | 12/1996 | Felgner et al. |
| 5,591,737 A | 1/1997 | Doherty et al. |
| 5,625,047 A | 4/1997 | Been et al. |
| 5,629,304 A | 5/1997 | Murakata et al. |
| 5,656,606 A | 8/1997 | Nargund et al. |
| 5,672,596 A | 9/1997 | Wyvratt et al. |
| 5,712,128 A | 1/1998 | Been et al. |
| 5,747,485 A | 5/1998 | Doherty et al. |
| 5,755,903 A | 5/1998 | Garant et al. |
| 5,766,903 A | 6/1998 | Sarnow |
| 5,773,244 A | 6/1998 | Ares, Jr. et al. |
| 5,972,964 A | 10/1999 | Perregaard |
| 6,043,026 A | 3/2000 | Patchett et al. |
| 6,210,931 B1 | 4/2001 | Feldstein et al. |
| 6,211,174 B1 | 4/2001 | Devita et al. |
| 6,368,802 B1 | 4/2002 | Kool |
| 6,576,628 B1 | 6/2003 | Grams et al. |
| 6,620,597 B1 | 9/2003 | Chen et al. |

(Continued)

FOREIGN PATENT DOCUMENTS

| | | |
|---|---|---|
| CN | 101016264 A | 8/2007 |
| CN | 105176981 A | 12/2015 |

(Continued)

OTHER PUBLICATIONS

Harrer, D. et al., BMC Cancer, 2017, vol. 17: 17 pages.*
Oberli, M. et al., Nano Lett, 2017, vol. 17: pp. 1326-1335.*
Badelt et al. "Computational Design of a Circular RNA with Prionlike Behavior," Artif Life., 2016, 22(2):172-84.
Barrett et al. "Circular RNAs: analysis, expression and potential functions," Development, 2016, 1143(11):1838-47.
Borchardt et al. "Inducing circular RNA formation using the CRISPR endoribonuclease Csy4," RNA, 2017, 23(5):619-627.
Branch et al. "Unusual properties of two branched RNA's with circular and linear components," Nucleic Acids Res., 1985, 13(13):4889-903.

(Continued)

Primary Examiner — Michael D Burkhart
(74) Attorney, Agent, or Firm — Goodwin Procter LLP

(57) ABSTRACT

Circular RNA and transfer vehicles, along with related compositions and methods are described herein. In some embodiments, the inventive circular RNA comprises group I intron fragments, spacers, an IRES, duplex forming regions, and an expression sequence. In some embodiments, the expression sequence encodes a chimeric antigen receptor (CAR). In some embodiments, circular RNA of the invention has improved expression, functional stability, immunogenicity, ease of manufacturing, and/or half-life when compared to linear RNA. In some embodiments, inventive methods and constructs result in improved circularization efficiency, splicing efficiency, and/or purity when compared to existing RNA circularization approaches.

8 Claims, 68 Drawing Sheets

Specification includes a Sequence Listing.

(56) References Cited

U.S. PATENT DOCUMENTS

| | | |
|---|---|---|
| 8,829,170 B2 | 9/2014 | Dale et al. |
| 11,203,767 B2 | 12/2021 | Anderson et al. |
| 11,603,396 B2 | 3/2023 | Wesselhoeft et al. |
| 2006/0199851 A1 | 9/2006 | Kempf et al. |
| 2010/0137407 A1 | 6/2010 | Abe et al. |
| 2010/0305197 A1 | 12/2010 | Che |
| 2011/0019782 A1 | 1/2011 | Kobayashi et al. |
| 2015/0079630 A1 | 3/2015 | Abe et al. |
| 2016/0083747 A1 | 3/2016 | Kruse |
| 2016/0194368 A1 | 7/2016 | Hoge et al. |
| 2016/0331828 A1 | 11/2016 | Ciaramella et al. |
| 2017/0204422 A1 | 7/2017 | Nelson et al. |
| 2018/0010175 A1 | 1/2018 | Cheng |
| 2018/0311343 A1 | 11/2018 | Huang et al. |
| 2018/0326045 A1 | 11/2018 | Ciaramella et al. |
| 2019/0290694 A1 | 9/2019 | Gautron et al. |
| 2019/0314291 A1 | 10/2019 | Besin et al. |
| 2019/0328769 A1 | 10/2019 | Uchida et al. |
| 2019/0345503 A1 | 11/2019 | Chang et al. |
| 2020/0040370 A1 | 2/2020 | Eber et al. |
| 2020/0080106 A1 | 3/2020 | Anderson et al. |
| 2021/0085719 A1 | 3/2021 | Jensen |
| 2021/0198688 A1 | 7/2021 | Anderson et al. |
| 2021/0363540 A1 | 11/2021 | Anderson et al. |
| 2021/0371494 A1 | 12/2021 | Wesselhoeft et al. |
| 2021/0403944 A1 | 12/2021 | Anderson et al. |
| 2022/0025395 A1 | 1/2022 | Anderson et al. |
| 2022/0106259 A1 | 4/2022 | Benenato et al. |
| 2022/0177540 A1 | 6/2022 | Wesselhoeft et al. |
| 2023/0050306 A1 | 2/2023 | Anderson et al. |
| 2023/0058784 A1 | 2/2023 | Goodman et al. |
| 2023/0062665 A1 | 3/2023 | Goodman et al. |

FOREIGN PATENT DOCUMENTS

| | | |
|---|---|---|
| CN | 106801050 A | 6/2017 |
| EP | 2819377 A1 | 12/2014 |
| EP | 3630966 A1 | 4/2020 |
| EP | 3819377 A1 | 5/2021 |
| GB | 2308064 A | 6/1997 |
| JP | 2016/521133 A | 7/2016 |
| JP | 2017043556 A | 3/2017 |
| JP | 6284181 B2 | 2/2018 |
| KR | 2011/0095439 A | 8/2011 |
| WO | 1995/011029 A1 | 4/1995 |
| WO | 1995/024207 A1 | 9/1995 |
| WO | 2005/044201 A2 | 5/2005 |
| WO | 2005/079803 A1 | 9/2005 |
| WO | 2006/138380 A2 | 12/2006 |
| WO | 2007/044627 A2 | 4/2007 |
| WO | 2009/035541 A1 | 3/2009 |
| WO | 2010/084371 A1 | 7/2010 |
| WO | 2010/138652 A1 | 12/2010 |
| WO | 2010/138659 A1 | 12/2010 |
| WO | 2010/138685 A1 | 12/2010 |
| WO | 2010/138695 A1 | 12/2010 |
| WO | 2010/138706 A1 | 12/2010 |
| WO | 2010/138758 A1 | 12/2010 |
| WO | 2013/076509 A1 | 5/2013 |
| WO | 2013/118878 A1 | 8/2013 |
| WO | 2014/144871 A1 | 9/2014 |
| WO | 2014/186334 A1 | 11/2014 |
| WO | 2014/193857 A1 | 12/2014 |
| WO | 2015/034925 A1 | 3/2015 |
| WO | 2015/095340 A1 | 6/2015 |
| WO | 2016/020373 A1 | 2/2016 |
| WO | 2016/197121 A1 | 12/2016 |
| WO | 2017/046203 A1 | 3/2017 |
| WO | 2017/049245 A2 | 3/2017 |
| WO | 2017/055487 A2 | 4/2017 |
| WO | 2017/059357 A1 | 4/2017 |
| WO | 2017/118734 A1 | 7/2017 |
| WO | 2017/201332 A1 | 11/2017 |
| WO | 2017/201333 A1 | 11/2017 |
| WO | 2017/201340 A2 | 11/2017 |
| WO | 2017/201342 A1 | 11/2017 |
| WO | 2017/201346 A1 | 11/2017 |
| WO | 2017/201348 A1 | 11/2017 |
| WO | 2017/201349 A1 | 11/2017 |
| WO | 2017/201350 A1 | 11/2017 |
| WO | 2017/222911 A1 | 12/2017 |
| WO | 2018/144775 A1 | 8/2018 |
| WO | 2018/157009 A1 | 8/2018 |
| WO | 2018/170260 A1 | 9/2018 |
| WO | 2018/170306 A1 | 9/2018 |
| WO | 2018/191722 A1 | 10/2018 |
| WO | 2018/237372 A1 | 12/2018 |
| WO | 2019/118919 A1 | 6/2019 |
| WO | 2019/213308 A1 | 11/2019 |
| WO | 2019/222275 A2 | 11/2019 |
| WO | 2019/236673 A1 | 12/2019 |
| WO | 2020/010242 A1 | 1/2020 |
| WO | 2020/023595 A1 | 1/2020 |
| WO | 2020/035070 A1 | 2/2020 |
| WO | 2020/061367 A1 | 3/2020 |
| WO | 2020/198403 A2 | 10/2020 |
| WO | 2020/237227 A1 | 11/2020 |
| WO | 2020/252436 A1 | 12/2020 |
| WO | 2021/041541 A1 | 3/2021 |
| WO | 2021/055849 A1 | 3/2021 |
| WO | 2021/113777 A2 | 6/2021 |

OTHER PUBLICATIONS

Chen et al. "Promising diagnostic and therapeutic circRNAs for skeletal and chondral disorders," Int J Biol Sci., 2021, 17(5):1428-1439.

Chen et al. "Sensing Self and Foreign Circular RNAs by Intron Identify," Molecular Cell, 2017, 67:228-238.

Costello et al. "Reinventing the Wheel: Synthetic Circular RNAs for Mammalian Cell Engineering." Trends Biotechnol., 2020, 38(2):217-230.

Foster et al. "Purification of mRNA Encoding Chimeric Antigen Receptor Is Critical for Generation of a Robust T-Cell Response," Hum Gene Ther, 2019, 30(2):168-178.

Holdt et al. "Circular RNAs as Therapeutic Agents and Targets," Front Physiol., 2018, 9:1262.

International Preliminary Report on Patentability and Written Opinion for International Application No. PCT/US2019/035531, dated Dec. 8, 2020, 8 pages.

International Search Report and Written Opinion for International Application No. PCT/US2020/034418, dated Sep. 28, 2020, 15 pages.

Invitation to Pay Additional Fees and, Where Applicable, Protest Fee for International Application No. PCT/US2020/063494, dated Apr. 28, 2021, 12 pages.

Jeck et al. "Detecting and characterizing circular RNAs," Nat Biotechnol., 2014, 32(5):453-61.

Kaczmarek et al. "Advances in the Delivery of RNA Therapeutics: from Concept to Clinical Reality," Genome Medicine, 2017, 9(1):60.

Li et al. "The Biogenesis, Functions, and Challenges of Circular RNAs," Mol Cell., 2018, 71(3):428-442.

Litke et al. "Trans ligation of RNAs to generate hybrid circular RNAs using highly efficient autocatalytic transcripts," Methods, 2021, S1046-2023(21)00135-3.

Miao et al. "Biological roles and therapeutic potential of circular RNAs in osteoarthritis," Mol Ther Nucleic Acids, 2021, 24:856-867.

Meganck et al. "Engineering highly efficient backsplicing and translation of synthetic circRNAs," Mol Ther Nucleic Acids, 2021, 23:821-834.

Nakamoto et al. "Chemical Synthesis of Circular RNAs with Phosphoramidate Linkages for Rolling-Circle Translation," Curr Protoc., 2021, 1(3):e43.

Obi et al. "The design and synthesis of circular RNAs," Methods, 2021, S1046-2023(21)00065-7.

Petkovic et al. "RNA Circularization Strategies in vivo and in vitro," Nucleic Acids Research, 2015, 43(4):2454-2465.

(56) References Cited

OTHER PUBLICATIONS

Puttaraju et al. "Group I Permuted Intron-exon (PIE) Sequences Self-splice to Produce Circular Exons," Nucleic Acids Research, 1992, 20(20):5357-5364.

Rausch et al. "Characterizing and circumventing sequence restrictions for synthesis of circular RNA in vitro," Nucleic Acids Res., 2021, 49(6):e35.

Sullenger et al. "From the RNA world to the clinic," Science, 2016, 352(6292):1417-1420.

Umekage et al. "In vivo circular RNA production using a constitutive promoter for high-level expression," J Biosci Bioeng, 2009, 108(4):354-6.

Wesselhoeft et al. "Engineering Circular RNA for Potent and Stable Translation in Eukaryotic Cells," Nature Communications, 2018, 9(1):2629, 10 pages.

Wesselhoeft et al. "RNA Circulation Diminishes Immunogenicity and can Extend Translation Duration In Vivo," Molecular Cell, 2019, 74(3):508-520.

Wiesinger et al. "Clinical-Scale Production of CAR-T Cells for the Treatment of Melanoma Patients by mRNA Transfection of a CSPG4-Specific CAR under Full GMP Compliance," Cancers (Basel), 2019, 11(8):1198.

Xue et al. "Lipid-based nanocarriers for RNA delivery," Curr Pharm Des, 2015, 21(22):3140-7.

Yang et al. "Circular RNAs: Expression, localization, and therapeutic potentials," Mol Ther, 2021, 29(5):1683-1702.

Bail et al. "Tri—to be mono—for bacterial mRNA decay," Structure, 2009, 17(3):317-9.

Bohjanen, P. R. et al., "A small circular TAR RNA decoy specifically inhibits Tat-activated HIV-1 transcription,", Nucleic Acids Res., vol. 24; No. 19; 3733-3738 (1996).

Bohjanen, P. R., et al., "TAR RNA decoys inhibit Tat-activated HIV-1 transcription after preinitiation complex formation", Nucleic Acids Res., vol. 25; 4481-4486 (1997).

Cech, T.R., "Self-Splicing of Group 1 Introns," Ann. Rev. Biochem., vol. 59; 543-568 (1990).

Chen, C. and Sarnow, P., "Initiation of protein synthesis by the eukaryotic translational apparatus on circular RNAs," America Association for the Advancement of Science, Abstract 268.5209; p. 415 (1995).

Dahlman, J.E., et al., "Barcoded nanoparticles for high throughput in vivo discovery of targeted therapeutics," PNAS, vol. 114; No. 8; 2060-2065 (2017).

Devaux, Y. et al., "Circular RNAs in heart failure", European Journal of Heart Failure, vol. 19; 701-709 (2017).

Durymanov, M. and Reineke, J., "Non-viral Delivery of Nucleic Acids: Insight Into Mechanisms of Overcoming Intracellular Barriers," Frontiers in Pharmacology, vol. 9; Article 971; 15 pages (2018).

Examination Report issued in EP19739422.4 dated Mar. 17, 2022. 6 pages.

Fenton et al., "Customizable Lipid Nanoparticle Materials for the Delivery of siRNAs and mRNAs," Angew Chem Int Ed Engl. 57(41):13582-86 (2018).

Final Office Action for U.S. Appl. No. 17/191,697, dated Sep. 30, 2021.

Final Office Action for U.S. Appl. No. 17/202,223, dated Mar. 7, 2022.

Greene, J. et al., "Circular RNAs: Biogenesis, Function and Role in Human Diseases", Frontiers in Molecular Biosciences, vol. 4; Article 38; 11 pages (2017).

Han et al. "Multi-antigen-targeted chimeric antigen receptor T cells for cancer therapy," J Hematol Oncol., 2019, 12(1):128.

He, J. et al., "Cicular RNAs and cancer", Cancer Letters, vol. 396, 138-144 (2017).

International Preliminary Report on Patentability for International Application No. PCT/US2019/035531, entitled: "Circular RNA for Translation in Eukaryotic Cells," dated Dec. 17, 2020 (9 pages).

International Preliminary Report on Patentability for International Application No. PCT/US2020/034418 dated Nov. 16, 2021. 8 pages.

International Search Report and Written Opinion for International Application No. PCT/US2019/035531, entitled: "Circular RNA for Translation in Eukaryotic Cells," dated Sep. 27, 2019 (17 pages).

International Search Report and Written Opinion for International Application No. PCT/US2020/063494, dated Aug. 6, 2021, 24 pages.

International Search Report and Written Opinion for International Application No. PCT/US2021/023540 dated Oct. 11, 2021.

International Search Report and Written Opinion for International Application No. PCT/US2021/031629 dated Feb. 4, 2022.

International Search Report and Written Opinion for International Appliction No. PCT/US2021/033276 dated Oct. 18, 2021.

Jemielity et al. "Synthetic mRNA cap analogs with a modified triphosphate bridge—synthesis, applications and prospects," New Journal of Chemistry, 2010, 34:829-844.

Kariko, K. et al., "Generating the optimal mRNA for therapy: HPLC purification eliminates immune activation and improves translation of nucleoside-modified, protein-encoding mRNA", Nucleic Acids Research, vol. 39; No. 21; e142, 10 pages (2011).

Kariko, K. et al., "Incorporation of Pseudouridine Into mRNA Yields Superior Nonimmunogenic Vector With Increased Translational Capacity and Biological Stability," Molecular Therapy, Vo. 16; No. 11; 1833-1840 (2008).

Kauffman, K.J. et al., "Efficacy and Immunogenicity of Unmodified and Pseudouridine-Modified mRNA Delivered Systemically with Lipid Nanoparticles in Vivo," Biomaterials, vol. 109; 78-87 (2016).

Kauffman, K.J. et al., "Rapid, Single-cell Analysis and Discovery of Vectored mRNA Transfection in Vivo wth a loxP-Flanked tdTomato Reporter Mouse," Molecular Therapy: Nucleic Acids, vol. 10; 55-63 (2018).

Kauffman, K.J., "Optimization and analysis of lipid nanoparticles for in vivo mRNA delivery," Ph.D. Thesis, Massachusetts Institute of Technology, Department of Chemical Engineering; 167 pages (2017).

Kotterman, M.A. and Schaffer, D.V., "Engineering adeno-associated viruses for clinical gene therapy," Nature Reviews, vol. 15; 445-451 (2014).

Legnini, I. et al., "Circ-ZNF609 Is a Circular RNA that Can Be Translated and Functions in Myogenesis," Molecular Cell, vol. 66; No. 1; 22-37 (2017).

Lenzi et al., "Gene Transfer Research: The Evolution of the Clinical Science," NCBI Bookshelf, A Service of the National Library of Medicine, National Institutes of Health, 16 pages (2014).

Memczak, S. et al., "Circular RNAs and a large class of animal RNAs with regulatory potency," Nature, vol. 495; 333-338 (2013).

Metzgar et al. "Abrupt emergence of diverse species B adenoviruses at US military recruit training centers," J Infect Dis. 2007, 196(10):1465-73.

Mu, X. et al., "An origin of the immunogenicity of in vitro transcribed RNA," Nucleic Acids Research, vol. 46; No. 10; 5239-5249 (2018).

Non-Final Office Action for U.S. Appl. No. 17/191,697, dated Jun. 18, 2021.

Non-Final Office Action for U.S. Appl. No. 17/374,497, dated Dec. 7, 2021.

Non-Final Office Action for U.S. Appl. No. 17/468,100, dated Dec. 8, 2021.

Non-Final Office Action for U.S. Appl. No. 17/492,512, dated Mar. 1, 2022.

Non-Final Office Action for U.S. Appl. No. 17/202,223, dated Apr. 18, 2022.

Non-Final Office Action for U.S. Appl. No. 17/202,223, dated Aug. 20, 2021.

Non-Final Office Action for U.S. Appl. No. 17/548,247, dated Apr. 1, 2022.

Notice of Allowance for U.S. Appl. No. 17/191,697, dated Nov. 2, 2021.

Notice of Allowance for U.S. Appl. No. 17/374,497, dated Apr. 13, 2022.

(56) References Cited

OTHER PUBLICATIONS

Notice of Allowance for U.S. Appl. No. 17/468,100, dated Apr. 8, 2022.
Ochi, A., et al., Nucleic Acids Symp. Ser. vol. 53, pp. 275-276 (2009).
Pamudurti, N.R. et al., "Translation of CircRNAs," Molecular Cell, vol. 66; No. 1; 9-21 (2017).
Puttaraju, M. and Been, M. D., Circular Ribozymes Generated in *Escherichia coli* Using Group I Self-splicing Permuted Intron-Exon Sequences, J. Biol. Chem., vol. 271, pp. 26081-26087 (1996).
Rafiq et al. "Targeted delivery of a PD-1-blocking scFv by CAR-T cells enhances anti-tumor efficacy in vivo," Nat Biotechnol., 2018, 36(9):847-856.
Sahin, U. et al., "mRNA-based therapeutics—developing a new class of drugs," Nature Reviews, vol. 13; 759-780 (2014).
Shim, G. et al., "Nonviral Delivery Systems for Cancer Gene Therapy: Strategies and Challenges," Current Gene Therapy, vol. 17; 18 pages (2017).
Umekage, U. et al., In Vivo Circular RNA Expression by the Permuted Intron-Exon Method, Innovations in Biotechnology, Chapter 4, 17 pages (2012).
Unpublished U.S. Appl. No. 17/202,223, entitled: "Circular RNA Compositions and Methods," filed Mar. 15, 2021; Inventors: Brian Goodman, Alexander Wesselhoeft, Allen T. Horhota, Jung-hoon Yang, and Kristen Ott.
Unpublished U.S. Appl. No. 17/374,497, entitled: "Circular RNA for Translation in Eukaryotic Cells," filed Jul. 13, 2021, Inventors: Daniel G. Anderson, Robert Alexander Wesselhoeft, and Piotr S. Kowalski.
Unpublished U.S. Appl. No. 17/468,100, entitled: "Circular RNA for Translation in Eukaryotic Cells," filed Sep. 7, 2021, Inventors: Daniel G. Anderson, Robert Alexander Wesselhoeft, and Piotr S. Kowalski.
Unpublished U.S. Appl. No. 17/492,512, entitled: "Circular RNA for Translation in Eukaryotic Cells," filed Oct. 1, 2021, Inventors: Daniel G. Anderson, Robert Alexander Wesselhoeft, and PiotrS. Kowalski.
Unpublished U.S. Appl. No. 17/503,208, entitled "Circular RNA Compositions and Methods," filed Oct. 15, 2021; Inventors: Brian Goodman, Alexander Wesselhoeft, Allen Horhota, and Junghoon Yang.
Unpublished U.S. Appl. No. 17/548,241, entitled "Circular RNA Compositions and Methods," filed Dec. 10, 2021; Inventors: Brian Goodman, Alexander Wesselhoeft, Allen Horhota, and Junghoon Yang.
Unpublished U.S. Appl. No. 17/548,247, entitled "Circular RNA Compositions and Methods," filed Dec. 10, 2021; Inventors: Alexander Wesselhoeft, Daniel G. Anderson, Shinichiro Fuse, Brian Goodman, Allen Horhota, and Raffaella Squilloni.
Valdmanis, P.N. and Kay, M.A., "The Expanding Repertoire of Circular RNAs," The American Society of Gene and Cell Therapy, vol. 21; No. 6; 1112-1114 (2013).
Wang, Y. and Wang, Z., "Efficient backsplicing produces translatable circular mRNAs," RNA, vol. 21; No. 2; 172-179 (2014).
Yang, E. et al., "Decay Rates of Human mRNAs: Correlation with Functional Characteristics and Sequence Attributes," Genome Research, vol. 13; 1863-1872 (2003).
Yeku et al. "Armored CAR T-cells: utilizing cytokines and pro-inflammatory ligands to enhance CAR T-cell anti-tumour efficacy," Biochem Soc Trans, 2016, 44(2):412-8.
Zeng et al., "A Circular RNA Binds to and Activates AKT Phosphorylation and Nuclear Localization Reducing Apoptosis and Enhancing Cardia Repair," Theranostics 7(16):3842-3855 (2017).
U.S. Appl. No. 17/894,141, filed Aug. 23, 2022, Daniel G. Anderson et al., Pending.
U.S. Appl. No. 17/853,576, filed Jun. 29, 2022, Robert Alexander Wesselhoeft et al., Pending.
Benenato, Ciaramella, and Huang. "Structures of Lipids," 2022, 28 pages.

Final Office Action for U.S. Appl. No. 17/503,208, dated Aug. 30, 2022.
Final Office Action for U.S. Appl. No. 17/548,241, dated Sep. 28, 2022.
Koos et al. "Influence of structure on antimicrobial activity of some heterocycles. IV. 1-(3-alkylamino-2-hydroxypropyl)-2-methyl-5-nitroimidazoles," Chem Papers. 1994, 48(1):54-57.
Liang et al. "Short intronic repeat sequences facilitate circular RNA production," Genes & Development, 2014, 28:2233-2247.
Liang et al. "The Output of Protein-Coding Genes Shifts to Circular RNAs When the Pre-mRNA Processing Machinery Is Limiting," Molecular Cell, 2017, 68:940-954.
Non-Final Office Action for U.S. Appl. No. 17/503,208, dated May 5, 2022.
Non-Final Office Action for U.S. Appl. No. 17/548,241, dated May 24, 2022.
Notice of Allowance for U.S. Appl. No. 17/548,247, dated Jul. 22, 2022.
Starke et al. "Exon Circularization Requires Canonical Splice Signals," Cell Reports, 2015, 10:103-111.
STN Registry Database Entry for 1333432-38-4 entered STN Sep. 27, 2011.
STN Registry Database Entry for 1333626-46-2 entered STN Sep. 28, 2011.
STN Registry Database Entry for 156811-31-3 entered STN Aug. 5, 1994.
STN Registry Database Entry for 157493-54-4 entered STN Sep. 7, 1994.
STN Registry Database Entry for 1609534-48-6 entered STN Jun. 4, 2014.
STN Registry Database Entry for 2086785-24-0 entered STN Mar. 17, 2017.
STN Registry Database Entry for 2086785-25-1 entered STN Mar. 17, 2017.
STN Registry Database Entry for 2086785-26-2 entered STN Mar. 17, 2017.
STN Registry Database Entry for 2086785-27-3 entered STN Mar. 17, 2017.
STN Registry Database Entry for 2086785-32-0 entered STN Mar. 17, 2017.
STN Registry Database Entry for 2086785-33-1 entered STN Mar. 17, 2017.
STN Registry Database Entry for 2089251-16-9 entered STN Apr. 10, 2017.
STN Registry Database Entry for 79111-60-7 entered STN Nov. 16, 1984.
Unpublished U.S. Appl. No. 17/853,576, entitled "Circular RNA Vectors Encoding Chimeric Antigen Receptors Targeting BCMA," filed Jun. 29, 2022; Inventors: Robert Alexander Wesselhoeft, Kristen Ott, Thomas Barnes, Gregory Motz, Amy M. Becker, Allen T. Horhota, and Brian Goodman.
Unpublished U.S. Appl. No. 17/894,141, entitled "Circular RNA for Translation in Eukaryotic Cells," filed Aug. 23, 2022; Inventors: Daniel G. Anderson, Robert Alexander Wesselhoeft, and Piotr S. Kowalski.
Van Esch et al. "Aggregation behavior and copper-binding properties of surfactants containing imidazole and pyrazole ligands," Recl Trav Chim Pays-Bas. 1994, 113(4):186-193.
Wang et al. "Combinatorially designed lipid-like nanoparticles for intracellular delivery of cytotoxic protein for cancer therapy," Angew Chem Int Ed Engl. 2014, 53(11):2893-2898.
Notice of Allowance for U.S. Appl. No. 17/202,223, dated Nov. 16, 2022.
Notice of Allowance for U.S. Appl. No. 17/503,208, dated Jan. 19, 2023.
Notice of Allowance for U.S. Appl. No. 17/548,241, dated Feb. 27, 2023.
Notice of Allowance for U.S. Appl. No. 17/548,247, dated Nov. 14, 2022.
Zhang et al. "A novel protein encoded by the circular form of the SHPRH gene suppresses glioma tumorigenesis," Oncogene, 2018, 37(13):1805-1814.

(56) References Cited

OTHER PUBLICATIONS

Unpublished U.S. Appl. No. 18/069,621, entitled "Circular RNA Compositions and Methods," filed Dec. 21, 2022; Inventors: Robert Alexander Wesselhoeft, Daniel G. Anderson, Shinichiro Fuse, Brian Goodman, Allen T. Horhota, and Raffaella Squilloni.
U.S. Appl. No. 18/069,621, filed Dec. 21, 2022, Robert Alexander Wesselhoeft et al., Pending.

* cited by examiner a) No homology arms b) Weak homology arms    c) Strong homology arms

CIRCULAR RNA COMPOSITIONS AND METHODS

CROSS-REFERENCE TO RELATED APPLICATIONS

This application is a continuation of International Patent Application No. PCT/US2020/034418, filed on May 22, 2020, which claims the benefit of and priority to U.S. Provisional Patent Application No. 62/851,548, filed May 22, 2019; U.S. Provisional Patent Application No. 62/857,121, filed Jun. 4, 2019; International Patent Application No. PCT/US2019/035531, filed Jun. 5, 2019, U.S. Provisional Patent Application No. 62/943,796, filed Dec. 4, 2019; U.S. Provisional Patent Application No. 62/943,779, filed Dec. 4, 2019; and U.S. Provisional Patent Application No. 62/972,194, filed Feb. 10, 2020, the disclosures of which are hereby incorporated by reference in their entireties for all purposes.

SEQUENCE LISTING

The instant application contains a Sequence Listing which has been submitted electronically in ASCII format and is hereby incorporated by reference in its entirety. Said ASCII copy, created on Jan. 7, 2021, is named OBS_101WOC1_Sequence_Listing.txt and is 232,801 bytes in size.

BACKGROUND

Conventional gene therapy involves the use of DNA for insertion of desired genetic information into host cells. The DNA introduced into the cell is usually integrated to a certain extent into the genome of one or more transfected cells, allowing for long-lasting action of the introduced genetic material in the host. While there may be substantial benefits to such sustained action, integration of exogenous DNA into a host genome may also have many deleterious effects. For example, it is possible that the introduced DNA will be inserted into an intact gene, resulting in a mutation which impedes or even totally eliminates the function of the endogenous gene. Thus, gene therapy with DNA may result in the impairment of a vital genetic function in the treated host, such as e.g., elimination or deleteriously reduced production of an essential enzyme or interruption of a gene critical for the regulation of cell growth, resulting in unregulated or cancerous cell proliferation. In addition, with conventional DNA-based gene therapy, it is necessary for effective expression of the desired gene product to include a strong promoter sequence, which again may lead to undesirable changes in the regulation of normal gene expression in the cell. It is also possible that the DNA-based genetic material will result in the induction of undesired anti-DNA antibodies, which in turn, may trigger a possibly fatal immune response. Gene therapy approaches using viral vectors can also result in an adverse immune response. In some circumstances, the viral vector may even integrate into the host genome. In addition, production of clinical grade viral vectors also is expensive and time consuming. Targeting delivery of the introduced genetic material using viral vectors can also be difficult to control. Thus, while DNA-based gene therapy has been evaluated for delivery of secreted proteins using viral vectors (U.S. Pat. No. 6,066,626; US2004/0110709), these approaches may be limited for these various reasons.

In contrast to DNA, the use of RNA as a gene therapy agent is substantially safer because RNA does not involve the risk of being stably integrated into the genome of the transfected cell, thus eliminating the concern that the introduced genetic material will disrupt the normal functioning of an essential gene, or cause a mutation that results in deleterious or oncogenic effects, and extraneous promoter sequences are not required for effective translation of the encoded protein, again avoiding possible deleterious side effects. In addition, it is not necessary for mRNA to enter the nucleus to perform its function, while DNA must overcome this major barrier.

Circular RNA is useful in the design and production of stable forms of RNA. The circularization of an RNA molecule provides an advantage to the study of RNA structure and function, especially in the case of molecules that are prone to folding in an inactive conformation (Wang and Ruffner, 1998). Circular RNA can also be particularly interesting and useful for in vivo applications, especially in the research area of RNA-based control of gene expression and therapeutics, including protein replacement therapy and vaccination.

Use of T cells genetically modified to express Chimeric Antigen Receptors (CARs) and recombinant T Cell Receptors (TCRs) targeting antigens on cancer cells is an attractive therapeutic strategy for the treatment of cancer. However, current methods of modifying T cells to express CARs and TCRs and the resulting therapies are associated with toxicity in the form of Cytokine Release Syndrome (CRS) and other complications. There remains a need for safer methods of engineering cells to express CARs and recombinant TCRs.

Prior to this invention, there were three main techniques for making circularized RNA in vitro: the splint-mediated method, the permuted intron-exon method, and the RNA ligase-mediated method. However, the existing methodologies are limited by the size of RNA that can be circularized, thus limiting their therapeutic application.

SUMMARY

In one aspect, provided herein is a pharmaceutical composition comprising: a circular RNA polynucleotide comprising, in the following order, a 3' group I intron fragment, an Internal Ribosome Entry Site (IRES), an expression sequence encoding a chimeric antigen receptor (CAR) or T cell receptor (TCR) complex protein, and a 5' group I intron fragment, and a transfer vehicle comprising at least one of (i) an ionizable lipid, (ii) a structural lipid, and (iii) a PEG-modified lipid, wherein the transfer vehicle is capable of delivering the circular RNA polynucleotide to a human immune cell present in a human subject, such that the CAR is translated in the human immune cell and expressed on the surface of the human immune cell.

In some embodiments, the pharmaceutical composition is formulated for intravenous administration to the human subject in need thereof. In some embodiments, the 3' group I intron fragment and 5' group I intron fragment are Anabaena group I intron fragments.

In certain embodiments, the 3' intron fragment and 5' intron fragment are defined by the L9a-5 permutation site in the intact intron. In certain embodiments, the 3' intron fragment and 5' intron fragment are defined by the L8-2 permutation site in the intact intron.

In some embodiments, the IRES is from Taura syndrome virus, *Triatoma* virus, Theiler's encephalomyelitis virus, Simian Virus 40, *Solenopsis invicta* virus 1, *Rhopalosiphum padi* virus, Reticuloendotheliosis virus, Human poliovirus 1, *Plautia stali* intestine virus, Kashmir bee virus, Human rhinovirus 2, *Homalodisca coagulata* virus-1, Human Immunodeficiency Virus type 1, *Homalodisca coagulata* virus-1, Himetobi P virus, Hepatitis C virus, Hepatitis A virus, Hepatitis GB virus, Foot and mouth disease virus, Human enterovirus 71, Equine rhinitis virus, *Ectropis obliqua* picorna-like virus, Encephalomyocarditis virus, *Drosophila* C Virus, Human coxsackievirus B3, Crucifer tobamovirus, Cricket paralysis virus, Bovine viral diarrhea virus 1, Black Queen Cell Virus, Aphid lethal paralysis virus, Avian encephalomyelitis virus, Acute bee paralysis virus, Hibiscus chlorotic ringspot virus, Classical swine fever virus, Human FGF2, Human SFTPA1, Human AML1/RUNX1, *Drosophila* antennapedia, Human AQP4, Human AT1R, Human BAG-1, Human BCL2, Human BiP, Human c-IAP1, Human c-myc, Human eIF4G, Mouse NDST4L, Human LEF1, Mouse HIF1 alpha, Human n.myc, Mouse Gtx, Human p27kip1, Human PDGF2/c-sis, Human p53, Human Pim-1, Mouse Rbm3, *Drosophila* reaper, Canine Scamper, *Drosophila* Ubx, Human UNR, Mouse UtrA, Human VEGF-A, Human XIAP, *Drosophila* hairless, *S. cerevisiae* TFIID, *S. cerevisiae* YAP1, tobacco etch virus, turnip crinkle virus, EMCV-A, EMCV-B, EMCV-Bf, EMCV-Cf, EMCV pEC9, Picobirnavirus, HCV QC64, Human Cosavirus E/D, Human Cosavirus F, Human Cosavirus JMY, Rhinovirus NAT001, HRV14, HRV89, HRVC-02, HRV-A21, Salivirus A SH1, Salivirus FHB, Salivirus NG-J1, Human Parechovirus 1, Crohivirus B, Yc-3, Rosavirus M-7, Shanbavirus A, Pasivirus A, Pasivirus A 2, Echovirus E14, Human Parechovirus 5, Aichi Virus, Hepatitis A Virus HA16, Phopivirus, CVA10, Enterovirus C, Enterovirus D, Enterovirus J, Human Pegivirus 2, GBV-C GT110, GBV-C K1737, GBV-C Iowa, Pegivirus A 1220, Pasivirus A 3, Sapelovirus, Rosavirus B, Bakunsa Virus, Tremovirus A, Swine Pasivirus 1, PLV-CHN, Pasivirus A, Sicinivirus, Hepacivirus K, Hepacivirus A, BVDV1, Border Disease Virus, BVDV2, CSFV-PK15C, SF573 Dicistrovirus, Hubei Picorna-like Virus, CRPV, Salivirus A BNS, Salivirus A BN2, Salivirus A 02394, Salivirus A GUT, Salivirus A CH, Salivirus A SZ1, Salivirus FHB, CVB3, CVB1, Echovirus 7, CVBS, EVA71, CVA3, CVA12, EV24 or an aptamer to eIF4G.

In some embodiments, the IRES comprises a CVB3 IRES or a fragment or variant thereof, or wherein the IRES comprises a sequence according to SEQ ID NO: 65. In some embodiments, the IRES comprises a salivirus SZ1 IRES or a fragment or variant thereof. In certain embodiments, the IRES comprises a sequence according to SEQ ID NO: 63. In some embodiments, the pharmaceutical composition comprises a first internal spacer between the 3' group I intron fragment and the IRES, and a second internal spacer between the expression sequence and the 5' group I intron fragment. In certain embodiments, the first and second internal spacers each have a length of about 10 to about 60 nucleotides.

In some embodiments, the CAR or TCR complex protein comprises an antigen binding domain specific for an antigen selected from the group: CD19, CD123, CD22, CD30, CD171, CS-1, C-type lectin-like molecule-1, CD33, epidermal growth factor receptor variant III (EGFRvIII), disialoganglioside GD2, disaloganglioside GD3, TNF receptor family member, B cell maturation antigen (BCMA), Tn antigen ((Tn Ag) or (GaINAca-Ser/Thr)), prostate-specific membrane antigen (PSMA), Receptor tyrosine kinase-like orphan receptor 1 (ROR1), Fms-Like Tyrosine Kinase 3 (FLT3), Tumor-associated glycoprotein 72 (TAG72), CD38, CD44v6, Carcinoembryonic antigen (CEA), Epithelial cell adhesion molecule (EPCAM), B7H3 (CD276), KIT (CD117), Interleukin-13 receptor subunit alpha-2, mesothelin, Interleukin 11 receptor alpha (IL-11Ra), prostate stem cell antigen (PSCA), Protease Serine 21, vascular endothelial growth factor receptor 2 (VEGFR2), Lewis(Y) antigen, CD24, Platelet-derived growth factor receptor beta (PDGFR-beta), Stage-specific embryonic antigen-4 (SSEA-4), CD20, Folate receptor alpha, HER2, HER3, Mucin 1, cell surface associated (MUC1), epidermal growth factor receptor (EGFR), neural cell adhesion molecule (NCAM), Prostase, prostatic acid phosphatase (PAP), elongation factor 2 mutated (ELF2M), Ephrin B2, fibroblast activation protein alpha (FAP), insulin-like growth factor 1 receptor (IGF-I receptor), carbonic anhydrase IX (CAIX), Proteasome (Prosome, Macropain) Subunit, Beta Type, 9 (LMP2), glycoprotein 100 (gp100), oncogene fusion protein consisting of breakpoint cluster region (BCR) and Abelson murine leukemia viral oncogene homolog 1 (Abl) (bcr-abl), tyrosinase, ephrin type-A receptor 2 (EphA2), Fucosyl GM1, sialyl Lewis adhesion molecule (sLe), ganglioside GM3, transglutaminase 5 (TGS5), high molecular weight-melanoma-associated antigen (HMWMAA), o-acetyl-GD2 ganglioside (OAcGD2), Folate receptor beta, tumor endothelial marker 1 (TEM1/CD248), tumor endothelial marker 7-related (TEM7R), claudin 6 (CLDN6), claudin 18.2 (CLDN18.2), thyroid stimulating hormone receptor (TSHR), G protein-coupled receptor class C group 5, member D (GPRC5D), chromosome X open reading frame 61 (CXORF61), CD97, and CD179a.

In some embodiments, the CAR or TCR complex protein comprises a CAR comprising an antigen binding domain specific for CD19. In some embodiments, the CAR or TCR complex protein comprises a CAR comprising a costimulatory domain selected from the group CD28, 4-1BB, OX40, CD27, CD30, ICOS, GITR, CD40, CD2, SLAM, and combinations thereof. In some embodiments, the CAR or TCR complex protein comprises a CAR comprising a CD3zeta signaling domain. In some embodiments, the CAR or TCR complex protein comprises a CAR comprising a CH2CH3, CD28, and/or CD8 spacer domain. In some embodiments, the CAR or TCR complex protein comprises a CAR comprising a CD28 or CD8 transmembrane domain.

In some embodiments, the CAR or TCR complex protein comprises a CAR comprising: an antigen binding domain, a spacer domain, a transmembrane domain, a costimulatory domain, and an intracellular T cell signaling domain.

In some embodiments, the CAR or TCR complex protein comprises a multispecific CAR comprising antigen binding domains for at least 2 different antigens. In some embodiments, the CAR or TCR complex protein comprises a TCR complex protein selected from the group TCRalpha, TCRbeta, TCRgamma, and TCRdelta. In some embodiments, the transfer vehicle comprises a lipid nanoparticle, a core-shell nanoparticle, a biodegradable nanoparticle, a biodegradable lipid nanoparticle, a polymer nanoparticle, or a biodegradable polymer nanoparticle.

In some embodiments, the pharmaceutical composition further comprises a targeting moiety. In certain embodiments, the targeting moiety mediates receptor-mediated endocytosis or direct fusion into selected cells of a selected cell population or tissue in the absence of cell isolation or purification. In certain embodiments, the targeting moiety is capable of binding to a protein selected from the group CD3, CD4, CD8, CD5, CD7, PD-1, 4-1BB, CD28, C1q, and CD2. In certain embodiments, the targeting moiety comprises an antibody specific for a macrophage, dendritic cell, NK cell, NKT, or T cell antigen. In certain embodiments, the targeting moiety comprises a scFv, nanobody, peptide, minibody, polynucleotide aptamer, heavy chain variable region, light chain variable region or fragment thereof.

In some embodiments, the pharmaceutical composition is administered in an amount effective to treat cancer in the human subject. In some embodiments, the pharmaceutical composition has an enhanced safety profile when compared to a pharmaceutical composition comprising T cells or vectors comprising exogenous DNA encoding the same CAR.

In some embodiments, less than 1%, by weight, of the polynucleotides in the composition are double stranded RNA, DNA splints, or triphosphorylated RNA.

In some embodiments, less than 1%, by weight, of the polynucleotides and proteins in the pharmaceutical composition are double stranded RNA, DNA splints, triphosphorylated RNA, phosphatase proteins, protein ligases, and capping enzymes. In some embodiments, the transfer vehicle comprises more than one circular RNA polynucleotide.

In another aspect, the present disclosure provides a circular RNA polynucleotide comprising, in the following order, a 3' group I intron fragment, an Internal Ribosome Entry Site (IRES), an expression sequence encoding a chimeric antigen receptor (CAR) or TCR complex protein, and a 5' group I intron fragment.

In some embodiments, the 3' group I intron fragment and 5' group I intron fragment are Anabaena group I intron fragments. In certain embodiments, the 3' intron fragment and 5' intron fragment are defined by the L9a-5 permutation site in the intact intron. In certain embodiments, the 3' intron fragment and 5' intron fragment are defined by the L8-2 permutation site in the intact intron. In certain embodiments, the IRES comprises a CVB3 IRES or a fragment or variant thereof. In certain embodiments, the IRES has a sequence according to SEQ ID NO: 65. In certain embodiments, the IRES comprises a salivirus SZ1 IRES or a fragment or variant thereof. In certain embodiments, the IRES has a sequence according to SEQ ID NO: 63.

In some embodiments, the circular RNA polynucleotide comprises a first internal spacer between the 3' group I intron fragment and the IRES, and a second internal spacer between the expression sequence and the 5' group I intron fragment.

In certain embodiments, the first and second internal spacers each have a length of about 10 to about 60 nucleotides.

In some embodiments, the circular RNA polynucleotide consists of natural nucleotides. In some embodiments, the circular RNA polynucleotide further comprises a second expression sequence encoding a therapeutic protein. In some embodiments, the therapeutic protein comprises a checkpoint inhibitor. In certain embodiments, the therapeutic protein comprises a cytokine.

In some embodiments, the CAR or TCR complex protein comprises an antigen binding domain specific for an antigen selected from the group: CD19, CD123, CD22, CD30, CD171, CS-1, C-type lectin-like molecule-1, CD33, epidermal growth factor receptor variant III (EGFRvIII), disialoganglioside GD2, disialoganglioside GD3, TNF receptor family member, B cell maturation antigen (BCMA), Tn antigen ((Tn Ag) or (GaINAca-Ser/Thr)), prostate-specific membrane antigen (PSMA), Receptor tyrosine kinase-like orphan receptor 1 (ROR1), Fms-Like Tyrosine Kinase 3 (FLT3), Tumor-associated glycoprotein 72 (TAG72), CD38, CD44v6, Carcinoembryonic antigen (CEA), Epithelial cell adhesion molecule (EPCAM), B7H3 (CD276), KIT (CD117), Interleukin-13 receptor subunit alpha-2, mesothelin, Interleukin 11 receptor alpha (IL-11Ra), prostate stem cell antigen (PSCA), Protease Serine 21, vascular endothelial growth factor receptor 2 (VEGFR2), Lewis(Y) antigen, CD24, Platelet-derived growth factor receptor beta (PDGFR-beta), Stage-specific embryonic antigen-4 (SSEA-4), CD20, Folate receptor alpha, HER2, HER3, Mucin 1, cell surface associated (MUC1), epidermal growth factor receptor (EGFR), neural cell adhesion molecule (NCAM), Prostase, prostatic acid phosphatase (PAP), elongation factor 2 mutated (ELF2M), Ephrin B2, fibroblast activation protein alpha (FAP), insulin-like growth factor 1 receptor (IGF-I receptor), carbonic anhydrase IX (CAIX), Proteasome (Prosome, Macropain) Subunit, Beta Type, 9 (LMP2), glycoprotein 100 (gp100), oncogene fusion protein consisting of breakpoint cluster region (BCR) and Abelson murine leukemia viral oncogene homolog 1 (Abl) (bcr-abl), tyrosinase, ephrin type-A receptor 2 (EphA2), Fucosyl GM1, sialyl Lewis adhesion molecule (sLe), ganglioside GM3, transglutaminase 5 (TGS5), high molecular weight-melanoma-associated antigen (HMWMAA), o-acetyl-GD2 ganglioside (OAcGD2), Folate receptor beta, tumor endothelial marker 1 (TEM1/CD248), tumor endothelial marker 7-related (TEM7R), claudin 6 (CLDN6), claudin 18.2 (CLDN18.2), thyroid stimulating hormone receptor (TSHR), G protein-coupled receptor class C group 5, member D (GPRC5D), chromosome X open reading frame 61 (CXORF61), CD97, and CD179a In some embodiments, the CAR or TCR complex protein comprises a CAR comprising an antigen binding domain specific for CD19. In some embodiments, the CAR or TCR complex protein comprises a CAR comprising a costimulatory domain selected from the group CD28, 4-1BB, OX40, CD27, CD30, ICOS, GITR, CD40, CD2, SLAM, and combinations thereof. In some embodiments, the CAR or TCR complex protein comprises a CAR comprising a CD3zeta signaling domain. In some embodiments, the CAR or TCR complex protein comprises a CAR comprising a CH2CH3, CD28, and/or CD8 spacer domain. In some embodiments, the CAR or TCR complex protein comprises a CAR comprising a CD28 or CD8 transmembrane domain.

In some embodiments, the CAR or TCR complex protein comprises a CAR comprising: an antigen binding domain, a spacer domain, a transmembrane domain, a costimulatory domain, and an intracellular T cell signaling domain.

In some embodiments, the CAR or TCR complex protein comprises a multispecific CAR comprising antigen binding domains for at least 2 different antigens. In some embodiments, the CAR or TCR complex protein comprises a TCR complex protein selected from the group TCRalpha, TCRbeta, TCRgamma, and TCRdelta.

In some embodiments, the circular RNA polynucleotide consists of natural nucleotides.

In some embodiments, the circular RNA polynucleotide expression sequence is codon optimized. In some embodiments, the circular RNA polynucleotide is optimized to lack at least one microRNA binding site present in an equivalent pre-optimized polynucleotide. In some embodiments, the circular RNA polynucleotide is optimized to lack at least one endonuclease susceptible site present in an equivalent pre-optimized polynucleotide. In some embodiments, the circular RNA polynucleotide is optimized to lack at least one RNA-editing susceptible site present in an equivalent pre-optimized polynucleotide.

In some embodiments, the circular RNA polynucleotide has an in vivo functional half-life in humans greater than that of an equivalent linear RNA polynucleotide having the same expression sequence. In some embodiments, the circular RNA polynucleotide has a length of about 100 nucleotides to about 10 kilobases. In some embodiments, the circular RNA polynucleotide has a functional half-life of at least about 20 hours. In some embodiments, the circular RNA polynucleotide has a duration of therapeutic effect in a human cell of at least about 20 hours. In some embodiments, the circular RNA polynucleotide has a duration of therapeutic effect in a human cell greater than or equal to that of an equivalent linear RNA polynucleotide comprising the same expression sequence. In some embodiments, the circular RNA polynucleotide has a functional half-life in a human cell greater than or equal to that of an equivalent linear RNA polynucleotide comprising the same expression sequence.

In another aspect, the present disclosure provides a DNA vector comprising, in the following order, a 5' duplex forming region, an Anabaena 3' group I intron fragment with a first permutation site, an Internal Ribosome Entry Site (IRES), an expression sequence encoding a chimeric antigen receptor (CAR) polypeptide, an Anabaena 5' group I intron fragment with a second permutation site, and a 3' duplex forming region.

In some embodiments, the 3' group I intron fragment and 5' group I intron fragment are Anabaena group I intron fragments. In some embodiments, the 3' intron fragment and 5' intron fragment are defined by the L9a-5 permutation site in the intact intron. In some embodiments, the 3' intron fragment and 5' intron fragment are defined by the L8-2 permutation site in the intact intron. In some embodiments, the IRES comprises a CVB3 IRES or a fragment or variant thereof.

In some embodiments, the IRES encodes a sequence according to SEQ ID NO: 65. In some embodiments, the IRES comprises a salivirus SZ1 IRES or a fragment or variant thereof. In some embodiments, the IRES encodes a sequence according to SEQ ID NO: 63. In some embodiments, the circular RNA polynucleotide comprises, in the following order, 5' duplex forming region, a 3' group I intron fragment, an Internal Ribosome Entry Site (IRES), an expression sequence encoding a chimeric antigen receptor (CAR) or TCR complex protein, a 5' group I intron fragment, and a 3' duplex forming region. In some embodiments, the 5' duplex forming region and 3' duplex forming region each have about 70% GC nucleotides. In some embodiments, the 5' duplex forming region and 3' duplex forming region each have a length of about 30 nucleotides.

In some embodiments, the DNA vector comprises a first external spacer between the 5' duplex forming region and the 3' group I intron fragment, and a second external spacer between the 5' group I intron fragment and the 3' duplex forming region. In some embodiments, the first and second external spacers each have a length of about 10 to about 60 nucleotides. In some embodiments, the 5' duplex forming region is directly adjacent to the 3' group I intron fragment, and wherein the 5' group I intron fragment is directly adjacent to the 3' duplex forming region. In some embodiments, the DNA vector comprises a first internal spacer between the 3' group I intron fragment and the IRES, and a second internal spacer between the expression sequence and the 5' group I intron fragment. In some embodiments, the first and second internal spacers each have a length of about 10 to about 60 nucleotides.

In some embodiments, the CAR or TCR complex protein comprises an antigen binding domain specific for an antigen selected from the group: CD19, CD123, CD22, CD30, CD171, CS-1, C-type lectin-like molecule-1, CD33, epidermal growth factor receptor variant III (EGFRvIII), disialoganglioside GD2, disialoganglioside GD3, TNF receptor family member, B cell maturation antigen (BCMA), Tn antigen ((Tn Ag) or (GalNAca-Ser/Thr)), prostate-specific membrane antigen (PSMA), Receptor tyrosine kinase-like orphan receptor 1 (ROR1), Fms-Like Tyrosine Kinase 3 (FLT3), Tumor-associated glycoprotein 72 (TAG72), CD38, CD44v6, Carcinoembryonic antigen (CEA), Epithelial cell adhesion molecule (EPCAM), B7H3 (CD276), KIT (CD117), Interleukin-13 receptor subunit alpha-2, mesothelin, Interleukin 11 receptor alpha (IL-11Ra), prostate stem cell antigen (PSCA), Protease Serine 21, vascular endothelial growth factor receptor 2 (VEGFR2), Lewis(Y) antigen, CD24, Platelet-derived growth factor receptor beta (PDGFR-beta), Stage-specific embryonic antigen-4 (SSEA-4), CD20, Folate receptor alpha, HER2, HER3, Mucin 1, cell surface associated (MUC1), epidermal growth factor receptor (EGFR), neural cell adhesion molecule (NCAM), Prostase, prostatic acid phosphatase (PAP), elongation factor 2 mutated (ELF2M), Ephrin B2, fibroblast activation protein alpha (FAP), insulin-like growth factor 1 receptor (IGF-I receptor), carbonic anhydrase IX (CAIX), Proteasome (Prosome, Macropain) Subunit, Beta Type, 9 (LMP2), glycoprotein 100 (gp100), oncogene fusion protein consisting of breakpoint cluster region (BCR) and Abelson murine leukemia viral oncogene homolog 1 (Abl) (bcr-abl), tyrosinase, ephrin type-A receptor 2 (EphA2), Fucosyl GM1, sialyl Lewis adhesion molecule (sLe), ganglioside GM3, transglutaminase 5 (TGS5), high molecular weight-melanoma-associated antigen (HMWMAA), o-acetyl-GD2 ganglioside (OAcGD2), Folate receptor beta, tumor endothelial marker 1 (TEM1/CD248), tumor endothelial marker 7-related (TEM7R), claudin 6 (CLDN6), claudin 18.2 (CLDN18.2), thyroid stimulating hormone receptor (TSHR), G protein-coupled receptor class C group 5, member D (GPRC5D), chromosome X open reading frame 61 (CXORF61), CD97, and CD179a In some embodiments, the CAR or TCR complex protein comprises a CAR comprising an antigen binding domain specific for CD19. In some embodiments, the CAR or TCR complex protein comprises a CAR comprising a costimulatory domain selected from the group CD28, 4-1BB, OX40, CD27, CD30, ICOS, GITR, CD40, CD2, SLAM, and combinations thereof. In some embodiments, the CAR or TCR complex protein comprises a CAR comprising a CD3zeta signaling domain. In some embodiments, the CAR or TCR complex protein comprises a CAR comprising a CH2CH3, CD28, and/or CD8 spacer domain. In some embodiments, the CAR or TCR complex protein comprises a CAR comprising a CD28 or CD8 transmembrane domain.

In some embodiments, the CAR or TCR complex protein comprises a CAR comprising: an antigen binding domain, a spacer domain, a transmembrane domain, a costimulatory domain, and an intracellular T cell signaling domain.

In some embodiments, the CAR or TCR complex protein comprises a multispecific CAR comprising antigen binding domains for at least 2 different antigens. In some embodiments, the CAR or TCR complex protein comprises a TCR complex protein selected from the group TCRalpha, TCRbeta, TCRgamma, and TCRdelta.

In another aspect, the present disclosure provides a eukaryotic cell comprising a circular RNA polynucleotide comprising, in the following order, a 3' group I intron fragment, an Internal Ribosome Entry Site (IRES), an expression sequence encoding a chimeric antigen receptor (CAR) or TCR complex protein, and a 5' group I intron fragment. In some embodiments, the eukaryotic cell comprises a human cell. In some embodiments, the eukaryotic cell comprises an immune cell. In some embodiments, the eukaryotic cell comprises a T cell.

In another aspect, the present disclosure provides a population of eukaryotic cells comprising a circular RNA polynucleotide comprising, in the following order, a 3' group I intron fragment, an Internal Ribosome Entry Site (IRES), an expression sequence encoding a chimeric antigen receptor (CAR) or TCR complex protein, and a 5' group I intron fragment, wherein the population of eukaryotic cells express the CAR or TCR complex protein encoded by the circular RNA polynucleotide on its cell surface.

In some embodiments, the population of cells comprises NK cells, NKT cells, macrophages, dendritic cells, alphabeta T cells, gammadelta T cells, or combinations thereof. In some embodiments, the population of cells comprises T cells. In some embodiments, the population comprises CD3+ T cells. In some embodiments, the population comprises CD4+ T cells. In some embodiments, the population comprises CD8+ T cells. In some embodiments, the population of eukaryotic cells is administered in an amount effective to treat cancer in a human subject in need thereof. In some embodiments, the population of cells kills tumor cells more effectively or for longer than an equivalent population of eukaryotic cells comprising linear RNA encoding the same CAR.

In another aspect, provided herein is a method of making a population of eukaryotic cells comprising contacting cells in the population with a transfer vehicle comprising a circular RNA polynucleotide comprising, in the following order, a 3' group I intron fragment, an Internal Ribosome Entry Site (IRES), an expression sequence encoding a chimeric antigen receptor (CAR) or TCR complex protein, and a 5' group I intron fragment, wherein the transfer vehicle comprises (i) an ionizable lipid, (ii) a structural lipid, and (iii) a PEG-modified lipid, wherein the transfer vehicle is capable of delivering the circular RNA polynucleotide to a human immune cell, such that the CAR is translated in the human immune cell and expressed on the surface of the human immune cell.

In another aspect, provided herein is a method of treating a subject in need thereof comprising administering a therapeutically effective amount of a pharmaceutical composition comprising: a circular RNA polynucleotide comprising, in the following order, a 3' group I intron fragment, an Internal Ribosome Entry Site (IRES), an expression sequence encoding a chimeric antigen receptor (CAR) or TCR complex protein, and a 5' group I intron fragment, and a transfer vehicle comprising (i) an ionizable lipid, (ii) a structural lipid, and (iii) a PEG-modified lipid, wherein the transfer vehicle is capable of delivering the circular RNA polynucleotide to a human immune cell, such that the CAR is translated in the human immune cell and expressed on the surface of the human immune cell.

In some embodiments, the subject has a cancer selected from the group acute lymphocytic cancer, acute myeloid leukemia (AML), alveolar rhabdomyosarcoma, bladder cancer (e.g., bladder carcinoma), bone cancer, brain cancer (e.g., medulloblastoma), breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vulva, chronic lymphocytic leukemia, chronic myeloid cancer, colon cancer, esophageal cancer, cervical cancer, fibrosarcoma, gastrointestinal carcinoid tumor, head and neck cancer (e.g., head and neck squamous cell carcinoma), Hodgkin lymphoma, hypopharynx cancer, kidney cancer, larynx cancer, leukemia, liquid tumors, liver cancer, lung cancer (e.g., non-small cell lung carcinoma and lung adenocarcinoma), lymphoma, mesothelioma, mastocytoma, melanoma, multiple myeloma, nasopharynx cancer, non-Hodgkin lymphoma, B-chronic lymphocytic leukemia, hairy cell leukemia, acute lymphocytic leukemia (ALL), and Burkitt's lymphoma, ovarian cancer, pancreatic cancer, peritoneum, omentum, and mesentery cancer, pharynx cancer, prostate cancer, rectal cancer, renal cancer, skin cancer, small intestine cancer, soft tissue cancer, solid tumors, synovial sarcoma, gastric cancer, testicular cancer, thyroid cancer, and ureter cancer.

In another aspect, provided herein is an RNA polynucleotide comprising an Internal Ribosome Entry Site (IRES), an expression sequence encoding a chimeric antigen receptor (CAR) polypeptide, and at least one self-circularizing element.

In some embodiments, the RNA polynucleotide comprises a 5' duplex forming region, an Anabaena 3' group I intron fragment with a first permutation site, an Internal Ribosome Entry Site (IRES), an expression sequence encoding a chimeric antigen receptor (CAR) polypeptide, an Anabaena 5' group I intron fragment with a second permutation site, and a 3' duplex forming region. In some embodiments, the RNA polynucleotide comprises a 5' duplex forming region, a first permutation site, an Internal Ribosome Entry Site (IRES), an expression sequence encoding a chimeric antigen receptor (CAR) polypeptide, a second permutation site, and a 3' duplex forming region. In some embodiments, the self-circularizing element is a group I intron fragment. In some embodiments, a 3' group I intron fragment and a 5' intron fragment. In some embodiments, the 3' group I intron fragment and 5' group I intron fragment are Anabaena group I intron fragments. In some embodiments, the 3' intron fragment and 5' intron fragment are defined by the L9a-5 permutation site in the intact intron. In some embodiments, the 3' intron fragment and 5' intron fragment are defined by the L8-2 permutation site in the intact intron. In some embodiments, the RNA polynucleotide is capable of circularizing in the absence of an enzyme. In some embodiments, the RNA polynucleotide consists of natural nucleotides.

In another aspect, the present disclosures provides a DNA vector suitable for synthesizing the RNA polynucleotide of one of the above embodiments.

In some embodiments, a circular RNA polynucleotide of the present disclosure is delivered to a target cell in a non-lipid polymeric core-shell nanoparticle.

INCORPORATION BY REFERENCE

All publications, patents, and patent applications mentioned in this specification are herein incorporated by reference to the same extent as if each individual publication, patent, or patent application was specifically and individually indicated as being incorporated by reference herein.

BRIEF DESCRIPTION OF THE DRAWINGS

FIG. 40 shows the lysis of target and non-target cells by T cells electroporated with circRNA encoding anti-CD19 CAR.

FIG. 41 shows the efficacy of T-cells electroporated with anti-CD19 CAR-encoding circRNAs in lysing CD19+ Raji cells as compared to T-cells transduced with anti-CD19 CAR-encoding lentivirus.

DETAILED DESCRIPTION

Figure 1A:
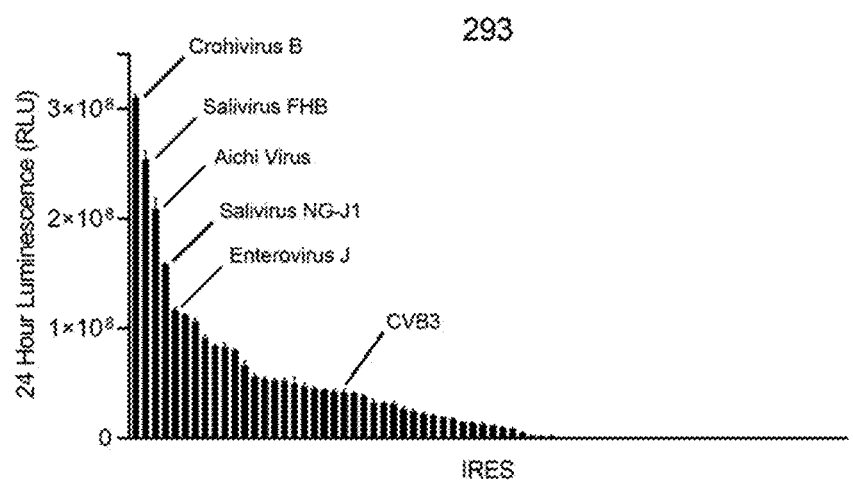
FIG. 1 depicts luminescence in supernatants of HEK293 (FIG. 1A), HepG2 (FIG. 1B), or 1C1C7 (FIG. 1C) cells 24 hours after transfection with circular RNA comprising a *Gaussia* luciferase expression sequence and various IRES sequences.

Provided herein are pharmaceutical compositions and transfer vehicles, e.g., lipid nanoparticles, comprising circular RNA. The circular RNA provided herein may be delivered and/or targeted to a cell in a transfer vehicle, e.g., a nanoparticle, or a composition comprising a transfer vehicle. In some embodiments, the circular RNA may also be delivered to a subject in a transfer vehicle or a composition comprising a transfer vehicle. In some embodiments, the transfer vehicle is a nanoparticle. In some embodiments, the nanoparticle is a lipid nanoparticle, a non-lipid polymeric core-shell nanoparticle, or a biodegradable nanoparticle. In some embodiments, the transfer vehicle comprises one or more ionizable lipids, PEG modified lipids, helper lipids, and/or structural lipids.

In some embodiments, a transfer vehicle encapsulates circular RNA and comprises an ionizable lipid, a structural lipid, and a PEG-modified lipid. In some embodiments, a transfer vehicle encapsulates circular RNA and comprises an ionizable lipid, a structural lipid, a PEG-modified lipid, and a helper lipid.

Without wishing to be bound by theory, it is thought that transfer vehicles described herein shield encapsulated circular RNA from degradation and provide for effective delivery of circular RNA to target cells in vivo and in vitro.

Embodiments of the present disclosure provide lipid compositions described according to the respective molar ratios of the component lipids in the formulation. In one embodiment, the mol-% of the ionizable lipid may be from about 10 mol-% to about 80 mol-%. In one embodiment, the mol-% of the ionizable lipid may be from about 20 mol-% to about 70 mol-%. In one embodiment, the mol-% of the ionizable lipid may be from about 30 mol-% to about 60 mol-%. In one embodiment, the mol-% of the ionizable lipid may be from about 35 mol-% to about 55 mol-%. In one embodiment, the mol-% of the ionizable lipid may be from about 40 mol-% to about 50 mol-%. In some embodiments, the ionizable lipid mol-% of the transfer vehicle batch will be ±30%, ±25%, ±20%, ±15%, ±10%, ±5%, or ±2.5% of the target mol-%. In certain embodiments, transfer vehicle inter-lot variability will be less than 15%, less than 10% or less than 5%.

In one embodiment, the mol-% of the helper lipid may be from about 1 mol-% to about 50 mol-%. In one embodiment, the mol-% of the helper lipid may be from about 2 mol-% to about 45 mol-%. In one embodiment, the mol-% of the helper lipid may be from about 3 mol-% to about 40 mol-%. In one embodiment, the mol-% of the helper lipid may be from about 4 mol-% to about 35 mol-%. In one embodiment, the mol-% of the helper lipid may be from about 5 mol-% to about 30 mol-%. In one embodiment, the mol-% of the helper lipid may be from about 10 mol-% to about 20 mol-%. In some embodiments, the helper lipid mol-% of the transfer vehicle batch will be ±30%, ±25%, ±20%, ±15%, ±10%, ±5%, or ±2.5% of the target mol-%.

In one embodiment, the mol-% of the structural lipid may be from about 10 mol-% to about 80 mol-%. In one embodiment, the mol-% of the structural lipid may be from about 20 mol-% to about 70 mol-%. In one embodiment, the mol-% of the structural lipid may be from about 30 mol-% to about 60 mol-%. In one embodiment, the mol-% of the structural lipid may be from about 35 mol-% to about 55 mol-%. In one embodiment, the mol-% of the structural lipid may be from about 40 mol-% to about 50 mol-%. In some embodiments, the structural lipid mol-% of the transfer vehicle batch will be ±30%, ±25%, ±20%, ±15%, ±10%, ±5%, or ±2.5% of the target mol-%.

In one embodiment, the mol-% of the PEG modified lipid may be from about 0.1 mol-% to about 10 mol-%. In one embodiment, the mol-% of the PEG modified lipid may be from about 0.2 mol-% to about 5 mol-%. In one embodiment, the mol-% of the PEG modified lipid may be from about 0.5 mol-% to about 3 mol-%. In one embodiment, the mol-% of the PEG modified lipid may be from about 1 mol-% to about 2 mol-%. In one embodiment, the mol-% of the PEG modified lipid may be about 1.5 mol-%. In some embodiments, the PEG modified lipid mol-% of the transfer vehicle batch will be ±30%, ±25%, ±20%, ±15%, ±10%, ±5%, or ±2.5% of the target mol-%.

Also contemplated are pharmaceutical compositions, and in particular transfer vehicles, that comprise one or more of the compounds disclosed herein. In certain embodiments, such transfer vehicles comprise one or more of a PEG-modified lipid, an ionizable lipid, a helper lipid, and/or a structural lipid disclosed herein. Also contemplated are transfer vehicles that comprise one or more of the compounds disclosed herein and that further comprise one or more additional lipids. In certain embodiments, such transfer vehicles are loaded with or otherwise encapsulate circular RNA.

Transfer vehicles of the invention encapsulate circular RNA. In certain embodiments, the polynucleotides encapsulated by the compounds or pharmaceutical and liposomal compositions of the invention include RNA encoding a protein or enzyme (e.g., circRNA encoding, for example, phenylalanine hydroxylase (PAH)). The present invention contemplates the use of such polynucleotides as a therapeutic that is capable of being expressed by target cells for the production (and in certain instances, the excretion) of a functional enzyme or protein as disclosed, for example, in International Application No. PCT/US2010/058457 and in U.S. Provisional Application No. 61/494,881, filed Jun. 8, 2011, the teachings of which are both incorporated herein by reference in their entirety. For example, in certain embodiments, upon the expression of one or more polynucleotides by target cells, the production of a functional enzyme or protein in which a subject is deficient (e.g., a urea cycle enzyme or an enzyme associated with a lysosomal storage disorder) may be observed. As another example, circular RNA encapsulated by a transfer vehicle may encode a T cell receptor protein or a chimeric antigen receptor (CAR).

Also provided herein are methods of treating a disease in a subject by administering an effective amount of a composition comprising circular RNA encoding a functional protein and a transfer vehicle described herein to the subject. In some embodiments, the circular RNA is encapsulated within the transfer vehicle. In certain embodiments, such methods may enhance (e.g., increase) the expression of a polynucleotide and/or increase the production and secretion of a functional polypeptide product in one or more target cells and tissues (e.g., hepatocytes). Generally, such methods comprise contacting the target cells with one or more compounds and/or transfer vehicles that comprise or otherwise encapsulate the circRNA.

In certain embodiments, the transfer vehicles (e.g., lipid nanoparticles) are formulated based in part upon their ability to facilitate the transfection (e.g., of a circular RNA) of a target cell. In another embodiment, the transfer vehicles (e.g., lipid nanoparticles) may be selected and/or prepared to optimize delivery of circular RNA to a target cell, tissue or organ. For example, if the target cell is a hepatocyte the properties of the pharmaceutical and/or liposomal compositions (e.g., size, charge and/or pH) may be optimized to effectively deliver such composition (e.g., lipid nanoparticles) to the target cell or organ, reduce immune clearance and/or promote retention in the target cell or organ. Alternatively, if the target tissue is the central nervous system, the selection and preparation of the transfer vehicle must consider penetration of, and retention within. the blood brain barrier and/or the use of alternate means of directly delivering such compositions (e.g., lipid nanoparticles) to such target tissue (e.g., via intracerebrovascular administration). In certain embodiments, the transfer vehicles may be combined with agents that facilitate the transfer of encapsulated materials across the blood brain barrier (e.g., agents which disrupt or improve the permeability of the blood brain barrier and thereby enhance the transfer of circular RNA to the target cells). While the transfer vehicles described herein (e.g., lipid nanoparticles) can facilitate introduction of circRNA into target cells, the addition of polycations (e.g., poly L-lysine and protamine) as a copolymer to one or more of the lipid nanoparticles that comprise the pharmaceutical compositions can in some instances markedly enhance the transfection efficiency of several types of transfer vehicles by 2-28 fold in a number of cell lines both in vitro and in vivo (See, N. J. Caplen, et al., Gene Ther. 1995; 2: 603; S. Li, et al., Gene Ther. 1997; 4, 891). In some embodiments, a target cell is an immune cell. In some embodiments, a target cell is a T cell.

In certain embodiments, the transfer vehicles described herein (e.g., lipid nanoparticles) are prepared by combining multiple lipid components (e.g., one or more of the compounds disclosed herein) with one or more polymer components. For example, a lipid nanoparticle may be prepared using HGT4003, DOPE, cholesterol and DMG-PEG2000. A lipid nanoparticle may be comprised of additional lipid combinations in various ratios, including for example, HGT4001, DOPE and DMG-PEG2000. The selection of ionizable lipids, helper lipids, structural lipids, and/or PEG-modified lipids which comprise the lipid nanoparticles, as well as the relative molar ratio of such lipids to each other, is based upon the characteristics of the selected lipid(s), the nature of the intended target cells or tissues and the characteristics of the materials or polynucleotides to be delivered by the lipid nanoparticle. Additional considerations include, for example, the saturation of the alkyl chain, as well as the size, charge, pH, pKa, fusogenicity and toxicity of the selected lipid(s).

Transfer vehicles described herein can allow the encapsulated polynucleotide to reach the target cell or may preferentially allow the encapsulated polynucleotide to reach the target cells or organs on a discriminatory basis (e.g., the transfer vehicles may concentrate in the liver or spleen of a subject to which such transfer vehicles are administered). Alternatively, the transfer vehicles may limit the delivery of encapsulated polynucleotides to other non-targeted cells or organs where the presence of the encapsulated polynucleotides may be undesirable or of limited utility.

Loading or encapsulating a polynucleotide, e.g., circRNA, into a transfer vehicle may serve to protect the polynucleotide from an environment (e.g., serum) which may contain enzymes or chemicals that degrade such polynucleotides and/or systems or receptors that cause the rapid excretion of such polynucleotides. Accordingly, in some embodiments, the compositions described herein are capable of enhancing the stability of the encapsulated polynucleotide(s), particularly with respect to the environments into which such polynucleotides will be exposed.

In certain embodiments, provided herein is a vector for making circular RNA, the vector comprising a 5' duplex forming region, a 3' group I intron fragment, optionally a first spacer, an Internal Ribosome Entry Site (IRES), an expression sequence, optionally a second spacer, a 5' group I intron fragment, and a 3' duplex forming region. In some embodiments, these elements are positioned in the vector in the above order. In some embodiments, the vector further comprises an internal 5' duplex forming region between the 3' group I intron fragment and the IRES and an internal 3' duplex forming region between the expression sequence and the 5' group I intron fragment. In some embodiments, the internal duplex forming regions are capable of forming a duplex between each other but not with the external duplex forming regions. In some embodiments, the internal duplex forming regions are part of the first and second spacers. Additional embodiments include circular RNA polynucleotides, including circular RNA polynucleotides made using the vectors provided herein, compositions comprising such circular RNA, cells comprising such circular RNA, methods of using and making such vectors, circular RNA, compositions and cells.

In some embodiments, provided herein are methods comprising administration of circular RNA polynucleotides provided herein into cells for therapy or production of useful proteins, such as chimeric antigen receptor (CAR) or T Cell Receptor (TCR) complex proteins. In some embodiments, the method is advantageous in providing the production of a desired polypeptide inside eukaryotic cells with a longer half-life than linear RNA, due to the resistance of the circular RNA to ribonucleases.

Circular RNA polynucleotides lack the free ends necessary for exonuclease-mediated degradation, causing them to be resistant to several mechanisms of RNA degradation and granting extended half-lives when compared to an equivalent linear RNA. Circularization allows for the stabilization of RNA polynucleotides that generally suffer from short half-lives and improves the overall efficacy of exogenous mRNA in a variety of applications. In an embodiment, the half-life of the circular RNA polynucleotides provided herein in eukaryotic cells (e.g., mammalian cells, such as human cells) is at least 20 hours (e.g., at least 80 hours).

1. Definitions

As used herein, the terms "circRNA" or "circular polyribonucleotide" or "circular RNA" are used interchangeably and refers to a polyribonucleotide that forms a circular structure through covalent bonds.

As used herein, the term "3' group I intron fragment" refers to a sequence with 75% or higher similarity to the 3'-proximal end of a natural group I intron including the splice site dinucleotide and optionally a stretch of natural exon sequence.

As used herein, the term "5' group I intron fragment" refers to a sequence with 75% or higher similarity to the 5'-proximal end of a natural group I intron including the splice site dinucleotide and optionally a stretch of natural exon sequence.

As used herein, the term "permutation site" refers to the site in a group I intron where a cut is made prior to permutation of the intron. This cut generates 3' and 5' group I intron fragments that are permuted to be on either side of a stretch of precursor RNA to be circularized.

As used herein, the term "splice site" refers to a dinucleotide that is partially or fully included in a group I intron and between which a phosphodiester bond is cleaved during RNA circularization.

As used herein, the term "therapeutic protein" refers to any protein that, when administered to a subject directly or indirectly in the form of a translated nucleic acid, has a therapeutic, diagnostic, and/or prophylactic effect and/or elicits a desired biological and/or pharmacological effect.

As used herein, the term "immunogenic" refers to a potential to induce an immune response to a substance. An immune response may be induced when an immune system of an organism or a certain type of immune cell is exposed to an immunogenic substance. The term "non-immunogenic" refers to a lack of or absence of an immune response above a detectable threshold to a substance. No immune response is detected when an immune system of an organism or a certain type of immune cell is exposed to a non-immunogenic substance. In some embodiments, a non-immunogenic circular polyribonucleotide as provided herein, does not induce an immune response above a pre-determined threshold when measured by an immunogenicity assay. In some embodiments, no innate immune response is detected when an immune system of an organism or a certain type of immune cell is exposed to a non-immunogenic circular polyribonucleotide as provided herein. In some embodiments, no adaptive immune response is detected when an immune system of an organism or a certain type of immune cell is exposed to a non-immunogenic circular polyribonucleotide as provided herein.

As used herein, the term "circularization efficiency" refers to a measurement of resultant circular polyribonucleotide as compared to its linear starting material.

As used herein, the term "translation efficiency" refers to a rate or amount of protein or peptide production from a ribonucleotide transcript. In some embodiments, translation efficiency can be expressed as amount of protein or peptide produced per given amount of transcript that codes for the protein or peptide.

The term "nucleotide" refers to a ribonucleotide, a deoxyribonucleotide, a modified form thereof, or an analog thereof. Nucleotides include species that comprise purines, e.g., adenine, hypoxanthine, guanine, and their derivatives and analogs, as well as pyrimidines, e.g., cytosine, uracil, thymine, and their derivatives and analogs. Nucleotide analogs include nucleotides having modifications in the chemical structure of the base, sugar and/or phosphate, including, but not limited to, 5'-position pyrimidine modifications, 8'-position purine modifications, modifications at cytosine exocyclic amines, and substitution of 5-bromo-uracil; and 2'-position sugar modifications, including but not limited to, sugar-modified ribonucleotides in which the 2'-OH is replaced by a group such as an H, OR, R, halo, SH, SR, NH2, NHR, NR2, or CN, wherein R is an alkyl moiety as defined herein. Nucleotide analogs are also meant to include nucleotides with bases such as inosine, queuosine, xanthine; sugars such as 2'-methyl ribose; non-natural phosphodiester linkages such as methylphosphonate, phosphorothioate and peptide linkages. Nucleotide analogs include 5-methoxyuridine, 1-methylpseudouridine, and 6-methyladenosine.

The term "nucleic acid" and "polynucleotide" are used interchangeably herein to describe a polymer of any length, e.g., greater than about 2 bases, greater than about 10 bases, greater than about 100 bases, greater than about 500 bases, greater than 1000 bases, or up to about 10,000 or more bases, composed of nucleotides, e.g., deoxyribonucleotides or ribonucleotides, and may be produced enzymatically or synthetically (e.g., as described in U.S. Pat. No. 5,948,902 and the references cited therein), which can hybridize with naturally occurring nucleic acids in a sequence specific manner analogous to that of two naturally occurring nucleic acids, e.g., can participate in Watson-Crick base pairing interactions. Naturally occurring nucleic acids are comprised of nucleotides including guanine, cytosine, adenine, thymine, and uracil (G, C, A, T, and U respectively).

The terms "ribonucleic acid" and "RNA" as used herein mean a polymer composed of ribonucleotides.

The terms "deoxyribonucleic acid" and "DNA" as used herein mean a polymer composed of deoxyribonucleotides.

"Isolated" or "purified" generally refers to isolation of a substance (for example, in some embodiments, a compound, a polynucleotide, a protein, a polypeptide, a polynucleotide composition, or a polypeptide composition) such that the substance comprises a significant percent (e.g., greater than 1%, greater than 2%, greater than 5%, greater than 10%, greater than 20%, greater than 50%, or more, usually up to about 90%-100%) of the sample in which it resides. In certain embodiments, a substantially purified component comprises at least 50%, 80%-85%, or 90%-95% of the sample. Techniques for purifying polynucleotides and polypeptides of interest are well-known in the art and include, for example, ion-exchange chromatography, affinity chromatography and sedimentation according to density. Generally, a substance is purified when it exists in a sample in an amount, relative to other components of the sample, that is more than as it is found naturally.

The terms "duplexed," "double-stranded" or "hybridized" as used herein refer to nucleic acids formed by hybridization of two single strands of nucleic acids containing complementary sequences. In most cases, genomic DNA is double-stranded. Sequences can be fully complementary or partially complementary.

As used herein, "unstructured" with regard to RNA refers to an RNA sequence that is not predicted by the RNAFold software or similar predictive tools to form a structure (e.g., a hairpin loop) with itself or other sequences in the same RNA molecule. In some embodiments, unstructured RNA can be functionally characterized using nuclease protection assays.

As used herein, "structured" with regard to RNA refers to an RNA sequence that is predicted by the RNAFold software or similar predictive tools to form a structure (e.g., a hairpin loop) with itself or other sequences in the same RNA molecule.

As used herein, two "duplex forming regions," "homology arms," or "homology regions," complement, or are complementary, to one another when the two regions share a sufficient level of sequence identity to one another's reverse complement to act as substrates for a hybridization reaction. As used herein polynucleotide sequences have "homology" when they are either identical or share sequence identity to a reverse complement or "complementary" sequence. The percent sequence identity between a homology region and a counterpart homology region's reverse complement can be any percent of sequence identity that allows for hybridization to occur. In some embodiments, an internal duplex forming region of an inventive polynucleotide is capable of forming a duplex with another internal duplex forming region and does not form a duplex with an external duplex forming region.

Linear nucleic acid molecules are said to have a "5'-terminus" (5' end) and a "3'-terminus" (3' end) because nucleic acid phosphodiester linkages occur at the 5' carbon and 3' carbon of the sugar moieties of the substituent mononucleotides. The end nucleotide of a polynucleotide at which a new linkage would be to a 5' carbon is its 5' terminal nucleotide. The end nucleotide of a polynucleotide at which a new linkage would be to a 3' carbon is its 3' terminal nucleotide. A terminal nucleotide, as used herein, is the nucleotide at the end position of the 3'- or 5'-terminus.

"Transcription" means the formation or synthesis of an RNA molecule by an RNA polymerase using a DNA molecule as a template. The invention is not limited with respect to the RNA polymerase that is used for transcription. For example, in some embodiments, a T7-type RNA polymerase can be used.

"Translation" means the formation of a polypeptide molecule by a ribosome based upon an RNA template.

It is to be understood that the terminology used herein is for the purpose of describing particular embodiments only, and is not intended to be limiting. As used in this specification and the appended claims, the singular forms "a," "an," and "the" include plural referents unless the content clearly dictates otherwise. Thus, for example, reference to "a cell" includes combinations of two or more cells, or entire cultures of cells; reference to "a polynucleotide" includes, as a practical matter, many copies of that polynucleotide. Unless specifically stated or obvious from context, as used herein, the term "or" is understood to be inclusive. Unless defined herein and below in the reminder of the specification, all technical and scientific terms used herein have the same meaning as commonly understood by one of ordinary skill in the art to which the invention pertains.

Unless specifically stated or obvious from context, as used herein, the term "about," is understood as within a range of normal tolerance in the art, for example within 2 standard deviations of the mean. "About" can be understood as within 10%, 9%, 8%, 7%, 6%, 5%, 4%, 3%, 2%, 1%, 0.9%, 0.8%, 0.7%, 0.6%, 0.5%, 0.4%, 0.3%, 0.2%, 0.1%, 0.09%, 0.08%, 0.07%, 0.06%, 0.05%, 0.04%, 0.03%, 0.02%, or 0.01% of the stated value. Unless otherwise clear from the context, all numerical values provided herein are modified by the term "about."

As used herein, the term "encode" refers broadly to any process whereby the information in a polymeric macromolecule is used to direct the production of a second molecule that is different from the first. The second molecule may have a chemical structure that is different from the chemical nature of the first molecule.

By "co-administering" is meant administering a therapeutic agent provided herein in conjunction with one or more additional therapeutic agents sufficiently close in time such that the therapeutic agent provided herein can enhance the effect of the one or more additional therapeutic agents, or vice versa.

The terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. The treatment or prevention provided by the method disclosed herein can include treatment or prevention of one or more conditions or symptoms of the disease. Also, for purposes herein, "prevention" can encompass delaying the onset of the disease, or a symptom or condition thereof.

As used herein, the term "expression sequence" can refer to a nucleic acid sequence that encodes a product, e.g., a peptide or polypeptide, regulatory nucleic acid, or non-coding nucleic acid. An exemplary expression sequence that codes for a peptide or polypeptide can comprise a plurality of nucleotide triads, each of which can code for an amino acid and is termed as a "codon".

As used herein, a "spacer" refers to a region of a polynucleotide sequence ranging from 1 nucleotide to hundreds or thousands of nucleotides separating two other elements along a polynucleotide sequence. The sequences can be defined or can be random. A spacer is typically non-coding. In some embodiments, spacers include duplex forming regions.

As used herein, "splice site" refers to the dinucleotide or dinucleotides between which cleavage of the phosphodiester bond occurs during a splicing reaction. A "5' splice site" refers to the natural 5' dinucleotide of the intron e.g., group I intron, while a "3' splice site" refers to the natural 3' dinucleotide of the intron.

As used herein, an "internal ribosome entry site" or "IRES" refers to an RNA sequence or structural element ranging in size from 10 nt to 1000 nt or more, capable of initiating translation of a polypeptide in the absence of a typical RNA cap structure. An IRES is typically about 500 nt to about 700 nt in length.

As used herein, an "miRNA site" refers to a stretch of nucleotides within a polynucleotide that is capable of forming a duplex with at least 8 nucleotides of a natural miRNA sequence.

As used herein, an "endonuclease site" refers to a stretch of nucleotides within a polynucleotide that is capable of being recognized and cleaved by an endonuclease protein.

As used herein, "bicistronic RNA" refers to a polynucleotide that includes two expression sequences coding for two distinct proteins. These expression sequences are often separated by a cleavable peptide such as a 2A site or an IRES sequence.

As used herein, the term "co-formulate" refers to a nanoparticle formulation comprising two or more nucleic acids or a nucleic acid and other active drug substance. Typically, the ratios are equimolar or defined in the ratiometric amount of the two or more nucleic acids or the nucleic acid and other active drug substance.

As used herein, "transfer vehicle" includes any of the standard pharmaceutical carriers, diluents, excipients, and the like, which are generally intended for use in connection with the administration of biologically active agents, including nucleic acids.

As used herein, the phrase "lipid nanoparticle" refers to a transfer vehicle comprising one or more lipids (e.g., in some embodiments, cationic lipids, non-cationic lipids, and PEG-modified lipids).

As used herein, the phrase "cationic lipid" refers to any of a number of lipid species that carry a net positive charge at a selected pH, such as physiological pH.

As used herein, the phrase "non-cationic lipid" refers to any neutral, zwitterionic or anionic lipid.

As used herein, the phrase "anionic lipid" refers to any of a number of lipid species that carry a net negative charge at a selected pH, such as physiological pH.

As used herein, the phrase "ionizable lipid" refers to any of a number of lipid species that carry a net positive charge at a selected pH, such as physiological pH 4 and a neutral charge at other pHs such as physiological pH 7.

In some embodiments, a lipid, e.g., an ionizable lipid, disclosed herein comprises one or more cleavable groups. The terms "cleave" and "cleavable" are used herein to mean that one or more chemical bonds (e.g., one or more of covalent bonds, hydrogen-bonds, van der Waals' forces and/or ionic interactions) between atoms in or adjacent to the subject functional group are broken (e.g., hydrolyzed) or are capable of being broken upon exposure to selected conditions (e.g., upon exposure to enzymatic conditions). In certain embodiments, the cleavable group is a disulfide functional group, and in particular embodiments is a disulfide group that is capable of being cleaved upon exposure to selected biological conditions (e.g., intracellular conditions). In certain embodiments, the cleavable group is an ester functional group that is capable of being cleaved upon exposure to selected biological conditions. For example, the disulfide groups may be cleaved enzymatically or by a hydrolysis, oxidation or reduction reaction. Upon cleavage of such disulfide functional group, the one or more functional moieties or groups (e.g., one or more of a head-group and/or a tail-group) that are bound thereto may be liberated. Exemplary cleavable groups may include, but are not limited to, disulfide groups, ester groups, ether groups, and any derivatives thereof (e.g., alkyl and aryl esters). In certain embodiments, the cleavable group is not an ester group or an ether group. In some embodiments, a cleavable group is bound (e.g., bound by one or more of hydrogen-bonds, van der Waals' forces, ionic interactions and covalent bonds) to one or more functional moieties or groups (e.g., at least one head-group and at least one tail-group). In certain embodiments, at least one of the functional moieties or groups is hydrophilic (e.g., a hydrophilic head-group comprising one or more of imidazole, guanidinium, amino, imine, enamine, optionally-substituted alkyl amino and pyridyl).

As used herein, the term "hydrophilic" is used to indicate in qualitative terms that a functional group is water-preferring, and typically such groups are water-soluble. For example, disclosed herein are compounds that comprise a cleavable disulfide (S—S) functional group bound to one or more hydrophilic groups (e.g., a hydrophilic head-group), wherein such hydrophilic groups comprise or are selected from the group consisting of imidazole, guanidinium, amino, imine, enamine, an optionally-substituted alkyl amino (e.g., an alkyl amino such as dimethylamino) and pyridyl.

In certain embodiments, at least one of the functional groups of moieties that comprise the compounds disclosed herein is hydrophobic in nature (e.g., a hydrophobic tail-group comprising a naturally-occurring lipid such as cholesterol). As used herein, the term "hydrophobic" is used to indicate in qualitative terms that a functional group is water-avoiding, and typically such groups are not water soluble. For example, disclosed herein are compounds that comprise a cleavable functional group (e.g., a disulfide (S—S) group) bound to one or more hydrophobic groups, wherein such hydrophobic groups comprise one or more naturally occurring lipids such as cholesterol, and/or an optionally substituted, variably saturated or unsaturated $C_6$-$C_{20}$ alkyl and/or an optionally substituted, variably saturated or unsaturated $C_6$-$C_{20}$ acyl.

In certain embodiments, the compounds disclosed herein comprise, for example, at least one hydrophilic head-group and at least one hydrophobic tail-group, each bound to at least one cleavable group, thereby rendering such compounds amphiphilic. As used herein to describe a compound or composition, the term "amphiphilic" means the ability to dissolve in both polar (e.g., water) and non-polar (e.g., lipid) environments. For example, in certain embodiments, the compounds disclosed herein comprise at least one lipophilic tail-group (e.g., cholesterol or a $C_6$-$C_{20}$ alkyl) and at least one hydrophilic head-group (e.g., imidazole), each bound to a cleavable group (e.g., disulfide).

It should be noted that the terms "head-group" and "tail-group" as used describe the compounds of the present invention, and in particular functional groups that comprise such compounds, are used for ease of reference to describe the orientation of one or more functional groups relative to other functional groups. For example, in certain embodiments a hydrophilic head-group (e.g., guanidinium) is bound (e.g., by one or more of hydrogen-bonds, van der Waals' forces, ionic interactions and covalent bonds) to a cleavable functional group (e.g., a disulfide group), which in turn is bound to a hydrophobic tail-group (e.g., cholesterol).

As used herein, the term "alkyl" refers to both straight and branched chain $C_1$-$C_{40}$ hydrocarbons (e.g., $C_6$-$C_{20}$ hydrocarbons), and include both saturated and unsaturated hydrocarbons. In certain embodiments, the alkyl may comprise one or more cyclic alkyls and/or one or more heteroatoms such as oxygen, nitrogen, or sulfur and may optionally be substituted with substituents (e.g., one or more of alkyl, halo, alkoxyl, hydroxy, amino, aryl, ether, ester or amide). In certain embodiments, a contemplated alkyl includes (9Z, 12Z)-octadeca-9,12-dien. The use of designations such as, for example, "$C_6$-$C_{20}$" is intended to refer to an alkyl (e.g., straight or branched chain and inclusive of alkenes and alkyls) having the recited range carbon atoms.

As used herein, the term "aryl" refers to aromatic groups (e.g., monocyclic, bicyclic and tricyclic structures) containing six to ten carbons in the ring portion. The aryl groups may be optionally substituted through available carbon atoms and in certain embodiments may include one or more heteroatoms such as oxygen, nitrogen or sulfur.

In certain embodiments the compounds and the transfer vehicles of which such compounds are a component (e.g., lipid nanoparticles) exhibit an enhanced (e.g., increased) ability to transfect one or more target cells. Accordingly, also provided herein are methods of transfecting one or more target cells. Such methods generally comprise the step of contacting the one or more target cells with the compounds and/or pharmaceutical compositions disclosed herein such that the one or more target cells are transfected with the circular RNA encapsulated therein. As used herein, the terms "transfect" or "transfection" refer to the intracellular introduction of one or more encapsulated materials (e.g., nucleic acids and/or polynucleotides) into a cell, or preferably into a target cell. The term "transfection efficiency" refers to the relative amount of such encapsulated material (e.g., polynucleotides) up-taken by, introduced into and/or expressed by the target cell which is subject to transfection. In some embodiments, transfection efficiency may be estimated by the amount of a reporter polynucleotide product produced by the target cells following transfection. In some embodiments, a transfer vehicle has high transfection efficiency. In some embodiments, a transfer vehicle has at least about 10%, 20%, 30%, 40%, 50%, 60%, 70%, 80%, or 90% transfection efficiency.

As used herein, the term "liposome" generally refers to a vesicle composed of lipids (e.g., amphiphilic lipids) arranged in one or more spherical bilayer or bilayers. In certain embodiments, the liposome is a lipid nanoparticle (e.g., a lipid nanoparticle comprising one or more of the ionizable lipid compounds disclosed herein). Such liposomes may be unilamellar or multilamellar vesicles which have a membrane formed from a lipophilic material and an aqueous interior that contains the encapsulated circRNA to be delivered to one or more target cells, tissues and organs. In certain embodiments, the compositions described herein comprise one or more lipid nanoparticles. Examples of suitable lipids (e.g., ionizable lipids) that may be used to form the liposomes and lipid nanoparticles contemplated include one or more of the compounds disclosed herein (e.g., HGT4001, HGT4002, HGT4003, HGT4004 and/or HGT4005). Such liposomes and lipid nanoparticles may also comprise additional ionizable lipids such as C12-200, DLin-KC2-DMA, and/or HGT5001, helper lipids, structural lipids, PEG-modified lipids, MC3, DLinDMA, DLinkC2DMA, cKK-E12, ICE, HGT5000, DODAC, DDAB, DMRIE, DOSPA, DOGS, DODAP, DODMA, DMDMA, DODAC, DLenDMA, DMRIE, CLinDMA, CpLinDMA, DMOBA, DOcarbDAP, DLinDAP, DLincarbDAP, DLinCDAP, KLin-K-DMA, DLin-K-XTC2-DMA, HGT4003, and combinations thereof.

As used herein, the phrases "non-cationic lipid", "non-cationic helper lipid", and "helper lipid" are used interchangeably and refer to any neutral, zwitterionic or anionic lipid.

As used herein, the phrase "anionic lipid" refers to any of a number of lipid species that carry a net negative charge at a selected pH, such as physiological pH.

As used herein, the phrase "biodegradable lipid" or "degradable lipid" refers to any of a number of lipid species that are broken down in a host environment on the order of minutes, hours, or days ideally making them less toxic and unlikely to accumulate in a host over time. Common modifications to lipids include ester bonds, and disulfide bonds among others to increase the biodegradability of a lipid.

As used herein, the phrase "biodegradable PEG lipid" or "degradable PEG lipid" refers to any of a number of lipid species where the PEG molecules are cleaved from the lipid in a host environment on the order of minutes, hours, or days ideally making them less immunogenic. Common modifications to PEG lipids include ester bonds, and disulfide bonds among others to increase the biodegradability of a lipid.

In certain embodiments of the present invention, the transfer vehicles (e.g., lipid nanoparticles) are prepared to encapsulate one or more materials or therapeutic agents (e.g., circRNA). The process of incorporating a desired therapeutic agent (e.g., circRNA) into a transfer vehicle is referred to herein as or "loading" or "encapsulating" (Lasic, et al., FEBS Lett., 312: 255-258, 1992). The transfer vehicle-loaded or -encapsulated materials (e.g., circRNA) may be completely or partially located in the interior space of the transfer vehicle, within a bilayer membrane of the transfer vehicle, or associated with the exterior surface of the transfer vehicle.

As used herein, the term "structural lipid" refers to sterols and also to lipids containing sterol moieties.

As defined herein, "sterols" are a subgroup of steroids consisting of steroid alcohols.

As used herein, the term "structural lipid" refers to sterols and also to lipids containing sterol moieties.

As used herein, the term "PEG" means any polyethylene glycol or other polyalkylene ether polymer.

As generally defined herein, a "PEG-OH lipid" (also referred to herein as "hydroxy-PEGylated lipid") is a PEGylated lipid having one or more hydroxyl (—OH) groups on the lipid.

As used herein, a "phospholipid" is a lipid that includes a phosphate moiety and one or more carbon chains, such as unsaturated fatty acid chains.

The term "antibody" (Ab) includes, without limitation, a glycoprotein immunoglobulin which binds specifically to an antigen. In general, and antibody may comprise at least two heavy (H) chains and two light (L) chains interconnected by disulfide bonds, or an antigen-binding molecule thereof. Each H chain comprises a heavy chain variable region (abbreviated herein as VH) and a heavy chain constant region. The heavy chain constant region comprises three constant domains, CH1, CH2 and CH3. Each light chain comprises a light chain variable region (abbreviated herein as VL) and a light chain constant region. The light chain constant region comprises one constant domain, CL. The VH and VL regions may be further subdivided into regions of hypervariability, termed complementarity determining regions (CDRs), interspersed with regions that are more conserved, termed framework regions (FR). Each VH and VL comprises three CDRs and four FRs, arranged from amino-terminus to carboxy-terminus in the following order: FR1, CDR1, FR2, CDR2, FR3, CDR3, and FR4. The variable regions of the heavy and light chains contain a binding domain that interacts with an antigen. The constant regions of the Abs may mediate the binding of the immunoglobulin to host tissues or factors, including various cells of the immune system (e.g., effector cells) and the first component of the classical complement system. Antibodies may include, for example, monoclonal antibodies, recombinantly produced antibodies, monospecific antibodies, multispecific antibodies (including bispecific antibodies), human antibodies, engineered antibodies, humanized antibodies, chimeric antibodies, immunoglobulins, synthetic antibodies, tetrameric antibodies comprising two heavy chain and two light chain molecules, an antibody light chain monomer, an antibody heavy chain monomer, an antibody light chain dimer, an antibody heavy chain dimer, an antibody light chain-antibody heavy chain pair, intrabodies, antibody fusions (sometimes referred to herein as "antibody conjugates"), heteroconjugate antibodies, single domain antibodies, monovalent antibodies, single chain antibodies or single-chain Fvs (scFv), camelized antibodies, affybodies, Fab fragments, F(ab')2 fragments, disulfide-linked Fvs (sdFv), anti-idiotypic (anti-id) antibodies (including, e.g., anti-anti-Id antibodies), minibodies, domain antibodies, synthetic antibodies (sometimes referred to herein as "antibody mimetics"), and antigen-binding fragments of any of the above. In some embodiments, antibodies described herein refer to polyclonal antibody populations.

An immunoglobulin may derive from any of the commonly known isotypes, including but not limited to IgA, secretory IgA, IgG and IgM. IgG subclasses are also well known to those in the art and include but are not limited to human IgG1, IgG2, IgG3 and IgG4. "Isotype" refers to the Ab class or subclass (e.g., IgM or IgG1) that is encoded by the heavy chain constant region genes. The term "antibody" includes, by way of example, both naturally occurring and non-naturally occurring Abs; monoclonal and polyclonal Abs; chimeric and humanized Abs; human or nonhuman Abs; wholly synthetic Abs; and single chain Abs. A nonhuman Ab may be humanized by recombinant methods to reduce its immunogenicity in man. Where not expressly stated, and unless the context indicates otherwise, the term "antibody" also includes an antigen-binding fragment or an antigen-binding portion of any of the aforementioned immunoglobulins, and includes a monovalent and a divalent fragment or portion, and a single chain Ab.

An "antigen binding molecule," "antigen binding portion," or "antibody fragment" refers to any molecule that comprises the antigen binding parts (e.g., CDRs) of the antibody from which the molecule is derived. An antigen binding molecule may include the antigenic complementarity determining regions (CDRs). Examples of antibody fragments include, but are not limited to, Fab, Fab', F(ab')2, and Fv fragments, dAb, linear antibodies, scFv antibodies, and multispecific antibodies formed from antigen binding molecules. Peptibodies (i.e. Fc fusion molecules comprising peptide binding domains) are another example of suitable antigen binding molecules. In some embodiments, the antigen binding molecule binds to an antigen on a tumor cell. In some embodiments, the antigen binding molecule binds to an antigen on a cell involved in a hyperproliferative disease or to a viral or bacterial antigen. In some embodiments, the antigen binding molecule binds to BCMA. In further embodiments, the antigen binding molecule is an antibody fragment that specifically binds to the antigen, including one or more of the complementarity determining regions (CDRs) thereof. In further embodiments, the antigen binding molecule is a single chain variable fragment (scFv). In some embodiments, the antigen binding molecule comprises or consists of avimers.

As used herein, the term "variable region" or "variable domain" is used interchangeably and are common in the art. The variable region typically refers to a portion of an antibody, generally, a portion of a light or heavy chain, typically about the amino-terminal 110 to 120 amino acids in the mature heavy chain and about 90 to 115 amino acids in the mature light chain, which differ extensively in sequence among antibodies and are used in the binding and specificity of a particular antibody for its particular antigen. The variability in sequence is concentrated in those regions called complementarity determining regions (CDRs) while the more highly conserved regions in the variable domain are called framework regions (FR). Without wishing to be bound by any particular mechanism or theory, it is believed that the CDRs of the light and heavy chains are primarily responsible for the interaction and specificity of the antibody with antigen. In some embodiments, the variable region is a human variable region. In some embodiments, the variable region comprises rodent or murine CDRs and human framework regions (FRs). In particular embodiments, the variable region is a primate (e.g., non-human primate) variable region. In some embodiments, the variable region comprises rodent or murine CDRs and primate (e.g., non-human primate) framework regions (FRs).

The terms "VL" and "VL domain" are used interchangeably to refer to the light chain variable region of an antibody or an antigen-binding molecule thereof.

The terms "VH" and "VH domain" are used interchangeably to refer to the heavy chain variable region of an antibody or an antigen-binding molecule thereof.

A number of definitions of the CDRs are commonly in use: Kabat numbering, Chothia numbering, AbM numbering, or contact numbering. The AbM definition is a compromise between the two used by Oxford Molecular's AbM antibody modelling software. The contact definition is based on an analysis of the available complex crystal structures. The term "Kabat numbering" and like terms are recognized in the art and refer to a system of numbering amino acid residues in the heavy and light chain variable regions of an antibody, or an antigen-binding molecule thereof. In certain aspects, the CDRs of an antibody may be determined according to the Kabat numbering system (see, e.g., Kabat E A & Wu T T (1971) Ann NY Acad Sci 190: 382-391 and Kabat E A et al., (1991) Sequences of Proteins of Immunological Interest, Fifth Edition, U.S. Department of Health and Human Services, NIH Publication No. 91-3242). Using the Kabat numbering system, CDRs within an antibody heavy chain molecule are typically present at amino acid positions 31 to 35, which optionally may include one or two additional amino acids, following 35 (referred to in the Kabat numbering scheme as 35A and 35B) (CDR1), amino acid positions 50 to 65 (CDR2), and amino acid positions 95 to 102 (CDR3). Using the Kabat numbering system, CDRs within an antibody light chain molecule are typically present at amino acid positions 24 to 34 (CDR1), amino acid positions 50 to 56 (CDR2), and amino acid positions 89 to 97 (CDR3). In a specific embodiment, the CDRs of the antibodies described herein have been determined according to the Kabat numbering scheme. In certain aspects, the CDRs of an antibody may be determined according to the Chothia numbering scheme, which refers to the location of immunoglobulin structural loops (see, e.g., Chothia C & Lesk A M, (1987), J Mol Biol 196: 901-917; Al-Lazikani B et al, (1997) J Mol Biol 273: 927-948; Chothia C et al., (1992) J Mol Biol 227: 799-817; Tramontano A et al, (1990) J Mol Biol 215(1): 175-82; and U.S. Pat. No. 7,709,226). Typically, when using the Kabat numbering convention, the Chothia CDR-H1 loop is present at heavy chain amino acids 26 to 32, 33, or 34, the Chothia CDR-H2 loop is present at heavy chain amino acids 52 to 56, and the Chothia CDR-H3 loop is present at heavy chain amino acids 95 to 102, while the Chothia CDR-L1 loop is present at light chain amino acids 24 to 34, the Chothia CDR-L2 loop is present at light chain amino acids 50 to 56, and the Chothia CDR-L3 loop is present at light chain amino acids 89 to 97. The end of the Chothia CDR-HI loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34). In a specific embodiment, the CDRs of the antibodies described herein have been determined according to the Chothia numbering scheme.

As used herein, the terms "constant region" and "constant domain" are interchangeable and have a meaning common in the art. The constant region is an antibody portion, e.g., a carboxyl terminal portion of a light and/or heavy chain which is not directly involved in binding of an antibody to antigen but which may exhibit various effector functions, such as interaction with the Fc receptor. The constant region of an immunoglobulin molecule generally has a more conserved amino acid sequence relative to an immunoglobulin variable domain.

"Binding affinity" generally refers to the strength of the sum total of non-covalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y may generally be represented by the dissociation constant (KD or Kd). Affinity may be measured and/or expressed in a number of ways known in the art, including, but not limited to, equilibrium dissociation constant (KD), and equilibrium association constant (KA or Ka). The KD is calculated from the quotient of koff/kon, whereas KA is calculated from the quotient of kon/koff. kon refers to the association rate constant of, e.g., an antibody to an antigen, and koff refers to the dissociation of, e.g., an antibody to an antigen. The kon and koff may be determined by techniques known to one of ordinary skill in the art, such as BIACORE® or KinExA.

As used herein, a "conservative amino acid substitution" is one in which the amino acid residue is replaced with an amino acid residue having a similar side chain. Families of amino acid residues having side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). In some embodiments, one or more amino acid residues within a CDR(s) or within a framework region(s) of an antibody or antigen-binding molecule thereof may be replaced with an amino acid residue with a similar side chain.

As, used herein, the term "heterologous" means from any source other than naturally occurring sequences.

As used herein, an "epitope" is a term in the art and refers to a localized region of an antigen to which an antibody may specifically bind. An epitope may be, for example, contiguous amino acids of a polypeptide (linear or contiguous epitope) or an epitope can, for example, come together from two or more non-contiguous regions of a polypeptide or polypeptides (conformational, non-linear, discontinuous, or non-contiguous epitope). In some embodiments, the epitope to which an antibody binds may be determined by, e.g., NMR spectroscopy, X-ray diffraction crystallography studies, ELISA assays, hydrogen/deuterium exchange coupled with mass spectrometry (e.g., liquid chromatography electrospray mass spectrometry), array-based oligo-peptide scanning assays, and/or mutagenesis mapping (e.g., site-directed mutagenesis mapping). For X-ray crystallography, crystallization may be accomplished using any of the known methods in the art (e.g., Giege R et al., (1994) Acta Crystallogr D Biol Crystallogr 50 (Pt 4): 339-350; McPherson A (1990) Eur J Biochem 189: 1-23; Chayen N E (1997) Structure 5: 1269-1274; McPherson A (1976) J Biol Chem 251: 6300-6303). Antibody: antigen crystals may be studied using well known X-ray diffraction techniques and may be refined using computer software such as X-PLOR (Yale University, 1992, distributed by Molecular Simulations, Inc.; see e.g. Meth Enzymol (1985) volumes 114 & 115, eds Wyckoff H W et al.; U.S. 2004/0014194), and BUSTER (Bricogne G (1993) Acta Crystallogr D Biol Crystallogr 49 (Pt 1): 37-60; Bricogne G (1997) Meth Enzymol 276A: 361-423, ed Carter C W; Roversi P et al., (2000) Acta Crystallogr D Biol Crystallogr 56 (Pt 10): 1316-1323).

As used herein, an antigen binding molecule, an antibody, or an antigen binding molecule thereof "cross-competes" with a reference antibody or an antigen binding molecule thereof if the interaction between an antigen and the first binding molecule, an antibody, or an antigen binding molecule thereof blocks, limits, inhibits, or otherwise reduces the ability of the reference binding molecule, reference antibody, or an antigen binding molecule thereof to interact with the antigen. Cross competition may be complete, e.g., binding of the binding molecule to the antigen completely blocks the ability of the reference binding molecule to bind the antigen, or it may be partial, e.g., binding of the binding molecule to the antigen reduces the ability of the reference binding molecule to bind the antigen. In some embodiments, an antigen binding molecule that cross-competes with a reference antigen binding molecule binds the same or an overlapping epitope as the reference antigen binding molecule. In other embodiments, the antigen binding molecule that cross-competes with a reference antigen binding molecule binds a different epitope as the reference antigen binding molecule. Numerous types of competitive binding assays may be used to determine if one antigen binding molecule competes with another, for example: solid phase direct or indirect radioimmunoas say (RIA); solid phase direct or indirect enzyme immunoassay (EIA); sandwich competition assay (Stahli et al., 1983, Methods in Enzymology 9:242-253); solid phase direct biotin-avidin EIA (Kirkland et al., 1986, J. Immunol. 137:3614-3619); solid phase direct labeled assay, solid phase direct labeled sandwich assay (Harlow and Lane, 1988, Antibodies, A Laboratory Manual, Cold Spring Harbor Press); solid phase direct label RIA using 1-125 label (Morel et al., 1988, Molec. Immunol. 25:7-15); solid phase direct biotin-avidin EIA (Cheung, et al., 1990, Virology 176:546-552); and direct labeled RIA (Moldenhauer et al., 1990, Scand. J. Immunol. 32:77-82).

As used herein, the terms "immunospecifically binds," "immunospecifically recognizes," "specifically binds," and "specifically recognizes" are analogous terms in the context of antibodies and refer to molecules that bind to an antigen (e.g., epitope or immune complex) as such binding is understood by one skilled in the art. For example, a molecule that specifically binds to an antigen may bind to other peptides or polypeptides, generally with lower affinity as determined by, e.g., immunoassays, BIACORE®, KinExA 3000 instrument (Sapidyne Instruments, Boise, ID), or other assays known in the art. In a specific embodiment, molecules that specifically bind to an antigen bind to the antigen with a KA that is at least 2 logs, 2.5 logs, 3 logs, 4 logs or greater than the KA when the molecules bind to another antigen.

An "antigen" refers to any molecule that provokes an immune response or is capable of being bound by an antibody or an antigen binding molecule. The immune response may involve either antibody production, or the activation of specific immunologically-competent cells, or both. A person of skill in the art would readily understand that any macromolecule, including virtually all proteins or peptides, may serve as an antigen. An antigen may be endogenously expressed, i.e. expressed by genomic DNA, or may be recombinantly expressed. An antigen may be specific to a certain tissue, such as a cancer cell, or it may be broadly expressed. In addition, fragments of larger molecules may act as antigens. In some embodiments, antigens are tumor antigens.

The term "autologous" refers to any material derived from the same individual to which it is later to be re-introduced. For example, the engineered autologous cell therapy (eACT™) method described herein involves collection of lymphocytes from a patient, which are then engineered to express, e.g., a CAR construct, and then administered back to the same patient.

The term "allogeneic" refers to any material derived from one individual which is then introduced to another individual of the same species, e.g., allogeneic T cell transplantation.

A "cancer" refers to a broad group of various diseases characterized by the uncontrolled growth of abnormal cells in the body. Unregulated cell division and growth results in the formation of malignant tumors that invade neighboring tissues and may also metastasize to distant parts of the body through the lymphatic system or bloodstream. A "cancer" or "cancer tissue" may include a tumor. Examples of cancers that may be treated by the methods disclosed herein include, but are not limited to, cancers of the immune system including lymphoma, leukemia, myeloma, and other leukocyte malignancies. In some embodiments, the methods disclosed herein may be used to reduce the tumor size of a tumor derived from, for example, bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, multiple myeloma, Hodgkin's Disease, non-Hodgkin's lymphoma (NHL), primary mediastinal large B cell lymphoma (PMBC), diffuse large B cell lymphoma (DLBCL), follicular lymphoma (FL), transformed follicular lymphoma, splenic marginal zone lymphoma (SMZL), cancer of the esophagus, cancer of the small intestine, cancer of the endocrine system, cancer of the thyroid gland, cancer of the parathyroid gland, cancer of the adrenal gland, cancer of the urethra, cancer of the penis, chronic or acute leukemia, acute myeloid leukemia, chronic myeloid leukemia, acute lymphoblastic leukemia (ALL) (including non T cell ALL), chronic lymphocytic leukemia (CLL), solid tumors of childhood, lymphocytic lymphoma, cancer of the bladder, cancer of the kidney or ureter, neoplasm of the central nervous system (CNS), primary CNS lymphoma, tumor angiogenesis, spinal axis tumor, brain stem glioma, pituitary adenoma, epidermoid cancer, squamous cell cancer, T cell lymphoma, environmentally induced cancers including those induced by asbestos, other B cell malignancies, and combinations of said cancers. In some embodiments, the methods disclosed herein may be used to reduce the tumor size of a tumor derived from, for example, sarcomas and carcinomas, fibrosarcoma, myxosarcoma, liposarcoma, chondrosarcoma, osteogenic sarcoma, Kaposi's sarcoma, sarcoma of soft tissue, and other sarcomas, synovioma, mesothelioma, Ewing's tumor, leiomyosarcoma, rhabdomyosarcoma, colon carcinoma, pancreatic cancer, breast cancer, ovarian cancer, prostate cancer, hepatocellular carcinomna, lung cancer, colorectal cancer, squamous cell carcinoma, basal cell carcinoma, adenocarcinoma (for example adenocarcinoma of the pancreas, colon, ovary, lung, breast, stomach, prostate, cervix, or esophagus), sweat gland carcinoma, sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, bladder carcinoma, carcinoma of the fallopian tubes, carcinoma of the endometrium, carcinoma of the cervix, carcinoma of the vagina, carcinoma of the vulva, carcinoma of the renal pelvis, CNS tumors (such as a glioma, astrocytoma, medulloblastoma, craniopharyogioma, ependymoma, pinealoma, hemangioblastoma, acoustic neuroma, oligodendroglioma, menangioma, melanoma, neuroblastoma and retinoblastoma). The particular cancer may be responsive to chemo- or radiation therapy or the cancer may be refractory. A refractor cancer refers to a cancer that is not amendable to surgical intervention and the cancer is either initially unresponsive to chemo- or radiation therapy or the cancer becomes unresponsive over time.

An "anti-tumor effect" as used herein, refers to a biological effect that may present as a decrease in tumor volume, a decrease in the number of tumor cells, a decrease in tumor cell proliferation, a decrease in the number of metastases, an increase in overall or progression-free survival, an increase in life expectancy, or amelioration of various physiological symptoms associated with the tumor. An anti-tumor effect may also refer to the prevention of the occurrence of a tumor, e.g., a vaccine.

A "cytokine," as used herein, refers to a non-antibody protein that is released by one cell in response to contact with a specific antigen, wherein the cytokine interacts with a second cell to mediate a response in the second cell. "Cytokine" as used herein is meant to refer to proteins released by one cell population that act on another cell as intercellular mediators. A cytokine may be endogenously expressed by a cell or administered to a subject. Cytokines may be released by immune cells, including macrophages, dendritic cells, B cells, T cells, and mast cells to propagate an immune response. Cytokines may induce various responses in the recipient cell. Cytokines may include homeostatic cytokines, chemokines, pro-inflammatory cytokines, effectors, and acute-phase proteins. For example, homeostatic cytokines, including interleukin (IL) 7 and IL-15, promote immune cell survival and proliferation, and pro-inflammatory cytokines may promote an inflammatory response. Examples of homeostatic cytokines include, but are not limited to, IL-2, IL-4, IL-5, IL-7, IL-10, IL-12p40, IL-12p'70, IL-15, and interferon (IFN) gamma. Examples of pro-inflammatory cytokines include, but are not limited to, IL-1a, IL-1b, IL-6, IL-13, IL-17a, IL-23, IL-27, tumor necrosis factor (TNF)-alpha, TNF-beta, fibroblast growth factor (FGF) 2, granulocyte macrophage colony-stimulating factor (GM-CSF), soluble intercellular adhesion molecule 1 (sICAM-1), soluble vascular adhesion molecule 1 (sVCAM-1), vascular endothelial growth factor (VEGF), VEGF-C, VEGF-D, and placental growth factor (PLGF). Examples of effectors include, but are not limited to, granzyme A, granzyme B, soluble Fas ligand (sFasL), TGF-beta, IL-35, and perforin. Examples of acute phase-proteins include, but are not limited to, C-reactive protein (CRP) and serum amyloid A (SAA).

The term "lymphocyte" as used herein includes natural killer (NK) cells, T cells, or B cells. NK cells are a type of cytotoxic (cell toxic) lymphocyte that represent a major component of the inherent immune system. NK cells reject tumors and cells infected by viruses. It works through the process of apoptosis or programmed cell death. They were termed "natural killers" because they do not require activation in order to kill cells. T cells play a major role in cell-mediated-immunity (no antibody involvement). Its T cell receptors (TCR) differentiate themselves from other lymphocyte types. The thymus, a specialized organ of the immune system, is primarily responsible for the T cell's maturation. There are six types of T cells, namely: Helper T cells (e.g., CD4+ cells), Cytotoxic T cells (also known as TC, cytotoxic T lymphocyte, CTL, T-killer cell, cytolytic T cell, CD8+ T cells or killer T cell), Memory T cells ((i) stem memory TSCM cells, like naive cells, are CD45RO−, CCR7+, CD45RA+, CD62L+ (L-selectin), CD27+, CD28+ and IL-7Ra+, but they also express large amounts of CD95, IL-2R[T CXCR3, and LFA-1, and show numerous functional attributes distinctive of memory cells); (ii) central memory TCM cells express L-selectin and the CCR7, they secrete IL-2, but not IFNγ or IL-4, and (iii) effector memory TEM cells, however, do not express L-selectin or CCR7 but produce effector cytokines like IFNγ and IL-4), Regulatory T cells (Tregs, suppressor T cells, or CD4+CD25+ or CD4+FoxP3+ regulatory T cells), Natural Killer T cells (NKT) and Gamma Delta T cells. B-cells, on the other hand, play a principal role in humoral immunity (with antibody involvement). It makes antibodies and antigens and performs the role of antigen-presenting cells (APCs) and turns into memory B-cells and plasma cells, both short-lived and long-lived, after activation by antigen interaction. In mammals, immature B-cells are formed in the bone marrow, where its name is derived from.

The term "genetically engineered" or "engineered" refers to a method of modifying the genome of a cell, including, but not limited to, deleting a coding or non-coding region or a portion thereof or inserting a coding region or a portion thereof. In some embodiments, the cell that is modified is a lymphocyte, e.g., a T cell, which may either be obtained from a patient or a donor. The cell may be modified to express an exogenous construct, such as, e.g., a chimeric antigen receptor (CAR) or a T cell receptor (TCR), which is incorporated into the cell's genome.

An "immune response" refers to the action of a cell of the immune system (for example, T lymphocytes, B lymphocytes, natural killer (NK) cells, macrophages, eosinophils, mast cells, dendritic cells and neutrophils) and soluble macromolecules produced by any of these cells or the liver (including Abs, cytokines, and complement) that results in selective targeting, binding to, damage to, destruction of, and/or elimination from a vertebrate's body of invading pathogens, cells or tissues infected with pathogens, cancerous or other abnormal cells, or, in cases of autoimmunity or pathological inflammation, normal human cells or tissues.

A "costimulatory signal," as used herein, refers to a signal, which in combination with a primary signal, such as TCR/CD3 ligation, leads to a T cell response, such as, but not limited to, proliferation and/or upregulation or down regulation of key molecules.

A "costimulatory ligand," as used herein, includes a molecule on an antigen presenting cell that specifically binds a cognate co-stimulatory molecule on a T cell. Binding of the costimulatory ligand provides a signal that mediates a T cell response, including, but not limited to, proliferation, activation, differentiation, and the like. A costimulatory ligand induces a signal that is in addition to the primary signal provided by a stimulatory molecule, for instance, by binding of a T cell receptor (TCR)/CD3 complex with a major histocompatibility complex (MHC) molecule loaded with peptide. A co-stimulatory ligand may include, but is not limited to, 3/TR6, 4-1BB ligand, agonist or antibody that binds Toll ligand receptor, B7-1 (CD80), B7-2 (CD86), CD30 ligand, CD40, CD7, CD70, CD83, herpes virus entry mediator (HVEM), human leukocyte antigen G (HLA-G), ILT4, immunoglobulin-like transcript (ILT) 3, inducible costimulatory ligand (ICOS-L), intercellular adhesion molecule (ICAM), ligand that specifically binds with B7-H3, lymphotoxin beta receptor, MHC class I chain-related protein A (MICA), MHC class I chain-related protein B (MICB), 0X40 ligand, PD-L2, or programmed death (PD) LI. A co-stimulatory ligand includes, without limitation, an antibody that specifically binds with a co-stimulatory molecule present on a T cell, such as, but not limited to, 4-1BB, B7-H3, CD2, CD27, CD28, CD30, CD40, CD7, ICOS, ligand that specifically binds with CD83, lymphocyte function-associated antigen-1 (LFA-1), natural killer cell receptor C (NKG2C), OX40, PD-1, or tumor necrosis factor superfamily member 14 (TNFSF14 or LIGHT).

A "costimulatory molecule" is a cognate binding partner on a T cell that specifically binds with a costimulatory ligand, thereby mediating a costimulatory response by the T cell, such as, but not limited to, proliferation. Costimulatory molecules include, but are not limited to, A "costimulatory molecule" is a cognate binding partner on a T cell that specifically binds with a costimulatory ligand, thereby mediating a costimulatory response by the T cell, such as, but not limited to, proliferation. Costimulatory molecules include, but are not limited to, 4-1BB/CD137, B7-H3, BAFFR, BLAME (SLAMF8), BTLA, CD 33, CD 45, CD100 (SEMA4D), CD103, CD134, CD137, CD154, CD16, CD160 (BY55), CD 18, CD19, CD19a, CD2, CD22, CD247, CD27, CD276 (B7-H3), CD28, CD29, CD3 (alpha; beta; delta; epsilon; gamma; zeta), CD30, CD37, CD4, CD4, CD40, CD49a, CD49D, CD49f, CD5, CD64, CD69, CD7, CD80, CD83 ligand, CD84, CD86, CD8alpha, CD8beta, CD9, CD96 (Tactile), CD1-1a, CD1-1b, CD1-1c, CD1-1d, CDS, CEACAM1, CRT AM, DAP-10, DNAM1 (CD226), Fc gamma receptor, GADS, GITR, HVEM (LIGHTR), IA4, ICAM-1, ICAM-1, ICOS, Ig alpha (CD79a), IL2R beta, IL2R gamma, IL7R alpha, integrin, ITGA4, ITGA4, ITGA6, IT GAD, ITGAE, ITGAL, ITGAM, ITGAX, ITGB2, ITGB7, ITGB1, KIRDS2, LAT, LFA-1, LFA-1, LIGHT, LIGHT (tumor necrosis factor superfamily member 14; TNFSF14), LTBR, Ly9 (CD229), lymphocyte function-associated antigen-1 (LFA-1 (CD1 la/CD18), MHC class I molecule, NKG2C, NKG2D, NKp30, NKp44, NKp46, NKp80 (KLRF1), 0X40, PAG/Cbp, PD-1, PSGL1, SELPLG (CD162), signaling lymphocytic activation molecule, SLAM (SLAMF1; CD150; IPO-3), SLAMF4 (CD244; 2B4), SLAMF6 (NTB-A; Ly108), SLAMF7, SLP-76, TNF, TNFr, TNFR2, Toll ligand receptor, TRANCE/RANKL, VLA1, or VLA-6, or fragments, truncations, or combinations thereof.

The recitations "sequence identity" or, for example, comprising a "sequence 50% identical to," as used herein, refer to the extent that sequences are identical on a nucleotide-by-nucleotide basis or an amino acid-by-amino acid basis over a window of comparison. Thus, a "percentage of sequence identity" may be calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. Included are nucleotides and polypeptides having at least about 50%, 55%, 60%, 65%, 70%, 75%, 80%, 85%, 90%, 95%, 96%, 97%, 98%, 99% or 100% sequence identity to any of the reference sequences described herein, typically where the polypeptide variant maintains at least one biological activity of the reference polypeptide.

2. Vectors, Precursor RNA, and Circular RNA

In certain aspects, provided herein are circular RNA polynucleotides comprising a 3' post splicing group I intron fragment, optionally a first spacer, an Internal Ribosome Entry Site (IRES), an expression sequence, optionally a second spacer, and a 5' post splicing group I intron fragment. In some embodiments, these regions are in that order. In some embodiments, the circular RNA is made by a method provided herein or from a vector provided herein.

In certain embodiments, transcription of a vector provided herein (e.g., comprising a 5' homology region, a 3' group I intron fragment, optionally a first spacer, an Internal Ribosome Entry Site (IRES), an expression sequence, optionally a second spacer, a 5' group I intron fragment, and a 3' homology region) results in the formation of a precursor linear RNA polynucleotide capable of circularizing. In some embodiments, this precursor linear RNA polynucleotide circularizes when incubated in the presence of guanosine nucleotide or nucleoside (e.g., GTP) and divalent cation (e.g., Mg2+).

In some embodiments, the vectors and precursor RNA polynucleotides provided herein comprise a first (5') duplex forming region and a second (3') duplex forming region. In certain embodiments, the first and second homology regions may form perfect or imperfect duplexes. Thus, in certain embodiments at least 75%, 80%, 85%, 90%, 91%, 92%, 93%, 94%, 95%, 96%, 97%, 98%, 99% or 100% of the first and second duplex forming regions may be base paired with one another. In some embodiments, the duplex forming regions are predicted to have less than 50% (e.g., less than 45%, less than 40%, less than 35%, less than 30%, less than 25%) base pairing with unintended sequences in the RNA (e.g., non-duplex forming region sequences). In some embodiments, including such duplex forming regions on the ends of the precursor RNA strand, and adjacent or very close to the group I intron fragment, bring the group I intron fragments in close proximity to each other, increasing splicing efficiency. In some embodiments, the duplex forming regions are 3 to 100 nucleotides in length (e.g., 3-75 nucleotides in length, 3-50 nucleotides in length, 20-50 nucleotides in length, 35-50 nucleotides in length, 5-25 nucleotides in length, 9-19 nucleotides in length). In some embodiments, the duplex forming regions are about 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 nucleotides in length. In some embodiments, the duplex forming regions have a length of about 9 to about 50 nucleotides. In one embodiment, the duplex forming regions have a length of about 9 to about 19 nucleotides. In some embodiments, the duplex forming regions have a length of about 20 to about 40 nucleotides. In certain embodiments, the duplex forming regions have a length of about 30 nucleotides.

Figure 25:
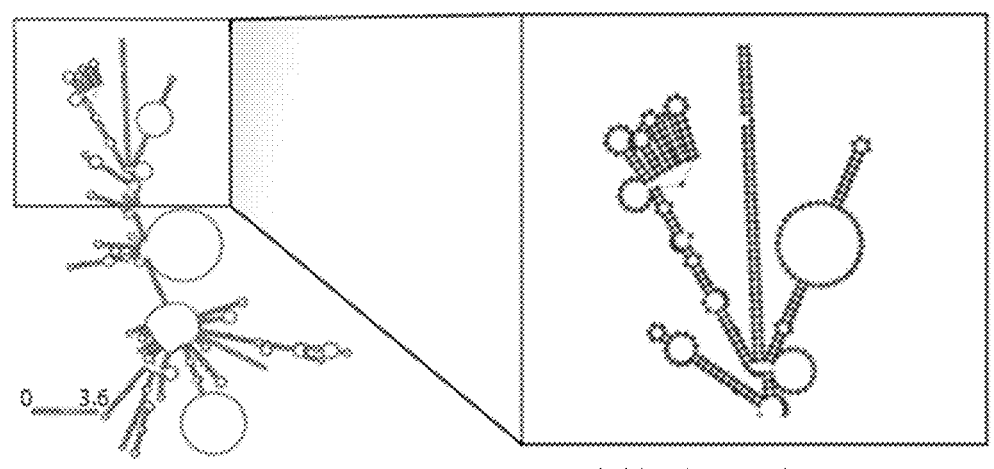
FIG. 25 depicts RNAFold predictions of precursor RNA secondary structure for homology arm design. Darker bases indicates higher base pairing probability. Without homology arms, no base pairing is predicted to occur between the ends of the precursor molecule.
Figure 25:
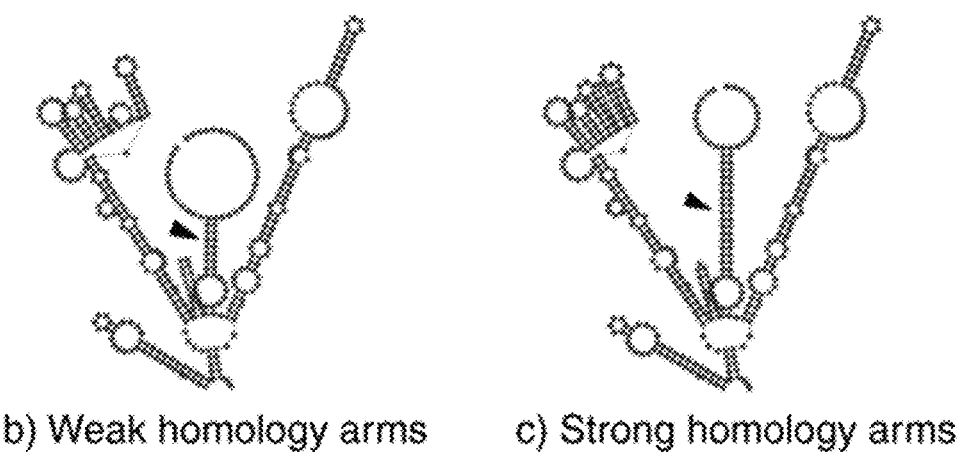

In certain embodiments, the vectors, precursor RNA and circular RNA provided herein comprise a first (5') and/or a second (3') spacer. In some embodiments, including a spacer between the 3' group I intron fragment and the IRES may conserve secondary structures in those regions by preventing them from interacting, thus increasing splicing efficiency. In some embodiments, the first (between 3' group I intron fragment and IRES) and second (between the expression sequence and 5' group I intron fragment) spacers comprise additional base pairing regions that are predicted to base pair with each other and not to the first and second duplex forming regions. In some embodiments, such spacer base pairing brings the group I intron fragments in close proximity to each other, further increasing splicing efficiency. Additionally, in some embodiments, the combination of base pairing between the first and second duplex forming regions, and separately, base pairing between the first and second spacers, promotes the formation of a splicing bubble containing the group I intron fragments flanked by adjacent regions of base pairing (FIG. 25). Typical spacers are contiguous sequences with one or more of the following qualities: 1) is predicted to avoid interfering with proximal structures, for example, the IRES, expression sequence, or intron; 2) is at least 7 nt long and no longer than 100 nt; 3) is located after and adjacent to the 3' intron fragment and/or before and adjacent to the 5' intron fragment; and 4) contains one or more of the following: a) an unstructured region at least 5 nt long, b) a region of base pairing at least 5 nt long to a distal sequence, including another spacer, and c) a structured region at least 7 nt long limited in scope to the sequence of the spacer. Spacers may have several regions, including an unstructured region, a base pairing region, a hairpin/structured region, and combinations thereof. In an embodiment, the spacer has a structured region with high GC content. In an embodiment, a region within a spacer base pairs with another region within the same spacer. In an embodiment, a region within a spacer base pairs with a region within another spacer. In an embodiment, a spacer comprises one or more hairpin structures. In an embodiment, a spacer comprises one or more hairpin structures with a stem of 4 to 12 nucleotides and a loop of 2 to 10 nucleotides. In an embodiment, there is an additional spacer between the 3' group I intron fragment and the IRES. In an embodiment, this additional spacer prevents the structured regions of the IRES from interfering with the folding of the 3' group I intron fragment or reduces the extent to which this occurs. In some embodiments, the 5' spacer sequence is at least 7, 8, 9, 10, 11, 12, 13, 14, 15, 16, 17, 18, 19, 20, 25 or 30 nucleotides in length. In some embodiments, the 5' spacer sequence is no more than 100, 90, 80, 70, 60, 50, 45, 40, 35 or 30 nucleotides in length. In some embodiments the 5' spacer sequence is between 5 and 50, 10 and 50, 20 and 50, 20 and 40, and/or 25 and 35 nucleotides in length. In certain embodiments, the 5' spacer sequence is 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 nucleotides in length. In one embodiment, the 5' spacer sequence is a polyA sequence. In another embodiment, the 5' spacer sequence is a polyAC sequence. In one embodiment, a spacer comprises about 10%, 20%, 30%, 40%, 50%, 60%, 70%, 80%, 90%, or 100% polyAC content. In one embodiment, a spacer comprises about 10%, 20%, 30%, 40%, 50%, 60%, 70%, 80%, 90%, or 100% polypyrimidine (C/T or C/U) content.

In certain embodiments, a 3' group I intron fragment is a contiguous sequence at least 75% homologous (e.g., at least 80%, 85%, 90%, 91%, 92%, 93%, 94%, 95%, 96%, 97%, 98%, 99% or 100% homologous) to a 3' proximal fragment of a natural group I intron including the 3' splice site dinucleotide and optionally the adjacent exon sequence at least 1 nt in length (e.g., at least 2, 3, 4, 5, 6, 7, 8, 9, 10, 15, 20, 25 or 30 nt in length) and at most the length of the exon. Typically, a 5' group I intron fragment is a contiguous sequence at least 75% homologous (e.g., at least 80%, 85%, 90%, 91%, 92%, 93%, 94%, 95%, 96%, 97%, 98%, 99% or 100% homologous) to a 5' proximal fragment of a natural group I intron including the 5' splice site dinucleotide and optionally the adjacent exon sequence at least 1 nt in length (e.g., at least 2, 3, 4, 5, 6, 7, 8, 9, 10, 15, 20, 25 or 30 nt in length) and at most the length of the exon. As described by Umekage et al. (2012), and illustrated in FIG. 33, external portions of the 3' group I intron fragment and 5' group I intron fragment are removed in circularization, causing the circular RNA provided herein to comprise only the portion of the 3' group I intron fragment formed by the optional exon sequence of at least 1 nt in length and 5' group I intron fragment formed by the optional exon sequence of at least 1 nt in length, if such sequences were present on the non-circularized precursor RNA. The part of the 3' group I intron fragment that is retained by a circular RNA is referred to herein as the post splicing 3' group I intron fragment. The part of the 5' group I intron fragment that is retained by a circular RNA is referred to herein as the post splicing 5' group I intron fragment.

In certain embodiments, the vectors, precursor RNA and circular RNA provided herein comprise an internal ribosome entry site (IRES). Inclusion of an IRES permits the translation of one or more open reading frames from a circular RNA (e.g., open reading frames that form the expression sequence). The IRES element attracts a eukaryotic ribosomal translation initiation complex and promotes translation initiation. See, e.g., Kaufman et al., Nuc. Acids Res. (1991) 19:4485-4490; Gurtu et al., Biochem. Biophys. Res. Comm. (1996) 229:295-298; Rees et al., BioTechniques (1996) 20: 102-110; Kobayashi et al., BioTechniques (1996) 21:399-402; and Mosser et al., BioTechniques 1997 22 150-161).

A multitude of IRES sequences are available and include sequences derived from a wide variety of viruses, such as from leader sequences of picornaviruses such as the encephalomyocarditis virus (EMCV) UTR (fang et al. J. Virol. (1989) 63: 1651-1660), the polio leader sequence, the hepatitis A virus leader, the hepatitis C virus IRES, human rhinovirus type 2 IRES (Dobrikova et al., Proc. Natl. Acad. Sci. (2003) 100(25): 15125-15130), an IRES element from the foot and mouth disease virus (Ramesh et al., Nucl. Acid Res. (1996) 24:2697-2700), a giardiavirus IRES (Garlapati et al., J. Biol. Chem. (2004) 279(5):3389-3397), and the like.

In some embodiments, the IRES is an IRES sequence of Taura syndrome virus, *Triatoma* virus, Theiler's encephalomyelitis virus, Simian Virus 40, *Solenopsis invicta* virus 1, *Rhopalosiphum padi* virus, Reticuloendotheliosis virus, Human poliovirus 1, *Plautia stali* intestine virus, Kashmir bee virus, Human rhinovirus 2, *Homalodisca coagulata* virus-1, Human Immunodeficiency Virus type 1, Himetobi P virus, Hepatitis C virus, Hepatitis A virus, Hepatitis GB virus, Foot and mouth disease virus, Human enterovirus 71, Equine rhinitis virus, *Ectropis obliqua* picorna-like virus, Encephalomyocarditis virus, *Drosophila* C Virus, Human coxsackievirus B3, Crucifer tobamovirus, Cricket paralysis virus, Bovine viral diarrhea virus 1, Black Queen Cell Virus, Aphid lethal paralysis virus, Avian encephalomyelitis virus, Acute bee paralysis virus, Hibiscus chlorotic ringspot virus, Classical swine fever virus, Human FGF2, Human SFTPA1, Human AML1/RUNX1, *Drosophila* antennapedia, Human AQP4, Human AT1R, Human BAG-1, Human BCL2, Human BiP, Human c-IAP1, Human c-myc, Human eIF4G, Mouse NDST4L, Human LEF1, Mouse HIF1 alpha, Human n.myc, Mouse Gtx, Human p27kip1, Human PDGF2/c-sis, Human p53, Human Pim-1, Mouse Rbm3, *Drosophila* reaper, Canine Scamper, *Drosophila* Ubx, Human UNR, Mouse UtrA, Human VEGF-A, Human XIAP, *Drosophila* hairless, *S. cerevisiae* TFIID, *S. cerevisiae* YAP1, tobacco etch virus, turnip crinkle virus, EMCV-A, EMCV-B, EMCV-Bf, EMCV-Cf, EMCV pEC9, Picobirnavirus, HCV QC64, Human Cosavirus E/D, Human Cosavirus F, Human Cosavirus JMY, Rhinovirus NAT001, HRV14, HRV89, HRVC-02, HRV-A21, Salivirus A SH1, Salivirus FHB, Salivirus NG-J1, Human Parechovirus 1, Crohivirus B, Yc-3, Rosavirus M-7, Shanbavirus A, Pasivirus A, Pasivirus A 2, Echovirus E14, Human Parechovirus 5, Aichi Virus, Hepatitis A Virus HA16, Phopivirus, CVA10, Enterovirus C, Enterovirus D, Enterovirus J, Human Pegivirus 2, GBV-C GT110, GBV-C K1737, GBV-C Iowa, Pegivirus A 1220, Pasivirus A 3, Sapelovirus, Rosavirus B, Bakunsa Virus, Tremovirus A, Swine Pasivirus 1, PLV-CHN, Pasivirus A, Sicinivirus, Hepacivirus K, Hepacivirus A, BVDV1, Border Disease Virus, BVDV2, CSFV-PK15C, SF573 Dicistrovirus, Hubei Picorna-like Virus, CRPV, Salivirus A BNS, Salivirus A BN2, Salivirus A 02394, Salivirus A GUT, Salivirus A CH, Salivirus A SZ1, Salivirus FHB, CVB3, CVB1, Echovirus 7, CVBS, EVA71, CVA3, CVA12, EV24 or an aptamer to eIF4G.

In some embodiments, the polynucleotides herein comprise an expression sequence. In some embodiments, the expression sequence encodes a CAR. In some embodiments, a polynucleotide comprises more than 1 expression sequence, e.g., 2, 3, 4, or 5 expression sequences. In some embodiments, one such expression sequence encodes a CAR and another encodes another therapeutic protein, such as a checkpoint inhibitor, e.g., an inhibitor of PD-1 inhibitor, a PD-L1 inhibitor, or a CTLA-4 inhibitor. In some embodiments, a polynucleotide comprises a first expression sequence encoding a CAR and a second expression sequence encoding an inhibitor of Programmed Death 1 (PD-1), PD-L1, PD-L2, Cytotoxic T-Lymphocyte Antigen 4

(CTLA-4), TIM-3, CEACAM (e.g., CEACAM-1, -3 and/or -5), VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GALS, adenosine, TGFR (e.g., TGFR beta), B7-H1, B7-H4 (VTCN1), OX-40, CD137, CD40, or LAGS. In some embodiments, an inhibitor is nivolumab, pembrolizumab, Ipilimumab, or atezolizumab. In some embodiments, an expression sequence encodes a protein that is cleaved into 2 or more functional units, e.g., a CAR and another therapeutic protein.

In certain embodiments, the polynucleotides provided herein comprise a CAR or TCR complex protein coding region. The CAR or TCR complex protein coding region is a sequence that encodes a chimeric antigen receptor (CAR) or any T cell receptor (TCR) complex protein. In some embodiments the CAR or TCR complex protein encodes a CAR. In some embodiments, the CAR or TCR complex protein coding region encodes two CARs in a bicistronic construct. In some embodiments, the CAR or TCR complex protein encodes TCRalpha, TCRbeta, TCRgamma, TCRdelta, CD3delta, CD3epsilon, CD3gamma, CD3zeta, CD4, and/or CD8. In some embodiments, the CAR or TCR complex protein encodes an artificial TCRalpha, TCRbeta, TCRgamma, TCRdelta, CD3delta, CD3epsilon, CD3gamma, CD3zeta, CD4, and/or CD8 variant. In some embodiments, the CAR or TCR complex protein encodes a natural TCRalpha, TCRbeta, TCRgamma, TCRdelta, CD3delta, CD3epsilon, CD3gamma, CD3zeta, CD4, and/or CD8 variant. In some embodiments, the CAR or TCR complex coding region concludes with a stop codon. In some embodiments, the CAR or TCR complex coding region concludes with a stop cassette.

In certain embodiments, the vectors provided herein comprise a 3' UTR. In some embodiments, the 3' UTR is from human beta globin, human alpha globin *xenopus* beta globin, *xenopus* alpha globin, human prolactin, human GAP-43, human eEF1a1, human Tau, human TNFα, dengue virus, hantavirus small mRNA, bunyavirus small mRNA, turnip yellow mosaic virus, hepatitis C virus, rubella virus, tobacco mosaic virus, human IL-8, human actin, human GAPDH, human tubulin, hibiscus chlorotic rinsgspot virus, woodchuck hepatitis virus post translationally regulated element, sindbis virus, turnip crinkle virus, tobacco etch virus, or Venezuelan equine encephalitis virus.

In some embodiments, the vectors provided herein comprise a 5' UTR. In some embodiments, the 5' UTR is from human beta globin, *Xenopus laevis* beta globin, human alpha globin, *Xenopus laevis* alpha globin, rubella virus, tobacco mosaic virus, mouse Gtx, dengue virus, heat shock protein 70 kDa protein 1A, tobacco alcohol dehydrogenase, tobacco etch virus, turnip crinkle virus, or the adenovirus tripartite leader.

In some embodiments, the vector provided herein comprises a polyA region. In some embodiments the polyA region is at least 30 nucleotides long or at least 60 nucleotides long.

In some embodiments, the DNA (e.g., vector), linear RNA (e.g., precursor RNA), and/or circular RNA polynucleotide provided herein is between 300 and 10000, 400 and 9000, 500 and 8000, 600 and 7000, 700 and 6000, 800 and 5000, 900 and 5000, 1000 and 5000, 1100 and 5000, 1200 and 5000, 1300 and 5000, 1400 and 5000, and/or 1500 and 5000 nucleotides in length. In some embodiments, the polynucleotide is at least 300 nt, 400 nt, 500 nt, 600 nt, 700 nt, 800 nt, 900 nt, 1000 nt, 1100 nt, 1200 nt, 1300 nt, 1400 nt, 1500 nt, 2000 nt, 2500 nt, 3000 nt, 3500 nt, 4000 nt, 4500 nt, or 5000 nt in length. In some embodiments, the polynucleotide is no more than 3000 nt, 3500 nt, 4000 nt, 4500 nt, 5000 nt, 6000 nt, 7000 nt, 8000 nt, 9000 nt, or 10000 nt in length. In some embodiments, the length of a DNA, linear RNA, and/or circular RNA polynucleotide provided herein is about 300 nt, 400 nt, 500 nt, 600 nt, 700 nt, 800 nt, 900 nt, 1000 nt, 1100 nt, 1200 nt, 1300 nt, 1400 nt, 1500 nt, 2000 nt, 2500 nt, 3000 nt, 3500 nt, 4000 nt, 4500 nt, 5000 nt, 6000 nt, 7000 nt, 8000 nt, 9000 nt, or 10000 nt.

In certain embodiments, the polynucleotides provided herein are circular RNA polynucleotides or are useful for making circular RNA polynucleotides. Such polynucleotides comprise CAR or TCR complex protein encoding domains. Certain current CAR and recombinant TCR treatments engineer cells with DNA encoding the CAR or recombinant TCR, causing greater toxicity when compared to transitory forms of CAR or recombinant TCR expression, and introducing the risk of harmful mutagenesis. An alternative is a linear RNA encoding a CAR or recombinant TCR complex protein. However, linear RNA suffers from short half-lives in vivo, limiting treatment efficacy. In certain embodiments, circular RNA polynucleotides provided herein encoding CARs or recombinant TCR complex proteins provides the toxicity advantages of transitory expression, while increasing the therapeutic efficacy of the treatment when compared to linear RNA. The methods of circularizing RNA described herein, including the addition of homology regions adjacent to the group I intron fragments, allow for high circularization efficiency and for the circularization of large RNA polynucleotides.

In some embodiments, provided herein is a vector. In certain embodiments, the vector comprises, in the following order, a) a 5' homology region, b) a 3' group I intron fragment, c) optionally, a first spacer sequence, d) an IRES, e) an expression sequence (e.g., CAR or TCR complex protein coding region), f) optionally, a second spacer sequence, g) a 5' group I intron fragment, and h) a 3' homology region. In some embodiments, the vector comprises a transcriptional promoter upstream of the 5' homology region.

In some embodiments, provided herein is a precursor RNA. In certain embodiments, the precursor RNA is a linear RNA produced by in vitro transcription of a vector provided herein. In some embodiments, the precursor RNA comprises, in the following order, a) a 5' homology region, b) a 3' group I intron fragment, c) optionally, a first spacer sequence, d) an IRES, e) an expression sequence (e.g., CAR or TCR complex protein coding region), f) optionally, a second spacer sequence, g) a 5' group I intron fragment, and h) a 3' homology region. The precursor RNA can be unmodified, partially modified or completely modified.

In certain embodiments, provided herein is a circular RNA. In certain embodiments, the circular RNA is a circular RNA produced by a vector provided herein. In some embodiments, the circular RNA is circular RNA produced by circularization of a precursor RNA provided herein. In some embodiments, the circular RNA comprises, in the following sequence, a) a first spacer sequence, b) an IRES, c) an expression sequence (e.g., CAR or TCR complex protein coding region), and d) a second spacer sequence. In some embodiments, the circular RNA further comprises the portion of the 3' group I intron fragment that is 3' of the 3' splice site. In some embodiments, the circular RNA further comprises the portion of the 5' group I intron fragment that is 5' of the 5' splice site. In some embodiments, the circular RNA is at least 500, 600, 700, 800, 900, 1000, 1500, 2000, 2500, 3000, 3500, 4000 or 4500 nucleotides in size. The circular RNA can be unmodified, partially modified or completely modified.

In some embodiments, the circular RNA provided herein has higher functional stability than mRNA comprising the same expression sequence. In some embodiments, the circular RNA provided herein has higher functional stability than mRNA comprising the same expression sequence, 5moU modifications, an optimized UTR, a cap, and/or a polyA tail.

In some embodiments, the circular RNA polynucleotide provided herein has a functional half-life of at least 5 hours, 10 hours, 15 hours, 20 hours. 30 hours, 40 hours, 50 hours, 60 hours, 70 hours or 80 hours. In some embodiments, the circular RNA polynucleotide provided herein has a functional half-life of 5-80, 10-70, 15-60, and/or 20-50 hours. In some embodiments, the circular RNA polynucleotide provided herein has a functional half-life greater than (e.g., at least 1.5-fold greater than, at least 2-fold greater than) that of an equivalent linear RNA polynucleotide encoding the same protein. In some embodiments, functional half-life can be assessed through the detection of functional protein synthesis.

In some embodiments, the circular RNA polynucleotide provided herein has a half-life of at least 5 hours, 10 hours, 15 hours, 20 hours. 30 hours, 40 hours, 50 hours, 60 hours, 70 hours or 80 hours. In some embodiments, the circular RNA polynucleotide provided herein has a half-life of 5-80, 10-70, 15-60, and/or 20-50 hours. In some embodiments, the circular RNA polynucleotide provided herein has a half-life greater than (e.g., at least 1.5-fold greater than, at least 2-fold greater than) that of an equivalent linear RNA polynucleotide encoding the same protein.

In some embodiments, the circular RNA provided herein may have a higher magnitude of expression than equivalent linear mRNA, e.g., a higher magnitude of expression 24 hours after administration of RNA to cells. In some embodiments, the circular RNA provided herein has a higher magnitude of expression than mRNA comprising the same expression sequence, 5moU modifications, an optimized UTR, a cap, and/or a polyA tail. In some embodiments, the circular RNA provided herein may have higher stability than an equivalent linear mRNA. In some embodiments, this may be shown by measuring receptor presence and density in vitro or in vivo post electroporation, with time points measured over 1 week. In some embodiments, this may be shown by measuring RNA presence via qPCR or ISH.

In some embodiments, the circular RNA provided herein may be less immunogenic than an equivalent mRNA when exposed to an immune system of an organism or a certain type of immune cell. In some embodiments, the circular RNA provided herein is associated with modulated production of cytokines when exposed to an immune system of an organism or a certain type of immune cell. For example, in some embodiments, the circular RNA provided herein is associated with reduced production of IFN-β1, RIG-I, IL-2, IL-6, IFNγ, and/or TNFα when exposed to an immune system of an organism or a certain type of immune cell as compared to mRNA comprising the same expression sequence. In some embodiments, the circular RNA provided herein is associated with less IFN-β1, RIG-I, IL-2, IL-6, IFNγ, and/or TNFα transcript induction when exposed to an immune system of an organism or a certain type of immune cell as compared to mRNA comprising the same expression sequence. In some embodiments, the circular RNA provided herein is less immunogenic than mRNA comprising the same expression sequence. In some embodiments, the circular RNA provided herein is less immunogenic than mRNA comprising the same expression sequence, 5moU modifications, an optimized UTR, a cap, and/or a polyA tail. In certain embodiments, the circular RNA provided herein may result in lower toxicity than viral, e.g. lentiviral, engineering using DNA when expressing CARs or TCR complex proteins on immune cells, e.g., T cells, due to cytokine release syndrome (CRS). In some embodiments, this may be shown by measuring cytokine, e.g. IL6, release post infection/transfection in vitro, assessed by ELISA and/or qPCR.

In certain embodiments, the circular RNA provided herein may result in lower toxicity than viral, e.g., lentiviral, engineering using DNA when expressing CARs or TCR complex proteins on immune cells, e.g., T cells, due to cytokine release syndrome (CRS). In some embodiments, this may be shown by measuring cytokine, e.g., IL6, release post infection/transfection in vitro, assessed by ELISA and/or qPCR.

In some embodiments, the circular RNA provided herein may result in lower toxicity than viral, e.g., lentiviral, engineering using DNA when expressing CARs or TCR complex proteins on immune cells, e.g., T cells, due to a lack of insertional mutagenesis by circular RNA. In some embodiments, this may be shown by demonstrating that circular RNA does not integrate into the genome, while DNA delivered by lentiviruses does, by sequencing after administering circular RNA or DNA. In certain embodiments, the circular RNA provided herein can be transfected into a cell as is, or can be transfected in DNA vector form and transcribed in the cell. Transcription of circular RNA from a transfected DNA vector can be via added polymerases or polymerases encoded by nucleic acids transfected into the cell, or preferably via endogenous polymerases.

In certain embodiments, a circular RNA polynucleotide provided herein comprises modified RNA nucleotides and/or modified nucleosides. In some embodiments, the modified nucleoside is $m^5C$ (5-methylcytidine). In another embodiment, the modified nucleoside is $m^5U$ (5-methyluridine). In another embodiment, the modified nucleoside is $m^6A$ ($N^6$-methyladenosine). In another embodiment, the modified nucleoside is $s^2U$ (2-thiouridine). In another embodiment, the modified nucleoside is ψ (pseudouridine). In another embodiment, the modified nucleoside is Um (2'-O-methyluridine). In other embodiments, the modified nucleoside is $m^1A$ (1-methyladenosine); $m^2A$ (2-methyladenosine); Am (2'-O-methyladenosine); $ms^2 m^6A$ (2-methylthio-$N^6$-methyladenosine); $i^6A$ ($N^6$-isopentenyladenosine); $ms^2t^6A$ (2-methylthio-$N^6$ isopentenyladenosine); $io^6A$ ($N^6$-(cis-hydroxyisopentenyl)adenosine); $ms^2io^6A$ (2-methylthio-$N^6$-(cis-hydroxyisopentenyl)adenosine); $g^6A$ ($N^6$-glycinylcarbamoyladenosine); $t^6A$ ($N^6$-threonylcarbamoyladenosine); $ms^2t^6A$ (2-methylthio-$N^6$-threonyl carbamoyladenosine); $m^6t^6A$ ($N^6$-methyl-$N^6$-threonylcarbamoyladenosine); $hn^6A$ ($N^6$-hydroxynorvalylcarbamoyladenosine); $ms^2hn^6A$ (2-methylthio-$N^6$-hydroxynorvalyl carbamoyladenosine); Ar(p) (2'-O-ribosyladenosine (phosphate)); I (inosine); $m^1I$ (1-methylinosine); $m^1Im$ (1,2'-O-dimethylinosine); $m^3C$ (3-methylcytidine); Cm (2'-O-methylcytidine); $s^2C$ (2-thiocytidine); $ac^4C$ ($N^4$-acetylcytidine); $f^5C$ (5-formylcytidine); $m^5Cm$ (5,2'-O-dimethylcytidine); $ac^4Cm$ ($N^4$-acetyl-2'-O-methylcytidine); $k^2C$ (lysidine); $m^1G$ (1-methylguanosine); $m^2G$ ($N^2$-methylguanosine); $m^7G$ (7-methylguanosine); Gm (2'-O-methylguanosine); $m^2_2G$ ($N^2,N^2$-dimethylguanosine); $m^2Gm$ ($N^2,2'$-O-dimethylguanosine); $m^2_2Gm$ ($N^2,N^2,2'$-O-trimethylguanosine); Gr(p) (2'-O-ribosylguanosine(phosphate)); yW (wybutosine); o$_2$yW (peroxywybutosine); OHyW (hydroxywybutosine); OHyW* (undermodified hydroxywybutosine); imG (wyosine); mimG (methylwyosine); Q (queuosine); oQ (epoxyqueuosine); galQ (galactosyl-queuosine); manQ (mannosyl-queuosine); preQ$_0$ (7-cyano-7-deazaguanosine); preQ$_1$ (7-aminomethyl-7-deazaguanosine); (archaeosine); D (dihydrouridine); m$^5$Um (5,2'-O-dimethyluridine); s$^4$U (4-thiouridine); m$^5$s$^2$U (5-methyl-2-thiouridine); s$^2$Um (2-thio-2'-O-methyluridine); acp$^3$U (3-(3-amino-3-carboxypropyl)uridine); ho$^5$U (5-hydroxyuridine); mo$^5$U (5-methoxyuridine); cmo$^5$U (uridine 5-oxyacetic acid); mcmo$^5$U (uridine 5-oxyacetic acid methyl ester); chm$^5$U (5-(carboxyhydroxymethyl)uridine)); mchm$^5$U (5-(carboxyhydroxymethyl)uridine methyl ester); mcm$^5$U (5-methoxycarbonylmethyluridine); mcm$^5$Um (5-methoxycarbonylmethyl-2'-O-methyluridine); mcm$^5$s$^2$U (5-methoxycarbonylmethyl-2-thiouridine); nm$^5$S$^2$U (5-aminomethyl-2-thiouridine); mnm$^5$U (5-methylaminomethyluridine); mnm$^5$s$^2$U (5-methylaminomethyl-2-thiouridine); mnm$^5$se$^2$U (5-methylaminomethyl-2-selenouridine); ncm$^5$U (5-carbamoylmethyluridine); ncm$^5$Um (5-carbamoylmethyl-2'-O-methyluridine); cmnm$^5$U (5-carboxymethylaminomethyluridine); cmnm$^5$Um (5-carboxymethylaminomethyl-2'-O-methyluridine); cmnm$^5$s$^2$U (5-carboxymethylaminomethyl-2-thiouridine); m$^6_2$A (N$^6$,N$^6$-dimethyladenosine); Im (2'-O-methylinosine); m$^4$C (N$^4$-methylcytidine); m$^4$Cm (N$^4$,2'-O-dimethylcytidine); hm$^5$C (5-hydroxymethylcytidine); m$^3$U (3-methyluridine); cm$^5$U (5-carboxymethyluridine); m$^6$Am (N$^6$,2'-O-dimethyladenosine); m$^6_2$Am (N$^6$,N$^6$,O-2'-trimethyladenosine); m$^{2,7}$G (N$^2$,7-dimethylguanosine); m$^{2,2,7}$G (N$^2$,N$^2$,7-trimethylguanosine); m$^3$Um (3,2'-O-dimethyluridine); m$^5$D (5-methyldihydrouridine); f$^5$Cm (5-formyl-2'-O-methylcytidine); m$^1$Gm (1,2'-O-dimethylguanosine); m$^1$Am (1,2'-O-dimethyladenosine); τm$^5$U (5-taurinomethyluridine); τm$^5$s$^2$U (5-taurinomethyl-2-thiouridine)); imG-14 (4-demethylwyosine); imG2 (isowyosine); or ac$^6$A (N$^6$-acetyladenosine).

In some embodiments, the modified nucleoside may include a compound selected from the group of: pyridin-4-one ribonucleoside, 5-aza-uridine, 2-thio-5-aza-uridine, 2-thiouridine, 4-thio-pseudouridine, 2-thio-pseudouridine, 5-hydroxyuridine, 3-methyluridine, 5-carboxymethyl-uridine, 1-carboxymethyl-pseudouridine, 5-propynyl-uridine, 1-propynyl-pseudouridine, 5-taurinomethyluridine, 1-taurinomethyl-pseudouridine, 5-taurinomethyl-2-thio-uridine, 1-taurinomethyl-4-thio-uridine, 5-methyl-uridine, 1-methyl-pseudouridine, 4-thio-1-methyl-pseudouridine, 2-thio-1-methyl-pseudouridine, 1-methyl-1-deaza-pseudouridine, 2-thio-1-methyl-1-deaza-pseudouridine, dihydrouridine, dihydropseudouridine, 2-thio-dihydrouridine, 2-thio-dihydropseudouridine, 2-methoxyuridine, 2-methoxy-4-thio-uridine, 4-methoxy-pseudouridine, 4-m ethoxy-2-thio-pseudouridine, 5-aza-cytidine, pseudoisocytidine, 3-methylcytidine, N4-acetylcytidine, 5-formylcytidine, N4-methylcytidine, 5-hydroxymethylcytidine, 1-methyl-pseudoisocytidine, pyrrolo-cytidine, pyrrolo-pseudoisocytidine, 2-thio-cytidine, 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, 4-methoxy-1-methyl-pseudoisocytidine, 2-aminopurine, 2, 6-diaminopurine, 7-deaza-adenine, 7-deaza-8-aza-adenine, 7-deaza-2-aminopurine, 7-deaza-8-aza-2-aminopurine, 7-deaza-2,6-diaminopurine, 7-deaza-8-aza-2,6-diaminopurine, 1-methyladenosine, N6-methyladenosine, N6-isopentenyladenosine, N6-(cis-hydroxyisopentenyl)adenosine, 2-methylthio-N6-(cis-hydroxyisopentenyl) adenosine, N6-glycinylcarbamoyladenosine, N6-threonylcarbamoyladenosine, 2-methylthio-N6-threonyl carbamoyladenosine, N6,N6-dimethyladenosine, 7-methyladenine, 2-methylthio-adenine, 2-methoxy-adenine, inosine, 1-methyl-inosine, wyosine, wybutosine, 7-deaza-guanosine, 7-deaza-8-aza-guanosine, 6-thio-guanosine, 6-thio-7-deaza-guanosine, 6-thio-7-deaza-8-aza-guanosine, 7-methyl-guanosine, 6-thio-7-methyl-guanosine, 7-methylinosine, 6-methoxy-guanosine, 1-methylguanosine, N2-methylguanosine, N2,N2-dimethylguanosine, 8-oxo-guanosine, 7-methyl-8-oxo-guanosine, 1-methyl-6-thio-guanosine, N2-methyl-6-thio-guanosine, and N2,N2-dimethyl-6-thio-guanosine. In another embodiment, the modifications are independently selected from the group consisting of 5-methylcytosine, pseudouridine and 1-methylpseudouridine.

In some embodiments, the modified ribonucleosides include 5-methylcytidine, 5-methoxyuridine, 1-methylpseudouridine, N6-methyladenosine, and/or pseudouridine. In some embodiments, such modified nucleosides provide additional stability and resistance to immune activation.

In particular embodiments, polynucleotides may be codon-optimized. A codon optimized sequence may be one in which codons in a polynucleotide encoding a polypeptide have been substituted in order to increase the expression, stability and/or activity of the polypeptide. Factors that influence codon optimization include, but are not limited to one or more of: (i) variation of codon biases between two or more organisms or genes or synthetically constructed bias tables, (ii) variation in the degree of codon bias within an organism, gene, or set of genes, (iii) systematic variation of codons including context, (iv) variation of codons according to their decoding tRNAs, (v) variation of codons according to GC %, either overall or in one position of the triplet, (vi) variation in degree of similarity to a reference sequence for example a naturally occurring sequence, (vii) variation in the codon frequency cutoff, (viii) structural properties of mRNAs transcribed from the DNA sequence, (ix) prior knowledge about the function of the DNA sequences upon which design of the codon substitution set is to be based, and/or (x) systematic variation of codon sets for each amino acid. In some embodiments, a codon optimized polynucleotide may minimize ribozyme collisions and/or limit structural interference between the expression sequence and the IRES.

In certain embodiments circular RNA provided herein is produced inside a cell. In some embodiments, precursor RNA is transcribed using a DNA template (e.g., in some embodiments, using a vector provided herein) in the cytoplasm by a bacteriophage RNA polymerase, or in the nucleus by host RNA polymerase II and then circularized.

In certain embodiments, the circular RNA provided herein is injected into an animal (e.g., a human), such that a polypeptide encoded by the circular RNA molecule (e.g., a CAR or TCR complex protein) is expressed inside the animal.

3. Payload

In some embodiments, the expression sequence encodes a therapeutic protein. In some embodiments, the therapeutic protein is selected from the proteins listed in Table 1.

TABLE 1

Protein Expression Sequences and Delivery Formulations

| Payload | Sequence | Target cell / organ | Preferred delivery formulation |
|---|---|---|---|
| CD19 CAR | Any of SEQ ID NOs: 309-314 | T cells | [lipid structure] (50 mol %)<br>DSPC (10 mol %)<br>Beta-sitosterol (28.5% mol %)<br>Cholesterol (10 mol %)<br>PEG DMG (1.5 mol %) |
| BCMA CAR | MALPVTALLLPLALLLHAAR PDIVLTQSPASLAVSLGERAT INCRASESVSVIGAHLIHWY QQKPGQPPKLLIYLASNLET GVPARFSGSGSGTDFTLTISS LQAEDAAIYYCLQSRIFPRTF GQGTKLEIKGSTSGSGKPGS GEGSTKGQVQLVQSGSELK<br><br>KPGASVKVSCKASGYTFTDY SINWVRQAPGQGLEWMGWI NTETREPAYAYDFRGRFVFS LDTSVSTAYLQISSLKAEDTA VYYCARDYSYAMDYWGQG TLVTVSSAAATTTPAPRPPTP APTIASQPLSLRPEACRPAAG GAVHTRGLDFACDIYIWAPL AGTCGVLLLSLVITLYCKRG RKKLLYIFKQPFMRPVQTTQ EEDGCSCRFPEEEEGGCELR VKFSRSADAPAYQQGQNQL YNELNLGRREEYDVLDKRR GRDPEMGGKPRRKNPQEGL YNELQKDKMAEAYSEIGMK GERRRGKGHDGLYQGLSTA TKDTYDALHMQALPPR | T cells | [lipid structure] (50 mol %)<br>DSPC (10 mol %)<br>Beta-sitosterol (28.5% mol %)<br>Cholesterol (10 mol %)<br>PEG DMG (1.5 mol %) |
| MAGE-A4 TCR | TCR alpha chain:<br>KNQVEQSPQSLIILEGKNCTL QCNYTVSPFSNLRWYKQDT GRGPVSLTIMTFSENTKSNG RYTATLDADTKQSSLHITAS QLSDSASYICVVNHSGGSYIP TFGRGTSLIVHPYIQKPDPAV<br><br>YQLRDSKSSDKSVCLFTDFD SQTNVSQSKDSDVYITDKTV LDMRSMDFKSNSAVAWSNK SDFACANAFNNSIIPEDTFFPS PESS<br>TCR beta chain:<br>DVKVTQSSRYLVKRTGEKV FLECVQDMDHENMFWYRQ DPGLGLRLIYFSYDVKMKEK GDIPEGYSVSREKKERFSLIL ESASTNQTSMYLCASSFLMT SGDPYEQYFGPGTRLTVTED LKNVFPPEVAVFEPSEAEISH TQKATLVCLATGFYPDHVEL SWWVNGKEVHSGVSTDPQP LKEQPALNDSRYCLSSRLRV SATFWQNPRNHFRCQVQFY GLSENDEWTQDRAKPVTQIV SAEAWGRAD | T cells | [lipid structure] (50 mol %)<br>DSPC (10 mol %)<br>Beta-sitosterol (28.5% mol %)<br>Cholesterol (10 mol %)<br>PEG DMG (1.5 mol %) |

TABLE 1 -continued

Protein Expression Sequences and Delivery Formulations

| Payload | Sequence | Target cell / organ | Preferred delivery formulation |
|---|---|---|---|
| NY-ESO TCR | TCRalpha extracellular sequence<br>MQEVTQIPAALSVPEGENLV<br>LNCSFTDSAIYNLQWFRQDP<br>GKGLTSLLLIQSSQREQTSGR<br>LNASLDKSSGRSTLYIAASQP<br>GDSATYLCAVRPTSGGSYIP<br>TFGRGTSLIVHPY<br><br>TCRbeta extracellular sequence<br>MGVTQTPKFQVLKTGQSMT<br>LQCAQDMNHEYMSWYRQD<br>PGMGLRLIHYSVGAGITDQG<br>EVPNGYNVSRSTTEDFPLRL<br>LSAAPSQTSVYFCASSYVGN<br>TGELFFGEGSRLTVL | T cells | 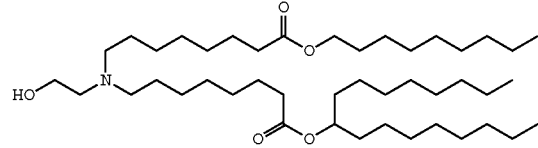 [SMILES: CCCCCCCCCOC(=O)CCCCCCCN(CCO)CCCCCCCC(=O)OC(CCCCCCCC)CCCCCCCC]<br>(50 mol %)<br>DSPC (10 mol %)<br>Beta-sitosterol (28.5% mol %)<br>Cholesterol (10 mol %)<br>PEG DMG (1.5 mol %) |
| EPO | APPRLICDSRVLERYLLEAKE<br>AENITTGCAEHCSLNENITVP<br>DTKVNFYAWKRMEVGQQA<br>VEVWQGLALLSEAVLRGQA<br>LLVNSSQPWEPLQLHVDKA<br>VSGLRSLTTLLRALGAQKEA<br>ISPPDAASAAPLRTITADTFR<br>KLFRVYSNFLRGKLKLYTGE<br>ACRTGDR | Kidney or bone marrow | |
| PAH | MSTAVLENPGLGRKLSDFGQ<br>ETSYIEDNCNQNGAISLIFSL<br>KEEVGALAKVLRLFEENDV<br>NLTHIESRPSRLKKDEYEFFT<br>HLDKRSLPALTNIIKILRHDIG<br>ATVHELSRDKKKDTVPWFP<br>RTIQELDRFANQILSYGAELD<br><br>ADHPGFKDPVYRARRKQFA<br>DIAYNYRHGQPIPRVEYMEE<br>EKKTWGTVFKTLKSLYKTH<br>ACYEYNHIFPLLEKYCGFHE<br>DNIPQLEDVSQFLQTCTGFRL<br>RPVAGLLSSRDFLGGLAFRV<br>FHCTQYIRHGSKPMYTPEPDI<br>CHELLGHVPLFSDRSFAQFS<br>QEIGLASLGAPDEYIEKLATI<br>YWFTVEFGLCKQGDSIKAY<br>GAGLLSSFGELQYCLSEKPK<br>LLPLELEKTAIQNYTVTEFQP<br>LYYVAESFNDAKEKVRNFA<br>ATIPRPFSVRYDPYTQRIEVL<br>DNTQQLKILADSINSEIGILCS<br>ALQKIK | Hepatic cells | 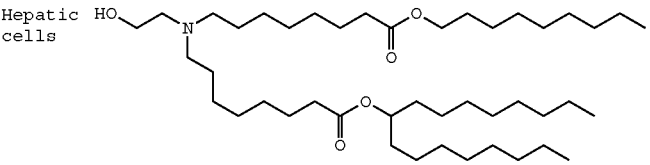<br>(50 mol %)<br>DSPC (10 mol %)<br>Cholesterol (38.5% mol %)<br>PEG-DMG (1.5%)<br>OR<br>MC3 (50 mol %)<br>DSPC (10 mol %)<br>Cholesterol (38.5% mol %)<br>PEG-DMG (1.5%) |
| CPS1 | LSVKAQTAHIVLEDGTKMK<br>GYSFGHPSSVAGEVVFNTGL<br>GGYPEAITDPAYKGQILTMA<br>NPIIGNGGAPDTTALDELGLS<br>KYLESNGIKVSGLLVLDYSK<br>DYNHWLATKSLGQWLQEEK<br>VPAIYGVDTRMLTKIIRDKG<br><br>TMLGKIEFEGQPVDFVDPNK<br>QNLIAEVSTKDVKVYGKGN<br>PTKVVAVDCGIKNNVIRLLV<br>KRGAEVHLVPWNHDFTKME<br>YDGILIAGGPGNPALAEPLIQ<br>NVRKILESDRKEPLFGISTGN<br>LITGLAAGAKTYKMSMANR<br>GQNQPVLNITNKQAFITAQN<br>HGYALDNTLPAGWKPLFVN<br>VNDQTNEGIMHESKPFFAVQ<br>FHPEVTPGPIDTEYLFDSFFSL<br>IKKGKATTITSVLPKPALVAS<br>RVEVSKVLILGSGGLSIGQA<br>GEFDYSGSQAVKAMKEENV | Hepatic cells | 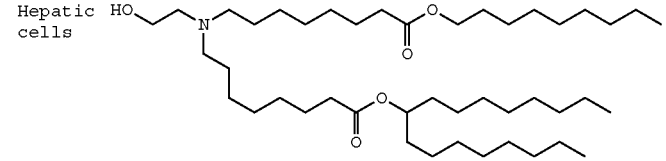<br>(50 mol %)<br>DSPC (10 mol %)<br>Cholesterol (38.5% mol %)<br>PEG-DMG (1.5%)<br>OR<br>MC3 (50 mol %)<br>DSPC (10 mol %)<br>Cholesterol (38.5% mol %)<br>PEG-DMG (1.5%) |

TABLE 1-continued

Protein Expression Sequences and Delivery Formulations

| Payload | Sequence | Target cell / organ | Preferred delivery formulation |
|---|---|---|---|
| | KTVLMNPNIASVQTNEVGLK QADTVYFLPITPQFVTEVIKA EQPDGLILGMGGQTALNCG VELFKRGVLKEYGVKVLGT SVESIMATEDRQLFSDKLNEI NEKIAPSFAVESIEDALKAAD TIGYPVMIRSAYALGGLGSGI CPNRETLMDLSTKAFAMTN QILVEKSVTGWKEIEYEVVR DADDNCVTVCNMENVDAM GVHTGDSVVVAPAQTLSNA EFQMLRRTSINVVRHLGIVG ECNIQFALHPTSMEYCIIEVN ARLSRSSALASKATGYPLAFI AAKIALGIPLPEIKNVVSGKT SACFEPSLDYMVTKIPRWDL DRFHGTSSRIGSSMKSVGEV MAIGRTFEESFQKALRMCHP SIEGFTPRLPMNKEWPSNLD LRKELSEPSSTRIYAIAKAID DNMSLDEIEKLTYIDKWFLY KMRDILNMEKTLKGLNSES MTEETLKRAKEIGFSDKQISK CLGLTEAQTRELRLKKNIHP WVKQIDTLAAEYPSVTNYL YVTYNGQEHDVNFDDHGM MVLGCGPYHIGSSVEFDWC AVSSIRTLRQLGKKTVVVNC NPETVSTDFDECDKLYFEEL SLERILDIYHQEACGGCIISV GGQIPNNLAVPLYKNGVKIM GTSPLQIDRAEDRSIFSAVLD ELKVAQAPWKAVNTLNEAL EFAKSVDYPCLLRPSYVLSG SAMNVVFSEDEMKKFLEEA TRVSQEHPVVLTKFVEGARE VEMDAVGKDGRVISHAISEH VEDAGVHSGDATLMLPTQTI SQGAIEKVKDATRKIAKAFA ISGPFNVQFLVKGNDVLVIEC NLRASRSFPFVSKTLGVDFID VATKVMIGENVDEKHLPTL DHPIIPADYVAIKAPMFSWPR LRDADPILRCEMASTGEVAC FGEGIHTAFLKAMLSTGFKIP QKGILIGIQQSFRPRFLGVAE QLHNEGFKLFATEATSDWL NANNVPATPVAWPSQEGQN PSLSSIRKLIRDGSIDLVINLP NNNTKFVHDNYVIRRTAVD SGIPLLTNFQVTKLFAEAVQ KSRKVDSKSLFHYRQYSAG KAA | | |
| Cas9 | MKRNYILGLDIGITSVGYGII DYETRDVIDAGVRLFKEANV ENNEGRRSKRGARRLKRRR RHRIQRVKKLLFDYNLLTDH SELSGINPYEARVKGLSQKLS EEEFSAALLHLAKRRGVHNV NEVEEDTGNELSTKEQISRNS KALEEKYVAELQLERLKKD GEVRGSINRFKTSDYVKEAK QLLKVQKAYHQLDQSFIDTY IDLLETRRTYYEGPGEGSPFG WKDIKEWYEMLMGHCTYFP EELRSVKYAYNADLYNALN DLNNLVITRDENEKLEYYEK FQIIENVFKQKKKPTLKQIAK EILVNEEDIKGYRVTSTGKPE FTNLKVYHDIKDITARKEIIE NAELLDQIAKILTIYQSSEDIQ EELTNLNSELTQEEIEQISNL | Immune cells | 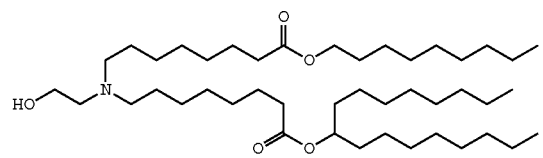 [SMILES: CCCCCCCCCOC(=O)CCCCCCCN(CCO)CCCCCCCC(=O)OC(CCCCCCCC)CCCCCCCC]

(50 mol %)<br>DSPC (10 mol %)<br>Beta-sitosterol (28.5% mol %)<br>Cholesterol (10 mol %)<br>PEG DMG (1.5 mol %) |

TABLE 1 -continued

Protein Expression Sequences and Delivery Formulations

| Payload | Sequence | Target cell / organ | Preferred delivery formulation |
|---|---|---|---|
| | KGYTGTHNLSLKAINLILDEL WHTNDNQIAIFNRLKLVPKK VDLSQQKEIPTTLVDDFILSP VVKRSFIQSIKVINAIIKKYGL PNDIIIELAREKNSKDAQKMI NEMQKRNRQTNERIEEIIRTT GKENAKYLIEKIKLHDMQEG KCLYSLEAIPLEDLLNNPFNY EVDHIIPRSVSFDNSFNNKVL VKQEENSKKGNRTPFQYLSS SDSKISYETFKKHIL TABLE 1 -continued Protein Expression Sequences and Delivery Formulations

| Payload | Sequence | Target cell / organ | Preferred delivery formulation |
|---|---|---|---|
| | LALENETCVPGADGLEAPVT<br>EGPGSVDEKLPAPEPCVGMS<br>CPPGWGHLDATSAGEKAPSP<br>WGSIRTGAQAAHVWTPAAG<br>SCSVSCGRGLMELRFLCMDS<br>ALRVPVQEELCGLASKPGSR<br>REVCQAVPCPARWQYKLAA<br>CSVSCGRGVVRRILYCARAH<br>GEDDGEEILLDTQCQGLPRP<br>EPQEACSLEPCPPRWKVMSL<br>GPCSASCGLGTARRSVACVQ<br>LDQGQDVEVDEAACAALVR<br>PEASVPCLIADCTYRWHVGT<br>WMECSVSCGDGIQRRRDTC<br>LGPQAQAPVPADFCQHLPKP<br>VTVRGCWAGPCVGQGTPSL<br>VPHEEAAAPGRTTATPAGAS<br>LEWSQARGLLFSPAPQPRRL<br>LPGPQENVQSSACGRQHLE<br>PTGTIDMRGPGQADCAVAIG<br>RPLGEVVTLRVLESSLNCSA<br>GDMLLLWGRLTWRKMCRK<br>LLDMTFSSKTNTLVVRQRCG<br>RPGGGVLLRYGSQLAPETFY<br>RECDMQLFGPWGEIVSPSLS<br>PATSNAGGCRLFINVAPHARI<br>AIHALATNMGAGTEGANAS<br>YILIRDTHSLRTTAFHGQQVL<br>YWESESSQAEMEFSEGFLKA<br>QASLRGQYWTLQSWVPEMQ<br>DPQSWKGKEGT | | |
| FOXP3 | MPNPRPGKPSAPSLALGPSP<br>GASPSWRAAPKASDLLGAR<br>GPGGTFQGRDLRGGAHASSS<br>SLNPMPPSQLQLPTLPLVMV<br>APSGARLGPLPHLQALLQDR<br>PHFMHQLSTVDAHARTPVL<br>QVHPLESPAMISLTPPTTATG | Immune cells | 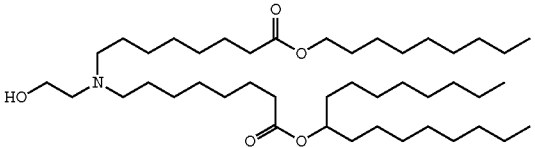 [SMILES: CCCCCCCCCOC(=O)CCCCCCCN(CCO)CCCCCCCC(=O)OC(CCCCCCCC)CCCCCCCC] |
| | VFSLKARPGLPPGINVASLE<br>WVSREPALLCTFPNPSAPRK<br>DSTLSAVPQSSYPLLANGVC<br>KWPGCEKVFEEPEDFLKHCQ<br>ADHLLDEKGRAQCLLQREM<br>VQSLEQQLVLEKEKLSAMQ<br>AHLAGKMALTKASSVASSD<br>KGSCCIVAAGSQGPVVPAWS<br>GPREAPDSLFAVRRHLWGSH<br>GNSTFPEFLHNMDYFKFHN<br>MRPPFTYATLIRWAILEAPEK<br>QRTLNEIYHWFTRMPAFFRN<br>HPATWKNAIRHNLSLHKCFV<br>RVESEKGAVWTVDELEFRK<br>KRSQRPSRCSNPTPGP | | (50 mol %)<br>DSPC (10 mol %)<br>Beta-sitosterol (28.5% mol %)<br>Cholesterol (10 mol %)<br>PEG DMG (1.5 mol %) |
| IL-10 | SPGQGTQSENSCTHFPGNLP<br>NMLRDLRDAFSRVKTFFQM<br>KDQLDNLLLKESLLEDFKGY<br>LGCQALSEMIQFYLEEVMPQ<br>AENQDPDIKAHVNSLGENLK<br>TLRLRLRRCHRFLPCENKSK<br>AVEQVKNAFNKLQEKGIYK | Immune cells | 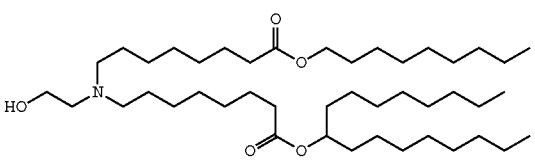 [SMILES: CCCCCCCCCOC(=O)CCCCCCCN(CCO)CCCCCCCC(=O)OC(CCCCCCCC)CCCCCCCC] |
| | AMSEFDIFINYIEAYMTMKIRN | | (50 mol %)<br>DSPC (10 mol %)<br>Beta-sitosterol (28.5% mol %)<br>Cholesterol (10 mol %)<br>PEG DMG (1.5 mol %) |

TABLE 1 -continued

Protein Expression Sequences and Delivery Formulations

| Payload | Sequence | Target cell / organ | Preferred delivery formulation |
|---|---|---|---|
| IL-2 | APTSSSTKKTQLQLEHLLLD LQMILNGINNYKNPKLTRML TFKFYMPKKATELKHLQCLE EELKPLEEVLNLAQSKNFHL RPRDLISNINVIVLELKGSETT FMCEYADETATIVEFLNRWI TFCQSIISTLT | Immune cells | 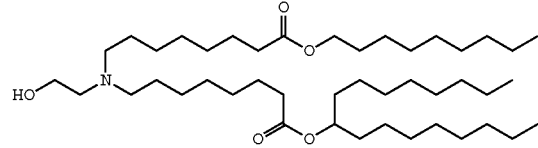 [SMILES: CCCCCCCCCOC(=O)CCCCCCCN(CCO)CCCCCCCC(=O)OC(CCCCCCCC)CCCCCCCC]<br>(50 mol %)<br>DSPC (10 mol %)<br>Beta-sitosterol (28.5% mol %)<br>Cholesterol (10 mol %)<br>PEG DMG (1.5 mol %) |

In some embodiments, a polynucleotide encodes a protein that is made up of subunits that are encoded by more than one gene. For example, the protein may be a heterodimer, wherein each chain or subunit of the protein is encoded by a separate gene. It is possible that more than one circRNA molecule is delivered in the transfer vehicle and each circRNA encodes a separate subunit of the protein. Alternatively, a single circRNA may be engineered to encode more than one subunit. In certain embodiments, separate circRNA molecules encoding the individual subunits may be administered in separate transfer vehicles.

4. Ionizable Lipids

In certain embodiments disclosed herein are lipids that may be used as a component of a transfer vehicle to facilitate or enhance the delivery and release of circular RNA to one or more target cells (e.g., by permeating or fusing with the lipid membranes of such target cells).

In some embodiments, a lipid or transfer vehicle is a lipid as described in pages 32-55 of International Patent Application No. PCT/US2010/061058, paragraphs 86-117 of US Application Publication No. US2019/0314524, pages 43-146 of International Patent Application No. PCT/US2018/058555, pages 46-51 of International Patent Application No. PCT/US2018/053569, paragraphs 195-217 of International Patent Application No. PCT/US2017/028981, paragraphs 82-95 of US Application Publication No. US2019/0321489, paragraphs 5-19 and/or 38-77 of US Application Publication No. US2019/0314284, Tables 1-4 of International Patent Application No. PCT/US2019/025246, paragraphs 92-107 of US Application Publication No 20190091164, pages 78-97, 109-164, and/or 190-217 of International Patent Application No. PCT/US2019/015913, the contents of each of which are herein incorporated by reference in their entireties.

In some embodiments, a lipid or transfer vehicle is an ionizable lipid. In certain embodiments, an ionizable lipid comprises one or more cleavable functional groups (e.g., a disulfide) that allow, for example, a hydrophilic functional head-group to dissociate from a lipophilic functional tail-group of the compound (e.g., upon exposure to oxidative, reducing or acidic conditions), thereby facilitating a phase transition in the lipid bilayer of the one or more target cells. In some embodiments, an ionizable lipid is a lipid as represented by formula 1 or as listed in Tables 1 or 2 of U.S. Pat. No. 9,708,628, the content of which is herein incorporated by reference in its entirety. In some embodiments, an ionizable lipid is as described in pages 7-13 of U.S. Pat. No. 9,765,022 or as represented by formula 1 of U.S. Pat. No. 9,765,022, the content of which is herein incorporated by reference in its entirety. In some embodiments, an ionizable lipid is described in pages 12-24 of International Patent Application No. PCT/US2019/016362 or as represented by formula 1 of International Patent Application PCT/US2019/016362, the contents of which are herein incorporated by reference in their entirety.

In some embodiments, a lipid or transfer vehicle is a lipid as described in International Patent Application Nos. PCT/US2010/061058, PCT/US2018/058555, PCT/US2018/053569, PCT/US2017/028981, PCT/US2019/025246, PCT/US2019/015913, PCT/US2019/016362, PCT/US2019/016362, US Application Publication Nos. US2019/0314524, US2019/0321489, US2019/0314284, and US2019/0091164, and U.S. Pat. Nos. 9,708,628 and 9,765,022, the contents of which are herein incorporated by reference in their entireties.

In some embodiments, a lipid that may be used as a component of a transfer vehicle to facilitate or enhance the delivery and release of circular RNA to one or more target cells may be one or more lipid listed in Table 2.

TABLE 2
Exemplary Lipids
| Number | Lipid Structure |
|---|---|
| 1 | 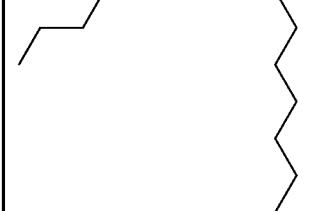 |
| 2 | 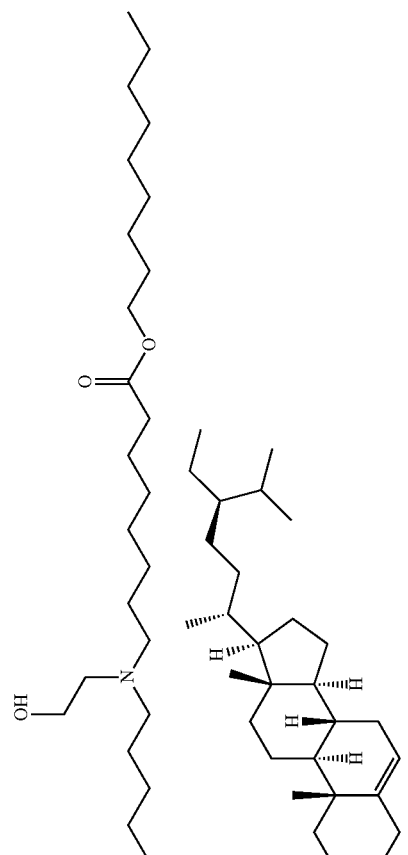 |
| 3 | 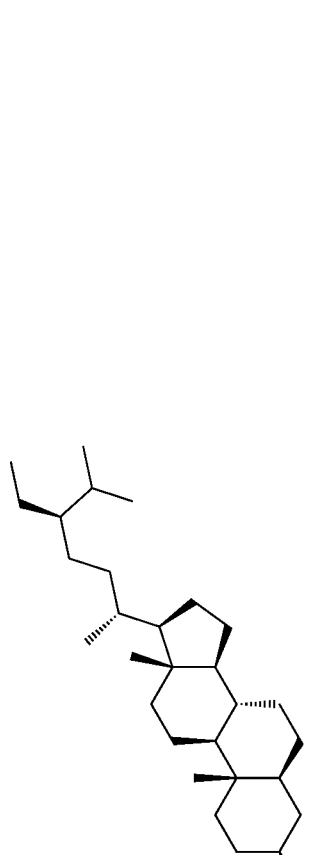 |

TABLE 2-continued
Exemplary Lipids
| Number | Lipid Structure |
|---|---|
| 4 | 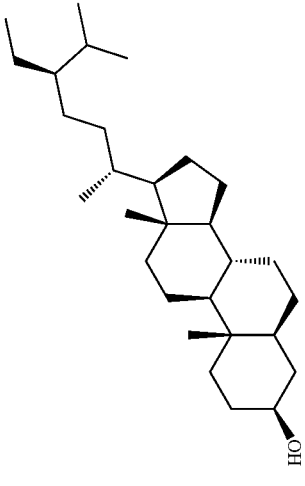 |
| 5 | 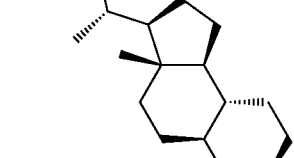 |
| 6 | 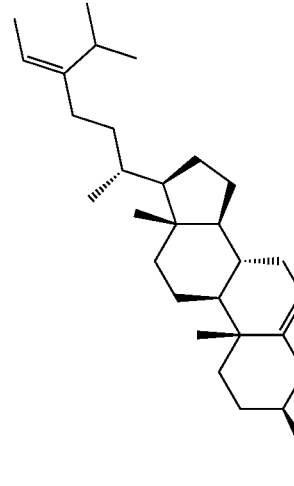 |

TABLE 2-continued

Exemplary Lipids

| Number | Lipid Structure |
|---|---|
| 7 | |
| 8 | |

TABLE 2-continued

Exemplary Lipids

| Number | Lipid Structure |
|---|---|
| 9 |  |
| 10 |  |
| 11 |  |

TABLE 2-continued

Exemplary Lipids

| Number | Lipid Structure |
|---|---|
| 12 | (structure) |
| 13 | (structure) |

TABLE 2-continued
Exemplary Lipids
| Number | Lipid Structure |
|---|---|
| 14 | 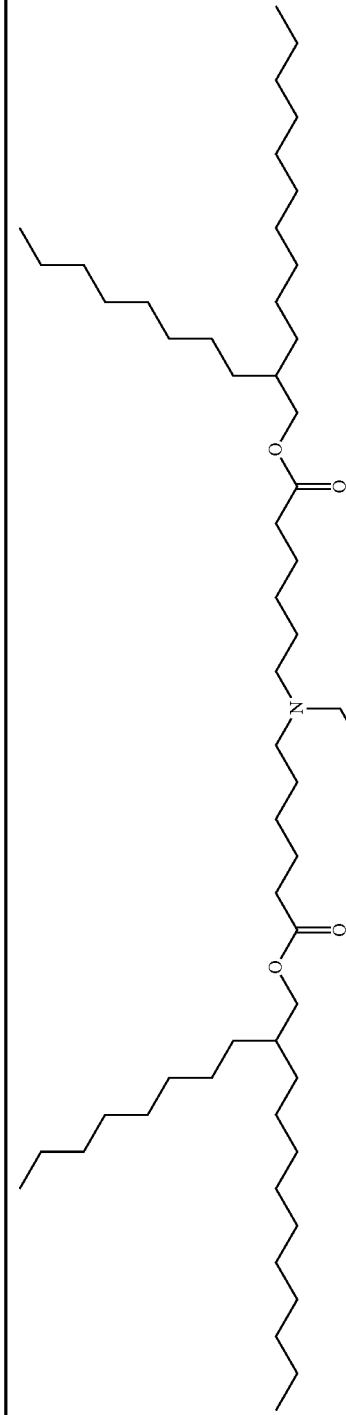 |
| 15 | 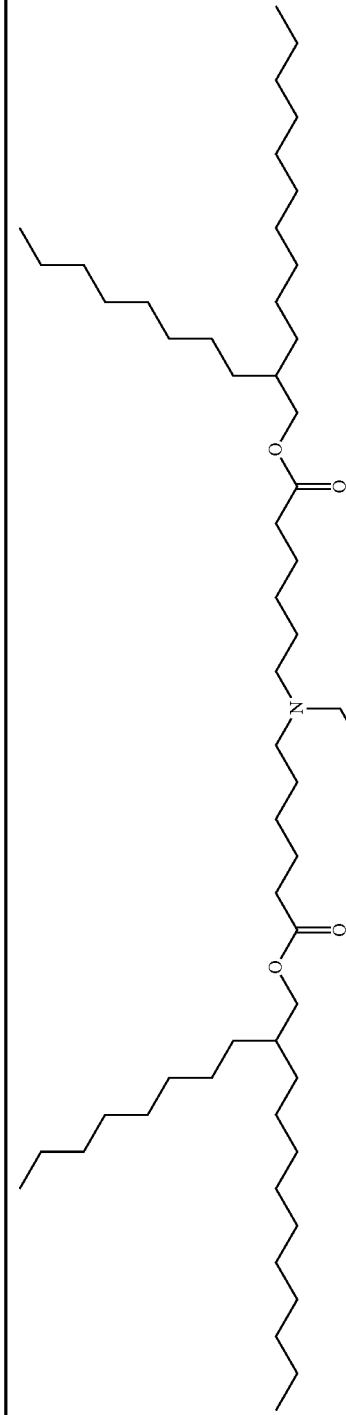 |
| 16 | 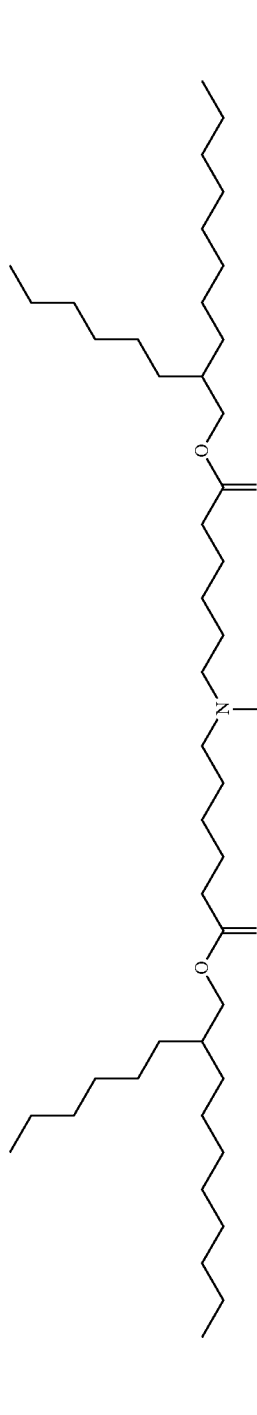 |

TABLE 2-continued
Exemplary Lipids
| Number | Lipid Structure |
|---|---|
| 17 |  |
| 18 |  |
| 19 | 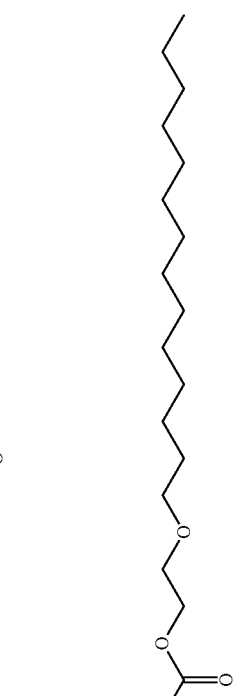 |
| 20 | 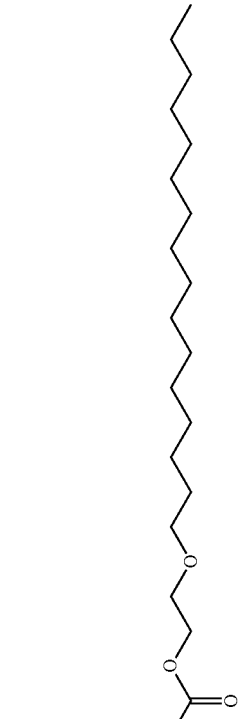 |
| 21 | 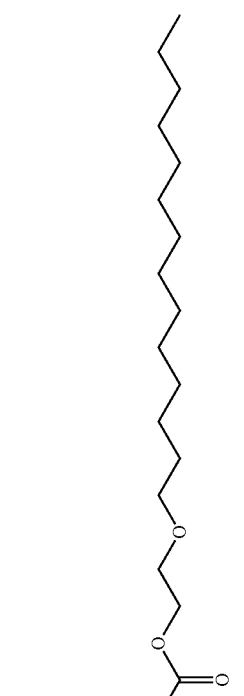 |

TABLE 2-continued
Exemplary Lipids
| Number | Lipid Structure |
|---|---|
| 22 | 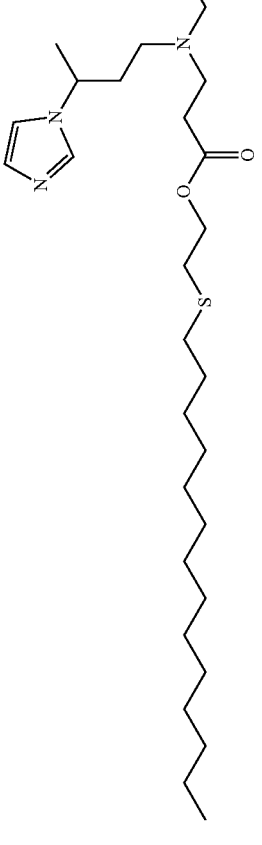 |
| 23 | 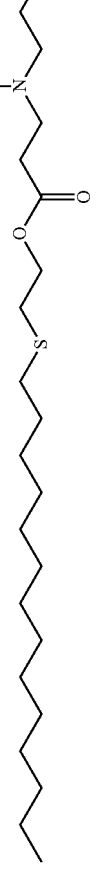 |
| 24 | 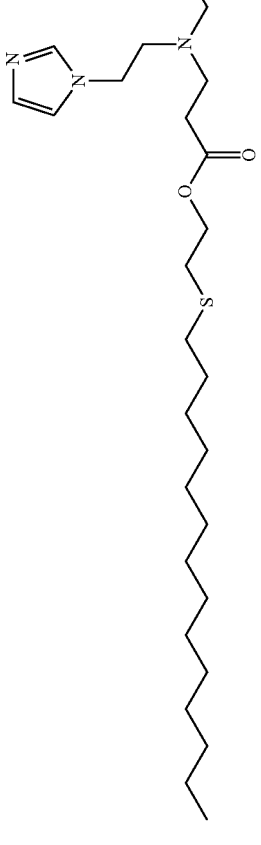 |
| 25 |  |

TABLE 2-continued
Exemplary Lipids
| Number | Lipid Structure |
|---|---|
| 26 | 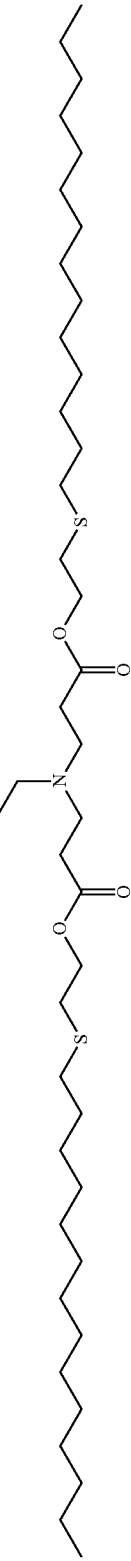 |
| 27 | 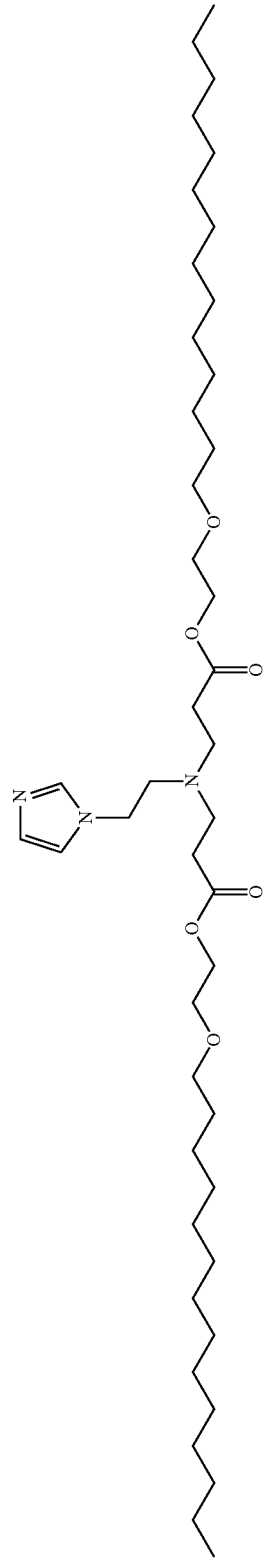 |
| 28 | 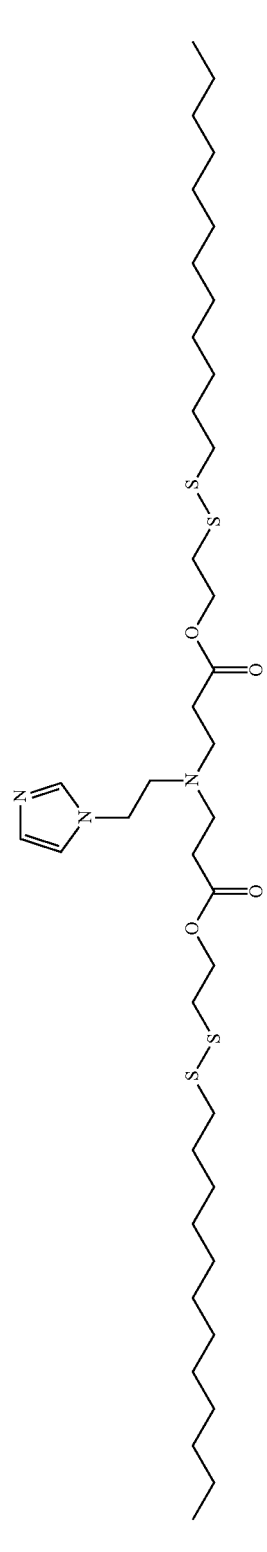 |

TABLE 2-continued

Exemplary Lipids

| Number | Lipid Structure |
|---|---|
| 29 | |
| 30 | |
| 31 | |

TABLE 2-continued
Exemplary Lipids
| Number | Lipid Structure |
|---|---|
| 32 | 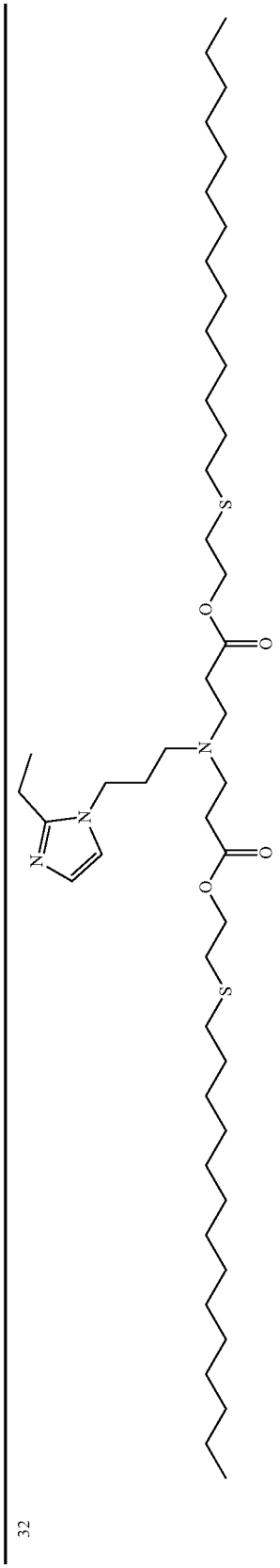 |
| 33 | 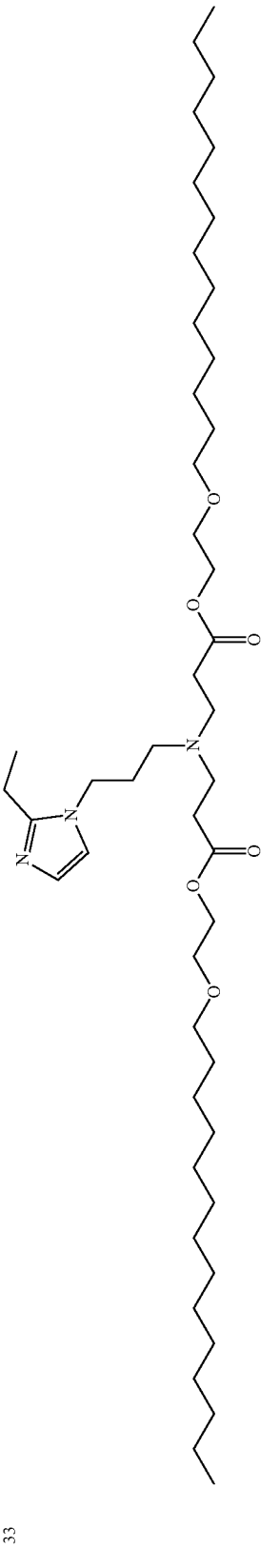 |
| 34 | 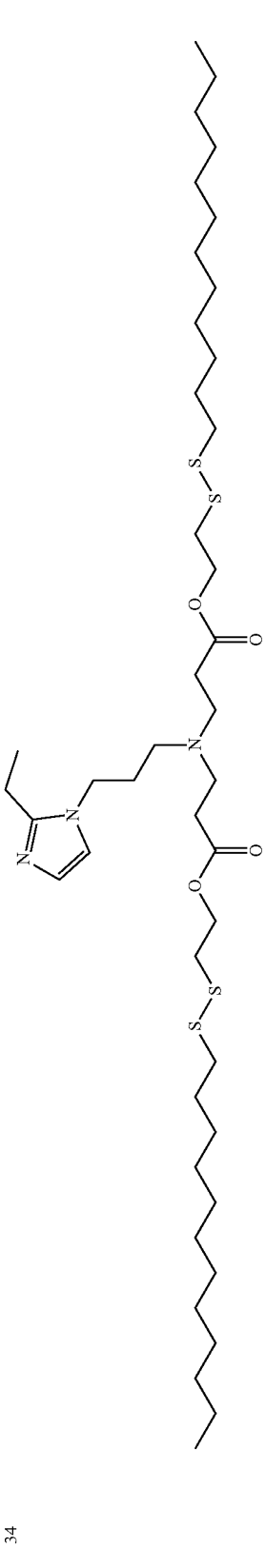 |

TABLE 2-continued
Exemplary Lipids
| Number | Lipid Structure |
|---|---|
| 35 | 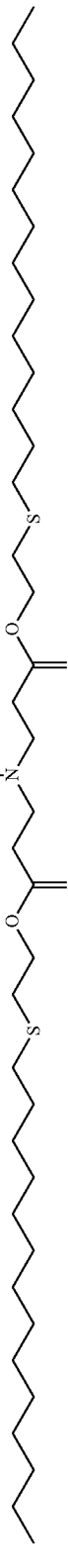 |
| 36 | 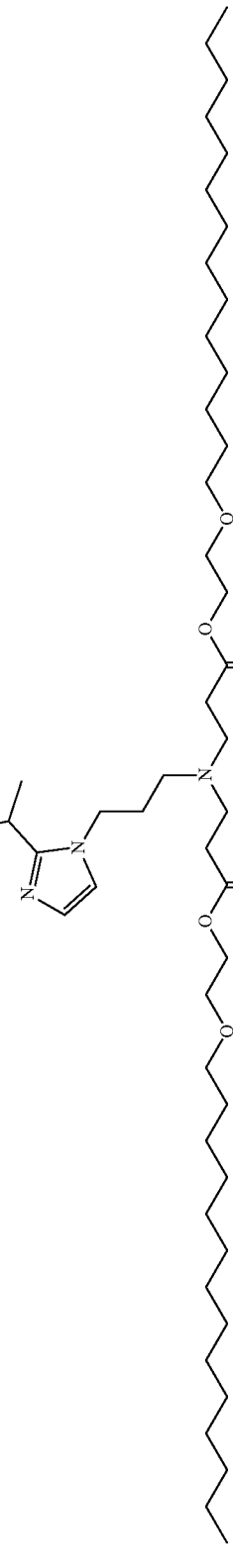 |
| 37 | 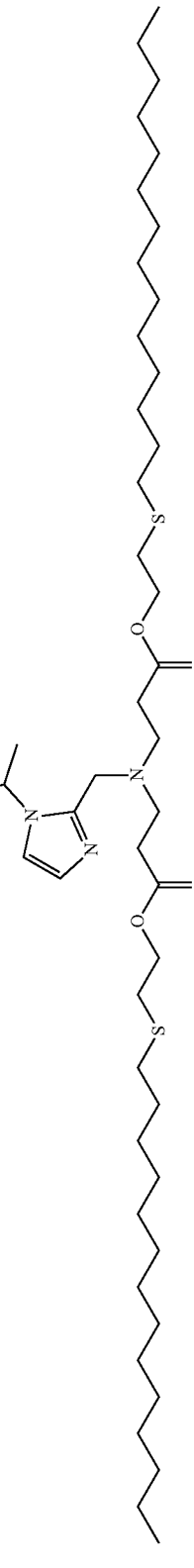 |

TABLE 2-continued
Exemplary Lipids
| Number | Lipid Structure |
|---|---|
| 38 | 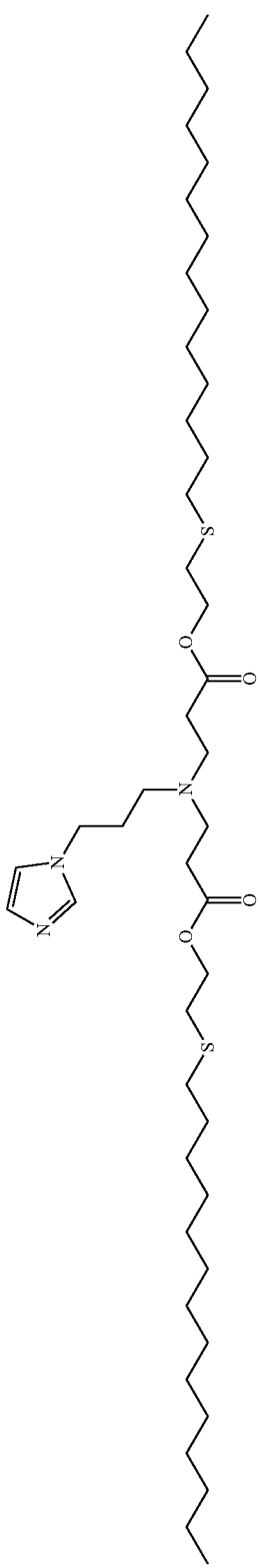 |
| 39 | 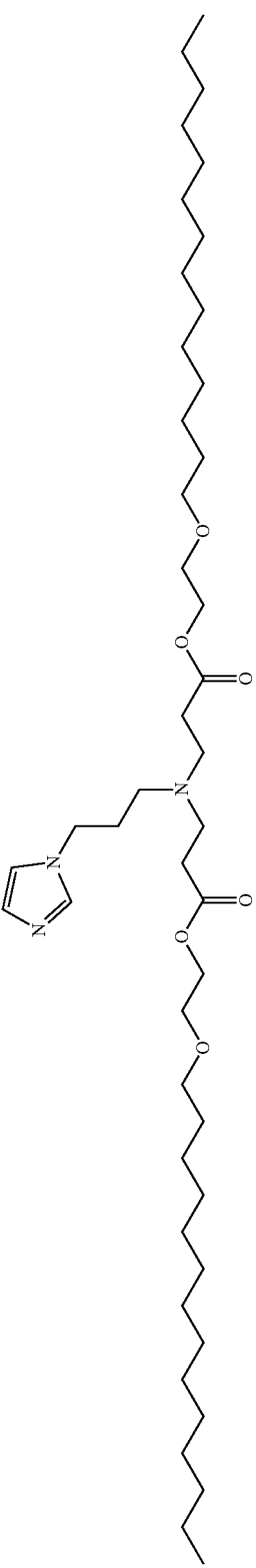 |
| 40 | 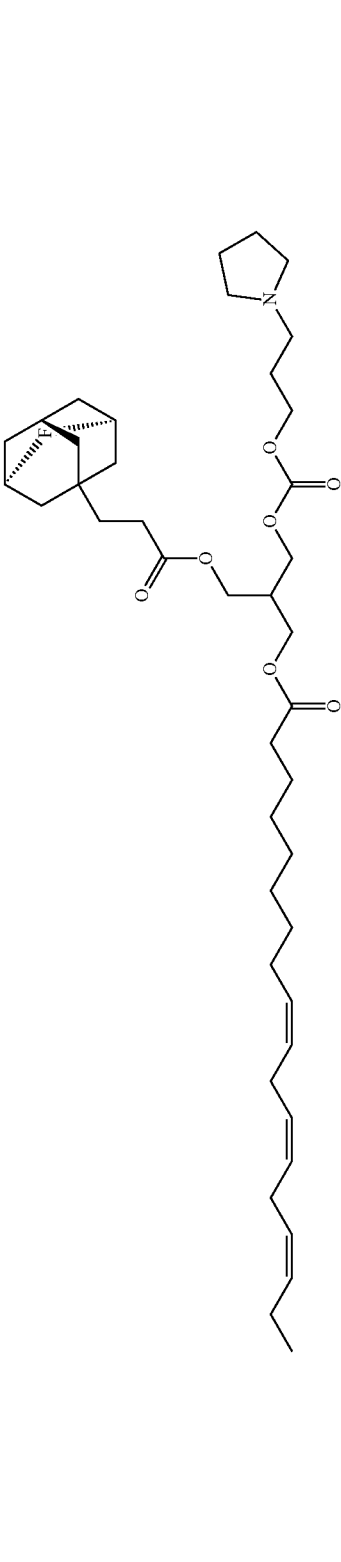 |

TABLE 2-continued
Exemplary Lipids
| Number | Lipid Structure |
|---|---|
| 41 | 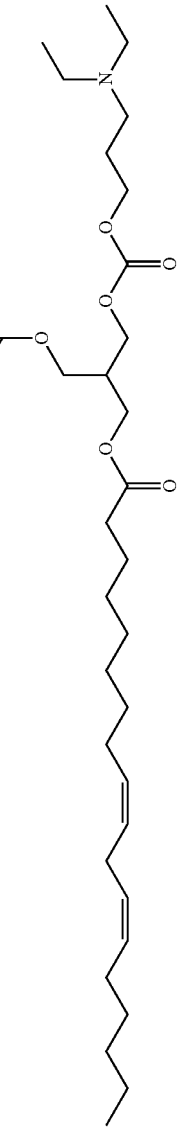 |
| 42 | 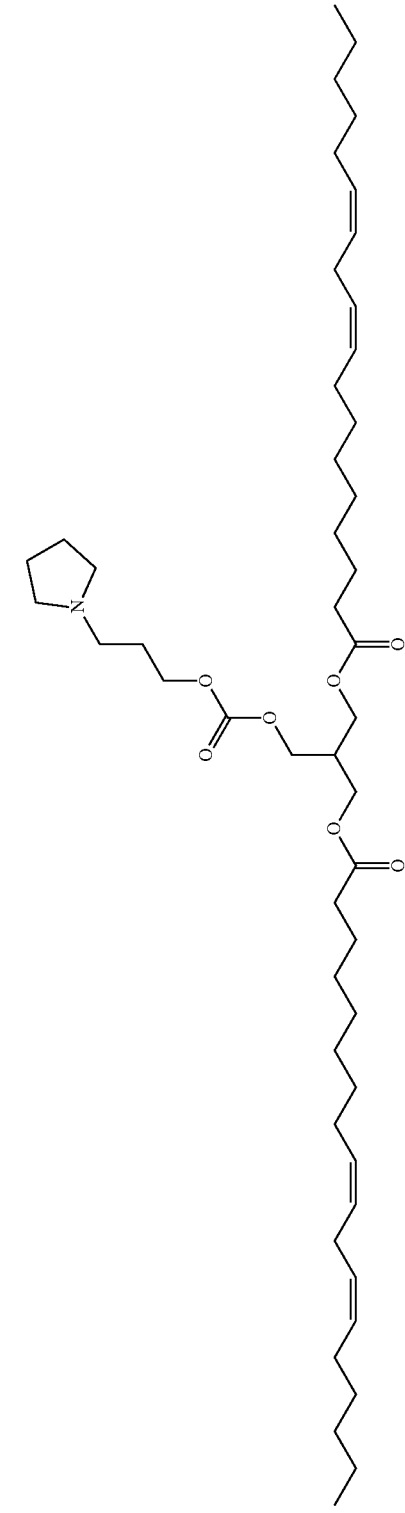 |

TABLE 2-continued
Exemplary Lipids
| Number | Lipid Structure |
|---|---|
| 43 | 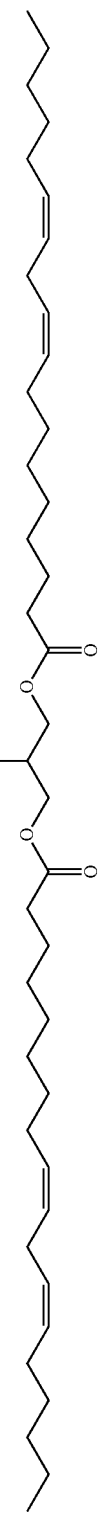 |
| 44 | 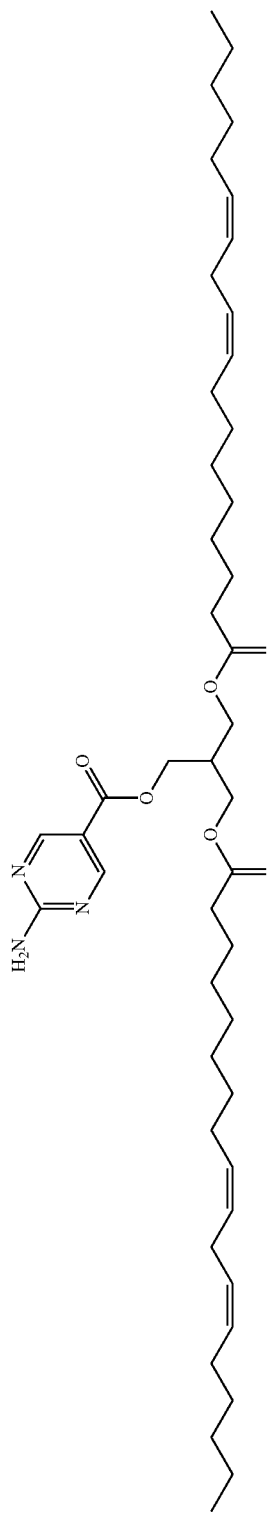 |
| 45 | 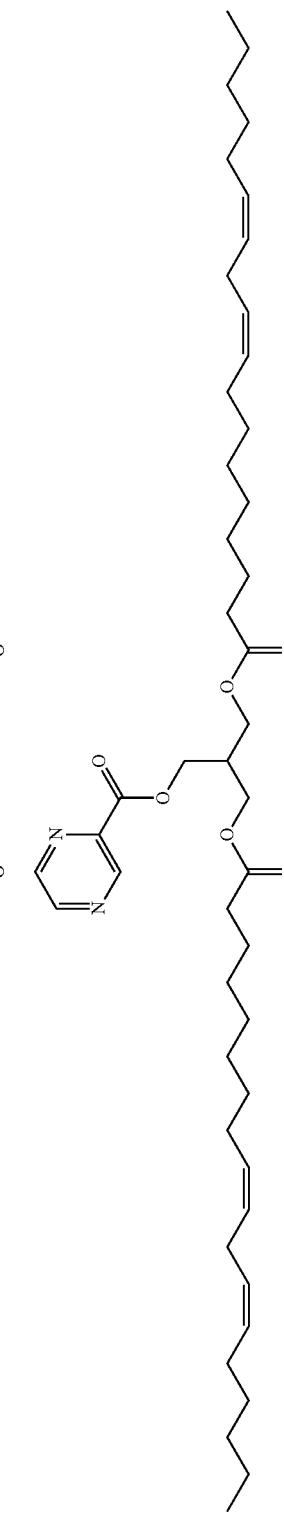 |

TABLE 2-continued

Exemplary Lipids

| Number | Lipid Structure |
|---|---|
| 46 | (structure) |
| 47 | (structure) |
| 48 | (structure) |

TABLE 2-continued
Exemplary Lipids
| Number | Lipid Structure |
|---|---|
| 49 | 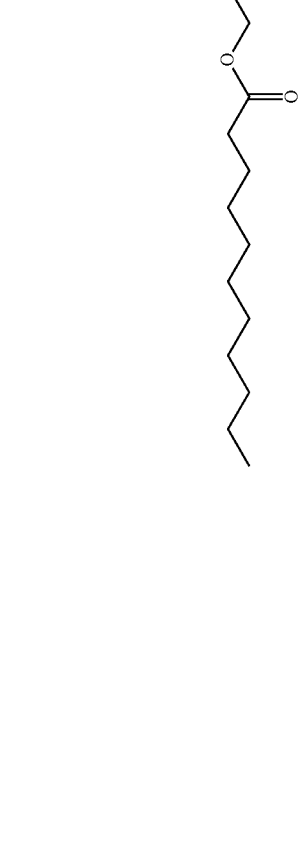 |
| 50 | 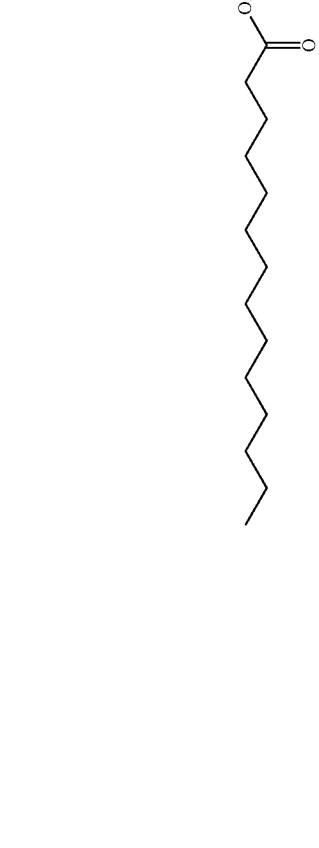 |
| 51 | 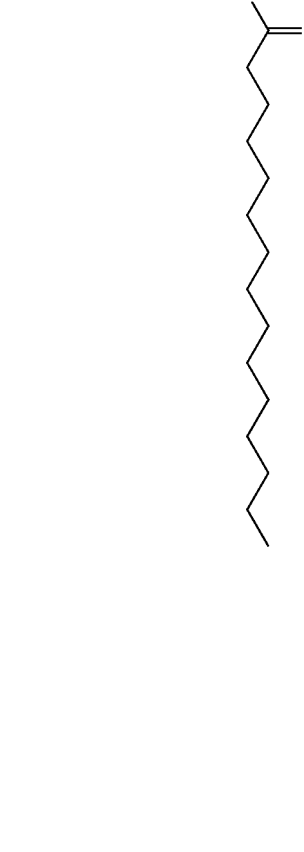 |

TABLE 2-continued

Exemplary Lipids

| Number | Lipid Structure |
|---|---|
| 52 | |
| 53 | |
| 54 | |
| 55 | |
| 56 | |

TABLE 2-continued

Exemplary Lipids

| Number | Lipid Structure |
|---|---|
| 57 | |
| 58 | |
| 59 | |

TABLE 2-continued
Exemplary Lipids
| Number | Lipid Structure |
|---|---|
| 60 | 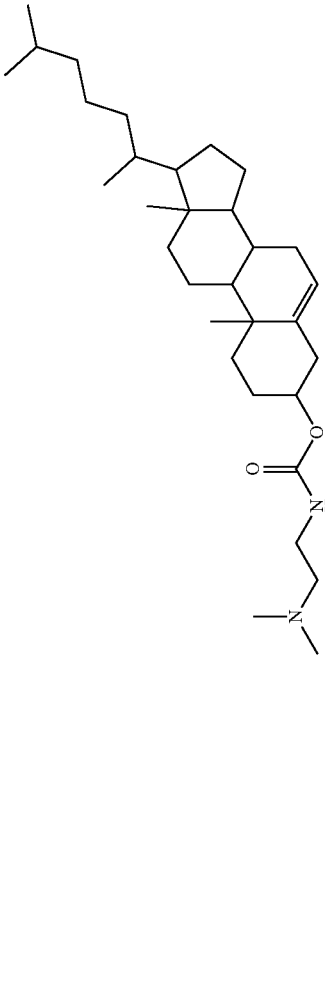 |
| 61 | 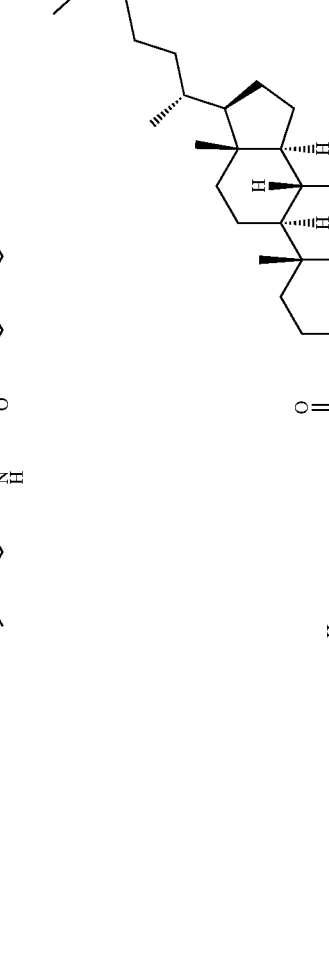 |

TABLE 2-continued
Exemplary Lipids
| Number | Lipid Structure |
|---|---|
| 62 |  |
| 63 | |

TABLE 2-continued
Exemplary Lipids
| Number | Lipid Structure |
|---|---|
| 64 | 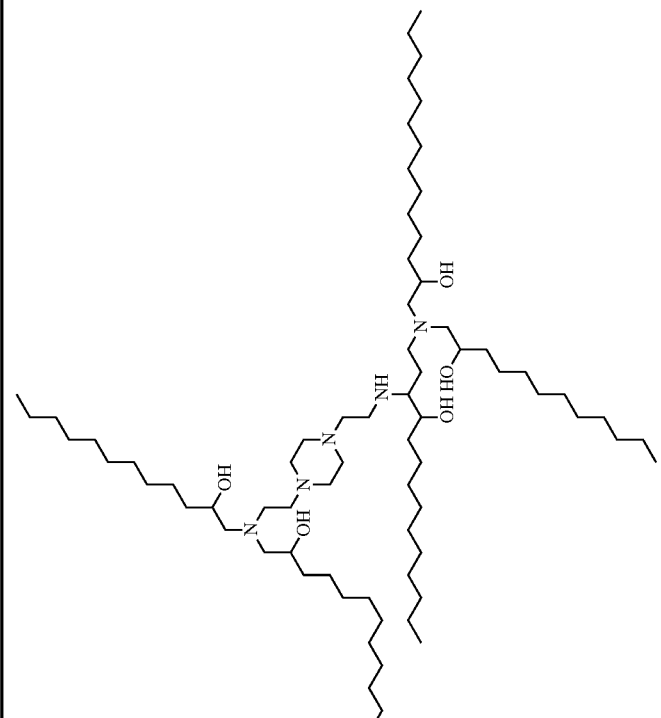 |

TABLE 2-continued
Exemplary Lipids
| Number | Lipid Structure |
|---|---|
| 65 | 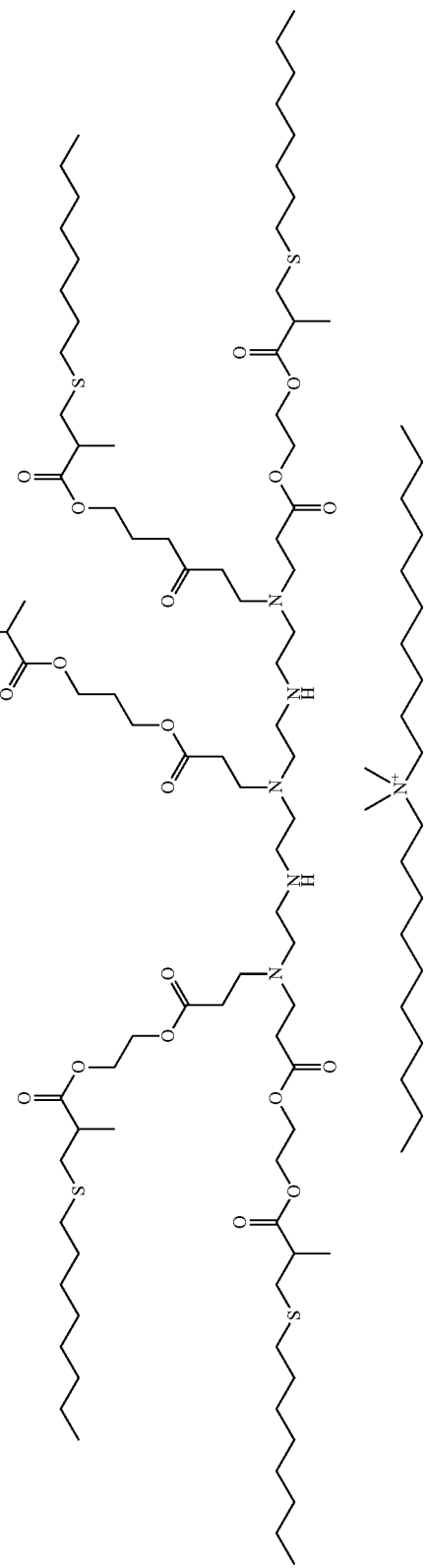 |
| 66 | |

TABLE 2-continued
Exemplary Lipids
| Number | Lipid Structure |
|---|---|
| 67 | 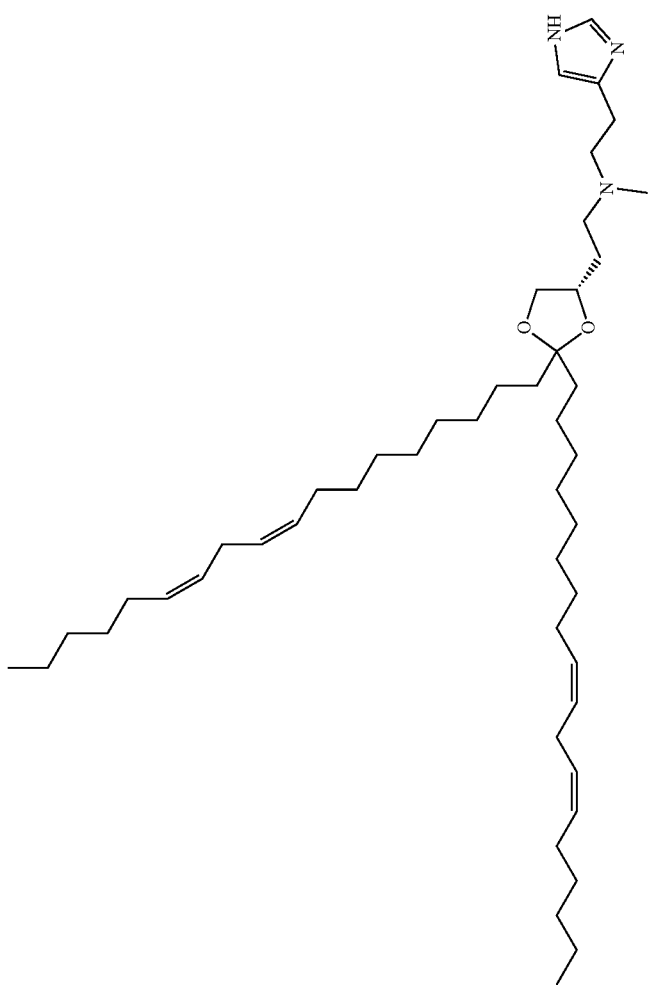 |

TABLE 2-continued

Exemplary Lipids

| Number | Lipid Structure |
|---|---|
| 68 | |

TABLE 2-continued

Exemplary Lipids

| Number | Lipid Structure |
|---|---|
| 69 | |

TABLE 2-continued

Exemplary Lipids

| Number | Lipid Structure |
|---|---|
| 70 | |

TABLE 2-continued
Exemplary Lipids
| Number | Lipid Structure |
|---|---|
| 71 | 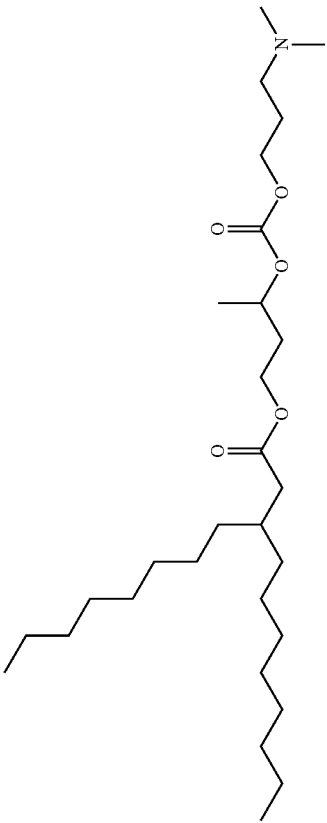 |

5. PEG Lipids

The use and inclusion of polyethylene glycol (PEG)-modified phospholipids and derivatized lipids such as derivatized ceramides (PEG-CER), including N-Octanoyl-Sphingosine-1-[Succinyl(Methoxy Polyethylene Glycol)-2000] (C8 PEG-2000 ceramide) in the liposomal and pharmaceutical compositions described herein is contemplated, preferably in combination with one or more of the compounds and lipids disclosed herein. Contemplated PEG-modified lipids include, but are not limited to, a polyethylene glycol chain of up to 5 kDa in length covalently attached to a lipid with alkyl chain(s) of C6-C20 length. In some embodiments, the PEG-modified lipid employed in the compositions and methods of the invention is 1,2-dimyristoyl-sn-glycerol, methoxypolyethylene Glycol (2000 MW PEG) "DMG-PEG2000." The addition of PEG-modified lipids to the lipid delivery vehicle may prevent complex aggregation and may also provide a means for increasing circulation lifetime and increasing the delivery of the lipid-polynucleotide composition to the target tissues, (Klibanov et al. (1990) FEBS Letters, 268 (1): 235-237), or they may be selected to rapidly exchange out of the formulation in vivo (see U.S. Pat. No. 5,885,613). Particularly useful exchangeable lipids are PEG-ceramides having shorter acyl chains (e.g., C14 or C18). The PEG-modified phospholipid and derivatized lipids of the present invention may comprise a molar ratio from about 0% to about 20%, about 0.5% to about 20%, about 1% to about 15%, about 4% to about 10%, or about 2% of the total lipid present in a liposomal lipid nanoparticle.

In an embodiment, a PEG-modified lipid is described in international patent application PCT/US2019/015913. In an embodiment, a transfer vehicle comprises one or more PEG-modified lipids.

Non-limiting examples of PEG-lipids include PEG-modified phosphatidylethanolamine and phosphatidic acid, PEG-ceramide conjugates (e.g., PEG-CerC14 or PEG-CerC20), PEG-modified dialkylamines and PEG-modified 1,2-diacyloxypropan-3-amines Such lipids are also referred to as PEGylated lipids. For example, a PEG lipid can be PEG-c-DOMG, PEG-DMG, PEG-DLPE, PEG-DMPE, PEG-DPPC, or a PEG-DSPE lipid.

In some embodiments, the PEG-lipid includes, but is not limited to 1,2-dimyristoyl-sn-glycerol methoxypolyethylene glycol (PEG-DMG), 1,2-distearoyl-sn-glycero-3-phosphoethanolamine-N-[amino(polyethylene glycol)] (PEG-DSPE), PEG-disteryl glycerol (PEG-DSG), PEG-dipalmetoleyl, PEG-dioleyl, PEG-distearyl, PEG-diacylglycamide (PEG-DAG), PEG-dipalmitoyl phosphatidylethanolamine (PEG-DPPE), or PEG-1,2-dimyristyloxlpropyl-3-amine (PEG-c-DMA).

In one embodiment, the PEG-lipid is selected from the group consisting of a PEG-modified phosphatidylethanolamine, a PEG-modified phosphatidic acid, a PEG-modified ceramide, a PEG-modified dialkylamine, a PEG-modified diacylglycerol, a PEG-modified dialkylglycerol, and mixtures thereof.

In some embodiments, the lipid moiety of the PEG-lipids includes those having lengths of from about $C_{14}$ to about $C_{22}$, such as from about $C_{14}$ to about $C_{16}$. In some embodiments, a PEG moiety, for example an mPEG-NH2, has a size of about 1000, 2000, 5000, 10,000, 15,000 or 20,000 daltons. In one embodiment, the PEG-lipid is PEG2k-DMG.

In one embodiment, the lipid nanoparticles described herein can comprise a PEG lipid which is a non-diffusible PEG. Non-limiting examples of non-diffusible PEGs include PEG-DSG and PEG-DSPE.

PEG-lipids are known in the art, such as those described in U.S. Pat. No. 8,158,601 and International Publ. No. WO 2015/130584 A2, which are incorporated herein by reference in their entirety.

In general, some of the other lipid components (e.g., PEG lipids) of various formulae, described herein may be synthesized as described International Patent Application No. PCT/US2016/000129, which is incorporated by reference in its entirety.

The lipid component of a lipid nanoparticle composition may include one or more molecules comprising polyethylene glycol, such as PEG or PEG-modified lipids. Such species may be alternately referred to as PEGylated lipids. A PEG lipid is a lipid modified with polyethylene glycol. A PEG lipid may be selected from the non-limiting group including PEG-modified phosphatidylethanolamines, PEG-modified phosphatidic acids, PEG-modified ceramides, PEG-modified dialkylamines, PEG-modified diacylglycerols, PEG-modified dialkylglycerols, and mixtures thereof. For example, a PEG lipid may be PEG-c-DOMG, PEG-DMG, PEG-DLPE, PEG-DMPE, PEG-DPPC, or a PEG-DSPE lipid.

In some embodiments the PEG-modified lipids are a modified form of PEG-DMG. PEG-DMG has the following structure:

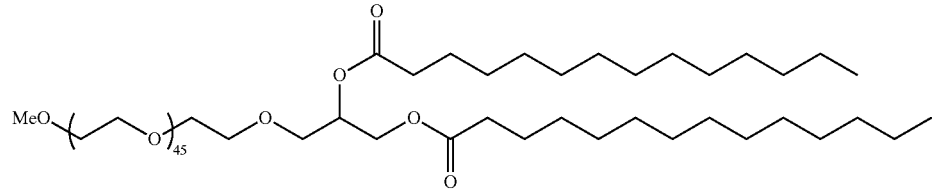

In one embodiment, PEG lipids useful in the present invention can be PEGylated lipids described in International Publication No. WO2012099755, the contents of which is herein incorporated by reference in its entirety. Any of these exemplary PEG lipids described herein may be modified to comprise a hydroxyl group on the PEG chain. In certain embodiments, the PEG lipid is a PEG-OH lipid. In certain embodiments, the PEG-OH lipid includes one or more hydroxyl groups on the PEG chain. In certain embodiments, a PEG-OH or hydroxy-PEGylated lipid comprises an —OH group at the terminus of the PEG chain. Each possibility represents a separate embodiment of the present invention.

In some embodiments, the PEG lipid is a compound of Formula (P1):

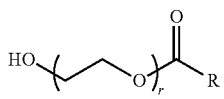

P1 or a salt or isomer thereof, wherein:
r is an integer between 1 and 100;
R is $C_{10-40}$ alkyl, $C_{10-40}$ alkenyl, or $C_{10-40}$ alkynyl; and optionally one or more methylene groups of R are independently replaced with $C_{3-10}$ carbocyclylene, 4 to 10 membered heterocyclylene, $C_{6-10}$ arylene, 4 to 10 membered heteroarylene, $-N(R^N)-$, $-O-$, $-S-$, $-C(O)-$, $-C(O)N(R^N)-$, $-NR^NC(O)-$, $-NR^NC(O)N(R^N)-$, $-C(O)O-$, $-OC(O)-$, $-OC(O)O-$, $-OC(O)N(R^N)-$, $-NR^NC(O)O-$, $-C(O)S-$, $-SC(O)-$, $-C(=NR^N)-$, $-C(=NR^N)N(R^N)-$, $-NR^NC(=NR^N)-$, $-NR^NC(=NR^N)N(R^N)-$, $-C(S)-$, $-C(S)N(R^N)-$, $-NR^NC(S)-$, $-NR^NC(S)N(R^N)-$, $-S(O)-$, $-OS(O)-$, $-S(O)O-$, $-OS(O)O-$, $-OS(O)_2-$, $-S(O)_2O-$, $-OS(O)_2O-$, $-N(R^N)S(O)-$, $-S(O)N(R^N)-$, $-N(R^N)S(O)N(R^N)-$, $-OS(O)N(R^N)-$, $-N(R^N)S(O)O-$, $-S(O)_2-$, $-N(R^N)S(O)_2-$, $-S(O)_2N(R^N)-$, $-N(R^N)S(O)_2N(R^N)-$, $-OS(O)_2N(R^N)-$, or $-N(R^N)S(O)_2O-$; and
each instance of $R^N$ is independently hydrogen, $C_{1-6}$ alkyl, or a nitrogen protecting group.

For example, R is C17 alkyl. For example, the PEG lipid is a compound of Formula (P1-a):

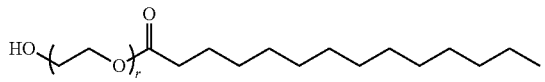

or a salt or isomer thereof, wherein r is an integer between 1 and 100.

For example, the PEG lipid is a compound of the following formula:

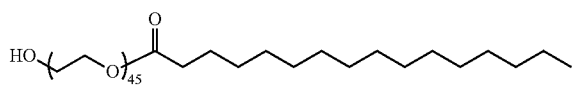

6. Helper Lipids

In some embodiments, the transfer vehicle (e.g., LNP) described herein comprises one or more non-cationic helper lipids. In some embodiments, the helper lipid is a phospholipid. In some embodiments, the helper lipid is a phospholipid substitute or replacement. In some embodiments, the phospholipid or phospholipid substitute can be, for example, one or more saturated or (poly)unsaturated phospholipids, or phospholipid substitutes, or a combination thereof. In general, phospholipids comprise a phospholipid moiety and one or more fatty acid moieties.

A phospholipid moiety can be selected, for example, from the non-limiting group consisting of phosphatidyl choline, phosphatidyl ethanolamine, phosphatidyl glycerol, phosphatidyl serine, phosphatidic acid, 2-lysophosphatidyl choline, and a sphingomyelin.

A fatty acid moiety can be selected, for example, from the non-limiting group consisting of lauric acid, myristic acid, myristoleic acid, palmitic acid, palmitoleic acid, stearic acid, oleic acid, linoleic acid, alpha-linolenic acid, erucic acid, phytanoic acid, arachidic acid, arachidonic acid, eicosapentaenoic acid, behenic acid, docosapentaenoic acid, and docosahexaenoic acid.

Phospholipids include, but are not limited to, glycerophospholipids such as phosphatidylcholines, phosphatidylethanolamines, phosphatidylserines, phosphatidylinositols, phosphatidy glycerols, and phosphatidic acids. Phospholipids also include phosphosphingolipid, such as sphingomyelin.

In some embodiments, the helper lipid is a 1,2-distearoyl-177-glycero-3-phosphocholine (DSPC) analog, a DSPC substitute, oleic acid, or an oleic acid analog.

In some embodiments, a helper lipid is a non-phosphatidyl choline (PC) zwitterionic lipid, a DSPC analog, oleic acid, an oleic acid analog, or a DSPC substitute.

In some embodiments, a helper lipid is described in PCT/US2018/053569. Helper lipids suitable for use in a lipid composition of the disclosure include, for example, a variety of neutral, uncharged or zwitterionic lipids. Such helper lipids are preferably used in combination with one or more of the compounds and lipids disclosed herein. Examples of helper lipids include, but are not limited to, 5-heptadecylbenzene-1,3-diol (resorcinol), dipalmitoylphosphatidylcholine (DPPC), distearoylphosphatidylcholine (DSPC), pohsphocholine (DOPC), dimyristoylphosphatidylcholine (DMPC), phosphatidylcholine (PLPC), 1,2-distearoylsn-glycero-3-phosphocholine (DAPC), phosphatidylethanolamine (PE), egg phosphatidylcholine (EPC), dilauryloylphosphatidylcholine (DLPC), dimyristoylphosphatidylcholine (DMPC), 1-myristoyl-2-palmitoyl phosphatidylcholine (MPPC), 1-paimitoyl-2-myristoyl phosphatidylcholine (PMPC), 1-palmitoyl-2-stearoyl phosphatidylcholine (PSPC), 1,2-diarachidoyl-sn-glycero-3-phosphocholine (DBPC), 1-stearoyl-2-palmitoyl phosphatidylcholine (SPPC), 1,2-dieicosenoyl-sn-glycero-3-phosphocholine (DEPC), paimitoyioieoyl phosphatidylcholine (POPC), lysophosphatidyl choline, dioleoyl phosphatidylethanol amine (DOPE) dilinoleoylphosphatidylcholine distearoylphosphatidylethanolamine (DSPE), dimyristoyl phosphatidylethanolamine (DMPE), dipalmitoyl phosphatidylethanolamine (DPPE), palmitoyloleoyl phosphatidylethanolamine (POPE), lysophosphatidylethanolamine and combinations thereof. In one embodiment, the helper lipid may be distearoylphosphatidylcholine (DSPC) or dimyristoyl phosphatidyl ethanolamine (DMPE). In another embodiment, the helper lipid may be distearoylphosphatidylcholine (DSPC). Helper lipids function to stabilize and improve processing of the transfer vehicles. Such helper lipids are preferably used in combination with other excipients, for example, one or more of the ionizable lipids disclosed herein. In some embodiments, when used in combination with an ionizable lipid, the helper lipid may comprise a molar ratio of 5% to about 90%, or about 10% to about 70% of the total lipid present in the lipid nanoparticle.

7. Structural Lipids

In an embodiment, a structural lipid is described in international patent application PCT/US2019/015913.

The transfer vehicles described herein comprise one or more structural lipids. Incorporation of structural lipids in the lipid nanoparticle may help mitigate aggregation of other lipids in the particle. Structural lipids can include, but are not limited to, cholesterol, fecosterol, ergosterol, bassicasterol, tomatidine, tomatine, ursolic, alpha-tocopherol, and mixtures thereof. In certain embodiments, the structural lipid is cholesterol. In certain embodiments, the structural lipid includes cholesterol and a corticosteroid (such as, for example, prednisolone, dexamethasone, prednisone, and hydrocortisone), or a combination thereof.

In some embodiments, the structural lipid is a sterol. In certain embodiments, the structural lipid is a steroid. In certain embodiments, the structural lipid is cholesterol. In certain embodiments, the structural lipid is an analog of cholesterol. In certain embodiments, the structural lipid is alpha-tocopherol.

The transfer vehicles described herein comprise one or more structural lipids. Incorporation of structural lipids in a transfer vehicle, e.g., a lipid nanoparticle, may help mitigate aggregation of other lipids in the particle. In certain embodiments, the structural lipid includes cholesterol and a corticosteroid (such as, for example, prednisolone, dexamethasone, prednisone, and hydrocortisone), or a combination thereof.

In some embodiments, the structural lipid is a sterol. Structural lipids can include, but are not limited to, sterols (e.g., phytosterols or zoosterols).

In certain embodiments, the structural lipid is a steroid. For example, sterols can include, but are not limited to, cholesterol, β-sitosterol, fecosterol, ergosterol, sitosterol, campesterol, stigmasterol, brassicasterol, ergosterol, tomatidine, tomatine, ursolic acid, or alpha-tocopherol.

8. Chimeric Antigen Receptors

Chimeric antigen receptors (CARs or CAR-Ts) are genetically-engineered receptors. These engineered receptors may be inserted into and expressed by immune cells, including T cells via circular RNA as described herein. With a CAR, a single receptor may be programmed to both recognize a specific antigen and, when bound to that antigen, activate the immune cell to attack and destroy the cell bearing that antigen. When these antigens exist on tumor cells, an immune cell that expresses the CAR may target and kill the tumor cell. In some embodiments, the CAR encoded by the polynucleotide comprises (i) an antigen-binding molecule that specifically binds to a target antigen, (ii) a hinge domain, a transmembrane domain, and an intracellular domain, and (iii) an activating domain.

In certain aspects, provided herein are vectors, precursor RNAs and circular RNA polynucleotides that comprise a protein coding region that encodes a chimeric antigen receptor (CAR) or a T cell receptor (TCR) complex protein.

A CAR is an artificially constructed hybrid protein or polypeptide containing an antigen binding domain (e.g., single chain variable fragment (scFv)) linked to T-cell signaling domains. Characteristics of CARs include their ability to redirect T-cell specificity and reactivity toward at least one selected target (e.g., in a non-MHC-restricted manner), exploiting the antigen-binding properties of monoclonal antibodies. The ability CARs to recognize non-MHC-restricted antigen gives T cells expressing CARs the ability to recognize an antigen independent of antigen processing, thus bypassing a major mechanism of tumor escape. A bispecific CAR is specific to two different antigens. In an embodiment, certain polynucleotides provided herein encode bispecific CARs.

In some embodiments, the CAR comprises a transmembrane domain. In an embodiment, the transmembrane domain comprises a CD8 transmembrane domain. In some embodiments, the CAR comprises a CD8a (CD8 alpha) hinge and transmembrane domain. In a preferred embodiment, the CD8 is human. The CAR may comprise less than the whole CD8 protein. In an embodiment, the transmembrane domain comprises a CD28 transmembrane domain. In some embodiments, the CAR comprises a CD28 hinge and transmembrane domain. In a preferred embodiment, the CD28 is human. The CAR may comprise less than the whole CD28 protein.

In some embodiments, an orientation of the CARs in accordance with the disclosure comprises an antigen binding domain (such as an scFv) in tandem with a costimulatory domain and an activating domain. The costimulatory domain may comprise one or more of an extracellular portion, a transmembrane portion, and an intracellular portion. In other embodiments, multiple costimulatory domains may be utilized in tandem.

In some embodiments, the CAR comprises a CAR protein spacer. The CAR protein spacer may be between any aforementioned domains. In an embodiment, the CAR comprises an IgG heavy chain constant domain (CH2CH3) spacer. In a further embodiment, the CAR protein spacer can be between the scFv and the transmembrane domain. In a preferred embodiment, the sequence of the spacer, e.g., CH2CH3, is human.

In some embodiments, the CAR or TCR complex protein is a TCR complex protein (i.e., a protein that makes up part of the TCR complex). In some embodiments, the TCR complex protein is a recombinant, naturally occurring protein. In some embodiments, the TCR complex protein is an artificial version of a protein that makes up part of the TCR complex. In some embodiments, the TCR complex protein is TCRalpha, TCRbeta, TCRgamma, TCRdelta, CD3epsilon, CD3gamma, CD3delta, CD3zeta, CD4, or CD8. In some embodiments, the TCR complex protein comprises an artificial binding domain, and/or a costimulatory domain.

In certain embodiments, the TCR complex protein comprises a sequence that is at least 90%, at least 91%, at least 92%, at least 93%, at least 94%, at least 95%, at least 96%, at least 97%, at least 98%, at least 99%, at least 99.5%, or 100% identical to an amino acid sequence of a natural TCR Vα, Vβ, Cα, and/or Cβ. In some embodiments, each CDR or the TCR complex protein comprises zero changes or at most one, two, or three changes, from a TCR or fragment or derivative thereof that specifically binds to a target of interest.

Antigen Binding Domain

CARs may be engineered to bind to an antigen (such as a cell-surface antigen) by incorporating an antigen binding molecule that interacts with that targeted antigen. In some embodiments, the antigen binding molecule is an antibody fragment thereof, e.g., one or more single chain antibody fragment (scFv). An scFv is a single chain antibody fragment having the variable regions of the heavy and light chains of an antibody linked together. See U.S. Pat. Nos. 7,741,465, and 6,319,494 as well as Eshhar et al., Cancer Immunol Immunotherapy (1997) 45: 131-136. An scFv retains the parent antibody's ability to specifically interact with target antigen. scFvs are useful in chimeric antigen receptors because they may be engineered to be expressed as part of a single chain along with the other CAR components. Id. See also Krause et al., J. Exp. Med., Volume 188, No. 4, 1998 (619-626); Finney et al., Journal of Immunology, 1998, 161: 2791-2797. It will be appreciated that the antigen binding molecule is typically contained within the extracellular portion of the CAR such that it is capable of recognizing and binding to the antigen of interest. Bispecific and multispecific CARs are contemplated within the scope of the invention, with specificity to more than one target of interest. In some embodiments, an antigen binding domain is an aptamer or nanobody specific for a target antigen.

In some embodiments, the antigen binding molecule comprises a single chain, wherein the heavy chain variable region and the light chain variable region are connected by a linker. In some embodiments, the VH is located at the N terminus of the linker and the VL is located at the C terminus of the linker. In other embodiments, the VL is located at the N terminus of the linker and the VH is located at the C terminus of the linker. In some embodiments, the linker comprises at least about 5, at least about 8, at least about 10, at least about 13, at least about 15, at least about 18, at least about 20, at least about 25, at least about 30, at least about 35, at least about 40, at least about 45, at least about 50, at least about 60, at least about 70, at least about 80, at least about 90, or at least about 100 amino acids.

In some embodiments, the CAR or TCR comprises an antigen binding domain specific for an antigen selected from the group CD19, CD123, CD22, CD30, CD171, CS-1, C-type lectin-like molecule-1, CD33, epidermal growth factor receptor variant III (EGFRvIII), ganglioside G2 (GD2), ganglioside GD3, TNF receptor family member B cell maturation (BCMA), Tn antigen ((Tn Ag) or (GalNAca-Ser/Thr)), prostate-specific membrane antigen (PSMA), Receptor tyrosine kinase-like orphan receptor 1 (ROR1), Fms-Like Tyrosine Kinase 3 (FLT3), Tumor-associated glycoprotein 72 (TAG72), CD38, CD44v6, Carcinoembryonic antigen (CEA), Epithelial cell adhesion molecule (EPCAM), B7H3 (CD276), KIT (CD117), Interleukin-13 receptor subunit alpha-2, mesothelin, Interleukin 11 receptor alpha (IL-11Ra), prostate stem cell antigen (PSCA), Protease Serine 21, vascular endothelial growth factor receptor 2 (VEGFR2), Lewis(Y) antigen, CD24, Platelet-derived growth factor receptor beta (PDGFR-beta), Stage-specific embryonic antigen-4 (SSEA-4), CD20, Folate receptor alpha, HER2, HER3, Mucin 1, cell surface associated (MUC1), epidermal growth factor receptor (EGFR), neural cell adhesion molecule (NCAM), Prostase, prostatic acid phosphatase (PAP), elongation factor 2 mutated (ELF2M), Ephrin B2, fibroblast activation protein alpha (FAP), insulin-like growth factor 1 receptor (IGF-I receptor), carbonic anhydrase IX (CAIX), Proteasome (Prosome, Macropain) Subunit, Beta Type, 9 (LMP2), glycoprotein 100 (gp100), oncogene fusion protein consisting of breakpoint cluster region (BCR) and Abelson murine leukemia viral oncogene homolog 1 (Abl) (bcr-abl), tyrosinase, ephrin type-A receptor 2 (EphA2), Fucosyl GM1, sialyl Lewis adhesion molecule (sLe), ganglioside GM3, transglutaminase 5 (TGS5), high molecular weight-melanoma-associated antigen (HMWMAA), o-acetyl-GD2 ganglioside (OAcGD2), Folate receptor beta, tumor endothelial marker 1 (TEM1/CD248), tumor endothelial marker 7-related (TEM7R), claudin 6 (CLDN6), claudin 18.2 (CLDN18.2), thyroid stimulating hormone receptor (TSHR), G protein-coupled receptor class C group 5, member D (GPRC5D), chromosome X open reading frame 61 (CXORF61), CD97, CD179a, anaplastic lymphoma kinase (ALK), Polysialic acid, placenta-specific 1 (PLAC1), hexasaccharide portion of globoH glycoceramide (GloboH), mammary gland differentiation antigen (NY-BR-1), uroplakin 2 (UPK2), Hepatitis A virus cellular receptor 1 (HAVCR1), adrenoceptor beta 3 (ADRB3), pannexin 3 (PANX3), G protein-coupled receptor 20 (GPR20), lymphocyte antigen 6 complex, locus K 9 (LY6K), Olfactory receptor 51E2 (OR51E2), TCR Gamma Alternate Reading Frame Protein (TARP), Wilms tumor protein (WT1), Cancer/testis antigen 1 (NY-ESO-1), Cancer/testis antigen 2 (LAGE-1a), MAGE family members (including MAGE-A1, MAGE-A3 and MAGE-A4), ETS translocation-variant gene 6, located on chromosome 12p (ETV6-AML), sperm protein 17 (SPA17), X Antigen Family, Member 1A (XAGE1), angiopoietin-binding cell surface receptor 2 (Tie 2), melanoma cancer testis antigen-1 (MAD-CT-1), melanoma cancer testis antigen-2 (MAD-CT-2), Fos-related antigen 1, tumor protein p53 (p53), p53 mutant, prostein, surviving, telomerase, prostate carcinoma tumor antigen-1, melanoma antigen recognized by T cells 1, Rat sarcoma (Ras) mutant, human Telomerase reverse transcriptase (hTERT), sarcoma translocation breakpoints, melanoma inhibitor of apoptosis (ML-IAP), ERG (transmembrane protease, serine 2 (TMPRSS2) ETS fusion gene), N-Acetyl glucosaminyl-transferase V (NA17), paired box protein Pax-3 (PAX3), Androgen receptor, Cyclin B1, v-myc avian myelocytomatosis viral oncogene neuroblastoma derived homolog (MYCN), Ras Homolog Family Member C (RhoC), Tyrosinase-related protein 2 (TRP-2), Cytochrome P450 1B1 (CYP1B1), CCCTC-Binding Factor (Zinc Finger Protein)-Like, Squamous Cell Carcinoma Antigen Recognized By T Cells 3 (SART3), Paired box protein Pax-5 (PAX5), proacrosin binding protein sp32 (OY-TES1), lymphocyte-specific protein tyrosine kinase (LCK), A kinase anchor protein 4 (AKAP-4), synovial sarcoma, X breakpoint 2 (SSX2), Receptor for Advanced Glycation Endproducts (RAGE-1), renal ubiquitous 1 (RU1), renal ubiquitous 2 (RU2), legumain, human papilloma virus E6 (HPV E6), human papilloma virus E7 (HPV E7), intestinal carboxyl esterase, heat shock protein 70-2 mutated (mut hsp70-2), CD79a, CD79b, CD72, Leukocyte-associated immunoglobulin-like receptor 1 (LAIR1), Fc fragment of IgA receptor (FCAR or CD89), Leukocyte immunoglobulin-like receptor subfamily A member 2 (LILRA2), CD300 molecule-like family member f (CD300LF), C-type lectin domain family 12 member A (CLEC12A), bone marrow stromal cell antigen 2 (BST2), EGF-like module-containing mucin-like hormone receptor-like 2 (EMR2), lymphocyte antigen 75 (LY75), Glypican-3 (GPC3), Fc receptor-like 5 (FCRL5), MUC16, 5T4, 8H9, αvβ0 integrin, αvβ6 integrin, alphafetoprotein (AFP), B7-H6, ca-125, CA9, CD44, CD44v7/8, CD52, E-cadherin, EMA (epithelial membrane antigen), epithelial glycoprotein-2 (EGP-2), epithelial glycoprotein-40 (EGP-40), ErbB4, epithelial tumor antigen (ETA), folate binding protein (FBP), kinase insert domain receptor (KDR), k-light chain, L1 cell adhesion molecule, MUC18, NKG2D, oncofetal antigen (h5T4), tumor/testis-antigen 1B, GAGE, GAGE-1, BAGE, SCP-1, CTZ9, SAGE, CAGE, CT10, MART-1, immunoglobulin lambda-like polypeptide 1 (IGLL1), Hepatitis B Surface Antigen Binding Protein (HBsAg), viral capsid antigen (VCA), early antigen (EA), EBV nuclear antigen (EBNA), HHV-6 p41 early antigen, HHV-6B U94 latent antigen, HHV-6B p98 late antigen, cytomegalovirus (CMV) antigen, large T antigen, small T antigen, adenovirus antigen, respiratory syncytial virus (RSV) antigen, haemagglutinin (HA), neuraminidase (NA), parainfluenza type 1 antigen, parainfluenza type 2 antigen, parainfluenza type 3 antigen, parainfluenza type 4 antigen, Human Metapneumovirus (HMPV) antigen, hepatitis C virus (HCV) core antigen, HIV p24 antigen, human T-cell lympotrophic virus (HTLV-1) antigen, Merkel cell polyoma virus small T antigen, Merkel cell polyoma virus large T antigen, and Kaposi sarcoma-associated herpesvirus (KSHV) lytic nuclear antigen and KSHV latent nuclear antigen.

Hinge/Spacer Domain

In some embodiments, a CAR of the instant disclosure comprises a hinge or spacer domain. In some embodiments, the hinge/spacer domain may comprise a truncated hinge/spacer domain (THD) the THD domain is a truncated version of a complete hinge/spacer domain ("CHD"). In some embodiments, an extracellular domain is from or derived from (e.g., comprises all or a fragment of) ErbB2, glycophorin A (GpA), CD2, CD3 delta, CD3 epsilon, CD3 gamma, CD4, CD7, CD8a, CD8[T CD1 la (IT GAL), CD1 lb (IT GAM), CD1 lc (ITGAX), CD1 ld (IT GAD), CD18 (ITGB2), CD19 (B4), CD27 (TNFRSF7), CD28, CD28T, CD29 (ITGB1), CD30 (TNFRSF8), CD40 (TNFRSF5), CD48 (SLAMF2), CD49a (ITGA1), CD49d (ITGA4), CD49f (ITGA6), CD66a (CEACAM1), CD66b (CEACAM8), CD66c (CEACAM6), CD66d (CEACAM3), CD66e (CEACAM5), CD69 (CLEC2), CD79A (B-cell antigen receptor complex-associated alpha chain), CD79B (B-cell antigen receptor complex-associated beta chain), CD84 (SLAMF5), CD96 (Tactile), CD100 (SEMA4D), CD103 (ITGAE), CD134 (0X40), CD137 (4-IBB), CD150 (SLAMF1), CD158A (KIR2DL1), CD158B1 (KIR2DL2), CD158B2 (KIR2DL3), CD158C (KIR3DP1), CD158D (KIRDL4), CD158F1 (KIR2DL5A), CD158F2 (KIR2DL5B), CD158K (KIR3DL2), CD160 (BY55), CD162 (SELPLG), CD226 (DNAM1), CD229 (SLAMF3), CD244 (SLAMF4), CD247 (CD3-zeta), CD258 (LIGHT), CD268 (BAFFR), CD270 (TNFSF14), CD272 (BTLA), CD276 (B7-H3), CD279 (PD-1), CD314 (NKG2D), CD319 (SLAMF7), CD335 (NK-p46), CD336 (NK-p44), CD337 (NK-p30), CD352 (SLAMF6), CD353 (SLAMF8), CD355 (CRT AM), CD357 (TNFRSF18), inducible T cell co-stimulator (ICOS), LFA-1 (CD1 la/CD18), NKG2C, DAP-10, ICAM-1, NKp80 (KLRF1), IL-2R beta, IL-2R gamma, IL-7R alpha, LFA-1, SLAMF9, LAT, GADS (GrpL), SLP-76 (LCβ2), PAG1/CBP, a CD83 ligand, Fc gamma receptor, MHC class 1 molecule, MHC class 2 molecule, a TNF receptor protein, an immunoglobulin protein, a cytokine receptor, an integrin, activating NK cell receptors, a Toll ligand receptor, and fragments or combinations thereof. A hinge or spacer domain may be derived either from a natural or from a synthetic source.

In some embodiments, a hinge or spacer domain is positioned between an antigen binding molecule (e.g., an scFv) and a transmembrane domain. In this orientation, the hinge/spacer domain provides distance between the antigen binding molecule and the surface of a cell membrane on which the CAR is expressed. In some embodiments, a hinge or spacer domain is from or derived from an immunoglobulin. In some embodiments, a hinge or spacer domain is selected from the hinge/spacer regions of IgG1, IgG2, IgG3, IgG4, IgA, IgD, IgE, and IgM, or a fragment thereof. In some embodiments, a hinge or spacer domain comprises, is from, or is derived from the hinge/spacer region of CD8 alpha. In some embodiments, a hinge or spacer domain comprises, is from, or is derived from the hinge/spacer region of CD28. In some embodiments, a hinge or spacer domain comprises a fragment of the hinge/spacer region of CD8 alpha or a fragment of the hinge/spacer region of CD28, wherein the fragment is anything less than the whole hinge/spacer region. In some embodiments, the fragment of the CD8 alpha hinge/spacer region or the fragment of the CD28 hinge/spacer region comprises an amino acid sequence that excludes at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, or at least 20 amino acids at the N-terminus or C-Terminus, or both, of the CD8 alpha hinge/spacer region, or of the CD28 hinge/spacer region.

Transmembrane Domain

The CAR of the present disclosure may further comprise a transmembrane domain and/or an intracellular signaling domain. The transmembrane domain may be designed to be fused to the extracellular domain of the CAR. It may similarly be fused to the intracellular domain of the CAR. In some embodiments, the transmembrane domain that naturally is associated with one of the domains in a CAR is used. In some instances, the transmembrane domain may be selected or modified (e.g., by an amino acid substitution) to avoid binding of such domains to the transmembrane domains of the same or different surface membrane proteins to minimize interactions with other members of the receptor complex. The transmembrane domain may be derived either from a natural or from a synthetic source. Where the source is natural, the domain may be derived from any membrane-bound or transmembrane protein.

Transmembrane regions may be derived from (i.e., comprise) a receptor tyrosine kinase (e.g., ErbB2), glycophorin A (GpA), 4-1BB/CD137, activating NK cell receptors, an Immunoglobulin protein, B7-H3, BAFFR, BFAME (SEAMF8), BTEA, CD100 (SEMA4D), CD103, CD160 (BY55), CD 18, CD 19, CD 19a, CD2, CD247, CD27, CD276 (B7-H3), CD28, CD29, CD3 delta, CD3 epsilon, CD3 gamma, CD30, CD4, CD40, CD49a, CD49D, CD49f, CD69, CD7, CD84, CD8alpha, CD8beta, CD96 (Tactile), CD1 la, CD1 lb, CD1 lc, CD1 ld, CDS, CEACAM1, CRT AM, cytokine receptor, DAP-10, DNAM1 (CD226), Fc gamma receptor, GADS, GITR, HVEM (EIGHTR), IA4, ICAM-1, ICAM-1, Ig alpha (CD79a), IE-2R beta, IE-2R gamma, IE-7R alpha, inducible T cell costimulator (ICOS), integrins, ITGA4, ITGA4, ITGA6, IT GAD, ITGAE, ITGAE, IT GAM, ITGAX, ITGB2, ITGB7, ITGB1, KIRDS2, EAT, LFA-1, LFA-1, a ligand that specifically binds with CD83, LIGHT, LIGHT, LTBR, Ly9 (CD229), lymphocyte function-associated antigen-1 (LFA-1; CD1-1a/CD18), MHC class 1 molecule, NKG2C, NKG2D, NKp30, NKp44, NKp46, NKp80 (KLRF1), OX-40, PAG/Cbp, programmed death-1 (PD-1), PSGL1, SELPLG (CD162), Signaling Lymphocytic Activation Molecules (SLAM proteins), SLAM (SLAMF1; CD150; IPO-3), SLAMF4 (CD244; 2B4), SLAMF6 (NTB-A; Ly108), SLAMF7, SLP-76, TNF receptor proteins, TNFR2, TNFSF14, a Toll ligand receptor, TRANCE/RANKL, VLA1, or VLA-6, or a fragment, truncation, or a combination thereof.

In some embodiments, a receptor tyrosine kinase may be derived from (e.g., comprise) Insulin receptor (InsR), Insulin-like growth factor I receptor (IGF1R), Insulin receptor-related receptor (IRR), platelet derived growth factor receptor alpha (PDGFRa), platelet derived growth factor receptor beta (PDGFRfi). KIT proto-oncogene receptor tyrosine kinase (Kit), colony stimulating factor 1 receptor (CSFR), fms related tyrosine kinase 3 (FLT3), fms related tyrosine kinase 1 (VEGFR-1), kinase insert domain receptor (VEGFR-2), fms related tyrosine kinase 4 (VEGFR-3), fibroblast growth factor receptor 1 (FGFR1), fibroblast growth factor receptor 2 (FGFR2), fibroblast growth factor receptor 3 (FGFR3), fibroblast growth factor receptor 4 (FGFR4), protein tyrosine kinase 7 (CCK4), neurotrophic receptor tyrosine kinase 1 (trkA), neurotrophic receptor tyrosine kinase 2 (trkB), neurotrophic receptor tyrosine kinase 3 (trkC), receptor tyrosine kinase like orphan receptor 1 (ROR1), receptor tyrosine kinase like orphan receptor 2 (ROR2), muscle associated receptor tyrosine kinase (MuSK), MET proto-oncogene, receptor tyrosine kinase (MET), macrophage stimulating 1 receptor (Ron), AXL receptor tyrosine kinase (Axl), TYR03 protein tyrosine kinase (Tyro3), MER proto-oncogene, tyrosine kinase (Mer), tyrosine kinase with immunoglobulin like and EGF like domains 1 (TIE1), TEK receptor tyrosine kinase (TIE2), EPH receptor A1 (EphA1), EPH receptor A2 (EphA2), (EPH receptor A3) EphA3, EPH receptor A4 (EphA4), EPH receptor A5 (EphA5), EPH receptor A6 (EphA6), EPH receptor A7 (EphA7), EPH receptor A8 (EphA8), EPH receptor A10 (EphA10), EPH receptor B1 (EphB1), EPH receptor B2 (EphB2), EPH receptor B3 (EphB3), EPH receptor B4 (EphB4), EPH receptor B6 (EphB6), ret proto oncogene (Ret), receptor-like tyrosine kinase (RYK), discoidin domain receptor tyrosine kinase 1 (DDR1), discoidin domain receptor tyrosine kinase 2 (DDR2), c-ros oncogene 1, receptor tyrosine kinase (ROS), apoptosis associated tyrosine kinase (Lmr1), lemur tyrosine kinase 2 (Lmr2), lemur tyrosine kinase 3 (Lmr3), leukocyte receptor tyrosine kinase (LTK), ALK receptor tyrosine kinase (ALK), or serine/threonine/tyrosine kinase 1 (STYK1).

Costimulatory Domain

In certain embodiments, the CAR comprises a costimulatory domain. In some embodiments, the costimulatory domain comprises 4-1BB (CD137), CD28, or both, and/or an intracellular T cell signaling domain. In a preferred embodiment, the costimulatory domain is human CD28, human 4-1BB, or both, and the intracellular T cell signaling domain is human CD3 zeta (ξ). The 4-1BB, CD28, CD3 zeta, or any of these may comprise less than the whole 4-1BB, CD28 or CD3 zeta, respectively. Chimeric antigen receptors may incorporate costimulatory (signaling) domains to increase their potency. See U.S. Pat. Nos. 7,741,465, and 6,319,494, as well as Krause et al. and Finney et al. (supra), Song et al., Blood 119:696-706 (2012); Kalos et al., Sci Transl. Med. 3:95 (2011); Porter et al., N. Engl. J. Med. 365:725-33 (2011), and Gross et al., Amur. Rev. Pharmacol. Toxicol. 56:59-83 (2016).

In some embodiments, a costimulatory domain comprises the amino acid sequence of SEQ ID NO: 318 or 320.

Intracellular Signaling Domain

The intracellular (signaling) domain of the engineered T cells disclosed herein may provide signaling to an activating domain, which then activates at least one of the normal effector functions of the immune cell. Effector function of a T cell, for example, may be cytolytic activity or helper activity including the secretion of cytokines.

In some embodiments, suitable intracellular signaling domains include (e.g., comprise), but are not limited to 4-1BB/CD137, activating NK cell receptors, an Immunoglobulin protein, B7-H3, BAFFR, BLAME (SLAMF8), BTLA, CD100 (SEMA4D), CD103, CD160 (BY55), CD18, CD19, CD 19a, CD2, CD247, CD27, CD276 (B7-H3), CD28, CD29, CD3 delta, CD3 epsilon, CD3 gamma, CD30, CD4, CD40, CD49a, CD49D, CD49f, CD69, CD7, CD84, CD8alpha, CD8beta, CD96 (Tactile), CD1 la, CD1 lb, CD1 lc, CD1 Id, CDS, CEACAM1, CRT AM, cytokine receptor, DAP-10, DNAM1 (CD226), Fc gamma receptor, GADS, GITR, HVEM (LIGHTR), IA4, ICAM-1, ICAM-1, Ig alpha (CD79a), IL-2R beta, IL-2R gamma, IL-7R alpha, inducible T cell costimulator (ICOS), integrins, ITGA4, ITGA4, ITGA6, IT GAD, ITGAE, ITGAL, IT GAM, ITGAX, ITGB2, ITGB7, ITGB1, KIRDS2, LAT, LFA-1, LFA-1, ligand that specifically binds with CD83, LIGHT, LIGHT, LTBR, Ly9 (CD229), Ly108), lymphocyte function-associated antigen-1 (LFA-1; CD1-1a/CD18), MHC class 1 molecule, NKG2C, NKG2D, NKp30, NKp44, NKp46, NKp80 (KLRF1), OX-40, PAG/Cbp, programmed death-1 (PD-1), PSGL1, SELPLG (CD162), Signaling Lymphocytic Activation Molecules (SLAM proteins), SLAM (SLAMF1; CD150; IPO-3), SLAMF4 (CD244; 2B4), SLAMF6 (NTB-A, SLAMF7, SLP-76, TNF receptor proteins, TNFR2, TNFSF14, a Toll ligand receptor, TRANCE/RANKL, VLA1, or VLA-6, or a fragment, truncation, or a combination thereof.

CD3 is an element of the T cell receptor on native T cells, and has been shown to be an important intracellular activating element in CARs. In some embodiments, the CD3 is CD3 zeta. In some embodiments, the activating domain comprises an amino acid sequence at least about 60%, at least about 65%, at least about 70%, at least about 75%, at least about 80%, at least about 85%, at least about 90%, at least about 95%, at least about 96%, at least about 97%, at least about 98%, at least about 99%, or about 100% identical to the polypeptide sequence of SEQ ID NO: 319.

9. Production of Polynucleotides

The vectors provided herein can be made using standard techniques of molecular biology. For example, the various elements of the vectors provided herein can be obtained using recombinant methods, such as by screening cDNA and genomic libraries from cells, or by deriving the polynucleotides from a vector known to include the same.

The various elements of the vectors provided herein can also be produced synthetically, rather than cloned, based on the known sequences. The complete sequence can be assembled from overlapping oligonucleotides prepared by standard methods and assembled into the complete sequence. See, e.g., Edge, Nature (1981) 292:756; Nambair et al., Science (1984) 223: 1299; and Jay et al., J. Biol. Chem. (1984) 259:631 1.

Thus, particular nucleotide sequences can be obtained from vectors harboring the desired sequences or synthesized completely, or in part, using various oligonucleotide synthesis techniques known in the art, such as site-directed mutagenesis and polymerase chain reaction (PCR) techniques where appropriate. One method of obtaining nucleotide sequences encoding the desired vector elements is by annealing complementary sets of overlapping synthetic oligonucleotides produced in a conventional, automated polynucleotide synthesizer, followed by ligation with an appropriate DNA ligase and amplification of the ligated nucleotide sequence via PCR. See, e.g., Jayaraman et al., Proc. Natl. Acad. Sci. USA (1991) 88:4084-4088. Additionally, oligonucleotide-directed synthesis (Jones et al., Nature (1986) 54:75-82), oligonucleotide directed mutagenesis of preexisting nucleotide regions (Riechmann et al., Nature (1988) 332:323-327 and Verhoeyen et al., Science (1988) 239: 1534-1536), and enzymatic filling-in of gapped oligonucleotides using T4 DNA polymerase (Queen et al., Proc. Natl. Acad. Sci. USA (1989) 86: 10029-10033) can be used.

The precursor RNA provided herein can be generated by incubating a vector provided herein under conditions permissive of transcription of the precursor RNA encoded by the vector. For example, in some embodiments a precursor RNA is synthesized by incubating a vector provided herein that comprises an RNA polymerase promoter upstream of its 5' duplex forming region and/or expression sequence with a compatible RNA polymerase enzyme under conditions permissive of in vitro transcription. In some embodiments, the vector is incubated inside of a cell by a bacteriophage RNA polymerase or in the nucleus of a cell by host RNA polymerase II.

In certain embodiments, provided herein is a method of generating precursor RNA by performing in vitro transcription using a vector provided herein as a template (e.g., a vector provided herein with a RNA polymerase promoter positioned upstream of the 5' homology region).

In certain embodiments, the resulting precursor RNA can be used to generate circular RNA (e.g., a circular RNA polynucleotide provided herein) by incubating it in the presence of magnesium ions and guanosine nucleotide or nucleoside at a temperature at which RNA circularization occurs (e.g., between 20° C. and 60° C.).

Thus, in certain embodiments provided herein is a method of making circular RNA. In certain embodiments, the method comprises synthesizing precursor RNA by transcription (e.g., run-off transcription) using a vector provided herein (e.g., a vector comprising, in the following order, a 5' homology region, a 3' group I intron fragment, a first spacer, an Internal Ribosome Entry Site (IRES), an expression sequence, a second spacer, a 5' group I intron fragment, and a 3' homology region) as a template, and incubating the resulting precursor RNA in the presence of divalent cations (e.g., magnesium ions) and GTP such that it circularizes to form circular RNA. In some embodiments, an inventive precursor RNA is capable of circularizing in the absence of magnesium ions and GTP and/or without the step of incubation with magnesium ions and GTP. In some embodiments, transcription is carried out in the presence of an excess of GMP.

In some embodiments, a composition comprising circular RNA has been purified. Circular RNA may be purified by any known method commonly used in the art, such as column chromatography, gel filtration chromatography, and size exclusion chromatography. In some embodiments, purification comprises one or more of the following steps: phosphatase treatment, HPLC size exclusion purification, and RNase R digestion. In some embodiments, purification comprises the following steps in order: RNase R digestion, phosphatase treatment, and HPLC size exclusion purification. In some embodiments, purification comprises reverse phase HPLC. In some embodiments, a purified composition contains less double stranded RNA, DNA splints, triphosphorylated RNA, phosphatase proteins, protein ligases, capping enzymes and/or nicked RNA than unpurified RNA. In some embodiments, a purified composition is less immunogenic than an unpurified composition. In some embodiments, immune cells exposed to a purified composition produce less IFN-$\beta$1, RIG-I, IL-2, IL-6, IFN$\gamma$, and/or TNF$\alpha$ than immune cells exposed to an unpurified composition.

10. Nanoparticles

In certain aspects, provided herein are pharmaceutical compositions comprising the circular RNA provided herein. In certain embodiments, such pharmaceutical compositions are formulated with nanoparticles to facilitate delivery.

In certain embodiments, the circular RNA provided herein may be delivered and/or targeted to a cell in a transfer vehicle, e.g., a nanoparticle, or a composition comprising a nanoparticle. In some embodiments, the circular RNA may also be delivered to a subject in a transfer vehicle or a composition comprising a transfer vehicle. In some embodiments, the transfer vehicle is a nanoparticle. In some embodiments, the nanoparticle is a lipid nanoparticle, a non-lipid polymeric core-shell nanoparticle, or a biodegradable nanoparticle. In some embodiments, the transfer vehicle comprises one or more cationic lipids, non-cationic lipids, ionizable lipids, PEG-modified lipids, polyglutamic acid lipids, Hyaluronic acid lipids, poly $\beta$-amino esters, poly beta amino peptides, or positively charged peptides.

In one embodiment, the transfer vehicle may be selected and/or prepared to optimize delivery of the circRNA to a target cell. For example, if the target cell is a hepatocyte the properties of the transfer vehicle (e.g., size, charge and/or pH) may be optimized to effectively deliver such transfer vehicle to the target cell, reduce immune clearance and/or promote retention in that target cell. Alternatively, if the target cell is the central nervous system (e.g., circRNA administered for the treatment of neurodegenerative diseases may specifically target brain or spinal tissue), selection and preparation of the transfer vehicle must consider penetration of; and retention within the blood brain barrier and/or the use of alternate means of directly delivering such transfer vehicle to such target cell. In one embodiment, the compositions of the present invention may be combined with agents that facilitate the transfer of exogenous circRNA (e.g., agents which disrupt or improve the permeability of the blood brain barrier and thereby enhance the transfer of exogenous circRNA to the target cells).

The use of transfer vehicles to facilitate the delivery of nucleic acids to target cells is contemplated by the present invention. Liposomes (e.g., liposomal lipid nanoparticles) are generally useful in a variety of applications in research, industry, and medicine, particularly for their use as transfer vehicles of diagnostic or therapeutic compounds in vivo (Lasic, Trends Biotechnol., 16: 307-321, 1998; Drummond et al., Pharmacol. Rev., 51: 691-743, 1999) and are usually characterized as microscopic vesicles having an interior aqueous space sequestered from an outer medium by a membrane of one or more bilayers. Bilayer membranes of liposomes are typically formed by amphiphilic molecules, such as lipids of synthetic or natural origin that comprise spatially separated hydrophilic and hydrophobic domains (Lasic, Trends Biotechnol., 16: 307-321, 1998). Bilayer membranes of the liposomes can also be formed by amphiphilic polymers and surfactants (e.g., polymerosomes, niosomes, etc.).

In the context of the present invention, a transfer vehicle typically serves to transport the circRNA to the target cell. For the purposes of the present invention, the transfer vehicles are prepared to contain the desired nucleic acids. The process of incorporation of a desired entity (e.g., a nucleic acid) into a liposome is often referred to as loading (Lasic, et al., FEBS Lett., 312: 255-258, 1992). The liposome-incorporated nucleic acids may be completely or partially located in the interior space of the liposome, within the bilayer membrane of the liposome, or associated with the exterior surface of the liposome membrane. The purpose of incorporating a circRNA into a transfer vehicle, such as a liposome, is often to protect the nucleic acid from an environment which may contain enzymes or chemicals that degrade nucleic acids and/or systems or receptors that cause the rapid excretion of the nucleic acids. Accordingly, in an embodiment of the present invention, the selected transfer vehicle is capable of enhancing the stability of the circRNA contained therein. The liposome can allow the encapsulated circRNA to reach the target cell and/or may allow the encapsulated circRNA to reach the target cell, or alternatively limit the delivery of such circRNA to other sites or cells where the presence of the administered circRNA may be useless or undesirable. Furthermore, incorporating the circRNA into a transfer vehicle, such as for example, a cationic liposome, also facilitates the delivery of such circRNA into a target cell.

Ideally, transfer vehicles are prepared to encapsulate one or more desired circRNA such that the compositions demonstrate a high transfection efficiency and enhanced stability. While liposomes can facilitate introduction of nucleic acids into target cells, the addition of polycations (e.g., poly L-lysine and protamine), as a copolymer can facilitate, and in some instances markedly enhance the transfection efficiency of several types of cationic liposomes by 2-28 fold in a number of cell lines both in vitro and in vivo. (See N J. Caplen, et al., Gene Ther. 1995; 2: 603; S. Li, et al., Gene Ther. 1997; 4, 891.)

In an embodiment of the present invention, the transfer vehicle is formulated as a lipid nanoparticle. In an embodiment, the lipid nanoparticles are formulated to deliver one or more circRNA to one or more target cells. Examples of suitable lipids include the phosphatidyl compounds (e.g., phosphatidylglycerol, phosphatidylcholine, phosphatidylserine, phosphatidylethanolamine, sphingolipids, cerebrosides, and gangliosides). Also contemplated is the use of polymers as transfer vehicles, whether alone or in combination with other transfer vehicles. Suitable polymers may include, for example, polyacrylates, polyalkycyanoacrylates, polylactide, polylactide-polyglycolide copolymers, polycaprolactones, dextran, albumin, gelatin, alginate, collagen, chitosan, cyclodextrins, dendrimers and polyethylenimine. In an embodiment, the transfer vehicle is formulated as a lipid as described in U.S. patent application Ser. No. 16/065,067, incorporated herein in its entirety. In one embodiment, the transfer vehicle is selected based upon its ability to facilitate the transfection of a circRNA to a target cell.

The invention contemplates the use of lipid nanoparticles as transfer vehicles comprising a cationic lipid to encapsulate and/or enhance the delivery of circRNA into the target cell that will act as a depot for protein production. The contemplated lipid nanoparticles may be prepared by including multi-component lipid mixtures of varying ratios employing one or more cationic lipids, non-cationic lipids and PEG-modified lipids. Several cationic lipids have been described in the literature, many of which are commercially available.

Suitable cationic lipids for use in the compositions and methods of the invention include those described in international patent publication WO 2010/053572 and/or U.S. patent application Ser. No. 15/809,680, e.g., C12-200. In certain embodiments, the compositions and methods of the invention employ a lipid nanoparticles comprising an ionizable cationic lipid described in U.S. provisional patent application 61/617,468, filed Mar. 29, 2012 (incorporated herein by reference), such as, e.g, (15Z,18Z)—N,N-dimethyl-6-(9Z,12Z)-octadeca-9,12-dien-1-yl)tetracosa-15,18-dien-1-amine (HGT5000), (15Z,18Z)—N,N-dimethyl-6-((9Z,12Z)-octadeca-9,12-dien-1-yl)tetracosa-4,15,18-trien-1-amine (HGT5001), and (15Z,18Z)—N,N-dimethyl-6-((9Z,12Z)-octadeca-9,12-dien-1-yl)tetracosa-5,15,18-trien-1-amine (HGT5002).

In some embodiments, the cationic lipid N-[1-(2,3-dioleyloxy)propyl]-N,N,N-trimethylammonium chloride or "DOTMA" is used. (Felgner et al. (Proc. Nat'l Acad. Sci. 84, 7413 (1987); U.S. Pat. No. 4,897,355). DOTMA can be formulated alone or can be combined with the neutral lipid, dioleoylphosphatidyl-ethanolamine or "DOPE" or other cationic or non-cationic lipids into a transfer vehicle or a lipid nanoparticle, and such liposomes can be used to enhance the delivery of nucleic acids into target cells. Other suitable cationic lipids include, for example, 5-carboxyspermylglycinedioctadecylamide or "DOGS," 2,3-dioleyloxy-N-[2 (spermine-carboxamido)ethyl]-N,N-dimethyl-1-propanaminium or "DOSPA" (Behr et al. Proc. Nat.'l Acad. Sci. 86, 6982 (1989); U.S. Pat. Nos. 5,171,678; 5,334,761), 1,2-Dioleoyl-3-Dimethylammonium-Propane or "DODAP," 1,2-Dioleoyl-3-Trimethylammonium-Propane or "DOTAP." Contemplated cationic lipids also include 1,2-distearyloxy-N,N-dimethyl-3-aminopropane or "DSDMA", 1,2-dioleyloxy-N,N-dimethyl-3-aminopropane or "DODMA," 1,2-dilinoleyloxy-N,N-dimethyl-3-aminopropane or "DLinDMA," 1,2-dilinolenyloxy-N,N-dimethyl-3-aminopropane or "DLenDMA," N-dioleyl-N,N-dimethylammonium chloride or "DODAC," N,N-distearyl-N,N-dimethylammonium bromide or "DDAB," N-(1,2-dimyristyloxyprop-3-yl)-N,N-dimethyl-N-hydroxyethyl ammonium bromide or "DMRIE," 3-dimethylamino-2-(cholest-5-en-3-beta-oxybutan-4-oxy)-1-(cis,cis-9,12-octadecadienoxy)propane or "CLinDMA," 2-[5'-(cholest-5-en-3-beta-oxy)-3'-oxapentoxy)-3-dimethy 1-1-(cis,cis-9', 1-2'-octadecadienoxy)propane or "CpLinDMA," N,N-dimethyl-3,4-dioleyloxybenzylamine or "DMOBA," 1,2-N,N'-dioleylcarbamyl-3-dimethylaminopropane or "DOcarbDAP," 2,3-Dilinoleoyloxy-N,N-dimethylpropylamine or "DLinDAP," 1,2-N,N'-Dilinoleylcarbamyl-3-dimethylaminopropane or "DLincarbDAP," 1,2-Dilinoleoylcarbamyl-3-dimethylaminopropane or "DLinCDAP," 2,2-dilinoleyl-4-dimethylaminomethyl-[1,3]-dioxolane or "DLin-K-DMA," 2,2-dilinoleyl-4-dimethylaminoethyl-[1,3]-dioxolane or "DLin-K-XTC2-DMA," and 2-(2,2-di((9Z,12Z)-octadeca-9,12-dien-1-yl)-1,3-dioxolan-4-yl)-N,N-dimethylethanamine (DLin-KC2-DMA)) (See, WO 2010/042877; Semple et al., Nature Biotech. 28:172-176 (2010)), or mixtures thereof. (Heyes, J., et al., J Controlled Release 107: 276-287 (2005); Morrissey, D V., et al., Nat. Biotechnol. 23(8): 1003-1007 (2005); PCT Publication WO2005/121348A1).

The use of cholesterol-based cationic lipids is also contemplated by the present invention. Such cholesterol-based cationic lipids can be used, either alone or in combination with other cationic or non-cationic lipids. Suitable cholesterol-based cationic lipids include, for example, GL67, DC-Chol (N,N-dimethyl-N-ethylcarboxamidocholesterol), 1,4-bis(3-N-oleylamino-propyl)piperazine (Gao, et al. Biochem. Biophys. Res. Comm. 179, 280 (1991); Wolf et al. BioTechniques 23, 139 (1997); U.S. Pat. No. 5,744,335), or ICE.

In addition, several reagents are commercially available to enhance transfection efficacy. Suitable examples include LIPOFECTIN (DOTMA:DOPE) (Invitrogen, Carlsbad, CA), LIPOFECTAMINE (DOSPA:DOPE) (Invitrogen), LIPOFECTAMINE2000. (Invitrogen), FUGENE (Promega, Madison, WI), TRANSFECTAM (DOGS) (Promega), and EFFECTENE (Qiagen, Valencia, CA).

Also contemplated are cationic lipids such as the dialkylamino-based, imidazole-based, and guanidinium-based lipids, such as those described in U.S. Pat. No. 10,413,618.

In other embodiments the compositions and methods described herein are directed to lipid nanoparticles comprising one or more cleavable lipids, such as, for example, one or more cationic lipids or compounds that comprise a cleavable disulfide (S—S) functional group (e.g., HGT4001, HGT4002, HGT4003, HGT4004 and HGT4005), as further described in U.S. Provisional Application No. 61/494,745, the entire teachings of which are incorporated herein by reference in their entirety.

The use of polyethylene glycol (PEG)-modified phospholipids and derivatized lipids such as derivatized ceramides (PEG-CER), including N-Octanoyl-Sphingosine-1-[Succinyl(Methoxy Polyethylene Glycol)-2000] (C8 PEG-2000 ceramide) is also contemplated by the present invention, either alone or in combination with other lipids together which comprise the transfer vehicle (e.g., a lipid nanoparticle). Contemplated PEG-modified lipids include, but are not limited to, a polyethylene glycol chain of up to 5 kDa in length covalently attached to a lipid with alkyl chain(s) of C6-C20 length. The addition of such components may prevent complex aggregation and may also provide a means for increasing circulation lifetime and increasing the delivery of the lipid-nucleic acid composition to the target cell, (Klibanov et al. (1990) FEBS Letters, 268 (1): 235-237), or they may be selected to rapidly exchange out of the formulation in vivo (see U.S. Pat. No. 5,885,613). Particularly useful exchangeable lipids are PEG-ceramides having shorter acyl chains (e.g., C14 or C18). The PEG-modified phospholipid and derivatized lipids of the present invention may comprise a molar ratio from about 0% to about 20%, about 0.5% to about 20%, about 1% to about 15%, about 4% to about 10%, or about 2% of the total lipid present in the transfer vehicle.

The present invention also contemplates the use of non-cationic lipids including those described in U.S. patent application Ser. No. 15/809,680. Non-cationic lipids include, but are not limited to, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoylphosphatidylethanolamine (DOPE), palmitoyloleoylphosphatidylcholine (POPC), palmitoyloleoyl-phosphatidylethanolamine (POPE), dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidyl-ethanolamine (DSPE), 16-O-monomethyl PE, 16-O-dimethyl PE, 18-1-trans PE, 1-stearoyl-2-oleoyl-phosphatidyethanolamine (SOPE), cholesterol, or a mixture thereof. Such non-cationic lipids may be used alone or in combination with other excipients, for example, cationic lipids. When used in combination with a cationic lipid, the non-cationic lipid may comprise a molar ratio of 5% to about 90%, or about 10% to about 70% of the total lipid present in the transfer vehicle.

The transfer vehicle (e.g., a lipid nanoparticle) may be prepared by combining multiple lipid and/or polymer components. For example, a transfer vehicle may be prepared using C12-200, DOPE, cholesterol, DMG-PEG2K at a molar ratio of 40:30:25:5, or DODAP, DOPE, cholesterol, DMG-PEG2K at a molar ratio of 18:56:20:6, or HGT5000, DOPE, cholesterol, DMG-PEG2K at a molar ratio of 40:20:35:5, or HGT5001, DOPE, cholesterol, DMG-PEG2K at a molar ratio of 40:20:35:5. The selection of cationic lipids, non-cationic lipids and/or PEG-modified lipids which comprise the lipid nanoparticle, as well as the relative molar ratio of such lipids to each other, is based upon the characteristics of the selected lipid(s), the nature of the intended target cells, the characteristics of the circRNA to be delivered. Additional considerations include, for example, the saturation of the alkyl chain, as well as the size, charge, pH, pKa, fusogenicity and toxicity of the selected lipid(s). Thus, the molar ratios may be adjusted accordingly. For example, in some embodiments, the percentage of cationic lipid in the lipid nanoparticle may be greater than 10%, greater than 20%, greater than 30%, greater than 40%, greater than 50%, greater than 60%, or greater than 70%. The percentage of non-cationic lipid in the lipid nanoparticle may be greater than 5%, greater than 10%, greater than 20%, greater than 30%, or greater than 40%. The percentage of cholesterol in the lipid nanoparticle may be greater than 10%, greater than 20%, greater than 30%, or greater than 40%. The percentage of PEG-modified lipid in the lipid nanoparticle may be greater than 1%, greater than 2%, greater than 5%, greater than 10%, or greater than 20%.

The transfer vehicles for use in the compositions of the invention can be prepared by various techniques which are presently known in the art. Multi-lamellar vesicles (MLV) may be prepared using conventional techniques, for example, by depositing a selected lipid on the inside wall of a suitable container or vessel, dissolving the lipid in an appropriate solvent, and then evaporating the solvent to leave a thin film on the inside of the vessel or by spray-drying. An aqueous phase may then be added to the vessel with a vortexing motion which results in the formation of MLVs. Uni-lamellar vesicles (ULV) can then be formed by homogenization, sonication or extrusion of the multi-lamellar vesicles. In addition, ULV can be formed by detergent removal techniques.

In certain embodiments of this invention, the compositions of the present invention comprise a transfer vehicle wherein the circRNA is associated on both the surface of the transfer vehicle and encapsulated within the same transfer vehicle. For example, during preparation of the compositions of the present invention, cationic transfer vehicles may associate with the circRNA through electrostatic interactions.

In certain embodiments, the compositions of the invention may be loaded with diagnostic radionuclide, fluorescent materials or other materials that are detectable in both in vitro and in vivo applications. For example, suitable diagnostic materials for use in the present invention may include Rhodamine-dioleoylphosphatidylethanolamine (Rh-PE), Green Fluorescent Protein circRNA (GFP circRNA), *Renilla* Luciferase circRNA and Firefly Luciferase circRNA.

In some embodiments, selection of the appropriate size of a transfer vehicle takes into consideration the site of the target cell or tissue and to some extent the application for which the liposome is being made. In some embodiments, it may be desirable to limit transfection of the circRNA to certain cells or tissues. For example, to target hepatocytes a transfer vehicle may be sized such that its dimensions are smaller than the fenestrations of the endothelial layer lining hepatic sinusoids in the liver. Accordingly, the appropriately-sized transfer vehicle can readily penetrate such endothelial fenestrations to reach the target hepatocytes. Alternatively, a transfer vehicle may be sized such that the dimensions of the liposome are of a sufficient diameter to limit or expressly avoid distribution into certain cells or tissues. For example, a transfer vehicle may be sized such that its dimensions are larger than the fenestrations of the endothelial layer lining hepatic sinusoids to thereby limit distribution of the transfer vehicle to hepatocytes. Generally, the size of the transfer vehicle is within the range of about 25 to 250 nm. In some embodiments, the size of the transfer vehicle is less than about 250 nm, 175 nm, 150 nm, 125 nm, 100 nm, 75 nm, 50 nm, 25 nm or 10 nm.

A variety of alternative methods known in the art are available for sizing of a population of transfer vehicles. One such sizing method is described in U.S. Pat. No. 4,737,323, incorporated herein by reference. Sonicating a liposome suspension either by bath or probe sonication produces a progressive size reduction down to small ULV less than about 0.05 microns in diameter. Homogenization is another method that relies on shearing energy to fragment large liposomes into smaller ones. In a typical homogenization procedure, MLV are recirculated through a standard emulsion homogenizer until selected liposome sizes, typically between about 0.1 and 0.5 microns, are observed. The size of the liposomal vesicles may be determined by quasi-electric light scattering (QELS) as described in Bloomfield, Ann. Rev. Biophys. Bioeng 10:421-450 (1981), incorporated herein by reference. Average liposome diameter may be reduced by sonication of formed liposomes. Intermittent sonication cycles may be alternated with QELS assessment to guide efficient liposome synthesis.

Additionally, in certain embodiments, the circular RNA provided herein can be formulated using one or more liposomes, lipoplexes, or lipid nanoparticles. In one embodiment, the circular RNA may be formulated in a lipid nanoparticle such as those described in International Publication No. WO2012170930, herein incorporated by reference in its entirety. In one embodiment, the lipid may be a cleavable lipid such as those described in International Publication No. WO2012170889, herein incorporated by reference in its entirety. In one embodiment, the pharmaceutical compositions of the circular RNA may include at least one of the PEGylated lipids described in International Publication No. 2012099755, herein incorporated by reference. In one embodiment, a lipid nanoparticle formulation may be formulated by the methods described in International Publication Nos. WO2011127255 or WO2008103276, each of which is herein incorporated by reference in their entirety. A lipid nanoparticle may be coated or associated with a co-polymer such as, but not limited to, a block co-polymer, such as a branched polyether-polyamide block copolymer described in International Publication No. WO2013012476, herein incorporated by reference in its entirety. Liposomes, lipoplexes, or lipid nanoparticles may be used to improve the efficacy of circular RNA directed protein production as these formulations may be able to increase cell transfection by the circular RNA, increase the in vivo or in vitro half-life of the circular RNA, and/or allow for controlled release.

In embodiments, a polynucleotide encodes a protein that is made up of subunits that are encoded by more than one gene. For example, the protein may be a heterodimer, wherein each chain or subunit of the protein is encoded by a separate gene. It is possible that more than one circRNA molecule is delivered in the transfer vehicle and each circRNA encodes a separate subunit of the protein. Alternatively, a single circRNA may be engineered to encode more than one subunit (e.g. in the case of a single-chain Fv antibody). In certain embodiments, separate circRNA molecules encoding the individual subunits may be administered in separate transfer vehicles.

The present invention also contemplates the discriminatory targeting of target cells and tissues by both passive and active targeting means. The phenomenon of passive targeting exploits the natural distributions patterns of a transfer vehicle in vivo without relying upon the use of additional excipients or means to enhance recognition of the transfer vehicle by target cells. For example, transfer vehicles which are subject to phagocytosis by the cells of the reticuloendothelial system are likely to accumulate in the liver or spleen, and accordingly, may provide a means to passively direct the delivery of the compositions to such target cells.

Alternatively, the present invention contemplates active targeting, which involves the use of targeting moieties that may be bound (either covalently or non-covalently) to the transfer vehicle to encourage localization of such transfer vehicle at certain target cells or target tissues. For example, targeting may be mediated by the inclusion of one or more endogenous targeting moieties in or on the transfer vehicle to encourage distribution to the target cells or tissues. Recognition of the targeting moiety by the target tissues actively facilitates tissue distribution and cellular uptake of the transfer vehicle and/or its contents in the target cells and tissues (e.g., the inclusion of an apolipoprotein-E targeting ligand in or on the transfer vehicle encourages recognition and binding of the transfer vehicle to endogenous low density lipoprotein receptors expressed by hepatocytes). As provided herein, the composition can comprise a moiety capable of enhancing affinity of the composition to the target cell. Targeting moieties may be linked to the outer bilayer of the lipid particle during formulation or post-formulation. These methods are well known in the art. In addition, some lipid particle formulations may employ fusogenic polymers such as PEAA, hemagglutinin, other lipopeptides (see U.S. patent application Ser. No. 08/835,281, and 60/083,294, which are incorporated herein by reference) and other features useful for in vivo and/or intracellular delivery. In other some embodiments, the compositions of the present invention demonstrate improved transfection efficacies, and/or demonstrate enhanced selectivity towards target cells or tissues of interest. Contemplated therefore are compositions which comprise one or more moieties (e.g., peptides, aptamers, oligonucleotides, a vitamin or other molecules) that are capable of enhancing the affinity of the compositions and their nucleic acid contents for the target cells or tissues. Suitable moieties may optionally be bound or linked to the surface of the transfer vehicle. In some embodiments, the targeting moiety may span the surface of a transfer vehicle or be encapsulated within the transfer vehicle. Suitable moieties and are selected based upon their physical, chemical or biological properties (e.g., selective affinity and/or recognition of target cell surface markers or features). Cell-specific target sites and their corresponding targeting ligand can vary widely. Suitable targeting moieties are selected such that the unique characteristics of a target cell are exploited, thus allowing the composition to discriminate between target and non-target cells. For example, compositions of the invention may include surface markers (e.g., apolipoprotein-B or apolipoprotein-E) that selectively enhance recognition of, or affinity to hepatocytes (e.g., by receptor-mediated recognition of and binding to such surface markers). As an example, the use of galactose as a targeting moiety would be expected to direct the compositions of the present invention to parenchymal hepatocytes, or alternatively the use of mannose containing sugar residues as a targeting ligand would be expected to direct the compositions of the present invention to liver endothelial cells (e.g., mannose containing sugar residues that may bind preferentially to the asialoglycoprotein receptor present in hepatocytes). (See Hillery A M, et al. "Drug Delivery and Targeting: For Pharmacists and Pharmaceutical Scientists" (2002) Taylor & Francis, Inc.) The presentation of such targeting moieties that have been conjugated to moieties present in the transfer vehicle (e.g., a lipid nanoparticle) therefore facilitate recognition and uptake of the compositions of the present invention in target cells and tissues. Examples of suitable targeting moieties include one or more peptides, proteins, aptamers, vitamins and oligonucleotides.

In particular embodiments, a transfer vehicle comprises a targeting moiety. In some embodiments, the targeting moiety mediates receptor-mediated endocytosis selectively into a specific population of cells. In some embodiments, the targeting moiety is capable of binding to a T cell antigen. In some embodiments, the targeting moiety is capable of binding to a NK, NKT, dendritic cell, or macrophage antigen. In some embodiments, the targeting moiety is capable of binding to a protein selected from the group CD3, CD4, CD8, PD-1, 4-1BB, CD5, CD7, C1q, and CD2. In some embodiments, the targeting moiety is an single chain Fv (scFv) fragment, nanobody, peptide, peptide-based macrocycle, minibody, heavy chain variable region, light chain variable region or fragment thereof. In some embodiments, the targeting moiety is selected from anti T-cell receptor motif antibodies, anti T-cell α chain antibodies, anti T-cell β chain antibodies, anti T-cell γ chain antibodies, anti T-cell δ chain antibodies, anti CCR7 antibodies, anti CD3 antibodies, anti CD4 antibodies, anti CD5 antibodies, anti CD7 antibodies, anti CD8 antibodies, anti CD11b antibodies, anti CD11c antibodies, anti CD16 antibodies, anti CD19 antibodies, anti CD20 antibodies, anti CD21 antibodies, anti CD22 antibodies, anti CD25 antibodies, anti CD28 antibodies, anti CD34 antibodies, anti CD35 antibodies, anti CD40 antibodies, anti CD45RA antibodies, anti CD45RO antibodies, anti CD52 antibodies, anti CD56 antibodies, anti CD62L antibodies, anti CD68 antibodies, anti CD80 antibodies, anti CD95 antibodies, anti CD117 antibodies, anti CD127 antibodies, anti CD133 antibodies, anti CD137 (4-1BB) antibodies, anti CD163 antibodies, anti $C_1q$ antibodies, anti F4/80 antibodies, anti IL-4Ra antibodies, anti Sca-1 antibodies, anti CTLA-4 antibodies, anti GITR antibodies anti GARP antibodies, anti LAP antibodies, anti granzyme B antibodies, anti LFA-1 antibodies, anti transferrin receptor antibodies, and fragments thereof.

In some embodiments, circular RNA is formulated according to a process described in U.S. patent application Ser. No. 15/809,680. In some embodiments, the present invention provides a process of encapsulating circular RNA in lipid nanoparticles comprising the steps of forming lipids into pre-formed lipid nanoparticles (i.e., formed in the absence of RNA) and then combining the pre-formed lipid nanoparticles with RNA. In some embodiments, the novel formulation process results in an RNA formulation with higher potency (peptide or protein expression) and higher efficacy (improvement of a biologically relevant endpoint) both in vitro and in vivo with potentially better tolerability as compared to the same RNA formulation prepared without the step of preforming the lipid nanoparticles (e.g., combining the lipids directly with the RNA). In some embodiments, the targeting moiety is a small molecule binder of an ectoenzyme on lymphocytes. Small molecule binders of ectoenzymes include A2A inhibitors CD73 inhibitors, CD39 or adesines receptors A2aR and A2bR. Potential small molecules include AB928.

In some embodiments, transfer vehicles are formulated and/or targeted as described in Shobaki N, Sato Y, Harashima H. Mixing lipids to manipulate the ionization status of lipid nanoparticles for specific tissue targeting. Int J Nanomedicine. 2018; 13:8395-8410. Published 2018 Dec. 10. In some embodiments, a transfer vehicle is made up of 3 lipid types. In some embodiments, a transfer vehicle is made up of 4 lipid types. In some embodiments, a transfer vehicle is made up of 5 lipid types. In some embodiments, a transfer vehicle is made up of 6 lipid types.

For certain cationic lipid nanoparticle formulations of RNA, in order to achieve high encapsulation of RNA, the RNA in buffer (e.g., citrate buffer) has to be heated. In those processes or methods, the heating is required to occur before the formulation process (i.e., heating the separate components) as heating post-formulation (post-formation of nanoparticles) does not increase the encapsulation efficiency of the RNA in the lipid nanoparticles. In contrast, in some embodiments of the processes of the present invention, the order of heating of RNA does not appear to affect the RNA encapsulation percentage. In some embodiments, no heating (i.e. maintaining at ambient temperature) of one or more of the solution comprising the pre-formed lipid nanoparticles, the solution comprising the RNA and the mixed solution comprising the lipid nanoparticle encapsulated RNA is required to occur before or after the formulation process.

RNA may be provided in a solution to be mixed with a lipid solution such that the RNA may be encapsulated in lipid nanoparticles. A suitable RNA solution may be any aqueous solution containing RNA to be encapsulated at various concentrations. For example, a suitable RNA solution may contain an RNA at a concentration of or greater than about 0.01 mg/ml, 0.05 mg/ml, 0.06 mg/ml, 0.07 mg/ml, 0.08 mg/ml, 0.09 mg/ml, 0.1 mg/ml, 0.15 mg/ml, 0.2 mg/ml, 0.3 mg/ml, 0.4 mg/ml, 0.5 mg/ml, 0.6 mg/ml, 0.7 mg/ml, 0.8 mg/ml, 0.9 mg/ml, or 1.0 mg/ml. In some embodiments, a suitable RNA solution may contain an RNA at a concentration in a range from about 0.01-1.0 mg/ml, 0.01-0.9 mg/ml, 0.01-0.8 mg/ml, 0.01-0.7 mg/ml, 0.01-0.6 mg/ml, 0.01-0.5 mg/ml, 0.01-0.4 mg/ml, 0.01-0.3 mg/ml, 0.01-0.2 mg/ml, 0.01-0.1 mg/ml, 0.05-1.0 mg/ml, 0.05-0.9 mg/ml, 0.05-0.8 mg/ml, 0.05-0.7 mg/ml, 0.05-0.6 mg/ml, 0.05-0.5 mg/ml, 0.05-0.4 mg/ml, 0.05-0.3 mg/ml, 0.05-0.2 mg/ml, 0.05-0.1 mg/ml, 0.1-1.0 mg/ml, 0.2-0.9 mg/ml, 0.3-0.8 mg/ml, 0.4-0.7 mg/ml, or 0.5-0.6 mg/ml.

Typically, a suitable RNA solution may also contain a buffering agent and/or salt. Generally, buffering agents can include HEPES, ammonium sulfate, Tris, sodium bicarbonate, sodium citrate, sodium acetate, potassium phosphate or sodium phosphate. In some embodiments, a suitable concentration of the buffering agent may be in a range from about 0.1 mM to 100 mM, 0.5 mM to 90 mM, 1.0 mM to 80 mM, 2 mM to 70 mM, 3 mM to 60 mM, 4 mM to 50 mM, 5 mM to 40 mM, 6 mM to 30 mM, 7 mM to 20 mM, 8 mM to 15 mM, or 9 to 12 mM.

Exemplary salts can include sodium chloride, magnesium chloride, and potassium chloride. In some embodiments, suitable concentration of salts in an RNA solution may be in a range from about 1 mM to 500 mM, 5 mM to 400 mM, 10 mM to 350 mM, 15 mM to 300 mM, 20 mM to 250 mM, 30 mM to 200 mM, 40 mM to 190 mM, 50 mM to 180 mM, 50 mM to 170 mM, 50 mM to 160 mM, 50 mM to 150 mM, or 50 mM to 100 mM.

In some embodiments, a suitable RNA solution may have a pH in a range from about 3.5-6.5, 3.5-6.0, 3.5-5.5, 3.5-5.0, 3.5-4.5, 4.0-5.5, 4.0-5.0, 4.0-4.9, 4.0-4.8, 4.0-4.7, 4.0-4.6, or 4.0-4.5.

Various methods may be used to prepare an RNA solution suitable for the present invention. In some embodiments, RNA may be directly dissolved in a buffer solution described herein. In some embodiments, an RNA solution may be generated by mixing an RNA stock solution with a buffer solution prior to mixing with a lipid solution for encapsulation. In some embodiments, an RNA solution may be generated by mixing an RNA stock solution with a buffer solution immediately before mixing with a lipid solution for encapsulation.

According to the present invention, a lipid solution contains a mixture of lipids suitable to form transfer vehicles for encapsulation of RNA. In some embodiments, a suitable lipid solution is ethanol based. For example, a suitable lipid solution may contain a mixture of desired lipids dissolved in pure ethanol (i.e. 100% ethanol). In another embodiment, a suitable lipid solution is isopropyl alcohol based. In another embodiment, a suitable lipid solution is dimethylsulfoxide-based. In another embodiment, a suitable lipid solution is a mixture of suitable solvents including, but not limited to, ethanol, isopropyl alcohol and dimethylsulfoxide.

A suitable lipid solution may contain a mixture of desired lipids at various concentrations. In some embodiments, a suitable lipid solution may contain a mixture of desired lipids at a total concentration in a range from about 0.1-100 mg/ml, 0.5-90 mg/ml, 1.0-80 mg/ml, 1.0-70 mg/ml, 1.0-60 mg/ml, 1.0-50 mg/ml, 1.0-40 mg/ml, 1.0-30 mg/ml, 1.0-20 mg/ml, 1.0-15 mg/ml, 1.0-10 mg/ml, 1.0-9 mg/ml, 1.0-8 mg/ml, 1.0-7 mg/ml, 1.0-6 mg/ml, or 1.0-5 mg/ml.

Any desired lipids may be mixed at any ratios suitable for encapsulating RNAs. In some embodiments, a suitable lipid solution contains a mixture of desired lipids including cationic lipids, helper lipids (e.g., non cationic lipids and/or cholesterol lipids) and/or PEGylated lipids. In some embodiments, a suitable lipid solution contains a mixture of desired lipids including one or more cationic lipids, one or more helper lipids (e.g., non cationic lipids and/or cholesterol lipids) and one or more PEGylated lipids.

11. Target Cells

In some embodiments, the target cells are deficient in a protein or enzyme of interest. For example, where it is desired to deliver a nucleic acid to a hepatocyte, the hepatocyte represents the target cell. In some embodiments, the compositions of the invention transfect the target cells on a discriminatory basis (i.e., do not transfect non-target cells). The compositions of the invention may also be prepared to preferentially target a variety of target cells, which include, but are not limited to, hepatocytes, epithelial cells, hematopoietic cells, epithelial cells, endothelial cells, lung cells, bone cells, stem cells, mesenchymal cells, neural cells (e.g., meninges, astrocytes, motor neurons, cells of the dorsal root ganglia and anterior horn motor neurons), photoreceptor cells (e.g., rods and cones), retinal pigmented epithelial cells, secretory cells, cardiac cells, adipocytes, vascular smooth muscle cells, cardiomyocytes, skeletal muscle cells, beta cells, pituitary cells, synovial lining cells, ovarian cells, testicular cells, fibroblasts, B cells, T cells, dendritic cells, macrophages, reticulocytes, leukocytes, granulocytes and tumor cells.

The compositions of the invention may be prepared to preferentially distribute to target cells such as in the heart, lungs, kidneys, liver, and spleen. In some embodiments, the compositions of the invention distribute into the cells of the liver to facilitate the delivery and the subsequent expression of the circRNA comprised therein by the cells of the liver (e.g., hepatocytes). The targeted cells may function as a biological "reservoir" or "depot" capable of producing, and systemically excreting a functional protein or enzyme. Accordingly, in one embodiment of the invention the transfer vehicle may target hepatocytes and/or preferentially distribute to the cells of the liver upon delivery. In an embodiment, following transfection of the target hepatocytes, the circRNA loaded in the vehicle are translated and a functional protein product is produced, excreted and systemically distributed. In other embodiments, cells other than hepatocytes (e.g., lung, spleen, heart, ocular, or cells of the central nervous system) can serve as a depot location for protein production.

In one embodiment, the compositions of the invention facilitate a subject's endogenous production of one or more functional proteins and/or enzymes. In an embodiment of the present invention, the transfer vehicles comprise circRNA which encode a deficient protein or enzyme. Upon distribution of such compositions to the target tissues and the subsequent transfection of such target cells, the exogenous circRNA loaded into the transfer vehicle (e.g., a lipid nanoparticle) may be translated in vivo to produce a functional protein or enzyme encoded by the exogenously administered circRNA (e.g., a protein or enzyme in which the subject is deficient). Accordingly, the compositions of the present invention exploit a subject's ability to translate exogenously- or recombinantly-prepared circRNA to produce an endogenously-translated protein or enzyme, and thereby produce (and where applicable excrete) a functional protein or enzyme. The expressed or translated proteins or enzymes may also be characterized by the in vivo inclusion of native post-translational modifications which may often be absent in recombinantly-prepared proteins or enzymes, thereby further reducing the immunogenicity of the translated protein or enzyme.

The administration of circRNA encoding a deficient protein or enzyme avoids the need to deliver the nucleic acids to specific organelles within a target cell. Rather, upon transfection of a target cell and delivery of the nucleic acids to the cytoplasm of the target cell, the circRNA contents of a transfer vehicle may be translated and a functional protein or enzyme expressed.

In some embodiments, a circular RNA comprises one or more miRNA binding sites. In some embodiments, a circular RNA comprises one or more miRNA binding sites recognized by miRNA present in one or more non-target cells or non-target cell types (e.g., Kupffer cells) and not present in one or more target cells or target cell types (e.g., hepatocytes). In some embodiments, a circular RNA comprises one or more miRNA binding sites recognized by miRNA present in an increased concentration in one or more non-target cells or non-target cell types (e.g., Kupffer cells) compared to one or more target cells or target cell types (e.g., hepatocytes). miRNAs are thought to function by pairing with complementary sequences within RNA molecules, resulting in gene silencing.

12. Pharmaceutical Compositions

In certain embodiments, provided herein are compositions (e.g. pharmaceutical compositions) comprising a therapeutic agent provided herein. In some embodiments, the therapeutic agent is a circular RNA polynucleotide provided herein. In some embodiments the therapeutic agent is a vector provided herein. In some embodiments, the therapeutic agent is a cell comprising a circular RNA or vector provided herein (e.g., a human cell, such as a human T cell). In certain embodiments, the composition further comprises a pharmaceutically acceptable carrier. In some embodiments, the compositions provided herein comprise a therapeutic agent provided herein in combination with other pharmaceutically active agents or drugs, such as anti-inflammatory drugs or antibodies capable of targeting B cell antigens, e.g., anti-CD20 antibodies, e.g., rituximab, chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, vincristine, etc. In a preferred embodiment, the pharmaceutical composition comprises a cell provided herein or populations thereof.

With respect to pharmaceutical compositions, the pharmaceutically acceptable carrier can be any of those conventionally used and is limited only by chemico-physical considerations, such as solubility and lack of reactivity with the active agent(s), and by the route of administration. The pharmaceutically acceptable carriers described herein, for example, vehicles, adjuvants, excipients, and diluents, are well-known to those skilled in the art and are readily available to the public. It is preferred that the pharmaceutically acceptable carrier be one which is chemically inert to the therapeutic agent(s) and one which has no detrimental side effects or toxicity under the conditions of use.

The choice of carrier will be determined in part by the particular therapeutic agent, as well as by the particular method used to administer the therapeutic agent. Accordingly, there are a variety of suitable formulations of the pharmaceutical compositions provided herein.

In certain embodiments, the pharmaceutical composition comprises a preservative. In certain embodiments, suitable preservatives may include, for example, methylparaben, propylparaben, sodium benzoate, and benzalkonium chloride. Optionally, a mixture of two or more preservatives may be used. The preservative or mixtures thereof are typically present in an amount of about 0.0001% to about 2% by weight of the total composition.

In some embodiments, the pharmaceutical composition comprises a buffering agent. In some embodiments, suitable buffering agents may include, for example, citric acid, sodium citrate, phosphoric acid, potassium phosphate, and various other acids and salts. A mixture of two or more buffering agents optionally may be used. The buffering agent or mixtures thereof are typically present in an amount of about 0.001% to about 4% by weight of the total composition.

In some embodiments, the concentration of therapeutic agent in the pharmaceutical composition can vary, e.g., less than about 1%, or at least about 1%, 2%, 3%, 4%, 5%, 6%, 7%, 8%, 9% 10%, 15%, 20%, 25%, 30%, 35%, 40%, 45%, or about 50% or more by weight, and can be selected primarily by fluid volumes, and viscosities, in accordance with the particular mode of administration selected.

The following formulations for oral, aerosol, parenteral (e.g., subcutaneous, intravenous, intraarterial, intramuscular, intradermal, intraperitoneal, and intrathecal), and topical administration are merely exemplary and are in no way limiting. More than one route can be used to administer the therapeutic agents provided herein, and in certain instances, a particular route can provide a more immediate and more effective response than another route.

Formulations suitable for oral administration can comprise or consist of (a) liquid solutions, such as an effective amount of the therapeutic agent dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol and the polyethylene alcohols, either with or without the addition of a pharmaceutically acceptable surfactant. Capsule forms can be of the ordinary hard or soft shelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and other pharmacologically compatible excipients. Lozenge forms can comprise the therapeutic agent with a flavorant, usually sucrose, acacia or tragacanth. Pastilles can comprise the therapeutic agent with an inert base, such as gelatin and glycerin, or sucrose and acacia, emulsions, gels, and the like containing, in addition to, such excipients as are known in the art.

Formulations suitable for parenteral administration include aqueous and nonaqueous isotonic sterile injection solutions, which can contain antioxidants, buffers, bacteriostats, and solutes that render the formulation isotonic with the blood of the intended recipient, and aqueous and nonaqueous sterile suspensions that can include suspending agents, solubilizers, thickening agents, stabilizers, and preservatives. In some embodiments, the therapeutic agents provided herein can be administered in a physiologically acceptable diluent in a pharmaceutical carrier, such as a sterile liquid or mixture of liquids including water, saline, aqueous dextrose and related sugar solutions, an alcohol such as ethanol or hexadecyl alcohol, a glycol such as propylene glycol or polyethylene glycol, dimethylsulfoxide, glycerol, ketals such as 2,2-dimethyl-1,3-dioxolane-4-methanol, ethers, poly(ethyleneglycol) 400, oils, fatty acids, fatty acid esters or glycerides, or acetylated fatty acid glycerides with or without the addition of a pharmaceutically acceptable surfactant such as a soap or a detergent, suspending agent such as pectin, carbomers, methylcellulose, hydroxypropylmethylcellulose, or carboxymethylcellulose, or emulsifying agents and other pharmaceutical adjuvants.

Oils, which can be used in parenteral formulations in some embodiments, include petroleum, animal oils, vegetable oils, or synthetic oils. Specific examples of oils include peanut, soybean, sesame, cottonseed, corn, olive, petrolatum, and mineral oil. Suitable fatty acids for use in parenteral formulations include oleic acid, stearic acid, and isostearic acid. Ethyl oleate and isopropyl myristate are examples of suitable fatty acid esters.

Suitable soaps for use in certain embodiments of parenteral formulations include fatty alkali metal, ammonium, and triethanolamine salts, and suitable detergents include (a) cationic detergents such as, for example, dimethyl dialkyl ammonium halides. and alkyl pyridinium halides, (b) anionic detergents such as, for example, alkyl, aryl, and olefin sulfonates, alky, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-β-aminopropionates, and 2-alkyl-imidazoline quaternary ammonium salts, and (e) mixtures thereof.

In some embodiments, the parenteral formulations will contain, for example, from about 0.5% to about 25% by weight of the therapeutic agent in solution. Preservatives and buffers may be used. In order to minimize or eliminate irritation at the site of injection, such compositions may contain one or more nonionic surfactants having, for example, a hydrophile-lipophile balance (HLB) of from about 12 to about 17. The quantity of surfactant in such formulations will typically range, for example, from about 5% to about 15% by weight. Suitable surfactants include polyethylene glycol, sorbitan fatty acid esters such as sorbitan monooleate, and high molecular weight adducts of ethylene oxide with a hydrophobic base formed by the condensation of propylene oxide with propylene glycol. The parenteral formulations can be presented in unit-dose or multi-dose sealed containers, such as ampoules or vials, and can be stored in a freeze-dried (lyophilized) condition requiring only the addition of a sterile liquid excipient, for example, water, for injections, immediately prior to use. Extemporaneous injection solutions and suspensions can be prepared from sterile powders, granules, and tablets of the kind previously described.

In certain embodiments, injectable formulations are provided herein. The requirements for effective pharmaceutical carriers for injectable compositions are well-known to those of ordinary skill in the art (see, e.g., Pharmaceutics and Pharmacy Practice, J.B. Lippincott Company, Philadelphia, PA, Banker and Chalmers, eds., pages 238-250 (1982), and ASHP Handbook on Injectable Drugs, Toissel, 4th ed, pages 622-630 (1986)).

In some embodiments, topical formulations are provided herein. Topical formulations, including those that are useful for transdermal drug release, are suitable in the context of certain embodiments provided herein for application to skin. In some embodiments, the therapeutic agent alone or in combination with other suitable components, can be made into aerosol formulations to be administered via inhalation. These aerosol formulations can be placed into pressurized acceptable propellants, such as dichlorodifluoromethane, propane, nitrogen, and the like. They also may be formulated as pharmaceuticals for non-pressured preparations, such as in a nebulizer or an atomizer. Such spray formulations also may be used to spray mucosa.

In certain embodiments, the therapeutic agents provided herein can be formulated as inclusion complexes, such as cyclodextrin inclusion complexes, or liposomes. Liposomes can serve to target the therapeutic agents to a particular tissue. Liposomes also can be used to increase the half-life of the therapeutic agents. Many methods are available for preparing liposomes, as described in, for example, Szoka et al., Ann. Rev. Biophys. Bioeng., 9, 467 (1980) and U.S. Pat. Nos. 4,235,871, 4,501,728, 4,837,028, and 5,019,369.

In some embodiments, the therapeutic agents provided herein are formulated in time-released, delayed release, or sustained release delivery systems such that the delivery of the composition occurs prior to, and with sufficient time to cause, sensitization of the site to be treated. Such systems can avoid repeated administrations of the therapeutic agent, thereby increasing convenience to the subject and the physician, and may be particularly suitable for certain composition embodiments provided herein. In one embodiment, the compositions of the invention are formulated such that they are suitable for extended-release of the circRNA contained therein. Such extended-release compositions may be conveniently administered to a subject at extended dosing intervals. For example, in one embodiment, the compositions of the present invention are administered to a subject twice a day, daily or every other day. In an embodiment, the compositions of the present invention are administered to a subject twice a week, once a week, every ten days, every two weeks, every three weeks, every four weeks, once a month, every six weeks, every eight weeks, every three months, every four months, every six months, every eight months, every nine months or annually.

In some embodiments, a protein encoded by an inventive polynucleotide is produced by a target cell for sustained amounts of time. For example, the protein may be produced for more than one hour, more than four, more than six, more than 12, more than 24, more than 48 hours, or more than 72 hours after administration. In some embodiments the polypeptide is expressed at a peak level about six hours after administration. In some embodiments the expression of the polypeptide is sustained at least at a therapeutic level. In some embodiments the polypeptide is expressed at least at a therapeutic level for more than one, more than four, more than six, more than 12, more than 24, more than 48, or more than 72 hours after administration. In some embodiments, the polypeptide is detectable at a therapeutic level in patient serum or tissue (e.g., liver or lung). In some embodiments, the level of detectable polypeptide is from continuous expression from the circRNA composition over periods of time of more than one, more than four, more than six, more than 12, more than 24, more than 48, or more than 72 hours after administration.

In certain embodiments, a protein encoded by an inventive polynucleotide is produced at levels above normal physiological levels. The level of protein may be increased as compared to a control. In some embodiments, the control is the baseline physiological level of the polypeptide in a normal individual or in a population of normal individuals. In other embodiments, the control is the baseline physiological level of the polypeptide in an individual having a deficiency in the relevant protein or polypeptide or in a population of individuals having a deficiency in the relevant protein or polypeptide. In some embodiments, the control can be the normal level of the relevant protein or polypeptide in the individual to whom the composition is administered. In other embodiments, the control is the expression level of the polypeptide upon other therapeutic intervention, e.g., upon direct injection of the corresponding polypeptide, at one or more comparable time points.

In certain embodiments, the levels of a protein encoded by an inventive polynucleotide are detectable at 3 days, 4 days, 5 days, or 1 week or more after administration. Increased levels of secreted protein may be observed in the serum and/or in a tissue (e.g., liver or lung).

In some embodiments, the method yields a sustained circulation half-life of a protein encoded by an inventive polynucleotide. For example, the protein may be detected for hours or days longer than the half-life observed via subcutaneous injection of the protein or mRNA encoding the protein. In some embodiments, the half-life of the protein is 1 day, 2 days, 3 days, 4 days, 5 days, or 1 week or more.

Many types of release delivery systems are available and known to those of ordinary skill in the art. They include polymer based systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are lipids including sterols such as cholesterol, cholesterol esters, and fatty acids or neutral fats such as mono-di- and tri-glycerides; hydrogel release systems; sylastic systems; peptide based systems: wax coatings; compressed tablets using conventional binders and excipients; partially fused implants; and the like. Specific examples include, but are not limited to: (a) erosional systems in which the active composition is contained in a form within a matrix such as those described in U.S. Pat. Nos. 4,452,775, 4,667,014, 4,748,034, and 5,239,660 and (b) diffusional systems in which an active component permeates at a controlled rate from a polymer such as described in U.S. Pat. Nos. 3,832,253 and 3,854,480. In addition, pump-based hardware delivery systems can be used, some of which are adapted for implantation.

In some embodiments, the therapeutic agent can be conjugated either directly or indirectly through a linking moiety to a targeting moiety. Methods for conjugating therapeutic agents to targeting moieties is known in the art. See, for instance, Wadwa et al., J, Drug Targeting 3:111 (1995) and U.S. Pat. No. 5,087,616.

In some embodiments, the therapeutic agents provided herein are formulated into a depot form, such that the manner in which the therapeutic agent is released into the body to which it is administered is controlled with respect to time and location within the body (see, for example, U.S. Pat. No. 4,450,150). Depot forms of therapeutic agents can be, for example, an implantable composition comprising the therapeutic agents and a porous or non-porous material, such as a polymer, wherein the therapeutic agents are encapsulated by or diffused throughout the material and/or degradation of the non-porous material. The depot is then implanted into the desired location within the body and the therapeutic agents are released from the implant at a predetermined rate.

13. Therapeutic Methods

In certain aspects, provided herein is a method of treating and/or preventing a condition, e.g., cancer, comprising introducing pharmaceutical composition provided herein into a subject in need thereof (e.g., a subject with cancer). In some embodiments, the pharmaceutical composition comprises a circular RNA polynucleotide provided herein. In some embodiments, the pharmaceutical composition comprises a vector provided herein. In some embodiments, the pharmaceutical composition comprises a cell (e.g., human cell, such as a human T cell) comprising a polynucleotide provided herein (e.g., a circular RNA or a vector provided herein).

Thus, in certain embodiments, provided herein are methods of treating and/or preventing a disease in a subject (e.g., mammalian subject, such as a human subject). Without being bound to a particular theory or mechanism, the CARs and TCR complex proteins have biological activity, e.g., ability to recognize an antigen, e.g., CD19, such that the CAR or TCR, when expressed by a cell, is able to mediate an immune response against the cell expressing the antigen, e.g., CD19, for which the CAR or TCR is specific. In this regard, an embodiment provided herein provides a method of treating or preventing cancer in a mammal, comprising administering to the mammal the therapeutic agents thereof, and/or the pharmaceutical compositions provided herein in an amount effective to treat or prevent cancer in the mammal.

In certain embodiments, the therapeutic agents provided herein are coadministered with one or more additional therapeutic agents (e.g., in the same pharmaceutical composition or in separate pharmaceutical compositions). In some embodiments, the therapeutic agent provided herein can be administered first and the one or more additional therapeutic agents can be administered second, or vice versa. Alternatively, the therapeutic agent provided herein and the one or more additional therapeutic agents can be administered simultaneously. In some embodiments, the additional therapeutic agent that can be co-administered with the therapeutic agents provided herein is a T cell active cytokine, such as IL-2, IL-7, IL-15 and/or IL-21.

In certain embodiments, the therapeutic agent is a cell or population of cells comprising a circular RNA or a vector provided herein that expresses a CAR or TCR complex protein encoded by the circular RNA or vector. In some embodiments, the administered cells are allogeneic to the subject being treated. In some embodiments, the administered cells are autologous to the subject being treated.

In certain embodiments, the methods further comprise lymphodepleting the subject prior to administering the therapeutic agent. Examples of lymphodepletion include, but may not be limited to, nonmyeloablative lymphodepleting chemotherapy, myeloablative lymphodepleting chemotherapy, total body irradiation, etc.

In some embodiments, the subject is a mammal. In some embodiments, the mammal referred to herein can be any mammal, including, but not limited to, mammals of the order Rodentia, such as mice and hamsters, or mammals of the order Logomorpha, such as rabbits. The mammals may be from the order Carnivora, including Felines (cats) and Canines (dogs). The mammals may be from the order Artiodactyla, including Bovines (cows) and Swines (pigs), or of the order Perssodactyla, including Equines (horses). The mammals may be of the order Primates, Ceboids, or Simoids (monkeys) or of the order Anthropoids (humans and apes). Preferably, the mammal is a human.

14. Sequences

TABLE 3

Exemplary IRES sequences.

| SEQ ID NO: | IRES | Sequence |
|---|---|---|
| 1 | EMCV-A | cccccctctccctccccccctaacgttactggccgaagccgcttggaataaggccggt gtgcgtttgtctatatgttattttccaccatattgccgtcttttggcaatgtgagggcccgg aaacctggccctgtcttcttgacgagcattcctaggggtctttcccctctcgccaaagg aatgcaaggtctgttgaatgtcgtgaaggaagcagttcctctggaagcttcttgaagac aaacaacgtctgtagcgaccctttgcaggcagcggaaccccccacctggcgacagg tgcctctgcggccaaaagccacgtgtataagatacacctgcaaaggcggcacaacc ccagtgccacgttgtgagttggatagttgtggaaagagtcaaatggctctcctcaagc gtattcaacaaggggctgaaggatgcccagaaggtacccccattgtatgggatctgatc tggggcctcggtgcacatgctttacatgtgtttagtcgaggttaaaaaacgtctaggcc ccccgaaccacggggacgtggttttcctttgaaaaacacgatgataatatggccacaa cc |
| 2 | EMCV-B | ctccccctcccccccttactatactggccgaagccacttggaataaggccggtgtgc gtttgtctacatgctattttctaccgcattaccgtcttatggtaatgtgagggtccagaacc tgaccctgtcttcttgacgaacactcctaggggtctttcccctctcgacaaaggagtgta aggtctgttgaatgtcgtgaaggaagcagttcctctggaagcttcttaaagacaaacaa cgtctgtagcgaccctttgcaggcagcggaaccccccacctggtgacaggtgcctct gcggccaaaagccacgtgtataagatacacctgcaaaggcggcacaacccccagtgc cacgttgtgagttggatagttgtggaaagagtcaaatggctctcctcaagcgtattcaa caaggggctgaaggatgcccagaaggtacccccattgtatgggatctgatctggggcc tcggtgcacgtgctttacacgtgttgagtcgaggtgaaaaaacgtctaggccccccga accacggggacgtggttttcctttgaaaaccacgattacaat |

TABLE 3-continued

Exemplary IRES sequences.

| SEQ ID NO: | IRES | Sequence |
|---|---|---|
| 3 | EMCV-Bf | ttgccagtctgctcgatatcgcaggctgggtccgtgactacccactcccccttttcaacg<br>tgaaggctacgatagtgccagggcgggtactgccgtaagtgccaccccaaacaaca<br>acaacaaaacaaactccccctccccccccttactatactggccgaagccacttggaat<br>aaggccggtgtgcgtttgtctacatgctatttctaccgcattaccgtcttatggtaatgtg<br>agggtccagaacctgaccctgtcttcttgacgaacactcctagggggtcttccccctctc<br>gacaaaggagtgtaaggtctgttgaatgtcgtgaaggaagcagttcctctggaagctt<br>cttaaagacaaacaacgtctgtagcgaccctttgcaggcagcggaaccccccacctg<br>gtgacaggtgcctctgcggccaaaagccacgtgtataagatacacctgcaaaggcg<br>gcacaaccccagtgccacgttgtgagttggatagttgtggaaagagtcaaatggctct<br>cctcaagcgtattcaacaaggggctgaaggatgcccagaaggtaccccattgtatgg<br>gatctgatctggggcctcggtgcacgtgctttacacgtgttgagtcgaggtgaaaaaa<br>cgtctaggcccccgaaccacggggacgtggttttcctttgaaaaccacgattacaat |
| 4 | EMCV-Cf | ttgccagtctgctcgatatcgcaggctgggtccgtgactacccactcccccttttcaacg<br>tgaaggctacgatagtgccagggcgggtactgccgtaagtgccaccccaaaacaac<br>aacaaccccccctctccctccTccccccctaacgttactggccgaagccgcttggaa<br>taaggccggtgtgcgtttgtctatatgttattttccaccatattgccgtcttttggcaatgtg<br>agggcccggaaacctggccctgtcttcttgacgagcattcctagggggtctttcccctct<br>cgccaaaggaatgcaaggtctgttgaatgtcgtgaaggaagcagttcctctggaagct<br>tcttgaagacaaacaacgtctgtagcgaccctttgcaggcagcggaaccccccacct<br>ggcgacaggtgcctctgcggccaaaagccacgtgtataagatacacctgcaaaggc<br>ggcacaaccccagtgccacgttgtgagttggatagttgtggaaagagtcaaatggctc<br>tcctcaagcgtattcaacaaggggctgaaggatgcccagaaggtaccccattgtatgg<br>gatctgatctggggcctcggtgcacatgctttacatgtgtttagtcgaggttaaaaaacg<br>tctaggcccccgaaccacggggacgtggttttcctttgaaaaacacgatgataat |
| 5 | EMCV pEC9 | cccccccctaacgttactggccgaagccgcttggaataaggccggtgtgcgtttgtc<br>tatatgttattttccaccatattgccgtcttttggcaatgtgagggcccggaaacctggcc<br>ctgtcttcttgacgagcattcctagggggtctttcccctctcgccaaaggaatgcaaggt<br>ctgttgaatgtcgtgaaggaagcagttcctctggaagcttcttgaagacaaacaacgtct<br>gtagcgaccctttgcaggcagcggaaccccccacctggcgacaggtgcctctgcgg<br>ccaaaagccacgtgtataagatacacctgcaaaggcggcacaaccccagtgccacg<br>ttgtgagttggatagttgtggaaagagtcaaatggctctcctcaagcgtattcaacaag<br>gggctgaaggatgcccagaaggtaccccattgtatgggatctgatctggggcctcgg<br>tgcacatgctttacatgtgtttagtcgaggttaaaaaacgtctaggcccccgaaccac<br>ggggacgtggttttcctttgaaaaacacgatgataat |
| 6 | Picobirnavirus | gtaaattaaatgctatttacaaaatttaaacagaaaggagagatgttatgaaccggtttta<br>caaggtttcatacatcgaaaatagcactacctggggcagccgacacactaacatcgtc<br>tgtttaaccagaagtgttactgaaaggaggttattta |
| 7 | HCV QC64 | acctgccctaatagggcgacactccgccatgaatcactccctgtgaggaactact<br>gtcttcacgcagaaagcgtctagccatggcgttagtatgagtgtcgtacagcctccag<br>gccccccctcccgggagagccatagtggtctgcggaaccggtgagtacaccgga<br>attgccgggaagactgggtcctttcttggataaacccactctatgcccggacatttggg<br>cgtgccccgcaagactgctagccgagtagcgttgggttgcgaaaggccttgtggta<br>ctgcctgatagggtgcttgcgagtgccccgggaggtctcgtagaccgtgcatc |
| 8 | Human Cosavirus E/D | ctacaagctttgtgtaaacaaacttttgtttggcttttctcaagcttctctcacatcaggccc<br>caaagatgtcctgaaggtaccccgtgtatctgaggatgagcaccatcgactacccgg<br>acctgcaaaattttgcaaacgcatgtggtatcccagcccctcctctcggggaggggg<br>ctttgctcactcagcacaggatctgatcaggagatccacctccggtgctttacaccggg<br>gcgtggatttaaaaattgcccaaggcctggcgcacaacctaggggactaggttttcctt<br>atattttaaagctgtcaat |
| 9 | Human Cosavirus F | gtcttaggacgacgcatgtggtatcccagcccccgcctacattggcggggcttttga<br>agcaccagacactggatctgatcaggaggagggtagctgctttacagcccctcttaaa<br>aattgcccaaggtccggccacccaacctaggggactaggttttccttttatttttaaattg<br>tcatt |
| 10 | Human Cosavirus JMY | acatggggagactgcatgtggcagtcttgaaacgtgtggtttgacgtctaccttatat<br>ggcagtgggtggagtactgcaaagatgtcaccgtgctttacacggtttttgaaccccac<br>accggctgtttgacgctcgtagggcagcaggtttattttcattaaaattcttactttctagc<br>tgcatgagttctattcatgcagacggagtgatactcccgttccttcttggacaggttgcct<br>ccacgcccttgtggatcttaaggtgaccaagtcactggtgttggaggtgaagataga<br>gagtcctcttgggaatgtcatgtggctgtgccaggggttgtagcgatgccattcgtgtg<br>tgcggatttcctctcgtggtgacacgagcctcacaggccaaaagcccgtccgaaag<br>gaccccgaatggtggagtgaccctgactcccccctgcatagttttgtgattaggaacttg<br>aggaatttctgtcataaatctctatcacatcaggcccccaaagatgtcctgaaggtaccct<br>gtgtatctgaggatgagcaccaccgactacccggacttgcattagcagacacatgtgg<br>ttgcccagccccacctcttcagaggtggggctttgctcactcagcacaggatctgatca<br>ggagccccgctcgtgtgcttacactcgacgcggggttaaaaattgcccaaggcctg<br>gcacaacaacctaggggactaggttttcctattttttgtaaattatgtcaat |

TABLE 3-continued

Exemplary IRES sequences.

| SEQ ID NO: | IRES | Sequence |
| --- | --- | --- |
| 11 | Rhinovirus NAT001 | gtgacaatcagccagattgttaacggtcaagcacttctgtttccccggtaccttgtata cgcttcacccgaggcgaaaagtgaggttatcgttatccgcaaagtgcctacgagaag cctagtagcacttttgaagcctatggctggtcgctcaactgtttacccagcagtagcct ggcagatgaggctagatgttccccaccagcgatggtgatctagcctgcgtggctgcct gcacactctattgagtgtgaagccagaaagtggacaaggtgtgaagagcctattgtgc tcactttgagtcctccggcccctgaatgtggctaatcctaaccccgtagctgttgcatgt aatccaacatgtctgcagtcgtaatgggcaactatgggatggaaccaactactttgggt gtccgtgtttcttgttttctttatgcttgcttatggtgacaactgtagttattacatttgttacc |
| 12 | HRV14 | ttaaaacagcggatgggtatcccaccattcgacccattgggtgtagtactctggtactat gtacctttgtacgcctgtttctcccaaccacccttccttaaaattcccacccatgaaacg ttagaagcttgacattaaagtacaataggtggcgcatatccaatggtgtctatgtacaa gcacttctgtttcccaggagcgaggtataggctgtacccactgccaaaagcctttaacc gttatccgccaaccaactacgtaacagttagtaccatcttgttcttgactggacgttcgat caggtggattttccctccactagtttggtcgatgaggctaggaattccccacgggtgac cgtgtcctagcctgcgtggcggccaacccagcttatgctgggacgccttttaaggac atggtgtgaagactcgcatgtgcttggttgtgagtcctccggcccctgaatgcggctaa ccttaaccctagagcctatgccacgatccagtggttgtaaggtcgtaatgagcaattc cgggacgggaccgactacttgggtgtccgtgtttctcattttcttcatattgtcttatggt cacagcatatatatacatatactgtgatc |
| 13 | HRV89 | ttaaaactgggagtgggttgttcccactcactccacccatgcggtgttgtactctgttatt acgtaactttgtacgccagttttcccaccctttcccataatgtaacttagaagtttgtac aatatgaccaataggtgacaatcatccagactgtcaaaggtcaagcacttctgtttccc cggtcaatgaggatatgcttacccaaggcaaaaaccttagagatcgttatccccacac tgcctacacagagcccagtaccatttttgatataattgggttggtcgctccctgcaaacc cagcagtagacctggcagatgaggctggacattccccactggcgacagtggtccag cctgcgtggctgcctgctcacccttcttgggtgagaagcctaattattgacaaggtgtg aagagccgcgtgtgctcagtgtgcttcctccggcccctgaatgtggctaaccttaacc ctgcagccgttgcccataatccaatgggtttgcggtcgtaatgcgtaagtgcgggatg ggaccaactactttgggtgtccgtgtttcctgttttctttttgattgcatttttatggtgacaatt tatagtgtatagattgtcatc |
| 14 | HRVC-02 | ttaaaactgggtacaggttgttcccacctgtatcacccacgtggtgtggtgctcttgtatt ccggtacacttgcacgccagtttgccaccccctcacccgtcgtaacttagaagctaaca actcgaccaacaggcggtggtaaaccataccacttacggtcaagcactcctgtttccc cggtatgcgaggaatagactcctacagggttgaagcctcaagtatcgttatccgcattg gtactacgcaaagcttagtagtgccttgaaagtccctttggttggtcgctccgctagtttc ccctagtagacctggcagatgaggcaggacactccccactggcgacagtggtcctg cctgcgtggctgcctgcgcacccttaggggtgcgaagccaagtgacagacaaggtg tgaagagcccccgtgtgctaccaatgagtcctccggcccctgaatgcggctaatccaa ccccacagctattgcacacaagccagtgtatgtagtcgtaatgagcaattgtggga cggaaccgactacttgggtgtccgtgtttccttttattcttatcattctgcttatggtgaca atactgtgaaatagtgttgttacc |
| 15 | HRV-A21 | taaaaactggatccaggttgttcccacctggatctcctattgggagttgtactctattattcc ggtaattttgtacgccagttttatcttcccccctcccaattgtaacttagaaaggttatcaata cgaccaataggtggtagttagccaaactaccaaaggtcaagcacttctgtttcccccggt caaagttgatatgctccaacagggcaaaaacaactgagatcgttatccgcaaagtgcc tacgcaaaagcctagtaacacctttgaagattttatggttggtcgttccgctatttcccatag tagacctggcagatgaggctagaaatcccccactggcgacagtgctctagcctgcgt ggctgcctgcgcacccctttgggtgcgaagccatacattggacaaggtgtgaagagc ccgtgtgctcactttgagtcctccggcccctgaatgtggctaaccttaaccctgcagc tagtgcatgtaatccaacatgttgctagtcgtaatgagtaattgcgggacgggaccaac tactttgggtgtccgtgtttcacttttccttttaatattgcttatggtgacaatatatatagct atatatattgacacc |
| 16 | Salivirus A SH1 | ttcccctgcaaccattacgcttactcgcatgtgcattgagtggtgcatgtgttgaacaaa cagctacactcacatggggcgggtttcccgccctacggcttctcgcgaggccac ccctcccttctctcccataactacagtgctttggtaggtaagcatcctgatccccgcgg aagctgctcacgtggcaactgtggggacccagacaggttatcaaaggcacccggtct ttccgccttcaggagtatccctgctagcgaattctagtagggctctgcttggtgccaacc tcccccaaatgcgcgctgcgggagtgctcttcccaactcaccctagtatcctctcatg tgtgtgcttggtcagcatatctgagacgatgttccgctgtcccagaccagtccagtaat ggacgggccagtgtgcgtagtcgtcttccggcttgtccggcgcatgtttggtgaaccg gtggggtaaggttggtgtgcccaacgcccgtactcaggggatacctcaaggcaccc aggaatgccagggaggtaccccgcttcacagcgggatctgaccctggggtaaatgt ctgcgggggtcttcttggcccacttctcagtactttcagg |
| 17 | Salivurus FHB | acatggggggtctgcggacggcttcggcccaccccgcgacaagaatgccgtcatctg tcctcattacccgtattccttccctccccccgcaacccaccaccacgcttactcgcgcacgtgtt gagtggcacgtgcgttgtccaaacagctacacccacaccctcggggcgggtttgtc ccgccctcgggttcctgcgggaaccccccctccctctctctcttctatccgccctcac ttcccataactacagtgctttggtaggtgagcaccctgacccccgcggaagctgcta acgtggcaactgtggggatccaggcaggttatcaaaggcacccggtctttccgccttc aggagtatctctgccggtgaattccggtagggctctgcttggtgccaacctcccccaa |

TABLE 3-continued

Exemplary IRES sequences.

| SEQ ID NO: | IRES | Sequence |
|---|---|---|
| | | atgcgcgctgcgggagtgctcttccccaactcatcttagtaacctctcatgtgtgtgctt<br>ggtcagcatatctgaggcgacgttccgctgtcccagaccagtccagcaatggacggg<br>ccagtgtgcgtagtcgctttccggttttccggcgcatgtttggcgaaacgctgaggtaa<br>ggttggtgtgcccaacgcccgtaatttggtgatacctcaagaccacccaggaatgcca<br>gggaggtaccccacttcggtgggatctgaccctgggctaattgtctacggtggttcttc<br>ttgcttccacttctcttttttctggcatg |
| 18 | Salivirus NG-J1 | tatggcaggcgggcttgtggacggcttcggcccacccacagcaagaatgccatcatc<br>tgtcctcacccccaatttttcccttttcttcccctgcaaccattacgcttactcgcatgtgcat<br>tgagtggtgcatgtgttgaacaaacagctacactcacatgggggcgggttttcccgcc<br>ctacggcctctcgcgaggccacccccttccctccccttataactacagtgctttggtag<br>gtaagcatcctgatccccgcggaagctgctcacgtggcaactgtggggacccaga<br>caggttatcaaaggcaccggtctttccgccttcaggagtatccctactagtgaattcta<br>gcggggctctgcttggtgccaacctcccccaaatgcgcgctgcgggagtgctcttcc<br>ccaactcaccctagtatcctctcatgtgtgtgcttggtcagcatatctgagacgatgttcc<br>gctgtcccagaccagtccagtaatggacgggccagtgcgtgtagtcgtcttccggctt<br>gtccggggcatgtttggtgaaccggtggggtaaggttggtgtgcccaacgcccgtac<br>tttggtgacacctcaagaccacccaggaatgccagggaggtaccccacctcacggtg<br>gatctgaccctgggctaattgtctacggtggttcttcttgcttccacttctttcttctgttca<br>cg |
| 19 | Human Parechovirus 1 | tttgaaaggggtctcctagagagcttggccgtcgggccttataccccgacttgctgagt<br>ttctctaggagagcccttttcccagccctgaggcggctggtcaataaaagcctcaaac<br>gtaactaacacctaagaagatcatgtaaaccctatgcctggtctccactattcgaaggc<br>aacttgcaataagaagagtgggatcaagacgcttaaagcatagagacagttttcttttct<br>aacccacatttgtgtggggtggcagatggcgtgccataactctaatagtgagatacca<br>cgcttgtggaccttatgctcacacagccatcctctagtaagtttgtgagacgtctggtga<br>cgtgtgggaacttattggaaacaacattttgctgcaaagcatcctactgccagcggaaa<br>aacacctggtaacaggtgcctctggggccaaaagccaaggtttaacagacccttag<br>gattggttctaaacctgagatgttgtggaagatatttagtacctgctgatctggtagttatg<br>caaacactagttgtaaggcccatgaaggatgcccagaaggtacccgtaggtaacaag<br>tgacactatggatctgatttggggccagatacctctatcttggtgatctggttaaaaaac<br>atctaatgggccaaaccggggggggatcccccggtttcctcttattctatcaatgccact |
| 20 | Crohivirus B | gtataagagacaggtgtttgccttgtcttcggactggcatcttgggaccaaccccccttt<br>tccccagccatgggttaaatggcaataaaaggacgtaacaacttttgtaaccattaagctttt<br>gtaattttgtaaccactaagctttgtgcacataatgtaaccatcaagcttgttagtcccag<br>caggaggtttgcatgcttgtagccgaaatggggctcgaccccccccatgtaggatactt<br>gattttgcattccattgtggacctgcaaactctacacatagaggctttgtcttgcatctaaa<br>cacctgagtacagtgtgtacctagacccctatagtacgggaggaccgtttgtttcctcaat<br>aaccctacataataggctaggtgggcatgcccaatttgcaagatcccagactgggggt<br>cggtctgggcagggttagatccctgttagctactgcctgatagggtggtgctcaaccat<br>gtgtagtttaaattgagctgttcatatacc |
| 21 | Yc-3 | actgaagatcctacagtaactactgccccaatgaacgccacagatgggtctgctgatg<br>actacctatcttagtgctagtttgagggtttgaagtgagccggttttttagaagaaccagtttc<br>tgaacattatcatcccccagcatctattctatacgcacaagatagatagtcatcagcagac<br>acatctgtgctactgcttgatagagagttggctggtcaacttagattggtataaccagttg<br>agtggcaa |
| 22 | Rosavirus M-7 | tatgcatcactggacggcctaacctcggtcgtggcttcttgccgatttcagcgctacca<br>ggctttctggtctcgccaggcgttgattagtaggtgcactgtctaagtgaagacagcag<br>tgctctctgtgaaaagttgatgacactcttcaggtttgtagcgatcactcaaggctagcg<br>gatttccccgtgtggtaacacacgcctctaggcccagaaggcacggtgttgacagca<br>cccttgagtggctggtcttccccaccagcacctgatttgtggattcttcctagtaacgg<br>acaagcatggctgctcttaagcattcagtgcgtccggggctgaaggatgcccagaag<br>gtacccgcaggtaacgataagctcactgtggatctgatctggggctgcgggctgggt<br>gtctttccacccagccaaaacccgtaaaacggtagtcgcagttaaaaaacgtctaggc<br>cccacccccccagggatgggggggttccctttaaaccctcacaagttcaac |
| 23 | Shanbavirus A | tgaaaaggggggcgcagggtggtggtggttactaaatacccaccatcgccctgcactt<br>ccctttttccctgtggctcagggtcacttagccccctctttgggttaccagtagttttctac<br>ccctgggcacagggttaactatgcaagacggaacaacaatctcttagtccccctcgcc<br>gatagtgggctcgacccccatgtgtaggagtggataagggacggagtgagccgata<br>cggggaagagtgtgcggtcacaccttaattccatgagcgctgcgaagaaggaagct<br>gtgaacaatggcgacctgaaccgtacacatggagctccacaggcatggtactcgtta<br>gactacgcagcctggttgggagtgggtatacccctgggtgagccgccagtgaatggg<br>agttcactggttaacacactgcctgatagggtcagggcctcctgtccccgccgtaat<br>gaggtagaccatatgcc |
| 24 | Pasivirus A | gcggctggatattctggccgtgcaactgcttttgaccagtggctctgggtaacttagcc<br>aaagtgtccttctcctttcccttattatgtgttttatggctttgtctggtcttgtt-<br>tagtttatata<br>taagatccttccgccgatatagacctcgacagtctagtgtaggaggattggtgatatta<br>atttgccccagaagagtgaccgtgacacatagaaaccatgagtacatgtgtatccgtg<br>gaggatcgccgggactggattccatatcccattgccatcccaacaagcggagggta |

TABLE 3-continued

Exemplary IRES sequences.

| SEQ ID NO: | IRES | Sequence |
|---|---|---|
| | | tacccactatgtgcacgtctgcagtgggagtctgcagatttagtcatactgcctgatag
ggtgtgggcctgcactctggggtactcaggctgtttatataat |
| 25 | Pasivirus A 2 | gctggactttctggctgcgcaactgcttttaaccagtggctctggttacttagccaaaa
cccccctttccccgtaccctagtttgtgtgtgtattattattttgttgttgttttgtaaat-
ttttata
taagatcctttccgccgatatagacctcgacagtctagtgtaggaggattggtgatatta
atatgccccagaagagtgaccgtgacacatagaaaccatgagtacatgtgtatccgtg
gaggatcgcccgggactggattccatatcccattgccatcccaacaaacggagggta
tacccgctatgtgcgcgtctacagtgggaatctgtagatttagtcatactgcctgatagg
gtgtgggcctgcactctggggtactcaggctgtttatataat |
| 26 | Echovirus E14 | ttaaaacagcctgtgggttgttcccatccacagggcccactgggcgccagcactctgg
tattgcggtaccttagtgcgcctgtttttatataccccgtcccccaaacgtaacttagacgc
atgtcaacgaagaccaatagtaagcgcagcacaccagctgtgttccggtcaagcactt
ctgttaccccggaccgagtatcaataagctactcacgtggctgaaggagaaaacgttc
gttacccgaccaattacttcaagaaacctagtaacaccatgaaggttgcgcagtgtttc
gctccgcacaaccccagtgtagatcaggtcgatgagtcaccgcattccccacgggtg
accgtggcggtggctgcgctggcggcctgccatgggaaacccatgggacgcttc
aatactgacatggtgcgaagagtctattgagctaattggtagtcctccggccctgaat
gcggctaatcctaactgcggagcagataccacacaccagtgggcagtctgtcgtaa
cgggcaactctgcagcggaaccgactacttgggtgtccgtgtttctctttatccttatac
tggctgcttatggtgacaattgagagattgttaccatatagctattggattggccatccg
gtgacaaatagagcaattgtgtatttgtttgttggtttcgtgccattaaattacaaggttcta
aacacccttaatcttattatagcattcaacacaacaaa |
| 27 | Human Parechovirus 5 | gtacattagatgcgtcatctgcaactttagtcaataaattacctccaatgtcattaccaac
attccctacctttttcactaacacctaagacaacaagtacctatgcctggtctccactattc
gaaggcaacttgcaataagaagagtggaattaagacgcttaaagcatagagctagtta
tcttttctaacccacaaagttttgtgggtggcagatggcgtgccataactctattagtga
gataccatgcttgtggatcttatgctcacacagccatcctctagtaagttgataaggtgtc
tggtgatatgtgggaactcacatgaaccattaatttaccgtaaggtatcctatagccagc
ggaatcacatctggtgacagatgcctctggggccgaaagccaaggtttaacagaccc
tataggattggtttcaaaacctgaattgatgtggattgtgtatagtacctgttgatctggta
acagtgtcaacactagttgtaaggcccacgaaggatgcccagaagtacccgtaggt
aacaagtgacactatggatctgatctggggccagctacctctatcatggtgagttggtt
aaaaaacgtctagtgggccaaacccaggggggatccctggtttccttttacctaatcaa
agccact |
| 28 | Aichi Virus | tttgaaaaggggtggggggcctcggcccccctcaccctcttttccggtggtctggtc
ccggaccaccgttactccattcagcttcttcggaacctgttcggaggaattaaacgggc
acccatactcccccaccccccttttgtaactaagtatgtgtgctcgtgatcttgactccc
acggaacggaccgatccgttggtgaacaaacagctaggtccacatcctcccttccct
gggagggccccgccctcccacatcctccccccagcctgacgtatcacaggctgtgt
gaagccccgcgaaagctgctcacgtggcaattgtgggtcccccctttcatcaagaca
ccaggtctcttcctccttaaggctagccccggcgtgtgaattcacgttgggcaactagtg
gtgtcactgtgcgctcccaatctcggccgcggagtgctgttcccaagccaaaccct
ggcccttcactatgtgcctggcaagcatatctgagaaggtgttccgctgtggctgccaa
cctggtgacaggtgcccagtgtgcgtaaccttcttccgtctccggacggtagtgattg
gttaagatttggtgtaaggttcatgtgccaacgccctgtgcgggatgaaacctctactg
ccctaggaatgccaggcaggtaccccacctccgggtgggatctgagcctgggctaat
tgtctacgggtagtttcatttccaatcctttatgtcggagtc |
| 29 | Hepatitis A Virus HA16 | ttcaagagggggtctccggagttttccggaaccccctcttggaagtccatggtgaggga
cttgatacctcaccgccgtttgcctaggctataggctaaatttccccttttccctgtccttccc
ctatttccttttgttttgtttgtaaatattaattcctgcaggttcagggttctt-
taatctgtttctc
tataagaacactcaattttttcacgctttctgtctcctttcttccagggctctccccttgccct
aggctctggccgttgcgcccggcggggtcaactccatgattagcatggagctgtagg
agtctaaattggggacgcagatgtttgggacgtcgccttgcagtgttaacttggctttca
tgaacctctttgatcttccacaaggggtaggctacgggtgaaacctcttaggctaatact
tcaatgaagagatggcttgataggtaacagcggcggatattggtgagttgttaaga
caaaaaccattcaacgccggaggactggctctcatccagtggatgcattgagggaatt
gattgtcagggctgtctctaggtttaatctcagacctctctgtgcttagggcaaaacactat
ttggccttaaatgggatcctgtgagaggggtccctccattgacagctggactgttctttt
ggggccttatgtggtgtttgcctctgaggtactcaggggcatttaggttttttcctcattctt
aaataata |
| 30 | Phopivirus | gggagtaaacctcaccaccgtttgccgtggtttacggctacctattttttggatgtaaatat
taattcctgcaggttcaggtctcttgaattatgtccacgctagtggcactctcttacccata
agtacgccttagcggaaccttttctacacttgatgtggttaggggttacattattttccctg
ggccttcttggccctttttccctgcactatcattcttttcttccggggctctcagcatgcca
atgttccgaccggtgcgcccgcgggggttaactccatggttagcatggagctgtagg
ccctaaaagtgctgacactggaactggactattgaagcatacactgttaactgaaacat
gtaactccaatcgatcttctacaaggggtaggctacgggtgaaaccccttaggttaata
ctcatattgagagatacttctgataggttaaggttgctggataatggtgagtttaacgaca |

TABLE 3-continued

Exemplary IRES sequences.

| SEQ ID NO: | IRES | Sequence |
|---|---|---|
| | | aaaaccattcaacagctgtgggccaacctcatcaggtagatgcttttggagccaagtg<br>cgtaggggtgtgtgtggaaatgcttcagtggaaggtgccctcccgaaaggtcgtagg<br>ggtaatcaggggcagttaggtttccacaattacaatttgaa |
| 31 | CVA10 | gctcttccgatctgggttgttcccaccccacagggcccactgggcgccagcactctgat<br>tccacggaatctttgtgcgcctgttttacaacccttcccaatttgtaacgtagaagcaata<br>cacactactgatcaatagtaggcatggcgcgccagtcatgtcatgatcaagcacttctg<br>ttcccccggactgagtatcaatagactgctcacgcggttgaaggagaaaacgttcgtt<br>acccggctaactacttcgagaaaacctagtagcaccatggaagctgcggagtgtttcgc<br>tcagcactttccccgtgtagatcaggtcgatgagtcactgcaatcccacgggcgacc<br>gtggcagtggctgcgttggcggcctgcctatggggcaacccataggacgctctaatg<br>tggacatggtgcgaagagtctattgagctagttagtagtcctccggcccctgaatgcg<br>gctaatcctaactgcggagcacatgccttcaacccaggaggtggtgtcgtaacgg<br>gtaactctgcagcggaaccgactactttgggtgtccgtgtttccttttatccttatattggc<br>tgcttatggtgacaatcacggaattgttgccatatagctattggattggccatccggtgtc<br>taacagagctattgtatacctatttgttggatttactcccctatcatacaaatctctgaaca<br>ctttgtgctttatactgaacttaaacacacgaaa |
| 32 | Enterovirus<br>C | ttaaaacagctctggggttgttcccaccccagaggcccacgtggcggccagtacacc<br>ggtaccacggtacccttgtacgcctgttttatactcccctcccgtaaactagaagcac<br>gaaacacaagttcaatagaaggggggtacagaccagtaccaccacgaacaagcactt<br>ctgttccccggtgaggtcacatagactgtccccacggtcaaaagtgactgatccgtta<br>tccgctcacgtacttcggaaagcctagtaccacccttggaatctacgatgcgttgcgctc<br>agcactcgaccccggagtgtagcttaggctgatgagtctgacgttccccactggtga<br>cagtggtccaggctgcgttggcggcctacctgtggtccaaaaccacaggacgctagt<br>agtgaacaaggtgtgaagagcccactgagctacctgagaatcctccggcccctgaat<br>gcggctaatcccaaccacggagcaggtaatcgcaaaccagcggtcagcctgtcgta<br>acgcgtaagtctgtggcggaaccgactactttgggtgtccgtgtttccttttattttatgg<br>tggctgcttatggtgacaatcatagattgttatcataaagcaaattggattggccatccg<br>gagtgagctaaactatctatttctctgagtgttggattcgtttcacccacattctgaacaat<br>cagcctcattagtgttaccctgttaataagacgatatcatcacg |
| 33 | Enterovirus<br>D | ttaaaacagctctggggttgttcccaccccagaggcccacgtggcggctagtactccg<br>gtaccccggtacccttgtacgcctgttttatactccctttcccaagtagttttagaagaaa<br>taaactaatgttcaacaggagggggtacaaaccagtaccaccacgaacacacacttct<br>gtttccccggtgaagttgcatagactgtacccacggttgaaagcgatgaatccgttacc<br>cgcttaggtacttcgagaagcctagtatcatccttggaatcttcgatgcgttgcgatcagc<br>actctaccccgagtgtagctttgggtcgatgagtctgacacccccacacggcgacgt<br>ggtccaggctgcgttggcggcctacccatggctagcaccatgggacgctagttgtga<br>acaaggtgcgaagagcctattgagctacctgagagtcctccggcccctgaatgcggc<br>taatcccaaccacggagcaaatgctcacaatccagtgagtggtttgtcgtaatgcgca<br>agtctgtggcggaaccgactactttgggtgtccgtgtttccttttattttattatggctgctt<br>atggtgacaatctgagattgttatcatatagctattggattagccatccggtgatatcttga<br>aattttgccataactttttcacaaatcctacaacattacactacactttctcttgaataattga<br>gacaactcata |
| 34 | Enterovirus<br>J | ttaaaatagcctcagggttgttcccaccctgagggcccacgtggtgtagtactctggta<br>ttacggtacctttgtacgcctatttttatacccccttccccaagtaatttagaagcaagcac<br>aaaccagttcagtagtaagcagtacaatccagtactgtaatgaacaagtacttctgttac<br>cccggaagggtctatcggtaagctgtacccacggctgaagaatgacctaccgttaac<br>cggctacctacttcgagaagcctagtaatgccgttgaagttttattgacgttacgctcag<br>cacactacccgtgtgtagtttggctgatgagtcacggcactccccacgggcgaccg<br>tggccgtggctgcgttggcggcaaccaaggagtgcaagctccttggacgtcatatta<br>cagacatggtgtgaagagcctattgagctaggtggtagtcctccggcccctgaatgcg<br>gctaatcctaactccggagcatatcggtgcgaaccagcacttggtgtgttgtaatacgt<br>aagtctggagcggaaccgactactttgggtgtccgtgtttcctgttttaacttttatggctg<br>cttatggtgacaatttaacattgttaccatatagctgttgggttggccatccggattttgtta<br>taaaaccatttcctcgtgccttgacctttaacacatttgtgaacttctttaaatccttttatta<br>gtccttaaatactaaga |
| 35 | Human<br>Pegivirus 2 | aactgttgttgtagcaatgcgcatattgctacttcggtacgcctaattggtaggcgcccg<br>gccgaccggccccgcaagggcctagtaggacgtgtgacaatgccatgagggatcat<br>gacactggggtgagcggaggcagcaccgaagtcgggtgaactcgactcccagtgc<br>gaccacctggcttggtcgttcatggagggcatgcccacgggaacgctgatcgtgcaa<br>agggatgggtccctgcactggtgccatgcgcggcaccactccgtacagcctgatag<br>ggtggcggcgggccccccagtgtgacgtccgtgggagcgcaac |
| 36 | GBV-C<br>GT110 | tgacgtggggggggttgatTTTccccccccggcactgggtgcaagcccccagaaac<br>cgacgcctatctaagtagacgcaatgactcggcgccgactcggcgaccggccaaaa<br>ggtggtggatgggtgatgacagggttggtaggtcgtaaatcccggtcatcctggtagc<br>cactataggtgggtcttaagagaaggtcaagattcctcttacgcctgcggcgagaccg<br>cgcacggtccacaggtgttggccctaccggtgtgaataagggcccgacatcaggc |
| 37 | GBV-C<br>K1737 | gacgtggggggggttgatcccccccccTTTggcactgggtgcaagcccccagaaacc<br>gacgcctatttaaacagacgttaagaaccggcgccgactcggcgaccggccaaaa<br>ggtggtggatgggtgatgccaggggttggtaggtcgtaaatcccggtcatcttggtagc |

TABLE 3-continued

Exemplary IRES sequences.

| SEQ ID NO: | IRES | Sequence |
|---|---|---|
| | | cactataggtgggtcttaagggttggttaaggtccctctggcgcttgtggcgagaaag<br>cgcacggtccacaggtgttggccctaccggtgtgaataagggcccgacgtcaggct<br>cgtcgttaaaccgagcccactacccacctgggcaaacaacgcccacgtacggtcca<br>cgtcgcccttcaatgtctctcttgaccaataggcttagccggcgagttgacaaggacca<br>gtgggggctgggcggtaggggaaggaccccctgccgctgcccttcccggtggagtg<br>ggaaatgc |
| 38 | GBV-C<br>Iowa | tgacgtggggggggttgatccGcccccccccggcactCggtgcaagcccccataaacc<br>gacgcctatctaagtagacgcaatgactcggcgccgactcggcgaccggccaaaag<br>gtggtggatgggtggtgacaggggttggtaggtcgtaaatcccggtcatcctggtagcc<br>actataggtgggtcttaagagaaggtcaagactcctcttgtgcctgcggcgagaccgc<br>gcacggtccacaggtgctggccctaccggtgtgaataagggcccgacgtcaggctc<br>gtcgttaaaccgagcccgtcacccacctgggcaaacgacgcccacgtacggtccac<br>gtcgcccttca |
| 39 | Pegivirus A<br>1220 | tgtagcaatgcgcatattgctacttcggtacgcctaattggtaggcgcccggccgacc<br>ggccccgcaagggcctagtaggacgtgtgacaatgccatgcgggatcatgacactg<br>gggtgagcggaggcagcaccgaagtcgggtgaactcgactcccagtgcgaccacc<br>tggcttggtcgttcatggagggcatgcccacgggaacgctgatcgtgcaaagggatg<br>ggtccctgcactggtgccatgcgcggcaccactccgtacagcctgatagggtggcg<br>gcgggccccccagtgtgacgtccgtggagcgcaac |
| 40 | Pasivirus A<br>3 | attttctggccgtgtagctgcttttgaccagtggctctggttacttagccaaatcccccctt<br>ccttcacccttttaaatttgatggtctgtgttgtttgttttgtcttgtctaaataatatataagat<br>cctccccgccgatacagacctcgacagtctggtgtaggagggttggtgttattaatttgc<br>cccagaagagtgaccgtgacacatagaaaccatgagtacatgtgtatccgtggagga<br>tcgcccgggactggattccatatcccattgccatcccaacaagcggagggtatacccca<br>ctatgtgcgcgtttgcagtgggaatctgcaaatttagtcatactgcctgatagggtgtgg<br>gcctgcactctggggtactcaggctgttcatataat |
| 41 | Sapelovirus | cccctccacccttaaggtggttgtatcccacataccccaccctcccttccaaagtggac<br>ggacaactggattttgactaacggcaagtctgaatggtatgatttggatacgtttaaacg<br>gcagtagcgtggcgagctatggaaaaatcgcaattgtcgatagccatgttagtgacgc<br>gcttcggcgtgctcctttggtgattcggcgactggttacaggagagtaggcagtgagc<br>tatgggcaaacctctacagtattacttagagggaatgtgcaattgagacttgacgagcg<br>tctctttgagatgtggcgcatgctcttggcattaccatagtgagcttccaggttgggaaa<br>cctggactgggcctatactacctgatagggtcgcggctggccgcctgtaactagtata<br>gtcagttgaaaccccccc |
| 42 | Rosavirus B | gtctcttagtgtctatgcttcagagagcggtgaactgacaccgttgcttcttgcacagc<br>ccttcgtgccggtctttccggttctcgacagcgttgggcatcatggctagttaggctaag<br>atagtggatgatctagtgaacagttttggattgtttggagtttttgtagcgatgctagtagtg<br>tgtgtggacctccccacgtggtaacacgtgccccacaggccaaaagccaaggtgttg<br>aaagcaccccactagtcccagactcacccatctgggaactcctctcatgaaaaatctt<br>agtaacttttgattcggctattcatcaacctctctagtcaagggctgaaggatgcccgga<br>aggtacccgcaggtaacgataagctcactgtgatctgatccggggctttggtgcgac<br>cgtctgtccggcgtagccagagttaaaaaacgtctaggcccttccaccccaagggatt<br>gggggtttcccaatcatttgaaagttcact |
| 43 | Bakunsa<br>Virus | ttttgaacgccacctcggagcgatatccggggaccccctccccttttttcttcctaccttc<br>ttcccaaatttccctcttcccttgttattttggtttggatttcctggacatgactcggacgga<br>tctatctcatttgctttgtgtctgctccaccagtggcatggtcgaaagatcatcaacactg<br>gacgtgtactgtaatggccaaacgtgcccacaggggaaaccatgccggtcgctgtag<br>cggcgggtggacgtggtggacccctctccctgctcataaactttgggtaggtgaagg<br>gttcaagcgacgcttgccgtgagggcgcatccggatggtgggaaccaacaaactag<br>gctgtaatggccgacctcaggtggatgagctagggctgctgcaccaaaagggactc<br>gattcgatatcccggcctggtagcctagtcagtggactcgtagttgggaatctacga<br>ctggcctagtacagggtgatagccccgtttcccacgcccacctgttgtagggacaccc<br>ccccc |
| 44 | Tremovirus<br>A | tttgaaagaggcctccggagtgtccggaggctctcttttcgacccaacccatactgggg<br>ggtgtgtgggaccgtacctggagtgcacggtatatatgcattcccgcatggcaaggg<br>cgtgctaccttgcccttgacgcatggtatgcgtcatcatttgccttggttaagcccata<br>gaaacgaggcgtcacgtgccgaaaatcccttttgcgtttcacagaaccatcctaaccat<br>gggtagtagtgggaatcgtgtatgggatgattaggatctctcgtagagggataggt<br>gtgccattcaaatccagggagtactctggctctgacattgggacatttgatgtaaccgg<br>acctggttcagtatccggggttgtcctgtattgttacggtgtatccgtcttggcacactgaa<br>agggtattttgggtaatcctttcctactgcctgatagggtggcgtgcccggccacgag<br>agattaagggtagcaatttaaac |
| 45 | Swine<br>Pasivirus 1 | gcttttgaccagtggctctgggttacttagccaagtcccttttctcttattttcactagtttatg<br>ttgtgtgttgtctgttttgtttttgtttaaattgtatacaagatcctttcccgccgacacagacct<br>cgacagtctggtgtaggagggttggtgatattaatttgccccaaaagagtgaccgtgat<br>acgtggaaaccatgagtacatgtgtatccgtggaggatcgcccgggactggattccat<br>atcccattgccatcccaacaaacggagggtatacccaccacgtgcgcgtttgcagtg |

TABLE 3-continued

Exemplary IRES sequences.

| SEQ ID NO: | IRES | Sequence |
|---|---|---|
| | | ggaatctgcaaatttagtcatactgcctgatagggtgtgggcctgcactttggggtactc aggctgttcatataat |
| 46 | PLV-CHN | acatggggtatgttgtctgtcctgttttgttgaaacaatatataagatccttccgccgata tagacctcgacagtctagtgtaggaggattggtgatagtaacttgccccagaagagtg accgtgacacatagaaaccatgagtacatgtgtatccgtggaggatcgcccgggact ggattccatatcccattgccatcccaacaaacggagggtatacccactatgtgcgcgtt tgcagtgggagcctgcaaatttagtcatactgcctgatagggtgtgggcctgcactctg gggtactcaggctgtttatataat |
| 47 | Pasivirus A (longer) | tgaaaaagtggttgtgcagctggattttccggctgtgcaactgcttttgaccagtggctc tgggttacttagccaaattcctttcccttatccctattggtttgtgttgtgtgttgtttgttttgt tttgtcttaactatatacaagatccttcccgccgatacagacctcgacagtctggtgtag gaggggttggtgttattaatttgccccaaaagagtgaccgtgacacgtggaaaccatga gtacatgtgtatccgtggaggatcgcccgggactggattccatatcccattgccatccc aacaaacggagggtatacccaccacgtgcgcgtttgcagtgggaatctgcaaatttag tcatactgcctgatagggtgtgggcctgcacttggggtactcaggctgtttatataat |
| 48 | Sicinivirus | gtgtcattaaggtgtgtttggaagttcgaattagctggtttgtggtgattagtagaccccc tggaggtacccaattcggatctgaccagggacccgtgactataccgctccggtaattc gggtttaaaacaatgaacgtcaccacacaattacttttctcattttatttttcatcattgtcttc ctatttaccgattacactcgatttccttggatgttcctggagatttccctggttacctggac cctcattattgttgttgtttcacccagcgagctgtcccaattgcttattatttgcgcttacaa cttcgtcctaatattttttctggttgatcgggttgattgagctcccgggctatcctgccattc aac |
| 49 | Hepacivirus K | gggaacaatggtccgtccgcggaacgactctagccatgagtctagtacgagtgcgtg ccacccattagcacaaaaaccactgactgagccacacccctcccggaatcctgagta caggacattcgctcggacgacgcatgagcctccatgccgagaaaattgggtatacc acgggtaaggggtggccaccagcgggaatctgggggctggtcactgactatggta cagcctgataggatgctgccgcagcgtcagtggatatgcggctgttcatggaac |
| 50 | Hepacivirus A | acctccgtgctaggcacggtgcgttgtcagcgttttgcgcttgcatgcgctacacgcgt cgtccaacgcggagggaacttcacatcaccatgtgtcactcccccctatgagggttcc acccccgcttacacggaaatgggttaaccataccaaagtacggggtatgcgggtcctc ctagggcccccccggcaggtcgagggagctggaattcgtgaattcgtgagtacacg aaaatcgcggcttgaacgtctttgaccttcggagccgaaatttgggcgtgccccacga aggaaggcgggggcggtgttgggccgccgccccctttatcccacggtctgatagga tgcttgcgagggcacctgccggtctcgtagaccataggac |
| 51 | BVDV1 | gtatacgagaatttgcctaggacctcgtttacaatatgggcaatctaaaattataattagg cctaagggacaaatcctcctcagcgaaggccgaaaagaggctagccatgcccttagt aggactagcaaaataaggggggtagcaacagtggtgagtcgttggatggctgaag ccctgagtacaggggtagtcgtcagtggttcgacgcttcggaggacaagcctcgagat accacgtggacgagggcatgcccacagcacatcttaacctggacggggtcgttca ggtgaaaacggtttaaccaaccgctacgaatacagcctgataggtgctgcagaggc ccactgtattgctactgaaaatctctgctgtacatggcac |
| 52 | Border Disease Virus | gtatacgggagtagctcatgcccgtatacaaaattggatattccaaaactcgattgggtt agggagccctcctagcgacggccgaaccgtgttaaccatacacgtagtaggactag cagacgggaggactagccatcgtggtgagatccctgagcagtctaaatcctgagtac aggatagtcgtcagtagttcaacgcaggcacggttctgccttgagatgctacgtggac gagggcatgcccaagacttgctttaatctcggcgggggtcgccgaggtgaaaacac ctaacggtgttggggttacagcctgataggtgctgcagaggcccacgaataggcta gtataaaaatctctgctgtacatggcac |
| 53 | BVDV2 | gtatacgagattagctaaagtactcgtatatggattggacgtcaacaaatttttaattggc aacgtagggaaccttcccctcagcgaaggccgaaaagaggctagccatgcccttag taggactagcaaaagtaggggggactagcggtagcggtgagttcgttggatggccga accccctgagtacaggggagtcgtcaatggttcgacactccattagtcgaggagtctcg agatgccatgtggacgagggcatgcccacggcacatcttaacccatgcgggggttg catgggtgaaagcgctaatcgtggcgttatggacacagcctgataggtgtagcaga gacctgctattccgctagtaaaaaactctgctgtacatggcac |
| 54 | CSFV-PK15C | gtatacgaggttagttcattctcgtatgcattattggacaaatcaaaattttcaatttggttca gggcctcctccagcgacggccgaactgggctagccatgcccatagtaggactagc aaacggagggactagccgtagtggcgagctccctgggtcttctaagtcctggataca ggacagtcgtcagtagttcgacgtgagcagaagcccacctcgagatgctatgtggac gagggcatgcccaagacgcaccttaaccctagcgggggtcgctagggtgaaatcac accacgtgatgggagtccgacctgataggtgctgcagaggctcactattaggctagt ataaaaatctctgctgtacatggcac |
| 55 | SF573 Dicistrovirus | aaaaccgaccccagagatcagaaagtcgttgacgcgatcttttattagaggacgttgc gctggcgcgagctttaattagcagacgccaaaaataaacaacaaaatgctgatcgcg agacttaattgtcagacgattggccaaatcgatgtgatctttgctgctcccagattgcc gaaataggagtagtag |

TABLE 3-continued

Exemplary IRES sequences.

| SEQ ID NO: | IRES | Sequence |
|---|---|---|
| 56 | Hubei Picorna-like Virus | ccccaaaaccccccccttaaactcaacactgtagtggattcattttccgttgcaaaacaa aacattactacccgcatttatgtaggctctgtgttttctatgcgaccgttacattaatctcta ctctgacccactagtttataaaaccgaagacctgaatgaaacgattttccttcttttcaac ctctaacgaacctctgacggcttgagaaacctgaagttagtaattatgtgtttaaaagaaag gaaagtcaaacgcgatgactcttacatccctattccataccgttgctccacaatgtgag cgatgcgaggtcgggactgcagtattagggggaacgagctcatggagagttaattat ctctcccctcctacgggagtctcatgtgagctgtagaaaagcggttggcacctctcgtta cctcgcctgtacatgatcc |
| 57 | CRPV | aaaagcaaaaatgtgatcttgcttgtaaatacaattttgagaggttaataaattacaagta gtgctattttttgtatttaggttagctatttagctttacgttccaggatgcctagtggcagcc cacaatatccaggaagccctctctgcggttttcagattaggtagtcgaaaaacctaag aaatttacct |
| 58 | Salivirus A BN5 | tttcctcctttcgaccgccttacggcaggcgggtccgcggacggcttcggcctacccg cgacaagaatgccgtcatctgtccttatcacccatattctttcccttcccccgcaaccatc acgcttactcgcgcacgtgttgagtggcacgtgcgttgtccaaacagttacactcacac ccttggggcgggtttgtcccgccctcgggttcctcgcggaaccctccctcttctctctcc cttctatccgccttcactttccataactacagtgctttggtaggtaagcatcctgaccc ccgcggaagctgccaacgtggcaactgtggggatccaggcaggttatcaaaggcac ccggtctttccgccttcaggagtatccctgccggtgaattccgacagggctctgcttgg tgccaaccccccccaaatgcgcgctgcgggagtgctcttccccaactcatcttagtaac ctctcatgtgtgtgcttggtcagcatatctgaggcgacgttccgctgtcccagaccagt ccagcaatggacgggccagtgtgcgtagtcgctttccggtttccggccgcatgtttgg cgaaacgctgaggtaaggttggtgtgcccaatgcccgtaatttggtgacacctcaaga ccacccaggaatgccagggaggtaccccacttcggtgggatctgaccctgggctaat tgtctacggtggttcttcttgcttccacttctctttttctggcatg |
| 59 | Salivirus A BN2 | tatggcaggcgggcttgtggacggcttcggcccacccacagcaagaatgccatcatc tgtcctcaccccatgtttccctttctttccctgcaaccgttacgcttactcgcaggtgc atttgagtggtgcacgtgttgaataaacagctacactcacatgggggcgggttttcccg ccctgcggcctctcgcgaggccacccctcccttcctcccataactacagtgctttgg taggtaagcatcctgatcccccgcggaagctgctcacgtggcaactgtggggaccca gacaggttatcaaaggcacccggtctttccgccttcaggagtatccctgctagtgaatt ctagtagggctctgcttggtgccaacctcccccaaatgcgcgctgcgggagtgctctt ccccaactcaccctagtatcctctcatgtgtgtgcttggtcagcatatctgagacgatgtt ccgctgtcccagaccagtccagtaatggacgggccagtgtgcgtagtcgtcttccgg ctttttccggcgcatgtttggtgaaccggtggggtaaggttggtgtgcccaacgcccgt actttggtgatacctcaagaccacccaggaatgccagggaggtaccccgcttcacag cgggatctgaccctgggctaattgtctacggtggttcttcttgcttccacttctttctactgt tc |
| 60 | Salivirus A 02394 | tttcgaccgccttatggcaggcgggcttgtggacggcttcggcccacccacagcaag aatgccatcatctgtcctcaccccatttctccctccttcccctgcaaccattacgctta ctcgcatgtgcattgagtggtgcacgtgttgaacaaacagctacactcacgtggggc gggttttcccgcccttcggcctctcgcgaggccaccccttcccctcctcccataacta cagtgctttggtaggtaagcatcctgatcccccgcggaagctgctcgcgtggcaactg tggggacccagacaggttatcaaaggcacccggtctttccgcctccaggagtatccct gctagtgaattctagtggggctctgcttggtgccaacctcccccaaatgcgcgctgcg ggagtgctcttccccaactcaccctagtatcctctcatgtgtgtgcttggtcagcatatct gagacgatgttccgctgtcccagaccagtccagcaatggacgggccagtgtgcgta gtcgtcttccggcttgtccggcgcatgtttggtgaaccggtggggtaaggttggtgtgc ccaacgcccgtactttggtgacaactcaagaccacccaggaatgccagggaggtac ccgcctcacggcggatctgaccctgggctaattgtctacggtggttcttcttgcttcc atttcttcttctgttc |
| 61 | Salivirus A GUT | tatggcaggcgggcttgtggacggtttcggcccacccacagcaagaatgccatcatc tgtcctcaccccaatttttcctttcttccctgcaatcatcacgcttactcgcatgtgcatt gagtggtgcatgtgttgaacaaacagctacactcacatggggcgggttttcccgccc tacggcctctcgcgaggccaccctttccctcccttataactacagtgctttggcagg taagcatcctgatcccccgcggaagctgctcacgtggcaactgtggggacccagac aggttatcaaaggcacccggtctttccgccttcaggagcatccccactagtgaattcta gtggggctctgcttggtgccaacctcccccaaatgcgcgctgcgggagtgctcttccc caacccatcctagtatcctctcatgtgtgtgcttggtcagcatatctgagacgacgttcc gctgtcccagaccagtccagtaatggacgggccagtgtgcgtagtcgtcttccggctt gtccggcgcatgtttggtgaaccggtggggtaaggttggtgtgcccaacgcccgtact ttggtgacacctcaagaccacccaggaatgccagggaggtaccccgcctcacggcg gatctgaccctgggctaattgtctacggtggttcttcttgcttccacttctttctt |
| 62 | Salivirus A CH | ttctcctgcaaccattacgcttaatcgcatgtgcattgagtggtgcatgtgttgaacaaac agctacaatcacatggggcgggttttcccgcccacggcttctcgcgaggcccatc cctcccttttctcccataactacagtgctttggtaggtaagcatcccgatctcccgcgga agctgctcacgtggcaactgtggggacccagacaggttatcaaaggcacccggtctt tccgccttcaggagtatccctgctagcgaattctagtaggggctctgcttggtgccaacct ctcccaaatgcgcgctgcgggagtgctcttccccaaatcacccagtatcctctcatgt |

TABLE 3-continued

Exemplary IRES sequences.

| SEQ ID NO: | IRES | Sequence |
|---|---|---|
|  |  | gtgtgcctggtcagcatatctgagacgatgttccgctgtcccagaccagtccagtaatg gacgggccagtgtgcgtagtcgtcctccggcttgtccggcgcatgtttggtgaaccgg tggggtaaggttggtgtgcccaacgcccgtaatcaggggatacctcaaggcaccca ggaatgccagggaggtatcccgcctcacagcgggatctgaccctggggtaaatgtct gcgggggtcctcttggcccaattctcagtaattttcagg |
| 63 | Salivirus A SZ1 | tctgtcctcaccccatcttcccttctttcctgcaccgttacgcttactcgcatgtgcattga gtggtgcacgtgcttgaacaaacagctacactcacatgggggcgggttttcccgccct gcggcctctcgcgaggcccaccccctccccttcctcccataactacagtgctttggtag gtaagcatcctgatccccgcggaagctgctcacgtggcaactgtggggacccaga caggttatcaaaggcaccggtctttccgccttcaggagtatccctgctagtgaattcta gtagggctctgcttggtgccaacctcccccaaatgcgcgctgcgggagtgctcttccc caactcaccctagtatcctctcatgtgtgtgcttggtcagcatatctgagacgatgttccg ctgtcccagaccagtccagtaatggacgggccagtgtgcgtagtcgtcttccggcttg tccggcgcatgtttggtgaaccggtggggtaaggttggtgtgcccaacgcccgtactt tggtgatacctcaagaccacccaggaatgccagggaggtaccccgcttcacagcgg gatctgaccctgggctaattgtctacggtggttcttcttgcttccacttctttctactgttcat g |
| 64 | Salivirus FHB | acatgggggtctgcggacggcttcggcccacccgcgacaagaatgccgtcatctg tcctcattacccgtattccttccctctccccgcaaccaccacgcttactcgcgcacgtgtt gagtggcacgtgcgttgtccaaacagctacacccacaccctttcggggcgggtttgtc ccgccctcgggttcctcgcggaaccccccctccctctctctctttctatccgccctcac ttcccataactacagtgctttggtaggtgagcaccctgaccccccgcggaagctgcta acgtggcaactgtggggatccaggcaggttatcaaaggcaccggtctttccgccac aggagtatctctgccggtgaattccggtagggctctgcttggtgccaacctcccccaa atgcgcgctgcgggagtgctcttcccaactcatcttagtaacctctcatgtgtgtgcttg gtcagcatatctgaggcgacgttccgctgtcccagaccagtccagcaatggacggg ccagtgtgcgtagtcgctttccggttttccggcgcatgtttggcgaaacgctgaggtaa ggttggtgtgcccaacgcccgtaatttggtgatacctcaagaccacccaggaatgcca gggaggtaccccacttcggtgggatctgaccctgggctaattgtctacggtggttcttc ttgcttccacttctctttttctggcatg |
| 65 | CVB3 | ttaaaacagcctgtgggttgatcccacccacaggcccattgggcgctagcactctggt atcacggtacctttgtgcgcctgttttataccccctcccccaactgtaacttagaagtaac acaccgatcaacagtcagcgtggcacaccagccacgttttgatcaagcacttctgtt accccggactgagtatcaatagactgctcacgcggttgaaggagaaagcgttcgttat ccggccaactacttcgaaaaacctagtaacaccgtggaagttgcagagtgtttcgctc agcactaccccagtgtagatcaggtcgatgagtcaccgcattcccacgggcgaccg tggcggtggctgcgttggcggcctgcccatggggaaacccatgggacgctctaatac agacatggtgcgaagagtctattgagctagttggtagtcctccggcccctgaatgcgg ctaatcctaactgcggagcacacacccctcaagccagaagggcagtgtgtcgtaacgg gcaactctgcagcggaaccgactactttgggtgtccgtgtttcattttattcctatactgg ctgcttatggtgacaattgagagatcgttaccatatagctattggattggccatccggtg actaatagagctattatatatcccttttgtgggtttataccacttagcttgaaagaggttaa aacattacaattcattgttaagttgaatacagcaaa |
| 66 | CVB1 | ttaaaacagcctgtgggttgttcccacccacaggcccattgggcgctagcactctggt atcacggtacctttgtgcgcctgttttacatcccctcccccaaattgtaatttagaagtttca cacaccgatcattagcaagcgtggcacaccagccatgttttgatcaagcacttctgtta cccggactgagtatcaatagacgctaacgcggtgaaggagaaaacgttcgttac ccggccaactacttcgaaaaacctagtaacaccatggaagttgcggagtgtttcgctc agcactaccccagtgtagatcaggtcgatgagtcaccgcgttcccacgggcgacc gtggcggtggctgcgttggcggcctgcctacggggaaacccgtaggacgctctaat acagacatggtgcgaagagtctattgagctagttggtaatcctccggcccctgaatgc ggctaatcctaactgcggagcacataccctcaaaccaggggcagtgtgtcgtaacg ggcaactctgcagcggaaccgactactttgggtgtccgtgtttcattttattcctatactg gctgcttatggtgacaattgacaggttgttaccatatagttattggattggccatccggtg actaacagagcaattatatatctctttgagggtttataccacttagcttgaaagaggttaa aacactacatctcatcattaaactaaatacaacaaa |
| 67 | Echovirus 7 | ttaaaacagcctgtgggttgttcccacccacagggcccattgggcgtcagcaccctgg tatcacggtacctttgtgcgcctgttttatatcccttcccccaattgtaacttagaagaaac acaccgatcaacagcaagcgtggcacaccagccatgttttggtcaagcacttctgt taccccggactgagtatcaatagactgctcacgcggttgaaggagaaagcgtccgtta tccggccagctacttcgagaaacctagtaacaccatggaagttgcggagtgtttcgct cagcactaccccagtgtagatcaggtcgatgagtcaccgcctttcccacgggcgacc gtggcggtggctgcgttggcggcctgcctatggggaacccataggacgctctaata cagacatggtgcgaagagtctattgagctagctggtattcctccggcccctgaatgcg gctaatcctaactgtggagcacatgccctaatccaagggtagtgtgtcgtaatgag caattccgcagcggaaccgactactttgggtgtccgtgtttcctcttattcttgtactggct gcttatggtgacaattgagagattgttaccatatagctattggattggccatccggtgact aatagagctattgtgtatctctttgttggatttgtaccacttaatttgaaagaaatcaggac actacgctacattttactattgaacaccgcaaa |

TABLE 3-continued

Exemplary IRES sequences.

| SEQ ID NO: | IRES | Sequence |
|---|---|---|
| 68 | CVB5 | ttaaaacagcctgtgggttgtacccacccacagggcccactgggcgctagcactctg gtatcacggtaccttttgtgcgcctgttttatgccccctccccaattgaaacttagaagtt acacacaccgatcaacagcgggcgtggcataccagccgcgtcttgatcaagcactc ctgtttcccggaccgagtatcaatagactgctcacgcggttgaaggagaaaacgttc gttacccggctaactacttcgagaaacctagtagcatcatgaaagttgcgaagcgtttc gctcagcacatccccagtgtagatcaggtcgatgagtcaccgcattccccacgggcg accgtggcggtgctgcgttggcggcctgcctacggggcaacccgtaggacgcttc aatacagacatggtgcgaagagtcgattgagctagttagtagtcctccggcccctgaa tccggctaatcctaactgcggagcacataccctcaacccaggggcattgtgtcgtaa cgggtaactctgcagcggaaccgactactttgggtgtccgtgtttccttttattcttataat ggctgcttatggtgacaattgaaagattgttaccatatagctattggattggccatccggt gtctaacagagctattatatacctctttgttggatttgtaccacttgatctaaaggaagtca agacactacaattcatcatacaattgaacacagcaaa |
| 69 | EVA71 | ttaaaacagcctgtgggttgcacccactcacagggcccactgggcgcaagcactctg gcacttcggtaccttttgtgcgcctgttttatatcccctcccccaatgaaatttagaagcag caaaacccgatcaatagcaggcataacgcttccagttatgtcttgatcaagcacttctgtt tccccggactgagtatcaatagactgctcacgcggttgaaggagaaaacgttcgttat ccggctaactacttcggaaagcctagtaacaccatggaagttgcggagagtttcgttc agcacttcccagtgtagatcaggtcgatgagtcaccgcattccccacgggcgaccg tggcggtggctgcgttggcggcctgcccatggggtaacccatgggacgctctaatac ggacatggtgtgaagagtctactgagctagttagtagtcctccggcccctgaatgcgg ctaatcccaactgcggagcacacgcccacaagccagtgggtagtgtgtcgtaacgg gcaactctgcagcggaaccgactactttgggtgtccgtgtttccttttattcttatgttggc tgcttatggtgacaattaaagagagttaccatatagctattggattggccatccggtgtg caacagagcgatcgtttacctatttattggttttgtaccattgacactgaagtctgtgatca cccttaatttatcttaaccctcaacacagccaaac |
| 70 | CVA3 | ttaaaacagcctgtgggttgtacccacccacagggcccactgggcgctagcacactg gtattacggtaccttttgtgcgcctgttttatacccccccaacctcgaaacttagaagtaa agcaaacccgatcaatagcaggtgcggcgcaccagtcgcatcttgatcaagcacttct gtaaccccggaccgagtatcaatagactgctcacgcggttgaaggagaaaacgttcg ttacccggctaactacttcgagaaaccagtagcatcatgaaagttgcagagtgtttcg ctcagcactaccccgtgtagatcaggccgatgagtcaccgcacttccccacgggcg accgtggcggtgctgcgttggcggcctgcctatggggcaacccataggacgctcta atacgacatggtgcgaagagtctattgagctagttagtagtcctccggcccctgaatg cggctaatcctaactgcggagcacatacccttaatccaaagggcagtgtgtcgtaacg ggtaactctgcagcggaaccgactactttgggtgtccgtgtttccttttaattttttactggc tgcttatggtgacaattgaggaattgttgccatatagctattggattggccatccggtga ctaacagagctattgtgttccaatttgttggatttaccccgctcacactcacagtcgtaag aacccttcattacgtgttatttctcaactcaagaaa |
| 71 | CVA12 | ttaaaacagcctgtgggttgtacccacccacagggcccactgggcgctagcactctg gtactacggtaccttttgtgtgcctgttttaagcccctaccccccactcgtaacttagaag gcttctcacactcgatcaatagtaggtgtggcacgccagtcacaccgtgatcaagcac ttctgttaccccggtctgagtaccaataagctgctaacgcggctgaagggggaaaacga tcgttatccggctaactacttcgagaaacccagtaccaccatgaacgttgcagggtgtt tcgctcggcacaaccccagtgtagatcaggtcgatgagtcaccgtattccccacggg cgaccgtggcggtggctgcgttggcggcctgcccatggggtgacccatggacgct ctaatactgacatggtgcgaagagtctattgagctagttagtagtcctccggcccctga atgcggctaatcctaactgcggagcacatacccttaatccaaagggcagtgtgtcgta acgggcaactctgcagcggaaccgactactttgggtgtccgtgtttccttttattcttaca ttggctgcttatggtgacaattgaaagttgttaccatatagctattggattggccatccg gtgacaaatagagctattgtatatcttttgttggttacgtaccccttaattacaaagtggtt tcaactttgaaatacatcctaacactaaattgtagaaa |
| 72 | EV24 | ttaaaacagcctgtgggttgcacccacccacagggcccacagggcgctagcactctg gtatcacggtaccttgtgcgcctgttttattaccccttccccaattgaaaattagaagca atgcacaccgatcaacagcaggcgtggcgcaccagtcacgtctcgatcaagcacttc tgtttcccggaccgagtatcaatagactgctcacgcggttgaaggagaaagtgttcgt tatccggctaaccacttcgagaaacccagtaacaccatgaaagttgcagggtgtttcg ctcagcacttcccagtgtagatcaggtcgatgagtcaccgcgttcccacgggcga ccgtggcggtggctgcgttggcggcctgcctatgggttaacccataggacgctctaat acagacatggtgcgaagagtttattgagctggttagtatccctccggcccctgaatgcg gctaatcctaactgcggagcacgtgcctccaatccaggggggttgcatgtcgtaacgg gtaactctgcagcggaaccgactactttgggtgtccgtgtttccttttattcttatactggc tgcttatggtgacaatcgaggaattgttaccatatagctattggattggccatccggtgtc taacagagcgattatatacctctttgttggatttatgcagctcaataccaccaactttaaca cattgaaatatatcttaaagttaaacacagcaaa |

In some embodiments, an IRES of the invention is an IRES having a sequence as listed in Table 3 (SEQ ID NO: 1-72). In some embodiments, an IRES is a Salivirus IRES. In some embodiments, an IRES is a Salivirus SZ1 IRES.

TABLE 4

Anabaena permutation site 5' intron fragment sequences.

| SEQ ID NO. | Permutation site | Sequence |
|---|---|---|
| 73 | L2-1 | GAAGAAATTCTTTAAGTGGATGCTCTCAAACTCAGG<br>GAAACCTAAATCTAGTTATAGACAAGGCAATCCTG<br>AGCCAAGCCGAAGTAGTAATTAGTAAGTTAACAAT<br>AGATGACTTACAACTAATCGGAAGGTGCAGAGACT<br>CGACGGGAGCTACCCTAACGTCAAGACGAGGGTAA<br>AGAGAGAGTCCAATTCTCAAAGCCAATAGGCAGTA<br>GCGAAAGCTGCAAGAGAATGAAAATCCGT |
| 74 | L2-2 | AAGAAATTCTTTAAGTGGATGCTCTCAAACTCAGGG<br>AAACCTAAATCTAGTTATAGACAAGGCAATCCTGA<br>GCCAAGCCGAAGTAGTAATTAGTAAGTTAACAATA<br>GATGACTTACAACTAATCGGAAGGTGCAGAGACTC<br>GACGGGAGCTACCCTAACGTCAAGACGAGGGTAAA<br>GAGAGAGTCCAATTCTCAAAGCCAATAGGCAGTAG<br>CGAAAGCTGCAAGAGAATGAAAATCCGT |
| 75 | L2-3 | AGAAATTCTTTAAGTGGATGCTCTCAAACTCAGGGA<br>AACCTAAATCTAGTTATAGACAAGGCAATCCTGAGC<br>CAAGCCGAAGTAGTAATTAGTAAGTTAACAATAGA<br>TGACTTACAACTAATCGGAAGGTGCAGAGACTCGA<br>CGGGAGCTACCCTAACGTCAAGACGAGGGTAAAGA<br>GAGAGTCCAATTCTCAAAGCCAATAGGCAGTAGCG<br>AAAGCTGCAAGAGAATGAAAATCCGT |
| 76 | L5-1 | GTTATAGACAAGGCAATCCTGAGCCAAGCCGAAGT<br>AGTAATTAGTAAGTTAACAATAGATGACTTACAACT<br>AATCGGAAGGTGCAGAGACTCGACGGGAGCTACCC<br>TAACGTCAAGACGAGGGTAAAGAGAGAGTCCAATT<br>CTCAAAGCCAATAGGCAGTAGCGAAAGCTGCAAGA<br>GAATGAAAATCCGT |
| 77 | L5-2 | TTATAGACAAGGCAATCCTGAGCCAAGCCGAAGTA<br>GTAATTAGTAAGTTAACAATAGATGACTTACAACTA<br>ATCGGAAGGTGCAGAGACTCGACGGGAGCTACCCT<br>AACGTCAAGACGAGGGTAAAGAGAGAGTCCAATTC<br>TCAAAGCCAATAGGCAGTAGCGAAAGCTGCAAGAG<br>AATGAAAATCCGT |
| 78 | L5-3 | TATAGACAAGGCAATCCTGAGCCAAGCCGAAGTAG<br>TAATTAGTAAGTTAACAATAGATGACTTACAACTAA<br>TCGGAAGGTGCAGAGACTCGACGGGAGCTACCCTA<br>ACGTCAAGACGAGGGTAAAGAGAGAGTCCAATTCT<br>CAAAGCCAATAGGCAGTAGCGAAAGCTGCAAGAGA<br>ATGAAAATCCGT |
| 79 | L5-4 | ATAGACAAGGCAATCCTGAGCCAAGCCGAAGTAGT<br>AATTAGTAAGTTAACAATAGATGACTTACAACTAAT<br>CGGAAGGTGCAGAGACTCGACGGGAGCTACCCTAA<br>CGTCAAGACGAGGGTAAAGAGAGAGTCCAATTCTC<br>AAAGCCAATAGGCAGTAGCGAAAGCTGCAAGAGAA<br>TGAAAATCCGT |
| 80 | L5-5 | TAGACAAGGCAATCCTGAGCCAAGCCGAAGTAGTA<br>ATTAGTAAGTTAACAATAGATGACTTACAACTAATC<br>GGAAGGTGCAGAGACTCGACGGGAGCTACCCTAAC<br>GTCAAGACGAGGGTAAAGAGAGAGTCCAATTCTCA<br>AAGCCAATAGGCAGTAGCGAAAGCTGCAAGAGAAT<br>GAAAATCCGT |
| 81 | L6-1 | ACAATAGATGACTTACAACTAATCGGAAGGTGCAG<br>AGACTCGACGGGAGCTACCCTAACGTCAAGACGAG<br>GGTAAAGAGAGAGTCCAATTCTCAAAGCCAATAGG<br>CAGTAGCGAAAGCTGCAAGAGAATGAAAATCCGT |
| 82 | L6-2 | CAATAGATGACTTACAACTAATCGGAAGGTGCAGA<br>GACTCGACGGGAGCTACCCTAACGTCAAGACGAGG<br>GTAAAGAGAGAGTCCAATTCTCAAAGCCAATAGGC<br>AGTAGCGAAAGCTGCAAGAGAATGAAAATCCGT |

TABLE 4-continued

Anabaena permutation site 5' intron fragment sequences.

| SEQ ID NO. | Permutation site | Sequence |
|---|---|---|
| 83 | L6-3 | AATAGATGACTTACAACTAATCGGAAGGTGCAGAG ACTCGACGGGAGCTACCCTAACGTCAAGACGAGGG TAAAGAGAGAGTCCAATTCTCAAAGCCAATAGGCA GTAGCGAAAGCTGCAAGAGAATGAAAATCCGT |
| 84 | L6-4 | ATAGATGACTTACAACTAATCGGAAGGTGCAGAGA CTCGACGGGAGCTACCCTAACGTCAAGACGAGGGT AAAGAGAGAGTCCAATTCTCAAAGCCAATAGGCAG TAGCGAAAGCTGCAAGAGAATGAAAATCCGT |
| 85 | L6-5 | TAGATGACTTACAACTAATCGGAAGGTGCAGAGAC TCGACGGGAGCTACCCTAACGTCAAGACGAGGGTA AAGAGAGAGTCCAATTCTCAAAGCCAATAGGCAGT AGCGAAAGCTGCAAGAGAATGAAAATCCGT |
| 86 | L6-6 | AGATGACTTACAACTAATCGGAAGGTGCAGAGACT CGACGGGAGCTACCCTAACGTCAAGACGAGGGTAA AGAGAGAGTCCAATTCTCAAAGCCAATAGGCAGTA GCGAAAGCTGCAAGAGAATGAAAATCCGT |
| 87 | L6-7 | GATGACTTACAACTAATCGGAAGGTGCAGAGACTC GACGGGAGCTACCCTAACGTCAAGACGAGGGTAAA GAGAGAGTCCAATTCTCAAAGCCAATAGGCAGTAG CGAAAGCTGCAAGAGAATGAAAATCCGT |
| 88 | L6-8 | ATGACTTACAACTAATCGGAAGGTGCAGAGACTCG ACGGGAGCTACCCTAACGTCAAGACGAGGGTAAAG AGAGAGTCCAATTCTCAAAGCCAATAGGCAGTAGC GAAAGCTGCAAGAGAATGAAAATCCGT |
| 89 | L6-9 | TGACTTACAACTAATCGGAAGGTGCAGAGACTCGA CGGGAGCTACCCTAACGTCAAGACGAGGGTAAAGA GAGAGTCCAATTCTCAAAGCCAATAGGCAGTAGCG AAAGCTGCAAGAGAATGAAAATCCGT |
| 90 | L8-1 | CAAGACGAGGGTAAAGAGAGAGTCCAATTCTCAAA GCCAATAGGCAGTAGCGAAAGCTGCAAGAGAATGA AAATCCGT |
| 91 | L8-2 | AAGACGAGGGTAAAGAGAGAGTCCAATTCTCAAAG CCAATAGGCAGTAGCGAAAGCTGCAAGAGAATGAA AATCCGT |
| 92 | L8-3 | AGACGAGGGTAAAGAGAGAGTCCAATTCTCAAAGC CAATAGGCAGTAGCGAAAGCTGCAAGAGAATGAAA ATCCGT |
| 93 | L8-4 | GACGAGGGTAAAGAGAGAGTCCAATTCTCAAAGCC AATAGGCAGTAGCGAAAGCTGCAAGAGAATGAAAA TCCGT |
| 94 | L8-5 | ACGAGGGTAAAGAGAGAGTCCAATTCTCAAAGCCA ATAGGCAGTAGCGAAAGCTGCAAGAGAATGAAAAT CCGT |
| 95 | L9a-1 | AATAGGCAGTAGCGAAAGCTGCAAGAGAATGAAAA TCCGT |
| 96 | L9a-2 | ATAGGCAGTAGCGAAAGCTGCAAGAGAATGAAAAT CCGT |
| 97 | L9a-3 | TAGGCAGTAGCGAAAGCTGCAAGAGAATGAAAATC CGT |
| 98 | L9a-4 | AGGCAGTAGCGAAAGCTGCAAGAGAATGAAAATCC GT |
| 99 | L9a-5 | GGCAGTAGCGAAAGCTGCAAGAGAATGAAAATCCG T |
| 100 | L9-1 | GAAAGCTGCAAGAGAATGAAAATCCGT |
| 101 | L9-2 | AAAGCTGCAAGAGAATGAAAATCCGT |
| 102 | L9-3 | AAGCTGCAAGAGAATGAAAATCCGT |

TABLE 4-continued

Anabaena permutation site 5' intron fragment sequences.

| SEQ ID NO. | Permutation site | Sequence |
|---|---|---|
| 103 | L9-4 | AGCTGCAAGAGAATGAAAATCCGT |
| 104 | L9-5 | GCTGCAAGAGAATGAAAATCCGT |
| 105 | L9-6 | CTGCAAGAGAATGAAAATCCGT |
| 106 | L9-7 | AAGAGAATGAAAATCCGT |
| 107 | L9-8 | AGAGAATGAAAATCCGT |
| 108 | L9-9 | GAGAATGAAAATCCGT |
| 109 | L9a-6 | GCAGTAGCGAAAGCTGCAAGAGAATGAAAATCCGT |
| 110 | L9a-7 | AGTAGCGAAAGCTGCAAGAGAATGAAAATCCGT |
| 111 | L9a-8 | GTAGCGAAAGCTGCAAGAGAATGAAAATCCGT |

In some embodiments, a 5' intron fragment is a fragment having a sequence listed in Table 4. Typically, a construct containing a 5' intron fragment listed in Table 4 will contain a corresponding 3' intron fragment as listed in Table 5 (e.g., both representing fragments with the L9a-8 permutation site).

TABLE 5

Anabaena permutation site 3' intron fragment sequences.

| SEQ ID NO. | Permutation site | Sequence |
|---|---|---|
| 112 | L2-1 | ACGGACTTAAATAATTGAGCCTTAAA |
| 113 | L2-2 | ACGGACTTAAATAATTGAGCCTTAAAG |
| 114 | L2-3 | ACGGACTTAAATAATTGAGCCTTAAAGA |
| 115 | L5-1 | ACGGACTTAAATAATTGAGCCTTAAAGAAGAAATTCTTTAAGTGGATGCTCTCAAACTCAGGGAAACCTAAATCTA |
| 116 | L5-2 | ACGGACTTAAATAATTGAGCCTTAAAGAAGAAATTCTTTAAGTGGATGCTCTCAAACTCAGGGAAACCTAAATCTAG |
| 117 | L5-3 | ACGGACTTAAATAATTGAGCCTTAAAGAAGAAATTCTTTAAGTGGATGCTCTCAAACTCAGGGAAACCTAAATCTAGT |
| 118 | L5-4 | ACGGACTTAAATAATTGAGCCTTAAAGAAGAAATTCTTTAAGTGGATGCTCTCAAACTCAGGGAAACCTAAATCTAGTT |
| 119 | L5-5 | ACGGACTTAAATAATTGAGCCTTAAAGAAGAAATTCTTTAAGTGGATGCTCTCAAACTCAGGGAAACCTAAATCTAGTTA |
| 120 | L6-1 | ACGGACTTAAATAATTGAGCCTTAAAGAAGAAATTCTTTAAGTGGATGCTCTCAAACTCAGGGAAACCTAAATCTAGTTATAGACAAGGCAATCCTGAGCCAAGCCGAAGTAGTAATTAGTAAGTTA |
| 121 | L6-2 | ACGGACTTAAATAATTGAGCCTTAAAGAAGAAATTCTTTAAGTGGATGCTCTCAAACTCAGGGAAACCTAAATCTAGTTATAGACAAGGCAATCCTGAGCCAAGCCGAAGTAGTAATTAGTAAGTTAA |

TABLE 5-continued

Anabaena permutation site 3' intron fragment sequences.

| SEQ ID NO. | Permutation site | Sequence |
|---|---|---|
| 122 | L6-3 | ACGGACTTAAATAATTGAGCCTTAAAGAAGAAATT<br>CTTTAAGTGGATGCTCTCAAACTCAGGGAAACCTAA<br>ATCTAGTTATAGACAAGGCAATCCTGAGCCAAGCC<br>GAAGTAGTAATTAGTAAGTTAAC |
| 123 | L6-4 | ACGGACTTAAATAATTGAGCCTTAAAGAAGAAATT<br>CTTTAAGTGGATGCTCTCAAACTCAGGGAAACCTAA<br>ATCTAGTTATAGACAAGGCAATCCTGAGCCAAGCC<br>GAAGTAGTAATTAGTAAGTTAACA |
| 124 | L6-5 | ACGGACTTAAATAATTGAGCCTTAAAGAAGAAATT<br>CTTTAAGTGGATGCTCTCAAACTCAGGGAAACCTAA<br>ATCTAGTTATAGACAAGGCAATCCTGAGCCAAGCC<br>GAAGTAGTAATTAGTAAGTTAACAA |
| 125 | L6-6 | ACGGACTTAAATAATTGAGCCTTAAAGAAGAAATT<br>CTTTAAGTGGATGCTCTCAAACTCAGGGAAACCTAA<br>ATCTAGTTATAGACAAGGCAATCCTGAGCCAAGCC<br>GAAGTAGTAATTAGTAAGTTAACAAT |
| 126 | L6-7 | ACGGACTTAAATAATTGAGCCTTAAAGAAGAAATT<br>CTTTAAGTGGATGCTCTCAAACTCAGGGAAACCTAA<br>ATCTAGTTATAGACAAGGCAATCCTGAGCCAAGCC<br>GAAGTAGTAATTAGTAAGTTAACAATA |
| 127 | L6-8 | ACGGACTTAAATAATTGAGCCTTAAAGAAGAAATT<br>CTTTAAGTGGATGCTCTCAAACTCAGGGAAACCTAA<br>ATCTAGTTATAGACAAGGCAATCCTGAGCCAAGCC<br>GAAGTAGTAATTAGTAAGTTAACAATAG |
| 128 | L6-9 | ACGGACTTAAATAATTGAGCCTTAAAGAAGAAATT<br>CTTTAAGTGGATGCTCTCAAACTCAGGGAAACCTAA<br>ATCTAGTTATAGACAAGGCAATCCTGAGCCAAGCC<br>GAAGTAGTAATTAGTAAGTTAACAATAGA |
| 129 | L8-1 | ACGGACTTAAATAATTGAGCCTTAAAGAAGAAATT<br>CTTTAAGTGGATGCTCTCAAACTCAGGGAAACCTAA<br>ATCTAGTTATAGACAAGGCAATCCTGAGCCAAGCC<br>GAAGTAGTAATTAGTAAGTTAACAATAGATGACTTA<br>CAACTAATCGGAAGGTGCAGAGACTCGACGGGAGC<br>TACCCTAACGT |
| 130 | L8-2 | ACGGACTTAAATAATTGAGCCTTAAAGAAGAAATT<br>CTTTAAGTGGATGCTCTCAAACTCAGGGAAACCTAA<br>ATCTAGTTATAGACAAGGCAATCCTGAGCCAAGCC<br>GAAGTAGTAATTAGTAAGTTAACAATAGATGACTTA<br>CAACTAATCGGAAGGTGCAGAGACTCGACGGGAGC<br>TACCCTAACGTC |
| 131 | L8-3 | ACGGACTTAAATAATTGAGCCTTAAAGAAGAAATT<br>CTTTAAGTGGATGCTCTCAAACTCAGGGAAACCTAA<br>ATCTAGTTATAGACAAGGCAATCCTGAGCCAAGCC<br>GAAGTAGTAATTAGTAAGTTAACAATAGATGACTTA<br>CAACTAATCGGAAGGTGCAGAGACTCGACGGGAGC<br>TACCCTAACGTCA |
| 132 | L8-4 | ACGGACTTAAATAATTGAGCCTTAAAGAAGAAATT<br>CTTTAAGTGGATGCTCTCAAACTCAGGGAAACCTAA<br>ATCTAGTTATAGACAAGGCAATCCTGAGCCAAGCC<br>GAAGTAGTAATTAGTAAGTTAACAATAGATGACTTA<br>CAACTAATCGGAAGGTGCAGAGACTCGACGGGAGC<br>TACCCTAACGTCAA |
| 133 | L8-5 | ACGGACTTAAATAATTGAGCCTTAAAGAAGAAATT<br>CTTTAAGTGGATGCTCTCAAACTCAGGGAAACCTAA<br>ATCTAGTTATAGACAAGGCAATCCTGAGCCAAGCC<br>GAAGTAGTAATTAGTAAGTTAACAATAGATGACTTA<br>CAACTAATCGGAAGGTGCAGAGACTCGACGGGAGC<br>TACCCTAACGTCAAG |
| 134 | L9a-1 | ACGGACTTAAATAATTGAGCCTTAAAGAAGAAATT<br>CTTTAAGTGGATGCTCTCAAACTCAGGGAAACCTAA<br>ATCTAGTTATAGACAAGGCAATCCTGAGCCAAGCC<br>GAAGTAGTAATTAGTAAGTTAACAATAGATGACTTA |

TABLE 5-continued

Anabaena permutation site 3' intron fragment sequences.

| SEQ ID NO. | Permutation site | Sequence |
|---|---|---|
|  |  | CAACTAATCGGAAGGTGCAGAGACTCGACGGGAGC<br>TACCCTAACGTCAAGACGAGGGTAAAGAGAGAGTC<br>CAATTCTCAAAGCC |
| 135 | L9a-2 | ACGGACTTAAATAATTGAGCCTTAAAGAAGAAATT<br>CTTTAAGTGGATGCTCTCAAACTCAGGGAAACCTAA<br>ATCTAGTTATAGACAAGGCAATCCTGAGCCAAGCC<br>GAAGTAGTAATTAGTAAGTTAACAATAGATGACTTA<br>CAACTAATCGGAAGGTGCAGAGACTCGACGGGAGC<br>TACCCTAACGTCAAGACGAGGGTAAAGAGAGAGTC<br>CAATTCTCAAAGCCA |
| 136 | L9a-3 | ACGGACTTAAATAATTGAGCCTTAAAGAAGAAATT<br>CTTTAAGTGGATGCTCTCAAACTCAGGGAAACCTAA<br>ATCTAGTTATAGACAAGGCAATCCTGAGCCAAGCC<br>GAAGTAGTAATTAGTAAGTTAACAATAGATGACTTA<br>CAACTAATCGGAAGGTGCAGAGACTCGACGGGAGC<br>TACCCTAACGTCAAGACGAGGGTAAAGAGAGAGTC<br>CAATTCTCAAAGCCAA |
| 137 | L9a-4 | ACGGACTTAAATAATTGAGCCTTAAAGAAGAAATT<br>CTTTAAGTGGATGCTCTCAAACTCAGGGAAACCTAA<br>ATCTAGTTATAGACAAGGCAATCCTGAGCCAAGCC<br>GAAGTAGTAATTAGTAAGTTAACAATAGATGACTTA<br>CAACTAATCGGAAGGTGCAGAGACTCGACGGGAGC<br>TACCCTAACGTCAAGACGAGGGTAAAGAGAGAGTC<br>CAATTCTCAAAGCCAAT |
| 138 | L9a-5 | ACGGACTTAAATAATTGAGCCTTAAAGAAGAAATT<br>CTTTAAGTGGATGCTCTCAAACTCAGGGAAACCTAA<br>ATCTAGTTATAGACAAGGCAATCCTGAGCCAAGCC<br>GAAGTAGTAATTAGTAAGTTAACAATAGATGACTTA<br>CAACTAATCGGAAGGTGCAGAGACTCGACGGGAGC<br>TACCCTAACGTCAAGACGAGGGTAAAGAGAGAGTC<br>CAATTCTCAAAGCCAATA |
| 139 | L9-1 | ACGGACTTAAATAATTGAGCCTTAAAGAAGAAATT<br>CTTTAAGTGGATGCTCTCAAACTCAGGGAAACCTAA<br>ATCTAGTTATAGACAAGGCAATCCTGAGCCAAGCC<br>GAAGTAGTAATTAGTAAGTTAACAATAGATGACTTA<br>CAACTAATCGGAAGGTGCAGAGACTCGACGGGAGC<br>TACCCTAACGTCAAGACGAGGGTAAAGAGAGAGTC<br>CAATTCTCAAAGCCAATAGGCAGTAGC |
| 140 | L9-2 | ACGGACTTAAATAATTGAGCCTTAAAGAAGAAATT<br>CTTTAAGTGGATGCTCTCAAACTCAGGGAAACCTAA<br>ATCTAGTTATAGACAAGGCAATCCTGAGCCAAGCC<br>GAAGTAGTAATTAGTAAGTTAACAATAGATGACTTA<br>CAACTAATCGGAAGGTGCAGAGACTCGACGGGAGC<br>TACCCTAACGTCAAGACGAGGGTAAAGAGAGAGTC<br>CAATTCTCAAAGCCAATAGGCAGTAGCG |
| 141 | L9-3 | ACGGACTTAAATAATTGAGCCTTAAAGAAGAAATT<br>CTTTAAGTGGATGCTCTCAAACTCAGGGAAACCTAA<br>ATCTAGTTATAGACAAGGCAATCCTGAGCCAAGCC<br>GAAGTAGTAATTAGTAAGTTAACAATAGATGACTTA<br>CAACTAATCGGAAGGTGCAGAGACTCGACGGGAGC<br>TACCCTAACGTCAAGACGAGGGTAAAGAGAGAGTC<br>CAATTCTCAAAGCCAATAGGCAGTAGCGA |
| 142 | L9-4 | ACGGACTTAAATAATTGAGCCTTAAAGAAGAAATT<br>CTTTAAGTGGATGCTCTCAAACTCAGGGAAACCTAA<br>ATCTAGTTATAGACAAGGCAATCCTGAGCCAAGCC<br>GAAGTAGTAATTAGTAAGTTAACAATAGATGACTTA<br>CAACTAATCGGAAGGTGCAGAGACTCGACGGGAGC<br>TACCCTAACGTCAAGACGAGGGTAAAGAGAGAGTC<br>CAATTCTCAAAGCCAATAGGCAGTAGCGAA |
| 143 | L9-5 | ACGGACTTAAATAATTGAGCCTTAAAGAAGAAATT<br>CTTTAAGTGGATGCTCTCAAACTCAGGGAAACCTAA<br>ATCTAGTTATAGACAAGGCAATCCTGAGCCAAGCC<br>GAAGTAGTAATTAGTAAGTTAACAATAGATGACTTA<br>CAACTAATCGGAAGGTGCAGAGACTCGACGGGAGC<br>TACCCTAACGTCAAGACGAGGGTAAAGAGAGAGTC<br>CAATTCTCAAAGCCAATAGGCAGTAGCGAAA |

TABLE 5-continued

Anabaena permutation site 3' intron fragment sequences.

| SEQ ID NO. | Permutation site | Sequence |
|---|---|---|
| 144 | L9-6 | ACGGACTTAAATAATTGAGCCTTAAAGAAGAAATT<br>CTTTAAGTGGATGCTCTCAAACTCAGGGAAACCTAA<br>ATCTAGTTATAGACAAGGCAATCCTGAGCCAAGCC<br>GAAGTAGTAATTAGTAAGTTAACAATAGATGACTTA<br>CAACTAATCGGAAGGTGCAGAGACTCGACGGGAGC<br>TACCCTAACGTCAAGACGAGGGTAAAGAGAGAGTC<br>CAATTCTCAAAGCCAATAGGCAGTAGCGAAAG |
| 145 | L9-7 | ACGGACTTAAATAATTGAGCCTTAAAGAAGAAATT<br>CTTTAAGTGGATGCTCTCAAACTCAGGGAAACCTAA<br>ATCTAGTTATAGACAAGGCAATCCTGAGCCAAGCC<br>GAAGTAGTAATTAGTAAGTTAACAATAGATGACTTA<br>CAACTAATCGGAAGGTGCAGAGACTCGACGGGAGC<br>TACCCTAACGTCAAGACGAGGGTAAAGAGAGAGTC<br>CAATTCTCAAAGCCAATAGGCAGTAGCGAAAGCTG<br>C |
| 146 | L9-8 | ACGGACTTAAATAATTGAGCCTTAAAGAAGAAATT<br>CTTTAAGTGGATGCTCTCAAACTCAGGGAAACCTAA<br>ATCTAGTTATAGACAAGGCAATCCTGAGCCAAGCC<br>GAAGTAGTAATTAGTAAGTTAACAATAGATGACTTA<br>CAACTAATCGGAAGGTGCAGAGACTCGACGGGAGC<br>TACCCTAACGTCAAGACGAGGGTAAAGAGAGAGTC<br>CAATTCTCAAAGCCAATAGGCAGTAGCGAAAGCTG<br>CA |
| 147 | L9-9 | ACGGACTTAAATAATTGAGCCTTAAAGAAGAAATT<br>CTTTAAGTGGATGCTCTCAAACTCAGGGAAACCTAA<br>ATCTAGTTATAGACAAGGCAATCCTGAGCCAAGCC<br>GAAGTAGTAATTAGTAAGTTAACAATAGATGACTTA<br>CAACTAATCGGAAGGTGCAGAGACTCGACGGGAGC<br>TACCCTAACGTCAAGACGAGGGTAAAGAGAGAGTC<br>CAATTCTCAAAGCCAATAGGCAGTAGCGAAAGCTG<br>CAA |
| 148 | L9a-6 | ACGGACTTAAATAATTGAGCCTTAAAGAAGAAATT<br>CTTTAAGTGGATGCTCTCAAACTCAGGGAAACCTAA<br>ATCTAGTTATAGACAAGGCAATCCTGAGCCAAGCC<br>GAAGTAGTAATTAGTAAGTTAACAATAGATGACTTA<br>CAACTAATCGGAAGGTGCAGAGACTCGACGGGAGC<br>TACCCTAACGTCAAGACGAGGGTAAAGAGAGAGTC<br>CAATTCTCAAAGCCAATAG |
| 149 | L9a-7 | ACGGACTTAAATAATTGAGCCTTAAAGAAGAAATT<br>CTTTAAGTGGATGCTCTCAAACTCAGGGAAACCTAA<br>ATCTAGTTATAGACAAGGCAATCCTGAGCCAAGCC<br>GAAGTAGTAATTAGTAAGTTAACAATAGATGACTTA<br>CAACTAATCGGAAGGTGCAGAGACTCGACGGGAGC<br>TACCCTAACGTCAAGACGAGGGTAAAGAGAGAGTC<br>CAATTCTCAAAGCCAATAGGC |
| 150 | L9a-8 | ACGGACTTAAATAATTGAGCCTTAAAGAAGAAATT<br>CTTTAAGTGGATGCTCTCAAACTCAGGGAAACCTAA<br>ATCTAGTTATAGACAAGGCAATCCTGAGCCAAGCC<br>GAAGTAGTAATTAGTAAGTTAACAATAGATGACTTA<br>CAACTAATCGGAAGGTGCAGAGACTCGACGGGAGC<br>TACCCTAACGTCAAGACGAGGGTAAAGAGAGAGTC<br>CAATTCTCAAAGCCAATAGGCA |

In some embodiments, a 3' intron fragment is a fragment having a sequence listed in Table 5. In some embodiments, a construct containing a 3' intron fragment listed in Table 5 will contain a corresponding 5' intron fragment as listed in Table 4 (e.g., both representing fragments with the L9a-8 permutation site).

TABLE 6

Non-anabaena permutation site 5' intron fragment sequences.

| SEQ ID NO. | Intron | Sequence |
|---|---|---|
| 151 | Azop1 | tgcgccgatgaaggtgtagagactagacggcacccacctaaggcaaacgctatggt<br>gaaggcatagtccagggagtggcgaaagtcacacaaaccggaatccgt |

TABLE 6-continued

Non-anabaena permutation site 5' intron fragment sequences.

| SEQ ID NO. | Intron | Sequence |
|---|---|---|
| 152 | Azop2 | ccgggcgtatggcaacgccgagccaagcttcggcgcctgcgccgatgaaggtgta gagactagacggcacccacctaaggcaaacgctatggtgaaggcatagtccaggga gtggcgaaagtcacacaaaccggaatccgt |
| 153 | Azop3 | acggcacccacctaaggcaaacgctatggtgaaggcatagtccagggagtggcga aagtcacacaaaccggaatccgt |
| 154 | Azop4 | acgctatggtgaaggcatagtccagggagtggcgaaagtcacacaaaccggaatcc gt |
| 155 | S795p1 | attaaagttatagaattatcagagaatgatatagtccaagccttatggtaacatgagggc acttgaccctggtag |
| 156 | Twortp1 | aagatgtaggcaatcctgagctaagctcttagtaataagagaaagtgcaacgactattc cgataggaagtagggtcaagtgactcgaaatggggattaccttctagggtagtgata tagtctgaacatatatgaaacatatagaaggataggagtaacgaacctattcgtaaca taattgaacttttagttat |
| 157 | Twortp2 | taataagagaaagtgcaacgactattccgataggaagtagggtcaagtgactcgaaat ggggattaccttctagggtagtgatatagtctgaacatatatggaaacatatagaagg ataggagtaacgaacctattcgtaacataattgaacttttagttat |
| 158 | Twortp3 | taggaagtagggtcaagtgactcgaaatggggattaccttctagggtagtgatatagt ctgaacatatatggaaacatatagaaggataggagtaacgaacctattcgtaacataat tgaacttttagttat |
| 159 | Twortp4 | ctagggtagtgatatagtctgaacatatatggaaacatatagaaggataggagtaacg aacctattcgtaacataattgaacttttagttat |
| 160 | LSUp1 | agttaataaagatgatgaaatagtctgaaccattttgagaaaagtggaaataaaagaaa atcttttatgataacataaattgaacaggctaa |
| 161 | Phip1 | caaagactgatgatatagtccgacactcctagtaataggagaatacagaaaggatgaa atcc |
| 162 | Nostoc | agtcgagggtaaagggagagtccaattctcaaagcctattggcagtagcgaaagctg cgggagaatgaaaatccgt |
| 163 | Nostoc | agccgagggtaaagggagagtccaattctcaaagccaataggcagtagcgaaagct gcgggagaatgaaaatccgt |
| 164 | Nodularia | agccgagggtaaagggagagtccaattctcaaagccgaaggttattaaaacctggca gcagtgaaagctgcgggagaatgaaaatccgt |
| 165 | Pleurocapsa | agctgagggtaaagagagagtccaattctcaaagccagcagatggcagtagcgaaa gctgcgggagaatgaaaatccgt |
| 166 | Planktothrix | agccgagggtaaagagagagtccaattctcaaagccaattggtagtagcgaaagcta cgggagaatgaaaatccgt |

In some embodiments, a 5' intron fragment is a fragment having a sequence listed in Table 6. A construct containing a 5' intron fragment listed in Table 6 will contain a corresponding 3' intron fragment as listed in Table 7 (e.g., both representing fragments with the Azop1 intron).

TABLE 7

Non-anabaena permutation site 3' intron fragment sequences.

| SEQ ID NO. | Intron | Sequence |
|---|---|---|
| 167 | Azop1 | gcggactcatatttcgatgtgccttgcgccgggaaaccacgcaagggatggtgtcaa attcggcgaaacctaagcgcccgcccggcgtatggcaacgccgagccaagcttcg gcgcc |
| 168 | Azop2 | gcggactcatatttcgatgtgccttgcgccgggaaaccacgcaagggatggtgtcaa attcggcgaaacctaagcgcccgc |
| 169 | Azop3 | gcggactcatatttcgatgtgccttgcgccgggaaaccacgcaagggatggtgtcaa attcggcgaaacctaagcgcccgcccggcgtatggcaacgccgagccaagcttcg gcgcctgcgccgatgaaggtgtagagactag |

TABLE 7-continued

Non-anabaena permutation site 3' intron fragment sequences.

| SEQ ID NO. | Intron | Sequence |
|---|---|---|
| 170 | Azop4 | gcggactcatatttcgatgtgccttgcgccgggaaaccacgcaagggatggtgtcaa attcggcgaaacctaagcgcccgcccgggcgtatggcaacgccgagccaagcttcg gcgcctgcgccgatgaaggtgtagagactagacggcacccacctaaggcaa |
| 171 | S795p1 | aggattagatactacactaagtgtcccccagactggtgacagtctggtgtgcatccag ctatatcggtgaaacccc attggggtaataccgagggaagctatattatatatattaat aaatagccccgtagagactatgtaggtaaggagatagaagatgataaaatcaaaatca tc |
| 172 | Twortp1 | actactgaaagcataaataattgtgcctttatacagtaatgtatatcgaaaaatcctctaat tcagggaacacctaaacaaact |
| 173 | Twortp2 | actactgaaagcataaataattgtgcctttatacagtaatgtatatcgaaaaatcctctaat tcagggaacacctaaacaaactaagatgtaggcaatcctgagctaagctcttag |
| 174 | Twortp3 | actactgaaagcataaataattgtgcctttatacagtaatgtatatcgaaaaatcctctaat tcagggaacacctaaacaaactaagatgtaggcaatcctgagctaagctcttagtaata agagaaagtgcaacgactattccga |
| 175 | Twortp4 | actactgaaagcataaataattgtgcctttatacagtaatgtatatcgaaaaatcctctaat tcagggaacacctaaacaaactaagatgtaggcaatcctgagctaagctcttagtaata agagaaagtgcaacgactattccgataggaagtagggtcaagtgactcgaaatggg gattaccctt |
| 176 | LSUp1 | cgctagggatttataactgtgagtcctccaatattataaaatgttggtaatatattgggtaa atttcaaagacaacttttctccacgtcaggatatagtgtatttgaagcgaaacttattttag cagtgaaaaagcaaataaggacgttcaacgactaaaaggtgagtattgctaacaataa tccttttttttaatgcccaacatctttattaact |
| 177 | Phip1 | gtgggtgcataaactatttcattgtgcacattaaatctggtgaactcggtgaaaccctaat ggggcaataccgagccaagccataggaggatatatgagaggcaagaagttaattct tgaggccactgagactggctgtatcatccctacgtcacacaaacttaatgccgatggtt atttcagaaagaaaaccaatggcgtcttagagatgtatcacag aacggtgtggaagga gcataacggagacatacctgatggcttcgagatagaccataagtgtcgcaatagggct tgctgtaatatagagcatttacagatgcttgagggtacagcccacactgttaagaccaa tcgtgaacgctacgcagacagaaaggaaacagctagggaatactggctggagactg gatgtaccggcctagcactcggtgagaagtttggtgtgtcgttctcttctgcttgtaagtg gattagagaatggaaggcgtagagactatccgaaaggagtagggccgagggtgag actccctcgtaacccgaagcgccagacagtcaact |
| 178 | Nostoc | acggacttaagtaattgagccttaaagaagaaattctttaagtggcagctctcaaactca gggaaacctaaatctgttcacagacaaggcaatcctgagccaagccgaaagagtcat gagtgctgagtagtgagtaaaataaaagctcacaactcagaggttgtaactctaagcta gtcggaaggtgcagagactcgacgggagctaccctaacgtaa |
| 179 | Nostoc | acggacttaaactgaattgagccttagagaagaaattctttaagtgtcagctctcaaact cagggaaacctaaatctgttgacagacaaggcaatcctgagccaagccgagaactct aagttattcggaaggtgcagagactcgacgggagctaccctaacgtca |
| 180 | Nodularia | acggactagaaaactgagccttgatcgagaaatctttcaagtggaagctctcaaattc agggaaacctaaatctgtttacagatatggcaatcctgagccaagccgaaacaagtcc tgagtgttaaagctcataactcatcggaaggtgcagagactcgacgggagctaccta acgtta |
| 181 | Pleurocapsa | acggacttaaaaaaattgagccttggcagagaaatctgtcatgcgaacgctctcaaatt cagggaaacctaagtctggcaacagatatggcaatcctgagccaagccttaatcaag gaaaaaaacatttttaccttttaccttgaaaggaaggtgcagagactcaacgggagcta ccctaacaggtca |
| 182 | Planktothrix | acggacttaaagataaattgagccttgaggcgagaaatctctcaagtgtaagctgtcaa attcagggaaacctaaatctgtaaattcagacaaggcaatcctgagccaagcctaggg gtattagaaatgagggagtttccccaatctaagatcaatacctaggaaggtgcagaga ctcgacgggagctaccctaacgtta |

In some embodiments, a 3' intron fragment is a fragment having a sequence listed in Table 7. A construct containing a 3' intron fragment listed in Table 7 will contain the corresponding 5' intron fragment as listed in Table 6 (e.g., both representing fragments with the Azop1 intron).

TABLE 8

Spacer and Anabaena 5' intron fragment sequences.

| SEQ ID NO. | Spacer | Sequence |
|---|---|---|
| 183 | T25 L10 | agtatataagaaacaaaccacTAGATGACTTACAACTAATCGGA<br>AGGTGCAGAGACTCGACGGGAGCTACCCTAACGTC<br>AAGACGAGGGTAAAGAGAGAGTCCAATTCTCAAAG<br>CCAATAGGCAGTAGCGAAAGCTGCAAGAGAATGAA<br>AATCCGTggctcgcagc |
| 184 | T25 L20 | ctgaaattatacttatactcaaacaaaccacTAGATGACTTACAACTA<br>ATCGGAAGGTGCAGAGACTCGACGGGAGCTACCCT<br>AACGTCAAGACGAGGGTAAAGAGAGAGTCCAATTC<br>TCAAAGCCAATAGGCAGTAGCGAAAGCTGCAAGAG<br>AATGAAAATCCGTggctcgcagc |
| 185 | T25 L30<br>(I80-10)<br>[Control] | ctgaaattatacttatactcagtatatgacaaacaaaccacTAGATGACTTAC<br>AACTAATCGGAAGGTGCAGAGACTCGACGGGAGCT<br>ACCCTAACGTCAAGACGAGGGTAAAGAGAGAGTCC<br>AATTCTCAAAGCCAATAGGCAGTAGCGAAAGCTGC<br>AAGAGAATGAAAATCCGTggctcgcagc |
| 186 | T25 L40 | catcaacaatatgaaattatacttatactcagtatatgacaaacaaaccacTAGAT<br>GACTTACAACTAATCGGAAGGTGCAGAGACTCGAC<br>GGGAGCTACCCTAACGTCAAGACGAGGGTAAAGAG<br>AGAGTCCAATTCTCAAAGCCAATAGGCAGTAGCGA<br>AAGCTGCAAGAGAATGAAAATCCGTggctcgcagc |
| 187 | T25 L50 | catcaacaatatgaaactatacttatactcagtatatgaagcattatcgcaaacaa<br>accacTAGATGACTTACAACTAATCGGAAGGTGCAGAGAC<br>TCGACGGGAGCTACCCTAACGTCAAGACGAGGGTA<br>AAGAGAGAGTCCAATTCTCAAAGCCAATAGGCAGT<br>AGCGAAAGCTGCAAGAGAATGAAAATCCGTggctcgca<br>gc |
| 188 | T50 L10 | tagcgtcagcaaacaaacaaaTAGATGACTTACAACTAATCGG<br>AAGGTGCAGAGACTCGACGGGAGCTACCCTAACGT<br>CAAGACGAGGGTAAAGAGAGAGTCCAATTCTCAAA<br>GCCAATAGGCAGTAGCGAAAGCTGCAAGAGAATGA<br>AAATCCGTggctcgcagc |
| 189 | T50 L20 | atactcatactagcgtcagcaaacaaacaaaTAGATGACTTACAACTA<br>ATCGGAAGGTGCAGAGACTCGACGGGAGCTACCCT<br>AACGTCAAGACGAGGGTAAAGAGAGAGTCCAATTC<br>TCAAAGCCAATAGGCAGTAGCGAAAGCTGCAAGAG<br>AATGAAAATCCGTggctcgcagc |
| 190 | T50 L30 | gtgtgaagctatactcatactagcgtcagcaaacaaacaaaTAGATGACTT<br>ACAACTAATCGGAAGGTGCAGAGACTCGACGGGAG<br>CTACCCTAACGTCAAGACGAGGGTAAAGAGAGAGT<br>CCAATTCTCAAAGCCAATAGGCAGTAGCGAAAGCT<br>GCAAGAGAATGAAAATCCGTggctcgcagc |
| 191 | T50 L40 | cctcacctgagtgtgaagctatactcatactagcgtcagcaaacaaacaaaTAGA<br>TGACTTACAACTAATCGGAAGGTGCAGAGACTCGA<br>CGGGAGCTACCCTAACGTCAAGACGAGGGTAAAGA<br>GAGAGTCCAATTCTCAAAGCCAATAGGCAGTAGCG<br>AAAGCTGCAAGAGAATGAAAATCCGTggctcgcagc |
| 192 | T50 L50 | ccgaatgatgcctcacctgagtgtgaagctatactcatactagcgtcagcaaaca<br>aacaaaTAGATGACTTACAACTAATCGGAAGGTGCAGAG<br>ACTCGACGGGAGCTACCCTAACGTCAAGACGAGGG<br>TAAAGAGAGAGTCCAATTCTCAAAGCCAATAGGCA<br>GTAGCGAAAGCTGCAAGAGAATGAAAATCCGTggctc<br>gcagc |
| 193 | T75 L10 | cggtgcgagcaaacaaacaaaTAGATGACTTACAACTAATCGG<br>AAGGTGCAGAGACTCGACGGGAGCTACCCTAACGT<br>CAAGACGAGGGTAAAGAGAGAGTCCAATTCTCAAA<br>GCCAATAGGCAGTAGCGAAAGCTGCAAGAGAATGA<br>AAATCCGTggctcgcagc |

TABLE 8-continued

Spacer and Anabaena 5' intron fragment sequences.

| SEQ ID NO. | Spacer | Sequence |
|---|---|---|
| 194 | T75 L20 | cgctccgacccagtgcgagcaaacaaacaaaTAGATGACTTACAACT<br>AATCGGAAGGTGCAGAGACTCGACGGGAGCTACCC<br>TAACGTCAAGACGAGGGTAAAGAGAGAGTCCAATT<br>CTCAAAGCCAATAGGCAGTAGCGAAAGCTGCAAGA<br>GAATGAAAATCCGTggctcgcagc |
| 195 | T25 L30 1MM | ctgaaattatactAatactcagtatatgacaaacaaaccacTAGATGACTTA<br>CAACTAATCGGAAGGTGCAGAGACTCGACGGGAGC<br>TACCCTAACGTCAAGACGAGGGTAAAGAGAGAGTC<br>CAATTCTCAAAGCCAATAGGCAGTAGCGAAAGCTG<br>CAAGAGAATGAAAATCCGTggctcgcagc |
| 196 | T25 L30 3MM | ctgaaaAtatactAatactcaCtatatgacaaacaaaccacTAGATGACTT<br>ACAACTAATCGGAAGGTGCAGAGACTCGACGGGAG<br>CTACCCTAACGTCAAGACGAGGGTAAAGAGAGAGT<br>CCAATTCTCAAAGCCAATAGGCAGTAGCGAAAGCT<br>GCAAGAGAATGAAAATCCGTggctcgcagc |
| 197 | T25 L30 5MM | ctgaTaAtataGtAatactcaCtatatgacaaacaaaccacTAGATGACT<br>TACAACTAATCGGAAGGTGCAGAGACTCGACGGGA<br>GCTACCCTAACGTCAAGACGAGGGTAAAGAGAGAG<br>TCCAATTCTCAAAGCCAATAGGCAGTAGCGAAAGC<br>TGCAAGAGAATGAAAATCCGTggctcgcagc |
| 198 | T25 L30 8MM | ctgaTaAtaAaGtAatacAcaCtataAgacaaacaaaccacTAGATGA<br>CTTACAACTAATCGGAAGGTGCAGAGACTCGACGG<br>GAGCTACCCTAACGTCAAGACGAGGGTAAAGAGAG<br>AGTCCAATTCTCAAAGCCAATAGGCAGTAGCGAAA<br>GCTGCAAGAGAATGAAAATCCGTggctcgcagc |
| 199 | T25 L30 OffTarget 10 | ctgaaattatacttatactctctaagttacaaacaaaccacTAGATGACTTAC<br>AACTAATCGGAAGGTGCAGAGACTCGACGGGAGCT<br>ACCCTAACGTCAAGACGAGGGTAAAGAGAGAGTCC<br>AATTCTCAAAGCCAATAGGCAGTAGCGAAAGCTGC<br>AAGAGAATGAAAATCCGTggctcgcagc |
| 200 | T25 L30 OffTarget 20 | ctgaaattatgtgtgttacAtctaagttacaaacaaaccacTAGATGACTTA<br>CAACTAATCGGAAGGTGCAGAGACTCGACGGGAGC<br>TACCCTAACGTCAAGACGAGGGTAAAGAGAGAGTC<br>CAATTCTCAAAGCCAATAGGCAGTAGCGAAAGCTG<br>CAAGAGAATGAAAATCCGTggctcgcagc |
| 201 | T25 L30 OffTarget 30 | gttgatcggtgtgtgttacAtctaagttacaaacaaaccacTAGATGACTTA<br>CAACTAATCGGAAGGTGCAGAGACTCGACGGGAGC<br>TACCCTAACGTCAAGACGAGGGTAAAGAGAGAGTC<br>CAATTCTCAAAGCCAATAGGCAGTAGCGAAAGCTG<br>CAAGAGAATGAAAATCCGTggctcgcagc |
| 202 | T25 L30 I25-10 | ctgaaattatacttatactcagtatatgacaaacaaaccacTAGATGACTTAC<br>AACTAATCGGAAGGTGCAGAGACTCGACGGGAGCT<br>ACCCTAACGTCAAGACGAGGGTAAAGAGAGAGTCC<br>AATTCTCAAAGCCAATAGGCAGTAGCGAAAGCTGC<br>AAGAGAATGAAAATCCGTgattaaacag |
| 203 | T25 L30 I25-20 | ctgaaattatacttatactcagtatatgacaaacaaaccacTAGATGACTTAC<br>AACTAATCGGAAGGTGCAGAGACTCGACGGGAGCT<br>ACCCTAACGTCAAGACGAGGGTAAAGAGAGAGTCC<br>AATTCTCAAAGCCAATAGGCAGTAGCGAAAGCTGC<br>AAGAGAATGAAAATCCGTgattcacaatataaattacg |
| 204 | T25 L30 I50-10 | ctgaaattatacttatactcagtatatgacaaacaaaccacTAGATGACTTAC<br>AACTAATCGGAAGGTGCAGAGACTCGACGGGAGCT<br>ACCCTAACGTCAAGACGAGGGTAAAGAGAGAGTCC<br>AATTCTCAAAGCCAATAGGCAGTAGCGAAAGCTGC<br>AAGAGAATGAAAATCCGTggatcatagc |
| 205 | T25 L30 I50-20 | ctgaaattatacttatactcagtatatgacaaacaaaccacTAGATGACTTAC<br>AACTAATCGGAAGGTGCAGAGACTCGACGGGAGCT<br>ACCCTAACGTCAAGACGAGGGTAAAGAGAGAGTCC<br>AATTCTCAAAGCCAATAGGCAGTAGCGAAAGCTGC<br>AAGAGAATGAAAATCCGTggatcgcagcataatatccg |

TABLE 8-continued

Spacer and Anabaena 5' intron fragment sequences.

| SEQ ID NO. | Spacer | Sequence |
|---|---|---|
| 206 | T25 L30 I80-20 | ctgaaattatacttatactcagtatatgacaaacaaaccacTAGATGACTTAC AACTAATCGGAAGGTGCAGAGACTCGACGGGAGCT ACCCTAACGTCAAGACGAGGGTAAAGAGAGAGTCC AATTCTCAAAGCCAATAGGCAGTAGCGAAAGCTGC AAGAGAATGAAAATCCGTggctcgcagcgcgcctaccg |
| 207 | T25 L30 I80-20x2 | ctgaaattatacttatactcagtatatgacaaacaaaccacTAGATGACTTAC AACTAATCGGAAGGTGCAGAGACTCGACGGGAGCT ACCCTAACGTCAAGACGAGGGTAAAGAGAGAGTCC AATTCTCAAAGCCAATAGGCAGTAGCGAAAGCTGC AAGAGAATGAAAATCCGTggctcgcagcgcgcctaccgaaagcc ggcgtcgacgttagcgc |
| 208 | T25 L30 I50-20x2 | ctgaaattatacttatactcagtatatgacaaacaaaccacTAGATGACTTAC AACTAATCGGAAGGTGCAGAGACTCGACGGGAGCT ACCCTAACGTCAAGACGAGGGTAAAGAGAGAGTCC AATTCTCAAAGCCAATAGGCAGTAGCGAAAGCTGC AAGAGAATGAAAATCCGTggatcgcagcataatatccgaaacgag gatacaagtgacatgc |
| 209 | T25 L30 I25-20x2 | ctgaaattatacttatactcagtatatgacaaacaaaccacTAGATGACTTAC AACTAATCGGAAGGTGCAGAGACTCGACGGGAGCT ACCCTAACGTCAAGACGAGGGTAAAGAGAGAGTCC AATTCTCAAAGCCAATAGGCAGTAGCGAAAGCTGC AAGAGAATGAAAATCCGTgattcacaatctaaattacgaaacgataa atgataactctaac |
| 210 | T0 L0 | aaacaaaccacTAGATGACTTACAACTAATCGGAAGGTG CAGAGACTCGACGGGAGCTACCCTAACGTCAAGAC GAGGGTAAAGAGAGAGTCCAATTCTCAAAGCCAAT AGGCAGTAGCGAAAGCTGCAAGAGAATGAAAATCC GTggctcgcagc |
| 211 | T100 L5 | cgggcaaacaaacaaaTAGATGACTTACAACTAATCGGAAG GTGCAGAGACTCGACGGGAGCTACCCTAACGTCAA GACGAGGGTAAAGAGAGAGTCCAATTCTCAAAGCC AATAGGCAGTAGCGAAAGCTGCAAGAGAATGAAAA TCCGTggctcgcagc |
| 212 | T75 L30 | cgctccgacgagcttccggccagtgcgagcaaacaaacaaaTAGATGACT TACAACTAATCGGAAGGTGCAGAGACTCGACGGGA GCTACCCTAACGTCAAGACGAGGGTAAAGAGAGAG TCCAATTCTCAAAGCCAATAGGCAGTAGCGAAAGC TGCAAGAGAATGAAAATCCGTggctcgcagc |
| 213 | T0 L0a | aaacaaaccacGGCAGTAGCGAAAGCTGCAAGAGAATGA AAATCCGTggctcgcagc |
| 214 | T25 L10a | agtatataagaaacaaaccacGGCAGTAGCGAAAGCTGCAAGA GAATGAAAATCCGTggctcgcagc |
| 215 | T25 L20a | ctgaaattatacttatactcaaacaaaccacGGCAGTAGCGAAAGCTG CAAGAGAATGAAAATCCGTggctcgcagc |
| 216 | T25 L30a (I80-10) [Control] | ctgaaattatacttatactcagtatatgacaaacaaaccacGGCAGTAGCGA AAGCTGCAAGAGAATGAAAATCCGTggctcgcagc |
| 217 | T50 L10a | tagcgtcagcaaacaaacaaaGGCAGTAGCGAAAGCTGCAAGA GAATGAAAATCCGTggctcgcagc |
| 218 | T50 L20a | atactcatactagcgtcagcaaacaaacaaaGGCAGTAGCGAAAGCT GCAAGAGAATGAAAATCCGTggctcgcagc |
| 219 | T50 L30a | gtgtgaagctatactcatactagcgtcagcaaacaaacaaaGGCAGTAGCG AAAGCTGCAAGAGAATGAAAATCCGTggctcgcagc |
| 220 | T75 L10a | cggtgcgagcaaacaaacaaaGGCAGTAGCGAAAGCTGCAAG AGAATGAAAATCCGTggctcgcagc |
| 221 | T75 L20a | cgctccgacccagtgcgagcaaacaaacaaaGGCAGTAGCGAAAGC TGCAAGAGAATGAAAATCCGTggctcgcagc |
| 222 | T75 L30a | cgctccgacgagcttccggccagtgcgagcaaacaaacaaaGGCAGTAGC GAAAGCTGCAAGAGAATGAAAATCCGTggctcgcagc |

TABLE 8-continued

Spacer and Anabaena 5' intron fragment sequences.

| SEQ ID NO. | Spacer | Sequence |
|---|---|---|
| 223 | T0 L0b | aaacaaaccacAAGACGAGGGTAAAGAGAGAGTCCAATT<br>CTCAAAGCCAATAGGCAGTAGCGAAAGCTGCAAGA<br>GAATGAAAATCCGTggctcgcagc |
| 224 | T25 L10b | agtatataagaaacaaaccacAAGACGAGGGTAAAGAGAGAGT<br>CCAATTCTCAAAGCCAATAGGCAGTAGCGAAAGCT<br>GCAAGAGAATGAAAATCCGTggctcgcagc |
| 225 | T25 L20b | ctgaaattatacttatactcaaacaaaccacAAGACGAGGGTAAAGAG<br>AGAGTCCAATTCTCAAAGCCAATAGGCAGTAGCGA<br>AAGCTGCAAGAGAATGAAAATCCGTggctcgcagc |
| 226 | T25 L30b<br>(I80-10)<br>[Control] | ctgaaattatacttatactcagtatatgacaaacaaaccacAAGACGAGGGT<br>AAAGAGAGAGTCCAATTCTCAAAGCCAATAGGCAG<br>TAGCGAAAGCTGCAAGAGAATGAAAATCCGTggctcgc<br>agc |
| 227 | T50 L10b | tagcgtcagcaaacaaacaaaAAGACGAGGGTAAAGAGAGAG<br>TCCAATTCTCAAAGCCAATAGGCAGTAGCGAAAGC<br>TGCAAGAGAATGAAAATCCGTggctcgcagc |
| 228 | T50 L20b | atactcatactagcgtcagcaaacaaacaaaAAGACGAGGGTAAAGA<br>GAGAGTCCAATTCTCAAAGCCAATAGGCAGTAGCG<br>AAAGCTGCAAGAGAATGAAAATCCGTggctcgcagc |
| 229 | T50 L30b | gtgtgaagctatactcatactagcgtcagcaaacaaacaaaAAGACGAGGG<br>TAAAGAGAGAGTCCAATTCTCAAAGCCAATAGGCA<br>GTAGCGAAAGCTGCAAGAGAATGAAAATCCGTggctc<br>gcagc |
| 230 | T75 L10b | cggtgcgagcaaacaaacaaaAAGACGAGGGTAAAGAGAGAG<br>TCCAATTCTCAAAGCCAATAGGCAGTAGCGAAAGC<br>TGCAAGAGAATGAAAATCCGTggctcgcagc |
| 231 | T75 L20b | cgctccgacccagtgcgagcaaacaaacaaaAAGACGAGGGTAAAG<br>AGAGAGTCCAATTCTCAAAGCCAATAGGCAGTAGC<br>GAAAGCTGCAAGAGAATGAAAATCCGTggctcgcagc |
| 232 | T75 L30b | cgctccgacgagcttccggccagtgcgagcaaacaaacaaaAAGACGAGG<br>GTAAAGAGAGAGTCCAATTCTCAAAGCCAATAGGC<br>AGTAGCGAAAGCTGCAAGAGAATGAAAATCCGTggc<br>tcgcagc |
| 233 | T25 L30<br>I0-0 | ctgaaattatacttatactcagtatatgacaaacaaaccacTAGATGACTTAC<br>AACTAATCGGAAGGTGCAGAGACTCGACGGGAGCT<br>ACCCTAACGTCAAGACGAGGGTAAAGAGAGAGTCC<br>AATTCTCAAAGCCAATAGGCAGTAGCGAAAGCTGC<br>AAGAGAATGAAAATCCGT |
| 234 | T25 L30a<br>I0-0 | ctgaaattatacttatactcagtatatgacaaacaaaccacGGCAGTAGCGA<br>AAGCTGCAAGAGAATGAAAATCCGT |
| 235 | T25 L30a<br>I25-10 | ctgaaattatacttatactcagtatatgacaaacaaaccacGGCAGTAGCGA<br>AAGCTGCAAGAGAATGAAAATCCGTgattaaacag |
| 236 | T25 L30a<br>I25-20 | ctgaaattatacttatactcagtatatgacaaacaaaccacGGCAGTAGCGA<br>AAGCTGCAAGAGAATGAAAATCCGTgattcacaatataaatta<br>cg |
| 237 | T25 L30a<br>I50-10 | ctgaaattatacttatactcagtatatgacaaacaaaccacGGCAGTAGCGA<br>AAGCTGCAAGAGAATGAAAATCCGTggatcatagc |
| 238 | T25 L30a<br>I50-20 | ctgaaattatacttatactcagtatatgacaaacaaaccacGGCAGTAGCGA<br>AAGCTGCAAGAGAATGAAAATCCGTggatcgcagcataatat<br>ccg |
| 239 | T25 L30a<br>I80-20 | ctgaaattatacttatactcagtatatgacaaacaaaccacGGCAGTAGCGA<br>AAGCTGCAAGAGAATGAAAATCCGTggctcgcagcgcgcct<br>accg |
| 240 | T25 L30b<br>I0-0 | ctgaaattatacttatactcagtatatgacaaacaaaccacAAGACGAGGGT<br>AAAGAGAGAGTCCAATTCTCAAAGCCAATAGGCAG<br>TAGCGAAAGCTGCAAGAGAATGAAAATCCGT |
| 241 | T25 L30b<br>I25-10 | ctgaaattatacttatactcagtatatgacaaacaaaccacAAGACGAGGGT<br>AAAGAGAGAGTCCAATTCTCAAAGCCAATAGGCAG |

TABLE 8-continued

Spacer and Anabaena 5' intron fragment sequences.

| SEQ ID NO. | Spacer | Sequence |
|---|---|---|
|  |  | TAGCGAAAGCTGCAAGAGAATGAAAATCCGTgattaaa<br>cag |
| 242 | T25 L30b<br>I25-20 | ctgaaattatacttatactcagtatatgacaaacaaaccacAAGACGAGGGT<br>AAAGAGAGAGTCCAATTCTCAAAGCCAATAGGCAG<br>TAGCGAAAGCTGCAAGAGAATGAAAATCCGTgattcac<br>aatataaattacg |
| 243 | T25 L30b<br>I50-10 | ctgaaattatacttatactcagtatatgacaaacaaaccacAAGACGAGGGT<br>AAAGAGAGAGTCCAATTCTCAAAGCCAATAGGCAG<br>TAGCGAAAGCTGCAAGAGAATGAAAATCCGTggatcat<br>agc |
| 244 | T25 L30b<br>I50-20 | ctgaaattatacttatactcagtatatgacaaacaaaccacAAGACGAGGGT<br>AAAGAGAGAGTCCAATTCTCAAAGCCAATAGGCAG<br>TAGCGAAAGCTGCAAGAGAATGAAAATCCGTggatcgc<br>agcataatatccg |
| 245 | T25 L30b<br>I80-20 | ctgaaattatacttatactcagtatatgacaaacaaaccacAAGACGAGGGT<br>AAAGAGAGAGTCCAATTCTCAAAGCCAATAGGCAG<br>TAGCGAAAGCTGCAAGAGAATGAAAATCCGTggctcgc<br>agcgcgcctaccg |

In some embodiments, a spacer and 5' intron fragment are spacers and fragments having sequences as listed in Table 8.

TABLE 9

Spacer and Anabaena 3' intron fragment sequences.

| SEQ ID NO. | Spacer | Sequence |
|---|---|---|
| 246 | T25 L10 | gctgcgagccACGGACTTAAATAATTGAGCCTTAAAGAA<br>GAAATTCTTTAAGTGGATGCTCTCAAACTCAGGGAA<br>ACCTAAATCTAGTTATAGACAAGGCAATCCTGAGCC<br>AAGCCGAAGTAGTAATTAGTAAGTTAACAAcacaaaca<br>caacttatatact |
| 247 | T25 L20 | gctgcgagccACGGACTTAAATAATTGAGCCTTAAAGAA<br>GAAATTCTTTAAGTGGATGCTCTCAAACTCAGGGAA<br>ACCTAAATCTAGTTATAGACAAGGCAATCCTGAGCC<br>AAGCCGAAGTAGTAATTAGTAAGTTAACAAcacaaaca<br>caagagtataagtataatttcag |
| 248 | T25 L30<br>(I80-10)<br>[Control] | gctgcgagccACGGACTTAAATAATTGAGCCTTAAAGAA<br>GAAATTCTTTAAGTGGATGCTCTCAAACTCAGGGAA<br>ACCTAAATCTAGTTATAGACAAGGCAATCCTGAGCC<br>AAGCCGAAGTAGTAATTAGTAAGTTAACAAcacaaaca<br>caagtcatatactgagtataagtataatttcag |
| 249 | T25 L40 | gctgcgagccACGGACTTAAATAATTGAGCCTTAAAGAA<br>GAAATTCTTTAAGTGGATGCTCTCAAACTCAGGGAA<br>ACCTAAATCTAGTTATAGACAAGGCAATCCTGAGCC<br>AAGCCGAAGTAGTAATTAGTAAGTTAACAAcacaaaca<br>caagtcatatactgagtataagtataatttcatattgttgatg |
| 250 | T25 L50 | gctgcgagccACGGACTTAAATAATTGAGCCTTAAAGAA<br>GAAATTCTTTAAGTGGATGCTCTCAAACTCAGGGAA<br>ACCTAAATCTAGTTATAGACAAGGCAATCCTGAGCC<br>AAGCCGAAGTAGTAATTAGTAAGTTAACAAcacaaaca<br>caagcgataatgcttcatatactgagtataagtatagtttcat<br>attgttgatg |
| 251 | T50 L10 | gctgcgagccACGGACTTAAATAATTGAGCCTTAAAGAA<br>GAAATTCTTTAAGTGGATGCTCTCAAACTCAGGGAA<br>ACCTAAATCTAGTTATAGACAAGGCAATCCTGAGCC<br>AAGCCGAAGTAGTAATTAGTAAGTTAACAAaacaaaaa<br>caagctgacgcta |
| 252 | T50 L20 | gctgcgagccACGGACTTAAATAATTGAGCCTTAAAGAA<br>GAAATTCTTTAAGTGGATGCTCTCAAACTCAGGGAA<br>ACCTAAATCTAGTTATAGACAAGGCAATCCTGAGCC |

TABLE 9-continued

Spacer and Anabaena 3' intron fragment sequences.

| SEQ ID NO. | Spacer | Sequence |
|---|---|---|
| | | AAGCCGAAGTAGTAATTAGTAAGTTAACAAacaaaaa<br>caagctgacgctagtatgagtat |
| 253 | T50 L30 | gctgcgagccACGGACTTAAATAATTGAGCCTTAAAGAA<br>GAAATTCTTTAAGTGGATGCTCTCAAACTCAGGGAA<br>ACCTAAATCTAGTTATAGACAAGGCAATCCTGAGCC<br>AAGCCGAAGTAGTAATTAGTAAGTTAACAAaacaaaaa<br>caagctgacgctagtatgagtatagcttcacac |
| 254 | T50 L40 | gctgcgagccACGGACTTAAATAATTGAGCCTTAAAGAA<br>GAAATTCTTTAAGTGGATGCTCTCAAACTCAGGGAA<br>ACCTAAATCTAGTTATAGACAAGGCAATCCTGAGCC<br>AAGCCGAAGTAGTAATTAGTAAGTTAACAAaacaaaaa<br>caagctgacgctagtatgagtatagcttcacactcaggtgagg |
| 255 | T50 L50 | gctgcgagccACGGACTTAAATAATTGAGCCTTAAAGAA<br>GAAATTCTTTAAGTGGATGCTCTCAAACTCAGGGAA<br>ACCTAAATCTAGTTATAGACAAGGCAATCCTGAGCC<br>AAGCCGAAGTAGTAATTAGTAAGTTAACAAaacaaaaa<br>caagctgacgctagtatgagtatagcttcacactcaggtgagg<br>catcattcgg |
| 256 | T75 L10 | gctgcgagccACGGACTTAAATAATTGAGCCTTAAAGAA<br>GAAATTCTTTAAGTGGATGCTCTCAAACTCAGGGAA<br>ACCTAAATCTAGTTATAGACAAGGCAATCCTGAGCC<br>AAGCCGAAGTAGTAATTAGTAAGTTAACAAaacaaaaa<br>caagctcgcaccg |
| 257 | T75 L20 | gctgcgagccACGGACTTAAATAATTGAGCCTTAAAGAA<br>GAAATTCTTTAAGTGGATGCTCTCAAACTCAGGGAA<br>ACCTAAATCTAGTTATAGACAAGGCAATCCTGAGCC<br>AAGCCGAAGTAGTAATTAGTAAGTTAACAAaacaaaaa<br>caagctcgcactgggtcggagcg |
| 258 | T25 L30<br>1MM | gctgcgagccACGGACTTAAATAATTGAGCCTTAAAGAA<br>GAAATTCTTTAAGTGGATGCTCTCAAACTCAGGGAA<br>ACCTAAATCTAGTTATAGACAAGGCAATCCTGAGCC<br>AAGCCGAAGTAGTAATTAGTAAGTTAACAAacacaaaca<br>caagtcatatactgagtataagtataatttcag |
| 259 | T25 L30<br>3MM | gctgcgagccACGGACTTAAATAATTGAGCCTTAAAGAA<br>GAAATTCTTTAAGTGGATGCTCTCAAACTCAGGGAA<br>ACCTAAATCTAGTTATAGACAAGGCAATCCTGAGCC<br>AAGCCGAAGTAGTAATTAGTAAGTTAACAAacacaaaca<br>caagtcatatactgagtataagtataatttcag |
| 260 | T25 L30<br>5MM | gctgcgagccACGGACTTAAATAATTGAGCCTTAAAGAA<br>GAAATTCTTTAAGTGGATGCTCTCAAACTCAGGGAA<br>ACCTAAATCTAGTTATAGACAAGGCAATCCTGAGCC<br>AAGCCGAAGTAGTAATTAGTAAGTTAACAAacacaaaca<br>caagtcatatactgagtataagtataatttcag |
| 261 | T25 L30<br>8MM | gctgcgagccACGGACTTAAATAATTGAGCCTTAAAGAA<br>GAAATTCTTTAAGTGGATGCTCTCAAACTCAGGGAA<br>ACCTAAATCTAGTTATAGACAAGGCAATCCTGAGCC<br>AAGCCGAAGTAGTAATTAGTAAGTTAACAAacacaaaca<br>caagtcatatactgagtataagtataatttcag |
| 262 | T25 L30<br>OffTarget<br>10 | gctgcgagccACGGACTTAAATAATTGAGCCTTAAAGAA<br>GAAATTCTTTAAGTGGATGCTCTCAAACTCAGGGAA<br>ACCTAAATCTAGTTATAGACAAGGCAATCCTGAGCC<br>AAGCCGAAGTAGTAATTAGTAAGTTAACAAacacaaaca<br>caagtaacttagagagtataagtataatttcag |
| 263 | T25 L30<br>OffTarget<br>20 | gctgcgagccACGGACTTAAATAATTGAGCCTTAAAGAA<br>GAAATTCTTTAAGTGGATGCTCTCAAACTCAGGGAA<br>ACCTAAATCTAGTTATAGACAAGGCAATCCTGAGCC<br>AAGCCGAAGTAGTAATTAGTAAGTTAACAAacacaaaca<br>caagtaacttagaTgtaacacacataatttcag |
| 264 | T25 L30<br>OffTarget<br>30 | gctgcgagccACGGACTTAAATAATTGAGCCTTAAAGAA<br>GAAATTCTTTAAGTGGATGCTCTCAAACTCAGGGAA<br>ACCTAAATCTAGTTATAGACAAGGCAATCCTGAGCC<br>AAGCCGAAGTAGTAATTAGTAAGTTAACAAacacaaaca<br>caagtaacttagaTgtaacacacaccgatcaac |

TABLE 9-continued

Spacer and Anabaena 3' intron fragment sequences.

| SEQ ID NO. | Spacer | Sequence |
|---|---|---|
| 265 | T25 L30 I25-10 | ctgtttaatcACGGACTTAAATAATTGAGCCTTAAAGAAG<br>AAATTCTTTAAGTGGATGCTCTCAAACTCAGGGAAA<br>CCTAAATCTAGTTATAGACAAGGCAATCCTGAGCCA<br>AGCCGAAGTAGTAATTAGTAAGTTAACAAcacaaacaca<br>agtcatatactgagtataagtataatttcag |
| 266 | T25 L30 I25-20 | cgtaatttatattgtgaatcACGGACTTAAATAATTGAGCCTTAA<br>AGAAGAAATTCTTTAAGTGGATGCTCTCAAACTCAG<br>GGAAACCTAAATCTAGTTATAGACAAGGCAATCCT<br>GAGCCAAGCCGAAGTAGTAATTAGTAAGTTAACAAc<br>acaaacacaagtcatatactgagtataagtataatttcag |
| 267 | T25 L30 I50-10 | gctatgatccACGGACTTAAATAATTGAGCCTTAAAGAA<br>GAAATTCTTTAAGTGGATGCTCTCAAACTCAGGGAA<br>ACCTAAATCTAGTTATAGACAAGGCAATCCTGAGCC<br>AAGCCGAAGTAGTAATTAGTAAGTTAACAAcacaaaca<br>caagtcatatactgagtataagtataatttcag |
| 268 | T25 L30 I50-20 | cggatattatgctgcgatccACGGACTTAAATAATTGAGCCTTA<br>AAGAAGAAATTCTTTAAGTGGATGCTCTCAAACTCA<br>GGGAAACCTAAATCTAGTTATAGACAAGGCAATCC<br>TGAGCCAAGCCGAAGTAGTAATTAGTAAGTTAACA<br>Acacaaacacaagtcatatactgagtataagtataatttcag |
| 269 | T25 L30 I80-20 | cggtaggcgcgctgcgagccACGGACTTAAATAATTGAGCCTT<br>AAAGAAGAAATTCTTTAAGTGGATGCTCTCAAACTC<br>AGGGAAACCTAAATCTAGTTATAGACAAGGCAATC<br>CTGAGCCAAGCCGAAGTAGTAATTAGTAAGTTAAC<br>AAcacaaacacaagtcatatactgagtataagtataatttcag |
| 270 | T25 L30 I80-20x2 | gcgctaacgtcgacgccggcaaacggtaggcgcgctgcgagcc<br>ACGGACTTAAATAATTGAGCCTTAAAGAAGAAATTCTTTAAGT<br>GGATGCTCTCAAACTCAGGGAAACCTAAATCTAGTT<br>ATAGACAAGGCAATCCTGAGCCAAGCCGAAGTAGT<br>AATTAGTAAGTTAACAAcacaaacacaagtcatatactgagta<br>taagtataatttcag |
| 271 | T25 L30 I50-20x2 | gcatgtcacttgtatcctcgaaacggatattatgctgcgatcc<br>ACGGACTTAAATAATTGAGCCTTAAAGAAGAAATTCTTTAAGTGGA<br>TGCTCTCAAACTCAGGGAAACCTAAATCTAGTTATA<br>GACAAGGCAATCCTGAGCCAAGCCGAAGTAGTAAT<br>TAGTAAGTTAACAAcacaaacacaagtcatatactgagtataa<br>gtataatttcag |
| 272 | T25 L30 I25-20x2 | gttagagttatcatttatcgaaacgtaatttagattgtgaatcACG<br>GACTTAAATAATTGAGCCTTAAAGAAGAAATTCTTTAAGTGGAT<br>GCTCTCAAACTCAGGGAAACCTAAATCTAGTTATAG<br>ACAAGGCAATCCTGAGCCAAGCCGAAGTAGTAATT<br>AGTAAGTTAACAAcacaaacacaagtcatatactgagtataag<br>tataatttcag |
| 273 | T0 L0 | gctgcgagccACGGACTTAAATAATTGAGCCTTAAAGAA<br>GAAATTCTTTAAGTGGATGCTCTCAAACTCAGGGAA<br>ACCTAAATCTAGTTATAGACAAGGCAATCCTGAGCC<br>AAGCCGAAGTAGTAATTAGTAAGTTAACAAcacaaaca<br>caa |
| 274 | T100 L5 | gctgcgagccACGGACTTAAATAATTGAGCCTTAAAGAA<br>GAAATTCTTTAAGTGGATGCTCTCAAACTCAGGGAA<br>ACCTAAATCTAGTTATAGACAAGGCAATCCTGAGCC<br>AAGCCGAAGTAGTAATTAGTAAGTTAACAAaacaaaaa<br>caagcccg |
| 275 | T75 L30 | gctgcgagccACGGACTTAAATAATTGAGCCTTAAAGAA<br>GAAATTCTTTAAGTGGATGCTCTCAAACTCAGGGAA<br>ACCTAAATCTAGTTATAGACAAGGCAATCCTGAGCC<br>AAGCCGAAGTAGTAATTAGTAAGTTAACAAaacaaaaa<br>caagctcgcactggccggaagctcgtcggagcg |
| 276 | T0 L0a | gctgcgagccACGGACTTAAATAATTGAGCCTTAAAGAA<br>GAAATTCTTTAAGTGGATGCTCTCAAACTCAGGGAA<br>ACCTAAATCTAGTTATAGACAAGGCAATCCTGAGCC<br>AAGCCGAAGTAGTAATTAGTAAGTTAACAATAGAT<br>GACTTACAACTAATCGGAAGGTGCAGAGACTCGAC<br>GGGAGCTACCCTAACGTCAAGACGAGGGTAAAGAG<br>AGAGTCCAATTCTCAAAGCCAATAcacaaacacaa |

TABLE 9-continued

Spacer and Anabaena 3' intron fragment sequences.

| SEQ ID NO. | Spacer | Sequence |
|---|---|---|
| 277 | T25 L10a | gctgcgagccACGGACTTAAATAATTGAGCCTTAAAGAA<br>GAAATTCTTTAAGTGGATGCTCTCAAACTCAGGGAA<br>ACCTAAATCTAGTTATAGACAAGGCAATCCTGAGCC<br>AAGCCGAAGTAGTAATTAGTAAGTTAACAATAGAT<br>GACTTACAACTAATCGGAAGGTGCAGAGACTCGAC<br>GGGAGCTACCCTAACGTCAAGACGAGGGTAAAGAG<br>AGAGTCCAATTCTCAAAGCCAATAcacaaacacaacttatatact |
| 278 | T25 L20a | gctgcgagccACGGACTTAAATAATTGAGCCTTAAAGAA<br>GAAATTCTTTAAGTGGATGCTCTCAAACTCAGGGAA<br>ACCTAAATCTAGTTATAGACAAGGCAATCCTGAGCC<br>AAGCCGAAGTAGTAATTAGTAAGTTAACAATAGAT<br>GACTTACAACTAATCGGAAGGTGCAGAGACTCGAC<br>GGGAGCTACCCTAACGTCAAGACGAGGGTAAAGAG<br>AGAGTCCAATTCTCAAAGCCAATAcacaaacacaagagtataa<br>gtataatttcag |
| 279 | T25 L30a<br>(I80-10)<br>[Control] | gctgcgagccACGGACTTAAATAATTGAGCCTTAAAGAA<br>GAAATTCTTTAAGTGGATGCTCTCAAACTCAGGGAA<br>ACCTAAATCTAGTTATAGACAAGGCAATCCTGAGCC<br>AAGCCGAAGTAGTAATTAGTAAGTTAACAATAGAT<br>GACTTACAACTAATCGGAAGGTGCAGAGACTCGAC<br>GGGAGCTACCCTAACGTCAAGACGAGGGTAAAGAG<br>AGAGTCCAATTCTCAAAGCCAATAcacaaacacaagtcatata<br>ctgagtataagtataatttcag |
| 280 | T50 L10a | gctgcgagccACGGACTTAAATAATTGAGCCTTAAAGAA<br>GAAATTCTTTAAGTGGATGCTCTCAAACTCAGGGAA<br>ACCTAAATCTAGTTATAGACAAGGCAATCCTGAGCC<br>AAGCCGAAGTAGTAATTAGTAAGTTAACAATAGAT<br>GACTTACAACTAATCGGAAGGTGCAGAGACTCGAC<br>GGGAGCTACCCTAACGTCAAGACGAGGGTAAAGAG<br>AGAGTCCAATTCTCAAAGCCAATAaacaaaaacaagctgacg<br>cta |
| 281 | T50 L20a | gctgcgagccACGGACTTAAATAATTGAGCCTTAAAGAA<br>GAAATTCTTTAAGTGGATGCTCTCAAACTCAGGGAA<br>ACCTAAATCTAGTTATAGACAAGGCAATCCTGAGCC<br>AAGCCGAAGTAGTAATTAGTAAGTTAACAATAGAT<br>GACTTACAACTAATCGGAAGGTGCAGAGACTCGAC<br>GGGAGCTACCCTAACGTCAAGACGAGGGTAAAGAG<br>AGAGTCCAATTCTCAAAGCCAATAaacaaaaacaagctgacg<br>ctagtatgagtat |
| 282 | T50 L30a | gctgcgagccACGGACTTAAATAATTGAGCCTTAAAGAA<br>GAAATTCTTTAAGTGGATGCTCTCAAACTCAGGGAA<br>ACCTAAATCTAGTTATAGACAAGGCAATCCTGAGCC<br>AAGCCGAAGTAGTAATTAGTAAGTTAACAATAGAT<br>GACTTACAACTAATCGGAAGGTGCAGAGACTCGAC<br>GGGAGCTACCCTAACGTCAAGACGAGGGTAAAGAG<br>AGAGTCCAATTCTCAAAGCCAATAaacaaaaacaagctgacg<br>ctagtatgagtatagcttcacac |
| 283 | T75 L10a | gctgcgagccACGGACTTAAATAATTGAGCCTTAAAGAA<br>GAAATTCTTTAAGTGGATGCTCTCAAACTCAGGGAA<br>ACCTAAATCTAGTTATAGACAAGGCAATCCTGAGCC<br>AAGCCGAAGTAGTAATTAGTAAGTTAACAATAGAT<br>GACTTACAACTAATCGGAAGGTGCAGAGACTCGAC<br>GGGAGCTACCCTAACGTCAAGACGAGGGTAAAGAG<br>AGAGTCCAATTCTCAAAGCCAATAaacaaaaacaagctcgca<br>ccg |
| 284 | T75 L20a | gctgcgagccACGGACTTAAATAATTGAGCCTTAAAGAA<br>GAAATTCTTTAAGTGGATGCTCTCAAACTCAGGGAA<br>ACCTAAATCTAGTTATAGACAAGGCAATCCTGAGCC<br>AAGCCGAAGTAGTAATTAGTAAGTTAACAATAGAT<br>GACTTACAACTAATCGGAAGGTGCAGAGACTCGAC<br>GGGAGCTACCCTAACGTCAAGACGAGGGTAAAGAG<br>AGAGTCCAATTCTCAAAGCCAATAaacaaaaacaagctcgca<br>ctgggtcggagcg |
| 285 | T75 L30a | gctgcgagccACGGACTTAAATAATTGAGCCTTAAAGAA<br>GAAATTCTTTAAGTGGATGCTCTCAAACTCAGGGAA<br>ACCTAAATCTAGTTATAGACAAGGCAATCCTGAGCC<br>AAGCCGAAGTAGTAATTAGTAAGTTAACAATAGAT |

TABLE 9-continued

Spacer and Anabaena 3' intron fragment sequences.

| SEQ ID NO. | Spacer | Sequence |
|---|---|---|
| | | GACTTACAACTAATCGGAAGGTGCAGAGACTCGAC<br>GGGAGCTACCCTAACGTCAAGACGAGGGTAAAGAG<br>AGAGTCCAATTCTCAAAGCCAATAaacaaaaacaagctcgca<br>ctggccggaagctcgtcggagcg |
| 286 | T0 L0b | gctgcgagccACGGACTTAAATAATTGAGCCTTAAAGAA<br>GAAATTCTTTAAGTGGATGCTCTCAAACTCAGGGAA<br>ACCTAAATCTAGTTATAGACAAGGCAATCCTGAGCC<br>AAGCCGAAGTAGTAATTAGTAAGTTAACAATAGAT<br>GACTTACAACTAATCGGAAGGTGCAGAGACTCGAC<br>GGGAGCTACCCTAACGTCcacaaacacaa |
| 287 | T25 L10b | gctgcgagccACGGACTTAAATAATTGAGCCTTAAAGAA<br>GAAATTCTTTAAGTGGATGCTCTCAAACTCAGGGAA<br>ACCTAAATCTAGTTATAGACAAGGCAATCCTGAGCC<br>AAGCCGAAGTAGTAATTAGTAAGTTAACAATAGAT<br>GACTTACAACTAATCGGAAGGTGCAGAGACTCGAC<br>GGGAGCTACCCTAACGTCcacaaacacaacttatatact |
| 288 | T25 L20b | gctgcgagccACGGACTTAAATAATTGAGCCTTAAAGAA<br>GAAATTCTTTAAGTGGATGCTCTCAAACTCAGGGAA<br>ACCTAAATCTAGTTATAGACAAGGCAATCCTGAGCC<br>AAGCCGAAGTAGTAATTAGTAAGTTAACAATAGAT<br>GACTTACAACTAATCGGAAGGTGCAGAGACTCGAC<br>GGGAGCTACCCTAACGTCcacaaacacaagagtataagtataa<br>tttcag |
| 289 | T25 L30b<br>(I80-10)<br>[Control] | gctgcgagccACGGACTTAAATAATTGAGCCTTAAAGAA<br>GAAATTCTTTAAGTGGATGCTCTCAAACTCAGGGAA<br>ACCTAAATCTAGTTATAGACAAGGCAATCCTGAGCC<br>AAGCCGAAGTAGTAATTAGTAAGTTAACAATAGAT<br>GACTTACAACTAATCGGAAGGTGCAGAGACTCGAC<br>GGGAGCTACCCTAACGTCcacaaacacaagtcatatactgagt<br>ataagtataatttcag |
| 290 | T50 L10b | gctgcgagccACGGACTTAAATAATTGAGCCTTAAAGAA<br>GAAATTCTTTAAGTGGATGCTCTCAAACTCAGGGAA<br>ACCTAAATCTAGTTATAGACAAGGCAATCCTGAGCC<br>AAGCCGAAGTAGTAATTAGTAAGTTAACAATAGAT<br>GACTTACAACTAATCGGAAGGTGCAGAGACTCGAC<br>GGGAGCTACCCTAACGTCaacaaaaacaagctgacgcta |
| 291 | T50 L20b | gctgcgagccACGGACTTAAATAATTGAGCCTTAAAGAA<br>GAAATTCTTTAAGTGGATGCTCTCAAACTCAGGGAA<br>ACCTAAATCTAGTTATAGACAAGGCAATCCTGAGCC<br>AAGCCGAAGTAGTAATTAGTAAGTTAACAATAGAT<br>GACTTACAACTAATCGGAAGGTGCAGAGACTCGAC<br>GGGAGCTACCCTAACGTCaacaaaaacaagctgacgctagtat<br>gagtat |
| 292 | T50 L30b | gctgcgagccACGGACTTAAATAATTGAGCCTTAAAGAA<br>GAAATTCTTTAAGTGGATGCTCTCAAACTCAGGGAA<br>ACCTAAATCTAGTTATAGACAAGGCAATCCTGAGCC<br>AAGCCGAAGTAGTAATTAGTAAGTTAACAATAGAT<br>GACTTACAACTAATCGGAAGGTGCAGAGACTCGAC<br>GGGAGCTACCCTAACGTCaacaaaaacaagctgacgctagtat<br>gagtatagcttcacac |
| 293 | T75 L10b | gctgcgagccACGGACTTAAATAATTGAGCCTTAAAGAA<br>GAAATTCTTTAAGTGGATGCTCTCAAACTCAGGGAA<br>ACCTAAATCTAGTTATAGACAAGGCAATCCTGAGCC<br>AAGCCGAAGTAGTAATTAGTAAGTTAACAATAGAT<br>GACTTACAACTAATCGGAAGGTGCAGAGACTCGAC<br>GGGAGCTACCCTAACGTCaacaaaaacaagctcgcaccg |
| 294 | T75 L20b | gctgcgagccACGGACTTAAATAATTGAGCCTTAAAGAA<br>GAAATTCTTTAAGTGGATGCTCTCAAACTCAGGGAA<br>ACCTAAATCTAGTTATAGACAAGGCAATCCTGAGCC<br>AAGCCGAAGTAGTAATTAGTAAGTTAACAATAGAT<br>GACTTACAACTAATCGGAAGGTGCAGAGACTCGAC<br>GGGAGCTACCCTAACGTCaacaaaaacaagctcgcactgggtc<br>ggagcg |
| 295 | T75 L30b | gctgcgagccACGGACTTAAATAATTGAGCCTTAAAGAA<br>GAAATTCTTTAAGTGGATGCTCTCAAACTCAGGGAA<br>ACCTAAATCTAGTTATAGACAAGGCAATCCTGAGCC |

TABLE 9-continued

Spacer and Anabaena 3' intron fragment sequences.

| SEQ ID NO. | Spacer | Sequence |
|---|---|---|
| | | AAGCCGAAGTAGTAATTAGTAAGTTAACAATAGAT<br>GACTTACAACTAATCGGAAGGTGCAGAGACTCGAC<br>GGGAGCTACCCTAACGTCaacaaaaacaagctcgcactggccg<br>gaagctcgtcggagcg |
| 296 | T25 L30<br>I0-0 | ACGGACTTAAATAATTGAGCCTTAAAGAAGAAATT<br>CTTTAAGTGGATGCTCTCAAACTCAGGGAAACCTAA<br>ATCTAGTTATAGACAAGGCAATCCTGAGCCAAGCC<br>GAAGTAGTAATTAGTAAGTTAACAAcacaaacacaagtcata<br>tactgagtataagtataatttcag |
| 297 | T25 L30a<br>I0-0 | ACGGACTTAAATAATTGAGCCTTAAAGAAGAAATT<br>CTTTAAGTGGATGCTCTCAAACTCAGGGAAACCTAA<br>ATCTAGTTATAGACAAGGCAATCCTGAGCCAAGCC<br>GAAGTAGTAATTAGTAAGTTAACAATAGATGACTTA<br>CAACTAATCGGAAGGTGCAGAGACTCGACGGGAGC<br>TACCCTAACGTCAAGACGAGGGTAAAGAGAGTC<br>CAATTCTCAAAGCCAATAcacaaacacaagtcatatactgagt<br>ataagtataatttcag |
| 298 | T25 L30a<br>I25-10 | ctgtttaatcACGGACTTAAATAATTGAGCCTTAAAGAAG<br>AAATTCTTTAAGTGGATGCTCTCAAACTCAGGGAAA<br>CCTAAATCTAGTTATAGACAAGGCAATCCTGAGCCA<br>AGCCGAAGTAGTAATTAGTAAGTTAACAATAGATG<br>ACTTACAACTAATCGGAAGGTGCAGAGACTCGACG<br>GGAGCTACCCTAACGTCAAGACGAGGGTAAAGAGA<br>GAGTCCAATTCTCAAAGCCAATAcacaaacacaagtcatatac<br>tgagtataagtataatttcag |
| 299 | T25 L30a<br>I25-20 | cgtaatttatattgtgaatcACGGACTTAAATAATTGAGCCTTAA<br>AGAAGAAATTCTTTAAGTGGATGCTCTCAAACTCAG<br>GGAAACCTAAATCTAGTTATAGACAAGGCAATCCT<br>GAGCCAAGCCGAAGTAGTAATTAGTAAGTTAACAA<br>TAGATGACTTACAACTAATCGGAAGGTGCAGAGAC<br>TCGACGGGAGCTACCCTAACGTCAAGACGAGGGTA<br>AAGAGAGAGTCCAATTCTCAAAGCCAATAcacaaacaca<br>agtcatatactgagtataagtataatttcag |
| 300 | T25 L30a<br>I50-10 | gctatgatccACGGACTTAAATAATTGAGCCTTAAAGAA<br>GAAATTCTTTAAGTGGATGCTCTCAAACTCAGGGAA<br>ACCTAAATCTAGTTATAGACAAGGCAATCCTGAGCC<br>AAGCCGAAGTAGTAATTAGTAAGTTAACAATAGAT<br>GACTTACAACTAATCGGAAGGTGCAGAGACTCGAC<br>GGGAGCTACCCTAACGTCAAGACGAGGGTAAAGAG<br>AGAGTCCAATTCTCAAAGCCAATAcacaaacacaagtcatata<br>ctgagtataagtataatttcag |
| 301 | T25 L30a<br>I50-20 | cggatattatgctgcgatccACGGACTTAAATAATTGAGCCTTA<br>AAGAAGAAATTCTTTAAGTGGATGCTCTCAAACTCA<br>GGGAAACCTAAATCTAGTTATAGACAAGGCAATCC<br>TGAGCCAAGCCGAAGTAGTAATTAGTAAGTTAACA<br>ATAGATGACTTACAACTAATCGGAAGGTGCAGAGA<br>CTCGACGGGAGCTACCCTAACGTCAAGACGAGGGT<br>AAAGAGAGTCCAATTCTCAAAGCCAATAcacaaaca<br>caagtcatatactgagtataagtataatttcag |
| 302 | T25 L30a<br>I80-20 | cggtaggcgcgctgcgagccACGGACTTAAATAATTGAGCCTT<br>AAAGAAGAAATTCTTTAAGTGGATGCTCTCAAACTC<br>AGGGAAACCTAAATCTAGTTATAGACAAGGCAATC<br>CTGAGCCAAGCCGAAGTAGTAATTAGTAAGTTAAC<br>AATAGATGACTTACAACTAATCGGAAGGTGCAGAG<br>ACTCGACGGGAGCTACCCTAACGTCAAGACGAGGG<br>TAAAGAGAGTCCAATTCTCAAAGCCAATAcacaaac<br>acaagtcatatactgagtataagtataatttcag |
| 303 | T25 L30b<br>I0-0 | ACGGACTTAAATAATTGAGCCTTAAAGAAGAAATT<br>CTTTAAGTGGATGCTCTCAAACTCAGGGAAACCTAA<br>ATCTAGTTATAGACAAGGCAATCCTGAGCCAAGCC<br>GAAGTAGTAATTAGTAAGTTAACAATAGATGACTTA<br>CAACTAATCGGAAGGTGCAGAGACTCGACGGGAGC<br>TACCCTAACGTCcacaaacacaagtcatatactgagtataagt<br>ataatttcag |
| 304 | T25 L30b<br>I25-10 | ctgtttaatcACGGACTTAAATAATTGAGCCTTAAAGAAG<br>AAATTCTTTAAGTGGATGCTCTCAAACTCAGGGAAA<br>CCTAAATCTAGTTATAGACAAGGCAATCCTGAGCCA |

TABLE 9-continued

Spacer and Anabaena 3' intron fragment sequences.

| SEQ ID NO. | Spacer | Sequence |
|---|---|---|
| | | AGCCGAAGTAGTAATTAGTAAGTTAACAATAGATG<br>ACTTACAACTAATCGGAAGGTGCAGAGACTCGACG<br>GGAGCTACCCTAACGTCcacaaacacaagtcatatactgagta<br>taagtataatttcag |
| 305 | T25 L30b<br>I25-20 | cgtaatttatattgtgaatcACGGACTTAAATAATTGAGCCTTAA<br>AGAAGAAATTCTTTAAGTGGATGCTCTCAAACTCAG<br>GGAAACCTAAATCTAGTTATAGACAAGGCAATCCT<br>GAGCCAAGCCGAAGTAGTAATTAGTAAGTTAACAA<br>TAGATGACTTACAACTAATCGGAAGGTGCAGAGAC<br>TCGACGGGAGCTACCCTAACGTCcacaaacacaagtcatatact<br>gagtataagtataatttcag |
| 306 | T25 L30b<br>I50-10 | gctatgatccACGGACTTAAATAATTGAGCCTTAAAGAA<br>GAAATTCTTTAAGTGGATGCTCTCAAACTCAGGGAA<br>ACCTAAATCTAGTTATAGACAAGGCAATCCTGAGCC<br>AAGCCGAAGTAGTAATTAGTAAGTTAACAATAGAT<br>GACTTACAACTAATCGGAAGGTGCAGAGACTCGAC<br>GGGAGCTACCCTAACGTCcacaaacacaagtcatatactgagt<br>ataagtataatttcag |
| 307 | T25 L30b<br>I50-20 | cggatattatgctgcgatccACGGACTTAAATAATTGAGCCTTA<br>AAGAAGAAATTCTTTAAGTGGATGCTCTCAAACTCA<br>GGGAAACCTAAATCTAGTTATAGACAAGGCAATCC<br>TGAGCCAAGCCGAAGTAGTAATTAGTAAGTTAACA<br>ATAGATGACTTACAACTAATCGGAAGGTGCAGAGA<br>CTCGACGGGAGCTACCCTAACGTCcacaaacacaagtcatata<br>ctgagtataagtataatttcag |
| 308 | T25 L30b<br>I80-20 | cggtaggcgcgctgcgagccACGGACTTAAATAATTGAGCCTT<br>AAAGAAGAAATTCTTTAAGTGGATGCTCTCAAACTC<br>AGGGAAACCTAAATCTAGTTATAGACAAGGCAATC<br>CTGAGCCAAGCCGAAGTAGTAATTAGTAAGTTAAC<br>AATAGATGACTTACAACTAATCGGAAGGTGCAGAG<br>ACTCGACGGGAGCTACCCTAACGTCcacaaacacaagtcatat<br>actgagtataagtataatttcag |

In some embodiments, a spacer and 3' intron fragment is a spacer and intron fragment having sequences as listed in Table 9.

TABLE 10

CAR sequences.

| SEQ ID NO. | CAR | Sequence |
|---|---|---|
| 309 | FMC63-4-<br>1BB | ATGCTGCTGCTGGTCACATCTCTGCTGCTGTGCGAG<br>CTGCCCCATCCTGCCTTTCTGCTGATCCCCGACATCC<br>AGATGACCCAGACCACAAGCAGCCTGTCTGCCAGC<br>CTGGGCGATAGAGTGACCATCAGCTGTAGAGCCAG<br>CCAGGACATCAGCAAGTACCTGAACTGGTATCAGC<br>AAAAGCCCGACGGCACCGTGAAGCTGCTGATCTAC<br>CACACCAGCAGACTGCACAGCGGCGTGCCAAGCAG<br>ATTTTCTGGCAGCGGCTCTGGCACCGACTACAGCCT<br>GACAATCAGCAACCTGGAACAAGAGGATATCGCTA<br>CCTACTTCTGCCAGCAAGGCAACACCCTGCCTTACA<br>CCTTTGGCGGAGGCACCAAGCTGGAAATCACCGGC<br>TCTACAAGCGGCAGCGGCAAACCTGGATCTGGCGA<br>GGGATCTACCAAGGGCGAAGTGAAACTGCAAGAGT<br>CTGGCCCTGGACTGGTGGCCCCATCTCAGTCTCTGA<br>GCGTGACCTGTACAGTCAGCGGAGTGTCCCTGCCTG<br>ATTACGGCGTGTCCTGGATCAGACAGCCTCCTCGGA<br>AAGGCCTGGAATGGCTGGGAGTGATCTGGGCAGC<br>GAGACAACCTACTACAACAGCGCCCTGAAGTCCCG<br>GCTGACCATCATCAAGGACAACTCCAAGAGCCAGG<br>TGTTCCTGAAGATGAACAGCCTGCAGACCGACGAC<br>ACCGCCATCTACTATTGCGCCAAGCACTACTACTAC<br>GGCGGCAGCTACGCCATGGATTATTGGGGCCAGGG<br>CACCAGCGTGACCGTTTCTTCTGCCGCCGCTATCGA<br>AGTGATGTACCCTCCTCCTTACCTGGACAACGAGAA<br>GTCCAACGGCACCATCATCCACGTGAAGGGCAAGC<br>ACCTGTGTCCTTCTCCACTGTTCCCCGGACCTAGCA |

TABLE 10-continued

CAR sequences.

| SEQ ID NO. | CAR | Sequence |
|---|---|---|
|  |  | AGCCTTTCTGGGTGCTCGTTGTTGTTGGCGGCGTGC<br>TGGCCTGTTACAGCCTGCTGGTTACCGTGGCCTTCA<br>TCATCTTTTGGGTCAAGAGAGGCCGGAAGAAACTTC<br>TTTATATATTCAAGCAGCCCTTTATGCGACCCGTTC<br>AGACTACCCAAGAGGAAGATGGATGCAGTTGCCGC<br>TTTCCAGAAGAGGAGGAGGGCGGGTGCGAACTGtaa |
| 310 | FMC63-<br>CD28 | ATGCTGCTGCTGGTCACATCTCTGCTGCTGTGCGAG<br>CTGCCCCATCCTGCCTTTCTGCTGATCCCCGACATCC<br>AGATGACCCAGACCACAAGCAGCCTGTCTGCCAGC<br>CTGGGCGATAGAGTGACCATCAGCTGTAGAGCCAG<br>CCAGGACATCAGCAAGTACCTGAACTGGTATCAGC<br>AAAAGCCCGACGGCACCGTGAAGCTGCTGATCTAC<br>CACACCAGCAGACTGCACAGCGGCGTGCCAAGCAG<br>ATTTTCTGGCAGCGGCTCTGGCACCGACTACAGCCT<br>GACAATCAGCAACCTGGAACAAGAGGATATCGCTA<br>CCTACTTCTGCCAGCAAGGCAACACCCTGCCTTACA<br>CCTTTGGCGGAGGCACCAAGCTGGAAATCACCGGC<br>TCTACAAGCGGCAGCGGCAAACCTGGATCTGGCGA<br>GGGATCTACCAAGGGCGAAGTGAAACTGCAAGAGT<br>CTGGCCCTGGACTGGTGGCCCCATCTCAGTCTCTGA<br>GCGTGACCTGTACAGTCAGCGGAGTGTCCCTGCCTG<br>ATTACGGCGTGTCCTGGATCAGACAGCCTCCTCGGA<br>AAGGCCTGGAATGGCTGGGAGTGATCTGGGGCAGC<br>GAGACAACCTACTACAACAGCGCCCTGAAGTCCCG<br>GCTGACCATCATCAAGGACAACTCCAAGAGCCAGG<br>TGTTCCTGAAGATGAACAGCCTGCAGACCGACGAC<br>ACCGCCATCTACTATTGCGCCAAGCACTACTACTAC<br>GGCGGCAGCTACGCCATGGATTATTGGGGCCAGGG<br>CACCAGCGTGACCGTTTCTTCTGCCGCCGCTATCGA<br>AGTGATGTACCCTCCTCCTTACCTGGACAACGAGAA<br>GTCCAACGGCACCATCATCCACGTGAAGGGCAAGC<br>ACCTGTGTCCTTCTCCACTGTTCCCCGGACCTAGCA<br>AGCCTTTCTGGGTGCTCGTTGTTGTTGGCGGCGTGC<br>TGGCCTGTTACAGCCTGCTGGTTACCGTGGCCTTCA<br>TCATCTTTTGGGTCCGAAGCAAGCGGAGCCGGCTGC<br>TGCACTCCGACTACATGAACATGACCCCTAGACGGC<br>CCGGACCAACCAGAAAGCACTACCAGCCTTACGCT<br>CCTCCTAGAGACTTCGCCGCCTACCGGTCCtaa |
| 311 | FMC63-<br>CD28-zeta | ATGCTGCTGCTGGTCACATCTCTGCTGCTGTGCGAG<br>CTGCCCCATCCTGCCTTTCTGCTGATCCCCGACATCC<br>AGATGACCCAGACCACAAGCAGCCTGTCTGCCAGC<br>CTGGGCGATAGAGTGACCATCAGCTGTAGAGCCAG<br>CCAGGACATCAGCAAGTACCTGAACTGGTATCAGC<br>AAAAGCCCGACGGCACCGTGAAGCTGCTGATCTAC<br>CACACCAGCAGACTGCACAGCGGCGTGCCAAGCAG<br>ATTTTCTGGCAGCGGCTCTGGCACCGACTACAGCCT<br>GACAATCAGCAACCTGGAACAAGAGGATATCGCTA<br>CCTACTTCTGCCAGCAAGGCAACACCCTGCCTTACA<br>CCTTTGGCGGAGGCACCAAGCTGGAAATCACCGGC<br>TCTACAAGCGGCAGCGGCAAACCTGGATCTGGCGA<br>GGGATCTACCAAGGGCGAAGTGAAACTGCAAGAGT<br>CTGGCCCTGGACTGGTGGCCCCATCTCAGTCTCTGA<br>GCGTGACCTGTACAGTCAGCGGAGTGTCCCTGCCTG<br>ATTACGGCGTGTCCTGGATCAGACAGCCTCCTCGGA<br>AAGGCCTGGAATGGCTGGGAGTGATCTGGGGCAGC<br>GAGACAACCTACTACAACAGCGCCCTGAAGTCCCG<br>GCTGACCATCATCAAGGACAACTCCAAGAGCCAGG<br>TGTTCCTGAAGATGAACAGCCTGCAGACCGACGAC<br>ACCGCCATCTACTATTGCGCCAAGCACTACTACTAC<br>GGCGGCAGCTACGCCATGGATTATTGGGGCCAGGG<br>CACCAGCGTGACCGTTTCTTCTGCCGCCGCTATCGA<br>AGTGATGTACCCTCCTCCTTACCTGGACAACGAGAA<br>GTCCAACGGCACCATCATCCACGTGAAGGGCAAGC<br>ACCTGTGTCCTTCTCCACTGTTCCCCGGACCTAGCA<br>AGCCTTTCTGGGTGCTCGTTGTTGTTGGCGGCGTGC<br>TGGCCTGTTACAGCCTGCTGGTTACCGTGGCCTTCA<br>TCATCTTTTGGGTCCGAAGCAAGCGGAGCCGGCTGC<br>TGCACTCCGACTACATGAACATGACCCCTAGACGGC<br>CCGGACCAACCAGAAAGCACTACCAGCCTTACGCT<br>CCTCCTAGAGACTTCGCCGCCTACCGGTCCAGAGTG<br>AAGTTCAGCAGATCCGCCGATGCTCCCGCCTATCAG<br>CAGGGCCAAAACCAGCTGTACAACGAGCTGAACCT<br>GGGGAGAAGAGAAGAGTACGACGTGCTGGACAAGC<br>GGAGAGGCAGAGATCCTGAAATGGGCGGCAAGCCC |

TABLE 10-continued

CAR sequences.

| SEQ ID NO. | CAR | Sequence |
|---|---|---|
| | | AGACGGAAGAATCCTCAAGAGGGCCTGTATAATGA
GCTGCAGAAAGACAAGATGGCCGAGGCCTACAGCG
AGATCGGAATGAAGGGCGAGCGCAGAAGAGGCAA
GGGACACGATGGACTGTACCAGGGACTGAGCACCG
CCACCAAGGATACCTATGACGCCCTGCACATGCAG
GCCCTGCCTCCAAGAtaa |
| 312 | FMC63-zeta | ATGCTGCTGCTGGTCACATCTCTGCTGCTGTGCGAG
CTGCCCCATCCTGCCTTTCTGCTGATCCCCGACATCC
AGATGACCCAGACCACAAGCAGCCTGTCTGCCAGC
CTGGGCGATAGAGTGACCATCAGCTGTAGAGCCAG
CCAGGACATCAGCAAGTACCTGAACTGGTATCAGC
AAAAGCCCGACGGCACCGTGAAGCTGCTGATCTAC
CACACCAGCAGACTGCACAGCGGCGTGCCAAGCAG
ATTTTCTGGCAGCGGCTCTGGCACCGACTACAGCCT
GACAATCAGCAACCTGGAACAAGAGGATATCGCTA
CCTACTTCTGCCAGCAAGGCAACACCCTGCCTTACA
CCTTTGGCGGAGGCACCAAGCTGGAAATCACCGGC
TCTACAAGCGGCAGCGGCAAACCTGGATCTGGCGA
GGGATCTACCAAGGGCGAAGTGAAACTGCAAGAGT
CTGGCCCTGGACTGGTGGCCCCATCTCAGTCTCTGA
GCGTGACCTGTACAGTCAGCGGAGTGTCCCTGCCTG
ATTACGGCGTGTCCTGGATCAGACAGCCTCCTCGGA
AAGGCCTGGAATGGCTGGGAGTGATCTGGGCAGC
GAGACAACCTACTACAACAGCGCCCTGAAGTCCCG
GCTGACCATCATCAAGGACAACTCCAAGAGCCAGG
TGTTCCTGAAGATGAACAGCCTGCAGACCGACGAC
ACCGCCATCTACTATTGCGCCAAGCACTACTACTAC
GGCGGCAGCTACGCCATGGATTATTGGGGCCAGGG
CACCAGCGTGACCGTTTCTTCTGCCGCCGCTATCGA
AGTGATGTACCCTCCTCCTTACCTGGACAACGAGAA
GTCCAACGGCACCATCATCCACGTGAAGGGCAAGC
ACCTGTGTCCTTCTCCACTGTTCCCCGGACCTAGCA
AGCCTTTCTGGGTGCTCGTTGTTGTTGGCGGCGTGC
TGGCCTGTTACAGCCTGCTGGTTACCGTGGCCTTCA
TCATCTTTTGGGTCAGAGTGAAGTTCAGCAGATCCG
CCGATGCTCCCGCCTATCAGCAGGGCCAAAACCAG
CTGTACAACGAGCTGAACCTGGGGAGAAGAGAAGA
GTACGACGTGCTGGACAAGCGGAGAGGCAGAGATC
CTGAAATGGGCGGCAAGCCCAGACGGAAGAATCCT
CAAGAGGGCCTGTATAATGAGCTGCAGAAAGACAA
GATGGCCGAGGCCTACAGCGAGATCGGAATGAAGG
GCGAGCGCAGAAGAGGCAAGGGACACGATGGACTG
TACCAGGGACTGAGCACCGCCACCAAGGATACCTA
TGACGCCCTGCACATGCAGGCCCTGCCTCCAAGAtaa |
| 313 | CircKymriah-Q388 | ATGGCTCTCCCGGTCACAGCCCTTCTCCTGCCCCTG
GCACTCTTGCTGCATGCGGCACGACCCGACATCCAG
ATGACCCAGACCACAAGCAGCCTGTCTGCCAGCCTG
GGCGATAGAGTGACCATCAGCTGTAGAGCCAGCCA
GGACATCAGCAAGTACCTGAACTGGTATCAGCAAA
AGCCCGACGGCACCGTGAAGCTGCTGATCTACCAC
ACCAGCAGACTGCACAGCGGCGTGCCAAGCAGATT
TTCTGGCAGCGGCTCTGGCACCGACTACAGCCTGAC
AATCAGCAACCTGGAACAAGAGGATATCGCTACCT
ACTTCTGCCAGCAAGGCAACACCCTGCCTTACACCT
TTGGCGGAGGCACCAAGCTGGAAATCACCGGTGGA
GGTGGTTCTGGCGGAGGGGGATCTGGTGGAGGCGG
TTCAGAAGTGAAACTGCAAGAGTCTGGCCCTGGACT
GGTGGCCCCATCTCAGTCTCTGAGCGTGACCTGTAC
AGTCAGCGGAGTGTCCCTGCCTGATTACGGCGTGTC
CTGGATCAGACAGCCTCCTCGGAAAGGCCTGGAAT
GGCTGGGAGTGATCTGGGCAGCGAGACAACCTAC
TACAACAGCGCCCTGAAGTCCCGGCTGACCATCATC
AAGGACAACTCCAAGAGCCAGGTGTTCCTGAAGAT
GAACAGCCTGCAGACCGACGACACCGCCATCTACT
ATTGCGCCAAGCACTACTACTACGGCGGCAGCTACG
CCATGGATTATTGGGGCCAGGGCACCAGCGTGACC
GTTTCTTCTACCACAACGCCCGCCCCGCGACCGCCT
ACTCCCGCTCCCACAATTGCATCACAACCCCTGTCT
TGAGACCCGAAGCTTGTCGACCAGCTGCCGGTGGC
GCGGTTCACACGCGGGGCTCGATTTCGCCTGTGAT
ATATATATATGGGCCCCATTGGCTGAACATGCGGA
GTATTGCTTCTGAGCCTGGTGATTACCCTCTACTGTA
AGAGAGGCCGGAAGAAACTTCTTTATATATTCAAGC
AGCCCTTTATGCGACCCGTTCAGACTACCCAAGAGG |

TABLE 10-continued

CAR sequences.

| SEQ ID NO. | CAR | Sequence |
|---|---|---|
| | | AAGATGGATGCAGTTGCCGCTTTCCAGAAGAGGAG |
| | | GAGGGCGGGTGCGAACTGAGAGTGAAGTTCAGCAG |
| | | ATCCGCCGATGCTCCCGCCTATCAGCAGGGCCAAAA |
| | | CCAGCTGTACAACGAGCTGAACCTGGGGAGAAGAG |
| | | AAGAGTACGACGTGCTGGACAAGCGGAGAGGCAGA |
| | | GATCCTGAAATGGGCGGCAAGCCCAGACGGAAGAA |
| | | TCCTCAAGAGGGCCTGTATAATGAGCTGCAGAAAG |
| | | ACAAGATGGCCGAGGCCTACAGCGAGATCGGAATG |
| | | AAGGGCGAGCGCAGAAGAGGCAAGGGACACGATG |
| | | GACTGTACCAGGGACTGAGCACCGCCACCAAGGAT |
| | | ACCTATGACGCCCTGCACATGCAGGCCCTGCCTCCA |
| | | AGAtaa |
| 314 | CircKymriah-K388 | ATGGCTCTCCCGGTCACAGCCCTTCTCCTGCCCCTG |
| | | GCACTCTTGCTGCATGCGGCACGACCCGACATCCAG |
| | | ATGACCCAGACCACAAGCAGCCTGTCTGCCAGCCTG |
| | | GGCGATAGAGTGACCATCAGCTGTAGAGCCAGCCA |
| | | GGACATCAGCAAGTACCTGAACTGGTATCAGCAAA |
| | | AGCCCGACGGCACCGTGAAGCTGCTGATCTACCAC |
| | | ACCAGCAGACTGCACAGCGGCGTGCCAAGCAGATT |
| | | TTCTGGCAGCGGCTCTGGCACCGACTACGCCCTGAC |
| | | AATCAGCAACCTGGAACAAGAGGATATCGCTACCT |
| | | ACTTCTGCCAGCAAGGCAACACCCTGCCTTACACCT |
| | | TTGGCGGAGGCACCAAGCTGGAAATCACCGGTGGA |
| | | GGTGGTTCTGGCGGAGGGGGATCTGGTGGAGGCGG |
| | | TTCAGAAGTGAAACTGCAAGAGTCTGGCCCTGGACT |
| | | GGTGGCCCCATCTCAGTCTCTGAGCGTGACCTGTAC |
| | | AGTCAGCGGAGTGTCCCTGCCTGATTACGGCGTGTC |
| | | CTGGATCAGACAGCCTCCTCGGAAAGGCCTGGAAT |
| | | GGCTGGGAGTGATCTGGGGCAGCGAGACAACCTAC |
| | | TACAACAGCGCCCTGAAGTCCCGGCTGACCATCATC |
| | | AAGGACAACTCCAAGAGCCAGGTGTTCCTGAAGAT |
| | | GAACAGCCTGCAGACCGACGACACCGCCATCTACT |
| | | ATTGCGCCAAGCACTACTACTACGGCGGCAGCTACG |
| | | CCATGGATTATTGGGGCCAGGGCACCAGCGTGACC |
| | | GTTTCTTCTACCACAACGCCCGCCCCGCGACCGCCT |
| | | ACTCCCGCTCCCACAATTGCATCACAACCCCTGTCT |
| | | TTGAGACCCGAAGCTTGTCGACCAGCTGCCGGTGGC |
| | | GCGGTTCACACGCGGGGGCTCGATTTCGCCTGTGAT |
| | | ATATATATATGGGCCCCATTGGCTGGAACATGCGGA |
| | | GTATTGCTTCTGAGCCTGGTGATTACCCTCTACTGTA |
| | | AGAGAGGCCGGAAGAAACTTCTTTATATATTCAAGC |
| | | AGCCCTTTATGCGACCCGTTCAGACTACCCAAGAGG |
| | | AAGATGGATGCAGTTGCCGCTTTCCAGAAGAGGAG |
| | | GAGGGCGGGTGCGAACTGAGAGTGAAGTTCAGCAG |
| | | ATCCGCCGATGCTCCCGCCTATAAGCAGGGCCAAA |
| | | ACCAGCTGTACAACGAGCTGAACCTGGGGAGAAGA |
| | | GAAGAGTACGACGTGCTGGACAAGCGGAGAGGCAG |
| | | AGATCCTGAAATGGGCGGCAAGCCCAGACGGAAGA |
| | | ATCCTCAAGAGGGCCTGTATAATGAGCTGCAGAAA |
| | | GACAAGATGGCCGAGGCCTACAGCGAGATCGGAAT |
| | | GAAGGGCGAGCGCAGAAGAGGCAAGGGACACGAT |
| | | GGACTGTACCAGGGACTGAGCACCGCCACCAAGGA |
| | | TACCTATGACGCCCTGCACATGCAGGCCCTGCCTCC |
| | | AAGAtaa |
| 315 | CircM971-CD22 | ATGCTGCTGCTGGTCACATCTCTGCTGCTGTGCGAG |
| | | CTGCCCCATCCTGCCTTTCTGCTGATCCCCCAGGTTC |
| | | AACTCCAGCAGTCTGGTCCCGGCCTCGTTAAACCAA |
| | | GCCAGACTTTGTCTCTTACCTGTGCTATCAGTGGCG |
| | | ATAGCGTGTCTAGTAATTCAGCCGCATGGAACTGGA |
| | | TCCGACAATCACCGAGTAGGGGACTTGAATGGCTG |
| | | GGTAGAACCTATTACCGGTCCAAATGGTACAATGAC |
| | | TATGCAGTGTCTGTAAAAAGCAGGATCACGATCAA |
| | | CCCTGATACGTCTAAAAACCAGTTTTCTCTGCAACT |
| | | TAATAGTGTGACCCCTGAAGACACCGCTGTGTATTA |
| | | CTGTGCACGGGAGGTTACCGGTGATCTTGAAGATGC |
| | | TTTTGATATATGGGGCCAAGGTACGATGGTCACGGT |
| | | GTCTAGTggggaggcggcagcGACATACAGATGACGCAG |
| | | AGCCCATCCAGTCTCTCCGCGTCTGTTGGTGACAGA |
| | | GTGACTATTACATGTAGGGCGTCTCAGACCATTTGG |
| | | TCTTACCTCAATTGGTATCAACAGCGACCAGGCAAA |
| | | GCACCGAACTTGCTCATTTACGCTGCCAGCTCACTC |
| | | CAAAGTGGTGTGCCGTCCAGATTTAGTGGTAGGGGC |
| | | AGTGGCACTGATTTCACTCTGACTATTTCAAGTCTTC |
| | | AAGCTGAGGATTTTGCCACATACTACTGCCAGCAAA |

TABLE 10-continued

CAR sequences.

| SEQ ID NO. | CAR | Sequence |
|---|---|---|
| | | GTTACTCAATACCTCAGACTTTTGGACAGGGGACAA
AATTGGAGATTAAAtccggaACCACAACGCCCGCCCCG
CGACCGCCTACTCCCGCTCCCACAATTGCATCACAA
CCCCTGTCTTTGAGACCCGAAGCTTGTCGACCAGCT
GCCGGTGGCGCGGTTCACACGCGGGGCTCGATTTC
GCCTGTGATATATATATATGGGCCCCATTGGCTGGA
ACATGCGGAGTATTGCTTCTGAGCCTGGTGATTACC
CTCTACTGTAAGAGAGGCCGGAAGAAACTTCTTTAT
ATATTCAAGCAGCCCTTTATGCGACCCGTTCAGACT
ACCCAAGAGGAAGATGGATGCAGTTGCCGCTTTCC
AGAAGAGGAGGAGGGCGGGTGCGAACTGAGAGTG
AAGTTCAGCAGATCCGCCGATGCTCCCGCCTATAAG
CAGGGCCAAAACCAGCTGTACAACGAGCTGAACCT
GGGGAGAAGAGAAGAGTACGACGTGCTGGACAAGC
GGAGAGGCAGAGATCCTGAAATGGGCGGCAAGCCC
AGACGGAAGAATCCTCAAGAGGGCCTGTATAATGA
GCTGCAGAAAGACAAGATGGCCGAGGCCTACAGCG
AGATCGGAATGAAGGGCGAGCGCAGAAGAGGCAA
GGGACACGATGGACTGTACCAGGGACTGAGCACCG
CCACCAAGGATACCTATGACGCCCTGCACATGCAG
GCCCTGCCTCCAAGAtaa |
| 316 | CircCD19_
22
Bispecific
29 | ATGCTGCTGCTGGTCACATCTCTGCTGCTGTGCGAG
CTGCCCCATCCTGCCTTTCTGCTGATCCCCGACATCC
AGATGACCCAGACCACAAGCAGCCTGTCTGCCAGC
CTGGGCGATAGAGTGACCATCAGCTGTAGAGCCAG
CCAGGACATCAGCAAGTACCTGAACTGGTATCAGC
AAAAGCCCGACGGCACCGTGAAGCTGCTGATCTAC
CACACCAGCAGACTGCACAGCGGCGTGCCAAGCAG
ATTTTCTGGCAGCGGCTCTGGCACCGACTACAGCCT
GACAATCAGCAACCTGGAACAAGAGGATATCGCTA
CCTACTTCTGCCAGCAAGGCAACACCCTGCCTTACA
CCTTTGGCGGAGGCACCAAGCTGGAAATCACCggcgg
cggaggatccCAGGTTCAACTCCAGCAGTCTGGTCCCGG
CCTCGTTAAACCAAGCCAGACTTTGTCTCTTACCTG
TGCTATCAGTGGCGATAGCGTGTCTAGTAATTCAGC
CGCATGGAACTGGATCCGACAATCACCGAGTAGGG
GACTTGAATGGCTGGGTAGAACCTATTACCGGTCCA
AATGGTACAATGACTATGCAGTGTCTGTAAAAAGC
AGGATCACGATCAACCCTGATACGTCTAAAAACCA
GTTTTCTCTGCAACTTAATAGTGTGACCCCTGAAGA
CACCGCTGTGTATTACTGTGCACGGGAGGTTACCGG
TGATCTTGAAGATGCTTTTGATATATGGGGCCAAGG
TACGATGGTCACGGTGTCTAGTGGCTCTACAAGCGG
CAGCGGCAAACCTGGATCTGGCGAGGGATCTACCA
AGGGCGACATACAGATGACGCAGAGCCCATCCAGT
CTCTCCGCGTCTGTTGGTGACAGAGTGACTATTACA
TGTAGGGCGTCTCAGACCATTTGGTCTTACCTCAAT
TGGTATCAACAGCGACCAGGCAAAGCACCGAACTT
GCTCATTTACGCTGCCAGCTCACTCCAAAGTGGTGT
GCCGTCCAGATTTAGTGGTAGGGGCAGTGGCACTG
ATTTCACTCTGACTATTTCAAGTCTTCAAGCTGAGG
ATTTTGCCACATACTACTGCCAGCAAAGTTACTCAA
TACCTCAGACTTTTGGACAGGGGACAAAATTGGAG
ATTAAAgggggaggcggcagcGAAGTGAAACTGCAAGAGT
CTGGCCCTGGACTGGTGGCCCCATCTCAGTCTCTGA
GCGTGACCTGTACAGTCAGCGGAGTGTCCCTGCCTG
ATTACGGCGTGTCCTGGATCAGACAGCCTCCTCGGA
AAGGCCTGGAATGGCTGGGAGTGATCTGGGGCAGC
GAGACAACCTACTACAACAGCGCCCTGAAGTCCCG
GCTGACCATCATCAAGGACAACTCCAAGAGCCAGG
TGTTCCTGAAGATGAACAGCCTGCAGACCGACGAC
ACCGCCATCTACTATTGCGCCAAGCACTACTACTAC
GGCGGCAGCTACGCCATGGATTATTGGGGCCAGGG
CACCAGCGTGACCGTTTCTTCTtccggaACCACAACGC
CCGCCCCGCGACCGCCTACTCCCGCTCCCACAATTG
CATCACAACCCCTGTCTTTGAGACCCGAAGCTTGTC
GACCAGCTGCCGGTGGCGCGGTTCACACGCGGGGG
CTCGATTTCGCCTGTGATATATATATATGGGCCCCA
TTGGCTGGAACATGCGGAGTATTGCTTCTGAGCCTG
GTGATTACCCTCTACTGTAAGAGAGGCCGGAAGAA
ACTTCTTTATATATTCAAGCAGCCCTTTATGCGACCC
GTTCAGACTACCCAAGAGGAAGATGGATGCAGTTG
CCGCTTTCCAGAAGAGGAGGAGGGCGGGTGCGAAC
TGAGAGTGAAGTTCAGCAGATCCGCCGATGCTCCCG
CCTATAAGCAGGGCCAAAACCAGCTGTACAACGAG |

TABLE 10-continued

CAR sequences.

| SEQ ID NO. | CAR | Sequence |
|---|---|---|
| | | CTGAACCTGGGGAGAAGAGAAGAGTACGACGTGCT |
| | | GGACAAGCGGAGAGGCAGAGATCCTGAAATGGGCG |
| | | GCAAGCCCAGACGGAAGAATCCTCAAGAGGGCCTG |
| | | TATAATGAGCTGCAGAAAGACAAGATGGCCGAGGC |
| | | CTACAGCGAGATCGGAATGAAGGGCGAGCGCAGAA |
| | | GAGGCAAGGGACACGATGGACTGTACCAGGGACTG |
| | | AGCACCGCCACCAAGGATACCTATGACGCCCTGCA |
| | | CATGCAGGCCCTGCCTCCAAGAtaa |
| 317 | CircCD19_22 Bispecific 30 | ATGCTGCTGCTGGTCACATCTCTGCTGCTGTGCGAG |
| | | CTGCCCCATCCTGCCTTTCTGCTGATCCCCCAGGTTC |
| | | AACTCCAGCAGTCTGGTCCCGGCCTCGTTAAACCAA |
| | | GCCAGACTTTGTCTCTTACCTGTGCTATCAGTGGCG |
| | | ATAGCGTGTCTAGTAATTCAGCCGCATGGAACTGGA |
| | | TCCGACAATCACCGAGTAGGGGACTTGAATGGCTG |
| | | GGTAGAACCTATTACCGGTCCAAATGGTACAATGAC |
| | | TATGCAGTGTCTGTAAAAAGCAGGATCACGATCAA |
| | | CCCTGATACGTCTAAAAACCAGTTTTCTCTGCAACT |
| | | TAATAGTGTGACCCCTGAAGACACCGCTGTGTATTA |
| | | CTGTGCACGGGAGGTTACCGGTGATCTTGAAGATGC |
| | | TTTTGATATATGGGGCCAAGGTACGATGGTCACGGT |
| | | GTCTAGTggggaggcggcagcGACATACAGATGACGCAG |
| | | AGCCCATCCAGTCTCTCCGCGTCTGTTGGTGACAGA |
| | | GTGACTATTACATGTAGGGCGTCTCAGACCATTTGG |
| | | TCTTACCTCAATTGGTATCAACAGCGACCAGGCAAA |
| | | GCACCGAACTTGCTCATTTACGCTGCCAGCTCACTC |
| | | CAAAGTGGTGTGCCGTCCAGATTTAGTGGTAGGGGC |
| | | AGTGGCACTGATTTCACTCTGACTATTTCAAGTCTTC |
| | | AAGCTGAGGATTTTGCCACATACTACTGCCAGCAAA |
| | | GTTACTCAATACCTCAGACTTTTGGACAGGGGACAA |
| | | AATTGGAGATTAAAGGGGGAGGCGGATCCGGCGGT |
| | | GGTGGCTCCGGCGGTGGTGGTTCTGGAGGCGGCGG |
| | | AAGCGGTGGGGGTGGTAGCGACATCCAGATGACCC |
| | | AGACCACAAGCAGCCTGTCTGCCAGCCTGGGCGAT |
| | | AGAGTGACCATCAGCTGTAGAGCCAGCCAGGACAT |
| | | CAGCAAGTACCTGAACTGGTATCAGCAAAAGCCCG |
| | | ACGGCACCGTGAAGCTGCTGATCTACCACACCAGC |
| | | AGACTGCACAGCGGCGTGCCAAGCAGATTTTCTGGC |
| | | AGCGGCTCTGGCACCGACTACAGCCTGACAATCAG |
| | | CAACCTGGAACAAGAGGATATCGCTACCTACTTCTG |
| | | CCAGCAAGGCAACACCCTGCCTTACACCTTTGGCGG |
| | | AGGCACCAAGCTGGAAATCACCGGCTCTACAAGCG |
| | | GCAGCGGCAAACCTGGATCTGGCGAGGGATCTACC |
| | | AAGGGCGAAGTGAAACTGCAAGAGTCTGGCCCTGG |
| | | ACTGGTGGCCCCATCTCAGTCTCTGAGCGTGACCTG |
| | | TACAGTCAGCGGAGTGTCCCTGCCTGATTACGGCGT |
| | | GTCCTGGATCAGACAGCCTCCTCGGAAAGGCCTGG |
| | | AATGGCTGGGAGTGATCTGGGGCAGCGAGACAACC |
| | | TACTACAACAGCGCCCTGAAGTCCCGGCTGACCATC |
| | | ATCAAGGACAACTCCAAGAGCCAGGTGTTCCTGAA |
| | | GATGAACAGCCTGCAGACCGACGACACCGCCATCT |
| | | ACTATTGCGCCAAGCACTACTACTACGGCGGCAGCT |
| | | ACGCCATGGATTATTGGGGCCAGGGCACCAGCGTG |
| | | ACCGTTTCTTCTtccggaACCACAACGCCCGCCCCGCG |
| | | ACCGCCTACTCCCGCTCCCACAATTGCATCACAACC |
| | | CCTGTCTTTGAGACCCGAAGCTTGTCGACCAGCTGC |
| | | CGGTGGCGCGGTTCACACGCGGGGGCTCGATTTCGC |
| | | CTGTGATATATATATGGGCCCCATTGGCTGGAAC |
| | | ATGCGGAGTATTGCTTCTGAGCCTGGTGATTACCCT |
| | | CTACTGTAAGAGAGGCCGGAAGAAACTTCTTTATAT |
| | | ATTCAAGCAGCCCTTTATGCGACCCGTTCAGACTAC |
| | | CCAAGAGGAAGATGGATGCAGTTGCCGCTTTCCAG |
| | | AAGAGGAGGAGGGCGGGTGCGAACTGAGAGTGAA |
| | | GTTCAGCAGATCCGCCGATGCTCCCGCCTATAAGCA |
| | | GGGCCAAAACCAGCTGTACAACGAGCTGAACCTGG |
| | | GGAGAAGAGAAGAGTACGACGTGCTGGACAAGCGG |
| | | AGAGGCAGAGATCCTGAAATGGCGGCAAGCCCAG |
| | | ACGGAAGAATCCTCAAGAGGGCCTGTATAATGAGC |
| | | TGCAGAAAGACAAGATGGCCGAGGCCTACAGCGAG |
| | | ATCGGAATGAAGGGCGAGCGCAGAAGAGGCAAGG |
| | | GACACGATGGACTGTACCAGGGACTGAGCACCGCC |
| | | ACCAAGGATACCTATGACGCCCTGCACATGCAGGC |
| | | CCTGCCTCCAAGAtaa |

In some embodiments, a CAR has a sequence as listed in Table 10.

TABLE 11

CAR domain sequences.

| SEQ ID NO. | Protein | Sequence |
|---|---|---|
| 318 | 4-1BB | KRGRKKLLYIFKQPFMRPVQTTQEEDGCSCRFPEEEEGGCEL |
| 319 | CD3ζ intracellular domain | RVKFSRSADAPAYKQGQNQLYNELNLGRREEYDVLDKRRGRDPEMGGKPRRKNPQEGLYNELQKDKMAEAYSEIGMKGERRRGKGHDGLYQGLSTATKDTYDALHMQALPPR |
| 320 | CD28 intracellular signaling domain | QVQLVQSGAEVEKPGASVKVSCKASGYTFTDYYMHWVRQAPGQGLEWMGWINPNSGGTNYAQKFQGRVTMTRDTSISTAYMELSRLRSDDTAVYYCASGWDFDYWGQGTLVTVSSGGGGSGGGGSGGGGSGGGGSDIVMTQSPSSLSASVGDRVTITCRASQSIRYYLSWYQQKPGKAPKLLIYTASILQNGVPSRFSGSGSGTDFTLTISSLQPEDFATYYCLQTYTTPDFGPGTKVEIK |
| 321 | FMC63 VH | EVKLQESGPGLVAPSQSLSVTCTVSGVSLPDYGVSWIRQPPRKGLEWLGVIWGSETTYYNSALKSRLTIIKDNSKSQVFLKMNSLQTDDTAIYYCAKHYYYGGSYAMDYWGQGTSVTVSS |
| 322 | FMC63 VL | DIQMTQTTSSLSASLGDRVTISCRASQDISKYLNWYQQKPDGTVKLLIYHTSRLHSGVPSRFSGSGSGTDYSLTISNLEQEDIATYFCQQGNTLPYTFGGGTKLEIT |

In some embodiments, a CAR domain encoded by an inventive polynucleotide has a sequence as listed in Table 11.

Preferred embodiments are described herein. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

EXAMPLES

Wesselhoeft et al. (2019) RNA Circularization Diminishes Immunogenicity and Can Extend Translation Duration In Vivo. Molecular Cell. 74(3), 508-520 and Wesselhoeft et al. (2018) Engineering circular RNA for Potent and Stable Translation in Eukaryotic Cells. Nature Communications. 9, 2629 are incorporated by reference in their entirety.

The invention is further described in detail by reference to the following examples but are not intended to be limited to the following examples. These examples encompass any and all variations of the illustrations with the intention of providing those of ordinary skill in the art with complete disclosure and description of how to make and use the subject invention and are not intended to limit the scope of what is regarded as the invention.

EXAMPLE 1

Example 1A: External Homology Regions Allow for Circularization of Long Precursor RNA Using the Permuted Intron Exon (PIE) Circularization Strategy A 1.1 kb sequence containing a full-length encephalomyocarditis virus (EMCV) IRES, a *Gaussia* luciferase (GLuc) expression sequence, and two short exon fragments of the permuted intron-exon (PIE) construct were inserted between the 3' and 5' introns of the permuted group I catalytic intron in the thymidylate synthase (Td) gene of the T4 phage. Precursor RNA was synthesized by run-off transcription. Circularization was attempted by heating the precursor RNA in the presence of magnesium ions and GTP, but splicing products were not obtained.

Perfectly complementary 9 nucleotide and 19 nucleotide long homology regions were designed and added at the 5' and 3' ends of the precursor RNA. Addition of these homology arms increased splicing efficiency from 0 to 16% for 9 nucleotide homology regions and to 48% for 19 nucleotide homology regions as assessed by disappearance of the precursor RNA band.

The splicing product was treated with RNase R. Sequencing across the putative splice junction of RNase R-treated splicing reactions revealed ligated exons, and digestion of the RNase R-treated splicing reaction with oligonucleotide-targeted RNase H produced a single band in contrast to two bands yielded by RNase H-digested linear precursor. This shows that circular RNA is a major product of the splicing reactions of precursor RNA containing the 9 or 19 nucleotide long external homology regions.

Example 1B: Spacers that Conserve Secondary Structures of IRES and PIE Splice Sites Increase Circularization Efficiency A series of spacers was designed and inserted between the 3' PIE splice site and the IRES. These spacers were designed to either conserve or disrupt secondary structures within intron sequences in the IRES, 3' PIE splice site, and/or 5' splice site. The addition of spacer sequences designed to conserve secondary structures resulted in 87% splicing efficiency, while the addition of a disruptive spacer sequences resulted in no detectable splicing.

EXAMPLE 2

Example 2A: Internal Homology Regions in Addition to External Homology Regions Creates a Splicing Bubble and Allows for Translation of Several Expression Sequences Spacers were designed to be unstructured, non-homologous to the intron and IRES sequences, and to contain spacer-spacer homology regions. These were inserted between the 5' exon and IRES and between the 3' exon and expression sequence in constructs containing external homology regions, EMCV IRES, and expression sequences for *Gaussia* luciferase (total length: 1289 nt), Firefly luciferase (2384 nt), eGFP (1451 nt), human erythropoietin (1313 nt), and Cas9 endonuclease (4934 nt). Circularization of all 5 constructs was achieved. Circularization of constructs utilizing T4 phage and Anabaena introns were roughly equal. Circularization efficiency was higher for shorter sequences. To measure translation, each construct was transfected into HEK293 cells. *Gaussia* and Firefly luciferase transfected cells produced a robust response as measured by luminescence, human erythropoietin was detectable in the media of cells transfected with erythropoietin circRNA, and EGFP fluorescence was observed from cells transfected with EGFP circRNA. Co-transfection of Cas9 circRNA with sgRNA directed against GFP into cells constitutively expressing GFP resulted in ablated fluorescence in up to 97% of cells in comparison to an sgRNA-only control.

Example 2B: Use of CVB3 IRES Increases Protein Production

Constructs with internal and external homology regions and differing IRES containing either *Gaussia* luciferase or Firefly luciferase expression sequences were made. Protein production was measured by luminescence in the supernatant of HEK293 cells 24 hours after transfection. The Coxsackievirus B3 (CVB3) IRES construct produced the most protein in both cases.

Example 2C: Use of polyA or polyAC Spacers Increases Protein Production

Thirty nucleotide long polyA or polyAC spacers were added between the IRES and splice junction in a construct with each IRES that produced protein in example 2B. *Gaussia* luciferase activity was measured by luminescence in the supernatant of HEK293 cells 24 hours after transfection. Both spacers improved expression in every construct over control constructs without spacers.

EXAMPLE 3

HEK293 or HeLa Cells Transfected with Circular RNA Produce More Protein than Those Transfected with Comparable Unmodified or Modified Linear RNA HPLC-purified *Gaussia* luciferase-coding circRNA (CVB3-GLuc-pAC) was compared with a canonical unmodified 5' methylguanosine-capped and 3' polyA-tailed linear GLuc mRNA, and a commercially available nucleoside-modified (pseudouridine, 5-methylcytosine) linear GLuc mRNA (from Trilink). Luminescence was measured 24 h post-transfection, revealing that circRNA produced 811.2% more protein than the unmodified linear mRNA in HEK293 cells and 54.5% more protein than the modified mRNA. Similar results were obtained in HeLa cells and a comparison of optimized circRNA coding for human erythropoietin with linear mRNA modified with 5-methoxyuridine.

Luminescence data was collected over 6 days. In HEK293 cells, circRNA transfection resulted in a protein production half-life of 80 hours, in comparison with the 43 hours of unmodified linear mRNA and 45 hours of modified linear mRNA. In HeLa cells, circRNA transfection resulted in a protein production half-life of 116 hours, in comparison with the 44 hours of unmodified linear mRNA and 49 hours of modified linear mRNA. CircRNA produced substantially more protein than both the unmodified and modified linear mRNAs over its lifetime in both cell types.

EXAMPLE 4

Example 4A: Purification of circRNA by RNase Digestion, HPLC Purification, and Phosphatase Treatment Decreases Immunogenicity. Completely Purified Circular RNA is Significantly Less Immunogenic than Unpurified or Partially Purified Circular RNA. Protein Expression Stability and Cell Viability are Dependent on Cell Type and Circular RNA Purity Human embryonic kidney 293 (HEK293) and human lung carcinoma A549 cells were transfected with:

a. products of an unpurified GLuc circular RNA splicing reaction, b. products of RNase R digestion of the splicing reaction, c. products of RNase R digestion and HPLC purification of the splicing reaction, or d. products of RNase digestion, HPLC purification, and phosphatase treatment of the splicing reaction.

RNase R digestion of splicing reactions was insufficient to prevent cytokine release in A549 cells in comparison to untransfected controls.

The addition of HPLC purification was also insufficient to prevent cytokine release, although there was a significant reduction in interleukin-6 (IL-6) and a significant increase in interferon-α1 (IFN-α1) compared to the unpurified splicing reaction.

The addition of a phosphatase treatment after HPLC purification and before RNase R digestion dramatically reduced the expression of all upregulated cytokines assessed in A549 cells. Secreted monocyte chemoattractant protein 1 (MCP1), IL-6, IFN-α1, tumor necrosis factor α (TNFα), and IFNγ inducible protein-10 (IP-10) fell to undetectable or un-transfected baseline levels.

There was no substantial cytokine release in HEK293 cells. A549 cells had increased GLuc expression stability and cell viability when transfected with higher purity circular RNA. Completely purified circular RNA had a stability phenotype similar to that of transfected 293 cells.

Example 4B: Circular RNA does not Cause Significant Immunogenicity and is not a RIG-I Ligand A549 cells were transfected with the products of a splicing reaction.

A549 cells were transfected with:
a. unpurified circular RNA,
b. high molecular weight (linear and circular concatenations) RNA,
c. circular (nicked) RNA,
d. an early fraction of purified circular RNA (more overlap with nicked RNA peak),
e. a late fraction of purified circular RNA (less overlap with nicked RNA peak),
f. introns excised during circularization, or
g. vehicle (i.e. untransfected control).

Precursor RNA was separately synthesized and purified in the form of the splice site deletion mutant (DS) due to difficulties in obtaining suitably pure linear precursor RNA from the splicing reaction. Cytokine release and cell viability was measured in each case.

Robust IL-6, RANTES, and IP-10 release was observed in response to most of the species present within the splicing reaction, as well as precursor RNA. Early circRNA fractions elicited cytokine responses comparable to other non-circRNA fractions, indicating that even relatively small quantities of linear RNA contaminants are able to induce a substantial cellular immune response in A549 cells. Late circRNA fractions elicited no cytokine response in excess of that from untransfected controls. A549 cell viability 36 hours post-transfection was significantly greater for late circRNA fractions compared with all of the other fractions.

RIG-I and IFN-β1 transcript induction upon transfection of A549 cells with late circRNA HPLC fractions, precursor RNA or unpurified splicing reactions were analyzed. Induction of both RIG-I and IFN-β1 transcripts were weaker for late circRNA fractions than precursor RNA and unpurified splicing reactions. RNase R treatment of splicing reactions alone was not sufficient to ablate this effect. Addition of very small quantities of the RIG-I ligand 3p-hpRNA to circular RNA induced substantial RIG-I transcription. In HeLa cells, transfection of RNase R-digested splicing reactions induced RIG-I and IFN-β1, but purified circRNA did not. Overall, HeLa cells were less sensitive to contaminating RNA species than A549 cells.

A time course experiment monitoring RIG-I, IFN-β1, IL-6, and RANTES transcript induction within the first 8 hours after transfection of A549 cells with splicing reactions or fully purified circRNA did not reveal a transient response to circRNA. Purified circRNA similarly failed to induce pro-inflammatory transcripts in RAW264.7 murine macrophages.

A549 cells were transfected with purified circRNA containing an EMCV IRES and EGFP expression sequence. This failed to produce substantial induction of pro-inflammatory transcripts. These data demonstrate that non-circular components of the splicing reaction are responsible for the immunogenicity observed in previous studies and that circRNA is not a natural ligand for RIG-I.

EXAMPLE 5

Circular RNA Avoids Detection by TLRs

TLR 3, 7, and 8 reporter cell lines were transfected with multiple linear or circular RNA constructs and secreted embryonic alkaline phosphatase (SEAP) was measured. Linearized RNA was constructed by deleting the intron and homology arm sequences. The linear RNA constructs were then treated with phosphatase (in the case of capped RNAs, after capping) and purified by HPLC.

None of the attempted transfections produced a response in TLR7 reporter cells. TLR3 and TLR8 reporter cells were activated by capped linearized RNA, polyadenylated linearized RNA, the nicked circRNA HPLC fraction, and the early circRNA fraction. The late circRNA fraction and m1ψ-mRNA did not provoke TLR-mediated response in any cell line.

In a second experiment, circRNA was linearized using two methods: treatment of circRNA with heat in the presence of magnesium ions and DNA oligonucleotide-guided RNase H digestion. Both methods yielded a majority of full-length linear RNA with small amounts of intact circRNA. TLR3, 7, and 8 reporter cells were transfected with circular RNA, circular RNA degraded by heat, or circular RNA degraded by RNase H, and SEAP secretion was measured 36 hours after transfection. TLR8 reporter cells secreted SEAP in response to both forms of degraded circular RNA, but did not produce a greater response to circular RNA transfection than mock transfection. No activation was observed in TLR3 and TLR7 reporter cells for degraded or intact conditions, despite the activation of TLR3 by in vitro transcribed linearized RNA.

EXAMPLE 6

Unmodified Circular RNA Produces Increased Sustained In Vivo Protein Expression than Linear RNA Mice were injected and HEK293 cells were transfected with unmodified and m1ψ-modified human erythropoietin (hEpo) linear mRNAs and circRNAs. Equimolar transfection of m1ψ-mRNA and unmodified circRNA resulted in robust protein expression in HEK293 cells. hEpo linear mRNA and circRNA displayed similar relative protein expression patterns and cell viabilities in comparison to GLuc linear mRNA and circRNA upon equal weight transfection of HEK293 and A549 cells.

In mice, hEpo was detected in serum after the injection of hEpo circRNA or linear mRNA into visceral adipose. hEpo detected after the injection of unmodified circRNA decayed more slowly than that from unmodified or m1ψ-mRNA and was still present 42 hours post-injection. Serum hEpo rapidly declined upon the injection of unpurified circRNA splicing reactions or unmodified linear mRNA. Injection of unpurified splicing reactions produced a cytokine response detectable in serum that was not observed for the other RNAs, including purified circRNA.

EXAMPLE 7

Circular RNA can be Effectively Delivered In Vivo or In Vitro Via Lipid Nanoparticles Purified circular RNA was formulated into lipid nanoparticles (LNPs) with the ionizable lipidoid cKK-E12 (Dong et al., 2014; Kauffman et al., 2015). The particles formed uniform multilamellar structures with an average size, polydispersity index, and encapsulation efficiency similar to that of particles containing commercially available control linear mRNA modified with 5moU.

Purified hEpo circRNA displayed greater expression than 5moU-mRNA when encapsulated in LNPs and added to HEK293 cells. Expression stability from LNP-RNA in HEK293 cells was similar to that of RNA delivered by transfection reagent, with the exception of a slight delay in decay for both 5moU-mRNA and circRNA. Both unmodified circRNA and 5moU-mRNA failed to activate RIG-I/IFN-β1 in vitro.

In mice, LNP-RNA was delivered by local injection into visceral adipose tissue or intravenous delivery to the liver. Serum hEpo expression from circRNA was lower but comparable with that from 5moU-mRNA 6 hours after delivery in both cases. Serum hEpo detected after adipose injection of unmodified LNP-circRNA decayed more slowly than that from LNP-5moU-mRNA, with a delay in expression decay present in serum that was similar to that noted in vitro, but serum hEpo after intravenous injection of LNP-circRNA or LNP-5moU-mRNA decayed at approximately the same rate. There was no increase in serum cytokines or local RIG-I, TNFα, or IL-6 transcript induction in any of these cases.

EXAMPLE 8

Expression and Functional Stability by IRES in HEK293, HepG2, and 1C1C7 Cells

Figure 1B:
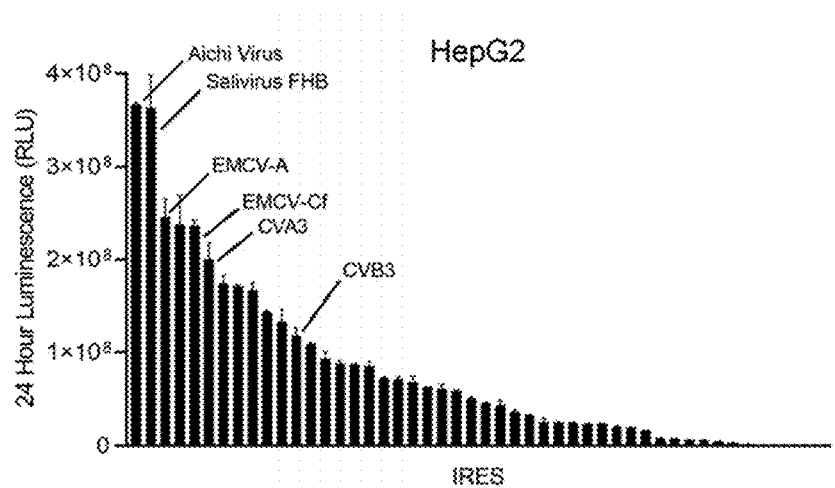
Figure 1C:
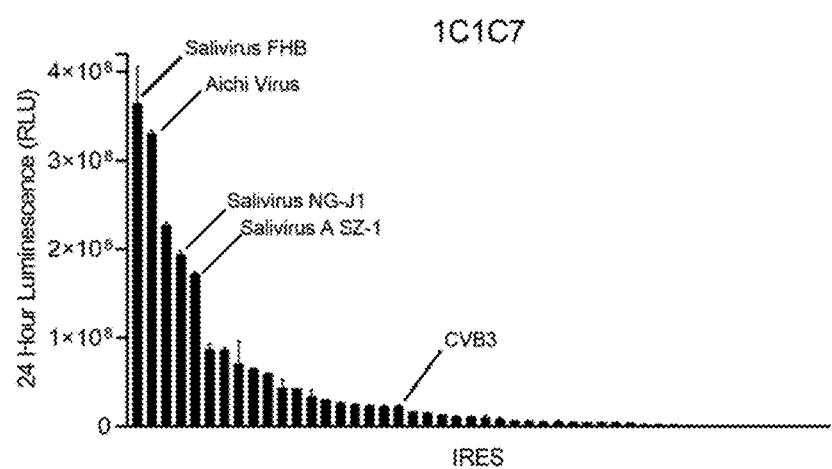

Constructs including anabaena intron/exon regions, a *Gaussia* luciferase expression sequence, and varying IRES were circularized. 100 ng of each circularization reaction was separately transfected into 20,000 HEK293 cells, HepG2 cells, and 1C1C7 cells using Lipofectamine MessengerMax. Luminescence in each supernatant was assessed after 24 hours as a measure of protein expression. In HEK293 cells, constructs including Crohivirus B, Salivirus FHB, Aichi Virus, Salivirus HG-J1, and Enterovirus J IRES produced the most luminescence at 24 hours (FIG. 1A). In HepG2 cells, constructs including Aichi Virus, Salivirus FHB, EMCV-Cf, and CVA3 IRES produced high luminescence at 24 hours (FIG. 1B). In 1C1C7 cells, constructs including Salivirus FHB, Aichi Virus, Salivirus NG-J1, and Salivirus A SZ-1 IRES produced high luminescence at 24 hours (FIG. 1C).

Figure 2A:
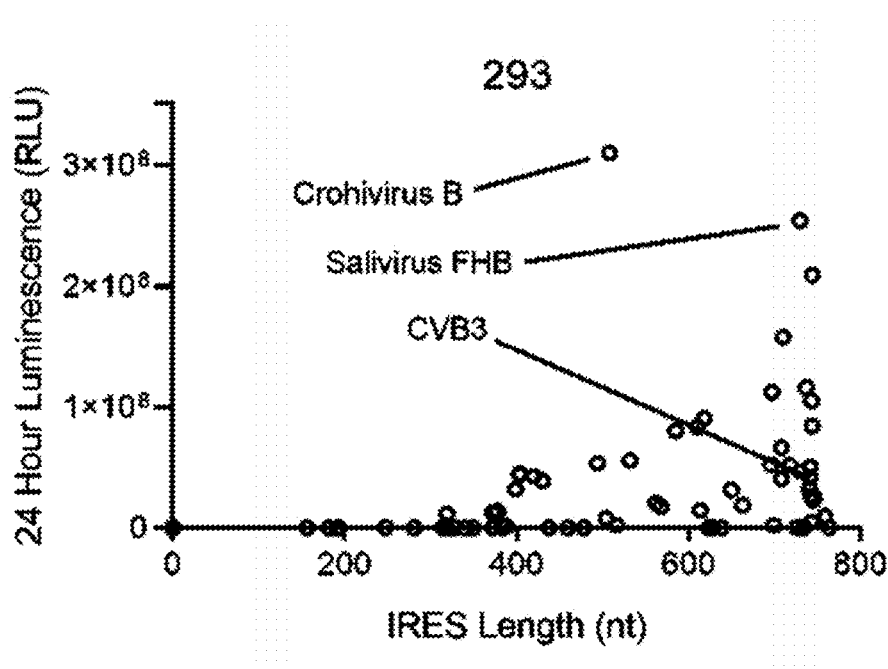
FIG. 2 depicts luminescence in supernatants of HEK293 (FIG. 2A), HepG2 (FIG. 2B), or 1C1C7 (FIG. 2C) cells 24 hours after transfection with circular RNA comprising a *Gaussia* luciferase expression sequence and various IRES sequences having different lengths.
Figure 2B:
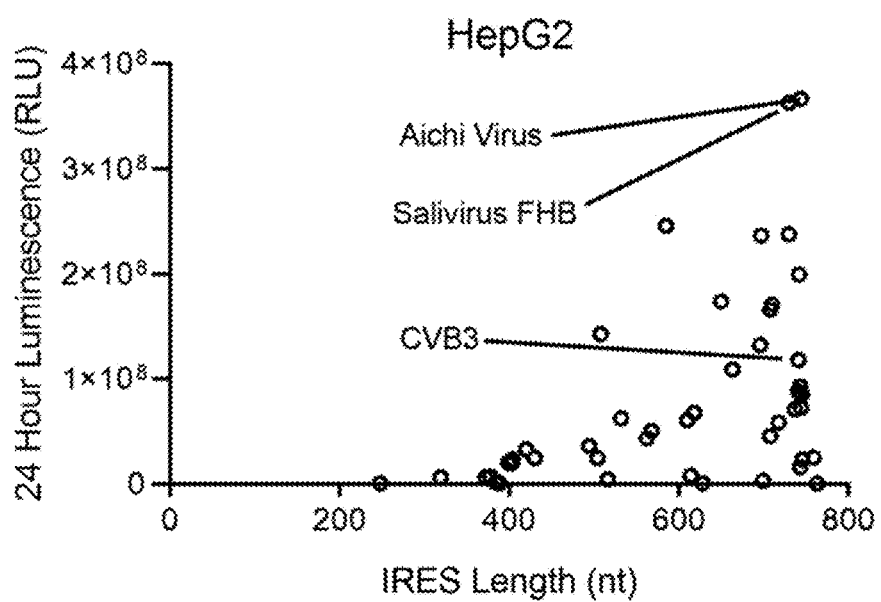
Figure 2C:
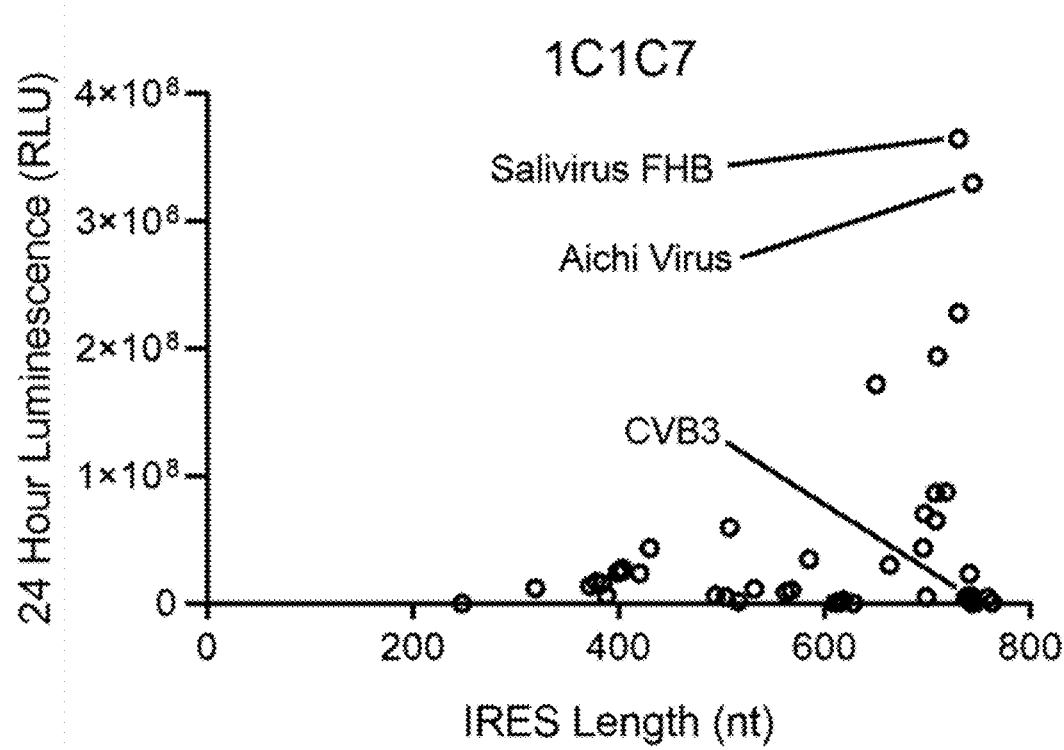

A trend of larger IRES producing greater luminescence at 24 hours was observed. Shorter total sequence length tends to increase circularization efficiency, so selecting a high expression and relatively short IRES may result in an improved construct. In HEK293 cells, a construct using the Crohivirus B IRES produced the highest luminescence, especially in comparison to other IRES of similar length (FIG. 2A). Expression from IRES constructs in HepG2 and 1C1C7 cells plotted against IRES size are in FIGS. 2B and 2C.

Figure 3A:
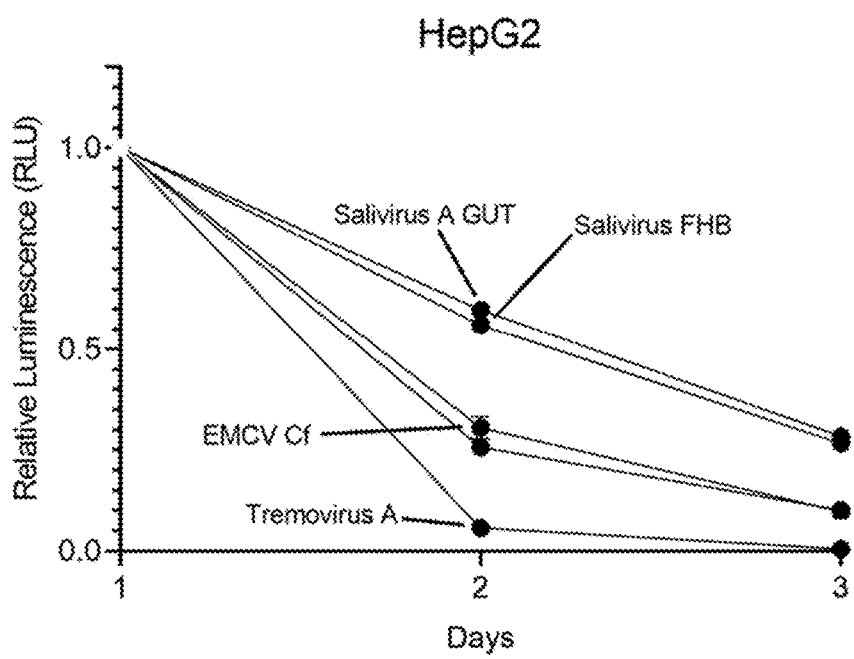
FIG. 3 depicts stability of select IRES constructs in HepG2 (FIG. 3A) or 1C1C7 (FIG. 3B) cells over 3 days as measured by luminescence.
Figure 3B:
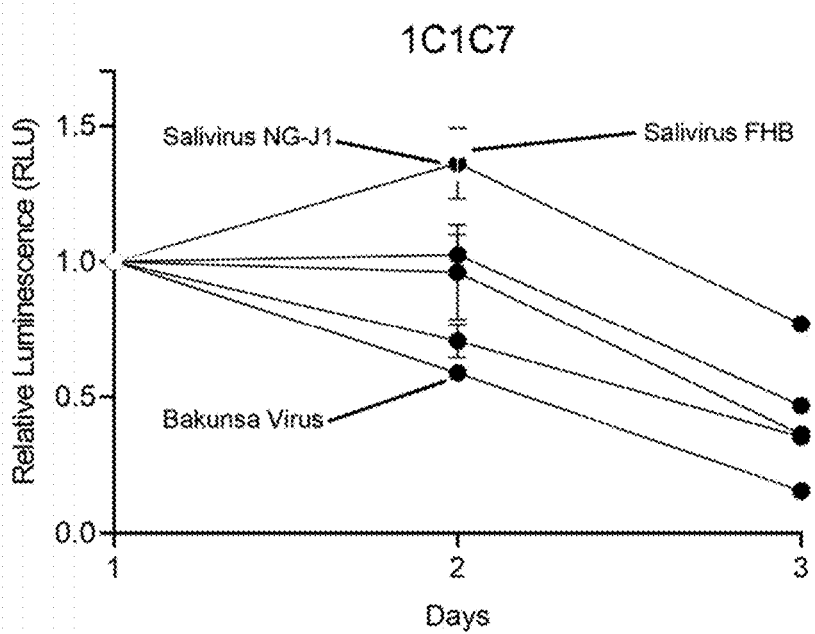

Functional stability of select IRES constructs in HepG2 and 1C1C7 cells were measured over 3 days. Luminescence from secreted *Gaussia* luciferase in supernatant was measured every 24 hours after transfection of 20,000 cells with 100 ng of each circularization reaction, followed by complete media replacement. Salivirus A GUT and Salivirus FHB exhibited the highest functional stability in HepG2 cells, and Salivirus N-J1 and Salivirus FHB produced the most stable expression in 1C1C7 cells (FIGS. 3A and 3B).

EXAMPLE 9

Figure 4A:
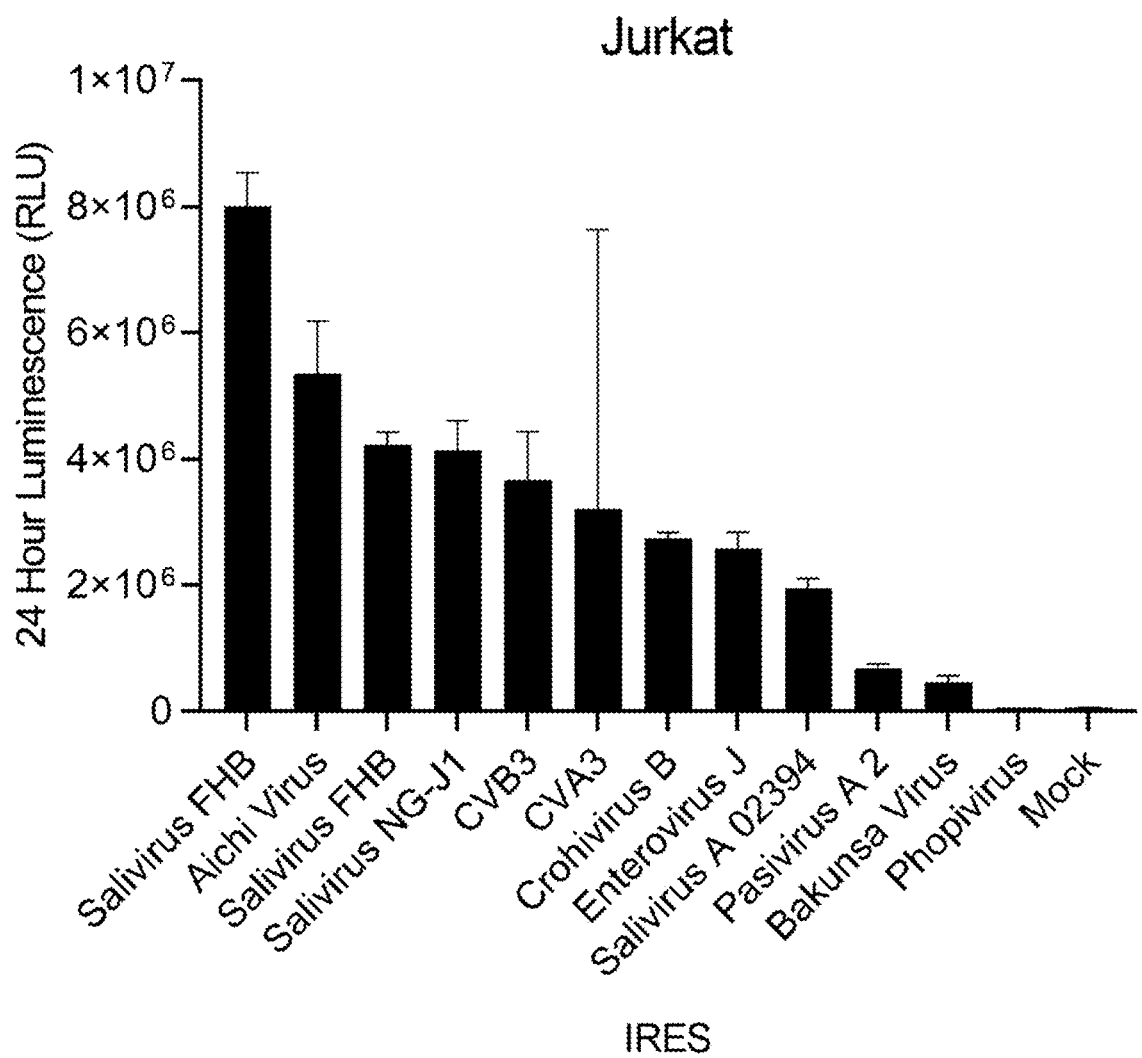
FIGS. 4A and 4B depict protein expression from select IRES constructs in Jurkat cells, as measured by luminescence from secreted *Gaussia* luciferase in cell supernatants.
Figure 4B:
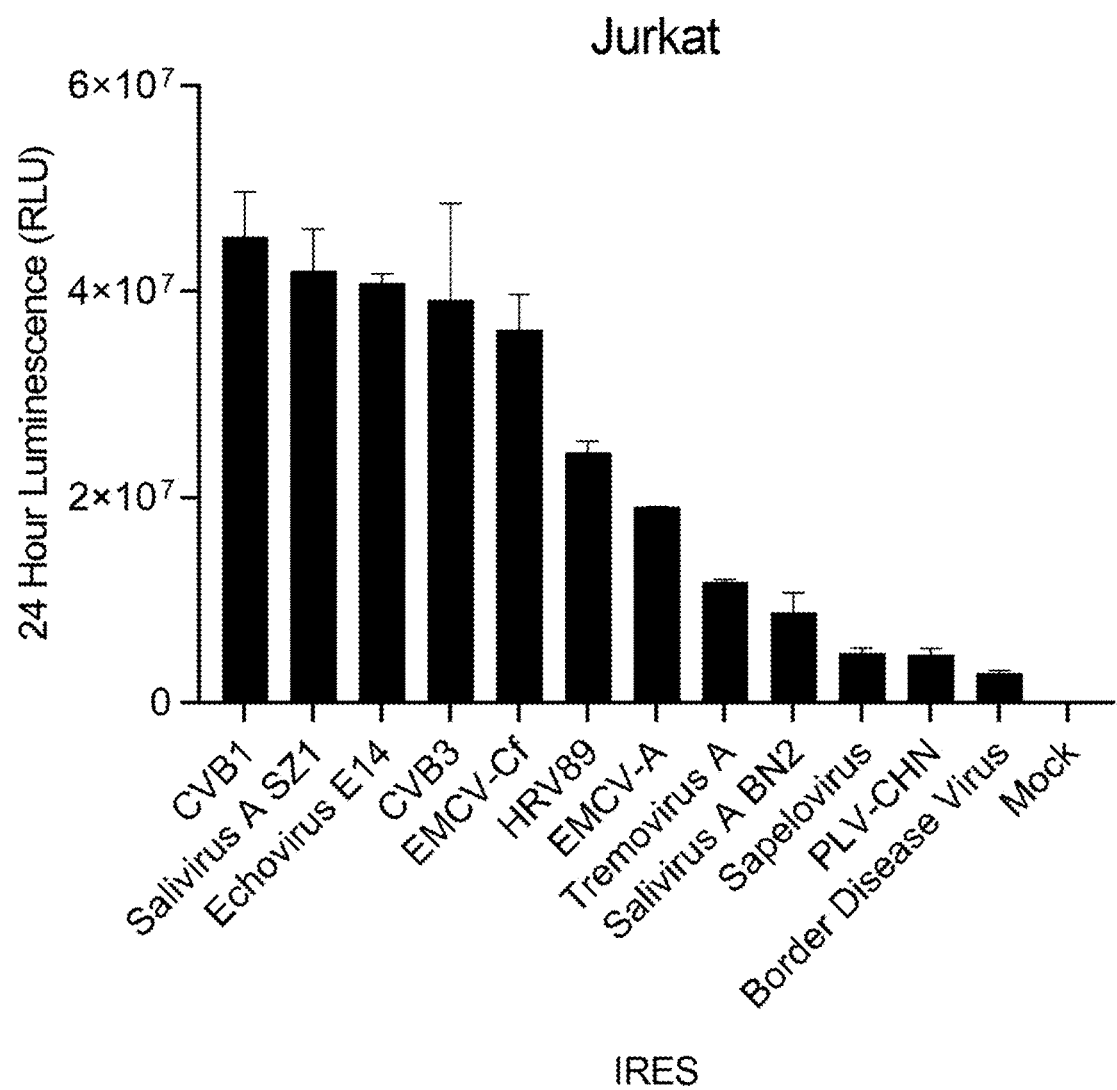

Expression and Functional Stability by IRES in Jurkat Cells 2 sets of constructs including anabaena intron/exon regions, a *Gaussia* luciferase expression sequence, and a subset of previously tested IRES were circularized. 60,000 Jurkat cells were electroporated with 1 μg of each circularization reaction. Luminescence from secreted *Gaussia* luciferase in supernatant was measured 24 hours after electroporation. A CVB3 IRES construct was included in both sets for comparison between sets and to previously defined IRES efficacy. CVB1 and Salivirus A SZ1 IRES constructs produced the most expression at 24 h. Data can be found in FIGS. 4A and 4B.

Figure 5A:
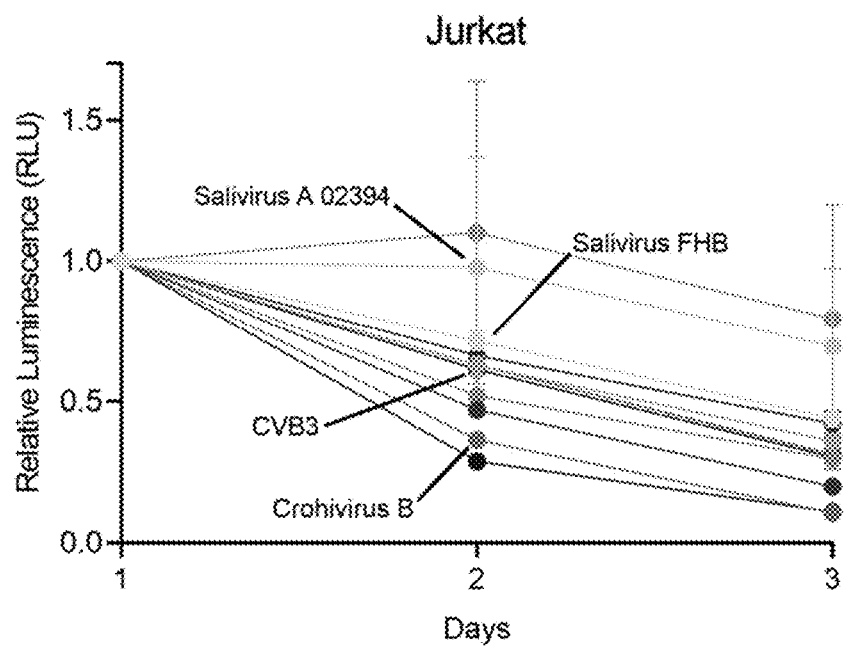
FIGS. 5A and 5B depict stability of select IRES constructs in Jurkat cells over 3 days as measured by luminescence.
Figure 5B:
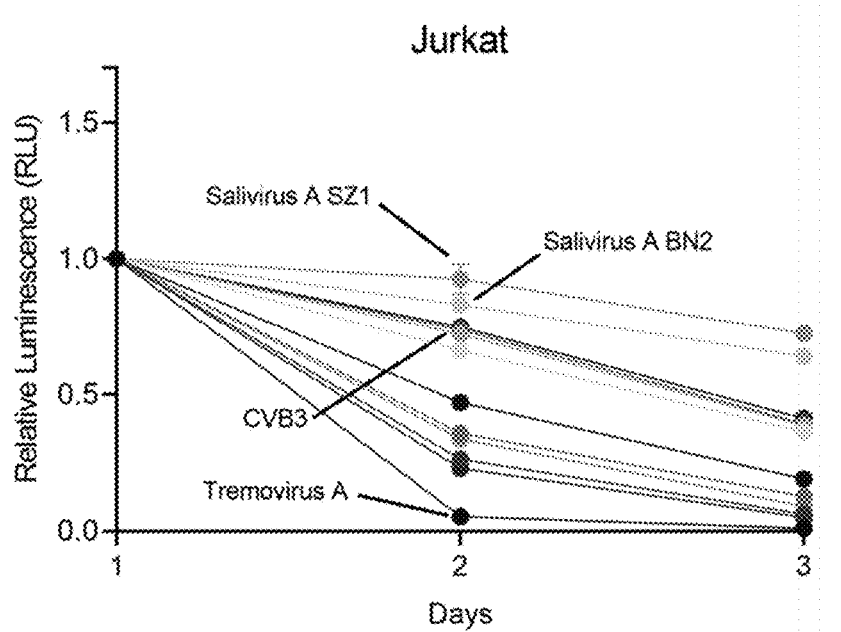

Functional stability of the IRES constructs in each round of electroporated Jurkat cells was measured over 3 days. Luminescence from secreted *Gaussia* luciferase in supernatant was measured every 24 hours after electroporation of 60,000 cells with 1 μg of each circularization reaction, followed by complete media replacement (FIGS. 5A and 5B).

Salivirus A SZ1 and Salivirus A BN2 IRES constructs had high functional stability compared to other constructs.

EXAMPLE 10

Figure 6A:
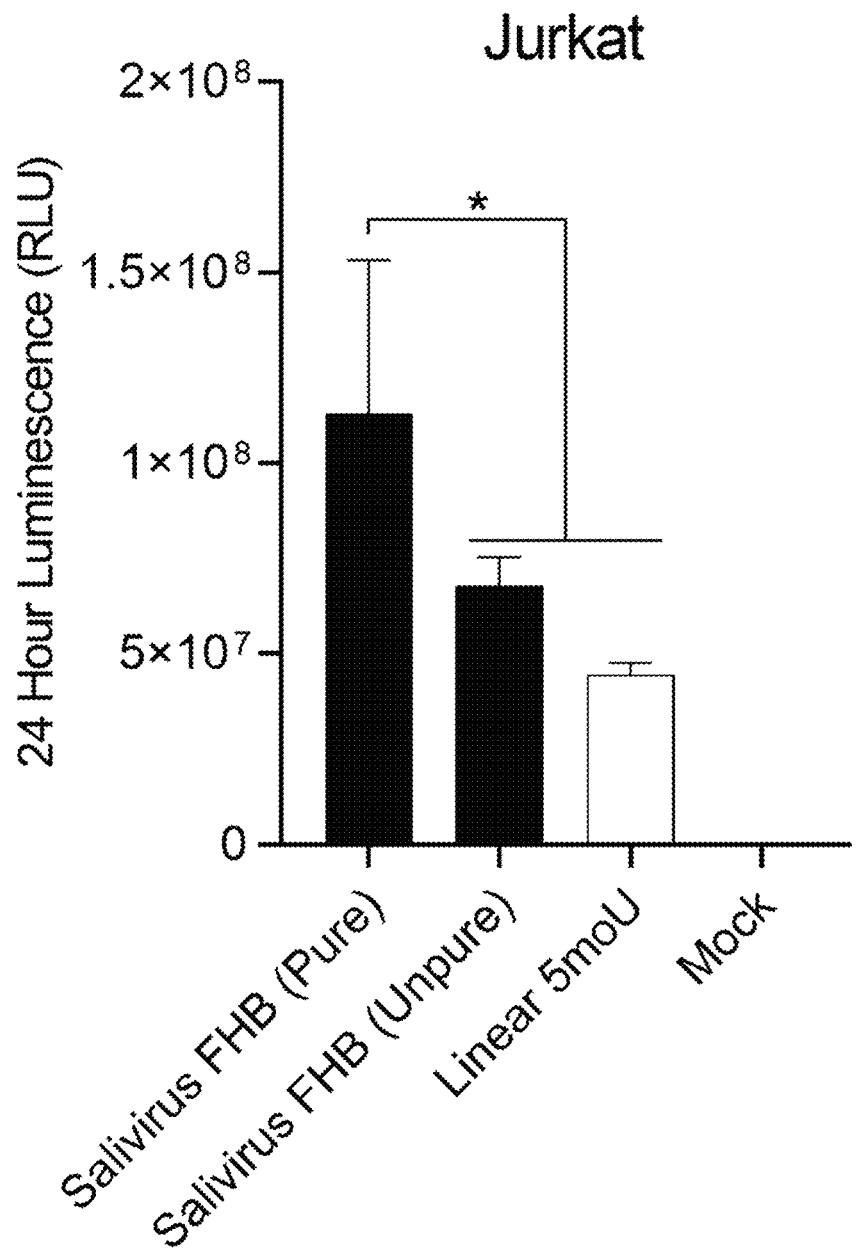
FIG. 6 depicts comparisons of 24 hour luminescence (FIG. 6A) or relative luminescence over 3 days (FIG. 6B) of modified linear, unpurified circular, or purified circular RNA encoding *Gaussia* luciferase.

Expression, Functional Stability, and Cytokine Release of Circular and Linear RNA in Jurkat Cells A construct including anabaena intron/exon regions, a *Gaussia* luciferase expression sequence, and a Salivirus FHB IRES was circularized. mRNA including a *Gaussia* luciferase expression sequence and a ~150 nt polyA tail, and modified to replace 100% of uridine with 5-methoxy uridine (5moU) is commercially available and was purchased from Trilink. 5moU nucleotide modifications have been shown to improve mRNA stability and expression (Bioconjug Chem. 2016 Mar. 16; 27(3):849-53). Expression of modified mRNA, circularization reactions (unpure), and circRNA purified by size exclusion HPLC (pure) in Jurkat cells were measured and compared (FIG. 6A). Luminescence from secreted *Gaussia* luciferase in supernatant was measured 24 hours after electroporation of 60,000 cells with 1 μg of each RNA species.

Figure 6B:
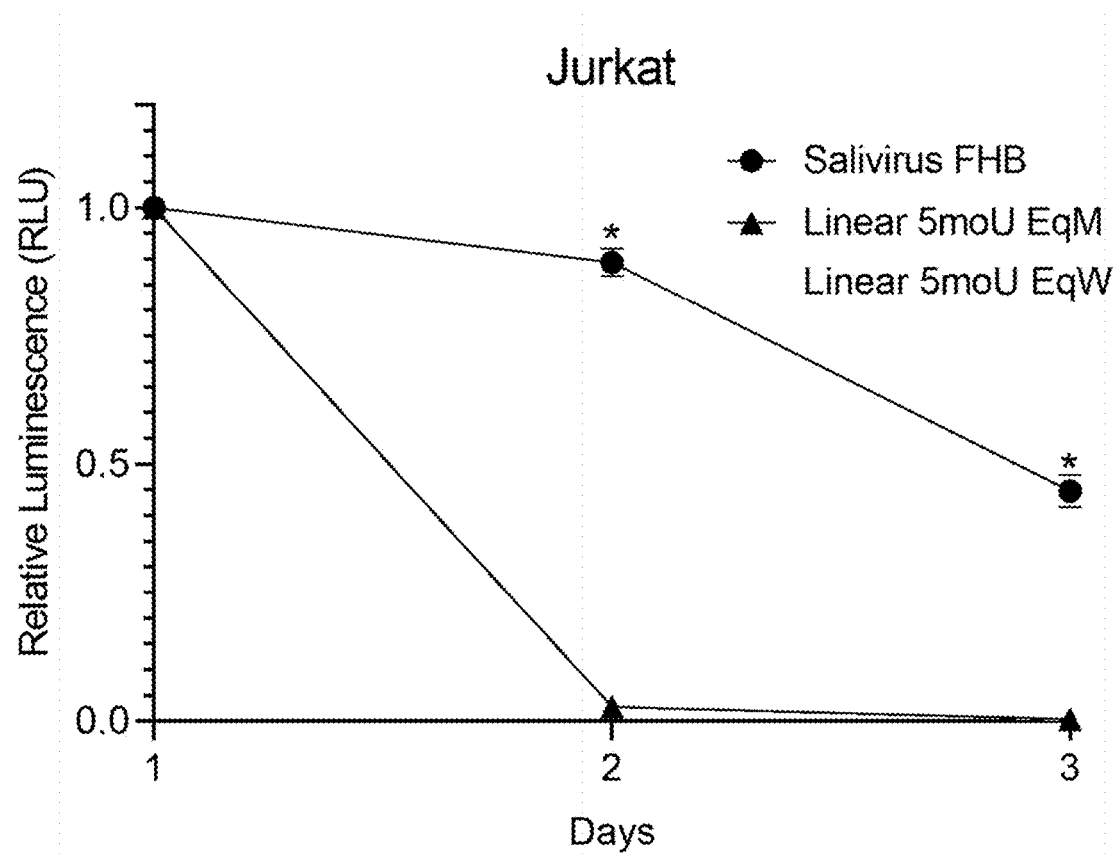

Luminescence from secreted *Gaussia* luciferase in supernatant was measured every 24 hours after electroporation of 60,000 cells with 1 ug of each RNA species, followed by complete media replacement. A comparison of functional stability data of modified mRNA and circRNA in Jurkat cells over 3 days is in FIG. 6B.

Figure 7A:
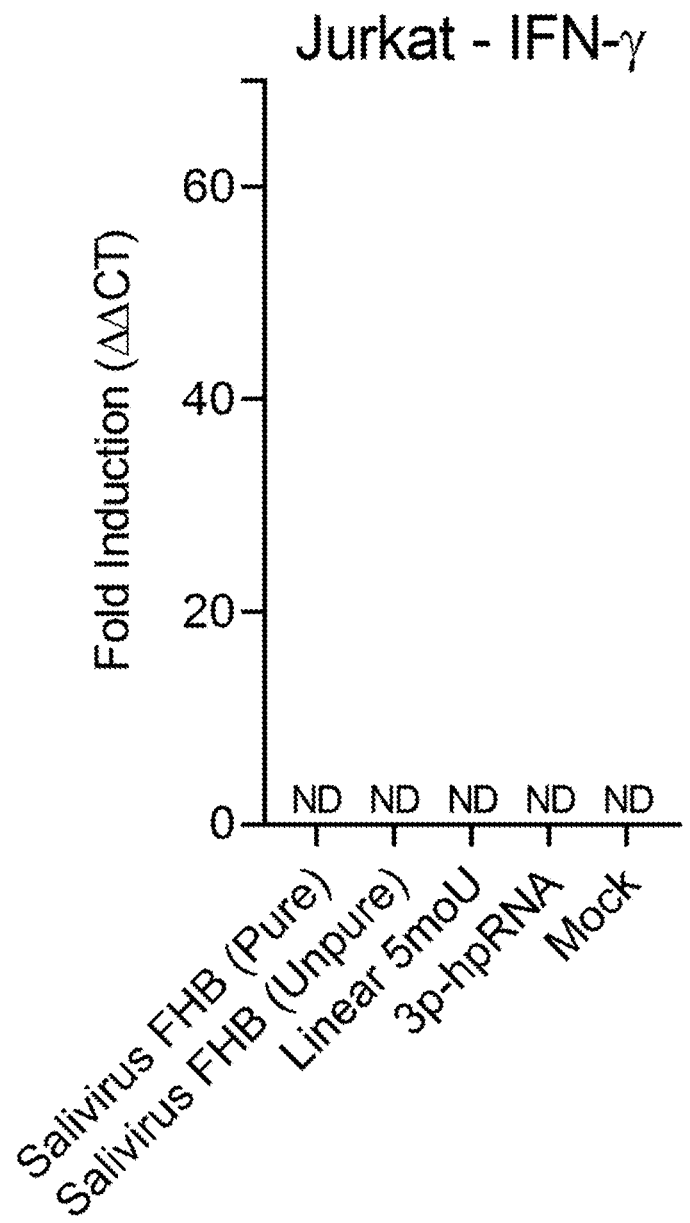
FIG. 7 depicts transcript induction of IFNγ (FIG. 7A), IL-6 (FIG. 7B), IL-2 (FIG. 7C), RIG-I (FIG. 7D), IFN-β1 (FIG. 7E), and TNFα (FIG. 7F) after electroporation of Jurkat cells with modified linear, unpurified circular, or purified circular RNA.
Figure 7B:
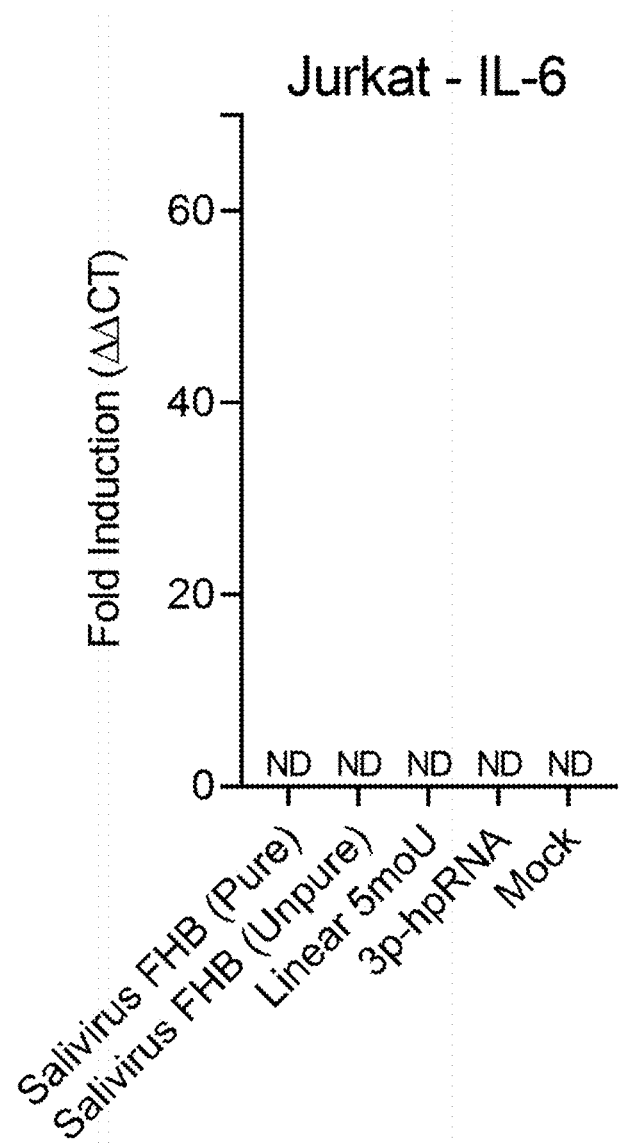
Figure 7C:
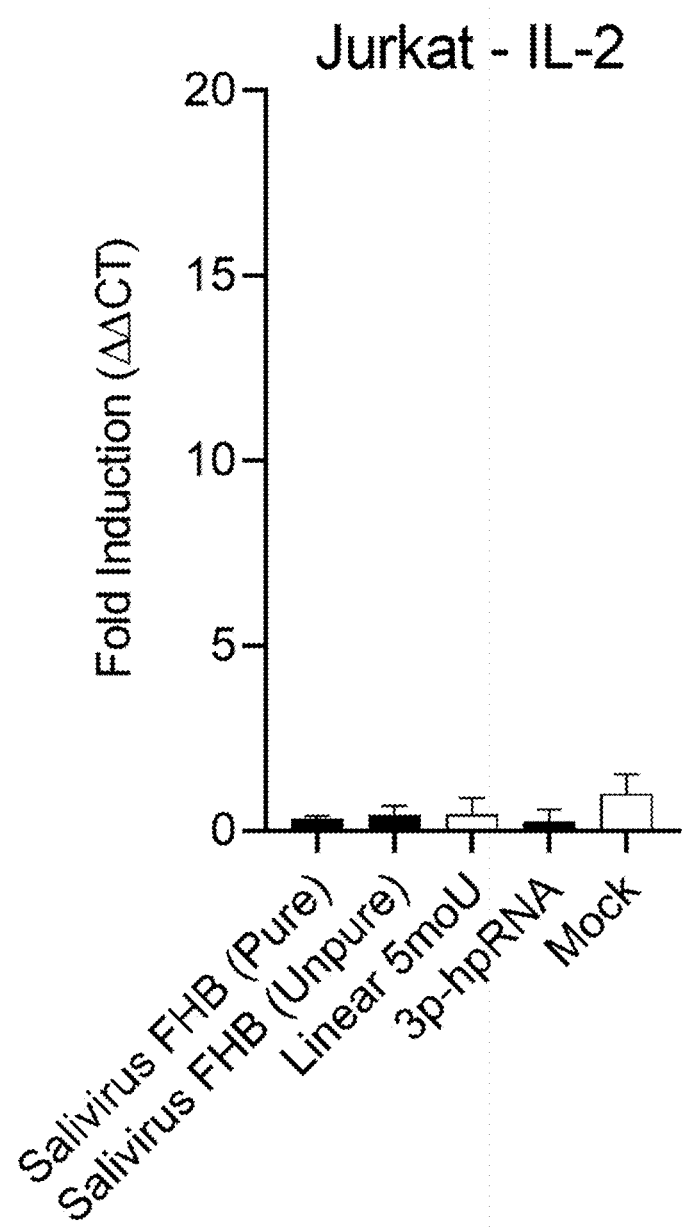
Figure 7D:
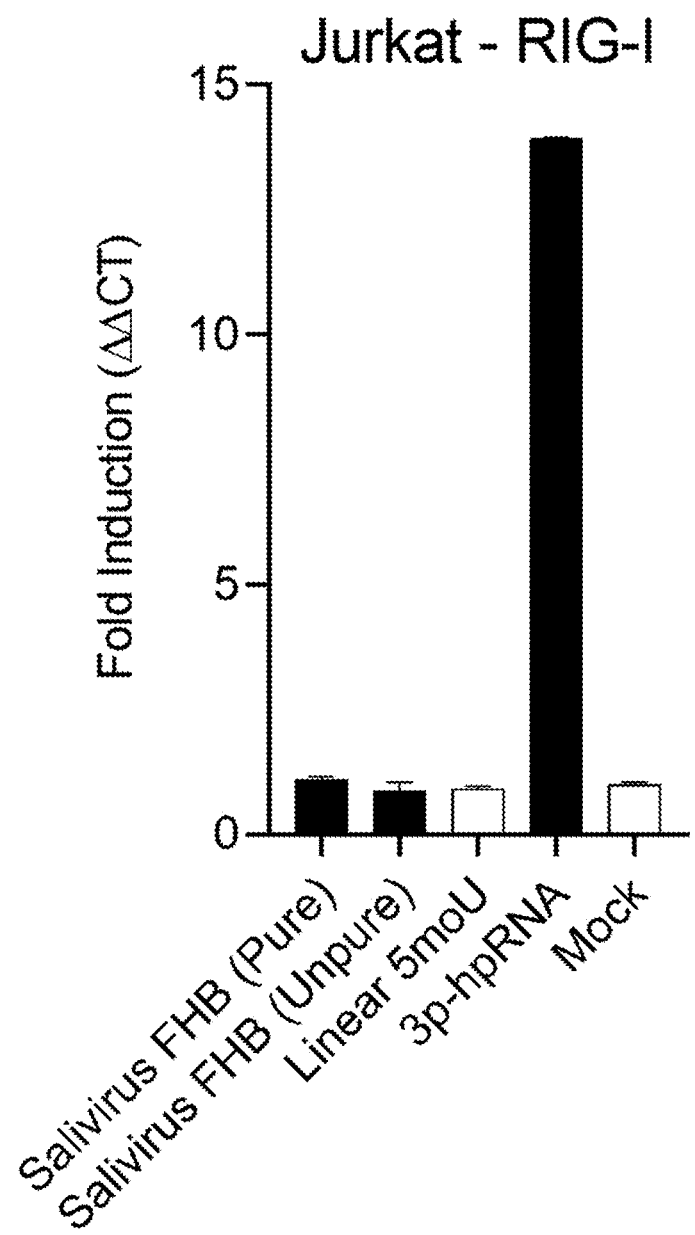
Figure 7E:
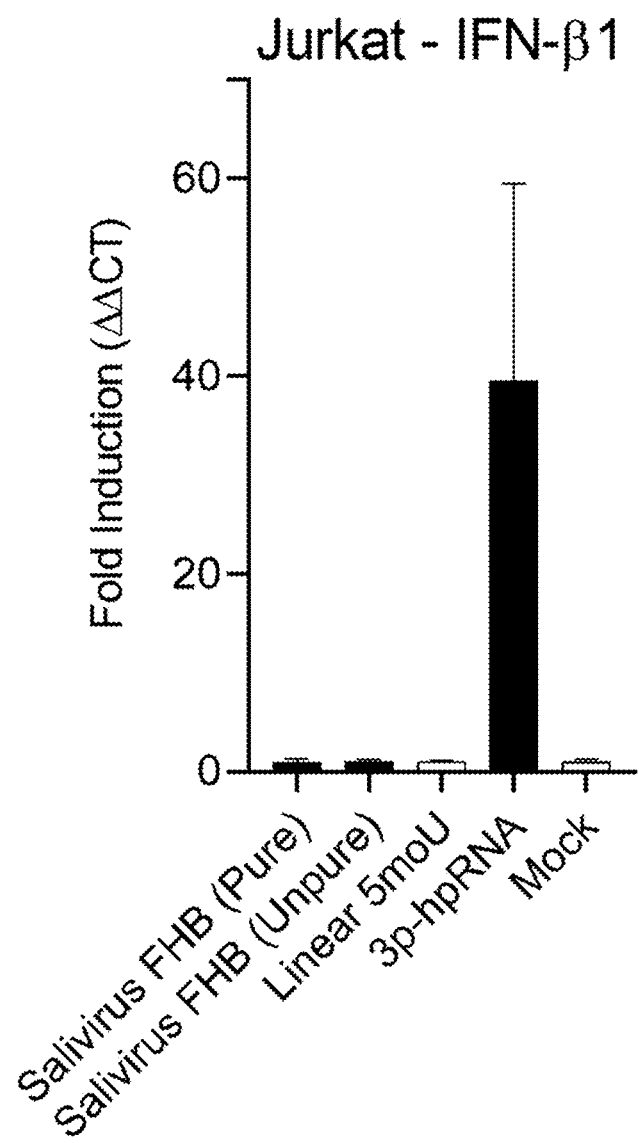
Figure 7F:
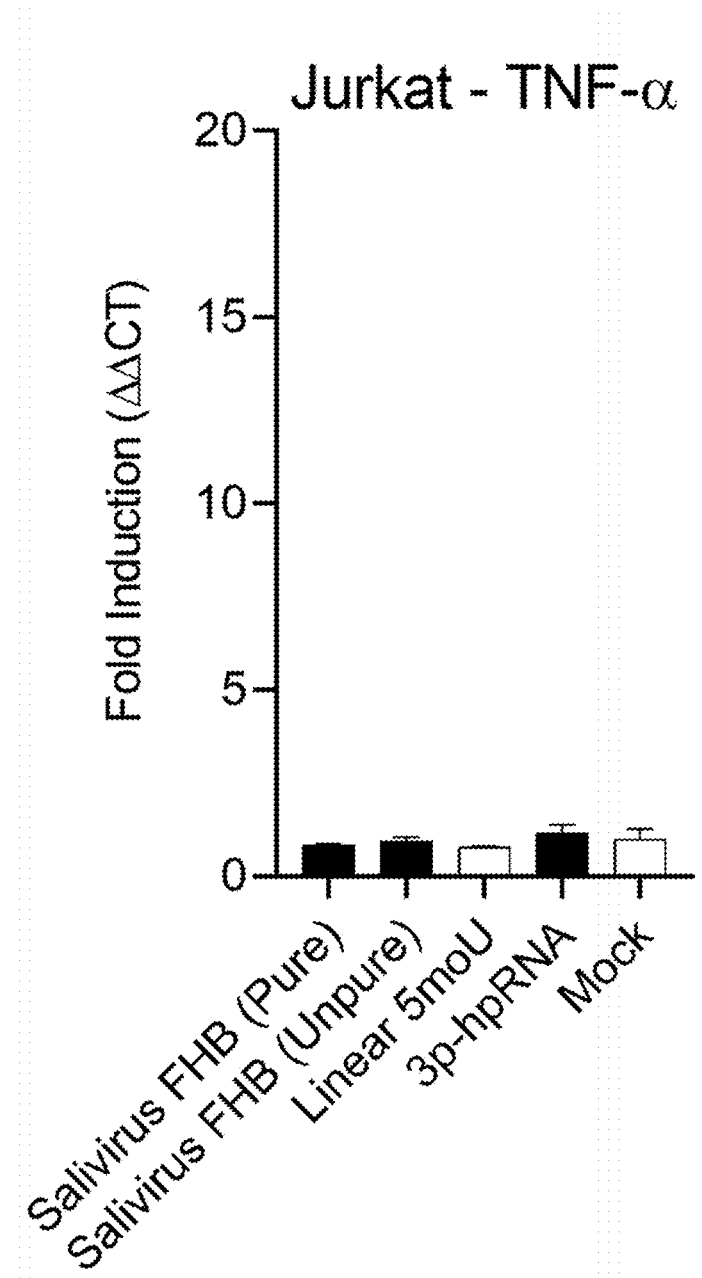

IFNγ (FIG. 7A), IL-6 (FIG. 7B), IL-2 (FIG. 7C), RIG-I (FIG. 7D), IFN-β1 (FIG. 7E), and TNFα (FIG. 7F) transcript induction was measured 18 hours after electroporation of 60,000 Jurkat cells with 1 μg of each RNA species described above and 3p-hpRNA (5' triphosphate hairpin RNA, which is a known RIG-I agonist).

EXAMPLE 11

Expression of Circular and Linear RNA in Monocytes and Macrophages

Figure 8A:
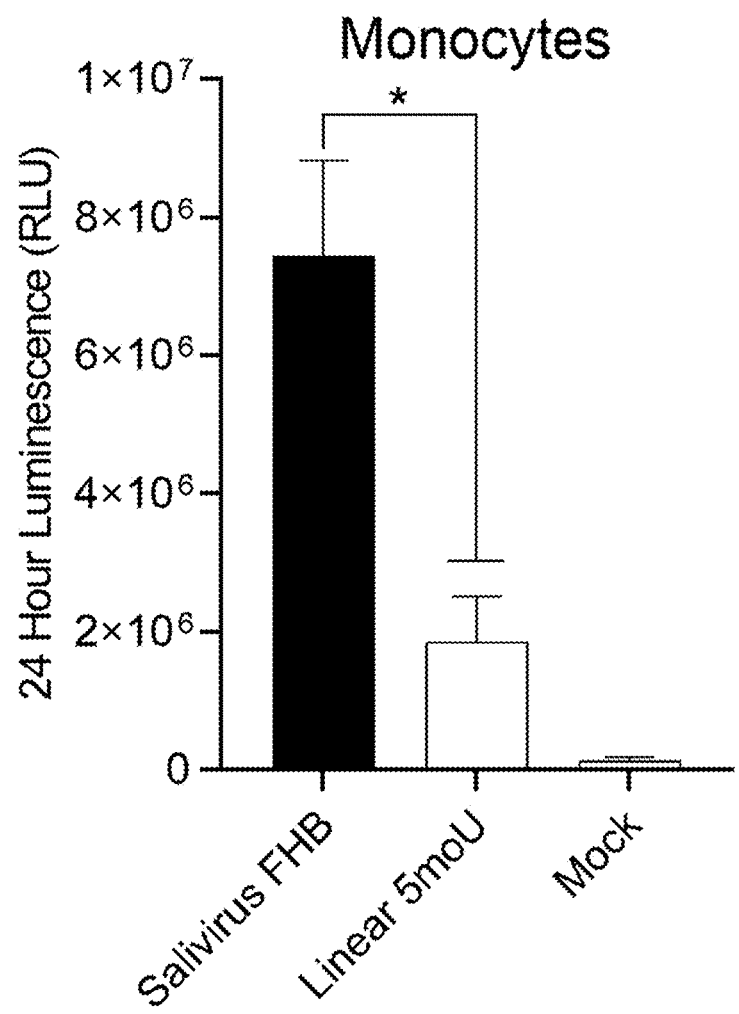
FIG. 8 depicts a comparison of luminescence of circular RNA and modified linear RNA encoding *Gaussia* luciferase in human primary monocytes (FIG. 8A) and macrophages (FIG. 8B and FIG. 8C).
Figure 8B:
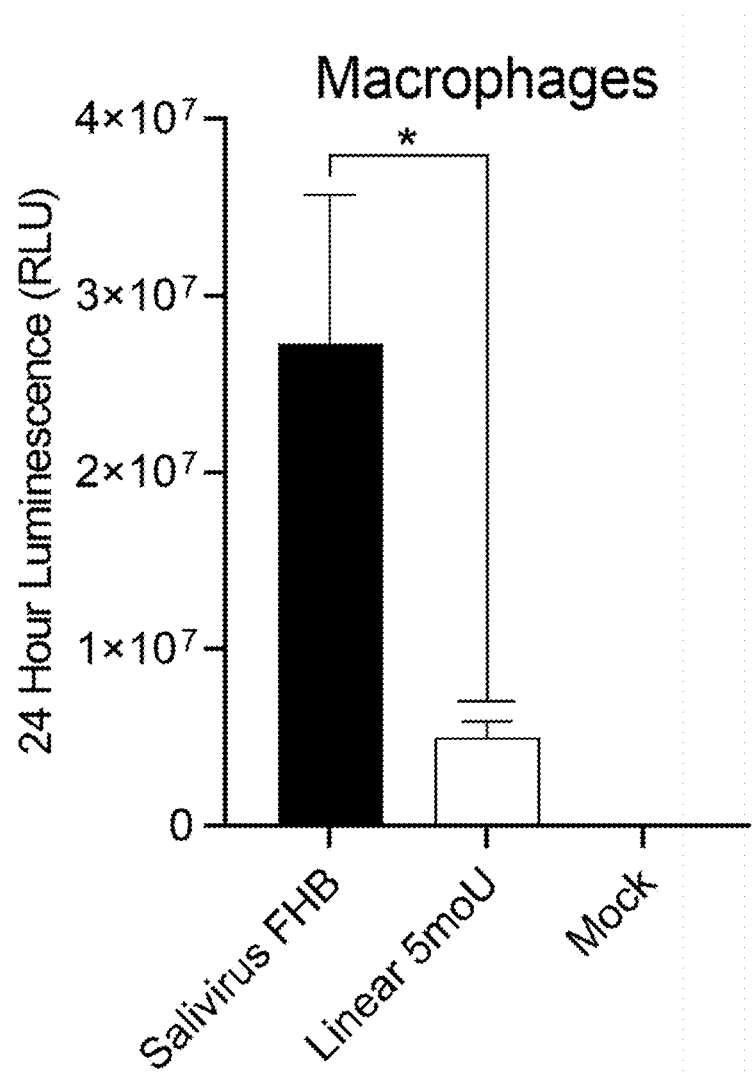
Figure 8C:
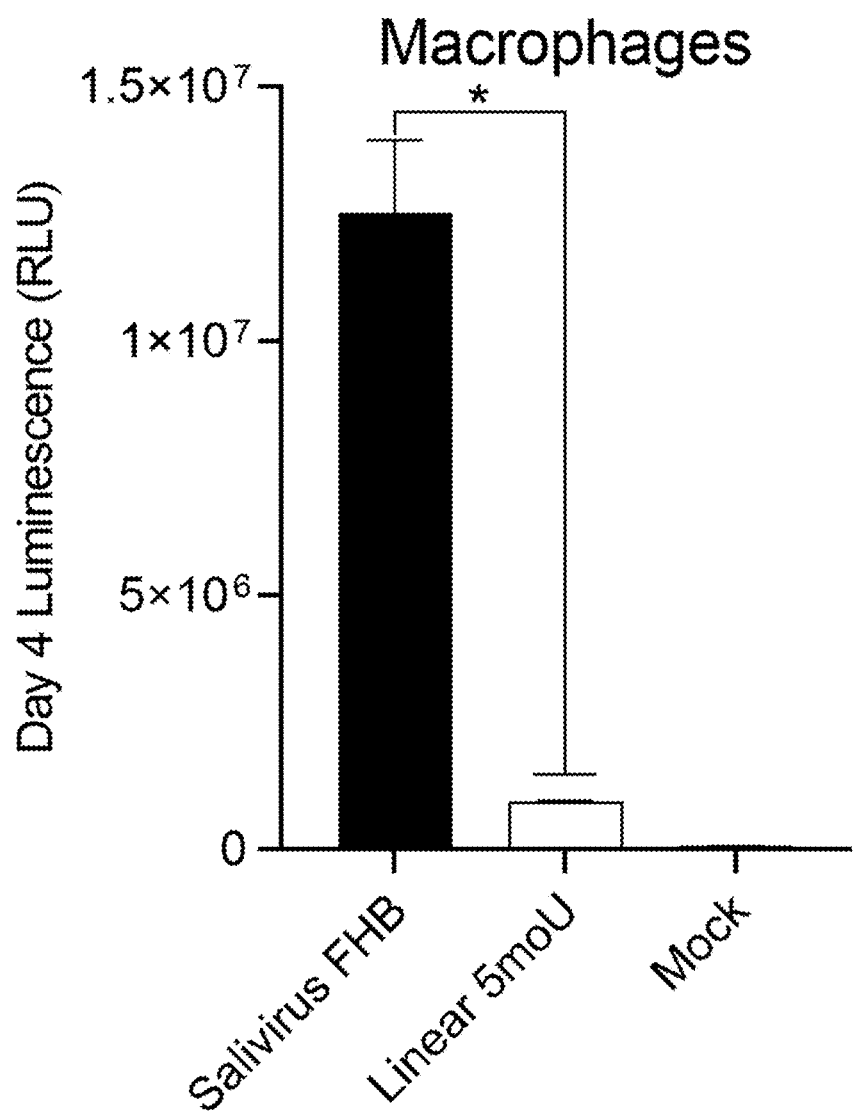

A construct including anabaena intron/exon regions, a *Gaussia* luciferase expression sequence, and a Salivirus FHB IRES was circularized. mRNA including a *Gaussia* luciferase expression sequence and a ~150 nt polyA tail, and modified to replace 100% of uridine with 5-methoxy uridine (5moU) was purchased from Trilink. Expression of circular and modified mRNA was measured in human primary monocytes (FIG. 8A) and human primary macrophages (FIG. 8B). Luminescence from secreted *Gaussia* luciferase in supernatant was measured 24 hours after electroporation of 60,000 cells with 1 μg of each RNA species. Luminescence was also measured 4 days after electroporation of human primary macrophages with media changes every 24

EXAMPLE 12

Expression and Functional Stability by IRES in Primary T Cells

Figure 9A:
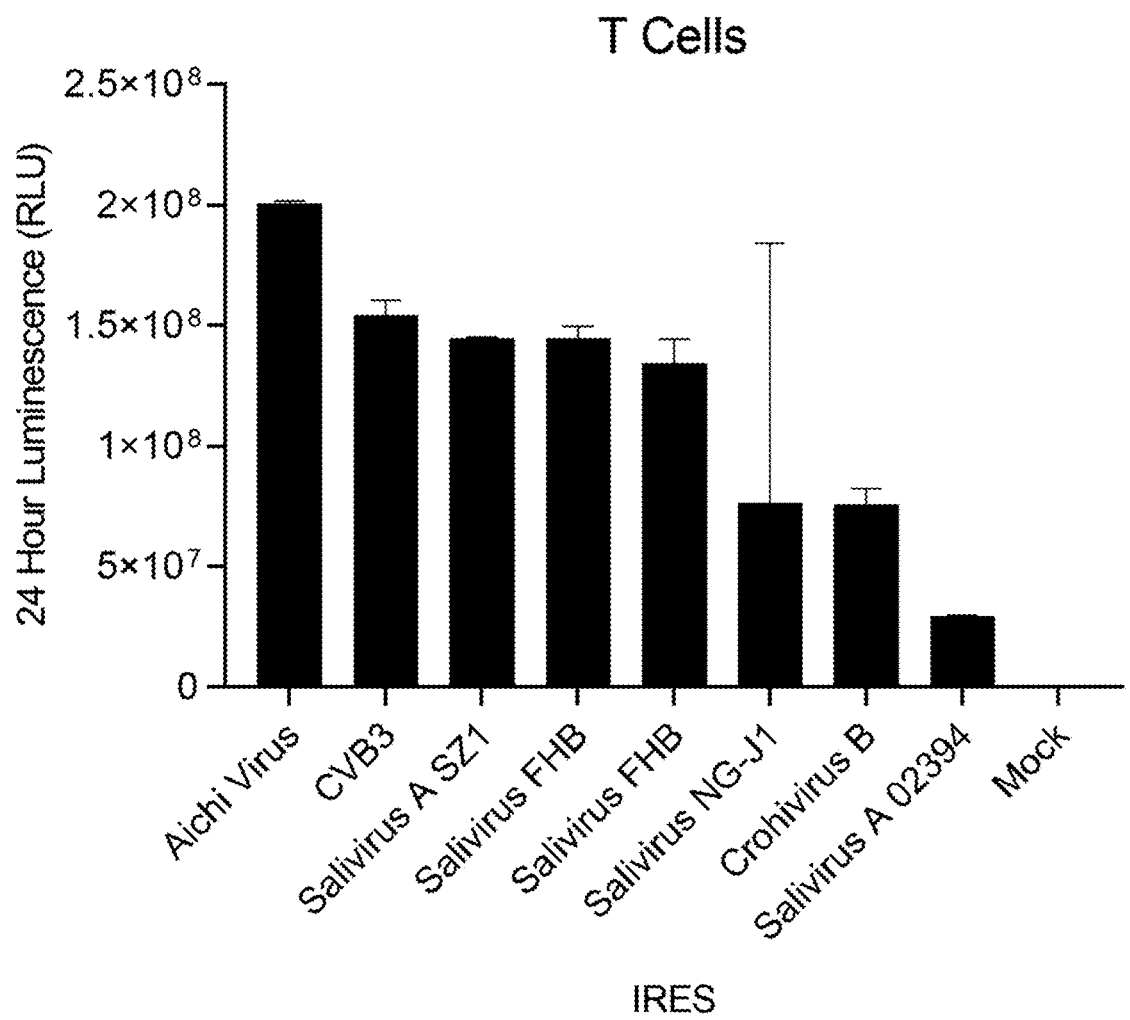
FIG. 9 depicts relative luminescence over 3 days (FIG. 9A) in supernatant of primary T cells after transduction with circular RNA comprising a *Gaussia* luciferase expression sequence and varying IRES sequences or 24 hour luminescence (FIG. 9B).

Constructs including anabaena intron/exon regions, a *Gaussia* luciferase expression sequence, and a subset of previously tested IRES were circularized and reaction products were purified by size exclusion HPLC. 150,000 primary human CD3+ T cells were electroporated with 1 µg of each circRNA. Luminescence from secreted *Gaussia* luciferase in supernatant was measured 24 hours after electroporation (FIG. 9A). Aichi Virus and CVB3 IRES constructs had the most expression at 24 hours.

Figure 9B:
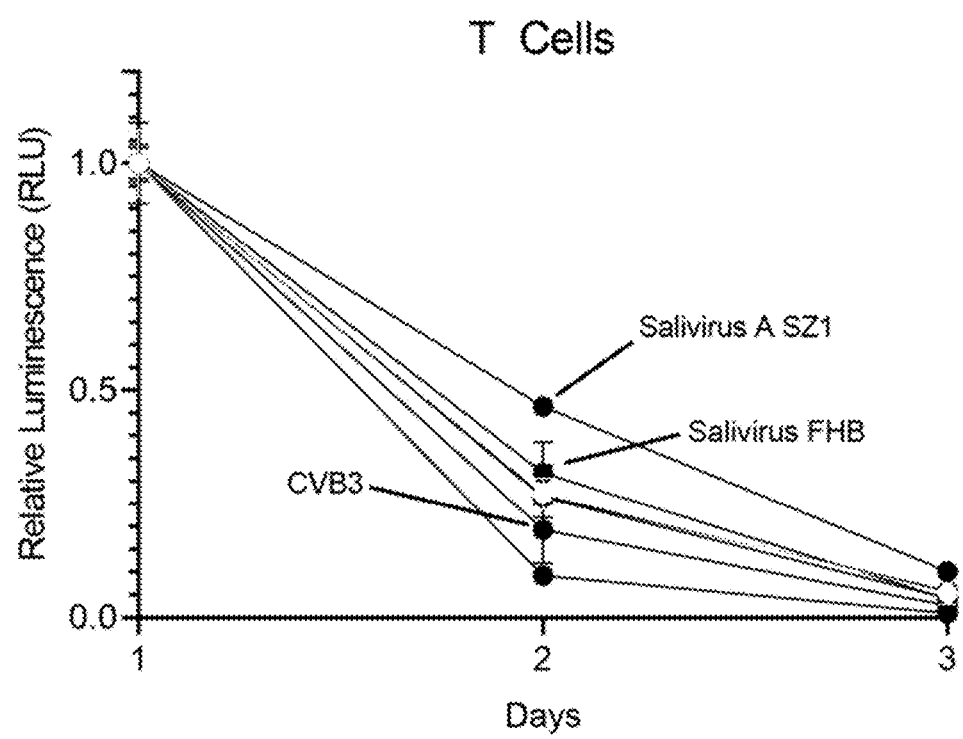

Luminescence was also measured every 24 hours after electroporation for 3 days in order to compare functional stability of each construct (FIG. 9B). The construct with a Salivirus A SZ1 IRES was the most stable.

EXAMPLE 13

Figure 10A:
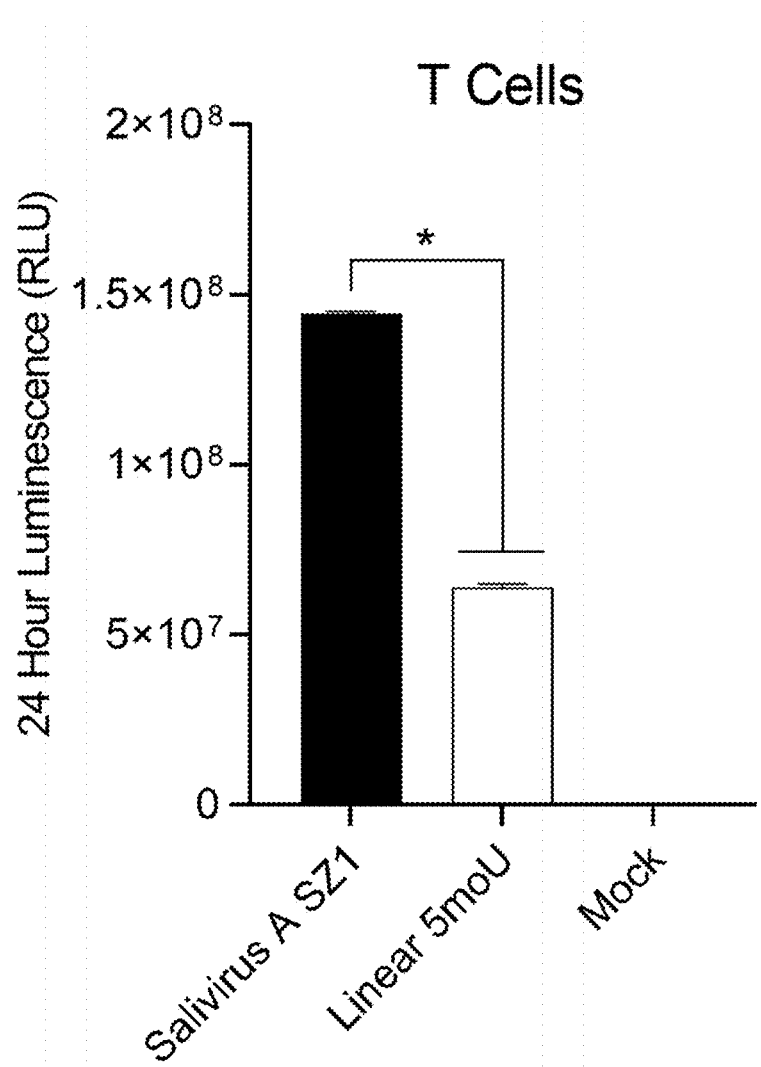
FIG. 10 depicts 24 hour luminescence in supernatant of primary T cells (FIG. 10A) after transduction with circular RNA or modified linear RNA comprising a *Gaussia* luciferase expression sequence, or relative luminescence over 3 days (FIG. 10B), and 24 hour luminescence in PBMCs (FIG. 10C).
Figure 10B:
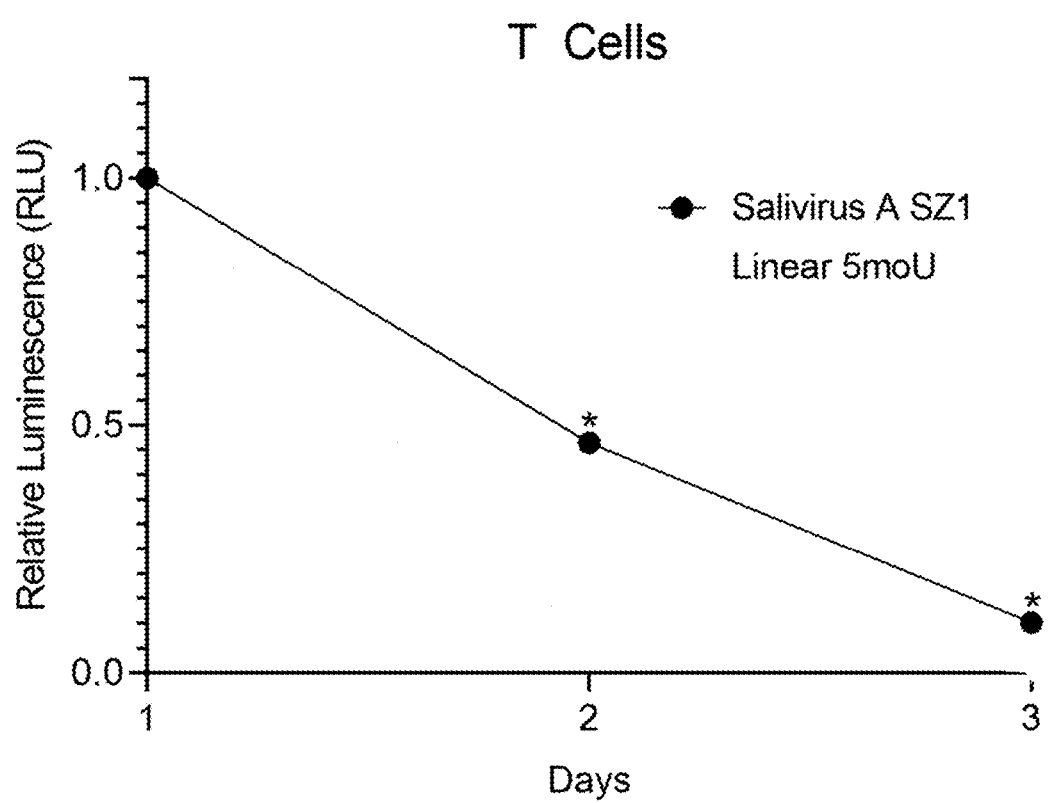
Figure 10C:
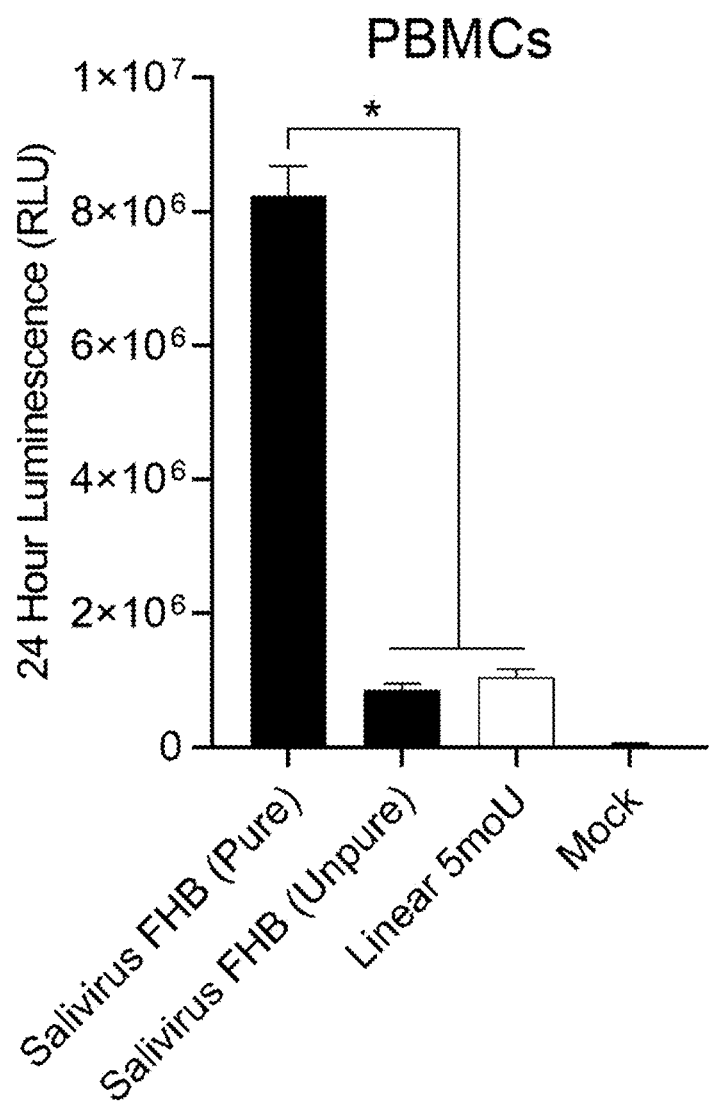

Expression and Functional Stability of Circular and Linear RNA in Primary T Cells and PBMCs Constructs including anabaena intron/exon regions, a *Gaussia* luciferase expression sequence, and a Salivirus A SZ1 IRES or Salivirus FHB IRES were circularized. mRNA including a *Gaussia* luciferase expression sequence and a ~150 nt polyA tail, and modified to replace 100% of uridine with 5-methoxy uridine (5moU) and was purchased from Trilink. Expression of Salivirus A SZ1 IRES HPLC purified circular and modified mRNA was measured in human primary CD3+ T cells. Expression of Salivirus FHB HPLC purified circular, unpurified circular and modified mRNA was measured in human PBMCs. Luminescence from secreted *Gaussia* luciferase in supernatant was measured 24 hours after electroporation of 150,000 cells with 1 µg of each RNA species. Data for primary human T cells is shown in FIGS. 10A and 10B, and data for PBMCs is shown in FIG. 10C. The difference in expression between the purified circular RNA and unpurified circular RNA or linear RNA was significant in each case (p<0.05).

Luminescence from secreted *Gaussia* luciferase in primary T cell supernatant was measured every 24 hours after electroporation over 3 days in order to compare construct functional stability. Data is shown in FIG. 10B. The difference in relative luminescence from the day 1 measurement between purified circular RNA and linear RNA was significant at both day 2 and day 3 for primary T cells.

EXAMPLE 14

Circularization Efficiency by Permutation Site in Anabaena Intron

Figure 11A:
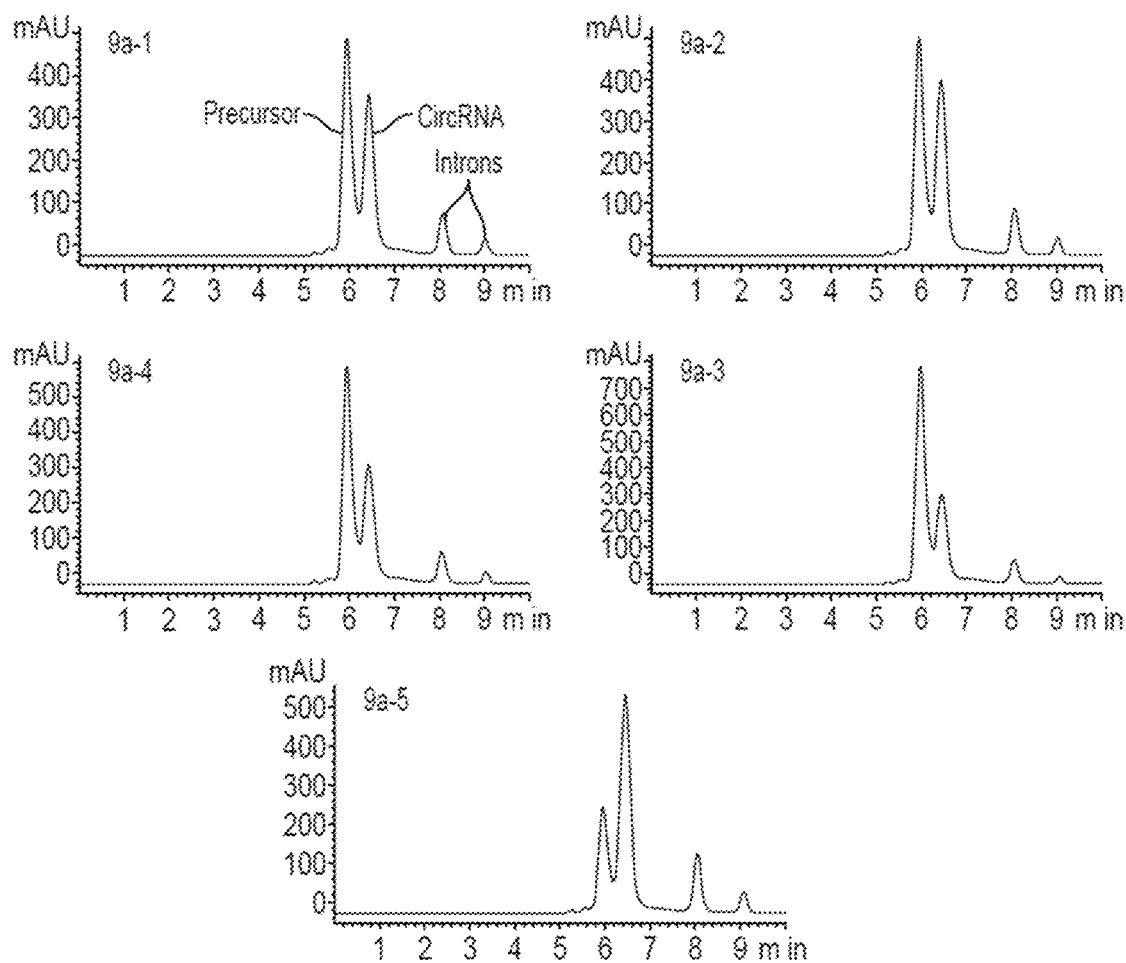
FIG. 11 depicts HPLC chromatograms (FIG. 11A) and circularization efficiencies (FIG. 11B) of RNA constructs having different permutation sites.

RNA constructs including a CVB3 IRES, a *Gaussia* luciferase expression sequence, anabaena intron/exon regions, spacers, internal homology regions, and homology arms were produced. Circularization efficiency of constructs using the traditional anabaena intron permutation site and 5 consecutive permutations sites in P9 was measured by HPLC. HPLC chromatograms for the 5 consecutive permutation sites in P9 are shown in FIG. 11A.

Figure 11B:
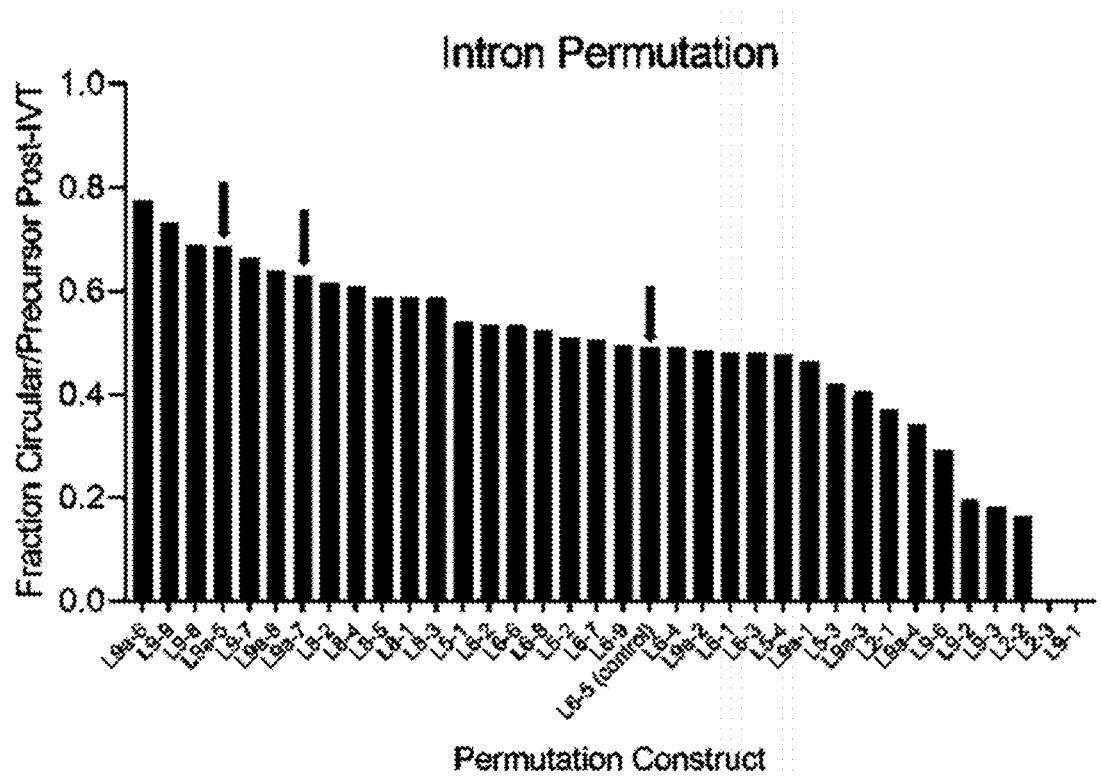

Circularization efficiency was measured at a variety of permutation sites. Circularization efficiency is defined as the area under the HPLC chromatogram curve for each of: circRNA/(circRNA+precursor RNA). Ranked quantification of circularization efficiency at each permutation site is in FIG. 11B. 3 permutation sites (indicated in FIG. 11B) were selected for further investigation.

Circular RNA in this example was circularized by in vitro transcription (IVT) then purified via spin column. Circularization efficiency for all constructs would likely be higher if the additional step of incubation with $Mg^{2+}$ and guanosine nucleotide were included; however, removing this step allowed for comparison between, and optimization of, circular RNA constructs. This level of optimization is especially useful for maintaining high circularization efficiency with large RNA constructs, such as those encoding chimeric antigen receptors.

EXAMPLE 15

Circularization Efficiency of Alternative Introns

Figure 12A:
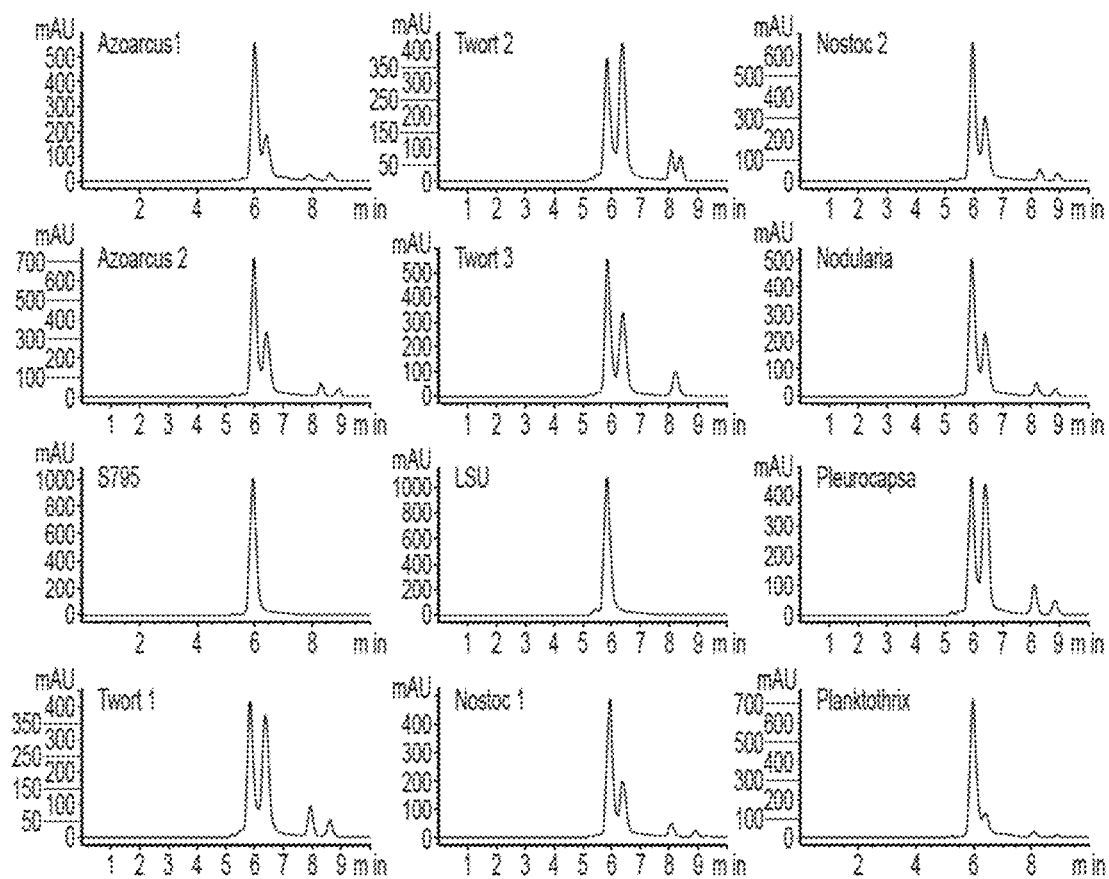
FIG. 12 depicts HPLC chromatograms (FIG. 12A) and circularization efficiencies (FIG. 12B) of RNA constructs having different introns and/or permutation sites.
Figure 12B:
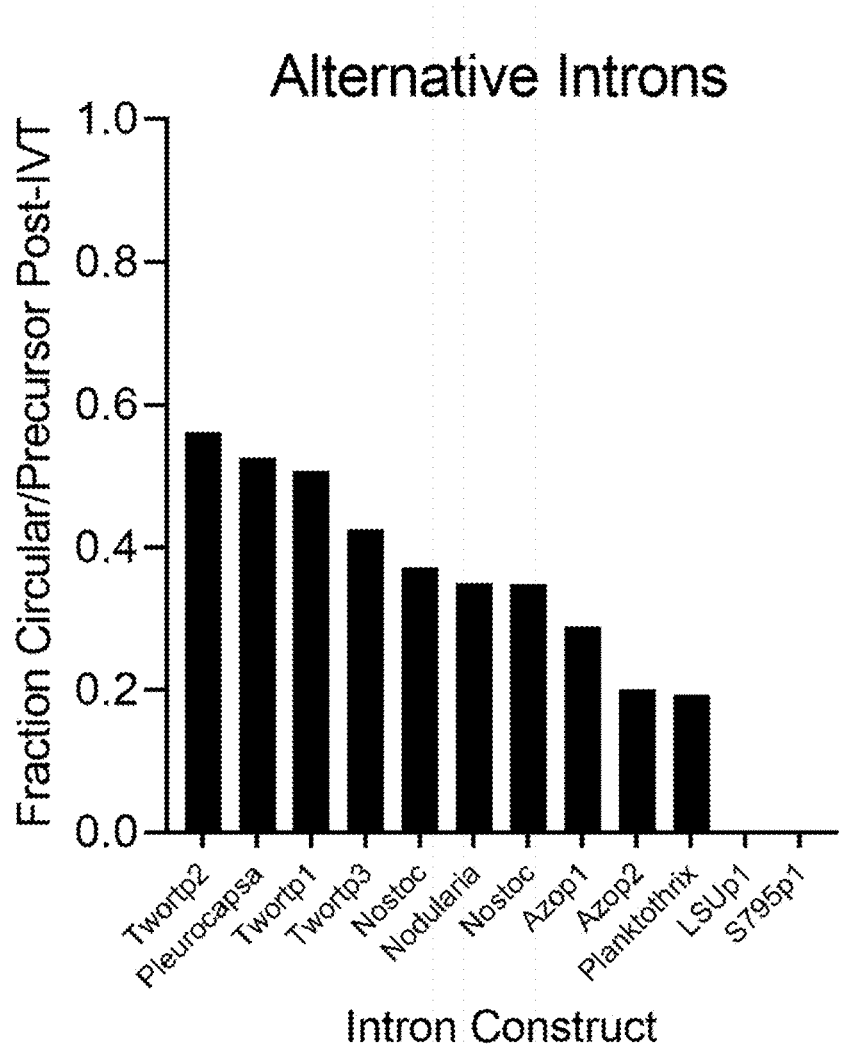

Precursor RNA containing a permuted group 1 intron of variable species origin or permutation site and several constant elements including: a CVB3 IRES, a *Gaussia* luciferase expression sequence, spacers, internal homology regions, and homology arms were created. Circularization data can be found in FIG. 12. FIG. 12A shows chromatograms resolving precursor, CircRNA and introns. FIG. 12B provides ranked quantification of circularization efficiency, based on the chromatograms shown in FIG. 12A, as a function of intron construct.

Circular RNA in this example was circularized by in vitro transcription (IVT) then spin column purification. Circularization efficiency for all constructs would likely be higher if the additional step of incubation with $Mg^{2+}$ and guanosine nucleotide were included; however, removing this step allows for comparison between, and optimization of, circular RNA constructs. This level of optimization is especially useful for maintaining high circularization efficiency with large RNA constructs, such as those encoding chimeric antigen receptors.

EXAMPLE 16

Circularization Efficiency by Homology Arm Presence or Length

Figure 13A:
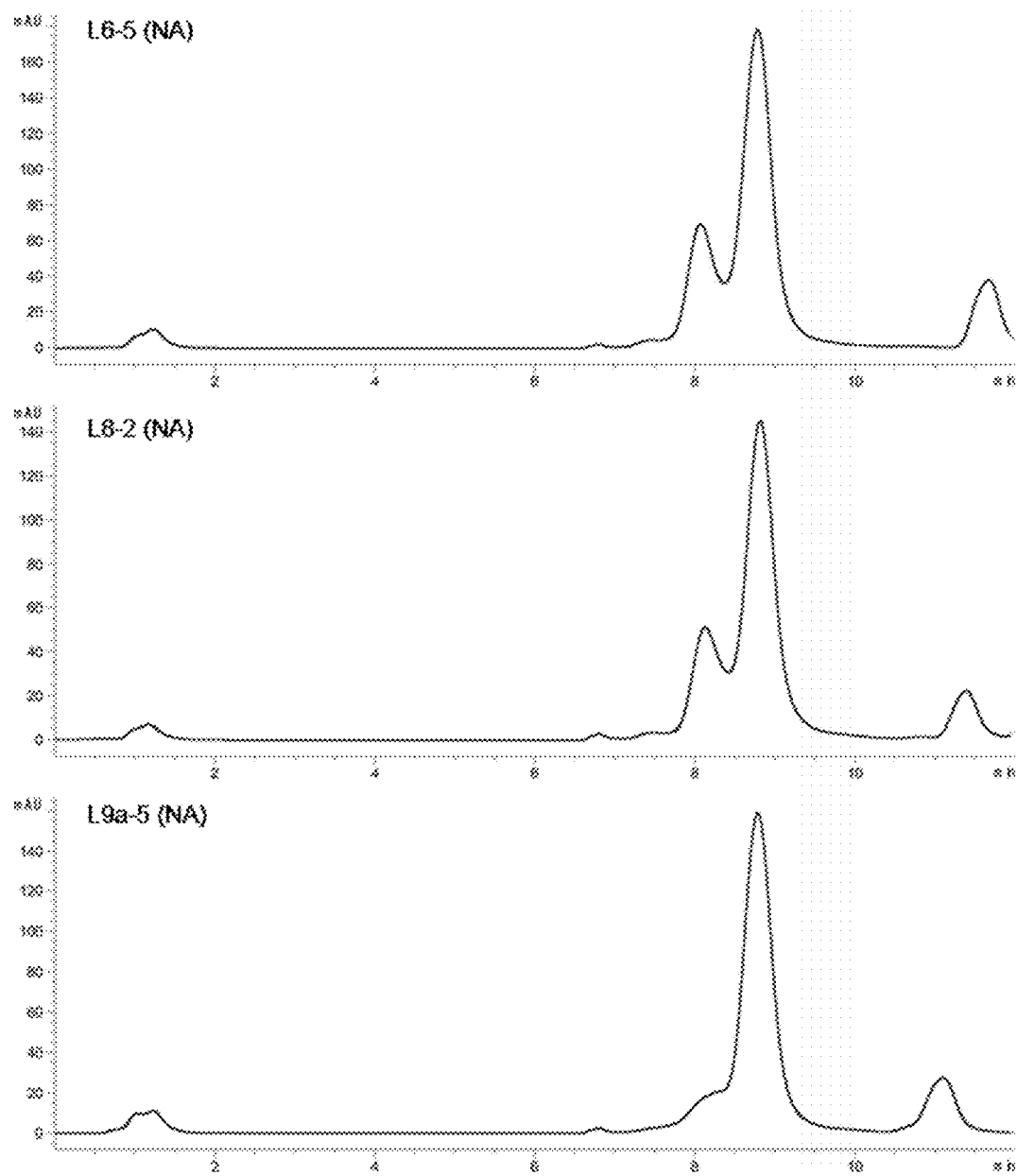
FIG. 13 depicts HPLC chromatograms (FIG. 13A) and circularization efficiencies (FIG. 13B) of 3 RNA constructs with or without homology arms.
Figure 13B:
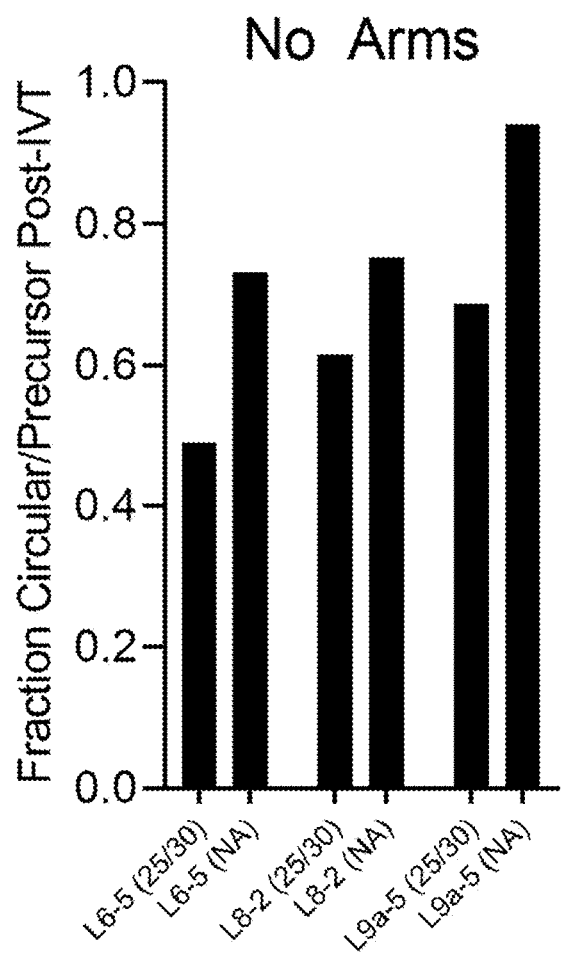

RNA constructs including a CVB3 IRES, a *Gaussia* luciferase expression sequence, anabaena intron/exon regions, spacers, and internal homology regions were produced. Constructs representing 3 anabaena intron permutation sites were tested with 30 nt, 25% GC homology arms or without homology arms ("NA"). These constructs were allowed to circularize without an $Mg^{2+}$ incubation step. Circularization efficiency was measured and compared. Data can be found in FIG. 13. Circularization efficiency was higher for each construct lacking homology arms. FIG. 13A provides ranked quantification of circularization efficiency; FIG. 13B provides chromatograms resolving precursor, circRNA and introns.

Figure 14:
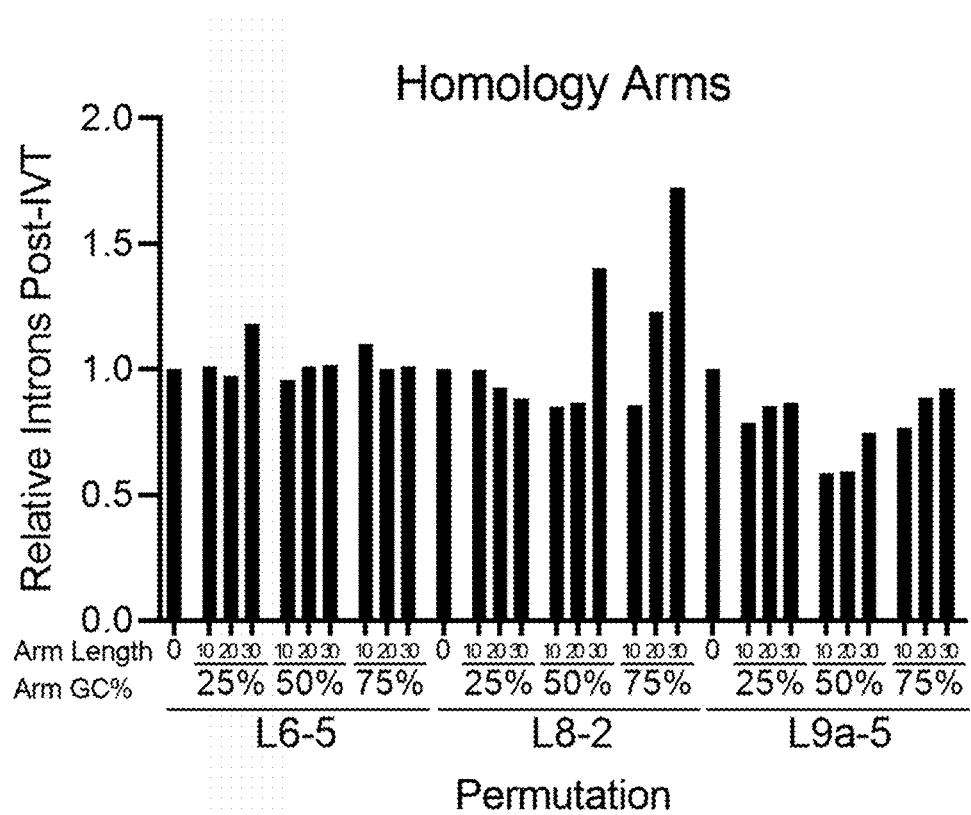
FIG. 14 depicts circularization efficiencies of 3 RNA constructs without homology arms or with homology arms having various lengths and GC content.

For each of the 3 permutation sites, constructs were created with 10 nt, 20 nt, and 30 nt arm lengths and 25%, 50%, and 75% GC content. Splicing efficiency of these constructs was measured and compared to constructs without homology arms (FIG. 14). Splicing efficiency is defined as the proportion of free introns relative to the total RNA in the splicing reaction.

Figure 15A:
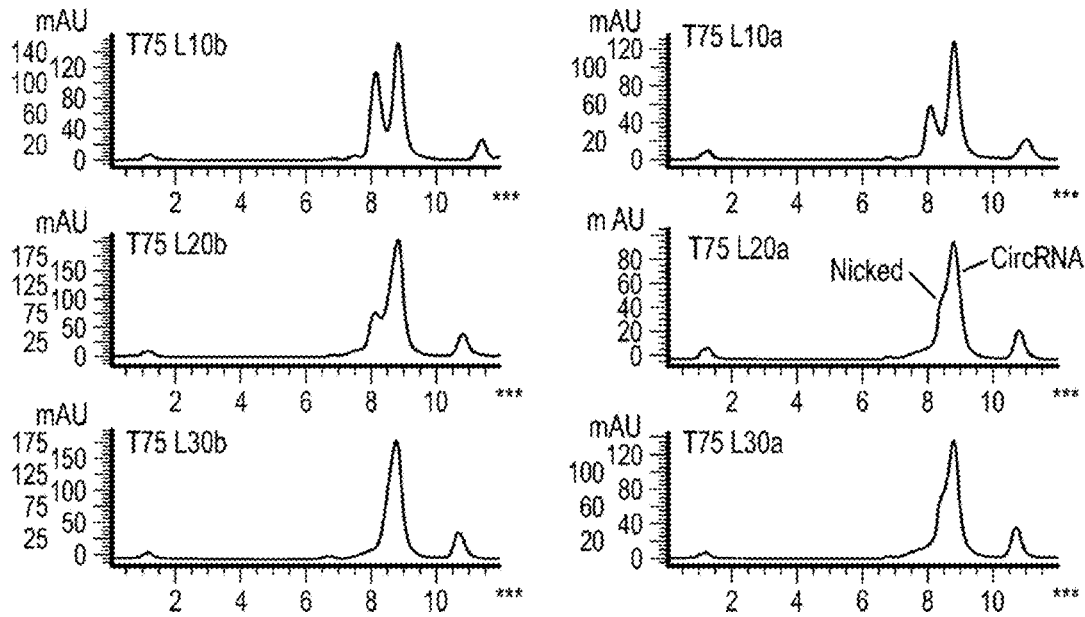
FIGS. 15A and 15B depict HPLC HPLC chromatograms showing the contribution of strong homology arms to improved splicing efficiency, the relationship between circularization efficiency and nicking in select constructs, and combinations of permutations sites and homology arms hypothesized to demonstrate improved circularization efficiency.
Figure 15B:
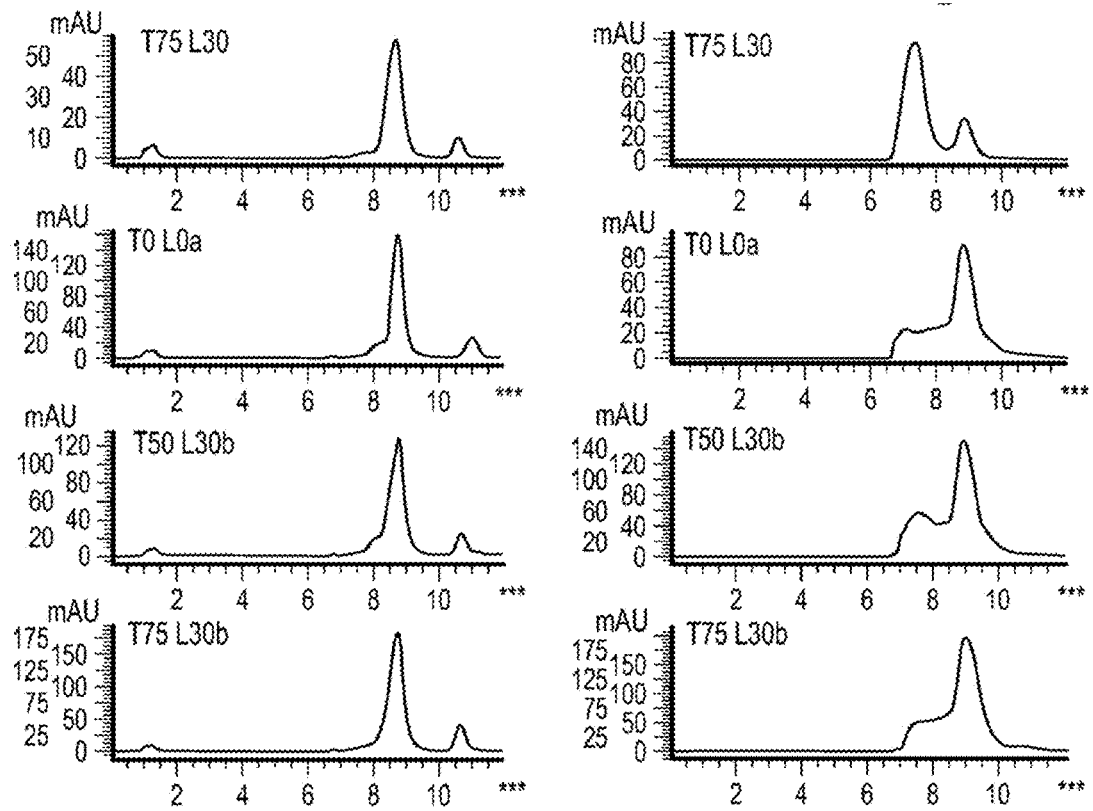

FIG. 15 A (left) shows HPLC chromatograms indicating the contribution of strong homology arms to improved splicing efficiency. Top left: 75% GC content, 10 nt homology arms. Center left: 75% GC content, 20 nt homology arms. Bottom left: 75% GC content, 30 nt homology arms.

FIG. 15 A (right) shows HPLC chromatograms showing increased splicing efficiency paired with increased nicking, appearing as a shoulder on the circRNA peak. Top right: 75% GC content, 10 nt homology arms. Center right: 75% GC content, 20 nt homology arms. Bottom right: 75% GC content, 30 nt homology arms.

FIG. 15 B (left) shows select combinations of permutation sites and homology arms hypothesized to demonstrate improved circularization efficiency.

FIG. 15 B (right) shows select combinations of permutation sites and homology arms hypothesized to demonstrate improved circularization efficiency, treated with *E. coli* polyA polymerase.

Circular RNA in this example was circularized by in vitro transcription (IVT) then spin-column purified. Circularization efficiency for all constructs would likely be higher if an additional $Mg^{2+}$ incubation step with guanosine nucleotide were included; however, removing this step allowed for comparison between, and optimization of, circular RNA constructs. This level of optimization is especially useful for maintaining high circularization efficiency with large RNA constructs, such as those encoding chimeric antigen receptors.

EXAMPLE 17

Circular RNA Encoding a CAR

Figure 16:
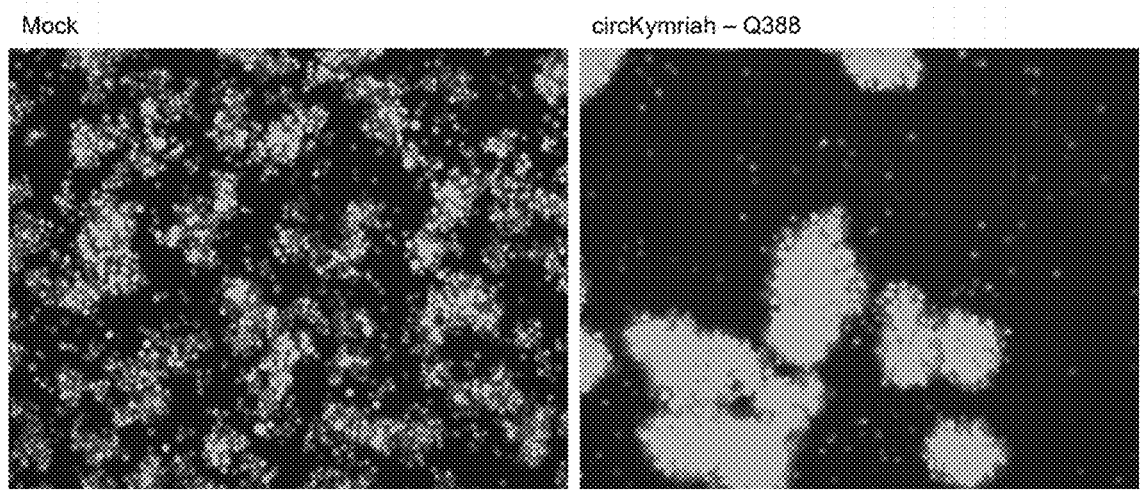
FIG. 16 shows fluorescent images of T cells mock electroporated (left) or electroporated with circular RNA encoding a CAR (right) and co-cultured with Raji cells expressing GFP and firefly luciferase.

Constructs including anabaena intron/exon regions, a Kymriah chimeric antigen receptor (CAR) expression sequence, and a CVB3 IRES were circularized. 100,000 human primary CD3+ T cells were electroporated with 500 ng of circRNA and co-cultured for 24 hours with Raji cells stably expressing GFP and firefly luciferase. Effector to target ratio (E:T ratio) 0.75:1. 100,000 human primary CD3+ T cells were mock electroporated and co-cultured as a control (FIG. 16).

Figure 17:
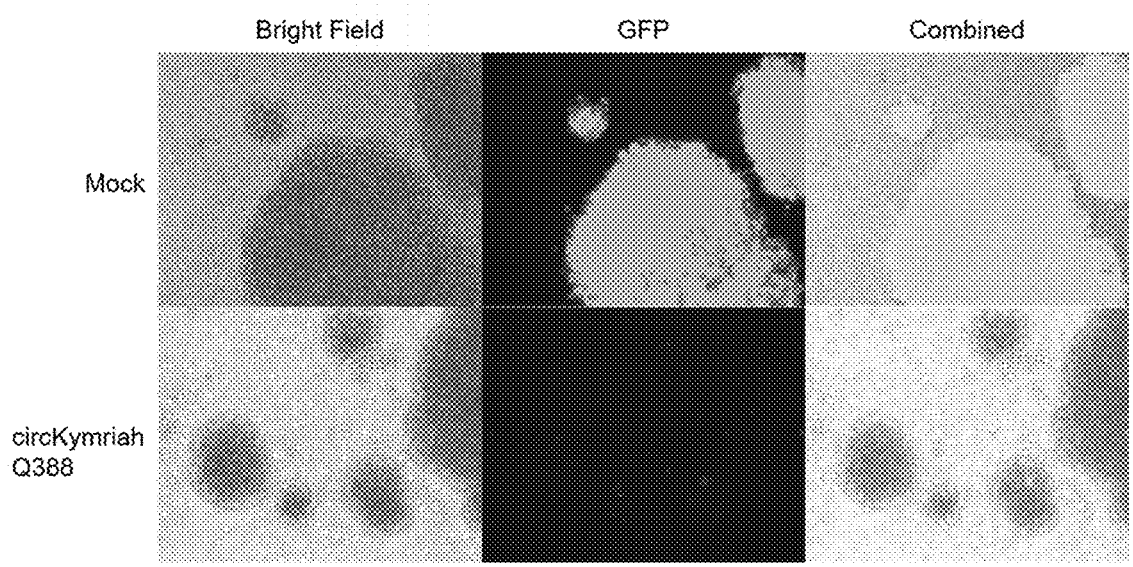
FIG. 17 shows bright field (left), fluorescent (center), and overlay (right) images of T cells mock electroporated (top) or electroporated with circular RNA encoding a CAR (bottom) and co-cultured with Raji cells expressing GFP and firefly luciferase.

Sets of 100,000 human primary CD3+ T cells were mock electroporated or electroporated with 1 μg of circRNA then co-cultured for 48 hours with Raji cells stably expressing GFP and firefly luciferase. E:T ratio 10:1 (FIG. 17).

Figure 18:
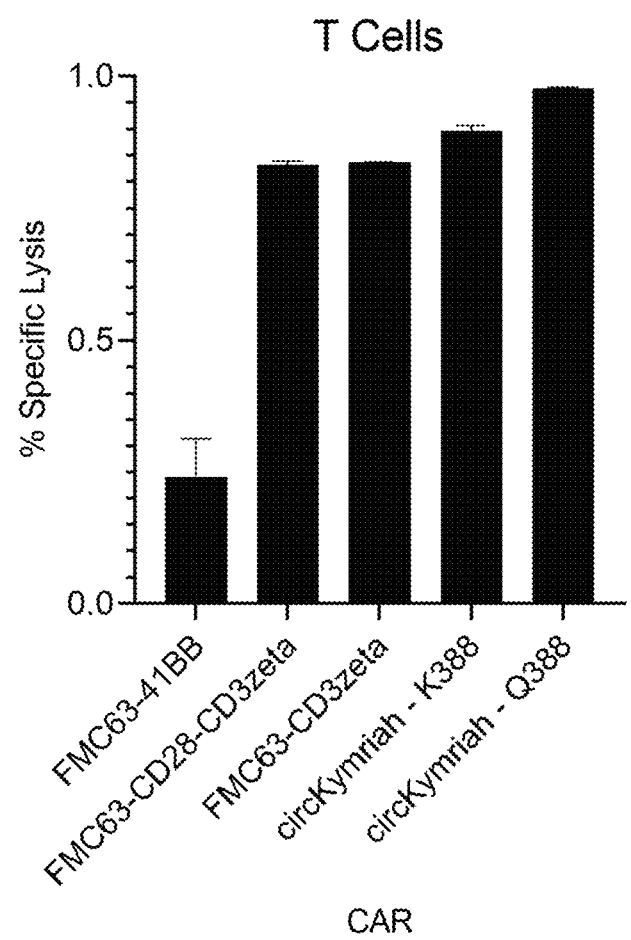
FIG. 18 depicts specific lysis of Raji target cells by T cells mock electroporated or electroporated with circular RNA encoding different CAR sequences.

Quantification of specific lysis of Raji target cells was determined by detection of firefly luminescence (FIG. 18). 100,000 human primary CD3+ T cells either mock electroporated or electroporated with circRNA encoding different CAR sequences were co-cultured for 48 hours with Raji cells stably expressing GFP and firefly luciferase. % Specific lysis defined as 1-[CAR condition luminescence]/[mock condition luminescence]. E:T ratio 10:1.

EXAMPLE 18

Figure 19A:
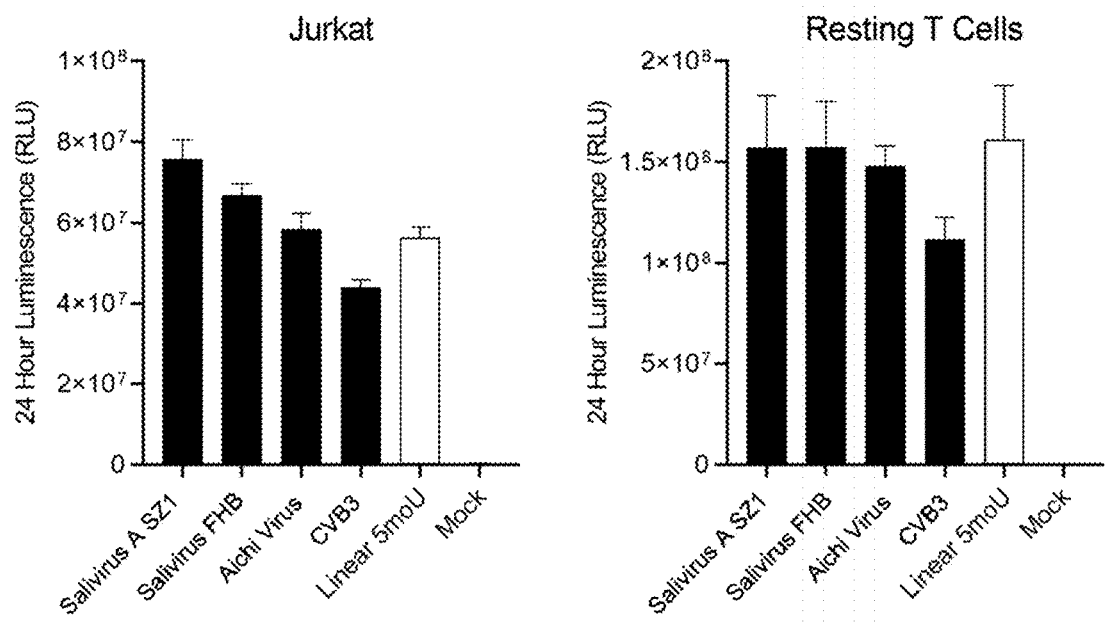
FIG. 19 depicts luminescence in supernatants of Jurkat cells (left) or resting primary human CD3+ T cells (right) 24 hours after transduction with linear or circular RNA comprising a *Gaussia* luciferase expression sequence and varying IRES sequences (FIG. 19A), and relative luminescence over 3 days (FIG. 19B).

Expression and Functional Stability of Circular and Linear RNA in Jurkat Cells and Resting Human T Cells Constructs including anabaena intron/exon regions, a *Gaussia* luciferase expression sequence, and a subset of previously tested IRES were circularized and reaction products were purified by size exclusion HPLC. 150,000 Jurkat cells were electroporated with 1 μg of circular RNA or 5moU-mRNA. Luminescence from secreted *Gaussia* luciferase in supernatant was measured 24 hours after electroporation (FIG. 19A left). 150,000 resting primary human CD3+ T cells (10 days post-stimulation) were electroporated with 1 μg of circular RNA or 5moU-mRNA. Luminescence from secreted *Gaussia* luciferase in supernatant was measured 24 hours after electroporation (FIG. 19A right).

Figure 19B:
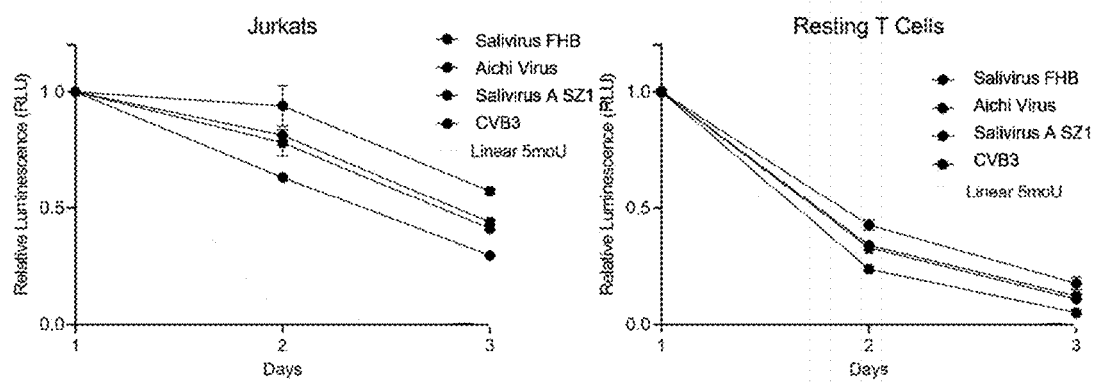

Luminescence from secreted *Gaussia* luciferase in supernatant was measured every 24 hours after electroporation, followed by complete media replacement. Functional stability data is shown in FIG. 19B. Circular RNA had more functional stability than linear RNA in each case, with a more pronounced difference in Jurkat cells.

EXAMPLE 19

Figure 20A:
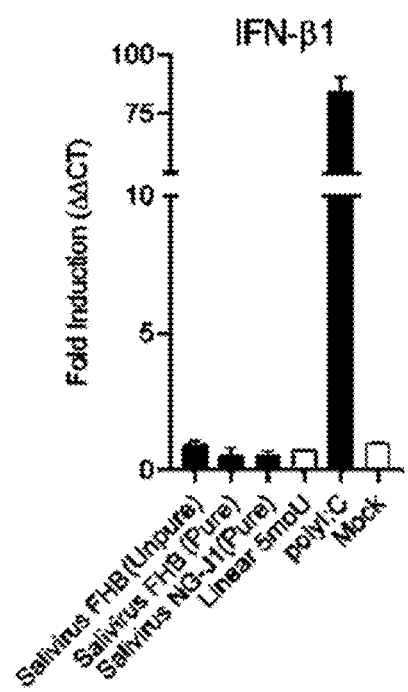
FIG. 20 depicts transcript induction of IFN-β1 (FIG. 20A), RIG-I (FIG. 20B), IL-2 (FIG. 20C), IL-6 (FIG. 20D), IFNγ (FIG. 20E), and TNFα (FIG. 20F) after electroporation of human CD3+ T cells with modified linear, unpurified circular, or purified circular RNA.
Figure 20B:
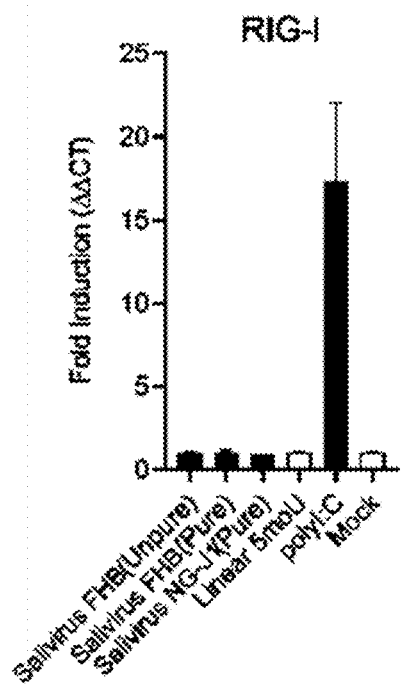
Figure 20C:
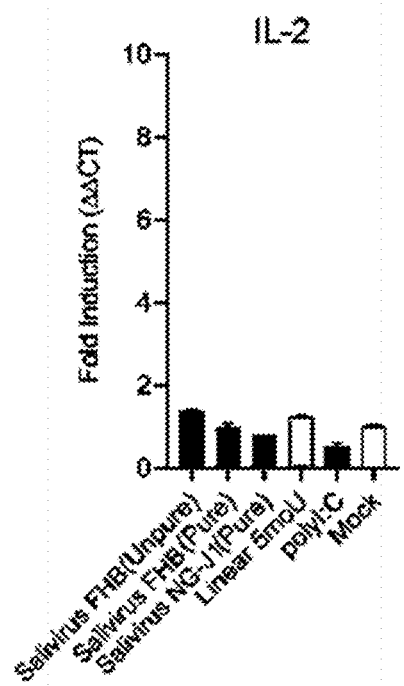
Figure 20D:
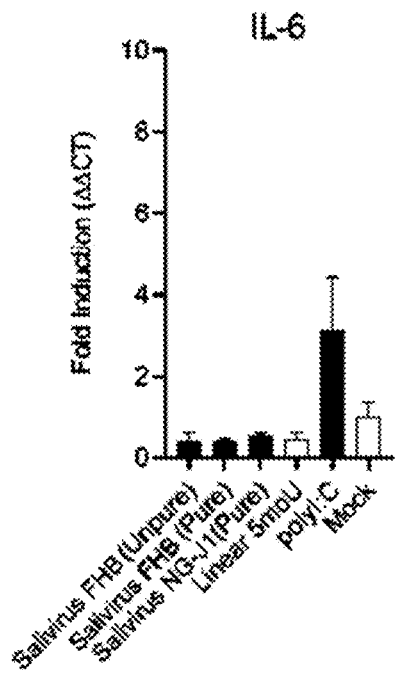
Figure 20E:
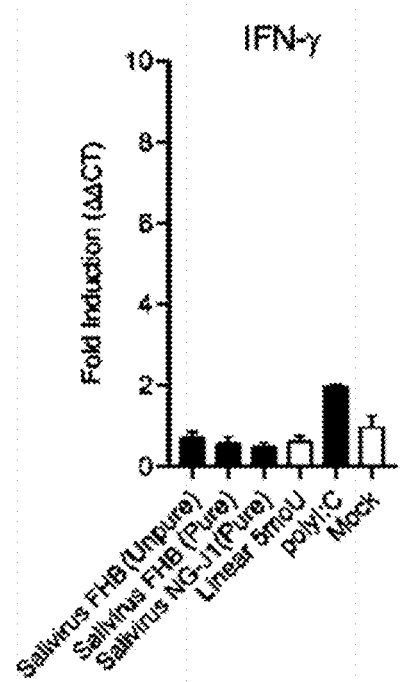
Figure 20F:
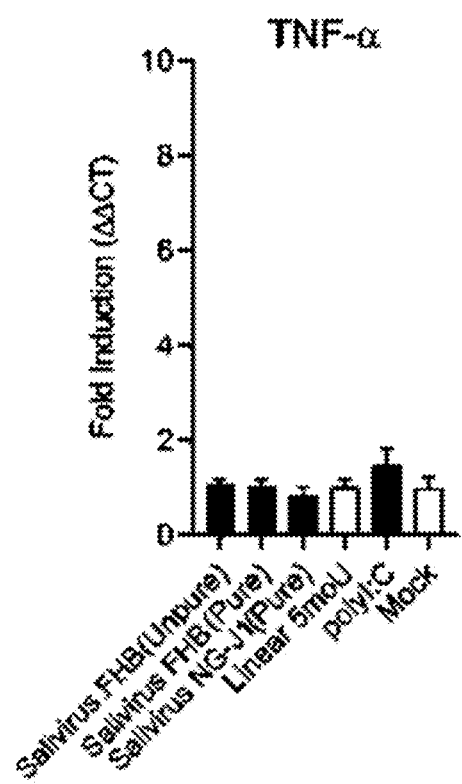

IFN-β1, RIG-I, IL-2, IL-6, IFNγ, and TNFα Transcript Induction of Cells Electroporated with Linear RNA or Varying Circular RNA Constructs Constructs including anabaena intron/exon regions, a *Gaussia* luciferase expression sequence, and a subset of previously tested IRES were circularized and reaction products were purified by size exclusion HPLC. 150,000 CD3+ human T cells were electroporated with 1 of circular RNA, 5moU-mRNA, or immunostimulatory positive control poly inosine:cytosine. IFN-β1 (FIG. 20A), RIG-I (FIG. 20B), IL-2 (FIG. 20C), IL-6 (FIG. 20D), IFN-γ (FIG. 20E), and TNF-α (FIG. 20F) transcript induction was measured 18 hours after electroporation.

EXAMPLE 20

Figure 21A:
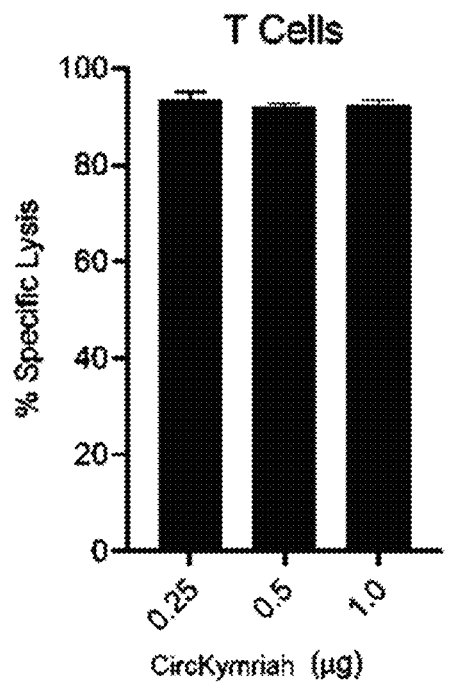
FIG. 21 depicts specific lysis of Raji target cells by human primary CD3+ T cells electroporated with circRNA encoding a CAR as determined by detection of firefly luminescence (FIG. 21A), and IFNγ transcript induction 24 hours after electroporation with different quantities of circular or linear RNA encoding a CAR sequence (FIG. 21B).
Figure 21B:
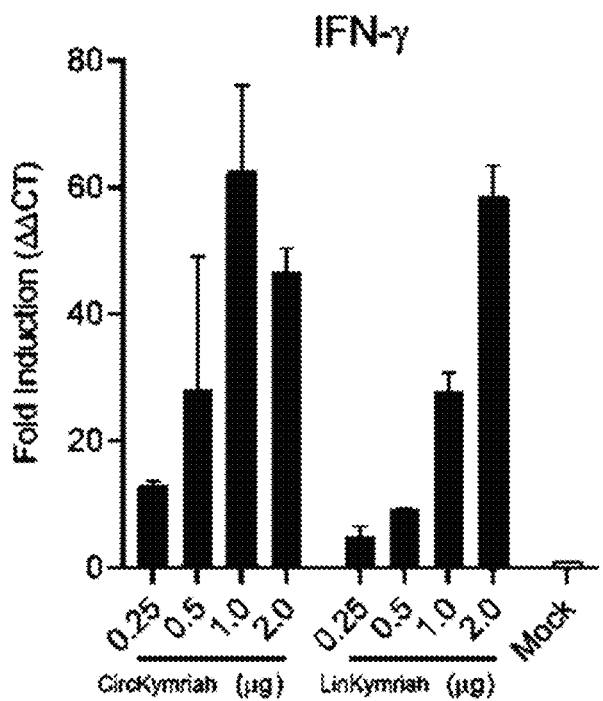

Specific Lysis of Target Cells and IFNγ Transcript Induction by CAR Expressing Cells Electroporated with Different Amounts of Circular or Linear RNA; Specific Lysis of Target and Non-Target Cells by CAR Expressing Cells at Different E:T Ratios Constructs including anabaena intron/exon regions, an anti-CD19 CAR expression sequence, and a CVB3 IRES were circularized and reaction products were purified by size exclusion HPLC. 150,000 human primary CD3+ T cells either mock electroporated or electroporated with different quantities of circRNA encoding an anti-CD19 CAR sequence were co-cultured for 12 hours with Raji cells stably expressing GFP and firefly luciferase at an E:T ratio of 2:1. % Specific lysis of Raji target cells was determined by detection of firefly luminescence (FIG. 21A). % Specific lysis was defined as 1-[CAR condition luminescence]/[mock condition luminescence]. IFNγ transcript induction was measured 24 hours after electroporation (FIG. 21B).

Figure 22A:
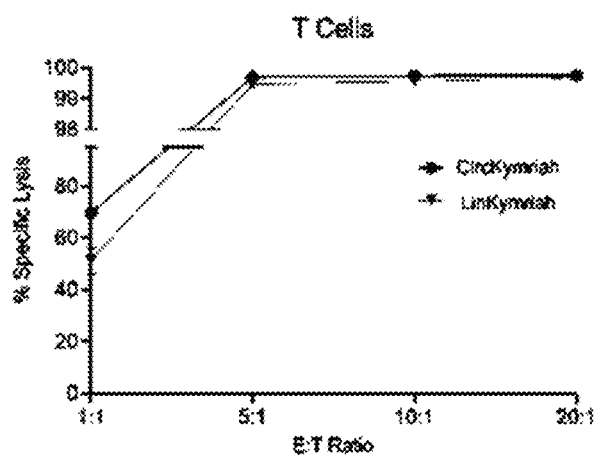
FIG. 22 depicts specific lysis of target or non-target cells by human primary CD3+ T cells electroporated with circular or linear RNA encoding a CAR at different E:T ratios (FIG. 22A and FIG. 22B) as determined by detection of firefly luminescence.

150,000 human primary CD3+ T cells were either mock electroporated or electroporated with 500 ng circRNA or m1ψ-mRNA encoding an anti-CD19 CAR sequence, then co-cultured for 24 hours with Raji cells stably expressing firefly luciferase at different E:T ratios. Specific lysis of Raji target cells was determined by detection of firefly luminescence (FIG. 22A). Specific lysis was defined as 1-[CAR condition luminescence]/[mock condition luminescence].

Figure 22B:
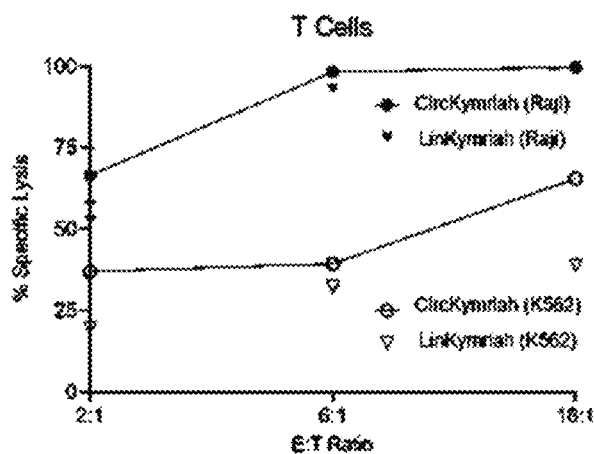

CAR expressing T cells were also co-cultured for 24 hours with Raji or K562 cells stably expressing firefly luciferase at different E:T ratios. Specific lysis of Raji target cells or K562 non-target cells was determined by detection of firefly luminescence (FIG. 22B). % Specific lysis is defined as 1-[CAR condition luminescence]/[mock condition luminescence].

EXAMPLE 21

Figure 23:
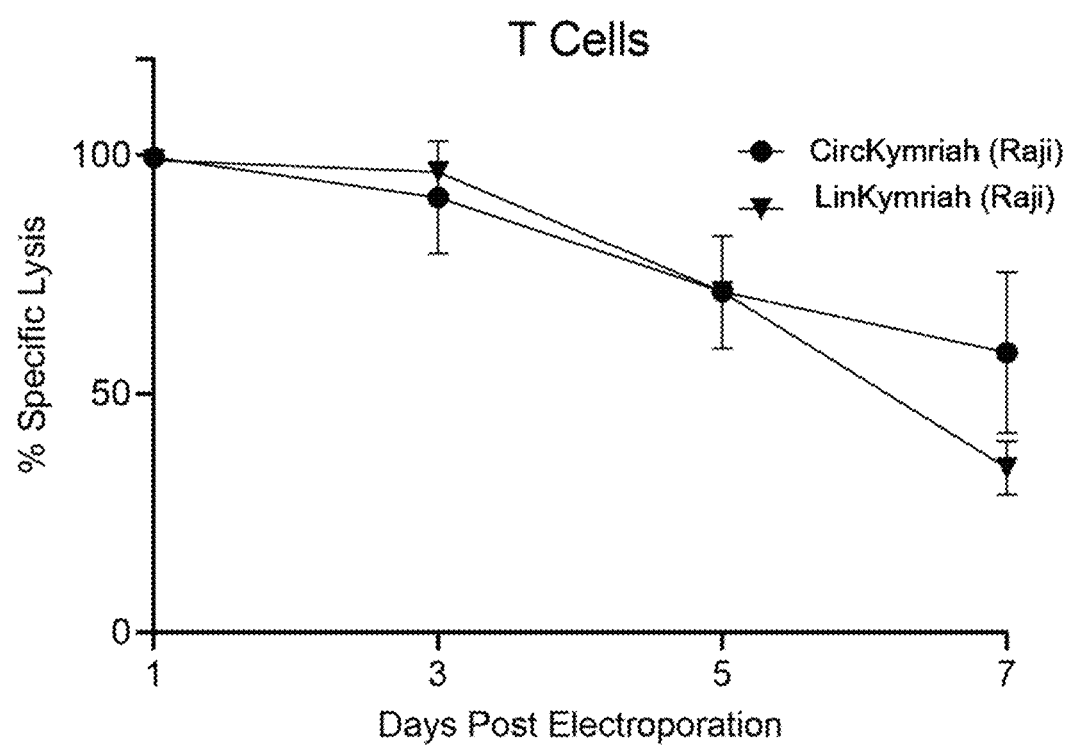
FIG. 23 depicts specific lysis of target cells by human CD3+ T cells electroporated with RNA encoding a CAR at 1, 3, 5, and 7 days post electroporation.

Specific Lysis of Target Cells by T Cells Electroporated with Circular RNA or Linear RNA Encoding a CAR Constructs including anabaena intron/exon regions, an anti-CD19 CAR expression sequence, and a CVB3 IRES were circularized and reaction products were purified by size exclusion HPLC. Human primary CD3+ T cells were electroporated with 500 ng of circular RNA or an equimolar quantity of m1ψ-mRNA, each encoding a CD19-targeted CAR. Raji cells were added to CAR-T cell cultures over 7 days at an E:T ratio of 10:1. % Specific lysis was measured for both constructs at 1, 3, 5, and 7 days (FIG. 23).

EXAMPLE 22

Figure 24:
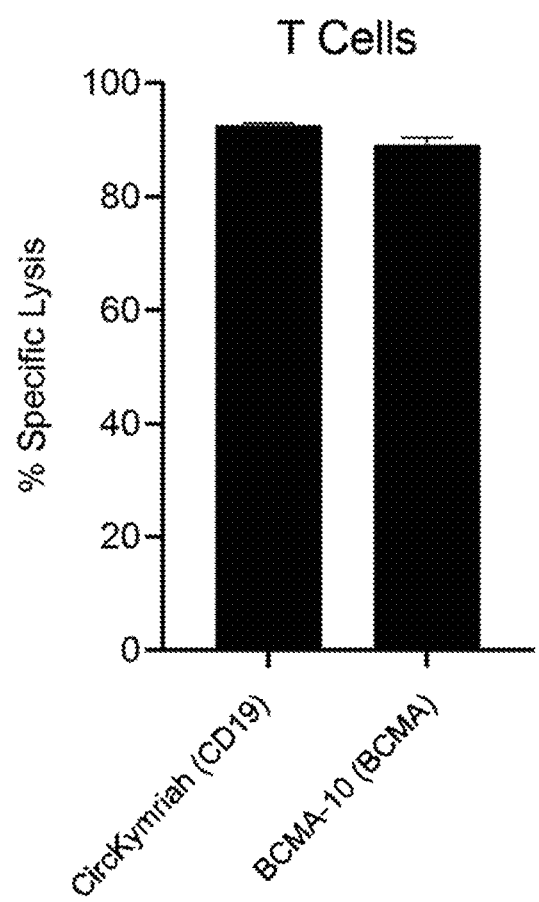
FIG. 24 depicts specific lysis of target cells by human CD3+ T cells electroporated with circular RNA encoding a CD19 or BCMA targeted CAR.

Specific Lysis of Raji Cells by T Cells Expressing an Anti-CD19 CAR or an Anti-BCMA CAR Constructs including anabaena intron/exon regions, anti-CD19 or anti-BCMA CAR expression sequence, and a CVB3 IRES were circularized and reaction products were purified by size exclusion HPLC. 150,000 primary human CD3+ T cells were electroporated with 500 ng of circRNA, then were co-cultured with Raji cells at an E:T ratio of 2:1. % Specific lysis was measured 12 hours after electroporation (FIG. 24).

EXAMPLE 23

Synthesis of Compounds

Synthesis of representative ionizable lipids of the invention are described in PCT applications PCT/US2016/052352, PCT/US2016/068300, PCT/US2010/061058, PCT/US2018/058555, PCT/US2018/053569, PCT/US2017/028981, PCT/US2019/025246, PCT/US2018/035419, PCT/US2019/015913, and US applications with publication numbers 20190314524, 20190321489, and 20190314284, the contents of each of which are incorporated herein by reference in their entireties.

EXAMPLE 24

Production of Nanoparticle Compositions

In order to investigate safe and efficacious nanoparticle compositions for use in the delivery of circular RNA to cells, a range of formulations are prepared and tested. Specifically, the particular elements and ratios thereof in the lipid component of nanoparticle compositions are optimized.

Nanoparticles can be made with mixing processes such as microfluidics and T-junction mixing of two fluid streams, one of which contains the circular RNA and the other has the lipid components.

Lipid compositions are prepared by combining an ionizable lipid, optionally a helper lipid (such as DOPE, DSPC, or oleic acid obtainable from Avanti Polar Lipids, Alabaster, AL), a PEG lipid (such as 1,2-dimyristoyl-sn-glycerol methoxypolyethylene glycol, also known as PEG-DMG, obtainable from Avanti Polar Lipids, Alabaster, AL), and a structural lipid such as cholesterol at concentrations of about, e.g., 50 mM in a solvent, e.g., ethanol. Solutions should be refrigerated for storage at, for example, −20° C. Lipids are combined to yield desired molar ratios (see, for example, Tables 12 and 13 below) and diluted with water and ethanol to a final lipid concentration of e.g., between about 5.5 mM and about 25 mM.

TABLE 12

| Formulation number | Description |
|---|---|
| 1 | Aliquots of 50 mg/mL ethanolic solutions of C12-200, DOPE, Chol and DMG-PEG2K (40:30:25:5) are mixed and diluted with ethanol to 3 mL final volume. Separately, an aqueous buffered solution (10 mM citrate/150 mM NaCl, pH 4.5) of circRNA is prepared from a 1 mg/mL stock. The lipid solution is injected rapidly into the aqueous circRNA solution and shaken to yield a final suspension in 20% ethanol. The resulting nanoparticle suspension is filtered, diafiltrated with 1 × PBS (pH 7.4), concentrated and stored at 2-8° C. |
| 2 | Aliquots of 50 mg/mL ethanolic solutions of DODAP, DOPE, cholesterol and DMG-PEG2K (18:56:20:6) are mixed and diluted with ethanol to 3 mL final volume. Separately, an aqueous buffered solution (10 mM citrate/150 mM NaCl, pH 4.5) of EPO circRNA is prepared from a 1 mg/mL stock. The lipid solution is injected rapidly into the aqueous circRNA solution and shaken to yield a final suspension in 20% ethanol. The resulting nanoparticle suspension is filtered, diafiltrated with 1 × PBS (pH 7.4), concentrated and stored at 2-8° C. Final concentration = 1.35 mg/mL EPO circRNA (encapsulated). Zave = 75.9 nm (Dv(50) = 57.3 nm; Dv(90 = 92.1 nm). |
| 3 | Aliquots of 50 mg/mL ethanolic solutions of HGT4003, DOPE, cholesterol and DMG-PEG2K (50:25:20:5) are mixed and diluted with ethanol to 3 mL final volume. Separately, an aqueous buffered solution (10 mM citrate/150 mM NaCl, pH 4.5) of circRNA is prepared from a 1 mg/mL stock. The lipid solution is injected rapidly into the aqueous circRNA solution and shaken to yield a final suspension in 20% ethanol. The resulting nanoparticle suspension is filtered, diafiltrated with 1 × PBS (pH 7.4), concentrated and stored at 2-8° C. |
| 4 | Aliquots of 50 mg/mL ethanolic solutions of ICE, DOPE and DMG-PEG2K (70:25:5) are mixed and diluted with ethanol to 3 mL final volume. Separately, an aqueous buffered solution (10 mM citrate/150 mM NaCl, pH 4.5) of circRNA is prepared from a 1 mg/mL stock. The lipid solution is injected rapidly into the aqueous circRNA solution and shaken to yield a |

TABLE 12-continued

| Formulation number | Description |
|---|---|
|  | final suspension in 20% ethanol. The resulting nanoparticle suspension is filtered, diafiltrated with 1 × PBS (pH 7.4), concentrated and stored at 2-8° C. |
| 5 | Aliquots of 50 mg/mL ethanolic solutions of HGT5000, DOPE, cholesterol and DMG-PEG2K (40:20:35:5) are mixed and diluted with ethanol to 3 mL final volume. Separately, an aqueous buffered solution (10 mM citrate/150 mM NaCl, pH 4.5) of EPO circRNA is prepared from a 1 mg/mL stock. The lipid solution is injected rapidly into the aqueous circRNA solution and shaken to yield a final suspension in 20% ethanol. The resulting nanoparticle suspension is filtered, diafiltrated with 1 × PBS (pH 7.4), concentrated and stored at 2-8° C. Final concentration = 1.82 mg/mL EPO mRNA (encapsulated). Zave = 105.6 nm (Dv(50) = 53.7 nm; Dv(90) = 157 nm). |
| 6 | Aliquots of 50 mg/mL ethanolic solutions of HGT5001, DOPE, cholesterol and DMG-PEG2K (40:20:35:5) are mixed and diluted with ethanol to 3 mL final volume. Separately, an aqueous buffered solution (10 mM citrate/150 mM NaCl, pH 4.5) of EPO circRNA is prepared from a 1 mg/mL stock. The lipid solution is injected rapidly into the aqueous circRNA solution and shaken to yield a final suspension in 20% ethanol. The resulting nanoparticle suspension is filtered, diafiltrated with 1 × PBS (pH 7.4), concentrated and stored at 2-8° C. |

In some embodiments, transfer vehicle has a formulation as described in Table 12.

TABLE 13

| Composition (mol %) | Components |
|---|---|
| 40:20:38.5:1.5 | Compound:Phospholipid:Phytosterol*:PEG-DMG |
| 40:20:38.5:1.5 | Compound:Phospholipid:Phytosterol*:PEG-DMG |
| 50:10:38.5:1.5 | Compound:Phospholipid:Phytosterol*:PEG-DMG |
| 55:5:38.5:1.5 | Compound:Phospholipid:Phytosterol*:PEG-DMG |

In some embodiments, transfer vehicle has a formulation as described in Table 13, where Compound refers to a circular RNA as described herein.

For nanoparticle compositions including circRNA, solutions of the circRNA at concentrations of 0.1 mg/ml in deionized water are diluted in a buffer, e.g., 50 mM sodium citrate buffer at a pH between 3 and 4 to form a stock solution.

Nanoparticle compositions including a circular RNA and a lipid component are prepared by combining the lipid solution with a solution including the circular RNA at lipid component to circRNA wt:wt ratios between about 5:1 and about 50:1. The lipid solution is rapidly injected using, e.g., a NanoAssemblr microfluidic based system at flow rates between about 10 ml/min and about 18 ml/min into the circRNA solution, to produce a suspension with a water to ethanol ratio between about 1:1 and about 4:1.

Nanoparticle compositions can be processed by dialysis to remove ethanol and achieve buffer exchange. Formulations are dialyzed twice against phosphate buffered saline (PBS), pH 7.4, at volumes 200 times that of the primary product using Slide-A-Lyzer cassettes (Thermo Fisher Scientific Inc., Rockford, IL) with a molecular weight cutoff of 10 kDa. The first dialysis is carried out at room temperature for 3 hours. The formulations are then dialyzed overnight at 4° C. The resulting nanoparticle suspension is filtered through 0.2 μm sterile filters (Sarstedt, Nümbrecht, Germany) into glass vials and sealed with crimp closures. Nanoparticle composition solutions of 0.01 mg/ml to 0.10 mg/ml are generally obtained.

The method described above induces nano-precipitation and particle formation.

Alternative processes including, but not limited to, T-junction and direct injection, may be used to achieve the same nano-precipitation. B. Characterization of nanoparticle compositions A Zetasizer Nano ZS (Malvern Instruments Ltd, Malvern, Worcestershire, UK) can be used to determine the particle size, the polydispersity index (PDI) and the zeta potential of the nanoparticle compositions in 1×PBS in determining particle size and 15 mM PBS in determining zeta potential.

Ultraviolet-visible spectroscopy can be used to determine the concentration of circRNA in nanoparticle compositions. 100 μL of the diluted formulation in 1×PBS is added to 900 μL of a 4:1 (v/v) mixture of methanol and chloroform. After mixing, the absorbance spectrum of the solution is recorded, for example, between 230 nm and 330 nm on a DU 800 spectrophotometer (Beckman Coulter, Beckman Coulter, Inc., Brea, CA). The concentration of circRNA in the nanoparticle composition can be calculated based on the extinction coefficient of the circRNA used in the composition and on the difference between the absorbance at a wavelength of, for example, 260 nm and the baseline value at a wavelength of, for example, 330 nm.

A QUANT-IT™ RIBOGREEN® RNA assay (Invitrogen Corporation Carlsbad, CA) can be used to evaluate the encapsulation of circRNA by the nanoparticle composition. The samples are diluted to a concentration of approximately 5 μg/mL in a TE buffer solution (10 mM Tris-HCl, 1 mM EDTA, pH 7.5). 50 μL of the diluted samples are transferred to a polystyrene 96 well plate and either 50 μL of TE buffer or 50 μL of a 2% Triton X-100 solution is added to the wells. The plate is incubated at a temperature of 37° C. for 15 minutes. The RIBOGREEN® reagent is diluted 1:100 in TE buffer, and 100 μL of this solution is added to each well. The fluorescence intensity can be measured using a fluorescence plate reader (Wallac Victor 1420 Multilabel Counter; Perkin Elmer, Waltham, MA) at an excitation wavelength of, for example, about 480 nm and an emission wavelength of, for example, about 520 nm. The fluorescence values of the reagent blank are subtracted from that of each of the samples and the percentage of free circRNA is determined by dividing the fluorescence intensity of the intact sample (without addition of Triton X-100) by the fluorescence value of the disrupted sample (caused by the addition of Triton X-100). C.

In Vivo Formulation Studies:

In order to monitor how effectively various nanoparticle compositions deliver circRNA to targeted cells, different nanoparticle compositions including circRNA are prepared and administered to rodent populations. Mice are intravenously, intramuscularly, intraarterially, or intratumorally administered a single dose including a nanoparticle composition with a lipid nanoparticle formulation. In some instances, mice may be made to inhale doses. Dose sizes may range from 0.001 mg/kg to 10 mg/kg, where 10 mg/kg describes a dose including 10 mg of a circRNA in a nanoparticle composition for each 1 kg of body mass of the mouse. A control composition including PBS may also be employed.

Upon administration of nanoparticle compositions to mice, dose delivery profiles, dose responses, and toxicity of particular formulations and doses thereof can be measured by enzyme-linked immunosorbent assays (ELISA), bioluminescent imaging, or other methods. Time courses of protein expression can also be evaluated. Samples collected from the rodents for evaluation may include blood and tissue (for example, muscle tissue from the site of an intramuscular injection and internal tissue); sample collection may involve sacrifice of the animals.

Higher levels of protein expression induced by administration of a composition including a circRNA will be indicative of higher circRNA translation and/or nanoparticle composition circRNA delivery efficiencies. As the non-RNA components are not thought to affect translational machineries themselves, a higher level of protein expression is likely indicative of a higher efficiency of delivery of the circRNA by a given nanoparticle composition relative to other nanoparticle compositions or the absence thereof.

EXAMPLE 25

Characterization of Nanoparticle Compositions

A Zetasizer Nano ZS (Malvern Instruments Ltd, Malvern, Worcestershire, UK) can be used to determine the particle size, the polydispersity index (PDI) and the zeta potential of the transfer vehicle compositions in 1×PBS in determining particle size and 15 mM PBS in determining zeta potential.

Ultraviolet-visible spectroscopy can be used to determine the concentration of a therapeutic and/or prophylactic (e.g., RNA) in transfer vehicle compositions. 100 µL of the diluted formulation in 1×PBS is added to 900 µL of a 4:1 (v/v) mixture of methanol and chloroform. After mixing, the absorbance spectrum of the solution is recorded, for example, between 230 nm and 330 nm on a DU 800 spectrophotometer (Beckman Coulter, Beckman Coulter, Inc., Brea, CA). The concentration of therapeutic and/or prophylactic in the transfer vehicle composition can be calculated based on the extinction coefficient of the therapeutic and/or prophylactic used in the composition and on the difference between the absorbance at a wavelength of, for example, 260 nm and the baseline value at a wavelength of, for example, 330 nm.

For transfer vehicle compositions including RNA, a QUANT-IT™ RIBOGREEN® RNA assay (Invitrogen Corporation Carlsbad, CA) can be used to evaluate the encapsulation of RNA by the transfer vehicle composition. The samples are diluted to a concentration of approximately 5 µg/mL in a TE buffer solution (10 mM Tris-HCl, 1 mM EDTA, pH 7.5). 50 µL of the diluted samples are transferred to a polystyrene 96 well plate and either 50 µL of TE buffer or 50 µL of a 2% Triton X-100 solution is added to the wells. The plate is incubated at a temperature of 37° C. for 15 minutes. The RIBOGREEN® reagent is diluted 1:100 in TE buffer, and 100 µL of this solution is added to each well. The fluorescence intensity can be measured using a fluorescence plate reader (Wallac Victor 1420 Multilablel Counter; Perkin Elmer, Waltham, MA) at an excitation wavelength of, for example, about 480 nm and an emission wavelength of, for example, about 520 nm. The fluorescence values of the reagent blank are subtracted from that of each of the samples and the percentage of free RNA is determined by dividing the fluorescence intensity of the intact sample (without addition of Triton X-100) by the fluorescence value of the disrupted sample (caused by the addition of Triton X-100).

EXAMPLE 26

T Cell Targeting

To target transfer vehicles to T-cells, T cell antigen binders, e.g., anti-CD8 antibodies, are coupled to the surface of the transfer vehicle. Anti-T cell antigen antibodies are mildly reduced with an excess of DTT in the presence of EDTA in PBS to expose free hinge region thiols. To remove DTT, antibodies are passed through a desalting column. The heterobifunctional cross-linker SM(PEG)24 is used to anchor antibodies to the surface of circRNA-loaded transfer vehicles (Amine groups are present in the head groups of PEG lipids, free thiol groups on antibodies were created by DTT, SM(PEG)24 cross-links between amines and thiol groups). Transfer vehicles are first incubated with an excess of SM(PEG)24 and centrifuged to remove unreacted cross-linker. Activated transfer vehicles are then incubated with an excess of reduced anti-T cell antigen antibody. Unbound antibody is removed using a centrifugal filtration device.

EXAMPLE 27

RNA Containing Transfer Vehicle Using RV88

In this example RNA containing transfer vehicles are synthesized using the 2-D vortex microfluidic chip with the cationic lipid RV88 for delivery of circRNA.

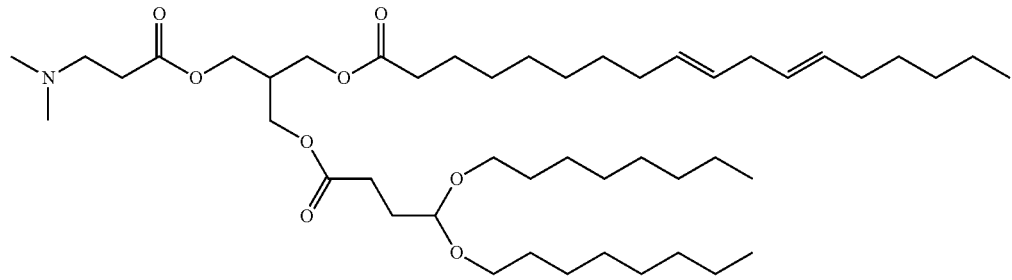

RV88

TABLE 14

| Materials and Instrument | Vendor | Cat # |
|---|---|---|
| 1M Tris-HCl, pH 8.0, Sterile | Teknova | T1080 |
| 5M Sodium Chloride solution | Teknova | S0250 |
| QB Citrate buffer, pH 6.0 (100 mM) | Teknova | Q2446 |
| Nuclease-free water | Ambion | AM9937 |
| Triton X-100 | Sigma-Aldrich | T8787- |
| RV88 | GVK bio | 100 ML |
| DSPC | Lipoid | 556500 |
| Cholesterol | Sigma | C3045-5G |
| PEG2K | Avanti Polar Lipids | 880150 |
| Ethanol | Acros Organic | 615090010 |
| 5 mL Borosillicate glass vials | Thermo Scientific | ST5-20 |
| PD MiniTrap G-25 Desalting Columns | GE Healthcare | VWR Cat. #95055-984 |
| Quant-iT RiboGreen RNA Assay kit | Molecular Probes/Life Technologies | R11490 |
| Black 96-well microplates | Greiner | 655900 |

RV88, DSPC, and cholesterol all being prepared in ethanol at a concentration of 10 mg/ml in borosilica vials. The lipid 14:0-PEG2K PE is prepared at a concentration of 4 mg/ml also in a borosilica glass vial. Dissolution of lipids at stock concentrations is attained by sonication of the lipids in ethanol for 2 min. The solutions are then heated on an orbital tilting shaker set at 170 rpm at 37° C. for 10 min. Vials are then equilibrated at 26° C. for a minimum of 45 min. The lipids are then mixed by adding volumes of stock lipid as shown in Table 15. The solution is then adjusted with ethanol such that the final lipid concentration was 7.92 mg/ml

TABLE 15

| Composition | MW | % | nmoles | mg | Stock (mg/ml) | ul | Ethanol (ul) |
|---|---|---|---|---|---|---|---|
| RV88 | 794.2 | 40% | 7200 | 5.72 | 10 | 571.8 | 155.3 |
| DSPC | 790.1 | 10% | 1800 | 1.42 | 10 | 142.2 | |
| Cholesterol | 386.67 | 48% | 8640 | 3.34 | 10 | 334.1 | |
| PEG2K | 2693.3 | 2% | 360 | 0.97 | 4 | 242.4 | |

RNA is prepared as a stock solution with 75 mM Citrate buffer at pH 6.0 and a concentration of RNA at 1.250 mg/ml. The concentration of the RNA is then adjusted to 0.1037 mg/ml with 75 mM citrate buffer at pH 6.0, equilibrated to 26° C. The solution is then incubated at 26° C. for a minimum of 25 min.

The microfluidic chamber is cleaned with ethanol and neMYSIS syringe pumps are prepared by loading a syringe with the RNA solution and another syringe with the ethanolic lipid. Both syringes are loaded and under the control of neMESYS software. The solutions are then applied to the mixing chip at an aqueous to organic phase ratio of 2 and a total flow rate of 22 ml/min (14.67 ml/min for RNA and 7.33 ml/min for the lipid solution. Both pumps are started synchronously. The mixer solution that flowed from the microfluidic chip is collected in 4×1 ml fractions with the first fraction being discarded as waste. The remaining solution containing the RNA-liposomes is exchanged by using G-25 mini desalting columns to 10 mM Tris-HCl, 1 mM EDTA, at pH 7.5. Following buffer exchange, the materials are characterized for size, and RNA entrapment through DLS analysis and Ribogreen assays, respectively.

EXAMPLE 28

RNA Containing Transfer Vehicle Using RV94

In this example, RNA containing liposome are synthesized using the 2-D vortex microfluidic chip with the cationic lipid RV94 for delivery of circRNA.

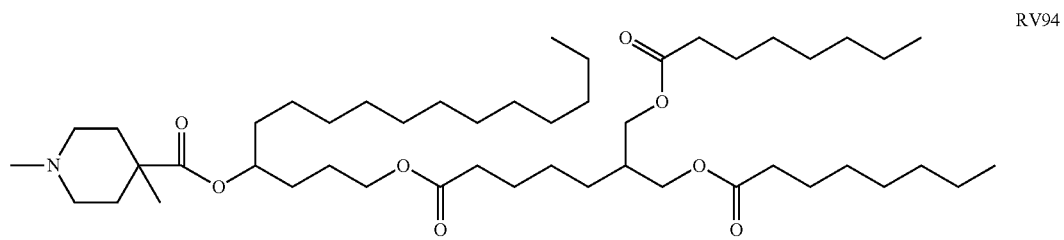 [SMILES: CCCCCCCCCCCCC(CCCOC(=O)CCCCC(COC(=O)CCCCCCC)COC(=O)CCCCCCC)OC(=O)C1(C)CCN(C)CC1]

RV94

TABLE 16

| Materials and Instrument | Vendor | Cat # |
|---|---|---|
| 1M Tris-HCl, pH 8.0, Sterile | Teknova | T1080 |
| 5M Sodium Chloride solution | Teknova | S0250 |
| QB Citrate buffer, pH 6.0 (100 mM) | Teknova | Q2446 |
| Nuclease-free water | Ambion | AM9937 |
| Triton X-100 | Sigma-Aldrich | T8787- |
| RV94 | GVKbio | 100 ML |
| DSPC | Lipoid | 556500 |
| Cholesterol | Sigma | C3045-5G |
| PEG2K | Avanti Polar Lipids | 880150 |
| Ethanol | Acros Organic | 615090010 |
| 5 mL Borosillicate glass vials | Thermo Scientific | ST5-20 |
| PD MiniTrap G-25 Desalting Columns | GE Healthcare | VWR Cat. #95055-984 |
| Quant-iT RiboGreen RNA Assay kit | Molecular Probes/Life Technologies | R11490 |
| Black 96-well microplates | Greiner | 655900 |

The lipids were prepared as in Example 27 using the material amounts named in Table 17 to a final lipid concentration of 7.92 mg/ml.

TABLE 17

| Composition | MW | % | nmoles | mg | Stock (mg/ml) | ul | Ethanol (ul) |
|---|---|---|---|---|---|---|---|
| RV94 | 808.22 | 40% | 2880 | 2.33 | 10 | 232.8 | 155.3 |
| DSPC | 790.15 | 10% | 720 | 0.57 | 10 | 56.9 | |
| Cholesterol | 386.67 | 48% | 3456 | 1.34 | 10 | 133.6 | |
| PEG2K | 2693.3 | 2% | 144 | 0.39 | 4 | 97.0 | |

The aqueous solution of circRNA is prepared as a stock solution with 75 mM Citrate buffer at pH 6.0 the circRNA at 1.250 mg/ml. The concentration of the RNA is then adjusted to 0.1037 mg/ml with 75 mM citrate buffer at pH 6.0, equilibrated to 26° C. The solution is then incubated at 26° C. for a minimum of 25 min.

The microfluidic chamber is cleaned with ethanol and neMYSIS syringe pumps are prepared by loading a syringe with the RNA solution and another syringe with the ethanolic lipid. Both syringes are loaded and under the control of neMESYS software. The solutions are then applied to the mixing chip at an aqueous to organic phase ratio of 2 and a total flow rate of 22 ml/min (14.67 ml/min for RNA and 7.33 ml/min for the lipid solution. Both pumps are started synchronously. The mixer solution that flowed from the microfluidic chip is collected in 4×1 ml fractions with the first fraction being discarded as waste. The remaining solution containing the circRNA-transfer vehicles is exchanged by using G-25 mini desalting columns to 10 mM Tris-HCl, 1 mM EDTA, at pH 7.5, as described above. Following buffer exchange, the materials are characterized for size, and RNA entrapment through DLS analysis and Ribogreen assays, respectively. The biophysical analysis of the liposomes is shown in Table 18.

TABLE 18

| Sample Name | N:P Ratio | TFR ml/min | Ratio (aqueous/org phase) | RNA encapsulation amount μg/ml | RNA encapsulation yield % | size d · nm | PDI |
|---|---|---|---|---|---|---|---|
| SAM-RV94 | 8 | 22 | 2 | 31.46 | 86.9 | 113.1 | 0.12 |

EXAMPLE 29

General Protocol for in Line Mixing

Individual and separate stock solutions are prepared—one containing lipid and the other circRNA. Lipid stock containing a desired lipid or lipid mixture, DSPC, cholesterol and PEG lipid is prepared by solubilized in 90% ethanol. The remaining 10% is low pH citrate buffer. The concentration of the lipid stock is 4 mg/mL. The pH of this citrate buffer can range between pH 3 and pH 5, depending on the type of lipid employed. The circRNA is also solubilized in citrate buffer at a concentration of 4 mg/mL. 5 mL of each stock solution is prepared.

Stock solutions are completely clear and lipids are ensured to be completely solubilized before combining with circRNA. Stock solutions may be heated to completely solubilize the lipids. The circRNAs used in the process may be unmodified or modified oligonucleotides and may be conjugated with lipophilic moieties such as cholesterol.

The individual stocks are combined by pumping each solution to a T-junction. A dual-head Watson-Marlow pump was used to simultaneously control the start and stop of the two streams. A 1.6 mm polypropylene tubing is further downsized to 0.8 mm tubing in order to increase the linear flow rate. The polypropylene line (ID=0.8 mm) are attached to either side of a T-junction. The polypropylene T has a linear edge of 1.6 mm for a resultant volume of 4.1 mm$^3$. Each of the large ends (1.6 mm) of polypropylene line is placed into test tubes containing either solubilized lipid stock or solubilized circRNA. After the T-junction, a single tubing is placed where the combined stream exited. The tubing is then extended into a container with 2× volume of PBS, which is rapidly stirred. The flow rate for the pump is at a setting of 300 rpm or 110 mL/min. Ethanol is removed and exchanged for PBS by dialysis. The lipid formulations are then concentrated using centrifugation or diafiltration to an appropriate working concentration.

C57BL/6 mice (Charles River Labs, MA) receive either saline or formulated circRNA via tail vein injection. At various time points after administration, serum samples are collected by retroorbital bleed. Serum levels of Factor VII protein are determined in samples using a chromogenic assay (Biophen FVTI, Aniara Corporation, OH). To determine liver RNA levels of Factor VII, animals are sacrificed and livers are harvested and snap frozen in liquid nitrogen. Tissue lysates are prepared from the frozen tissues and liver RNA levels of Factor VII are quantified using a branched DNA assay (QuantiGene Assay, Panomics, CA).

FVII activity is evaluated in FVTI siRNA-treated animals at 48 hours after intravenous (bolus) injection in C57BL/6 mice. FVII is measured using a commercially available kit for determining protein levels in serum or tissue, following the manufacturer's instructions at a microplate scale. FVII reduction is determined against untreated control mice, and the results are expressed as % Residual FVII. Two dose levels (0.05 and 0.005 mg/kg FVII siRNA) are used in the screen of each novel liposome composition.

EXAMPLE 30 circRNA Formulation Using Preformed Vesicles

Cationic lipid containing transfer vehicles are made using the preformed vesicle method. Cationic lipid, DSPC, cholesterol and PEG-lipid are solubilized in ethanol at a molar ratio of 40/10/40/10, respectively. The lipid mixture is added to an aqueous buffer (50 mM citrate, pH 4) with mixing to a final ethanol and lipid concentration of 30% (vol/vol) and 6.1 mg/mL respectively and allowed to equilibrate at room temperature for 2 min before extrusion. The hydrated lipids are extruded through two stacked 80 nm pore-sized filters (Nuclepore) at 22° C. using a Lipex Extruder (Northern Lipids, Vancouver, BC) until a vesicle diameter of 70-90 nm, as determined by Nicomp analysis, is obtained. For cationic lipid mixtures which do not form small vesicles, hydrating the lipid mixture with a lower pH buffer (50 mM citrate, pH 3) to protonate the phosphate group on the DSPC headgroup helps form stable 70-90 nm vesicles.

The FVII circRNA (solubilised in a 50 mM citrate, pH 4 aqueous solution containing 30% ethanol) is added to the vesicles, pre-equilibrated to 35° C., at a rate of ~5 mL/min with mixing. After a final target circRNA/lipid ratio of 0.06 (wt wt) is achieved, the mixture is incubated for a further 30 min at 35° C. to allow vesicle re-organization and encapsulation of the FVII RNA. The ethanol is then removed and the external buffer replaced with PBS (155 mM NaCl, 3 mM Na2HPO4, 1mM KH2PO4, pH 7.5) by either dialysis or tangential flow diafiltration. The final encapsulated circRNA-to-lipid ratio is determined after removal of unencapsulated RNA using size-exclusion spin columns or ion exchange spin columns.

EXAMPLE 31

Homology Regions Improves Precursor RNA Circularization

The engineered circular RNA was designed to optimize stability and is comparably more efficient in expressing proteins than linear mRNA (R. Wesselhoeft et al., 2018). This circular RNA was derived from a vector containing in the following order: a 5' homology region, a 3' group I intron fragment, a first spacer, an Internal Ribosome Entry Site (IRES), a protein coding region, a second spacer, a 5' group I intron fragment, and a 3' homology region.

Figure 26:
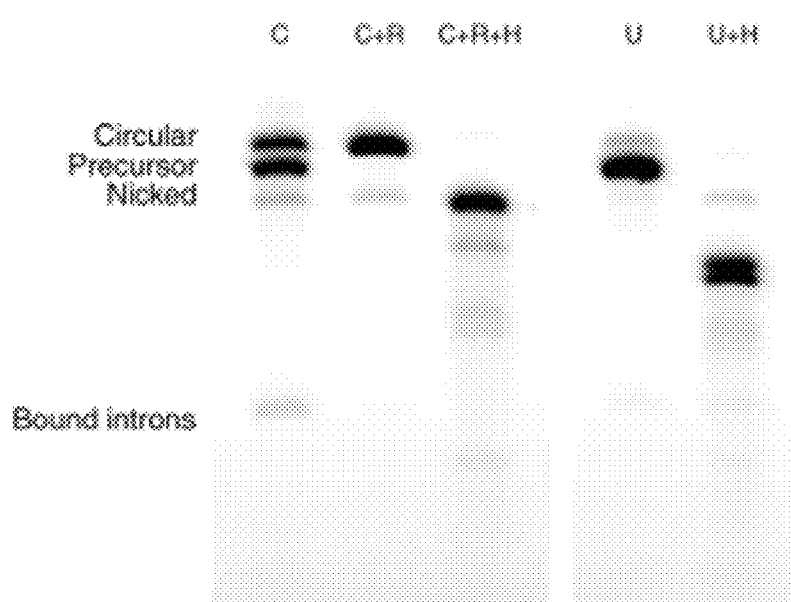
FIG. 26 depicts agarose gel confirmation of precursor RNA circularization. C: precursor RNA (with strong homology arms) subjected to circularization conditions. C+R: Lane C, digested with RNase R. C+R+H: Lane C+R, digested with oligonucleotide-guided RNase H. U: precursor RNA not subjected to circularization conditions. U+H: Lane U, digested with oligonucleotide-guided RNase H.
Figure 27:
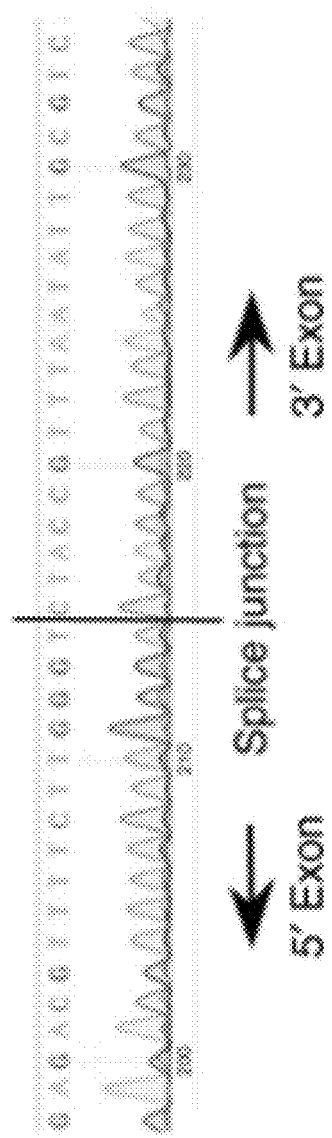
FIG. 27 depicts Sanger sequencing output of RT-PCR across the splice junction of the sample depicted in lane C+R from FIG. 26.

Both homology regions were created using the permuted intron exon method, which utilizes self-splicing group I catalytic introns, such as those from the T4 phage Td gene, to promote RNA circularization with only the addition of a guanosine nucleotide or nucleoside and Mg2+ (Petkovic S. and Muller S. (2015) RNA circularization strategies in vivo and in vitro. Nucleic Acids Research. 43, 2454-2465, which is incorporated by reference in its entirety). The resulting permuted intron-exon (PIE) regions allow for 5' and 3' ends of the RNA to covalently link and form a circular RNA. These PIE regions were engineered to have 5' and 3' ends that perfectly complement each other to form "homology regions." Nine nucleotide-long weak homology regions and 19 nucleotide-long strong homology regions were designed, and RNAFold was used to predict secondary structure (FIG. 25). Addition of these homology regions increased splicing efficiency of a construct containing a EMCV IRES and encoding Gaussia luciferase from 0% to 16% for weak homology regions and to 48% for strong homology regions. Effective circularization was confirmed by the presence of splicing products on an agarose gel (FIG. 26). In comparison, when the linear mRNA was treated with the same RNase H, the result comprises two products that did not effectively separate out circularized RNA (FIG. 27).

Figure 28:
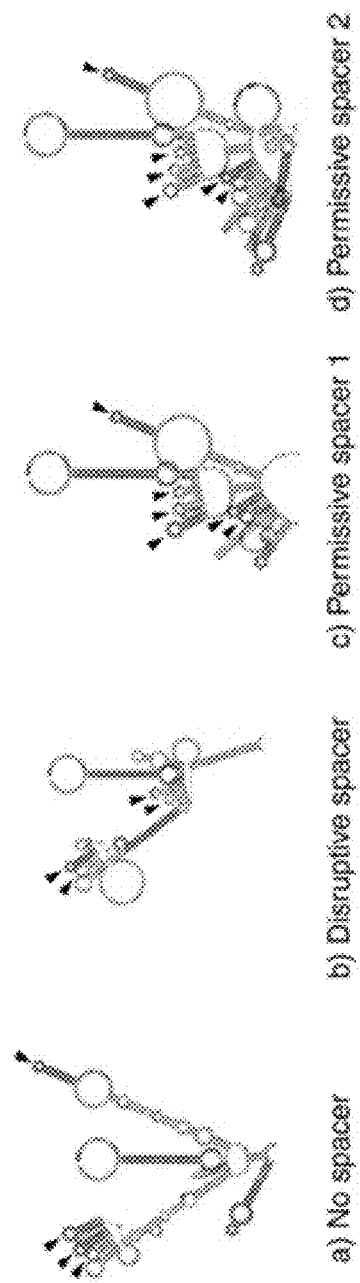
FIG. 28 depicts RNAFold predictions of precursor RNA secondary structure in the context of designed spacers. Secondary structures potentially important for ribozyme function are identified by black arrows.
Figure 29:
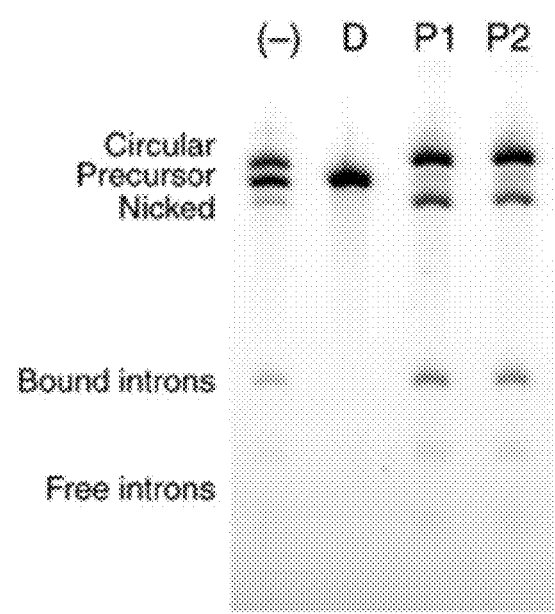
FIG. 29 depicts an agarose gel demonstrating the effect of spacers on splicing. (−): no spacer. D: disruptive spacer. P1: permissive spacer 1. P2: permissive spacer 2. c RNAFold predictions of precursor RNA secondary structure for internal homology region design. Lack of significant internal homology (Anabaena 1.0) and introduced internal homology (Anabaena 2.0) indicated by black arrows. Splicing bubble indicated as the region between homology arms and internal homology regions that contains the splicing ribozyme.
Figure 30:
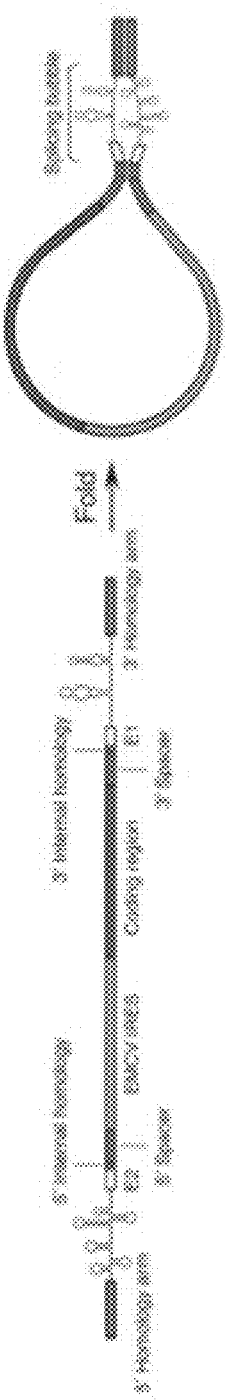
FIG. 30 is a schematic diagram showing elements of the engineered self-splicing precursor RNA design.

The two spacer regions were included to ensure that the structure will fold independently to form the circular RNA (FIG. 28). These spacer sequences were established to: (1) be unstructured and non-homologous to the proximal intron and IRES sequences; (2) separate intron and IRES secondary structures to allow each to independently fold from one another; and (3) contain a region of spacer-spacer complementary allowing formation of a sheltered splicing bubble (FIG. 30). The addition of spacer sequences that permit splicing increases splicing efficiency from 46 to 87%, while the disruptive spacer sequence completely abrogates splicing (FIG. 29). When the precursor RNA was tested with the homology regions, spacers, EMCV IRES, and coding regions, the sequences achieved circularization.

EXAMPLE 32

Engineered Circular RNA Provides More Stability than Linear RNA

Figure 31:
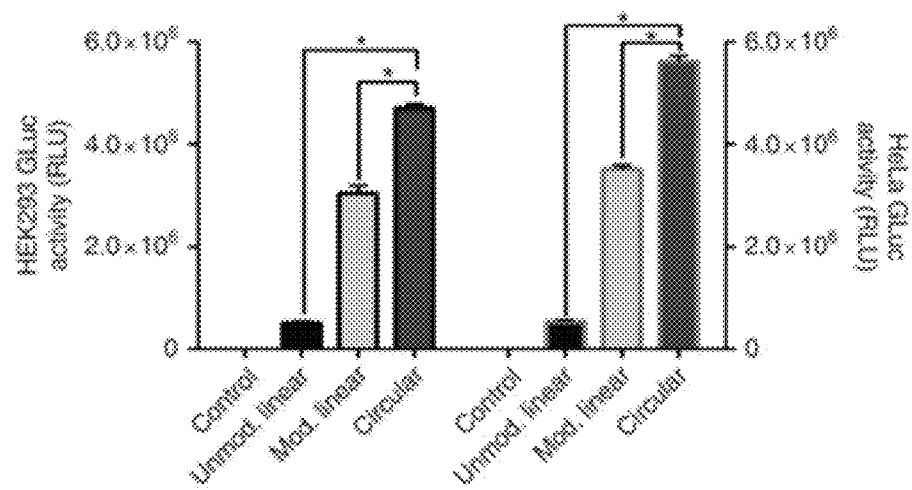
FIG. 31 shows luminescence in the supernatant of HEK293 (left, black outline) and HeLa (right, gray outline) cells 24 h after transfection with CVB3-GLuc-pAC circRNA or modified or unmodified linear GLuc mRNA (n=4 HEK293, n=3 HeLa).
Figure 32:
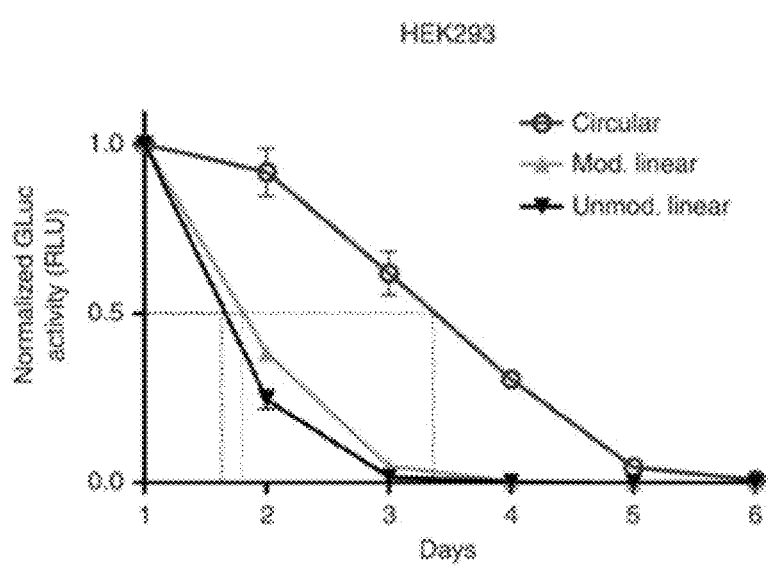
FIG. 32 shows luminescence in the supernatant of HEK293 cells starting 24 h after transfection with CVB3-GLuc-pAC circRNA or modified or unmodified linear GLuc mRNA and continuing for 6 days (n=4).

Stability of the circular RNA was determined using HPLC-purified engineered circular RNA (A. Wesselhoef, 2018). The circular RNA was a Gaussia luciferase-coding circular RNA (CVB3-GLuc-pAC). A canonical unmodified 5' methyl guanosine-capped and 3' polyA-tailed linear GLuc mRNA as well as a nucleoside-modified (pseudouridine, 5-methylcytosine) linear GLuc mRNA was as a linear comparison to the circular construct. Luminescence was performed in a supernatant of HEK293 and HeLa cells for 24 hours of transfection and then continuously monitored each day for 6 days for GLuc activity. Exogenous circular RNA produced 811.2% more protein than linear unmodified mRNA after 24 hours of transfection (FIG. 31). Within 24 hours, the circular RNA also produced more 54.5% more protein than the modified linear mRNA (FIG. 31). During the span of 6 days, circular RNA in HEK293 cells exhibited a protein production half-life of 80 hours, while the unmodified and modified linear mRNA performed half-lives of 43 and 45 hours respectively (FIG. 32). Since the circular RNA had a greater production of protein and a longer protein production half-life, circular RNA provides more stability than linear mRNA.

EXAMPLE 33

Figure 33:
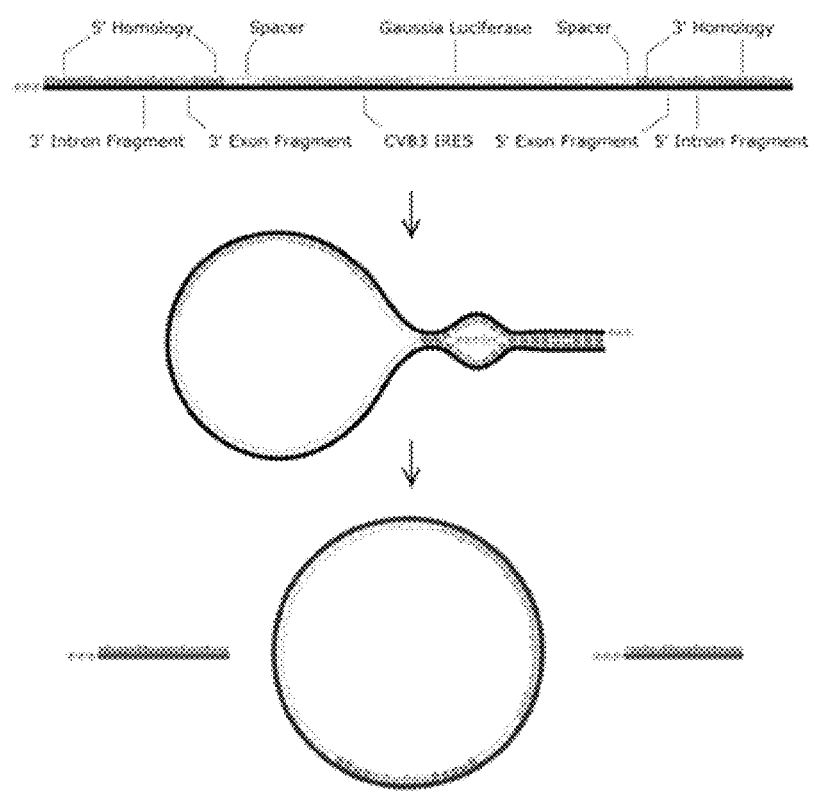
FIG. 33 gives an overview of precursor RNA design and self-splicing. Shading denotes different regions of RNAs described herein.
Figure 34:
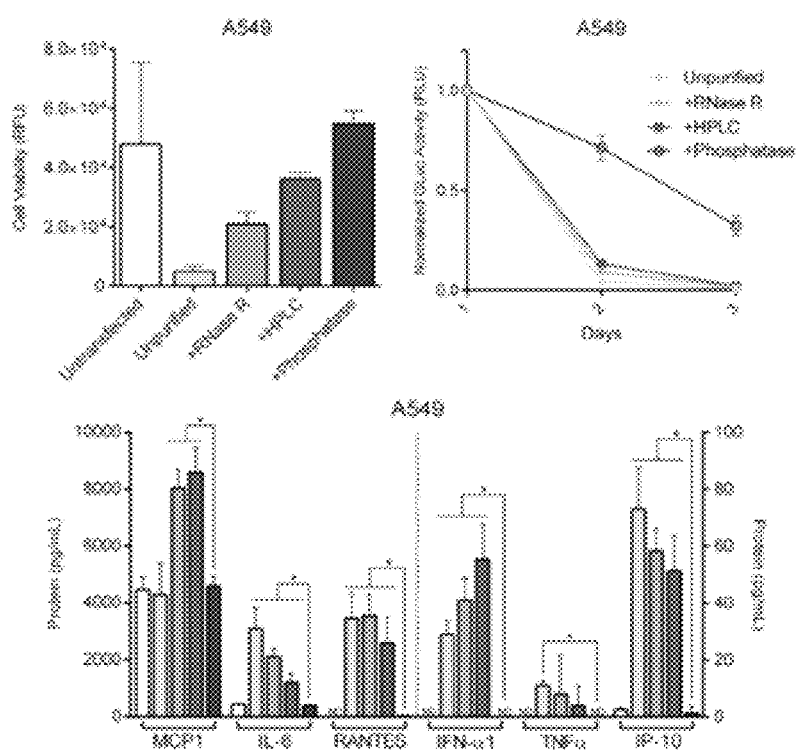
FIG. 34 depicts cell viability, circRNA expression stability, and cytokine release from A549 cells transfected with different circRNA preparations (+RNase R, unpurified circRNA digested with RNase R only; +HPLC, unpurified circRNA HPLC purified, and then digested with RNase R; +Phos, unpurified circRNA HPLC purified, treated with a phosphatase, and then digested with RNase R). Cell viability was assessed 3 days after transfection. Cytokine release was assessed 24 h after transfection (data presented as means+SDs; n=3; *p<0.05; ND, not detected).
Figure 35:
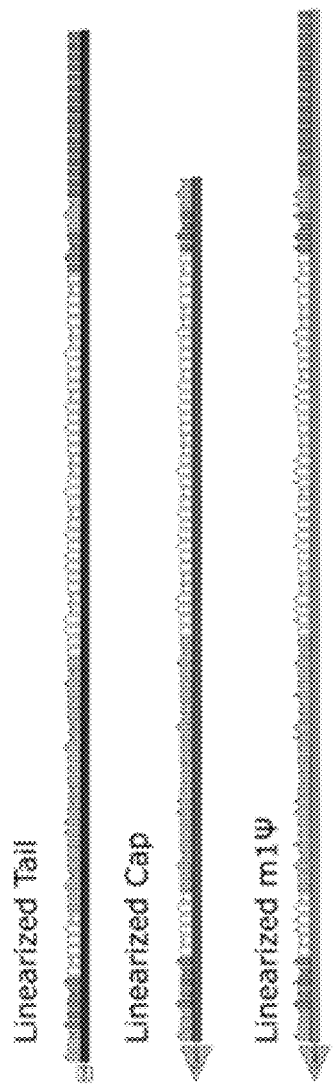
FIG. 35 depicts schematics of RNAs introduced and used for TLR experiments. Linearized circRNAs contain all of the same sequence elements as spliced circRNA due to deletions encompassing both the introns and the homology arms.

Purification of Circular RNA Encoding CARs Promotes an Effective Removal of Immunogenicity Using the engineered circular RNA, further steps of purification from the translation from the precursor RNA molecule diminishes immunogenicity (R. Wesselhoeft et al., 2019). Optimal purification during the splicing reaction included RNAse R, high-performance liquid chromatography (HPLC), digestion with oligonucleotide targeted RNAse H, and phosphatase to remove residual triphosphates. The effectiveness of circular RNA's immunogenicity, two cell lines (human embryotic kidney, 293; human lung carcinoma, A549) are observed for differential cell viability and CAR expression stability responses in circular RNA precursors containing a coxsackievirus B3 internal ribosome entry site (CVB3 IRES), a protein coding message, two designed spacer sequences, two short exon fragments from the PIE construct, and 3' and 5' intron segments of permuted Anabaena pre-tRNA group I intron (FIG. 33). For human lung carcinoma cell lines treatment, RNAse R and HPLC individually are not enough to reduce cytokine release of interleukin-6 (IL-6) (FIG. 34) and further lead to the significant increase of interferon-α1 (IFN-α1). Phosphatase treatment after HPLC and before RNAse digestion shows increased cell viability, greater normalized GLuc Activity and undetectable or un-transfected base line levels of monocyte chemoattractant protein 1 (MCP1), IL-6, IF-α, tumor necrosis factor α (TNF-α), and IFN-γ inducible protein-10 (IP-10) compared to a unpurified circular RNA.

EXAMPLE 34

Engineered Circular RNA Encoding CAR Avoids Toll-Like Receptor Degradation

Circular RNA can avoid Toll-Like Receptor (TLR) detection. When TLRs 3, 7, and 8 detect RNAs in endosomes, they bind to the RNA and lead to an inflammatory response (T. Kawasaki & T. Kawai, 2014). Linearized versions of circular RNA lacking the intron and homology arm sequences are treated with phosphatase and HPLC. TLRs 3 and 8 show a largely reduced relative SEAP activity when the RNA is circular instead of linear.

EXAMPLE 35

Example 35A—Circular RNA Delivery Through Lipid Nanoparticles Provide Effective Expression of Proteins In Vivo or In Vitro LNPs are synthesized by mixing 1 volume lipid mixture of MC3, DSPC (Avanti Polar Lipids, Alabaster, Ala.), Cholesterol (Sigma-Aldrich, Taufkirchen, Germany), DMG-PEG (NOF, Bouwelven, Belgium), and DSPE-PEG (50:10.5:38:1.4:0.5 mol ratio) in ethanol with 3 volumes of circular RNA (1:16 w/w circular RNA to lipid) in acetate buffer via injection in the micro fluidic mixing device Nanoassemblr® (Precision Nanosystems, Vancouver BC) at a combined flow rate of 2 mL/min (0.5 mL/min for ethanol and 1.5 mL/min for aqueous buffer). The resultant mixture is dialyzed against phosphate buffered saline (PBS) (pH 7.4) twice for 16 h at 200 times the primary volume with a Slide-A-Lyzer cassettes (10 kda cutoff, Thermo Fisher Scientific Inc. Rockford, Ill.) to remove ethanol. The resulting nanoparticle suspension was filtered through 0.2 μm sterile filter (Sarstedt, Numbrecht, Germany) into glass vials and sealed with a crimp closure.

Characterization of Formulations

A Zetasizer Nano ZS (Malvern Instruments Ltd, Malvern, Worcestershire, UK) is used to determine the particle size, the polydispersity index (PDI) and the zeta potential of the circular RNA nanoparticles in PBS in determining particle size and 15 mM PBS in determining zeta potential.

Ultraviolet-visible spectroscopy is used to determine the concentration of circular RNA nanoparticle formulation. LNPs are diluted 10 to 1 in 4:1 (v/v) mixture of methanol and chloroform solution. After mixing, the absorbance spectrum of the solution is recorded between 230 nm and 330 nm on a DU 800 spectrophotometer (Beckman Coulter, Beckman Coulter, Inc., Brea, Calif.). The circular RNA in the nanoparticle formulation is calculated based on the extinction coefficient of circular RNA used in the formulation and with the baseline subtracted out from the difference between the value of 260 nm wavelength and the baseline at 330 nm.

QUANT-IT™ RIBOGREEN® RNA assay (Invitrogen Corporation Carlsbad, Calif.) is used to evaluate the encapsulation of circular RNA by the nanoparticle. Samples are prepared per the manufacturer's instructions. The fluorescence intensity is measured using a fluorescence plate reader (Wallac Victor 1420 Multilabel Counter; Perkin Elmer, Waltham, Mass.) at an excitation wavelength of ~480 nm and an emission wavelength of ~520 nm. The fluorescence values of the reagent blank are subtracted from that of each of the samples and the percentage of free circular RNA is determined by dividing the fluorescence intensity of the intact sample (without addition of Triton X-100) by the fluorescence value of the disrupted sample (caused by the addition of Triton X-100).

Attaching a Targeting Ligand to the LNP.

First, nanobodies are selected for their binding capacity to CD3, CD4, or CD8. Preferably CD3 antibodies are used which bind, induce rapid internalization, but do not over stimulate T cells. Once a nanobody is selected, site directed mutagenesis using techniques known to one of ordinary skill in the art are used to generate a nanobody with a single surface exposed cysteine.

Nanobodies are first conjugated to an alkyne group for Click chemistry via the reactive cysteine. By mixing alkyne-maleimide with the nanobody devoid of reducing agent (no DTT or BME) of choice in a 10× molar ratio of alkyne-maleimide to nanobody, the single free cysteine is labeled (Hermanson, Bioconjugation techniques, 3rd addition, 2013, incorporated by reference). Free alkyne linker groups are dialyzed away with amicon filters with 2×100 volumes of PBS.

The purified nanobody alkyne is reacted with DSPE-PEG-azide via click chemistry and the addition of copper as a catalyst and is described in Presolski et al (Presolski et al 2011, Current protocols in chemical biology 3: 153-162). Once the nanobody is modified, 250 nm cholesterol is added to produce a micellar formulation of the lipid modified nanobody.

To incorporate the lipid modified nanobody micelles into the LNP, the lipid nanobody is incubated with LNPs for 48 hour at 4C at a ratio of 1:1 nanobody to circular RNA weight. The nanobody Labeled LNP is separated from free nanobody lipid via dialysis with a 1 MDa cutoff membrane (BioLabs, LTS). Nanobody incorporation is also measured via ELISA or western blot compared to a standard.

Example 35B—Formulation of Circular RNA into a Polymeric Nanoparticle for Delivery to T Cells PBAE Polymer Synthesis PBAE polymer is synthesized using methods previously (Mangraviti et al., ACS Nano 9, 1236-1249 (2015)). Briefly, 1,4-butanediol diacrylate was combined with 4-amino-1-butanol in a 1.1:1 molar ratio of diacrylate to amine monomer. After mixing, the reaction is at 90° C. for 24 h with stirring to produce acrylate-terminated poly(4-amino-1-butanol-co-1,4-butanediol diacrylate). The polymer is dissolved at a ratio of 1.15 g per ml tetrahydrofuran (THF). To form the piperazine-capped 447 polymer, 786 mg of 1-(3-aminopropyl)-4-methylpiperazine dissolved in 13 ml THF was added to the polymer/THF solution. The resulting mixture is incubated for 2 hours with stirring, then precipitated with 5 volumes of diethyl ether. After the solvent is decanted, the polymer is washed with 2 volumes of ether, and dried under vacuum for 2 days before used to form a stock of 100 mg/ml in DMSO. Polymer is stored at −20° C.

PGA-Antibody Conjugation.

15 kD poly-glutamic acid (from Alamanda Polymers) is dissolved in water to form 20 mg/ml and sonicated for 10 min. An equal volume of 4 mg/ml 1-ethyl-3-(3-dimethylaminopropyl) carbodiimide hydrochloride (Thermo Fisher) in water is added, mixed for 5 min at room temperature. The resulting activated PGA was then combined with antibodies at a 4:1 molar ratio in phosphate buffered saline (PBS) and mixed for 6 hrs at room temperature. To remove unlinked PGA, the solution was exchanged 3 times against PBS across a 50,000 NMWCO membrane (Millipore). Antibody concentrations are determined using a NanoDrop 2000 spectrophotometer (Thermo Scientific). The antibodies used for T cell experiments are anti-CD3 (clone OKT3), anti-CD4 (clone OKT4), anti-CD8 (clone OKT8), and anti-CD28 (clone 9.3, all from BioXCell). Clone C1.18.4 is used as a control antibody. For HSC transduction, polyclonal goat anti-mouse IgG and polyclonal goat anti-mouse CD105 antibodies (Fisher) are used.

Nanoparticle (NP) Preparation

Circular RNA stocks are diluted to 100 µg/ml in sterile, nuclease-free 25 mM sodium acetate buffer, pH 5.2 (NaOAc). PBAE-447 polymer in DMSO is diluted to 6 mg/ml in NaOAc, and added to circular RNA at a 60:1 (w:w) ratio. The Mixture is vortexed for 15 sec and incubated for 5 min at room temperature to form NPs. To add targeting elements to the nanoparticles, PGA-linked antibodies are diluted to 250 µg/ml in NaOAc and added at a 2.5:1 (w:w) ratio to the circular RNA. The mixture is vortexed for 15 sec and incubated for 5 min at room temperature to form NPs coated in PGA—antibody. PGA-PEG and other blocking agents can be mixed in as well to generate NP particles with greater half lives in serum.

The nanoparticles are lyophilized by mixing them with 60 mg/ml D-sucrose as a cryoprotectant, and flash-freezing them in liquid nitrogen, before processing them in a FreeZone 2.5 L Freeze Dry System (Labconco). The lyophilized NPs are stored at −80° C. until use. For application, lyophilized NPs are re-suspended in a volume of sterile water to restore their original concentration.

EXAMPLE 36

Introducing CAR Circular RNA into Cells In Vitro

Circular RNA can be introduced to the cytoplasm of eukaryotic cells using a lipid-polymeric transfection reagent. For example, 100 ng of circRNA in <5 uL water or storage buffer (pH 5-7) can be mixed with OptiMem (Gibco) to a final volume of 5 uL. Separately, 0.2 uL MessengerMax transfection reagent (Thermo Fisher) can be mixed with OptiMem (Gibco) to a final volume of 5 uL. This second mixture can then be added to the first mixture to produce a mixture of circRNA, OptiMem, and MessengerMax transfection reagent that can then be added to the culture medium of 10,000-50,000 eukaryotic cells after a short incubation (5-30 minutes) in order to promote cellular internalization of the circRNA. Alternatively, circRNA can be electroporated into eukaryotic cells using, for example, the Neon electroporation system (Thermo Fisher). 1 ug of circRNA can be electroporated into 200,000 T cells at 1,600V for 10 ms with 3 pulses in a volume of up to 100 uL. Alternatively, circRNA can be introduced into eukaryotic cells using a lipid nanoparticle or polymer complexed with circRNA.

EXAMPLE 37

Expression of CAR on T-Cells Transduced with Circular RNA

The engineered circular RNA encoding CAR are delivered by lipid nanoparticles to T-cells to generate CAR expressing T-Cells. To determine the efficiency of translation, the engineered circular RNA includes a CAR coding region. T cells are then transfected with CAR-coding circRNA. Flow cytometry is then used to analyze CAR expression on the cell surface (S. De Olivera et al., 2013). Fluorescein isothiocyanate conjugated polyclonal F(Ab')2 fragment goat antihuman IgG1Fcγ (Jackson ImmunoResearch Laboratories, West Grove, PA) (55.5 ng per 105 cells) is used to detect the presence of human IgG spacer in the CAR constructs located on the cell surface. Jurkat cells are stably transduced with the CD19-CAR, with an expression rate of above 96% to compare with the control T-Cells. The CAR expressing T-Cells are further washed with PBS. The flow cytometer results show the expression of CARs by the T cells.

EXAMPLE 38

Example 38A—Transfection of circRNA Encoding a CAR Results in Minimal Cytokine Release from T Cells Use of engineered circular RNA to express CARs produces less cytokine release than when lentiviruses are used. One of the main downfalls of using lentiviruses as a vector in gene therapy is the cytokine release that results from unstable packaging cells or expression of gag or pol genes of HIV that results in cascading cytotoxic effects (O. Merten, 2016). CAR-Transduced T-Cells generated using circular RNAs exert little to no cytokine release in comparison to lentiviral delivery of CARs.

Cytokine release can be determined through cytokine release assays. For example, a CRA is performed using therapeutic mAbs (S. Vessillier et al., 2015). Purified human IgG4κ and IgG1 are used as isotype controls (AMS Biotechnology Ltd, UK) and anti-CD28 agonist (Biolegend, UK) is used as a control to assess specificity for a CD28 superagonist. Sodium azide is removed from control mAbs using Amicon® Ultra-4 centrifugal filter units (Millipore Ltd, UK) and confirmed endotoxin-free using the limulus amebocyte lysate gel clot test. Since human FcγRI and FcγRIIIa bind murine IgG2a as per human IgG1, muromonab-CD3 responses are compared to human IgG1 isotype control. Phytohaemagglutinin (PHA; Sigma-Aldrich Ltd, UK) at 10 µg ml-1 is used as a positive control. PBMC SP CRAs are performed by wet coating wells of microtitre plates at a mAb concentration of 1 µg well-1 for 1 hour, followed by washing to remove unbound mAb and then the addition of PBMC for 48 hours (Eastwood et al., 2010, Eastwood et al., 2013). PBMC HDC CRAs are performed by addition of mAb at 1 µg ml-1, to PBMC pre-incubated at high density for 48 hours, and 24 hour-stimulation (Römer et al., 2011, Bartholomaeus et al., 2014). WB and 10% (v/v) WB CRAs are performed at a mAb concentration of 5 µg ml-1 and 48-hour stimulation, as previously described (Wolf et al., 2012, Bailey et al., 2013). All concentrations are chosen for comparability with previously published findings on cytokine release using these methods. Although not a published method, WB SP and 10% (v/v) WB SP CRAs are performed as per the PBMC SP CRA with a mAb coating concentration of 1 µg well-1, as controls. All assays are carried out in 96-well round bottom microtitre plates (Sigma Aldrich Ltd), PBMC SP and HDC CRA utilized 2×105 PBMC in 200 µl of complete media per well, the WB CRA utilized 200 µl of WB per well containing 0.7-2.0×106 WBCs and the 10% (v/v) WB CRA utilized a tenth of the latter in complete media at 200 µl well-1. CRA comparisons are performed using the same set of donors, except for the PBMC HDC CRA which utilized a different set of 8 donors. The effect of selective depletion of RBCs from heparinized WB are assessed, using EasySep™ glycophorin A positive cell depletion cocktail (Stemcell Technologies, UK) according to the manufacturer's instructions. Buffy coats are prepared from whole blood by centrifugation and incubated with anti-glycophorin A reagent for 15 minutes at room temperature before addition of magnetic nanoparticles added and a further incubation for 10 minutes. RBCs are then removed by immuno-magnetic separation. Depletion of 95-99% of RBCs are confirmed by visual assessment. The resultant white blood cell (WBC) suspension consisting almost entirely of plasma depleted polymorphonuclear leukocytes, lymphocytes and monocytes is adjusted to 1×106 ml-1 in complete media and used in a WBC SP CRA at 200 µl well-1 and a mAb coating concentration of 1 µg well-1 TGN1412. To investigate inhibition of TGN1412-associated cytokine release, WBCs are resuspended in autologous WB or 10-200 µg well-1 of GYPA (Sigma-Aldrich Ltd) is added. To assess the effect of IL-2 on TGN1412-associated cytokine release, daclizumab (IL-2R antagonist) at a concentration of 5 µg ml-1 is added to cells and pre-incubated for 10 min prior to plating in a PBMC SP CRA as described above. Concentrations of IFNγ, IL-2, IL-13 and IL-8 in culture supernatants are measured using custom made MSD plates, according to the manufacturer's instructions (Meso Scale Discovery, USA). TNFα and IL-17 concentrations are quantified by ELISA as previously described (Eastwood et al., 2010, Eastwood et al., 2013).

The cytokine release assay is completed for T cells engineered using the lentiviruses as well as using the engineered circular RNA in establishing CAR-Transduced T-cells. The T cells engineered circular RNA produces significantly less cytokines.

Example 38B—CAR-Transduced T-Cells Derived from Engineered Circular RNA Kill Tumor Cells CAR transduced T-cells created using engineered circular RNA are capable of killing tumor cells. Newborn mice, which are transgenic for human IL-3, SCF, and GM-CSF, are given an injection of fetal liver CD34+ or other hematopoietic stem cell to create humanized immune system (HIS) mice. After 5-6 weeks, engraftment of human hematopoiesis is confirmed. A killing assay is then performed to determine the effectiveness of these CAR transduced T cells. For example, UPN035, an oligoclonal population of primary CD3+ and CD8+ T cells is transfected to express a chimeric ScFv immunoreceptor that directs specific cytolysis of CD19+ target cells (L. Cao et al, "Development and application of a multiplexable flow-cytometry-based assay to quantify cell-mediated cytolysis," Cytometry Part A 77A(6): 534-545 (2010)). 4-h51Cr release assays are performed, for example, where 90-95% confluent U251T cells is labeled overnight in Dulbecco's Modified Eagle Medium (DMEM) solution with Na51CrO4 (C. Brown et al., "Biophotonic cytotoxicity assay for high-throughput screening of cytolytic killing," J. Immunol. Methods 297(1-2): 39-52 (2005)). The next day, the U251T cells are washed with EDTA solution, tyrpsinized, resuspended in DMEM, incubated for 60 minutes at 37° C., and then washed again with DMEM. The target cells are co-cultured with increasing numbers of CD8+ effector CTL in V-bottom 96-well micro-plates at 5% CO2 at 37° C. After 1-4 hours, 50% of the supernatant is removed and released 51Cr is counted with Cobra II autogamma (Packard). The percent lyse is calculated based on the combined positive score in comparison to the 100% lysed control determined by plating target cells in 1% SDS as well as the 0% lysed control determined by plating target cells in media without effector cells. The CAR transduced T-cells effectively kill tumor cells.

Example 38C—CAR-Transduced T-Cells Derived from Engineered Circular RNA Kill Tumor Cells A hematological cancer system is produced by injecting luciferase-expressing Eu-ALL01 leukemia cells into 4-6 week old female albino C57BL.6J-Tyr mice. One week following injection, mice are randomized into three groups. The mice in group 1 are treated with a control nanoparticle formulation containing circular RNA expressing eGFP. The mice in group 2 are treated with a test nanoparticle formulation containing circular RNA encoding a CD19-specific CAR. The mice in group 3 are treated with a test nanoparticle formulation containing linear modified RNA encoding a CD19-specific CAR.

Over time, luciferase-expressing leukemia is detected in the mice by intravenously administering D-luciferin and mice are imaged on a Xenogen IVIS spectrum imaging system (Xenogen) 10 min post injection of D-Luciferin. The mice in group 1 show rapid leukemia spread. The mice in group 2 show decreased amounts of leukemia luminescence at early time points and later time points compared to the mice in group 3. The mice in group 3 mice show leukemia rebound and an increase in the number of cancer cells sooner than group 2 mice due to the lower stability of the linear modified RNA construct compared to the circular RNA construct.

EXAMPLE 39

Detection of TCR Complex Protein Expression

Following delivery of circular RNA encoding a TCR complex protein using nanoparticles or electroporation, expression of the TCR complex protein is confirmed by flow cytometry. TCR complex protein may be detected by using the appropriate anti-target antibody (e.g., expression of a CD19-specific TCR complex protein may be detected with an anti-CD19 scFv antibody). T cells are washed in staining buffer and re-suspended in PBS. For dead cell exclusion, cells are incubated, for example, with LIVE/DEAD® Fixable Aqua Dead Cell Stain (Invitrogen) for 30 minutes on ice. Cells are washed with PBS and re-suspended in staining buffer. FACS buffer is added to each tube, and cells are pelleted by centrifugation. Surface expression of TCR complex proteins is detected by, for example, Zenon® R-Phycoerythrin-labeled human anti-tumor antigen IgG1 Fc or tumor antigen-Fc. Antibodies or soluble tumor antigen is added to the respective samples and incubated. Cells are then washed, and T cells stained for surface markers.

EXAMPLE 40

Recombinant TCR Complex Protein Expressing T Cell Treatment in an In Vivo Solid Tumor Xenograft Mouse Model T-cells expressing recombinant TCR that are created using engineered circular RNA. Primary human solid tumor cells are grown in immune compromised mice. Exemplary solid cancer cells include solid tumor cell lines, such as provided in The Cancer Genome Atlas (TCGA) and/or the Broad Cancer Cell Line Encyclopedia (CCLE, see Barretina et al., Nature 483:603 (2012)). Exemplary solid cancer cells include primary tumor cells isolated from lung cancer, ovarian cancer, melanoma, colon cancer, gastric cancer, renal cell carcinoma, esophageal carcinoma, glioma, urothelial cancer, retinoblastoma, breast cancer, Non-Hodgkin lymphoma, pancreatic carcinoma, Hodgkin's lymphoma, myeloma, hepatocellular carcinoma, leukemia, cervical carcinoma, cholangiocarcinoma, oral cancer, head and neck cancer, or mesothelioma. These mice are used to test the efficacy of T cells expressing the recombinant TCR complex protein in the human tumor xenograft models. Following an implant or injection of $1 \times 10^5$-$1 \times 10^7$ tumor cells subcutaneously, tumors are allowed to grow to 200-500 mm³ prior to initiation of treatment. The T-Cells expressing recombinant TCR are then introduced into the mice. Tumor shrinkage in response to treatment with human T cells comprising the inventive TCR complex proteins can be either assessed by caliper measurement of tumor size or by following the intensity of a luciferase protein (ffluc) signal emitted by ffluc-expressing tumor cells.

EXAMPLE 41

Engineering CAR Expression Using Circular RNA Results in Less Cytokine Release Syndrome Compared to Lentivirus The use of the engineered circular RNA to generate CAR expression is less susceptible to cytokine release syndrome than when lentivirus is used as a vector. Cells engineered to express a CD19-specific CAR using are compared to cells engineered to express CD19-specific CAR using lentivirus. Each type of vectors are transfected into T cells, which are then delivered to a mice to which a cell line expressing CD19 has been also administered. IL-6 expression by the mice is monitored over time by ELISA. Mice administered the CAR-T cells generated using circular RNA produce less IL-6 than mice administered CAR-T cells generated using lentivirus.

EXAMPLE 42

Example 42A—CAR-Expressing T Cells Produced Using Circular RNA Exhibit Functional Killing for Longer In Vitro than CAR-Expressing T Cells Produced Using Modified mRNA Eµ-ALL01 leukemia cells (or B16F10 melanoma tumor cells as controls) are labelled with the membrane dye PKH-26 (Sigma-Aldrich), washed with RPMI containing 10% fetal calf serum, and resuspended in the same medium at a concentration of $1 \times 10^5$ tumor cells per ml. T cells that have been transfected with either circular RNA CAR-T constructs encoding CD19 targeting CARs or modified mRNA constructs encoding CD19 targeting CARs are added to the suspension at varying effector-to-target cell ratios in 96-well plates (final volume, 200 µl) and incubated for 3 h at 37° C. Cells are transferred to V-bottom 96-well plates. The transduced T cells are tested for their ability to kill the CD19-expressing Eµ-ALL01 leukemia cells on days 1, 2, 3, 4, 6, 8, and 10 after transduction. CAR-expressing T cells produced using circular RNA functional in the cell killing of the CD19-expressing cells for longer compared to CAR-expressing T cells produced using modified mRNA.

Example 42B—CAR-Expressing T Cells Produced Using Circular RNA Exhibit Cytokine Secretion Longer In Vitro than CAR-Expressing T Cells Produced Using Modified mRNA CAR-T Cells are produced by transducing either a CD19-specific CAR-encoding circular RNA or a CD19-specific CAR-encoding modified mRNA. T-cell cytokine release is measured with ELISA (R&D Systems) 24 h (IL-2) or 48 h (IFN-γ and TNF-α) after stimulation on irradiated Eµ-ALL01 leukemia cells or B16F10 melanoma controls. T cells are stimulated and tested for cytokine release on day 1, 2, 3, 4, 6, 8, 10 after transduction to demonstrate that CAR-T cells generated using circular RNA produce more cytokines for longer periods of time compared to CAR-T cells produced using modified mRNA.

Furthermore expression of the CD19 CAR construct is measured by labeling the CAR-T transduced cells with an soluble CD19 fluorescently labeled protein. The cells are then washed in media and flow cytometry is used to assess the functional expression of the CD19 CAR. Circular RNA transduced CD19 CAR cells show functional expression for longer at later time points compared to modified mRNA transduced T cells.

EXAMPLE 43

Electroporation of Primary Human T-Cells with circRNA Encoding a CAR 150,000 primary human T-cell isolated from four different donors were electroporated with 250 ng of circRNA having anabaena intron/exon regions, an anti-CD19 CAR expression sequence, and a CVB3 IRES. After 24 hours of incubation, cells were analyzed for surface expression of anti-CD19 CAR by flow cytometry analysis using standard techniques and reagents known to persons of ordinary skill in the art.

Figure 36:
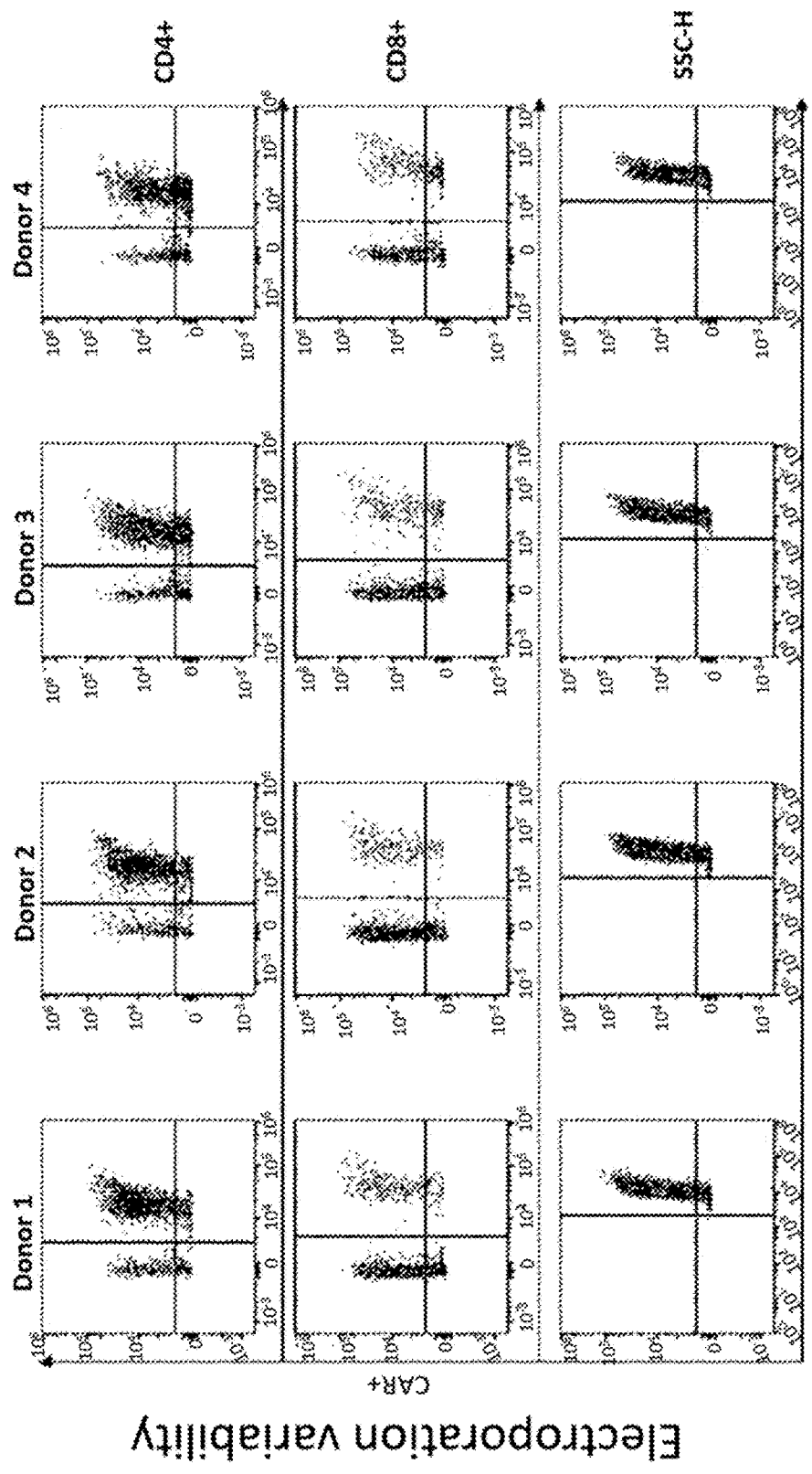
FIG. 36 shows the surface expression of anti-CD19 CAR on primary human T-cells isolated from four donors and electroporated with circRNA.
Figure 37A:
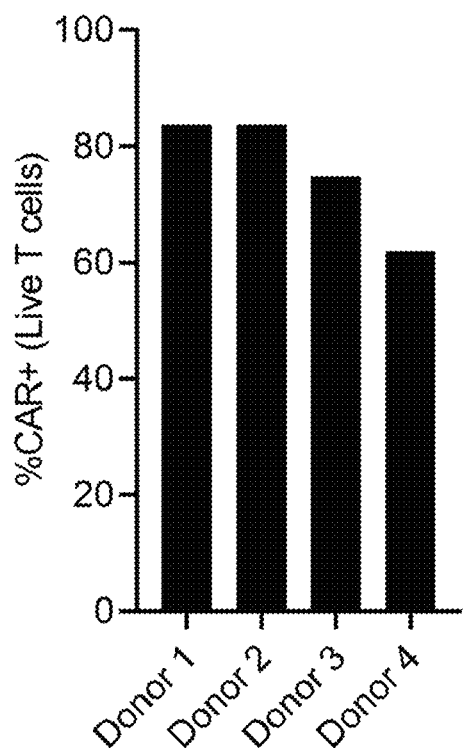
FIG. 37A shows the proportion of CAR+ of live T cells electroporated with circRNA (FIG. 37A) and the proportion of CD4 and CD8 positive T cells in the 4 human donors in FIG. 36 (FIG. 37B).
Figure 37B:
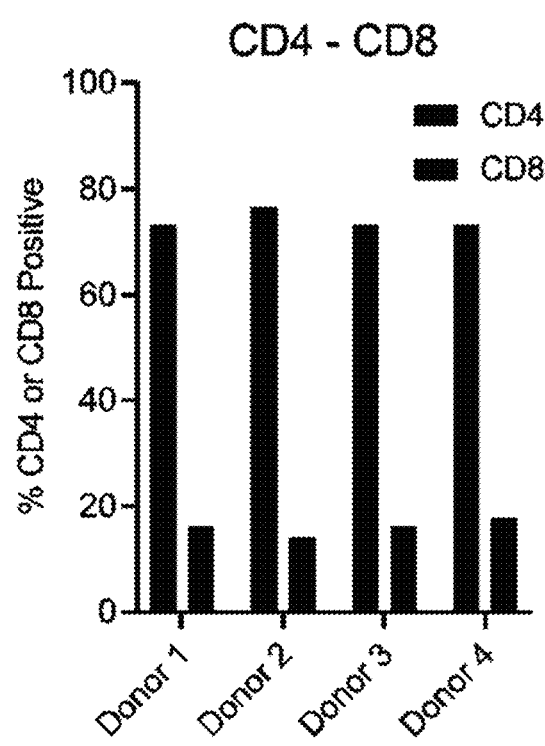

As shown in FIGS. 36 and 37, primary human T-cells can be electroporated to achieve significant surface CAR expression in the live T-cell population.

EXAMPLE 44

Efficacy of circRNA CAR T-Cell Against CD19+ Target Cells

Figure 38:
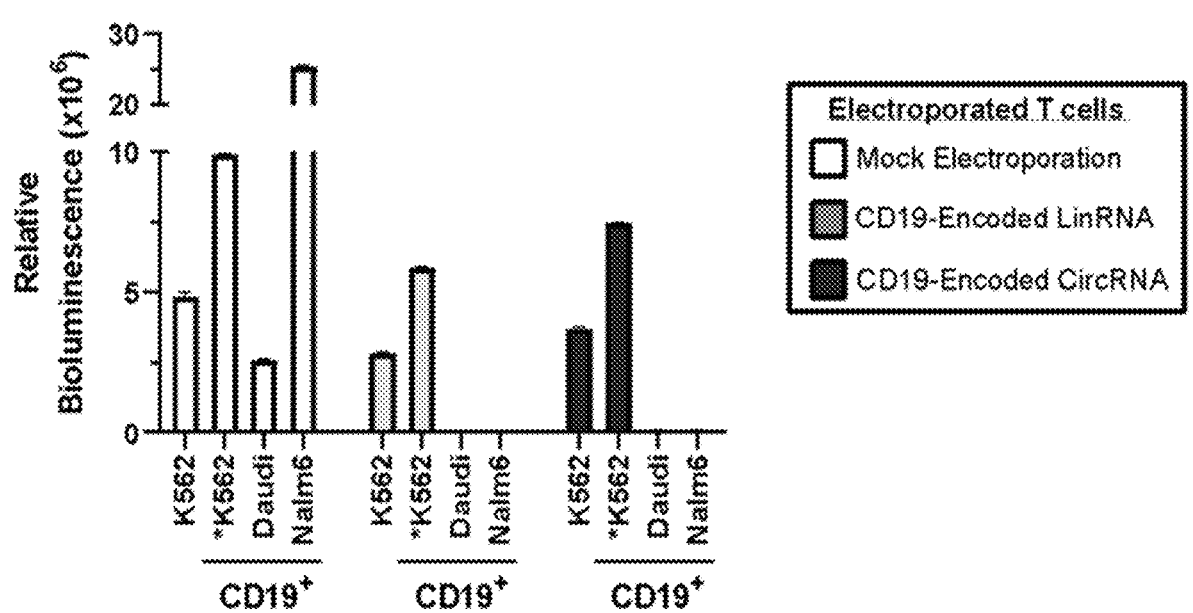
FIG. 38 shows the efficacy of T cells mock electroporated, or electroporated with anti-CD19 CAR-encoding circRNA or linear RNA, in reducing the bioluminescence of luciferase-expressing CD19+ target cells and CD19-non-target cells.

Constructs including anabaena intron/exon regions, and an anti-CD19 CAR expression sequence were circularized. 150,000 human primary CD3+ T cells were either mock electroporated or electroporated with 250 ng circRNA encoding a CAR against CD19. 1 day after electroporation, 10,000 T cells were cocultured with 10,000 target or non-target cells stably expressing firefly luciferase for 24 hours. Quantification of remaining cells of Daudi or Nalm6 target cells, or K562 non-target cells was determined by detection of firefly luminescence (FIG. 38).

EXAMPLE 45

Example 45A—Efficacy of circRNA CAR T Cells Having Different IRES Sequences 5 Days after Electroporation Constructs including anabaena intron/exon regions, an anti-CD19 CAR expression sequence, and a CVB3 IRES or a Salivirus SZ1 IRES were circularized. 150,000 human primary CD3+ T cells were either mock electroporated or electroporated with 250 ng circRNA. 10,000 cells were seeded for coculture experiments. 5 days after electroporation, 10,000 Raji or K562 cells stably expressing firefly luciferase were cocultured with seeded T cells for 24 hours.

Figure 39A:
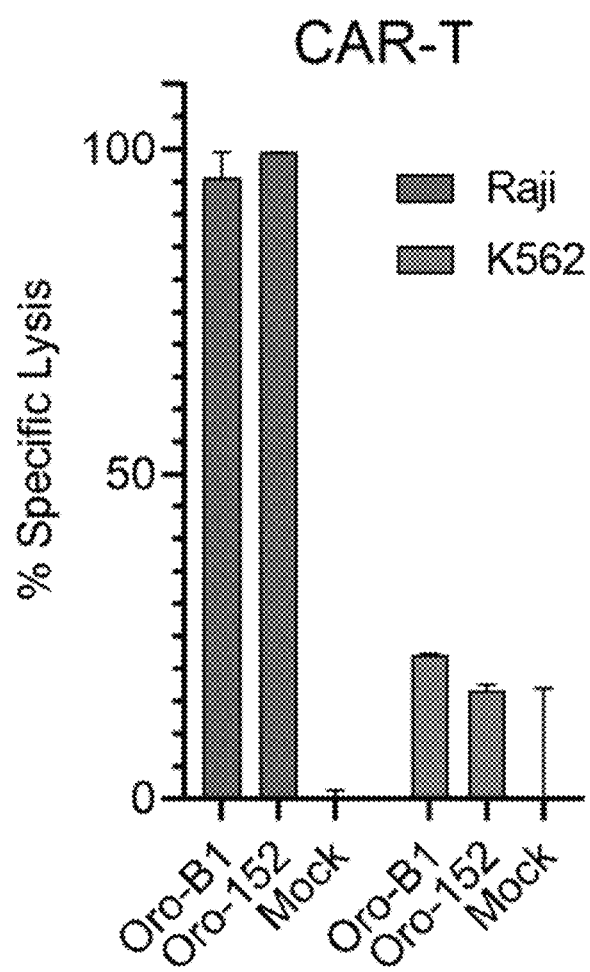
FIG. 39 shows the efficacy of T-cells electroporated with anti-CD19 CAR-encoding circRNAs having different IRES and co-cultured with luciferase-expressing Raji or K562 cells 5 days (FIG. 39A) or 1 day (FIG. 39B) after electroporation. (Oro-B1=circKymriah; CVB3 IRES, Oro-152=circKymriah; Salivirus SZ1 IRES, L9a-5 permutation site)

Specific lysis was defined as (1-[CAR condition luminescence]/[mock condition luminescence])*100 (FIG. 39A).

Example 45B—Efficacy of circRNA CAR T Cells 1 Day after Electroporation

Figure 39B:
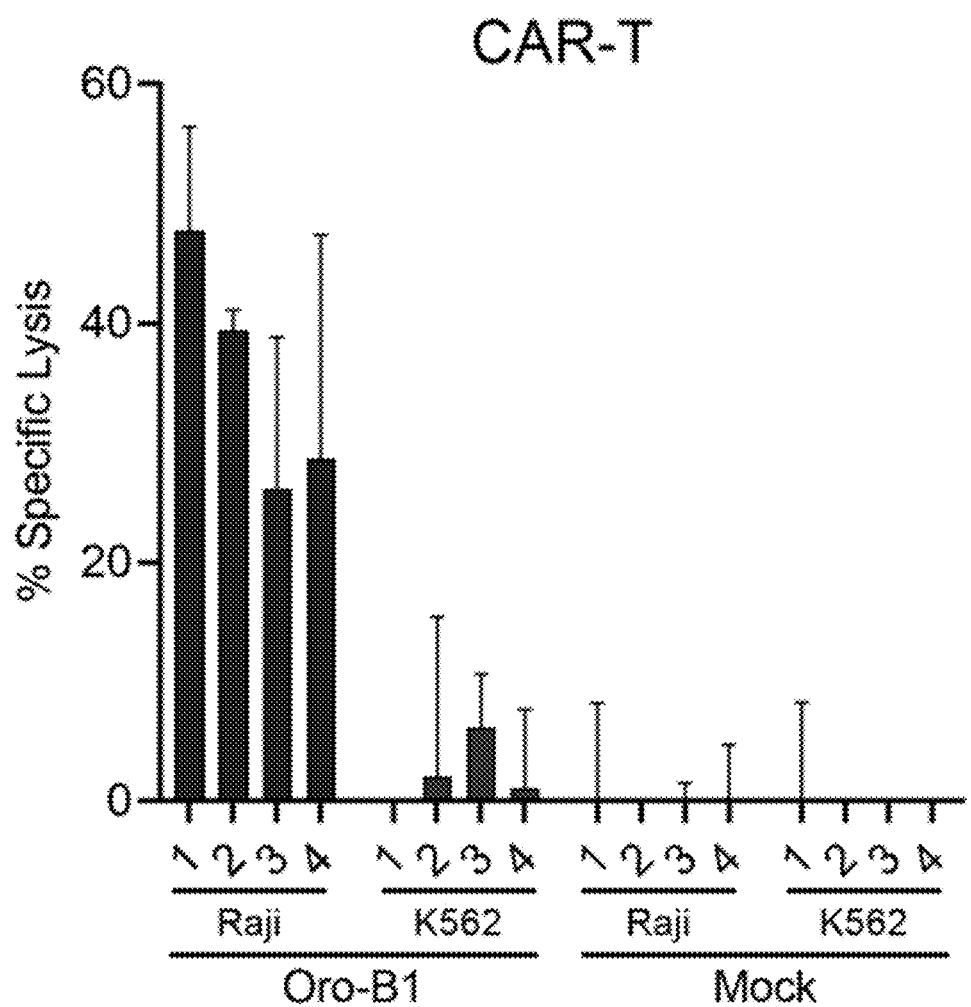

Constructs including anabaena intron/exon regions, an anti-CD19 CAR expression sequence, and a CVB3 IRES were circularized. 150,000 human primary CD3+ T cells from 4 different donors were either mock electroporated or electroporated with 250 ng circRNA. 10,000 cells were seeded for coculture experiments. 1 day after electroporation, 10,000 Raji (target) or K562 (non-target) cells stably expressing firefly luciferase were cocultured with seeded T cells for 24 hours. Specific lysis was defined as (1-[CAR condition luminescence]/[mock condition luminescence])*100 (FIG. 39B)

EXAMPLE 46

Example 46A—Lysis Kinetics of circRNA CAR T Cells

Figure 40A:
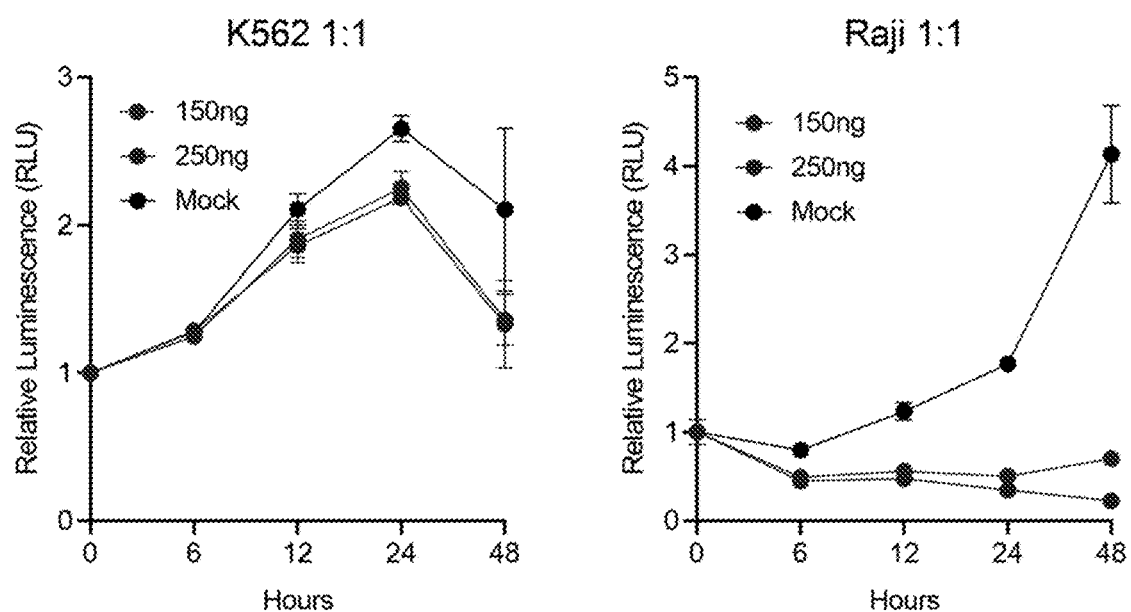
FIG. 40A shows the lysis of CD19+ Raji cells and CD19- K562 cells by primary human T cells electroporated with circRNA having an anti-CD19 CAR expression sequence and a CVB3 IRES or a Salivirus SZ1 IRES.

Constructs including anabaena intron/exon regions, an anti-CD19 CAR expression sequence, and a CVB3 IRES or a Salivirus SZ1 IRES were circularized. Human primary CD3+ T cells were electroporated with 150 ng or 250 ng of circRNA over 48 hours. Raji-luc on-target or K562-luc off-target cells were cocultured with the modified CD3+ T cells at a 1:1 ratio. Luminescence of Raji-luc and K562-luc cells was measured (FIG. 40A).

Example 46B—Lysis Kinetics of circRNA CAR T Cells

Figure 40B:
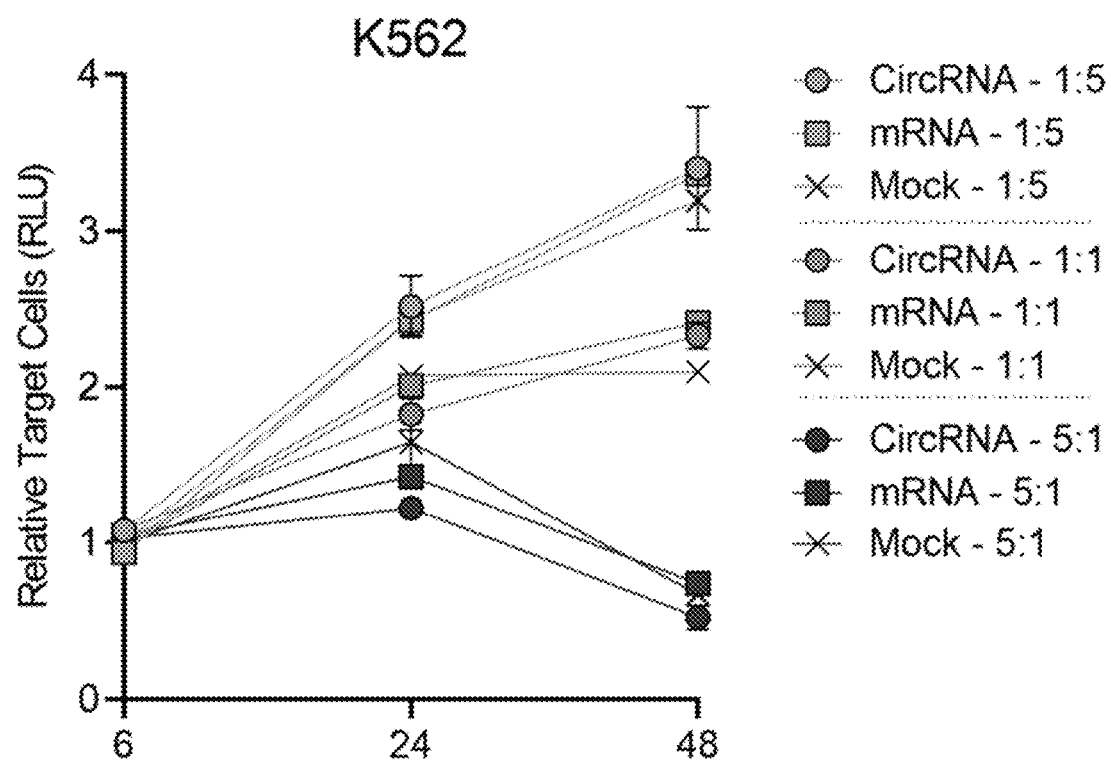
FIG. 40B shows the lysis of CD19+ Raji cells and CD19- K562 cells by primary human T cells electroporated with different ratios of circRNA having an anti-CD19 CAR expression sequence or linear mRNA.

Quantification of specific lysis of K562 target cells was determined by detection of firefly luminescence. 150,000 human primary CD3+ T cells were either mock electroporated or electroporated with 250 ng circRNA. 10,000 cells were seeded for coculture experiments. 1 day after electroporation, 2,000, 10,000, or 50,000 K562 cells stably expressing firefly luciferase were cocultured with seeded T cells for 24 hours. Specific lysis defined as (1-[CAR condition luminescence]/[mock condition luminescence])*100 (FIG. 40B).

Figure 40C:
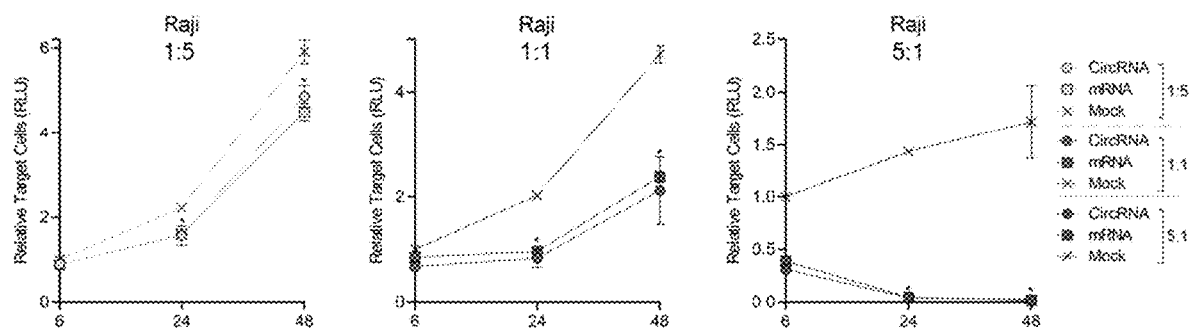
FIG. 40C shows the lysis of CD19+ Raji cells and CD19- K562 cells by different ratios of primary human T cells electroporated with circRNA having an anti-CD19 CAR expression sequence.

Example 46C—Effect of Co-Culture Ration on Lysis Kinetics of circRNA CAR T Cells Quantification of specific lysis of Raji target cells was determined by detection of firefly luminescence. 150,000 human primary CD3+ T cells were either mock electroporated or electroporated with 250 ng circRNA. 10,000 cells were seeded for coculture experiments. 1 day after electroporation, 2,000, 10,000, or 50,000 Raji cells stably expressing firefly luciferase were cocultured with seeded T cells for 24 hours. Specific lysis was defined as (1-[CAR condition luminescence]/[mock condition luminescence])*100 (FIG. 40c).

EXAMPLE 47

Figure 41A:
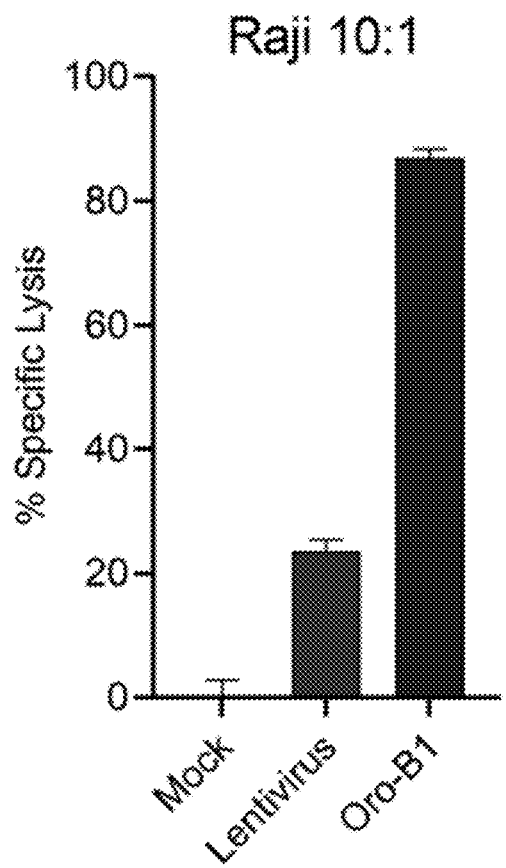
FIG. 41A shows the specific lysis of anti-CD19 CAR-encoding circRNAs in lysing CD19+ Raji cells as compared to T-cell transduced with anti-CD19 CAR-encoding lentivirus at a ratio of 10 Raji cells to one T-cell.
Figure 41B:
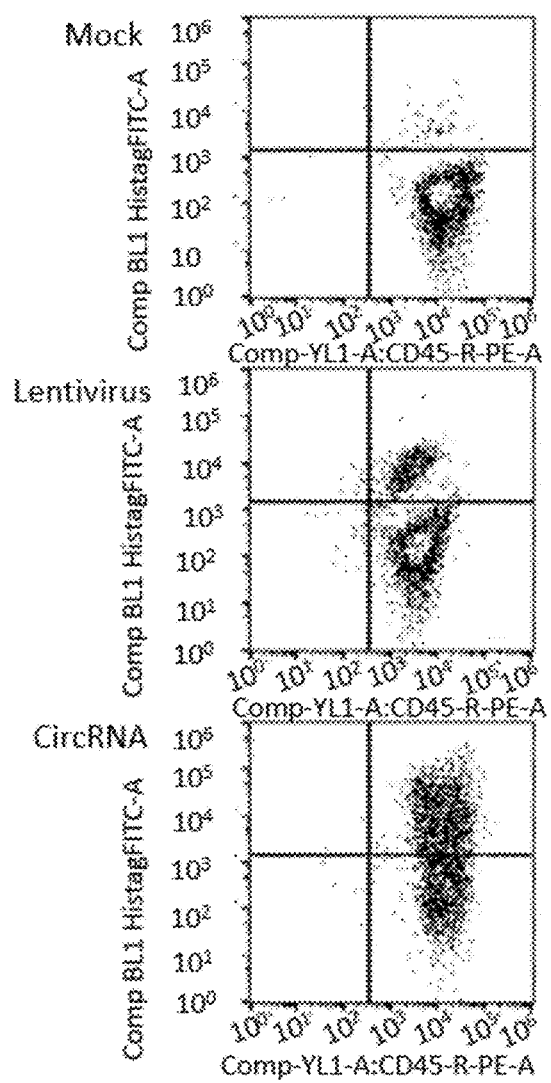
FIG. 41B shows the percentage of anti-CD19 CAR expressing T cells that were mock electroporated or electroporated with anti-CD19 CAR-encoding lentivirus or circRNA.
Figure 41C:
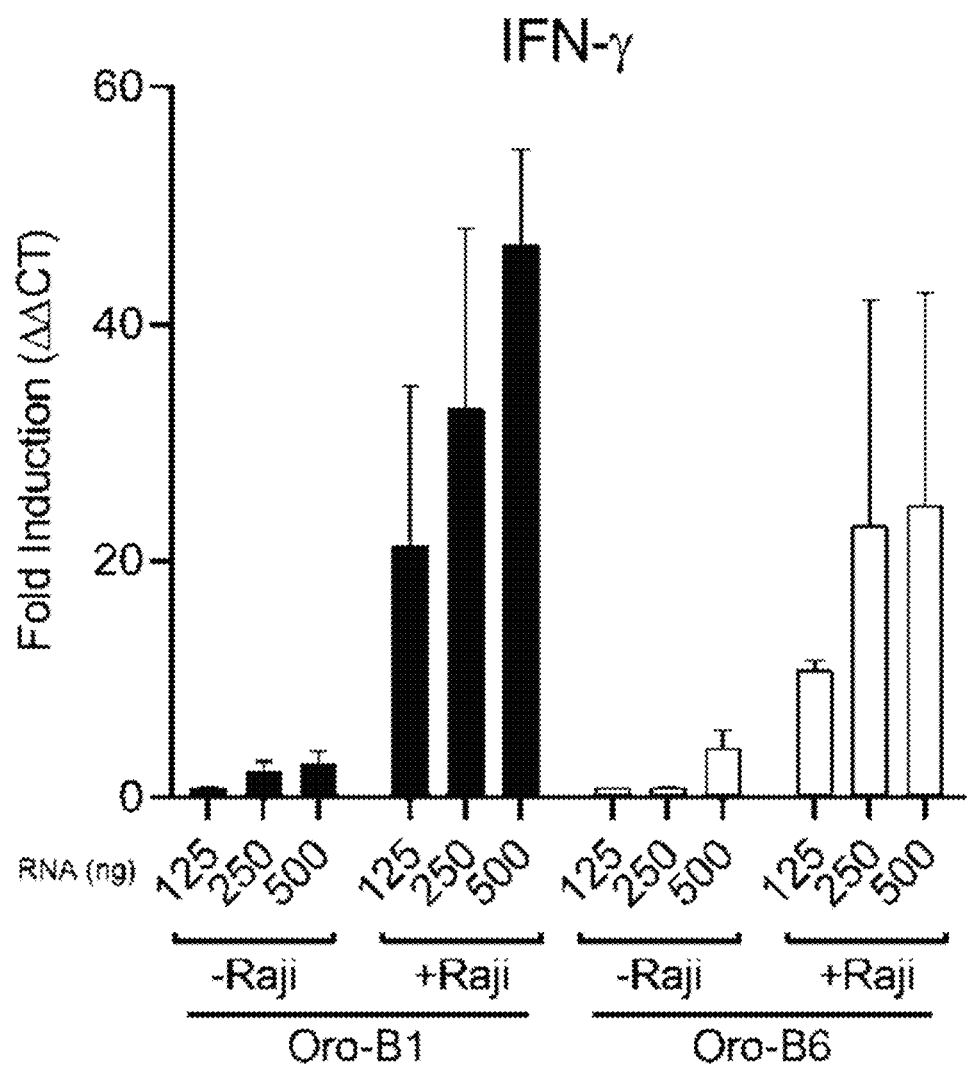
FIG. 41C shows the induction of interferon gamma mRNA in T-cells electroporated with anti-CD19 CAR-encoding circRNAs co-cultured in the presence or absence of CD19+ Raji cells. (Oro-B1=circKymriah; CVB3 IRES, Oro-B6=linKymriah)
Figure 42:
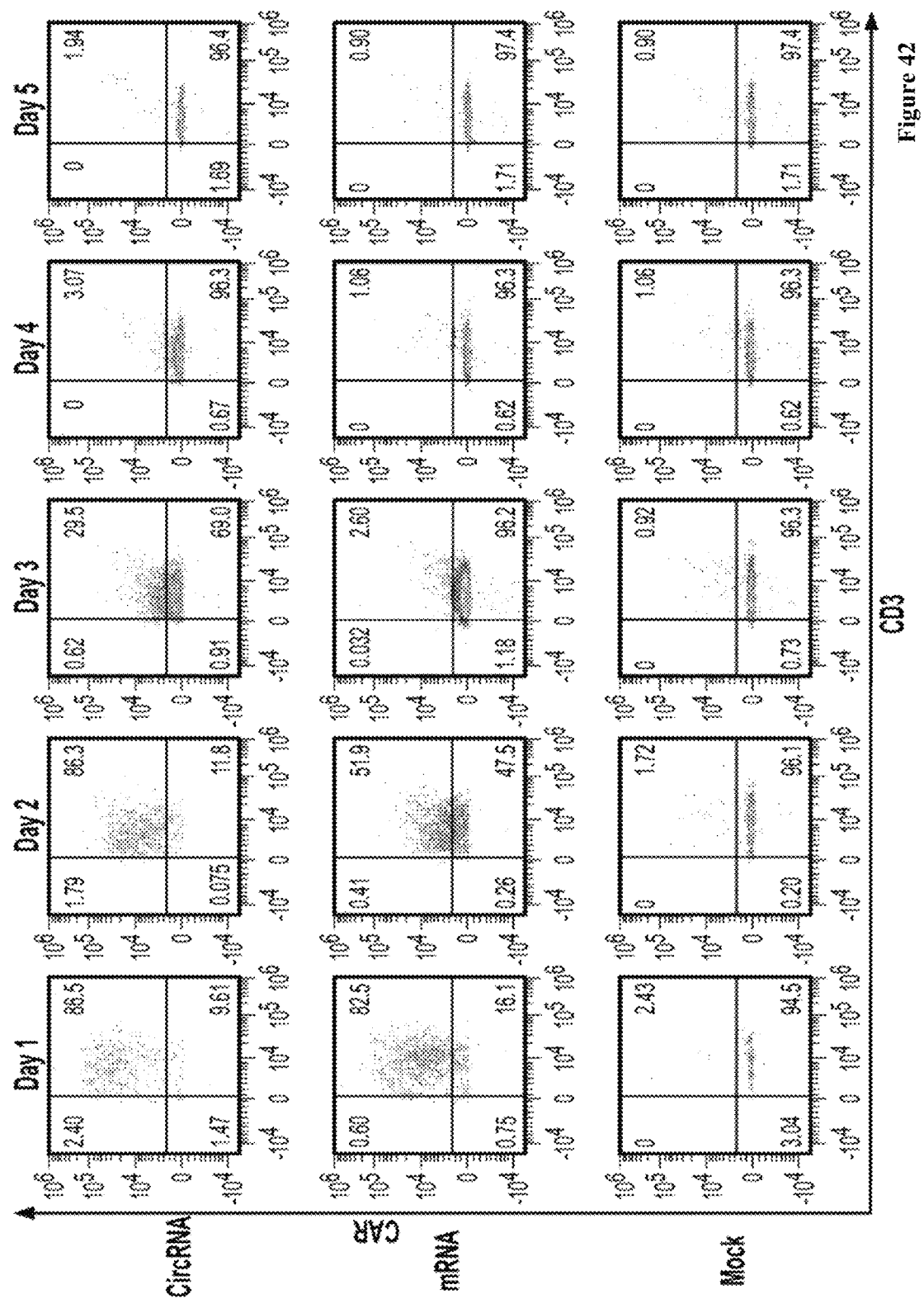
FIG. 42 shows the stability of anti-CD19 CAR expression in primary human CD3+ T cells electroporated with anti-CD19CAR-encoding circRNA or linear mRNA.

Comparison of circRNA CAR T Cells to Cells Electroporated with Linear CAR RNA or Transduced with CAR Lentivirus Constructs including anabaena intron/exon regions, an anti-CD19 CAR expression sequence, and a Salivirus SZ1 IRES were circularized. CD3+ primary human T cells were electroporated with circRNA or were infected with lentivirus encoding anti-CD19 CAR. Interferon gamma transcript induction was measured after 24 hours of culture with or without Raji target cells (FIG. 41A). Proportion of CAR+ T cells was also measured (FIG. 41B). Specific lysis of Raji target cells by human primary CD3+ T cells mock electroporated, electroporated with circRNA encoding a CAR against CD19, or infected with lentivirus encoding a CAR against CD19 was measured (FIG. 41C).

EXAMPLE 48

Stability of CircRNA

Constructs including anabaena intron/exon regions, an anti-CD19 CAR expression sequence, and a Salivirus SZ1 IRES were circularized. CAR surface expression was measured 1-5 days after electroporation of 150,000 primary human CD3+ T cells with 250 ng of linear mRNA or circRNA encoding an anti-CD19 CAR. T cells were electroporated 5 days after stimulation. Cell viability was assessed with DAPI. Live cells were analyzed for CD3 and CAR expression (FIG. 48).

EXAMPLE 49

CAR Expression in Human Monocytes

Figure 43:
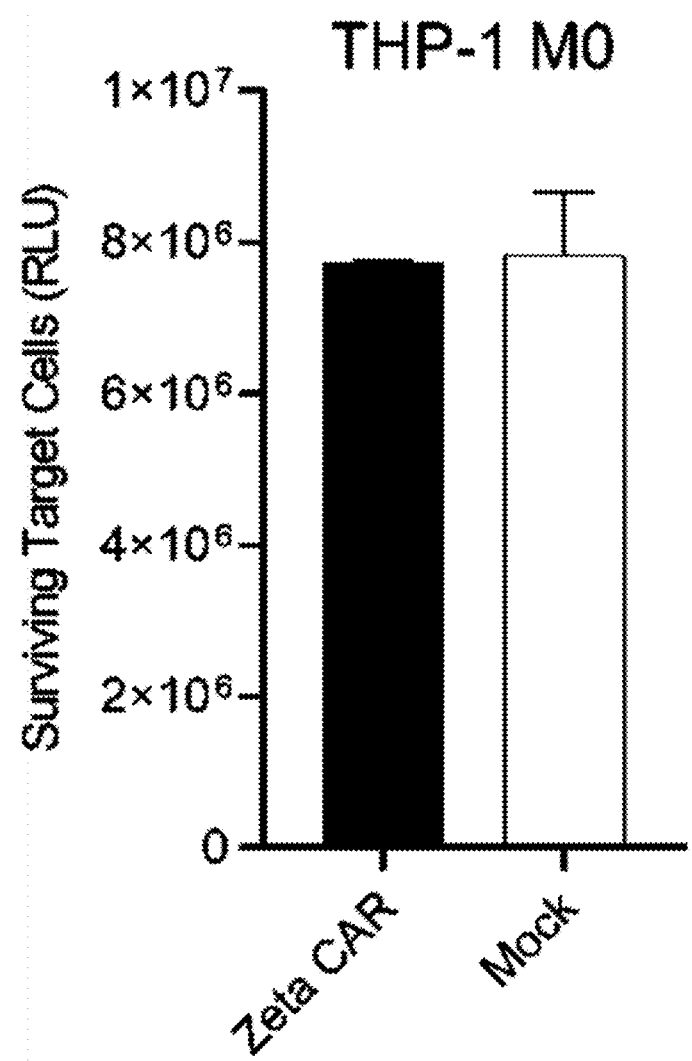
FIG. 43 shows the efficacy of THP-1 monocytes electroporated with a CAR-encoding circRNA in lysing luciferase-expressing Raji cells in co-culture experiments.

Constructs including anabaena intron/exon regions, and a CAR expression sequence were circularized. THP-1 MO cells were either mock electroporated or electroporated with 250 ng circRNA encoding a CAR. 10,000 cells were seeded for coculture experiments. 1 day after electroporation, 10,000 Raji cells stably expressing firefly luciferase were cocultured with seeded THP-1 MO cells for 24 hours. Quantification of surviving Raji target cells determined by detection of firefly luminescence. Luminescence was also measured in supernatant 24 or 48 hours after electroporation of THP-1 MO cells with circRNA encoding *Gaussia* luciferase and 0-90 ng of dsCircRNA. (FIG. 43).

EXAMPLE 50

CAR Expression in Human Monocytes

Figure 44:
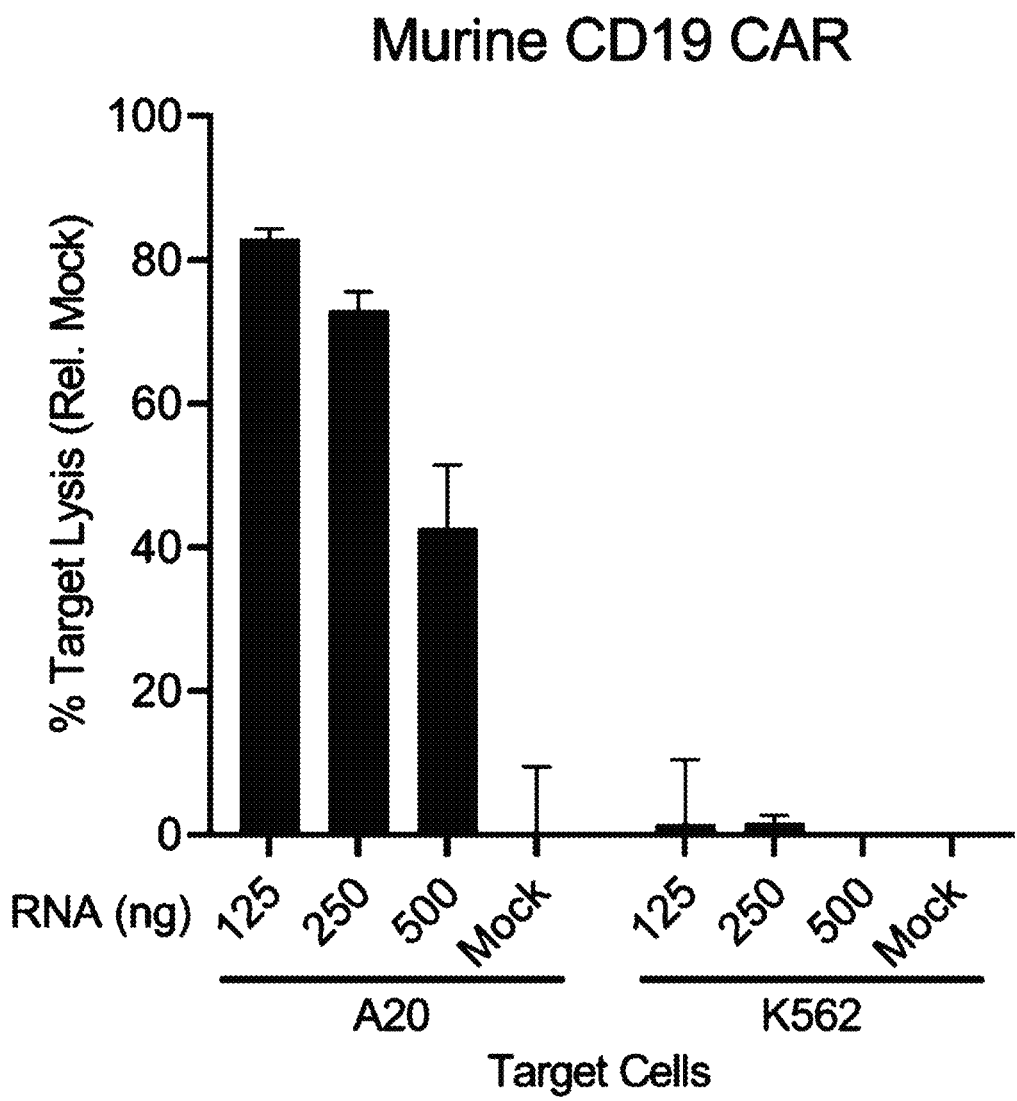
FIG. 44 shows the efficacy of T-cells electroporated with anti-murine CD19 CAR encoding circRNAs in lysing CD19+ A20 cells and CD19- K562 cells.

Constructs including anabaena intron/exon regions, and an anti-murine CD19 CAR expression sequence were circularized. CD3+ T cells were mock electroporated or electroporated with circular RNA and cocultured with A20 target cells or K462 non-target cells. Specific lysis was measured (FIG. 44).

What is claimed is:

1. A pharmaceutical composition formulated for intravenous administration, the pharmaceutical composition comprising:
   a. a circular RNA polynucleotide comprising a non-human post-splicing 3' group I intron fragment, an Internal Ribosome Entry Site (IRES), an expression sequence encoding a chimeric antigen receptor (CAR) or T cell receptor (TCR) complex protein, and a non-human post-splicing 5' group I intron fragment, wherein the post-splicing 3' group I intron fragment is not a T4 bacteriophage thymidylate synthase (Td) 3' group I intron fragment, and wherein the post-splicing 5' group I intron fragment is not a T4 bacteriophage Td 5' group I intron fragment, and
   b. a transfer vehicle comprising (i) an ionizable lipid, (ii) a structural lipid, and (iii) a PEG-modified lipid, wherein the transfer vehicle is capable of delivering the circular RNA polynucleotide to a human immune cell present in a human subject, such that the CAR or TCR is translated in the human immune cell and expressed on the surface of the human immune cell.

2. The pharmaceutical composition of claim 1, wherein the IRES is from Salivirus.

3. The pharmaceutical composition of claim 1, comprising a first internal spacer between the non-human post-splicing 3' group I intron fragment and the IRES, and a second internal spacer between the expression sequence and the non-human post-splicing 5' group I intron fragment.

4. The pharmaceutical composition of claim 3, wherein the first and second internal spacers each have a length of about 10 to about 60 nucleotides.

5. The pharmaceutical composition of claim 1, wherein the transfer vehicle comprises a lipid nanoparticle, a core-shell nanoparticle, a biodegradable nanoparticle, or a biodegradable lipid nanoparticle.

6. The pharmaceutical composition of claim 1, further comprising a targeting moiety.

7. The pharmaceutical composition of claim 1, wherein less than 1%, by weight, of the polynucleotides in the composition are double stranded RNA, DNA splints, or triphosphorylated RNA.

8. The pharmaceutical composition of claim 1, wherein the circular RNA polynucleotide comprises, in the following order, the non-human post-splicing 3' group I intron fragment, the IRES, the expression sequence encoding a CAR or TCR complex protein, and the non-human post-splicing 5' group I intron fragment.

* * * * *

SEQUENCE LISTING

<160> NUMBER OF SEQ ID NOS: 336

<210> SEQ ID NO 1
<211> LENGTH: 585
<212> TYPE: DNA

<213> ORGANISM: Encephalomyocarditis virus

<400> SEQUENCE: 1

```
cccccctctc cctccccccc taacgttact ggccgaagcc gcttggaata aggccggtgt     60
gcgtttgtct atatgttatt ttccaccata ttgccgtctt ttggcaatgt gagggcccgg    120
aaacctggcc ctgtcttctt gacgagcatt cctaggggtc tttcccctct cgccaaagga    180
atgcaaggtc tgttgaatgt cgtgaaggaa gcagttcctc tggaagcttc ttgaagacaa    240
acaacgtctg tagcgaccct ttgcaggcag cggaaccccc cacctggcga caggtgcctc    300
tgcggccaaa agccacgtgt ataagataca cctgcaaagg cggcacaacc ccagtgccac    360
gttgtgagtt ggatagttgt ggaaagagtc aaatggctct cctcaagcgt attcaacaag    420
gggctgaagg atgcccagaa ggtaccccat tgtatgggat ctgatctggg gcctcggtgc    480
acatgcttta catgtgttta gtcgaggtta aaaaacgtct aggccccccg aaccacgggg    540
acgtggtttt cctttgaaaa acacgatgat aatatggcca caacc                    585
```

<210> SEQ ID NO 2
<211> LENGTH: 568
<212> TYPE: DNA
<213> ORGANISM: Encephalomyocarditis virus

<400> SEQUENCE: 2

```
ctcccccctcc cccccccttac tatactggcc gaagccactt ggaataaggc cggtgtgcgt     60
ttgtctacat gctattttct accgcattac cgtcttatgg taatgtgagg gtccagaacc    120
tgaccctgtc ttcttgacga acactcctag gggtctttcc cctctcgaca aaggagtgta    180
aggtctgttg aatgtcgtga aggaagcagt tcctctggaa gcttcttaaa gacaaacaac    240
gtctgtagcg accctttgca ggcagcggaa ccccccacct ggtgacaggt gcctctgcgg    300
ccaaaagcca cgtgtataag atacacctgc aaaggcggca caaccccagt gccacgttgt    360
gagttggata gttgtggaaa gagtcaaatg gctctcctca agcgtattca acaaggggct    420
gaaggatgcc cagaaggtac cccattgtat gggatctgat ctggggcctc ggtgcacgtg    480
ctttacacgt gttgagtcga ggtgaaaaaa cgtctaggcc ccccgaacca cggggacgtg    540
gttttccttt gaaaaccacg attacaat                                       568
```

<210> SEQ ID NO 3
<211> LENGTH: 696
<212> TYPE: DNA
<213> ORGANISM: Encephalomyocarditis virus

<400> SEQUENCE: 3

```
ttgccagtct gctcgatatc gcaggctggg tccgtgacta cccactcccc ctttcaacgt     60
gaaggctacg atagtgccag ggcgggtact gccgtaagtg ccaccccaaa caacaacaac    120
aaaacaaact ccccctcccc cccettacta tactggccga agccacttgg aataaggccg    180
gtgtgcgttt gtctacatgc tattttctac cgcattaccg tcttatggta atgtgagggt    240
ccagaacctg accctgtctt cttgacgaac actcctaggg gtctttcccc tctcgacaaa    300
ggagtgtaag gtctgttgaa tgtcgtgaag gaagcagttc ctctggaagc ttcttaaaga    360
caaacaacgt ctgtagcgac cctttgcagg cagcggaacc ccccacctgg tgacaggtgc    420
ctctgcggcc aaaagccacg tgtataagat acacctgcaa aggcggcaca accccagtgc    480
cacgttgtga gttggatagt tgtggaaaga gtcaaatggc tctcctcaag cgtattcaac    540
aaggggctga aggatgccca gaaggtaccc cattgtatgg gatctgatct ggggcctcgg    600
```

-continued tgcacgtgct ttacacgtgt tgagtcgagg tgaaaaaacg tctaggcccc ccgaaccacg 660
gggacgtggt tttcctttga aaaccacgat tacaat 696

<210> SEQ ID NO 4
<211> LENGTH: 697
<212> TYPE: DNA
<213> ORGANISM: Encephalomyocarditis virus

<400> SEQUENCE: 4
ttgccagtct gctcgatatc gcaggctggg tccgtgacta cccactcccc ctttcaacgt 60
gaaggctacg atagtgccag ggcgggtact gccgtaagtg ccaccccaaa acaacaacaa 120 cccccccctct ccctcctccc cccctaacgt tactggccga agccgcttgg aataaggccg 180
gtgtgcgttt gtctatatgt tattttccac catattgccg tcttttggca atgtgagggc 240
ccggaaacct ggccctgtct tcttgacgag cattcctagg ggtctttccc ctctcgccaa 300
aggaatgcaa ggtctgttga atgtcgtgaa ggaagcagtt cctctggaag cttcttgaag 360
acaaacaacg tctgtagcga ccctttgcag gcagcggaac cccccacctg gcgacaggtg 420
cctctgcggc caaaagccac gtgtataaga tacacctgca aaggcggcac aaccccagtg 480
ccacgttgtg agttggatag ttgtggaaag agtcaaatgg ctctcctcaa gcgtattcaa 540
caaggggctg aaggatgccc agaaggtacc ccattgtatg ggatctgatc tggggcctcg 600
gtgcacatgc tttacatgtg tttagtcgag gttaaaaaac gtctaggccc cccgaaccac 660
ggggacgtgg ttttcctttg aaaaacacga tgataat 697

<210> SEQ ID NO 5
<211> LENGTH: 562
<212> TYPE: DNA
<213> ORGANISM: Encephalomyocarditis virus

<400> SEQUENCE: 5
ccccccccct aacgttactg gccgaagccg cttggaataa ggccggtgtg cgtttgtcta 60
tatgttattt tccaccatat tgccgtcttt tggcaatgtg agggcccgga aacctggccc 120
tgtcttcttg acgagcattc ctaggggtct ttcccctctc gccaaaggaa tgcaaggtct 180
gttgaatgtc gtgaaggaag cagttcctct ggaagcttct tgaagacaaa caacgtctgt 240
agcgaccctt tgcaggcagc ggaacccccc acctggcgac aggtgcctct gcggccaaaa 300
gccacgtgta taagatacac ctgcaaaggc ggcacaaccc cagtgccacg ttgtgagttg 360
gatagttgtg gaaagagtca aatggctctc ctcaagcgta ttcaacaagg ggctgaagga 420
tgcccagaag gtaccccatt gtatgggatc tgatctgggg cctcggtgca catgctttac 480
atgtgtttag tcgaggttaa aaaacgtcta ggccccccga accacgggga cgtggttttc 540
ctttgaaaaa cacgatgata at 562

<210> SEQ ID NO 6
<211> LENGTH: 156
<212> TYPE: DNA
<213> ORGANISM: Picobirnavirus sp.

<400> SEQUENCE: 6
gtaaattaaa tgctatttac aaaatttaaa cagaaaggag agatgttatg aaccggtttt 60
acaaggtttc atacatcgaa aatagcacta cctggggcag ccgacacact aacatcgtct 120
gtttaaccag aagtgttact gaaaggaggt tattta 156

<210> SEQ ID NO 7
<211> LENGTH: 340
<212> TYPE: DNA
<213> ORGANISM: Hepatitis C virus

<400> SEQUENCE: 7

| | | | | | | |
|---|---|---|---|---|---|---|
| acctgcccct | aatagggggcg | acactccgcc | atgaatcact | cccctgtgag | gaactactgt | 60 |
| cttcacgcag | aaagcgtcta | gccatggcgt | tagtatgagt | gtcgtacagc | ctccaggccc | 120 |
| cccctcccg | ggagagccat | agtggtctgc | ggaaccggtg | agtacaccgg | aattgccggg | 180 |
| aagactgggt | cctttcttgg | ataaacccac | tctatgcccg | gacatttggg | cgtgccccg | 240 |
| caagactgct | agccgagtag | cgttgggttg | cgaaaggcct | tgtggtactg | cctgataggg | 300 |
| tgcttgcgag | tgccccggga | ggtctcgtag | accgtgcatc | | | 340 |

<210> SEQ ID NO 8
<211> LENGTH: 315
<212> TYPE: DNA
<213> ORGANISM: Human Cosavirus

<400> SEQUENCE: 8

| | | | | | | |
|---|---|---|---|---|---|---|
| ctacaagctt | tgtgtaaaca | aacttttgtt | tggcttttct | caagcttctc | tcacatcagg | 60 |
| ccccaaagat | gtcctgaagg | taccccgtgt | atctgaggat | gagcaccatc | gactacccgg | 120 |
| acctgcaaaa | ttttgcaaac | gcatgtggta | tcccagcccc | ctcctctcgg | ggagggggct | 180 |
| ttgctcactc | agcacaggat | ctgatcagga | gatccacctc | cggtgcttta | caccggggcg | 240 |
| tggatttaaa | aattgcccaa | ggcctggcgc | acaacctagg | ggactaggtt | ttccttatat | 300 |
| tttaaagctg | tcaat | | | | | 315 |

<210> SEQ ID NO 9
<211> LENGTH: 182
<212> TYPE: DNA
<213> ORGANISM: Human Cosavirus

<400> SEQUENCE: 9

| | | | | | | |
|---|---|---|---|---|---|---|
| gtcttaggac | gacgcatgtg | gtatcccagc | ccccgcctac | attggcgggg | gcttttgaag | 60 |
| caccagacac | tggatctgat | caggaggagg | gtagctgctt | tacagcccct | cttaaaaatt | 120 |
| gcccaaggtc | cggccaccca | acctagggga | ctaggttttc | cttttatttt | taaattgtca | 180 |
| tt | | | | | | 182 |

<210> SEQ ID NO 10
<211> LENGTH: 759
<212> TYPE: DNA
<213> ORGANISM: Human Cosavirus

<400> SEQUENCE: 10

| | | | | | | |
|---|---|---|---|---|---|---|
| acatggggga | gactgcatgt | ggcagtcttg | aaacgtgtgg | tttgacgtct | accttatatg | 60 |
| gcagtgggtg | gagtactgca | aagatgtcac | cgtgctttac | acggttttg | aaccccacac | 120 |
| cggctgtttg | acgctcgtag | ggcagcaggt | ttattttcat | taaaattctt | actttctagc | 180 |
| tgcatgagtt | ctattcatgc | agacggagtg | atactcccgt | tccttcttgg | acaggttgcc | 240 |
| tccacgccct | ttgtggatct | taaggtgacc | aagtcactgg | tgttggaggt | gaagatagag | 300 |
| agtcctcttg | ggaatgtcat | gtggctgtgc | caggggttgt | agcgatgcca | ttcgtgtgtg | 360 |
| cggatttcct | ctcgtggtga | cacgagcctc | acaggccaaa | agcccgtcc | gaaaggaccc | 420 |
| gaatggtgga | gtgaccctga | ctcccccctg | catagttttg | tgattaggaa | cttgaggaat | 480 |

```
ttctgtcata aatctctatc acatcaggcc ccaaagatgt cctgaaggta ccctgtgtat    540
ctgaggatga gcaccaccga ctacccggac ttgcattagc agacacatgt ggttgcccag    600
ccccacctct tcagaggtgg ggctttgctc actcagcaca ggatctgatc aggagccccg    660
ctcgtgtgct ttacactcga cgcggggtta aaaattgccc aaggcctggc acaacaacct    720
aggggactag gttttcctat ttttgtaaat tatgtcaat                           759

<210> SEQ ID NO 11
<211> LENGTH: 478
<212> TYPE: DNA
<213> ORGANISM: Human rhinovirus

<400> SEQUENCE: 11
gtgacaatca gccagattgt taacggtcaa gcacttctgt ttccccggta cccttgtata     60
cgcttcaccc gaggcgaaaa gtgaggttat cgttatccgc aaagtgccta cgagaagcct    120
agtagcactt ttgaagccta tggctggtcg ctcaactgtt tacccagcag tagacctggc    180
agatgaggct agatgttccc caccagcgat ggtgatctag cctgcgtggc tgcctgcaca    240
ctctattgag tgtgaagcca gaaagtggac aaggtgtgaa gagcctattg tgctcacttt    300
gagtcctccg gcccctgaat gtggctaatc ctaaccccgt agctgttgca tgtaatccaa    360
catgtctgca gtcgtaatgg gcaactatgg atggaaccaa ctactttggg gtgtccgtgt    420
ttcttgtttt tctttatgct tgcttatggt gacaactgta gttattacat tgttacc       478

<210> SEQ ID NO 12
<211> LENGTH: 628
<212> TYPE: DNA
<213> ORGANISM: Human rhinovirus

<400> SEQUENCE: 12
ttaaaacagc ggatgggtat cccaccattc gacccattgg gtgtagtact ctggtactat     60
gtacctttgt acgcctgttt ctccccaacc acccttcctt aaaattccca cccatgaaac    120
gttagaagct tgacattaaa gtacaatagg tggcgccata tccaatggtg tctatgtaca    180
agcacttctg tttcccagga gcgaggtata ggctgtaccc actgccaaaa gcctttaacc    240
gttatccgcc aaccaactac gtaacagtta gtaccatctt gttcttgact ggacgttcga    300
tcaggtggat ttttccctcca ctagtttggt cgatgaggct aggaattccc cacgggtgac    360
cgtgtcctag cctgcgtggc ggccaaccca gcttatgctg ggacgcccct taaggacat     420 ggtgtgaaga ctcgcatgtg cttggttgtg agtcctccgg ccccctgaatg cggctaacct    480 taaccctaga gccttatgcc acgatccagt ggttgtaagg tcgtaatgag caattccggg    540
acgggaccga ctactttggg tgtccgtgtt tctcattttt cttcatattg tcttatggtc    600
acagcatata tatacatata ctgtgatc                                       628

<210> SEQ ID NO 13
<211> LENGTH: 618
<212> TYPE: DNA
<213> ORGANISM: Human rhinovirus

<400> SEQUENCE: 13
ttaaaactgg gagtgggttg ttcccactca ctccacccat gcggtgttgt actctgttat     60
tacggtaact ttgtacgcca gttttttccca cccttcccca taatgtaact tagaagtttg    120
tacaatatga ccaataggtg acaatcatcc agactgtcaa aggtcaagca cttctgtttc    180
```

```
cccggtcaat gaggatatgc tttacccaag gcaaaaacct tagagatcgt tatccccaca      240
ctgcctacac agagcccagt accatttttg atataattgg gttggtcgct ccctgcaaac      300
ccagcagtag acctggcaga tgaggctgga cattccccac tggcgacagt ggtccagcct      360
gcgtggctgc ctgctcaccc ttcttgggtg agaagcctaa ttattgacaa ggtgtgaaga      420
gccgcgtgtg ctcagtgtgc ttcctccggc ccctgaatgt ggctaacctt aaccctgcag      480
ccgttgccca taatccaatg ggtttgcggt cgtaatgcgc aagtgcggga tgggaccaac      540
tactttgggt gtccgtgttt cctgttttc ttttgattgc attttatggt gacaatttat      600
agtgtataga ttgtcatc                                                   618

<210> SEQ ID NO 14
<211> LENGTH: 610
<212> TYPE: DNA
<213> ORGANISM: Human rhinovirus

<400> SEQUENCE: 14
ttaaaactgg gtacaggttg ttcccacctg tatcacccac gtggtgtggt gctcttgtat       60
tccggtacac ttgcacgcca gtttgccacc cctcacccgt cgtaacttag aagctaacaa      120
ctcgaccaac aggcggtggt aaaccatacc acttacggtc aagcactcct gtttccccgg      180
tatgcgagga atagactcct acagggttga agcctcaagt atcgttatcc gcattggtac      240
tacgcaaagc ttagtagtgc cttgaaagtc ccttggttgg tcgctccgct agtttcccct      300
agtagacctg gcagatgagg caggacactc cccactggcg acagtggtcc tgcctgcgtg      360
gctgcctgcg cacccttagg ggtgcgaagc caagtgacag acaaggtgtg aagagccccg      420
tgtgctacca atgagtcctc cggcccctga atgcggctaa tccaacccca cagctattgc      480
acacaagcca gtgtgtatgt agtcgtaatg agcaattgtg ggacggaacc gactactttg      540
ggtgtccgtg tttcctttta ttcttatcat tctgcttatg gtgacaatac tgtgaaatag      600
tgttgttacc                                                            610

<210> SEQ ID NO 15
<211> LENGTH: 614
<212> TYPE: DNA
<213> ORGANISM: Human rhinovirus

<400> SEQUENCE: 15
taaaactgga tccaggttgt tcccacctgg atctcctatt gggagttgta ctctattatt       60
ccggtaattt tgtacgccag ttttatcttc ccctcccca attgtaactt agaaggttat      120
caatacgacc aataggtggt agttagccaa actaccaaag gtcaagcact tctgtttccc      180
cggtcaaagt tgatatgctc aacagggca aaaacaactg agatcgttat ccgcaaagtg      240
cctacgcaaa gcctagtaac acctttgaag atttatggtt ggtcgttccg ctatttccca      300
tagtagacct ggcagatgag gctagaaatc ccccactggc gacagtgctc tagcctgcgt      360
ggctgcctgc gcacccccttg ggtgcgaagc catacattgg acaaggtgtg aagagccccg      420
tgtgctcact ttgagtcctc cggcccctga atgtggctaa ccttaaccct gcagctagtg      480
catgtaatcc aacatgttgc tagtcgtaat gagtaattgc gggacgggac caactacttt      540
gggtgtccgt gtttcacttt ttccttttaa tattgcttat ggtgacaata tatatagcta      600
tatatattga cacc                                                       614

<210> SEQ ID NO 16
<211> LENGTH: 624
```

<212> TYPE: DNA
<213> ORGANISM: Salivirus A

<400> SEQUENCE: 16

```
ttcccctgca accattacgc ttactcgcat gtgcattgag tggtgcatgt gttgaacaaa    60
cagctacact cacatggggg cgggtttttcc cgccctacgg cttctcgcga ggcccacccc   120
tcccctttct cccataacta cagtgctttg gtaggtaagc atcctgatcc cccgcggaag   180
ctgctcacgt ggcaactgtg gggacccaga caggttatca aaggcacccg gtctttccgc   240
cttcaggagt atccctgcta gcgaattcta gtagggctct gcttggtgcc aacctccccc   300
aaatgcgcgc tgcgggagtg ctcttcccca actcacccta gtatcctctc atgtgtgtgc   360
ttggtcagca tatctgagac gatgttccgc tgtcccagac cagtccagta atggacgggc   420
cagtgtgcgt agtcgtcttc cggcttgtcc ggcgcatgtt tggtgaaccg gtggggtaag   480
gttggtgtgc ccaacgcccg tactcagggg atacctcaag gcacccagga atgccaggga   540
ggtaccccgc ttcacagcgg gatctgaccc tggggtaaat gtctgcgggg ggtcttcttg   600
gcccacttct cagtactttt cagg                                          624
```

<210> SEQ ID NO 17
<211> LENGTH: 730
<212> TYPE: DNA
<213> ORGANISM: Salivirus FHB

<400> SEQUENCE: 17

```
acatgggggg tctgcggacg gcttcggccc acccgcgaca agaatgccgt catctgtcct    60
cattcccgt attccttccc ttcccccgca accaccacgc ttactcgcgc acgtgttgag   120
tggcacgtgc gttgtccaaa cagctacacc cacaccttc ggggcgggtt tgtcccgccc   180
tcgggttcct cgcggaaccc cccctccct ctctctcttt ctatccgccc tcacttccca   240
taactacagt gctttggtag gtgagcaccc tgaccccccg cggaagctgc taacgtggca   300
actgtgggga tccaggcagg ttatcaaagg cacccggtct ttccgccttc aggagtatct   360
ctgccggtga attccggtag ggctctgctt ggtgccaacc tccccaaat gcgcgctgcg   420
ggagtgctct tccccaactc atcttagtaa cctctcatgt gtgtgcttgg tcagcatatc   480
tgaggcgacg ttccgctgtc ccagaccagt ccagcaatgg acgggccagt gtgcgtagtc   540
gctttccggt tttccggcgc atgtttggcg aaacgctgag gtaaggttgg tgtgcccaac   600
gcccgtaatt tggtgatacc tcaagaccac ccaggaatgc cagggaggta ccccacttcg   660
gtgggatctg accctgggct aattgtctac ggtggttctt cttgcttcca cttctctttt   720
ttctggcatg                                                         730
```

<210> SEQ ID NO 18
<211> LENGTH: 709
<212> TYPE: DNA
<213> ORGANISM: Salivirus NG-J1

<400> SEQUENCE: 18

```
tatggcaggc gggcttgtgg acggcttcgg cccacccaca gcaagaatgc catcatctgt    60
cctcaccccc aattttccct tttcttcccc tgcaaccatt acgcttactc gcatgtgcat   120
tgagtggtgc atgtgttgaa caaacagcta cactcacatg ggggcgggtt ttcccgccct   180
acggcctctc gcgaggccca ccccttccct cccttataa ctacagtgct ttggtaggta   240
agcatcctga tccccgcgg aagctgctca cgtggcaact gtggggaccc agacaggtta   300
```

| | | |
|---|---|---|
| tcaaaggcac ccggtctttc cgccttcagg agtatccctc ctagtgaatt ctagcggggc | 360 | |
| tctgcttggt gccaacctcc cccaaatgcg cgctgcggga gtgctcttcc ccaactcacc | 420 | |
| ctagtatcct ctcatgtgtg tgcttggtca gcatatctga gacgatgttc cgctgtccca | 480 | |
| gaccagtcca gtaatggacg ggccagtgcg tgtagtcgtc ttccggcttg tccggggcat | 540 | |
| gtttggtgaa ccggtggggt aaggttggtg tgcccaacgc ccgtactttg gtgacacctc | 600 | |
| aagaccaccc aggaatgcca gggaggtacc ccacctcacg gtgggatctg accctgggct | 660 | |
| aattgtctac ggtggttctt cttgcttcca cttctttctt ctgttcacg | 709 | |

<210> SEQ ID NO 19
<211> LENGTH: 708
<212> TYPE: DNA
<213> ORGANISM: Human Parechovirus

<400> SEQUENCE: 19

| | | |
|---|---|---|
| tttgaaaggg gtctcctaga gagcttggcc gtcgggcctt ataccccgac ttgctgagtt | 60 | |
| tctctaggag agccctttc ccagcccctga ggcggctggt caataaaagc ctcaaacgta | 120 | |
| actaacacct aagaagatca tgtaaaccct atgcctggtc tccactattc gaaggcaact | 180 | |
| tgcaataaga agagtgggat caagacgctt aaagcataga gacagttttc ttttctaacc | 240 | |
| cacatttgtg tggggtggca gatggcgtgc cataactcta atagtgagat accacgcttg | 300 | |
| tggaccttat gctcacacag ccatcctcta gtaagtttgt gagacgtctg gtgacgtgtg | 360 | |
| ggaacttatt ggaaacaaca ttttgctgca agcatcccta ctgccagcgg aaaaacacct | 420 | |
| ggtaacaggt gcctctgggg ccaaaagcca aggtttaaca gacccttag gattggttct | 480 | |
| aaacctgaga tgttgtggaa gatatttagt acctgctgat ctggtagtta tgcaaacact | 540 | |
| agttgtaagg cccatgaagg atgcccagaa ggtacccgta ggtaacaagt gacactatgg | 600 | |
| atctgatttg gggccagata cctctatctt ggtgatctgg ttaaaaaaca tctaatgggc | 660 | |
| caaacccggg ggggatcccc ggtttcctct tattctatca atgccact | 708 | |

<210> SEQ ID NO 20
<211> LENGTH: 508
<212> TYPE: DNA
<213> ORGANISM: Crohivirus B

<400> SEQUENCE: 20

| | | |
|---|---|---|
| gtataagaga caggtgtttg ccttgtcttc ggactggcat cttgggacca accccccttt | 60 | |
| tccccagcca tgggttaaat ggcaataaag gacgtaacaa cttttgtaacc attaagcttt | 120 | |
| gtaattttgt aaccactaag ctttgtgcac ataatgtaac catcaagctt gttagtccca | 180 | |
| gcaggaggtt tgcatgcttg tagccgaaat ggggctcgac ccccccatagt aggatacttg | 240 | |
| attttgcatt ccattgtgga cctgcaaact ctacacatag aggctttgtc ttgcatctaa | 300 | |
| acacctgagt acagtgtgta cctagaccct atagtacggg aggaccgttt gtttcctcaa | 360 | |
| taaccctaca taataggcta ggtgggcatg cccaatttgc aagatcccag actgggggtc | 420 | |
| ggtctgggca gggttagatc cctgttagct actgcctgat agggtggtgc tcaaccatgt | 480 | |
| gtagtttaaa ttgagctgtt catatacc | 508 | |

<210> SEQ ID NO 21
<211> LENGTH: 248
<212> TYPE: DNA
<213> ORGANISM: Picornaviridae sp.

<400> SEQUENCE: 21

```
actgaagatc ctacagtaac tactgcccca atgaacgcca cagatgggtc tgctgatgac    60
tacctatctt agtgctagtt gaggtttgaa gtgagccggt ttttagaaga accagtttct   120
gaacattatc atccccagca tctattctat acgcacaaga tagatagtca tcagcagaca   180
catctgtgct actgcttgat agagttgcgg ctggtcaact tagattggta taaccagttg   240
agtggcaa                                                            248
```

<210> SEQ ID NO 22
<211> LENGTH: 516
<212> TYPE: DNA
<213> ORGANISM: Rosavirus M-7

<400> SEQUENCE: 22

```
tatgcatcac tggacggcct aacctcggtc gtggcttctt gccgatttca gcgctaccag    60
gctttctggt ctcgccaggc gttgattagt aggtgcactg tctaagtgaa gacagcagtg   120
ctctctgtga aaagttgatg acactcttca ggtttgtagc gatcactcaa ggctagcgga   180
tttccccgtg tggtaacaca cgcctctagg cccagaaggc acggtgttga cagcacccct   240
tgagtggctg gtcttcccca ccagcacctg atttgtggat tcttcctagt aacgacaag    300 catggctgct cttaagcatt cagtgcgtcc ggggctgaag gatgcccaga aggtacccgc   360
aggtaacgat aagctcactg tggatctgat ctggggctgc gggctgggtg tctttccacc   420
cagccaaaac ccgtaaaacg gtagtcgcag ttaaaaaacg tctaggcccc accccccag    480 ggatgggggg ttcccttaaa ccctcacaag ttcaac                             516
```

<210> SEQ ID NO 23
<211> LENGTH: 478
<212> TYPE: DNA
<213> ORGANISM: Shanbavirus A

<400> SEQUENCE: 23

```
tgaaaggggg gcgcagggtg gtggtggtta ctaaatacccc accatcgccc tgcacttccc    60
ttttcccctg tggctcaggg tcacttagcc ccctctttgg gttaccagta gttttctacc   120
cctgggcaca gggttaacta tgcaagacgg aacaacaatc tcttagtccc cctcgccgat   180
agtgggctcg accccccatgt gtaggagtgg ataagggacg gagtgagccg atacggggaa   240
gagtgtgcgg tcacaccctta attccatgag cgctgcgaag aaggaagctg tgaacaatgg   300
cgacctgaac cgtacacatg gagctccaca ggcatggtac tcgttagact acgcagcctg   360
gttgggagtg gtatacccct gggtgagccg ccagtgaatg ggagttcact ggttaacaca   420
cactgcctga tagggtcagg gcctcctgtc cccgccgtaa tgaggtagac catatgcc    478
```

<210> SEQ ID NO 24
<211> LENGTH: 403
<212> TYPE: DNA
<213> ORGANISM: Pasivirus A

<400> SEQUENCE: 24

```
gcggctggat attctggccg tgcaactgct tttgaccagt ggctctgggt aacttagcca    60
aagtgtcctt ctcccttttcc ctattatatg ttttatggct tgtctggtc ttgtttagtt   120 tatatataag atccttttccg ccgatatga cctcgacagt ctagtgtagg aggattggtg   180
atattaattt gccccagaag agtgaccgtg acacatagaa accatgagta catgtgtatc   240
cgtggaggat cgcccgggac tggattccat atcccattgc catcccaaca agcggagggt   300
```

```
atacccacta tgtgcacgtc tgcagtggga gtctgcagat ttagtcatac tgcctgatag    360
ggtgtgggcc tgcactctgg ggtactcagg ctgtttatat aat                      403
```

<210> SEQ ID NO 25
<211> LENGTH: 404
<212> TYPE: DNA
<213> ORGANISM: Pasivirus A

<400> SEQUENCE: 25

```
gctggacttt ctggctgcgc aactgctttt aaccagtggc tctgggttac ttagccaaaa     60
ccccctttcc ccgtacccta gtttgtgtgt gtattattat tttgttgttg ttttgtaaat    120
ttttatataa gatcctttcc gccgatatag acctcgacag tctagtgtag gaggattggt    180
gatattaata tgccccagaa gagtgaccgt gacacataga aaccatgagt acatgtgtat    240
ccgtggagga tcgcccggga ctggattcca tatcccattg ccatcccaac aaacggaggg    300
tatacccgct atgtgcgcgt ctacagtggg aatctgtaga tttagtcata ctgcctgata    360
gggtgtgggc ctgcactctg gggtactcag gctgtttata taat                     404
```

<210> SEQ ID NO 26
<211> LENGTH: 744
<212> TYPE: DNA
<213> ORGANISM: Echovirus E14

<400> SEQUENCE: 26

```
ttaaaacagc ctgtgggttg ttcccatcca cagggcccac tgggcgccag cactctggta     60
ttgcggtacc ttagtgcgcc tgttttatat acccgtcccc caaacgtaac ttagacgcat    120
gtcaacgaag accaatagta agcgcagcac accagctgtg ttccggtcaa gcacttctgt    180
taccccggac cgagtatcaa taagctactc acgtggctga aggagaaaac gttcgttacc    240
cgaccaatta cttcaagaaa cctagtaaca ccatgaaggt tgcgcagtgt ttcgctccgc    300
acaaccccag tgtagatcag gtcgatgagt caccgcattc cccacgggtg accgtggcgg    360
tggctgcgct ggcggcctgc ccatggggaa acccatggga cgcttcaata ctgacatggt    420
gcgaagagtc tattgagcta attggtagtc ctccggcccc tgaatgcggc taatcctaac    480
tgcggagcag ataccacac accagtgggc agtctgtcgt aacgggcaac tctgcagcgg    540
aaccgactac tttgggtgtc cgtgtttctc tttatcctta tactggctgc ttatggtgac    600
aattgagaga ttgttaccat atagctattg gattggccat ccggtgacaa atagagcaat    660
tgtgtatttg tttgttggtt tcgtgccatt aaattacaag gttctaaaca cccttaatct    720
tattatagca ttcaacacaa caaa                                           744
```

<210> SEQ ID NO 27
<211> LENGTH: 663
<212> TYPE: DNA
<213> ORGANISM: Human Parechovirus

<400> SEQUENCE: 27

```
gtacattaga tgcgtcatct gcaactttag tcaataaatt acctccaatg tcattaccaa     60
cattccctac cttttcacta acacctaaga caacaagtac ctatgcctgg tctccactat    120
tcgaaggcaa cttgcaataa gaagagtgga attaagacgc ttaaagcata gagctagtta    180
tcttttctaa cccacaaagt tttgtggggt ggcagatggc gtgccataac tctattagtg    240
agataccatg cttgtggatc ttatgctcac acagccatcc tctagtaagt tgataaggtg    300
tctggtgata tgtgggaact cacatgaacc attaatttac cgtaaggtat cctatagcca    360
```

```
gcggaatcac atctggtgac agatgcctct ggggccgaaa gccaaggttt aacagaccct      420
ataggattgg tttcaaaacc tgaattgatg tggattgtgt atagtacctg ttgatctggt      480
aacagtgtca acactagttg taaggcccac gaaggatgcc cagaaggtac ccgtaggtaa      540
caagtgacac tatggatctg atctggggcc agctacctct atcatggtga gttggttaaa      600
aaacgtctag tgggccaaac ccagggggga tccctggttt cctttttacct aatcaaagcc     660 act                                                                    663
```

<210> SEQ ID NO 28
<211> LENGTH: 744
<212> TYPE: DNA
<213> ORGANISM: Aichi virus

<400> SEQUENCE: 28

```
tttgaaaagg gggtgggggg gcctcggccc cctcacctc ttttccggtg gtctggtccc       60
ggaccaccgt tactccattc agcttcttcg gaacctgttc ggaggaatta aacgggcacc     120
catactcccc ccaccccct tttgtaacta agtatgtgtg ctcgtgatct tgactcccac      180
ggaacggacc gatccgttgg tgaacaaaca gctaggtcca catcctccct tcccctggga    240
gggcccccgc cctcccacat cctcccccca gcctgacgta tcacaggctg tgtgaagccc    300
ccgcgaaagc tgctcacgtg gcaattgtgg gtccccctt catcaagaca ccaggtcttt    360
cctccttaag gctagccccg cgtgtgaat tcacgttggg caactagtgg tgtcactgtg     420
cgctcccaat ctcggccgcg gagtgctgtt ccccaagcca aaccctggc ccttcactat     480 gtgcctggca agcatatctg agaaggtgtt ccgctgtggc tgccaacctg gtgacaggtg   540
ccccagtgtg cgtaaccttc ttccgtctcc ggacggtagt gattggttaa gatttggtgt    600
aaggttcatg tgccaacgcc ctgtgcggga tgaaacctct actgccctag gaatgccagg  660
caggtacccc cctccgggt gggatctgag cctgggctaa ttgtctacgg gtagtttcat      720
ttccaatcct tttatgtcgg agtc                                            744
```

<210> SEQ ID NO 29
<211> LENGTH: 734
<212> TYPE: DNA
<213> ORGANISM: Hepatitis A virus

<400> SEQUENCE: 29

```
ttcaagaggg gtctccggag ttttccggaa ccctcttgg aagtccatgg tgaggggact      60
tgatacctca ccgccgtttg cctaggctat aggctaaatt tcccttccc tgtccttccc     120 ctatttcctt tgttttgtt tgtaaatatt aattcctgca ggttcagggt tctttaatct    180
gtttctctat aagaacactc aatttttcac gctttctgtc tcctttcttc cagggctctc    240
cccttgccct aggctctggc cgttgcgccc ggcggggtca actccatgat tagcatggag   300
ctgtaggagt ctaaattggg gacgcagatg tttgggacgt cgccttgcag tgttaacttg   360 gcttctcatga acctctttga tcttccacaa ggggtaggct acgggtgaaa cctcttaggc   420
taatacttca atgaagagat gccttggata gggtaacagc ggcggatatt ggtgagttgt   480
taagacaaaa accattcaac gccggaggac tggctctcat ccagtggatg cattgaggga   540
attgattgtc agggctgtct ctaggtttaa tctcagacct ctctgtgctt agggcaaaca    600
ctatttggcc ttaaatggga tcctgtgaga gggggtccct ccattgacag ctggactgtt   660
ctttggggcc ttatgtggtg tttgcctctg aggtactcag gggcatttag gttttttcctc   720
```
attcttaaat aata                                                        734

<210> SEQ ID NO 30
<211> LENGTH: 638
<212> TYPE: DNA
<213> ORGANISM: Unknown
<220> FEATURE:
<221> NAME/KEY: source
<223> OTHER INFORMATION: /note="Description of Unknown:
      unknown Phopivirus sequence"

<400> SEQUENCE: 30
gggagtaaac ctcaccaccg tttgccgtgg tttacggcta cctattttttg gatgtaaata     60
ttaattcctg caggttcagg tctcttgaat tatgtccacg ctagtggcac tctcttaccc    120
ataagtgacg ccttagcgga acctttctac acttgatgtg gttaggggtt acattatttc    180
cctgggcctt ctttggccct ttttcccctg cactatcatt cttttcttccg ggctctcagc   240
atgccaatgt tccgaccggt gcgcccgccg gggttaactc catggttagc atggagctgt    300
aggccctaaa agtgctgaca ctggaactgg actattgaag catacactgt taactgaaac    360
atgtaactcc aatcgatctt ctacaagggg taggctacgg gtgaaacccc ttaggttaat    420
actcatattg agagatactt ctgataggtt aaggttgctg gataatggtg agtttaacga    480
caaaaaccat tcaacagctg tgggccaacc tcatcaggta gatgcttttg agccaagtg     540
cgtaggggtg tgtgtggaaa tgcttcagtg gaaggtgccc tcccgaaagg tcgtaggggt    600
aatcaggggc agttaggttt ccacaattac aatttgaa                            638

<210> SEQ ID NO 31
<211> LENGTH: 743
<212> TYPE: DNA
<213> ORGANISM: Coxsackievirus A10

<400> SEQUENCE: 31
gctcttccga tctgggttgt tcccacccac agggcccact gggcgccagc actctgattc     60
cacggaatct ttgtgcgcct gttttacaac ccttcccaat ttgtaacgta gaagcaatac    120
acactactga tcaatagtag gcatggcgcg ccagtcatgt catgatcaag cacttctgtt    180
ccccccggact gagtatcaat agactgctca cgcggttgaa ggagaaaacg ttcgttaccc   240
ggctaactac ttcgagaaac ctagtagcac catggaagct gcggagtgtt tcgctcagca    300
cttttccccgt gtagatcagg tcgatgagtc actgcaatcc ccacgggcga ccgtggcagt    360
ggctgcgttg gcggcctgcc tatggggcaa cccataggac gctctaatgt ggacatggtg    420
cgaagagtct attgagctag ttagtagtcc tccggcccct gaatgcggct aatcctaact    480
gcggagcaca tgccttcaac ccaggaggtg gtgtgtcgta acgggtaact ctgcagcgga    540
accgactact ttgggtgtcc gtgtttcctt ttatccttat attggctgct tatggtgaca    600
atcacggaat tgttgccata tagctattgg attggccatc cggtgtctaa cagagctatt    660
gtatacctat ttgttggatt tactccccta tcatacaaat ctctgaacac tttgtgcttt    720
atactgaact taaacacacg aaa                                             743

<210> SEQ ID NO 32
<211> LENGTH: 746
<212> TYPE: DNA
<213> ORGANISM: Enterovirus C

<400> SEQUENCE: 32
ttaaaacagc tctgggggttg ttcccacccc agaggcccac gtggcggcca gtacaccggt     60

```
accacggtac ccttgtacgc ctgttttata ctcccctccc cgtaaactag aagcacgaaa        120
cacaagttca atagaagggg gtacagacca gtaccaccac gaacaagcac ttctgttccc        180
ccggtgaggt cacatagact gtccccacgg tcaaaagtga ctgatccgtt atccgctcac        240
gtacttcgga aagcctagta ccaccttgga atctacgatg cgttgcgctc agcactcgac        300
cccggagtgt agcttaggct gatgagtctg gacgttcccc actggtgaca gtggtccagg        360
ctgcgttggc ggcctacctg tggtccaaaa ccacaggacg ctagtagtga acaaggtgtg        420
aagagcccac tgagctacct gagaatcctc cggcccctga atgcggctaa tcccaaccac        480
ggagcaggta atcgcaaacc agcggtcagc ctgtcgtaac gcgtaagtct gtggcggaac        540
cgactacttt gggtgtccgt gtttcctttt attttatgg tggctgctta tggtgacaat        600
catagattgt tatcataaag caaattggat tggccatccg gagtgagcta aactatctat        660
ttctctgagt gttggattcg tttcacccac attctgaaca atcagcctca ttagtgttac        720
cctgttaata agacgatatc atcacg                                             746

<210> SEQ ID NO 33
<211> LENGTH: 726
<212> TYPE: DNA
<213> ORGANISM: Enterovirus D

<400> SEQUENCE: 33
ttaaaacagc tctggggttg ttcccacccc agaggcccac gtggcggcta gtactccggt         60
accccggtac ccttgtacgc ctgttttata ctcccttttcc caagtaactt tagaagaaat       120
aaactaatgt tcaacaggag ggggtacaaa ccagtaccac cacgaacaca cacttctgtt        180
tccccggtga agttgcatag actgtaccca cggttgaaag cgatgaatcc gttacccgct        240
taggtacttc gagaagccta gtatcatctt ggaatcttcg atgcgttgcg atcagcactc        300
taccccgagt gtagcttggg tcgatgagtc tggacacccc acaccggcga cgtggtccag        360
gctgcgttgg cggcctaccc atggctagca ccatgggacg ctagttgtga acaaggtgcg        420
aagagcctat tgagctacct gagagtcctc cggcccctga atgcggctaa tcccaaccac        480
ggagcaaatg ctcacaatcc agtgagtggt tgtcgtaat gcgcaagtct gtggcggaac        540
cgactacttt gggtgtccgt gtttcctttt attttatta tggctgctta tggtgacaat        600
ctgagattgt tatcatatag ctattggatt agccatccgg tgatatcttg aaattttgcc        660 ataactttt cacaaatcct acaacattac actacacttt ctcttgaata attgagacaa        720
ctcata                                                                   726

<210> SEQ ID NO 34
<211> LENGTH: 737
<212> TYPE: DNA
<213> ORGANISM: Enterovirus J

<400> SEQUENCE: 34
ttaaaatagc ctcagggttg ttcccaccct gagggcccac gtggtgtagt actctggtat         60
tacggtacct ttgtacgcct attttatacc cccttcccca gtaatttag aagcaagcac        120 aaaccagttc agtagtaagc agtacaatcc agtactgtaa tgaacaagta cttctgttac        180
cccggaaggg tctatcggta agctgtaccc acggctgaag aatgacctac cgttaaccgg        240
ctacctactt cgagaagcct agtaatgccg ttgaagtttt attgacgtta cgctcagcac        300 actacccgt gtgtagtttt ggctgatgag tcacggcact ccccacgggc gaccgtggcc        360
```

```
gtggctgcgt tggcggccaa ccaaggagtg caagctcctt ggacgtcata ttacagacat    420
ggtgtgaaga gcctattgag ctaggtggta gtcctccggc ccctgaatgc ggctaatcct    480
aactccggag catatcggtg cgaaccagca cttggtgtgt tgtaatacgt aagtctggag    540
cggaaccgac tactttgggt gtccgtgttt cctgttttaa cttttatggc tgcttatggt    600
gacaatttaa cattgttacc atatagctgt tgggttggcc atccggattt tgttataaaa    660
ccatttcctc gtgccttgac ctttaacaca tttgtgaact tctttaaatc cctttattta    720
gtccttaaat actaaga                                                    737

<210> SEQ ID NO 35
<211> LENGTH: 327
<212> TYPE: DNA
<213> ORGANISM: Human Pegivirus 2

<400> SEQUENCE: 35
aactgttgtt gtagcaatgc gcatattgct acttcggtac gcctaattgg taggcgcccg     60
gccgaccggc cccgcaaggg cctagtagga cgtgtgacaa tgccatgagg gatcatgaca    120
ctggggtgag cggaggcagc accgaagtcg ggtgaactcg actcccagtg cgaccacctg    180
gcttggtcgt tcatggaggg catgcccacg ggaacgctga tcgtgcaaag ggatgggtcc    240
ctgcactggt gccatgcgcg gcaccactcc gtacagcctg ataggggtggc ggcgggcccc    300 cccagtgtga cgtccgtgga gcgcaac                                          327

<210> SEQ ID NO 36
<211> LENGTH: 281
<212> TYPE: DNA
<213> ORGANISM: GB virus C

<400> SEQUENCE: 36
tgacgtgggg gggttgattt tccccccccg gcactgggtg caagccccag aaaccgacgc     60
ctatctaagt agacgcaatg actcggcgcc gactcggcga ccggccaaaa ggtggtggat    120
gggtgatgac agggttggta ggtcgtaaat cccggtcatc ctggtagcca ctataggtgg    180
gtcttaagag aaggtcaaga ttcctcttac gcctgcggcg agaccgcgca cggtccacag    240
gtgttggccc taccggtgtg aataagggcc cgacatcagg c                          281

<210> SEQ ID NO 37
<211> LENGTH: 459
<212> TYPE: DNA
<213> ORGANISM: GB virus C

<400> SEQUENCE: 37
gacgtggggg ggttgatccc ccccctttgg cactgggtgc aagccccaga aaccgacgcc     60
tatttaaaca gacgttaaga accggcgccg accggcgac cggccaaaag gtggtggatg    120
ggtgatgcca gggttggtag gtcgtaaatc ccggtcatct tggtagccac tataggtggg    180
tcttaagggt tggttaaggt ccctctggcg cttgtggcga aaagcgcac ggtccacagg    240 tgttggccct accggtgtga ataagggccc gacgtcaggc tcgtcgttaa ccgagcccca    300
ctacccacct gggcaaacaa cgcccacgta cggtccacgt cgcccttcaa tgtctctctt    360
gaccaatagg cttagccggc gagttgacaa ggaccagtgg gggctgggcg gtaggggaag    420 gaccctgcc gctgcccttc ccggtggagt gggaaatgc                            459

<210> SEQ ID NO 38
<211> LENGTH: 350
```

```
<212> TYPE: DNA
<213> ORGANISM: GB virus C

<400> SEQUENCE: 38
tgacgtgggg gggttgatcc gcccccccg gcactcggtg caagcccat aaaccgacgc      60
ctatctaagt agacgcaatg actcggcgcc gactcggcga ccggccaaaa ggtggtggat   120
gggtggtgac agggttggta ggtcgtaaat cccggtcatc ctggtagcca ctataggtgg   180
gtcttaagag aaggtcaaga ctcctcttgt gcctgcggcg agaccgcgca cggtccacag   240
gtgctggccc taccggtgtg aataagggcc cgacgtcagg ctcgtcgtta aaccgagccc   300
gtcacccacc tgggcaaacg acgcccacgt acggtccacg tcgcccttca              350

<210> SEQ ID NO 39
<211> LENGTH: 318
<212> TYPE: DNA
<213> ORGANISM: Pegivirus A

<400> SEQUENCE: 39
tgtagcaatg cgcatattgc tacttcggta cgcctaattg gtaggcgccc ggccgaccgg    60
ccccgcaagg gcctagtagg acgtgtgaca atgccatgcg ggatcatgac actggggtga   120
gcggaggcag caccgaagtc gggtgaactc gactcccagt gcgaccacct ggcttggtcg   180
ttcatggagg gcatgccac gggaacgctg atcgtgcaaa gggatgggtc cctgcactgg   240
tgccatgcgc ggcaccactc cgtacagcct gatagggtgg cggcgggccc cccagtgtg   300
acgtccgtgg agcgcaac                                                 318

<210> SEQ ID NO 40
<211> LENGTH: 399
<212> TYPE: DNA
<213> ORGANISM: Pasivirus A

<400> SEQUENCE: 40
attttctggc cgtgtagctg cttttgacca gtggctctgg gttacttagc caaatccccc    60
ttccttcacc cttttaaatt tgatggtctg tgttgtttgt tttgtcttgt ctaaataata   120
tataagatcc ttcccgccga tacagacctc gacagtctgg tgtaggaggg ttggtgttat   180
taatttgccc cagaagagtg accgtgacac atagaaacca tgagtacatg tgtatccgtg   240
gaggatcgcc cgggactgga ttccatatcc cattgccatc ccaacaagcg agggtatac   300
ccactatgtg cgcgtttgca gtgggaatct gcaaatttag tcatactgcc tgatagggtg   360
tgggcctgca ctctggggta ctcaggctgt tcatataat                           399

<210> SEQ ID NO 41
<211> LENGTH: 430
<212> TYPE: DNA
<213> ORGANISM: Sapelovirus sp.

<400> SEQUENCE: 41
cccctccacc cttaaggtgg ttgtatccca cataccccac cctcccttcc aaagtggacg    60
gacaactgga ttttgactaa cggcaagtct gaatggtatg atttggatac gtttaaacgg   120
cagtagcgtg gcgagctatg gaaaaatcgc aattgtcgat agccatgtta gtgacgcgct   180
tcggcgtgct cctttggtga ttcggcgact ggttacagga gagtaggcag tgagctatgg   240
gcaaaccctct acagtattac ttagagggaa tgtgcaattg agacttgacg agcgtctctt   300
tgagatgtgg cgcatgctct tggcattacc atagtgagct tccaggttgg gaaacctgga   360
```

```
ctgggcctat actacctgat agggtcgcgg ctggccgcct gtaactagta tagtcagttg    420
aaaccccccc                                                          430

<210> SEQ ID NO 42
<211> LENGTH: 504
<212> TYPE: DNA
<213> ORGANISM: Rosavirus B

<400> SEQUENCE: 42
gtctctttag tgtctatgct tcagagagcg gtgaactgac accgttgctt cttgcacagc    60
ccttcgtgcc ggtctttccg gttctcgaca gcgttgggca tcatggctag ttaggctaag   120
atagtggatg atctagtgaa cagttttgga ttgtttggag ttttgtagcg atgctagtag   180
tgtgtgtgga cctccccacg tggtaacacg tgccccacag gccaaaagcc aaggtgttga   240
aagcacccct actagtccca gactcaccca tctgggaact cctctcatga aaatcttag    300 taacttttga ttcggctatt catcaacctc tctagtcaag gctgaagga tgcccggaag    360 gtacccgcag gtaacgataa gctcactgtg gatctgatcc ggggctttgg tgcgaccgtc   420
tgtccggcgt agccagagtt aaaaaacgtc taggcccttc caccccaagg gattggggtt   480
tccccaatca tttgaaagtt cact                                          504

<210> SEQ ID NO 43
<211> LENGTH: 532
<212> TYPE: DNA
<213> ORGANISM: Bakunsa virus

<400> SEQUENCE: 43
ttttgaacgc cacctcggag cgatatccgg ggaccccctc ccctttttcc ttcctacctt    60
cttcccaaat ttccctcttc ccttgttatt ttggtttgga tttcctggac atgactcgga   120
cggatctatc tcatttgctt tgtgtctgct ccaccagtgg catggtcgaa agatcatcaa   180
cactggacgt gtactgtaat ggccaaacgt gcccacaggg gaaaccatgc cggtcgctgt   240
agcggcgggt ggacgtggtg gacccctctc cctgctcata aactttgggt aggtgaaggg   300
ttcaagcgac gcttgccgtg agggcgcatc cggatggtgg gaaccaacaa actaggctgt   360
aatggccgac ctcaggtgga tgagctaggg ctgctgcacc aaaagggact cgattcgata   420
tcccggcctg gtagcctagt gcagtggact cgtagttggg aatctacgac tggcctagta   480
cagggtgata gccccgtttc ccacgcccac ctgttgtagg gacacccccc cc            532

<210> SEQ ID NO 44
<211> LENGTH: 494
<212> TYPE: DNA
<213> ORGANISM: Tremovirus A

<400> SEQUENCE: 44
tttgaaagag gcctccggag tgtccggagg ctctctttcg acccaaccca tactgggggg    60
tgtgtgggac cgtacctgga gtgcacggta tatatgcatt cccgcatggc aagggcgtgc   120
taccttgccc cttgacgcat ggtatgcgtc atcatttgcc ttggttaagc cccatagaaa   180
cgaggcgtca cgtgccgaaa atcccttttgc gtttcacaga accatcctaa ccatgggtgt   240
agtatgggaa tcgtgtatgg ggatgattag gatctctcgt agagggatag gtgtgccatt   300
caaatccagg gagtactctg gctctgacat tgggacattt gatgtaaccg gacctggttc   360
agtatccggg ttgtcctgta ttgttacggt gtatccgtct tggcacactg aaagggtatt   420
tttgggtaat cctttcctac tgcctgatag ggtggcgtgc ccggccacga gagattaagg   480
```

```
gtagcaatttaaac                                                             494

<210> SEQ ID NO 45
<211> LENGTH: 378
<212> TYPE: DNA
<213> ORGANISM: Swine Pasivirus 1

<400> SEQUENCE: 45
gcttttgacc agtggctctg ggttacttag ccaagtccct ttctcttatt ttcactagtt        60
tatgttgtgt gttgtctgtt ttgttttgtt taaattgtat acaagatcct tcccgccgac       120
acagacctcg acagtctggt gtaggagggt tggtgatatt aatttgcccc aaaagagtga       180
ccgtgatacg tggaaaccat gagtacatgt gtatccgtgg aggatcgccc gggactggat       240
tccatatccc attgccatcc caacaaacgg agggtatacc caccacgtgc gcgtttgcag       300
tgggaatctg caaatttagt catactgcct gatagggtgt gggcctgcac tttggggtac       360
tcaggctgtt catataat                                                      378

<210> SEQ ID NO 46
<211> LENGTH: 319
<212> TYPE: DNA
<213> ORGANISM: Parechovirus-like virus PLV-CHN

<400> SEQUENCE: 46
acatggggta tgttgtctgt cctgttttgt tgaaacaata tataagatcc tttccgccga        60
tatagacctc gacagtctag tgtaggagga ttggtgatag taacttgccc cagaagagtg       120
accgtgacac atagaaacca tgagtacatg tgtatccgtg gaggatcgcc cgggactgga       180
ttccatatcc cattgccatc ccaacaaacg gagggtatac ccactatgtg cgcgtttgca       240
gtgggagcct gcaaatttag tcatactgcc tgatagggtg tgggcctgca ctctgggta       300 ctcaggctgt ttatataat                                                     319

<210> SEQ ID NO 47
<211> LENGTH: 420
<212> TYPE: DNA
<213> ORGANISM: Pasivirus A

<400> SEQUENCE: 47
tgaaaaagtg gttgtgcagc tggattttcc ggctgtgcaa ctgcttttga ccagtggctc        60
tgggttactt agccaaattc cttttcccta tccctattgg tttgtgttgt gtgttgtttg       120
ttttgttttg tcttaactat atacaagatc cttcccgccg atacagacct cgacagtctg       180
gtgtaggagg ttggtgtta ttaatttgcc ccaaaagagt gaccgtgaca cgtggaaacc       240
atgagtacat gtgtatccgt ggaggatcgc ccgggactgg attccatatc ccattgccat       300
cccaacaaac ggagggtata cccaccacgt gcgcgtttgc agtgggaatc tgcaaattta       360
gtcatactgc tgatagggt gtgggcctgc actttggggt actcaggctg tttatataat       420

<210> SEQ ID NO 48
<211> LENGTH: 373
<212> TYPE: DNA
<213> ORGANISM: Sicinivirus sp.

<400> SEQUENCE: 48
gtgtcattaa ggtgtgtttg gaagttcgaa ttagctggtt tgtggtgatt agtagacccc        60
ctggaggtac ccaattcgga tctgaccagg gacccgtgac tataccgctc cggtaattcg       120
```

```
ggtttaaaac aatgaacgtc accacacaat tactttctc attttatttt catcattgtc      180
ttcctattta ccgattacac tcgatttcct tggatgttcc tggagatttc cctggttacc    240
tggaccctca ttattgttgt tgtttcaccc agcgagctgt cccaattgct tattatttgc    300
gcttacaact tcgtcctaat attttttctgg ttgatcgggt tgattgagct cccgggctat    360
cctgccattc aac                                                        373
```

```
<210> SEQ ID NO 49
<211> LENGTH: 280
<212> TYPE: DNA
<213> ORGANISM: Hepacivirus K

<400> SEQUENCE: 49
gggaacaatg gtccgtccgc ggaacgactc tagccatgag tctagtacga gtgcgtgcca    60
cccattagca caaaaaccac tgactgagcc acacccctcc cggaatcctg agtacaggac    120
attcgctcgg acgacgcatg agcctccatg ccgagaaaat tgggtatacc cacgggtaag    180
gggtggccac ccagcgggaa tctgggggct ggtcactgac tatggtacag cctgataggg    240
tgctgccgca gcgtcagtgg tatgcggctg ttcatggaac                           280
```

```
<210> SEQ ID NO 50
<211> LENGTH: 384
<212> TYPE: DNA
<213> ORGANISM: Hepacivirus A

<400> SEQUENCE: 50
acctccgtgc taggcacggt gcgttgtcag cgttttgcgc ttgcatgcgc tacacgcgtc    60
gtccaacgcg gagggaactt cacatcacca tgtgtcactc ccctatgga gggttccacc    120 ccgcttacac ggaaatgggt taaccatacc caaagtacgg gtatgcgggt cctcctaggg    180 ccccccgc aggtcgaggg agctggaatt cgtgaattcg tgagtacacg aaaatcgcgg     240
cttgaacgtc tttgaccttc ggagccgaaa tttgggcgtg ccccacgaag gaaggcgggg    300
gcggtgttgg gccgccgccc cctttatccc acggtctgat aggatgcttg cgagggcacc    360
tgccggtctc gtagaccata ggac                                            384
```

```
<210> SEQ ID NO 51
<211> LENGTH: 384
<212> TYPE: DNA
<213> ORGANISM: Bovine viral diarrhea virus 1

<400> SEQUENCE: 51
gtatacgaga atttgcctag gacctcgttt acaatatggg caatctaaaa ttataattag    60
gcctaaggga caaatcctcc tcagcgaagg ccgaaaagag gctagccatg cccttagtag    120
gactagcaaa ataaggggg tagcaacagt ggtgagttcg ttggatggct gaagccctga    180
gtacagggta gtcgtcagtg gttcgacgct tcggaggaca agcctcgaga taccacgtgg    240
acgagggcat gcccacagca catcttaacc tggacggggg tcgttcaggt gaaaacggtt    300
taaccaaccg ctacgaatac agcctgatag ggtgctgcag aggcccactg tattgctact    360
gaaaatctct gctgtacatg gcac                                            384
```

```
<210> SEQ ID NO 52
<211> LENGTH: 372
<212> TYPE: DNA
<213> ORGANISM: Border Disease virus

<400> SEQUENCE: 52
```

```
gtatacggga gtagctcatg cccgtataca aaattggata ttccaaaact cgattgggtt    60
agggagccct cctagcgacg gccgaaccgt gttaaccata cacgtagtag gactagcaga   120
cgggaggact agccatcgtg gtgagatccc tgagcagtct aaatcctgag tacaggatag   180
tcgtcagtag ttcaacgcag gcacggttct gccttgagat gctacgtgga cgagggcatg   240
cccaagactt gctttaatct cggcgggggt cgccgaggtg aaaacaccta acggtgttgg   300
ggttacagcc tgatagggtg ctgcagaggc ccacgaatag gctagtataa aaatctctgc   360
tgtacatggc ac                                                       372

<210> SEQ ID NO 53
<211> LENGTH: 388
<212> TYPE: DNA
<213> ORGANISM: Bovine viral diarrhea virus 2

<400> SEQUENCE: 53
gtatacgaga ttagctaaag tactcgtata tggattggac gtcaacaaat ttttaattgg    60
caacgtaggg aaccttcccc tcagcgaagg ccgaaaagag gctagccatg ccctttagta   120
ggactagcaa aagtagggg actagcggta gcagtgagtt cgttggatgg ccgaaccct   180 gagtacaggg gagtcgtcaa tggttcgaca ctccattagt cgaggagtct cgagatgcca   240
tgtggacgag ggcatgccca cggcacatct taacccatgc gggggttgca tgggtgaaag   300
cgctaatcgt ggcgttatgg acacagcctg atagggtgta gcagagacct gctattccgc   360
tagtaaaaaa ctctgctgta catggcac                                      388

<210> SEQ ID NO 54
<211> LENGTH: 373
<212> TYPE: DNA
<213> ORGANISM: Classical swine fever virus

<400> SEQUENCE: 54
gtatacgagg ttagttcatt ctcgtatgca ttattggaca aatcaaaatt tcaatttggt    60
tcagggcctc cctccagcga cggccgaact gggctagcca tgcccatagt aggactagca   120
aacggaggga ctagccgtag tggcgagctc cctgggtgtt ctaagtcctg agtacaggac   180
agtcgtcagt agttcgacgt gagcagaagc ccacctcgag atgctatgtg gacgagggca   240
tgcccaagac gcaccttaac cctagcgggg gtcgctaggg tgaaatcaca ccacgtgatg   300
ggagtccgac ctgatagggt gctgcagagg ctcactatta ggctagtata aaatctctg   360 ctgtacatgg cac                                                      373

<210> SEQ ID NO 55
<211> LENGTH: 191
<212> TYPE: DNA
<213> ORGANISM: Human blood-associated dicistrovirus

<400> SEQUENCE: 55
aaaaccgacc ccagagatca gaaagtcgtt gacgcgatct tttattagag gacgttgcgc    60
tggcgcgagc tttaattagc agacgccaaa aataaacaac aaaatgctga tcgcgagact   120
taattgtcag acgattggcc aaatccgatg tgatctttgc tgctcccaga ttgccgaaat   180
aggagtagta g                                                        191

<210> SEQ ID NO 56
<211> LENGTH: 438
<212> TYPE: DNA
```

<213> ORGANISM: Hubei Picorna-like virus

<400> SEQUENCE: 56

| | | | | | | |
|---|---|---|---|---|---|---|
| ccccaaaacc | cccccttaa | actcaacact | gtagtggatt | cattttccgt | tgcaaaacaa | 60 |
| aacattacta | cccgcattta | tgtaggctct | gtgttttcta | tgcgaccgtt | acattaatct | 120 |
| ctactctgac | ccactagttt | ataaaaccga | agacctgaat | gaaacgattt | tccttctttt | 180 |
| caacctctaa | cgaacctctg | acggcttgag | aaacctgaag | ttagtaatta | tgtttaaaag | 240 |
| aaaggaaagt | caaacgcgat | gactcttaca | tccctattcc | ataccgttgc | tccacaatgt | 300 |
| gagcgatgcg | aggtcgggac | tgcagtatta | ggggaacgag | ctacatggag | agttaattat | 360 |
| ctctcccctc | ctacgggagt | ctcatgtgag | ctgtagaaag | cggttggcac | ctctcgttac | 420 |
| ctcgcctgta | catgatcc | | | | | 438 |

<210> SEQ ID NO 57
<211> LENGTH: 193
<212> TYPE: DNA
<213> ORGANISM: Cricket paralysis virus

<400> SEQUENCE: 57

| | | | | | | |
|---|---|---|---|---|---|---|
| aaaagcaaaa | atgtgatctt | gcttgtaaat | acaattttga | gaggttaata | aattacaagt | 60 |
| agtgctattt | ttgtatttag | gttagctatt | tagctttacg | ttccaggatg | cctagtggca | 120 |
| gccccacaat | atccaggaag | ccctctctgc | ggttttcag | attaggtagt | cgaaaaacct | 180 |
| aagaaattta | cct | | | | | 193 |

<210> SEQ ID NO 58
<211> LENGTH: 752
<212> TYPE: DNA
<213> ORGANISM: Salivirus A

<400> SEQUENCE: 58

| | | | | | | |
|---|---|---|---|---|---|---|
| tttcctcctt | tcgaccgcct | tacggcaggc | gggtccgcgg | acggcttcgg | cctacccgcg | 60 |
| acaagaatgc | cgtcatctgt | ccttatcacc | catattcttt | cccttccccc | gcaaccatca | 120 |
| cgcttactcg | cgcacgtgtt | gagtggcacg | tgcgttgtcc | aaacagttac | actcacaccc | 180 |
| ttggggcggg | tttgtcccgc | cctcgggttc | ctcgcggaac | cctccctctt | ctctctccct | 240 |
| ttctatccgc | cttcactttc | cataactaca | gtgcttggt | aggtaagcat | cctgaccccc | 300 |
| cgcggaagct | gccaacgtgg | caactgtggg | gatccaggca | ggttatcaaa | ggcacccggt | 360 |
| cttccgcct | tcaggagtat | ccctgccggt | gaattccgac | agggctctgc | ttggtgccaa | 420 |
| cctcccccaa | atgcgcgctg | cgggagtgct | cttccccaac | tcatcttagt | aacctctcat | 480 |
| gtgtgtgctt | ggtcagcata | tctgaggcga | cgttccgctg | tcccagacca | gtccagcaat | 540 |
| ggacgggcca | gtgtgcgtag | tcgctttccg | gtttcccggc | gcatgtttgg | cgaaacgctg | 600 |
| aggtaaggtt | ggtgtgccca | atgcccgtaa | tttggtgaca | cctcaagacc | acccaggaat | 660 |
| gccagggagg | tacccacttt | cggtgggatc | tgaccctggg | ctaattgtct | acggtggttc | 720 |
| ttcttgcttc | cacttctctt | ttttctggca | tg | | | 752 |

<210> SEQ ID NO 59
<211> LENGTH: 708
<212> TYPE: DNA
<213> ORGANISM: Salivirus A

<400> SEQUENCE: 59

| | | | | | | |
|---|---|---|---|---|---|---|
| tatggcaggc | gggcttgtgg | acggcttcgg | cccacccaca | gcaagaatgc | catcatctgt | 60 |

```
cctcaccccc atgtttcccc tttctttccc tgcaaccgtt acgcttactc gcaggtgcat      120
ttgagtggtg cacgtgttga ataaacagct acactcacat gggggcgggt tttcccgccc      180
tgcggcctct cgcgaggccc acccctcccc ttcctcccat aactacagtg ctttggtagg      240
taagcatcct gatccccgc ggaagctgct cacgtggcaa ctgtggggac ccagacaggt       300
tatcaaaggc acccggtctt tccgccttca ggagtatccc tgctagtgaa ttctagtagg     360
gctctgcttg gtgccaacct ccccaaatg cgcgctgcgg gagtgctctt ccccaactca     420
ccctagtatc ctctcatgtg tgtgcttggt cagcatatct gagacgatgt tccgctgtcc    480
cagaccagtc cagtaatgga cgggccagtg tgcgtagtcg tcttccggct tttccggcgc    540
atgtttggtg aaccggtggg gtaaggttgg tgtgcccaac gcccgtactt tggtgatacc    600
tcaagaccac ccaggaatgc cagggaggta ccccgcttca cagcgggatc tgaccctggg    660
ctaattgtct acggtggttc ttcttgcttc cacttctttc tactgttc                 708
```

```
<210> SEQ ID NO 60
<211> LENGTH: 718
<212> TYPE: DNA
<213> ORGANISM: Salivirus A

<400> SEQUENCE: 60
tttcgaccgc cttatggcag gcgggcttgt ggacggcttc ggcccaccca cagcaagaat      60
gccatcatct gtcctcaccc ccatttctcc cctccttccc ctgcaaccat tacgcttact     120
cgcatgtgca ttgagtggtg cacgtgttga acaaacagct acactcacgt ggggcgggt     180 tttcccgccc ttcggcctct cgcgaggccc acccttcccc ttcctcccat aactacagtg    240
ctttggtagg taagcatcct gatccccgc ggaagctgct cgcgtggcaa ctgtggggac    300
ccagacaggt tatcaaaggc acccggtctt tccgcctcca ggagtatccc tgctagtgaa    360
ttctagtggg gctctgcttg gtgccaacct ccccaaatg cgcgctgcgg gagtgctctt    420
ccccaactca ccctagtatc ctctcatgtg tgtgcttggt cagcatatct gagacgatgt    480
tccgctgtcc cagaccagtc cagcaatgga cgggccagtg tgcgtagtcg tcttccggct    540
tgtccggcgc atgtttggtg aaccggtggg gtaaggttgg tgtgcccaac gcccgtactt    600
tggtgacaac tcaagaccac ccaggaatgc cagggaggta ccccgcctca cggcgggatc    660
tgaccctggg ctaattgtct acggtggttc ttcttgcttc catttctttc ttctgttc      718
```

```
<210> SEQ ID NO 61
<211> LENGTH: 699
<212> TYPE: DNA
<213> ORGANISM: Salivirus A

<400> SEQUENCE: 61
tatggcaggc gggcttgtgg acggtttcgg cccacccaca gcaagaatgc catcatctgt      60
cctcaccccc aatttccct ttcttcccct gcaatcatca cgcttactcg catgtgcatt     120
gagtggtgca tgtgttgaac aaacagctac actcacatgg gggcgggttt tcccgcccta    180
cggcctctcg cgaggccac ccttcccctc cccttataac tacagtgctt tggcaggtaa    240
gcatcctgat ccccgcgga agctgctcac gtggcaactg tggggaccca gacaggttat    300
caaaggcacc cggtctttcc gccttcagga gcatcccac tagtgaattc tagtgggct    360 ctgcttggtg ccaaccctccc ccaaatgcgc gctgcgggag tgctcttccc caacccatcc    420
tagtatcctc tcatgtgtgt gcttggtcag catatctgag acgacgttcc gctgtcccag    480
```

```
accagtccag taatggacgg gccagtgtgc gtagtcgtct tccggcttgt ccggcgcatg    540
tttggtgaac cggtggggta aggttggtgt gcccaacgcc cgtactttgg tgacacctca    600
agaccaccca ggaatgccag ggaggtaccc cgcctcacgg cgggatctga ccctgggcta    660
attgtctacg gtggttcttc ttgcttccac ttctttctt                           699

<210> SEQ ID NO 62
<211> LENGTH: 624
<212> TYPE: DNA
<213> ORGANISM: Salivirus A

<400> SEQUENCE: 62
ttctcctgca accattacgc ttaatcgcat gtgcattgag tggtgcatgt gttgaacaaa     60
cagctacaat cacatggggg cgggttttcc cgccccacgg cttctcgcga ggcccatccc    120
tcccttttct cccataacta cagtgctttg gtaggtaagc atcccgatct cccgcggaag    180
ctgctcacgt ggcaactgtg gggacccaga caggttatca aaggcacccg gtctttccgc    240
cttcaggagt atccctgcta gcgaattcta gtagggctct gcttggtgcc aacctctccc    300
aaatgcgcgc tgcgggagtg ctcttcccca aatcacccca gtatcctctc atgtgtgtgc    360
ctggtcagca tatctgagac gatgttccgc tgtcccagac cagtccagta atggacgggc    420
cagtgtgcgt agtcgtcctc cggcttgtcc ggcgcatgtt tggtgaaccg gtggggtaag    480
gttggtgtgc ccaacgcccg taatcagggg atacctcaag cacccagga atgccaggga    540 ggtatcccgc tcacagcgg gatctgaccc tggggtaaat gtctgcgggg ggtcctcttg    600
gcccaattct cagtaatttt cagg                                           624

<210> SEQ ID NO 63
<211> LENGTH: 650
<212> TYPE: DNA
<213> ORGANISM: Salivirus A

<400> SEQUENCE: 63
tctgtcctca ccccatcttc ccttctttcc tgcaccgtta cgcttactcg catgtgcatt     60
gagtggtgca cgtgcttgaa caaacagcta cactcacatg ggggcgggtt ttcccgccct    120
gcggcctctc gcgaggccca cccctcccct tcctcccata actacagtgc tttggtaggt    180
aagcatcctg atccccgcg gaagctgctc acgtggcaac tgtggggacc cagacaggtt    240
atcaaaggca cccggtcttt ccgccttcag gagtatccct gctagtgaat ctagtaggg    300 ctctgcttgg tgccaacctc ccccaaatgc gcgctgcggg agtgctcttc cccaactcac    360
cctagtatcc tctcatgtgt gtgcttggtc agcatatctg agacgatgtt ccgctgtccc    420
agaccagtcc agtaatggac gggccagtgt gcgtagtcgt cttccggctt gtccggcgca    480
tgtttggtga accggtgggg taaggttggt gtgcccaacg cccgtacttt ggtgatacct    540
caagaccacc caggaatgcc agggaggtac cccgcttcac agcgggatct gaccctgggc    600
taattgtcta cggtggttct tcttgcttcc acttctttct actgttcatg               650

<210> SEQ ID NO 64
<211> LENGTH: 730
<212> TYPE: DNA
<213> ORGANISM: Salivirus FHB

<400> SEQUENCE: 64
acatgggggg tctgcggacg gcttcggccc accgcgacaa agaatgccgt catctgtcct     60
cattacccgt attccttccc ttcccccgca accaccacgc ttactcgcgc acgtgttgag    120
```

```
tggcacgtgc gttgtccaaa cagctacacc cacacccttc ggggcgggtt tgtcccgccc    180
tcgggttcct cgcggaaccc cccctccct  ctctctcttt  ctatccgccc tcacttccca    240
taactacagt gctttggtag gtgagcaccc tgaccccccg cggaagctgc taacgtggca    300
actgtgggga tccaggcagg ttatcaaagg cacccggtct ttccgccttc aggagtatct    360
ctgccggtga attccggtag ggctctgctt ggtgccaacc tcccccaaat gcgcgctgcg    420
ggagtgctct tccccaactc atcttagtaa cctctcatgt gtgtgcttgg tcagcatatc    480
tgaggcgacg ttccgctgtc ccagaccagt ccagcaatgg acgggccagt gtgcgtagtc    540
gctttccggt tttccggcgc atgtttggcg aaacgctgag gtaaggttgg tgtgcccaac    600
gcccgtaatt tggtgatacc tcaagaccac caggaatgc  agggaggta  ccccacttcg    660 gtgggatctg accctgggct aattgtctac ggtggttctt cttgcttcca cttctctttt    720
ttctggcatg                                                           730

<210> SEQ ID NO 65
<211> LENGTH: 741
<212> TYPE: DNA
<213> ORGANISM: Coxsackievirus B3

<400> SEQUENCE: 65
ttaaaacagc ctgtgggttg atcccaccca caggcccatt gggcgctagc actctggtat     60
cacggtacct ttgtgcgcct gttttatacc ccctccccca actgtaactt agaagtaaca    120
cacaccgatc aacagtcagc gtggcacacc agccacgttt tgatcaagca cttctgttac    180
cccggactga gtatcaatag actgctcacg cggttgaagg agaaagcgtt cgttatccgg    240
ccaactactt cgaaaaacct agtaacaccg tggaagttgc agagtgtttc gctcagcact    300
accccagtgt agatcaggtc gatgagtcac cgcattcccc acgggcgacc gtggcggtgg    360
ctgcgttggc ggcctgccca tggggaaacc catgggacgc tctaatacag acatggtgcg    420
aagagtctat tgagctagtt ggtagtcctc cggcccctga atgcggctaa tcctaactgc    480
ggagcacaca ccctcaagcc agagggcagt gtgtcgtaac gggcaactct gcagcggaac    540
cgactacttt gggtgtccgt gtttcatttt attcctatac tggctgctta tggtgacaat    600
tgagagatcg ttaccatata gctattggat tggccatccg gtgactaata gagctattat    660
atatcccttt gttgggttta taccacttag cttgaaagag gttaaaacat tacaattcat    720
tgttaagttg aatacagcaa a                                              741

<210> SEQ ID NO 66
<211> LENGTH: 741
<212> TYPE: DNA
<213> ORGANISM: Coxsackievirus B1

<400> SEQUENCE: 66
ttaaaacagc ctgtgggttg ttcccaccca caggcccatt gggcgctagc actctggtat     60
cacggtacct ttgtgcgcct gttttacatc ccctccccaa attgtaattt agaagtttca    120
cacaccgatc attagcaagc gtggcacacc agccatgttt tgatcaagca cttctgttac    180
cccggactga gtatcaatag accgctaacg cggttgaagg agaaaacgtt cgttacccgg    240
ccaactactt cgaaaaacct agtaacacca tggaagttgc ggagtgtttc gctcagcact    300
accccagtgt agatcaggtc gatgagtcac cgcgttcccc acgggcgacc gtggcggtgg    360
ctgcgttggc ggcctgccta cggggaaacc cgtaggacgc tctaatacag acatggtgcg    420
```

```
aagagtctat tgagctagtt ggtaatcctc cggcccctga atgcggctaa tcctaactgc    480
ggagcacata ccctcaaacc aggggggcagt gtgtcgtaac gggcaactct gcagcggaac   540
cgactacttt gggtgtccgt gtttcatttt attcctatac tggctgctta tggtgacaat   600
tgacaggttg ttaccatata gttattggat tggccatccg gtgactaaca gagcaattat   660
atatctcttt gttgggttta taccacttag cttgaaagag gttaaaacac tacatctcat   720
cattaaacta aatacaacaa a                                              741
```

<210> SEQ ID NO 67
<211> LENGTH: 742
<212> TYPE: DNA
<213> ORGANISM: Echovirus 7

<400> SEQUENCE: 67

```
ttaaaacagc ctgtgggttg ttcccaccca cagggcccat gggcgtcag cccctggta      60 tcacggtacc tttgtgcgcc tgttttatat cccttcccccc aattgtaact tagaagaaac  120
acacaccgat caacagcaag cgtggcacac cagccatgtt ttggtcaagc acttctgtta  180
ccccggactg agtatcaata gactgctcac gcggttgaag gagaaagcgt ccgttatccg  240
gccagctact tcgagaaacc tagtaacacc atggaagttg cggagtgttt cgctcagcac  300 tacccccagtg tagatcaggt cgatgagtca ccgctttccc cacgggcgac cgtggcggtg  360
gctgcgttgg cggcctgcct atgggggaac ccataggacg ctctaataca gacatggtgc  420
gaagagtcta ttgagctagc tggtattcct ccggcccctg aatgcggcta atcctaactg  480
tggagcacat gccctaatc caaggggtag tgtgtcgtaa tgagcaattc cgcagcggaa  540
ccgactactt gggtgtccg tgtttcctct tattcttgta ctggctgctt atggtgacaa  600
ttgagagatt gttaccatat agctattgga ttggccatcc ggtgactaat agagctattg  660
tgtatctctt gttggatttt gtaccactta atttgaaaga atcaggaca ctacgctaca  720 ttttactatt gaacaccgca aa                                            742
```

<210> SEQ ID NO 68
<211> LENGTH: 743
<212> TYPE: DNA
<213> ORGANISM: Coxsackievirus B5

<400> SEQUENCE: 68

```
ttaaaacagc ctgtgggttg tacccaccca cagggcccac tgggcgctag cactctggta    60
tcacggtacc tttgtgcgcc tgttttatgc ccccttcccc caattgaaac ttagaagtta   120
cacacaccga tcaacagcgg gcgtggcata ccagccgcgt cttgatcaag cactcctgtt   180
tccccggacc gagtatcaat agactgctca cgcggttgaa ggagaaaacg ttcgttaccc   240
ggctaactac ttcgagaaac ctagtagcat catgaaagtt gcgaagcgtt cgctcagca   300 catcccccagt gtagatcagg tcgatgagtc accgcattcc cacgggcga ccgtggcggt   360 ggctgcgttg gcggcctgcc tacggggcaa cccgtaggac gcttcaatac agacatggtg   420
cgaagagtcg attgagctag ttagtagtcc tccggcccct gaatccggct aatcctaact   480
gcggagcaca taccctcaac ccaggggggca ttgtgtcgta acgggtaact ctgcagcgga   540
accgactact ttgggtgtcc gtgtttcctt ttattcttat aatggctgct tatggtgaca   600
attgaaagat tgttaccata tagctattgg attggccatc cggtgtctaa cagagctatt   660 atatcctct ttgttggatt tgtaccactt gatctaaagg aagtcaagac actacaattc   720
atcatacaat tgaacacagc aaa                                            743
```

<210> SEQ ID NO 69
<211> LENGTH: 743
<212> TYPE: DNA
<213> ORGANISM: Enterovirus A71

<400> SEQUENCE: 69

| | | | | | |
|---|---|---|---|---|---|
| ttaaaacagc | ctgtgggttg | cacccactca | cagggcccac | tgggcgcaag | cactctggca | 60 |
| cttcggtacc | tttgtgcgcc | tgttttatat | ccctcccccc | aatgaaattt | agaagcagca | 120 |
| aaccccgatc | aatagcaggc | ataacgctcc | agttatgtct | tgatcaagca | cttctgtttc | 180 |
| cccggactga | gtatcaatag | actgctcacg | cggttgaagg | agaaaacgtt | cgttatccgg | 240 |
| ctaactactt | cggaaagcct | agtaacacca | tggaagttgc | ggagagtttc | gttcagcact | 300 |
| tccccagtgt | agatcaggtc | gatgagtcac | cgcattcccc | acgggcgacc | gtggcggtgg | 360 |
| ctgcgttggc | ggcctgccca | tggggtaacc | catgggacgc | tctaatacgg | acatggtgtg | 420 |
| aagagtctac | tgagctagtt | agtagtcctc | cggcccctga | atgcggctaa | tcccaactgc | 480 |
| ggagcacacg | cccacaagcc | agtgggtagt | gtgtcgtaac | gggcaactct | gcagcggaac | 540 |
| cgactacttt | gggtgtccgt | gtttcctttt | attcttatgt | tggctgctta | tggtgacaat | 600 |
| taaagagttg | ttaccatata | gctattggat | tggccatccg | gtgtgcaaca | gagcgatcgt | 660 |
| ttacctattt | attggttttg | taccattgac | actgaagtct | gtgatcaccc | ttaattttat | 720 |
| cttaaccctc | aacacagcca | aac | | | | 743 |

<210> SEQ ID NO 70
<211> LENGTH: 742
<212> TYPE: DNA
<213> ORGANISM: Coxsackievirus A3

<400> SEQUENCE: 70

| | | | | | |
|---|---|---|---|---|---|
| ttaaaacagc | ctgtgggttg | tacccaccca | cagggcccac | tgggcgctag | cacactggta | 60 |
| ttacggtacc | tttgtgcgcc | tgttttatac | cccccccaac | ctcgaaactt | agaagtaaag | 120 |
| caaacccgat | caatagcagg | tgcggcgcac | cagtcgcatc | ttgatcaagc | acttctgtaa | 180 |
| ccccggaccg | agtatcaata | gactgctcac | gcggttgaag | gagaaaacgt | tcgttacccg | 240 |
| gctaactact | tcgagaaacc | cagtagcatc | atgaaagttg | cagagtgttt | cgctcagcac | 300 |
| taccccgtg | tagatcaggc | cgatgagtca | ccgcacttcc | ccacgggcga | ccgtggcggt | 360 |
| ggctgcgttg | gcggcctgcc | tatggggcaa | cccataggac | gctctaatac | ggacatggtg | 420 |
| cgaagagtct | attgagctag | ttagtagtcc | tccggcccct | gaatgcggct | aatcctaact | 480 |
| gcggagcaca | tacccttaat | ccaaagggca | gtgtgtcgta | acgggtaact | ctgcagcgga | 540 |
| accgactact | ttgggtgtcc | gtgtttcctt | ttaattttta | ctggctgctt | atggtgacaa | 600 |
| ttgaggaatt | gttgccatat | agctattgga | ttggccatcc | ggtgactaac | agagctattg | 660 |
| tgttccaatt | tgttggattt | accccgctca | cactcacagt | cgtaagaacc | cttcattacg | 720 |
| tgttatttct | caactcaaga | aa | | | | 742 |

<210> SEQ ID NO 71
<211> LENGTH: 745
<212> TYPE: DNA
<213> ORGANISM: Coxsackievirus A12

<400> SEQUENCE: 71

| | | | | | |
|---|---|---|---|---|---|
| ttaaaacagc | ctgtgggttg | tacccaccca | cagggcccac | tgggcgctag | cactctggta | 60 |

```
ctacggtacc tttgtgtgcc tgttttaagc ccctacccccc cactcgtaac ttagaaggct    120
tctcacactc gatcaatagt aggtgtggca cgccagtcac accgtgatca agcacttctg    180
ttaccccggt ctgagtacca ataagctgct aacgcggctg aaggggaaaa cgatcgttat    240
ccggctaact acttcgagaa acccagtacc accatgaacg ttgcagggtg tttcgctcgg    300 cacaaccccca gtgtagatca ggtcgatgag tcaccgtatt ccccacgggc gaccgtggcg    360
gtggctgcgt tggcggcctg cccatggggt gacccatggg acgctctaat actgacatgg    420
tgcgaagagt ctattgagct agttagtagt cctccggccc ctgaatgcgg ctaatcctaa    480
ctgcggagca catacccctta atccaaaggg cagtgtgtcg taacgggcaa ctctgcagcg    540
gaaccgacta ctttgggtgt ccgtgtttcc ttttattctt acattggctg cttatggtga    600
caattgaaaa gttgttacca tatagctatt ggattggcca tccggtgaca aatagagcta    660
ttgtatatct ttttgttggt tacgtacccc ttaattacaa agtggtttca actttgaaat    720
acatcctaac actaaattgt agaaa                                          745
```

<210> SEQ ID NO 72
<211> LENGTH: 742
<212> TYPE: DNA
<213> ORGANISM: Echovirus E24

<400> SEQUENCE: 72

```
ttaaaacagc ctgtgggttg cacccaccca cagggcccac agggcgctag cactctggta     60
tcacggtacc tttgtgcgcc tgttttatta ccccttcccc aattgaaaat tagaagcaat    120
gcacaccgat caacagcagg cgtggcgcac cagtcacgtc tcgatcaagc acttctgttt    180
ccccggaccg agtatcaata gactgctcac gcggttgaag gagaaagtgt tcgttatccg    240
gctaaccact tcgagaaacc cagtaacacc atgaaagttg cagggtgttt cgctcagcac    300
ttccccagtg tagatcaggt cgatgagtca ccgcgttccc cacgggcgac cgtggcggtg    360
gctgcgttgg cggcctgcct atgggttaac cataggacg ctctaataca gacatggtgc    420
gaagagttta ttgagctggt tagtatccct ccggcccctg aatgcggcta atcctaactg    480
cggagcacgt gcctccaatc caggggggttg catgtcgtaa cgggtaactc tgcagcggaa    540
ccgactactt tgggtgtccg tgtttccttt tattcttata ctggctgctt atggtgacaa    600
tcgaggaatt gttaccatat agctattgga ttggccatcc ggtgtctaac agagcgatta    660
tatcctcttt tgttggattt atgcagctca ataccaccaa ctttaacaca ttgaaatata    720
tcttaaagtt aaacacagca aa                                             742
```

<210> SEQ ID NO 73
<211> LENGTH: 240
<212> TYPE: DNA
<213> ORGANISM: Anabaena sp.

<400> SEQUENCE: 73

```
gaagaaattc tttaagtgga tgctctcaaa ctcagggaaa cctaaatcta gttatagaca     60
aggcaatcct gagccaagcc gaagtagtaa ttagtaagtt aacaatagat gacttacaac    120
taatcggaag gtgcagagac tcgacgggag ctacccctaac gtcaagacga gggtaaagag    180
agagtccaat tctcaaagcc aataggcagt agcgaaagct gcaagagaat gaaaatccgt    240
```

<210> SEQ ID NO 74
<211> LENGTH: 239
<212> TYPE: DNA
<213> ORGANISM: Anabaena sp.

<400> SEQUENCE: 74
aagaaattct ttaagtggat gctctcaaac tcagggaaac ctaaatctag ttatagacaa      60
ggcaatcctg agccaagccg aagtagtaat tagtaagtta acaatagatg acttacaact     120
aatcggaagg tgcagagact cgacgggagc taccctaacg tcaagacgag ggtaaagaga     180
gagtccaatt ctcaaagcca ataggcagta gcgaaagctg caagagaatg aaaatccgt     239

<210> SEQ ID NO 75
<211> LENGTH: 238
<212> TYPE: DNA
<213> ORGANISM: Anabaena sp.

<400> SEQUENCE: 75
agaaattctt taagtggatg ctctcaaact cagggaaacc taaatctagt tatagacaag      60
gcaatcctga gccaagccga agtagtaatt agtaagttaa caatagatga cttacaacta     120
atcggaaggt gcagagactc gacgggagct accctaacgt caagacgagg gtaaagagag     180
agtccaattc tcaaagccaa taggcagtag cgaaagctgc aagagaatga aaatccgt     238

<210> SEQ ID NO 76
<211> LENGTH: 190
<212> TYPE: DNA
<213> ORGANISM: Anabaena sp.

<400> SEQUENCE: 76
gttatagaca aggcaatcct gagccaagcc gaagtagtaa ttagtaagtt aacaatagat      60
gacttacaac taatcggaag gtgcagagac tcgacgggag ctaccctaac gtcaagacga     120
gggtaaagag agagtccaat tctcaaagcc aataggcagt agcgaaagct gcaagagaat     180
gaaaatccgt                                                             190

<210> SEQ ID NO 77
<211> LENGTH: 189
<212> TYPE: DNA
<213> ORGANISM: Anabaena sp.

<400> SEQUENCE: 77
ttatagacaa ggcaatcctg agccaagccg aagtagtaat tagtaagtta acaatagatg      60
acttacaact aatcggaagg tgcagagact cgacgggagc taccctaacg tcaagacgag     120
ggtaaagaga gagtccaatt ctcaaagcca ataggcagta gcgaaagctg caagagaatg     180
aaaatccgt                                                              189

<210> SEQ ID NO 78
<211> LENGTH: 188
<212> TYPE: DNA
<213> ORGANISM: Anabaena sp.

<400> SEQUENCE: 78
tatagacaag gcaatcctga gccaagccga agtagtaatt agtaagttaa caatagatga      60
cttacaacta atcggaaggt gcagagactc gacgggagct accctaacgt caagacgagg     120
gtaaagagag agtccaattc tcaaagccaa taggcagtag cgaaagctgc aagagaatga     180
aaatccgt                                                               188

<210> SEQ ID NO 79
<211> LENGTH: 187
<212> TYPE: DNA

```
<213> ORGANISM: Anabaena sp.

<400> SEQUENCE: 79
atagacaagg caatcctgag ccaagccgaa gtagtaatta gtaagttaac aatagatgac    60
ttacaactaa tcggaaggtg cagagactcg acgggagcta ccctaacgtc aagacgaggg   120
taaagagaga gtccaattct caaagccaat aggcagtagc gaaagctgca agagaatgaa   180
aatccgt                                                             187

<210> SEQ ID NO 80
<211> LENGTH: 186
<212> TYPE: DNA
<213> ORGANISM: Anabaena sp.

<400> SEQUENCE: 80
tagacaaggc aatcctgagc caagccgaag tagtaattag taagttaaca atagatgact    60
tacaactaat cggaaggtgc agagactcga cgggagctac cctaacgtca agacgagggt   120
aaagagagag tccaattctc aaagccaata ggcagtagcg aaagctgcaa gagaatgaaa   180
atccgt                                                              186

<210> SEQ ID NO 81
<211> LENGTH: 139
<212> TYPE: DNA
<213> ORGANISM: Anabaena sp.

<400> SEQUENCE: 81
acaatagatg acttacaact aatcggaagg tgcagagact cgacgggagc taccctaacg    60
tcaagacgag ggtaaagaga gagtccaatt ctcaaagcca ataggcagta gcgaaagctg   120
caagagaatg aaaatccgt                                                139

<210> SEQ ID NO 82
<211> LENGTH: 138
<212> TYPE: DNA
<213> ORGANISM: Anabaena sp.

<400> SEQUENCE: 82
caatagatga cttacaacta atcggaaggt gcagagactc gacgggagct accctaacgt    60
caagacgagg gtaaagagag agtccaattc tcaaagccaa taggcagtag cgaaagctgc   120
aagagaatga aaatccgt                                                 138

<210> SEQ ID NO 83
<211> LENGTH: 137
<212> TYPE: DNA
<213> ORGANISM: Anabaena sp.

<400> SEQUENCE: 83
aatagatgac ttacaactaa tcggaaggtg cagagactcg acgggagcta ccctaacgtc    60
aagacgaggg taaagagaga gtccaattct caaagccaat aggcagtagc gaaagctgca   120
agagaatgaa aatccgt                                                  137

<210> SEQ ID NO 84
<211> LENGTH: 136
<212> TYPE: DNA
<213> ORGANISM: Anabaena sp.

<400> SEQUENCE: 84
atagatgact tacaactaat cggaaggtgc agagactcga cgggagctac cctaacgtca    60
```
agacgagggt aaagagagag tccaattctc aaagccaata ggcagtagcg aaagctgcaa    120
gagaatgaaa atccgt    136

<210> SEQ ID NO 85
<211> LENGTH: 135
<212> TYPE: DNA
<213> ORGANISM: Anabaena sp.

<400> SEQUENCE: 85
tagatgactt acaactaatc ggaaggtgca gagactcgac gggagctacc ctaacgtcaa    60
gacgagggta agagagagt ccaattctca agccaatag gcagtagcga aagctgcaag    120
agaatgaaaa tccgt    135

<210> SEQ ID NO 86
<211> LENGTH: 134
<212> TYPE: DNA
<213> ORGANISM: Anabaena sp.

<400> SEQUENCE: 86
agatgactta caactaatcg gaaggtgcag agactcgacg ggagctaccc taacgtcaag    60
acgagggtaa agagagagtc caattctcaa agccaatagg cagtagcgaa agctgcaaga    120
gaatgaaaat ccgt    134

<210> SEQ ID NO 87
<211> LENGTH: 133
<212> TYPE: DNA
<213> ORGANISM: Anabaena sp.

<400> SEQUENCE: 87
gatgacttac aactaatcgg aaggtgcaga gactcgacgg gagctaccct aacgtcaaga    60
cgagggtaaa gagagagtcc aattctcaaa gccaataggc agtagcgaaa gctgcaagag    120
aatgaaaatc cgt    133

<210> SEQ ID NO 88
<211> LENGTH: 132
<212> TYPE: DNA
<213> ORGANISM: Anabaena sp.

<400> SEQUENCE: 88
atgacttaca actaatcgga aggtgcagag actcgacggg agctacccta acgtcaagac    60
gagggtaaag agagagtcca attctcaaag ccaataggca gtagcgaaag ctgcaagaga    120
atgaaaatcc gt    132

<210> SEQ ID NO 89
<211> LENGTH: 131
<212> TYPE: DNA
<213> ORGANISM: Anabaena sp.

<400> SEQUENCE: 89
tgacttacaa ctaatcggaa ggtgcagaga ctcgacggga gctaccctaa cgtcaagacg    60
agggtaaaga gagagtccaa ttctcaaagc caataggcag tagcgaaagc tgcaagagaa    120
tgaaaatccg t    131

<210> SEQ ID NO 90
<211> LENGTH: 78
<212> TYPE: DNA

<213> ORGANISM: Anabaena sp.

<400> SEQUENCE: 90
caagacgagg gtaaagagag agtccaattc tcaaagccaa taggcagtag cgaaagctgc    60
aagagaatga aaatccgt    78

<210> SEQ ID NO 91
<211> LENGTH: 77
<212> TYPE: DNA
<213> ORGANISM: Anabaena sp.

<400> SEQUENCE: 91
aagacgaggg taaagagaga gtccaattct caaagccaat aggcagtagc gaaagctgca    60
agagaatgaa aatccgt    77

<210> SEQ ID NO 92
<211> LENGTH: 76
<212> TYPE: DNA
<213> ORGANISM: Anabaena sp.

<400> SEQUENCE: 92
agacgagggt aaagagagag tccaattctc aaagccaata ggcagtagcg aaagctgcaa    60
gagaatgaaa atccgt    76

<210> SEQ ID NO 93
<211> LENGTH: 75
<212> TYPE: DNA
<213> ORGANISM: Anabaena sp.

<400> SEQUENCE: 93
gacgagggta aagagagagt ccaattctca aagccaatag gcagtagcga aagctgcaag    60
agaatgaaaa tccgt    75

<210> SEQ ID NO 94
<211> LENGTH: 74
<212> TYPE: DNA
<213> ORGANISM: Anabaena sp.

<400> SEQUENCE: 94
acgagggtaa agagagagtc caattctcaa agccaatagg cagtagcgaa agctgcaaga    60
gaatgaaaat ccgt    74

<210> SEQ ID NO 95
<211> LENGTH: 40
<212> TYPE: DNA
<213> ORGANISM: Anabaena sp.

<400> SEQUENCE: 95
aataggcagt agcgaaagct gcaagagaat gaaaatccgt    40

<210> SEQ ID NO 96
<211> LENGTH: 39
<212> TYPE: DNA
<213> ORGANISM: Anabaena sp.

<400> SEQUENCE: 96
ataggcagta gcgaaagctg caagagaatg aaaatccgt    39

<210> SEQ ID NO 97
<211> LENGTH: 38

```
<212> TYPE: DNA
<213> ORGANISM: Anabaena sp.

<400> SEQUENCE: 97
taggcagtag cgaaagctgc aagagaatga aaatccgt                              38

<210> SEQ ID NO 98
<211> LENGTH: 37
<212> TYPE: DNA
<213> ORGANISM: Anabaena sp.

<400> SEQUENCE: 98
aggcagtagc gaaagctgca agagaatgaa aatccgt                               37

<210> SEQ ID NO 99
<211> LENGTH: 36
<212> TYPE: DNA
<213> ORGANISM: Anabaena sp.

<400> SEQUENCE: 99
ggcagtagcg aaagctgcaa gagaatgaaa atccgt                                36

<210> SEQ ID NO 100
<211> LENGTH: 27
<212> TYPE: DNA
<213> ORGANISM: Anabaena sp.

<400> SEQUENCE: 100
gaaagctgca agagaatgaa aatccgt                                          27

<210> SEQ ID NO 101
<211> LENGTH: 26
<212> TYPE: DNA
<213> ORGANISM: Anabaena sp.

<400> SEQUENCE: 101
aaagctgcaa gagaatgaaa atccgt                                           26

<210> SEQ ID NO 102
<211> LENGTH: 25
<212> TYPE: DNA
<213> ORGANISM: Anabaena sp.

<400> SEQUENCE: 102
aagctgcaag agaatgaaaa tccgt                                            25

<210> SEQ ID NO 103
<211> LENGTH: 24
<212> TYPE: DNA
<213> ORGANISM: Anabaena sp.

<400> SEQUENCE: 103
agctgcaaga gaatgaaaat ccgt                                             24

<210> SEQ ID NO 104
<211> LENGTH: 23
<212> TYPE: DNA
<213> ORGANISM: Anabaena sp.

<400> SEQUENCE: 104
gctgcaagag aatgaaaatc cgt                                              23

<210> SEQ ID NO 105
```

```
<211> LENGTH: 22
<212> TYPE: DNA
<213> ORGANISM: Anabaena sp.

<400> SEQUENCE: 105
ctgcaagaga atgaaaatcc gt                                              22

<210> SEQ ID NO 106
<211> LENGTH: 18
<212> TYPE: DNA
<213> ORGANISM: Anabaena sp.

<400> SEQUENCE: 106
aagagaatga aaatccgt                                                   18

<210> SEQ ID NO 107
<211> LENGTH: 17
<212> TYPE: DNA
<213> ORGANISM: Anabaena sp.

<400> SEQUENCE: 107
agagaatgaa aatccgt                                                    17

<210> SEQ ID NO 108
<211> LENGTH: 16
<212> TYPE: DNA
<213> ORGANISM: Anabaena sp.

<400> SEQUENCE: 108
gagaatgaaa atccgt                                                     16

<210> SEQ ID NO 109
<211> LENGTH: 35
<212> TYPE: DNA
<213> ORGANISM: Anabaena sp.

<400> SEQUENCE: 109
gcagtagcga aagctgcaag agaatgaaaa tccgt                                35

<210> SEQ ID NO 110
<211> LENGTH: 33
<212> TYPE: DNA
<213> ORGANISM: Anabaena sp.

<400> SEQUENCE: 110
agtagcgaaa gctgcaagag aatgaaaatc cgt                                  33

<210> SEQ ID NO 111
<211> LENGTH: 32
<212> TYPE: DNA
<213> ORGANISM: Anabaena sp.

<400> SEQUENCE: 111
gtagcgaaag ctgcaagaga atgaaaatcc gt                                   32

<210> SEQ ID NO 112
<211> LENGTH: 26
<212> TYPE: DNA
<213> ORGANISM: Anabaena sp.

<400> SEQUENCE: 112
acggacttaa ataattgagc cttaaa                                          26
```

```
<210> SEQ ID NO 113
<211> LENGTH: 27
<212> TYPE: DNA
<213> ORGANISM: Anabaena sp.

<400> SEQUENCE: 113
acggacttaa ataattgagc cttaaag                                          27

<210> SEQ ID NO 114
<211> LENGTH: 28
<212> TYPE: DNA
<213> ORGANISM: Anabaena sp.

<400> SEQUENCE: 114
acggacttaa ataattgagc cttaaaga                                         28

<210> SEQ ID NO 115
<211> LENGTH: 76
<212> TYPE: DNA
<213> ORGANISM: Anabaena sp.

<400> SEQUENCE: 115
acggacttaa ataattgagc cttaaagaag aaattcttta agtggatgct ctcaaactca      60
gggaaaccta aatcta                                                     76

<210> SEQ ID NO 116
<211> LENGTH: 77
<212> TYPE: DNA
<213> ORGANISM: Anabaena sp.

<400> SEQUENCE: 116
acggacttaa ataattgagc cttaaagaag aaattcttta agtggatgct ctcaaactca      60
gggaaaccta aatctag                                                    77

<210> SEQ ID NO 117
<211> LENGTH: 78
<212> TYPE: DNA
<213> ORGANISM: Anabaena sp.

<400> SEQUENCE: 117
acggacttaa ataattgagc cttaaagaag aaattcttta agtggatgct ctcaaactca      60
gggaaaccta aatctagt                                                   78

<210> SEQ ID NO 118
<211> LENGTH: 79
<212> TYPE: DNA
<213> ORGANISM: Anabaena sp.

<400> SEQUENCE: 118
acggacttaa ataattgagc cttaaagaag aaattcttta agtggatgct ctcaaactca      60
gggaaaccta aatctagtt                                                  79

<210> SEQ ID NO 119
<211> LENGTH: 80
<212> TYPE: DNA
<213> ORGANISM: Anabaena sp.

<400> SEQUENCE: 119
acggacttaa ataattgagc cttaaagaag aaattcttta agtggatgct ctcaaactca      60
gggaaaccta aatctagtta                                                 80
```

<210> SEQ ID NO 120
<211> LENGTH: 127
<212> TYPE: DNA
<213> ORGANISM: Anabaena sp.

<400> SEQUENCE: 120

```
acggacttaa ataattgagc cttaaagaag aaattcttta agtggatgct ctcaaactca    60
gggaaaccta aatctagtta tagacaaggc aatcctgagc caagccgaag tagtaattag   120
taagtta                                                             127
```

<210> SEQ ID NO 121
<211> LENGTH: 128
<212> TYPE: DNA
<213> ORGANISM: Anabaena sp.

<400> SEQUENCE: 121

```
acggacttaa ataattgagc cttaaagaag aaattcttta agtggatgct ctcaaactca    60
gggaaaccta aatctagtta tagacaaggc aatcctgagc caagccgaag tagtaattag   120
taagttaa                                                            128
```

<210> SEQ ID NO 122
<211> LENGTH: 129
<212> TYPE: DNA
<213> ORGANISM: Anabaena sp.

<400> SEQUENCE: 122

```
acggacttaa ataattgagc cttaaagaag aaattcttta agtggatgct ctcaaactca    60
gggaaaccta aatctagtta tagacaaggc aatcctgagc caagccgaag tagtaattag   120
taagttaac                                                           129
```

<210> SEQ ID NO 123
<211> LENGTH: 130
<212> TYPE: DNA
<213> ORGANISM: Anabaena sp.

<400> SEQUENCE: 123

```
acggacttaa ataattgagc cttaaagaag aaattcttta agtggatgct ctcaaactca    60
gggaaaccta aatctagtta tagacaaggc aatcctgagc caagccgaag tagtaattag   120
taagttaaca                                                          130
```

<210> SEQ ID NO 124
<211> LENGTH: 131
<212> TYPE: DNA
<213> ORGANISM: Anabaena sp.

<400> SEQUENCE: 124

```
acggacttaa ataattgagc cttaaagaag aaattcttta agtggatgct ctcaaactca    60
gggaaaccta aatctagtta tagacaaggc aatcctgagc caagccgaag tagtaattag   120
taagttaaca a                                                        131
```

<210> SEQ ID NO 125
<211> LENGTH: 132
<212> TYPE: DNA
<213> ORGANISM: Anabaena sp.

<400> SEQUENCE: 125

```
acggacttaa ataattgagc cttaaagaag aaattcttta agtggatgct ctcaaactca    60
```

```
gggaaaccta aatctagtta tagacaaggc aatcctgagc caagccgaag tagtaattag        120
taagttaaca at                                                             132

<210> SEQ ID NO 126
<211> LENGTH: 133
<212> TYPE: DNA
<213> ORGANISM: Anabaena sp.

<400> SEQUENCE: 126
acggacttaa ataattgagc cttaaagaag aaattcttta agtggatgct ctcaaactca         60
gggaaaccta aatctagtta tagacaaggc aatcctgagc caagccgaag tagtaattag        120
taagttaaca ata                                                            133

<210> SEQ ID NO 127
<211> LENGTH: 134
<212> TYPE: DNA
<213> ORGANISM: Anabaena sp.

<400> SEQUENCE: 127
acggacttaa ataattgagc cttaaagaag aaattcttta agtggatgct ctcaaactca         60
gggaaaccta aatctagtta tagacaaggc aatcctgagc caagccgaag tagtaattag        120
taagttaaca atag                                                           134

<210> SEQ ID NO 128
<211> LENGTH: 135
<212> TYPE: DNA
<213> ORGANISM: Anabaena sp.

<400> SEQUENCE: 128
acggacttaa ataattgagc cttaaagaag aaattcttta agtggatgct ctcaaactca         60
gggaaaccta aatctagtta tagacaaggc aatcctgagc caagccgaag tagtaattag        120
taagttaaca ataga                                                          135

<210> SEQ ID NO 129
<211> LENGTH: 188
<212> TYPE: DNA
<213> ORGANISM: Anabaena sp.

<400> SEQUENCE: 129
acggacttaa ataattgagc cttaaagaag aaattcttta agtggatgct ctcaaactca         60
gggaaaccta aatctagtta tagacaaggc aatcctgagc caagccgaag tagtaattag        120
taagttaaca atagatgact tacaactaat cggaaggtgc agagactcga cgggagctac        180
cctaacgt                                                                  188

<210> SEQ ID NO 130
<211> LENGTH: 189
<212> TYPE: DNA
<213> ORGANISM: Anabaena sp.

<400> SEQUENCE: 130
acggacttaa ataattgagc cttaaagaag aaattcttta agtggatgct ctcaaactca         60
gggaaaccta aatctagtta tagacaaggc aatcctgagc caagccgaag tagtaattag        120
taagttaaca atagatgact tacaactaat cggaaggtgc agagactcga cgggagctac        180
cctaacgtc                                                                 189
```

<210> SEQ ID NO 131
<211> LENGTH: 190
<212> TYPE: DNA
<213> ORGANISM: Anabaena sp.

<400> SEQUENCE: 131
acggacttaa ataattgagc cttaaagaag aaattcttta agtggatgct ctcaaactca    60
gggaaaccta atctagtta tagacaaggc aatcctgagc caagccgaag tagtaattag    120
taagttaaca atagatgact tacaactaat cggaaggtgc agagactcga cgggagctac   180
cctaacgtca                                                         190

<210> SEQ ID NO 132
<211> LENGTH: 191
<212> TYPE: DNA
<213> ORGANISM: Anabaena sp.

<400> SEQUENCE: 132
acggacttaa ataattgagc cttaaagaag aaattcttta agtggatgct ctcaaactca    60
gggaaaccta atctagtta tagacaaggc aatcctgagc caagccgaag tagtaattag    120
taagttaaca atagatgact tacaactaat cggaaggtgc agagactcga cgggagctac   180
cctaacgtca a                                                       191

<210> SEQ ID NO 133
<211> LENGTH: 192
<212> TYPE: DNA
<213> ORGANISM: Anabaena sp.

<400> SEQUENCE: 133
acggacttaa ataattgagc cttaaagaag aaattcttta agtggatgct ctcaaactca    60
gggaaaccta atctagtta tagacaaggc aatcctgagc caagccgaag tagtaattag    120
taagttaaca atagatgact tacaactaat cggaaggtgc agagactcga cgggagctac   180
cctaacgtca ag                                                      192

<210> SEQ ID NO 134
<211> LENGTH: 226
<212> TYPE: DNA
<213> ORGANISM: Anabaena sp.

<400> SEQUENCE: 134
acggacttaa ataattgagc cttaaagaag aaattcttta agtggatgct ctcaaactca    60
gggaaaccta atctagtta tagacaaggc aatcctgagc caagccgaag tagtaattag    120
taagttaaca atagatgact tacaactaat cggaaggtgc agagactcga cgggagctac   180
cctaacgtca agacgagggt aaagagagag tccaattctc aaagcc                 226

<210> SEQ ID NO 135
<211> LENGTH: 227
<212> TYPE: DNA
<213> ORGANISM: Anabaena sp.

<400> SEQUENCE: 135
acggacttaa ataattgagc cttaaagaag aaattcttta agtggatgct ctcaaactca    60
gggaaaccta atctagtta tagacaaggc aatcctgagc caagccgaag tagtaattag    120
taagttaaca atagatgact tacaactaat cggaaggtgc agagactcga cgggagctac   180
cctaacgtca agacgagggt aaagagagag tccaattctc aaagcca                227

<210> SEQ ID NO 136
<211> LENGTH: 228
<212> TYPE: DNA
<213> ORGANISM: Anabaena sp.

<400> SEQUENCE: 136

| | | |
|---|---|---|
| acggacttaa ataattgagc cttaaagaag aaattcttta agtggatgct ctcaaactca | 60 |
| gggaaaccta atctagttta tagacaaggc aatcctgagc caagccgaag tagtaattag | 120 |
| taagttaaca atagatgact tacaactaat cggaaggtgc agagactcga cgggagctac | 180 |
| cctaacgtca agacgagggt aaagagagag tccaattctc aaagccaa | 228 |

<210> SEQ ID NO 137
<211> LENGTH: 229
<212> TYPE: DNA
<213> ORGANISM: Anabaena sp.

<400> SEQUENCE: 137

| | | |
|---|---|---|
| acggacttaa ataattgagc cttaaagaag aaattcttta agtggatgct ctcaaactca | 60 |
| gggaaaccta atctagttta tagacaaggc aatcctgagc caagccgaag tagtaattag | 120 |
| taagttaaca atagatgact tacaactaat cggaaggtgc agagactcga cgggagctac | 180 |
| cctaacgtca agacgagggt aaagagagag tccaattctc aaagccaat | 229 |

<210> SEQ ID NO 138
<211> LENGTH: 230
<212> TYPE: DNA
<213> ORGANISM: Anabaena sp.

<400> SEQUENCE: 138

| | | |
|---|---|---|
| acggacttaa ataattgagc cttaaagaag aaattcttta agtggatgct ctcaaactca | 60 |
| gggaaaccta atctagttta tagacaaggc aatcctgagc caagccgaag tagtaattag | 120 |
| taagttaaca atagatgact tacaactaat cggaaggtgc agagactcga cgggagctac | 180 |
| cctaacgtca agacgagggt aaagagagag tccaattctc aaagccaata | 230 |

<210> SEQ ID NO 139
<211> LENGTH: 239
<212> TYPE: DNA
<213> ORGANISM: Anabaena sp.

<400> SEQUENCE: 139

| | | |
|---|---|---|
| acggacttaa ataattgagc cttaaagaag aaattcttta agtggatgct ctcaaactca | 60 |
| gggaaaccta atctagttta tagacaaggc aatcctgagc caagccgaag tagtaattag | 120 |
| taagttaaca atagatgact tacaactaat cggaaggtgc agagactcga cgggagctac | 180 |
| cctaacgtca agacgagggt aaagagagag tccaattctc aaagccaata ggcagtagc | 239 |

<210> SEQ ID NO 140
<211> LENGTH: 240
<212> TYPE: DNA
<213> ORGANISM: Anabaena sp.

<400> SEQUENCE: 140

| | | |
|---|---|---|
| acggacttaa ataattgagc cttaaagaag aaattcttta agtggatgct ctcaaactca | 60 |
| gggaaaccta atctagttta tagacaaggc aatcctgagc caagccgaag tagtaattag | 120 |
| taagttaaca atagatgact tacaactaat cggaaggtgc agagactcga cgggagctac | 180 |

```
cctaacgtca agacgagggt aaagagagag tccaattctc aaagccaata ggcagtagcg    240

<210> SEQ ID NO 141
<211> LENGTH: 241
<212> TYPE: DNA
<213> ORGANISM: Anabaena sp.

<400> SEQUENCE: 141
acggacttaa ataattgagc cttaaagaag aaattcttta agtggatgct ctcaaactca     60
gggaaaccta atctagtta tagacaaggc aatcctgagc caagccgaag tagtaattag    120
taagttaaca atagatgact tacaactaat cggaaggtgc agagactcga cgggagctac    180
cctaacgtca agacgagggt aaagagagag tccaattctc aaagccaata ggcagtagcg    240
a                                                                   241

<210> SEQ ID NO 142
<211> LENGTH: 242
<212> TYPE: DNA
<213> ORGANISM: Anabaena sp.

<400> SEQUENCE: 142
acggacttaa ataattgagc cttaaagaag aaattcttta agtggatgct ctcaaactca     60
gggaaaccta atctagtta tagacaaggc aatcctgagc caagccgaag tagtaattag    120
taagttaaca atagatgact tacaactaat cggaaggtgc agagactcga cgggagctac    180
cctaacgtca agacgagggt aaagagagag tccaattctc aaagccaata ggcagtagcg    240
aa                                                                  242

<210> SEQ ID NO 143
<211> LENGTH: 243
<212> TYPE: DNA
<213> ORGANISM: Anabaena sp.

<400> SEQUENCE: 143
acggacttaa ataattgagc cttaaagaag aaattcttta agtggatgct ctcaaactca     60
gggaaaccta atctagtta tagacaaggc aatcctgagc caagccgaag tagtaattag    120
taagttaaca atagatgact tacaactaat cggaaggtgc agagactcga cgggagctac    180
cctaacgtca agacgagggt aaagagagag tccaattctc aaagccaata ggcagtagcg    240
aaa                                                                 243

<210> SEQ ID NO 144
<211> LENGTH: 244
<212> TYPE: DNA
<213> ORGANISM: Anabaena sp.

<400> SEQUENCE: 144
acggacttaa ataattgagc cttaaagaag aaattcttta agtggatgct ctcaaactca     60
gggaaaccta atctagtta tagacaaggc aatcctgagc caagccgaag tagtaattag    120
taagttaaca atagatgact tacaactaat cggaaggtgc agagactcga cgggagctac    180
cctaacgtca agacgagggt aaagagagag tccaattctc aaagccaata ggcagtagcg    240
aaag                                                                244

<210> SEQ ID NO 145
<211> LENGTH: 248
<212> TYPE: DNA
<213> ORGANISM: Anabaena sp.
```

<400> SEQUENCE: 145

```
acggacttaa ataattgagc cttaaagaag aaattcttta agtggatgct ctcaaactca      60
gggaaaccta atctagtta tagacaaggc aatcctgagc caagccgaag tagtaattag     120
taagttaaca atagatgact tacaactaat cggaaggtgc agagactcga cgggagctac    180
cctaacgtca agacgagggt aaagagagag tccaattctc aaagccaata ggcagtagcg    240
aaagctgc                                                             248
```

<210> SEQ ID NO 146
<211> LENGTH: 249
<212> TYPE: DNA
<213> ORGANISM: Anabaena sp.

<400> SEQUENCE: 146

```
acggacttaa ataattgagc cttaaagaag aaattcttta agtggatgct ctcaaactca      60
gggaaaccta atctagtta tagacaaggc aatcctgagc caagccgaag tagtaattag     120
taagttaaca atagatgact tacaactaat cggaaggtgc agagactcga cgggagctac    180
cctaacgtca agacgagggt aaagagagag tccaattctc aaagccaata ggcagtagcg    240
aaagctgca                                                            249
```

<210> SEQ ID NO 147
<211> LENGTH: 250
<212> TYPE: DNA
<213> ORGANISM: Anabaena sp.

<400> SEQUENCE: 147

```
acggacttaa ataattgagc cttaaagaag aaattcttta agtggatgct ctcaaactca      60
gggaaaccta atctagtta tagacaaggc aatcctgagc caagccgaag tagtaattag     120
taagttaaca atagatgact tacaactaat cggaaggtgc agagactcga cgggagctac    180
cctaacgtca agacgagggt aaagagagag tccaattctc aaagccaata ggcagtagcg    240
aaagctgcaa                                                           250
```

<210> SEQ ID NO 148
<211> LENGTH: 231
<212> TYPE: DNA
<213> ORGANISM: Anabaena sp.

<400> SEQUENCE: 148

```
acggacttaa ataattgagc cttaaagaag aaattcttta agtggatgct ctcaaactca      60
gggaaaccta atctagtta tagacaaggc aatcctgagc caagccgaag tagtaattag     120
taagttaaca atagatgact tacaactaat cggaaggtgc agagactcga cgggagctac    180
cctaacgtca agacgagggt aaagagagag tccaattctc aaagccaata g             231
```

<210> SEQ ID NO 149
<211> LENGTH: 233
<212> TYPE: DNA
<213> ORGANISM: Anabaena sp.

<400> SEQUENCE: 149

```
acggacttaa ataattgagc cttaaagaag aaattcttta agtggatgct ctcaaactca      60
gggaaaccta atctagtta tagacaaggc aatcctgagc caagccgaag tagtaattag     120
taagttaaca atagatgact tacaactaat cggaaggtgc agagactcga cgggagctac    180
```

```
cctaacgtca agacgagggt aaagagagag tccaattctc aaagccaata ggc         233
```

```
<210> SEQ ID NO 150
<211> LENGTH: 234
<212> TYPE: DNA
<213> ORGANISM: Anabaena sp.

<400> SEQUENCE: 150
acggacttaa ataattgagc cttaaagaag aaattcttta agtggatgct ctcaaactca    60
gggaaaccta atctagtta tagacaaggc aatcctgagc caagccgaag tagtaattag    120
taagttaaca atagatgact tacaactaat cggaaggtgc agagactcga cgggagctac   180
cctaacgtca agacgagggt aaagagagag tccaattctc aaagccaata ggca         234
```

```
<210> SEQ ID NO 151
<211> LENGTH: 104
<212> TYPE: DNA
<213> ORGANISM: Azoarcus sp.

<400> SEQUENCE: 151
tgcgccgatg aaggtgtaga gactagacgg cacccaccta aggcaaacgc tatggtgaag    60
gcatagtcca gggagtggcg aaagtcacac aaaccggaat ccgt                    104
```

```
<210> SEQ ID NO 152
<211> LENGTH: 141
<212> TYPE: DNA
<213> ORGANISM: Azoarcus sp.

<400> SEQUENCE: 152
ccgggcgtat ggcaacgccg agccaagctt cggcgcctgc gccgatgaag gtgtagagac    60
tagacggcac ccacctaagg caaacgctat ggtgaaggca tagtccaggg agtggcgaaa    120
gtcacacaaa ccggaatccg t                                              141
```

```
<210> SEQ ID NO 153
<211> LENGTH: 78
<212> TYPE: DNA
<213> ORGANISM: Azoarcus sp.

<400> SEQUENCE: 153
acggcaccca cctaaggcaa acgctatggt gaaggcatag tccagggagt ggcgaaagtc    60
acacaaaccg gaatccgt                                                  78
```

```
<210> SEQ ID NO 154
<211> LENGTH: 58
<212> TYPE: DNA
<213> ORGANISM: Azoarcus sp.

<400> SEQUENCE: 154
acgctatggt gaaggcatag tccagggagt ggcgaaagtc acacaaaccg gaatccgt      58
```

```
<210> SEQ ID NO 155
<211> LENGTH: 75
<212> TYPE: DNA
<213> ORGANISM: Thiomargarita sp.

<400> SEQUENCE: 155
attaaagtta tagaattatc agagaatgat atagtccaag ccttatggta acatgagggc    60
acttgaccct ggtag                                                     75
```

```
<210> SEQ ID NO 156
<211> LENGTH: 195
<212> TYPE: DNA
<213> ORGANISM: Staphylococcus virus Twort

<400> SEQUENCE: 156
aagatgtagg caatcctgag ctaagctctt agtaataaga gaaagtgcaa cgactattcc      60
gataggaagt agggtcaagt gactcgaaat ggggattacc cttctagggt agtgatatag     120
tctgaacata tatggaaaca tatagaagga taggagtaac gaacctattc gtaacataat     180 tgaacttta gttat                                                      195

<210> SEQ ID NO 157
<211> LENGTH: 163
<212> TYPE: DNA
<213> ORGANISM: Staphylococcus virus Twort

<400> SEQUENCE: 157
taataagaga aagtgcaacg actattccga taggaagtag ggtcaagtga ctcgaaatgg      60
ggattaccct tctagggtag tgatatagtc tgaacatata tggaaacata tagaaggata    120
ggagtaacga acctattcgt aacataattg aactttagt tat                       163

<210> SEQ ID NO 158
<211> LENGTH: 133
<212> TYPE: DNA
<213> ORGANISM: Staphylococcus virus Twort

<400> SEQUENCE: 158
taggaagtag ggtcaagtga ctcgaaatgg ggattaccct tctagggtag tgatatagtc      60
tgaacatata tggaaacata tagaaggata ggagtaacga acctattcgt aacataattg    120 aactttagt tat                                                        133

<210> SEQ ID NO 159
<211> LENGTH: 92
<212> TYPE: DNA
<213> ORGANISM: Staphylococcus virus Twort

<400> SEQUENCE: 159
ctagggtagt gatatagtct gaacatatat ggaaacatat agaaggatag gagtaacgaa      60
cctattcgta acataattga actttagtt at                                    92

<210> SEQ ID NO 160
<211> LENGTH: 92
<212> TYPE: DNA
<213> ORGANISM: Unknown
<220> FEATURE:
<221> NAME/KEY: source
<223> OTHER INFORMATION: /note="Description of Unknown:
      LSUp1 sequence"

<400> SEQUENCE: 160
agttaataaa gatgatgaaa tagtctgaac catttttgaga aaagtggaaa taaaagaaaa      60 tctttttatga taacataaat tgaacaggct aa                                   92

<210> SEQ ID NO 161
<211> LENGTH: 62
<212> TYPE: DNA
<213> ORGANISM: Bacteriophage Phi I

<400> SEQUENCE: 161
```

```
caaagactga tgatatagtc cgacactcct agtaatagga gaatacagaa aggatgaaat      60
cc                                                                    62

<210> SEQ ID NO 162
<211> LENGTH: 76
<212> TYPE: DNA
<213> ORGANISM: Nostoc sp.

<400> SEQUENCE: 162
agtcgagggt aaagggagag tccaattctc aaagcctatt ggcagtagcg aaagctgcgg      60
gagaatgaaa atccgt                                                     76

<210> SEQ ID NO 163
<211> LENGTH: 76
<212> TYPE: DNA
<213> ORGANISM: Nostoc sp.

<400> SEQUENCE: 163
agccgagggt aaagggagag tccaattctc aaagccaata ggcagtagcg aaagctgcgg      60
gagaatgaaa atccgt                                                     76

<210> SEQ ID NO 164
<211> LENGTH: 89
<212> TYPE: DNA
<213> ORGANISM: Nodularia sp.

<400> SEQUENCE: 164
agccgagggt aaagggagag tccaattctc aaagccgaag gttattaaaa cctggcagca      60
gtgaaagctg cgggagaatg aaaatccgt                                       89

<210> SEQ ID NO 165
<211> LENGTH: 79
<212> TYPE: DNA
<213> ORGANISM: Pleurocapsa sp.

<400> SEQUENCE: 165
agctgagggt aaagagagag tccaattctc aaagccagca gatggcagta gcgaaagctg      60
cgggagaatg aaaatccgt                                                  79

<210> SEQ ID NO 166
<211> LENGTH: 76
<212> TYPE: DNA
<213> ORGANISM: Planktothrix sp.

<400> SEQUENCE: 166
agccgagggt aaagagagag tccaattctc aaagccaatt ggtagtagcg aaagctacgg      60
gagaatgaaa atccgt                                                     76

<210> SEQ ID NO 167
<211> LENGTH: 118
<212> TYPE: DNA
<213> ORGANISM: Azoarcus sp.

<400> SEQUENCE: 167
gcggactcat atttcgatgt gccttgcgcc gggaaaccac gcaagggatg gtgtcaaatt      60
cggcgaaacc taagcgcccg cccgggcgta tggcaacgcc gagccaagct tcggcgcc      118

<210> SEQ ID NO 168
<211> LENGTH: 81
```

<212> TYPE: DNA
<213> ORGANISM: Azoarcus sp.

<400> SEQUENCE: 168

```
gcggactcat atttcgatgt gccttgcgcc gggaaaccac gcaagggatg gtgtcaaatt    60
cggcgaaacc taagcgcccg c                                             81
```

<210> SEQ ID NO 169
<211> LENGTH: 144
<212> TYPE: DNA
<213> ORGANISM: Azoarcus sp.

<400> SEQUENCE: 169

```
gcggactcat atttcgatgt gccttgcgcc gggaaaccac gcaagggatg gtgtcaaatt    60
cggcgaaacc taagcgcccg cccgggcgta tggcaacgcc gagccaagct tcggcgcctg   120
cgccgatgaa ggtgtagaga ctag                                         144
```

<210> SEQ ID NO 170
<211> LENGTH: 164
<212> TYPE: DNA
<213> ORGANISM: Azoarcus sp.

<400> SEQUENCE: 170

```
gcggactcat atttcgatgt gccttgcgcc gggaaaccac gcaagggatg gtgtcaaatt    60
cggcgaaacc taagcgcccg cccgggcgta tggcaacgcc gagccaagct tcggcgcctg   120
cgccgatgaa ggtgtagaga ctagacggca cccacctaag gcaa                    164
```

<210> SEQ ID NO 171
<211> LENGTH: 179
<212> TYPE: DNA
<213> ORGANISM: Thiomargarita sp.

<400> SEQUENCE: 171

```
aggattagat actacactaa gtgtccccca gactggtgac agtctggtgt gcatccagct    60
atatcggtga acccccattg gggtaatacc gagggaagct atattatata tatattaata   120
aatagccccg tagagactat gtaggtaagg agatagaaga tgataaaatc aaaatcatc    179
```

<210> SEQ ID NO 172
<211> LENGTH: 84
<212> TYPE: DNA
<213> ORGANISM: Staphylococcus virus Twort

<400> SEQUENCE: 172

```
actactgaaa gcataaataa ttgtgccttt atacagtaat gtatatcgaa aaatcctcta    60
attcagggaa cacctaaaca aact                                          84
```

<210> SEQ ID NO 173
<211> LENGTH: 116
<212> TYPE: DNA
<213> ORGANISM: Staphylococcus virus Twort

<400> SEQUENCE: 173

```
actactgaaa gcataaataa ttgtgccttt atacagtaat gtatatcgaa aaatcctcta    60
attcagggaa cacctaaaca aactaagatg taggcaatcc tgagctaagc tcttag      116
```

<210> SEQ ID NO 174
<211> LENGTH: 146
<212> TYPE: DNA

<213> ORGANISM: Staphylococcus virus Twort

<400> SEQUENCE: 174

```
actactgaaa gcataaataa ttgtgccttt atacagtaat gtatatcgaa aaatcctcta      60
attcagggaa cacctaaaca aactaagatg taggcaatcc tgagctaagc tcttagtaat     120
aagagaaagt gcaacgacta ttccga                                          146
```

<210> SEQ ID NO 175
<211> LENGTH: 187
<212> TYPE: DNA
<213> ORGANISM: Staphylococcus virus Twort

<400> SEQUENCE: 175

```
actactgaaa gcataaataa ttgtgccttt atacagtaat gtatatcgaa aaatcctcta      60
attcagggaa cacctaaaca aactaagatg taggcaatcc tgagctaagc tcttagtaat     120
aagagaaagt gcaacgacta ttccgatagg aagtagggtc aagtgactcg aaatggggat     180
taccctt                                                               187
```

<210> SEQ ID NO 176
<211> LENGTH: 216
<212> TYPE: DNA
<213> ORGANISM: Unknown
<220> FEATURE:
<221> NAME/KEY: source
<223> OTHER INFORMATION: /note="Description of Unknown:
      LSUp1 sequence"

<400> SEQUENCE: 176

```
cgctagggat ttataactgt gagtcctcca atattataaa atgttggtaa tatattgggt      60
aaatttcaaa gacaactttt ctccacgtca ggatatagtg tatttgaagc gaaacttatt    120
ttagcagtga aaaagcaaat aaggacgttc aacgactaaa aggtgagtat tgctaacaat    180
aatccttttt tttaatgccc aacatcttta ttaact                              216
```

<210> SEQ ID NO 177
<211> LENGTH: 559
<212> TYPE: DNA
<213> ORGANISM: Bacteriophage Phi I

<400> SEQUENCE: 177

```
gtgggtgcat aaactatttc attgtgcaca ttaaatctgg tgaactcggt gaaaccctaa      60
tggggcaata ccgagccaag ccatagggag gatatatgag aggcaagaag ttaattcttg    120
aggccactga gactggctgt atcatcccta cgtcacacaa acttaatgcc gatggttatt    180
tcagaaagaa aaccaatggc gtcttagaga tgtatcacag aacggtgtgg aaggagcata    240
acggagacat acctgatggc ttcgagatag accataagtg tcgcaatagg gcttgctgta    300
atatagagca tttacagatg cttgagggta cagcccacac tgttaagacc aatcgtgaac    360
gctacgcaga cagaaaggaa acagctaggg aatactggct ggagactgga tgtaccggcc    420
tagcactcgg tgagaagttt ggtgtgtcgt tctcttctgc ttgtaagtgg attagagaat    480
ggaaggcgta gagactatcc gaaggagta gggccgaggg tgagactccc tcgtaacccg    540
aagcgccaga cagtcaact                                                 559
```

<210> SEQ ID NO 178
<211> LENGTH: 218
<212> TYPE: DNA
<213> ORGANISM: Nostoc sp.

<400> SEQUENCE: 178

```
acggacttaa gtaattgagc cttaaagaag aaattcttta agtggcagct ctcaaactca      60
gggaaaccta atctgttcca cagacaaggc aatcctgagc caagccgaaa gagtcatgag     120
tgctgagtag tgagtaaaat aaaagctcac aactcagagg ttgtaactct aagctagtcg     180
gaaggtgcag agactcgacg ggagctaccc taacgtaa                             218
```

<210> SEQ ID NO 179
<211> LENGTH: 165
<212> TYPE: DNA
<213> ORGANISM: Nostoc sp.

<400> SEQUENCE: 179

```
acggacttaa actgaattga gccttagaga agaaattctt taagtgtcag ctctcaaact      60
cagggaaacc taaatctgtt gacagacaag gcaatcctga gccaagccga gaactctaag     120
ttattcggaa ggtgcagaga ctcgacggga gctaccctaa cgtca                     165
```

<210> SEQ ID NO 180
<211> LENGTH: 181
<212> TYPE: DNA
<213> ORGANISM: Nodularia sp.

<400> SEQUENCE: 180

```
acggacttag aaaactgagc cttgatcgag aaatctttca gtggaagct ctcaaattca       60 gggaaaccta atctgtttta cagatatggc aatcctgagc caagccgaaa caagtcctga     120
gtgttaaagc tcataactca tcggaaggtg cagagactcg acgggagcta ccctaacgtt     180
a                                                                      181
```

<210> SEQ ID NO 181
<211> LENGTH: 188
<212> TYPE: DNA
<213> ORGANISM: Pleurocapsa sp.

<400> SEQUENCE: 181

```
acggacttaa aaaaattgag ccttggcaga gaaatctgtc atgcgaacgc tctcaaattc      60
agggaaacct aagtctggca acagatatgg caatcctgag ccaagcctta atcaaggaaa     120
aaaacatttt tacctttac cttgaaagga aggtgcagag actcaacggg agctacccta      180
acaggtca                                                               188
```

<210> SEQ ID NO 182
<211> LENGTH: 200
<212> TYPE: DNA
<213> ORGANISM: Planktothrix sp.

<400> SEQUENCE: 182

```
acggacttaa agataaattg agccttgagg cgagaaatct ctcaagtgta agctgtcaaa      60
ttcagggaaa cctaaatctg taaattcaga caaggcaatc ctgagccaag cctaggggta     120
ttagaaatga gggagtttcc ccaatctaag atcaatacct aggaaggtgc agagactcga     180
cgggagctac cctaacgtta                                                  200
```

<210> SEQ ID NO 183
<211> LENGTH: 166
<212> TYPE: DNA
<213> ORGANISM: Artificial Sequence
<220> FEATURE:

<221> NAME/KEY: source
<223> OTHER INFORMATION: /note="Description of Artificial Sequence:
      Synthetic polynucleotide"

<400> SEQUENCE: 183
agtatataag aaacaaacca ctagatgact tacaactaat cggaaggtgc agagactcga      60
cgggagctac cctaacgtca agacgagggt aaagagagag tccaattctc aaagccaata    120
ggcagtagcg aaagctgcaa gagaatgaaa atccgtggct cgcagc                   166

<210> SEQ ID NO 184
<211> LENGTH: 176
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 184
ctgaaattat acttatactc aaacaaacca ctagatgact tacaactaat cggaaggtgc      60
agagactcga cgggagctac cctaacgtca agacgagggt aaagagagag tccaattctc    120
aaagccaata ggcagtagcg aaagctgcaa gagaatgaaa atccgtggct cgcagc        176

<210> SEQ ID NO 185
<211> LENGTH: 186
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 185
ctgaaattat acttatactc agtatatgac aaacaaacca ctagatgact tacaactaat      60
cggaaggtgc agagactcga cgggagctac cctaacgtca agacgagggt aaagagagag    120
tccaattctc aaagccaata ggcagtagcg aaagctgcaa gagaatgaaa atccgtggct    180
cgcagc                                                              186

<210> SEQ ID NO 186
<211> LENGTH: 196
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 186
catcaacaat atgaaattat acttatactc agtatatgac aaacaaacca ctagatgact      60
tacaactaat cggaaggtgc agagactcga cgggagctac cctaacgtca agacgagggt    120
aaagagagag tccaattctc aaagccaata ggcagtagcg aaagctgcaa gagaatgaaa    180
atccgtggct cgcagc                                                   196

<210> SEQ ID NO 187
<211> LENGTH: 206
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 187

| catcaacaat atgaaactat acttatactc agtatatgaa gcattatcgc aaacaaacca | 60 |
| ctagatgact tacaactaat cggaaggtgc agagactcga cgggagctac cctaacgtca | 120 |
| agacgagggt aaagagagag tccaattctc aaagccaata ggcagtagcg aaagctgcaa | 180 |
| gagaatgaaa atccgtggct cgcagc | 206 |

<210> SEQ ID NO 188
<211> LENGTH: 166
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 188

| tagcgtcagc aaacaaacaa atagatgact tacaactaat cggaaggtgc agagactcga | 60 |
| cgggagctac cctaacgtca agacgagggt aaagagagag tccaattctc aaagccaata | 120 |
| ggcagtagcg aaagctgcaa gagaatgaaa atccgtggct cgcagc | 166 |

<210> SEQ ID NO 189
<211> LENGTH: 176
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 189

| atactcatac tagcgtcagc aaacaaacaa atagatgact tacaactaat cggaaggtgc | 60 |
| agagactcga cgggagctac cctaacgtca agacgagggt aaagagagag tccaattctc | 120 |
| aaagccaata ggcagtagcg aaagctgcaa gagaatgaaa atccgtggct cgcagc | 176 |

<210> SEQ ID NO 190
<211> LENGTH: 186
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 190

| gtgtgaagct atactcatac tagcgtcagc aaacaaacaa atagatgact tacaactaat | 60 |
| cggaaggtgc agagactcga cgggagctac cctaacgtca agacgagggt aaagagagag | 120 |
| tccaattctc aaagccaata ggcagtagcg aaagctgcaa gagaatgaaa atccgtggct | 180 |
| cgcagc | 186 |

<210> SEQ ID NO 191
<211> LENGTH: 196
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 191

```
cctcacctga gtgtgaagct atactcatac tagcgtcagc aaacaaacaa atagatgact     60
tacaactaat cggaaggtgc agagactcga cgggagctac cctaacgtca agacgagggt    120
aaagagagag tccaattctc aaagccaata ggcagtagcg aaagctgcaa gagaatgaaa    180
atccgtggct cgcagc                                                   196
```

<210> SEQ ID NO 192
<211> LENGTH: 206
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 192

```
ccgaatgatg cctcacctga gtgtgaagct atactcatac tagcgtcagc aaacaaacaa     60
atagatgact tacaactaat cggaaggtgc agagactcga cgggagctac cctaacgtca    120
agacgagggt aaagagagag tccaattctc aaagccaata ggcagtagcg aaagctgcaa    180
gagaatgaaa atccgtggct cgcagc                                        206
```

<210> SEQ ID NO 193
<211> LENGTH: 166
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 193

```
cggtgcgagc aaacaaacaa atagatgact tacaactaat cggaaggtgc agagactcga     60
cgggagctac cctaacgtca agacgagggt aaagagagag tccaattctc aaagccaata    120
ggcagtagcg aaagctgcaa gagaatgaaa atccgtggct cgcagc                  166
```

<210> SEQ ID NO 194
<211> LENGTH: 176
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 194

```
cgctccgacc cagtgcgagc aaacaaacaa atagatgact tacaactaat cggaaggtgc     60
agagactcga cgggagctac cctaacgtca agacgagggt aaagagagag tccaattctc    120
aaagccaata ggcagtagcg aaagctgcaa gagaatgaaa atccgtggct cgcagc       176
```

<210> SEQ ID NO 195
<211> LENGTH: 186
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 195

```
ctgaaattat actaatactc agtatatgac aaacaaacca ctagatgact tacaactaat     60
cggaaggtgc agagactcga cgggagctac cctaacgtca agacgagggt aaagagagag    120
```

```
tccaattctc aaagccaata ggcagtagcg aaagctgcaa gagaatgaaa atccgtggct    180
cgcagc                                                              186
```

<210> SEQ ID NO 196
<211> LENGTH: 186
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 196

```
ctgaaaatat actaatactc actatatgac aaacaaacca ctagatgact tacaactaat    60
cggaaggtgc agagactcga cgggagctac cctaacgtca agacgagggt aaagagagag   120
tccaattctc aaagccaata ggcagtagcg aaagctgcaa gagaatgaaa atccgtggct   180
cgcagc                                                              186
```

<210> SEQ ID NO 197
<211> LENGTH: 186
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 197

```
ctgataatat agtaatactc actatatgac aaacaaacca ctagatgact tacaactaat    60
cggaaggtgc agagactcga cgggagctac cctaacgtca agacgagggt aaagagagag   120
tccaattctc aaagccaata ggcagtagcg aaagctgcaa gagaatgaaa atccgtggct   180
cgcagc                                                              186
```

<210> SEQ ID NO 198
<211> LENGTH: 186
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 198

```
ctgataataa agtaatacac actataagac aaacaaacca ctagatgact tacaactaat    60
cggaaggtgc agagactcga cgggagctac cctaacgtca agacgagggt aaagagagag   120
tccaattctc aaagccaata ggcagtagcg aaagctgcaa gagaatgaaa atccgtggct   180
cgcagc                                                              186
```

<210> SEQ ID NO 199
<211> LENGTH: 186
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 199

```
ctgaaattat acttatactc tctaagttac aaacaaacca ctagatgact tacaactaat    60
```
cggaaggtgc agagactcga cgggagctac cctaacgtca agacgagggt aaagagagag    120
tccaattctc aaagccaata ggcagtagcg aaagctgcaa gagaatgaaa atccgtggct    180
cgcagc                                                              186

<210> SEQ ID NO 200
<211> LENGTH: 186
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 200
ctgaaattat gtgtgttaca tctaagttac aaacaaacca ctagatgact tacaactaat     60
cggaaggtgc agagactcga cgggagctac cctaacgtca agacgagggt aaagagagag    120
tccaattctc aaagccaata ggcagtagcg aaagctgcaa gagaatgaaa atccgtggct    180
cgcagc                                                              186

<210> SEQ ID NO 201
<211> LENGTH: 186
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 201
gttgatcggt gtgtgttaca tctaagttac aaacaaacca ctagatgact tacaactaat     60
cggaaggtgc agagactcga cgggagctac cctaacgtca agacgagggt aaagagagag    120
tccaattctc aaagccaata ggcagtagcg aaagctgcaa gagaatgaaa atccgtggct    180
cgcagc                                                              186

<210> SEQ ID NO 202
<211> LENGTH: 186
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 202
ctgaaattat acttatactc agtatatgac aaacaaacca ctagatgact tacaactaat     60
cggaaggtgc agagactcga cgggagctac cctaacgtca agacgagggt aaagagagag    120
tccaattctc aaagccaata ggcagtagcg aaagctgcaa gagaatgaaa atccgtgatt    180
aaacag                                                              186

<210> SEQ ID NO 203
<211> LENGTH: 196
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 203
ctgaaattat acttatactc agtatatgac aaacaaacca ctagatgact tacaactaat     60
cggaaggtgc agagactcga cgggagctac cctaacgtca agacgagggt aaagagagag      120
tccaattctc aaagccaata ggcagtagcg aaagctgcaa gagaatgaaa atccgtgatt      180
cacaatataa attacg                                                      196

<210> SEQ ID NO 204
<211> LENGTH: 186
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 204
ctgaaattat acttatactc agtatatgac aaacaaacca ctagatgact tacaactaat       60
cggaaggtgc agagactcga cgggagctac cctaacgtca agacgagggt aaagagagag      120
tccaattctc aaagccaata ggcagtagcg aaagctgcaa gagaatgaaa atccgtggat      180
catagc                                                                 186

<210> SEQ ID NO 205
<211> LENGTH: 196
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 205
ctgaaattat acttatactc agtatatgac aaacaaacca ctagatgact tacaactaat       60
cggaaggtgc agagactcga cgggagctac cctaacgtca agacgagggt aaagagagag      120
tccaattctc aaagccaata ggcagtagcg aaagctgcaa gagaatgaaa atccgtggat      180
cgcagcataa tatccg                                                      196

<210> SEQ ID NO 206
<211> LENGTH: 196
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 206
ctgaaattat acttatactc agtatatgac aaacaaacca ctagatgact tacaactaat       60
cggaaggtgc agagactcga cgggagctac cctaacgtca agacgagggt aaagagagag      120
tccaattctc aaagccaata ggcagtagcg aaagctgcaa gagaatgaaa atccgtggct      180
cgcagcgcgc ctaccg                                                      196

<210> SEQ ID NO 207
<211> LENGTH: 219
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 207

```
ctgaaattat acttatactc agtatatgac aaacaaacca ctagatgact tacaactaat    60
cggaaggtgc agagactcga cgggagctac cctaacgtca agacgagggt aaagagagag   120
tccaattctc aaagccaata ggcagtagcg aaagctgcaa gagaatgaaa atccgtggct   180
cgcagcgcgc ctaccgaaag ccggcgtcga cgttagcgc                          219
```

<210> SEQ ID NO 208
<211> LENGTH: 219
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 208

```
ctgaaattat acttatactc agtatatgac aaacaaacca ctagatgact tacaactaat    60
cggaaggtgc agagactcga cgggagctac cctaacgtca agacgagggt aaagagagag   120
tccaattctc aaagccaata ggcagtagcg aaagctgcaa gagaatgaaa atccgtggat   180
cgcagcataa tatccgaaac gaggatacaa gtgacatgc                          219
```

<210> SEQ ID NO 209
<211> LENGTH: 219
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 209

```
ctgaaattat acttatactc agtatatgac aaacaaacca ctagatgact tacaactaat    60
cggaaggtgc agagactcga cgggagctac cctaacgtca agacgagggt aaagagagag   120
tccaattctc aaagccaata ggcagtagcg aaagctgcaa gagaatgaaa atccgtgatt   180
cacaatctaa attacgaaac gataaatgat aactctaac                          219
```

<210> SEQ ID NO 210
<211> LENGTH: 156
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 210

```
aaacaaacca ctagatgact tacaactaat cggaaggtgc agagactcga cgggagctac    60
cctaacgtca agacgagggt aaagagagag tccaattctc aaagccaata ggcagtagcg   120
aaagctgcaa gagaatgaaa atccgtggct cgcagc                             156
```

<210> SEQ ID NO 211
<211> LENGTH: 161
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 211

```
cgggcaaaca aacaaataga tgacttacaa ctaatcggaa ggtgcagaga ctcgacggga    60
```

-continued gctaccctaa cgtcaagacg agggtaaaga gagagtccaa ttctcaaagc caataggcag    120
tagcgaaagc tgcaagagaa tgaaaatccg tggctcgcag c    161

<210> SEQ ID NO 212
<211> LENGTH: 186
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 212
cgctccgacg agcttccggc cagtgcgagc aaacaaacaa atagatgact tacaactaat    60
cggaaggtgc agagactcga cgggagctac cctaacgtca agacgagggt aaagagagag    120
tccaattctc aaagccaata ggcagtagcg aaagctgcaa gagaatgaaa atccgtggct    180
cgcagc    186

<210> SEQ ID NO 213
<211> LENGTH: 57
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 213
aaacaaacca cggcagtagc gaaagctgca agagaatgaa aatccgtggc tcgcagc    57

<210> SEQ ID NO 214
<211> LENGTH: 67
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 214
agtatataag aaacaaacca cggcagtagc gaaagctgca agagaatgaa aatccgtggc    60
tcgcagc    67

<210> SEQ ID NO 215
<211> LENGTH: 77
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 215
ctgaaattat acttatactc aaacaaacca cggcagtagc gaaagctgca agagaatgaa    60
aatccgtggc tcgcagc    77

<210> SEQ ID NO 216
<211> LENGTH: 87
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic oligonucleotide"

<400> SEQUENCE: 216
ctgaaattat acttatactc agtatatgac aaacaaacca cggcagtagc gaaagctgca    60
agagaatgaa aatccgtggc tcgcagc    87

<210> SEQ ID NO 217
<211> LENGTH: 67
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 217
tagcgtcagc aaacaaacaa aggcagtagc gaaagctgca agagaatgaa aatccgtggc    60
tcgcagc    67

<210> SEQ ID NO 218
<211> LENGTH: 77
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 218
atactcatac tagcgtcagc aaacaaacaa aggcagtagc gaaagctgca agagaatgaa    60
aatccgtggc tcgcagc    77

<210> SEQ ID NO 219
<211> LENGTH: 87
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 219
gtgtgaagct atactcatac tagcgtcagc aaacaaacaa aggcagtagc gaaagctgca    60
agagaatgaa aatccgtggc tcgcagc    87

<210> SEQ ID NO 220
<211> LENGTH: 67
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 220
cggtgcgagc aaacaaacaa aggcagtagc gaaagctgca agagaatgaa aatccgtggc    60
tcgcagc    67

<210> SEQ ID NO 221
<211> LENGTH: 77
<212> TYPE: DNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 221
cgctccgacc cagtgcgagc aaacaaacaa aggcagtagc gaaagctgca agagaatgaa    60
aatccgtggc tcgcagc                                                   77

<210> SEQ ID NO 222
<211> LENGTH: 87
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 222
cgctccgacg agcttccggc cagtgcgagc aaacaaacaa aggcagtagc gaaagctgca    60
agagaatgaa aatccgtggc tcgcagc                                        87

<210> SEQ ID NO 223
<211> LENGTH: 98
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 223
aaacaaacca caagacgagg gtaaagagag agtccaattc tcaaagccaa taggcagtag    60
cgaaagctgc aagagaatga aaatccgtgg ctcgcagc                            98

<210> SEQ ID NO 224
<211> LENGTH: 108
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 224
agtatataag aaacaaacca caagacgagg gtaaagagag agtccaattc tcaaagccaa    60
taggcagtag cgaaagctgc aagagaatga aaatccgtgg ctcgcagc                108

<210> SEQ ID NO 225
<211> LENGTH: 118
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 225
ctgaaattat acttatactc aaacaaacca caagacgagg gtaaagagag agtccaattc    60
tcaaagccaa taggcagtag cgaaagctgc aagagaatga aaatccgtgg ctcgcagc    118

<210> SEQ ID NO 226
<211> LENGTH: 128
<212> TYPE: DNA
<213> ORGANISM: Artificial Sequence
<220> FEATURE:
```

<210> SEQ ID NO 226 (continued)

<221> NAME/KEY: source
<223> OTHER INFORMATION: /note="Description of Artificial Sequence: Synthetic polynucleotide"

<400> SEQUENCE: 226

```
ctgaaattat acttatactc agtatatgac aaacaaacca caagacgagg gtaaagagag      60
agtccaattc tcaaagccaa taggcagtag cgaaagctgc aagagaatga aaatccgtgg     120
ctcgcagc                                                              128
```

<210> SEQ ID NO 227
<211> LENGTH: 108
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 227

```
tagcgtcagc aaacaaacaa aaagacgagg gtaaagagag agtccaattc tcaaagccaa      60
taggcagtag cgaaagctgc aagagaatga aaatccgtgg ctcgcagc                 108
```

<210> SEQ ID NO 228
<211> LENGTH: 118
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 228

```
atactcatac tagcgtcagc aaacaaacaa aaagacgagg gtaaagagag agtccaattc      60
tcaaagccaa taggcagtag cgaaagctgc aagagaatga aaatccgtgg ctcgcagc     118
```

<210> SEQ ID NO 229
<211> LENGTH: 128
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 229

```
gtgtgaagct atactcatac tagcgtcagc aaacaaacaa aaagacgagg gtaaagagag      60
agtccaattc tcaaagccaa taggcagtag cgaaagctgc aagagaatga aaatccgtgg    120
ctcgcagc                                                             128
```

<210> SEQ ID NO 230
<211> LENGTH: 108
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 230

```
cggtgcgagc aaacaaacaa aaagacgagg gtaaagagag agtccaattc tcaaagccaa      60
taggcagtag cgaaagctgc aagagaatga aaatccgtgg ctcgcagc                 108
```

<210> SEQ ID NO 231
<211> LENGTH: 118
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 231
cgctccgacc cagtgcgagc aaacaaacaa aaagacgagg gtaaagagag agtccaattc    60
tcaaagccaa taggcagtag cgaaagctgc aagagaatga aaatccgtgg ctcgcagc    118

<210> SEQ ID NO 232
<211> LENGTH: 128
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 232
cgctccgacg agcttccggc cagtgcgagc aaacaaacaa aaagacgagg gtaaagagag    60
agtccaattc tcaaagccaa taggcagtag cgaaagctgc aagagaatga aaatccgtgg   120
ctcgcagc                                                             128

<210> SEQ ID NO 233
<211> LENGTH: 176
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 233
ctgaaattat acttatactc agtatatgac aaacaaacca ctagatgact tacaactaat    60
cggaaggtgc agagactcga cgggagctac cctaacgtca agacgagggt aaagagagag   120
tccaattctc aaagccaata ggcagtagcg aaagctgcaa gagaatgaaa atccgt       176

<210> SEQ ID NO 234
<211> LENGTH: 77
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 234
ctgaaattat acttatactc agtatatgac aaacaaacca cggcagtagc gaaagctgca    60
agagaatgaa aatccgt                                                    77

<210> SEQ ID NO 235
<211> LENGTH: 87
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 235
ctgaaattat acttatactc agtatatgac aaacaaacca cggcagtagc gaaagctgca    60
agagaatgaa atccgtgat taaacag                                        87

<210> SEQ ID NO 236
<211> LENGTH: 97
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 236
ctgaaattat acttatactc agtatatgac aaacaaacca cggcagtagc gaaagctgca    60
agagaatgaa atccgtgat tcacaatata aattacg                             97

<210> SEQ ID NO 237
<211> LENGTH: 87
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 237
ctgaaattat acttatactc agtatatgac aaacaaacca cggcagtagc gaaagctgca    60
agagaatgaa atccgtgga tcatagc                                        87

<210> SEQ ID NO 238
<211> LENGTH: 97
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 238
ctgaaattat acttatactc agtatatgac aaacaaacca cggcagtagc gaaagctgca    60
agagaatgaa atccgtgga tcgcagcata atatccg                             97

<210> SEQ ID NO 239
<211> LENGTH: 97
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 239
ctgaaattat acttatactc agtatatgac aaacaaacca cggcagtagc gaaagctgca    60
agagaatgaa atccgtggc tcgcagcgcg cctaccg                             97

<210> SEQ ID NO 240
<211> LENGTH: 118
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 240

```
ctgaaattat acttatactc agtatatgac aaacaaacca caagacgagg gtaaagagag      60
agtccaattc tcaaagccaa taggcagtag cgaaagctgc aagagaatga aaatccgt       118
```

<210> SEQ ID NO 241
<211> LENGTH: 128
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 241

```
ctgaaattat acttatactc agtatatgac aaacaaacca caagacgagg gtaaagagag      60
agtccaattc tcaaagccaa taggcagtag cgaaagctgc aagagaatga aaatccgtga    120
ttaaacag                                                              128
```

<210> SEQ ID NO 242
<211> LENGTH: 138
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 242

```
ctgaaattat acttatactc agtatatgac aaacaaacca caagacgagg gtaaagagag      60
agtccaattc tcaaagccaa taggcagtag cgaaagctgc aagagaatga aaatccgtga    120
ttcacaatat aaattacg                                                   138
```

<210> SEQ ID NO 243
<211> LENGTH: 128
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 243

```
ctgaaattat acttatactc agtatatgac aaacaaacca caagacgagg gtaaagagag      60
agtccaattc tcaaagccaa taggcagtag cgaaagctgc aagagaatga aaatccgtgg    120
atcatagc                                                              128
```

<210> SEQ ID NO 244
<211> LENGTH: 138
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 244

```
ctgaaattat acttatactc agtatatgac aaacaaacca caagacgagg gtaaagagag      60
agtccaattc tcaaagccaa taggcagtag cgaaagctgc aagagaatga aaatccgtgg    120
atcgcagcat aatatccg                                                   138
```

<210> SEQ ID NO 245

```
<211> LENGTH: 138
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 245
ctgaaattat acttatactc agtatatgac aaacaaacca caagacgagg gtaaagagag      60
agtccaattc tcaaagccaa taggcagtag cgaaagctgc aagagaatga aaatccgtgg     120
ctcgcagcgc gcctaccg                                                   138

<210> SEQ ID NO 246
<211> LENGTH: 162
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 246
gctgcgagcc acggacttaa ataattgagc cttaaagaag aaattcttta agtggatgct      60
ctcaaactca gggaaaccta atctagtta tagacaaggc aatcctgagc caagccgaag     120
tagtaattag taagttaaca acacaaacac aacttatata ct                        162

<210> SEQ ID NO 247
<211> LENGTH: 172
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 247
gctgcgagcc acggacttaa ataattgagc cttaaagaag aaattcttta agtggatgct      60
ctcaaactca gggaaaccta atctagtta tagacaaggc aatcctgagc caagccgaag     120
tagtaattag taagttaaca acacaaacac aagagtataa gtataatttc ag             172

<210> SEQ ID NO 248
<211> LENGTH: 182
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 248
gctgcgagcc acggacttaa ataattgagc cttaaagaag aaattcttta agtggatgct      60
ctcaaactca gggaaaccta atctagtta tagacaaggc aatcctgagc caagccgaag     120
tagtaattag taagttaaca acacaaacac aagtcatata ctgagtataa gtataatttc    180
ag                                                                    182

<210> SEQ ID NO 249
<211> LENGTH: 192
<212> TYPE: DNA
<213> ORGANISM: Artificial Sequence
<220> FEATURE:
<221> NAME/KEY: source
```

<223> OTHER INFORMATION: /note="Description of Artificial Sequence:
      Synthetic polynucleotide"

<400> SEQUENCE: 249
gctgcgagcc acggacttaa ataattgagc cttaaagaag aaattcttta agtggatgct    60
ctcaaactca gggaaaccta aatctagtta tagacaaggc aatcctgagc caagccgaag  120
tagtaattag taagttaaca acacaaacac aagtcatata ctgagtataa gtataatttc  180
atattgttga tg                                                     192

<210> SEQ ID NO 250
<211> LENGTH: 202
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 250
gctgcgagcc acggacttaa ataattgagc cttaaagaag aaattcttta agtggatgct    60
ctcaaactca gggaaaccta aatctagtta tagacaaggc aatcctgagc caagccgaag  120
tagtaattag taagttaaca acacaaacac aagcgataat gcttcatata ctgagtataa  180
gtatagtttc atattgttga tg                                          202

<210> SEQ ID NO 251
<211> LENGTH: 162
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 251
gctgcgagcc acggacttaa ataattgagc cttaaagaag aaattcttta agtggatgct    60
ctcaaactca gggaaaccta aatctagtta tagacaaggc aatcctgagc caagccgaag  120
tagtaattag taagttaaca aaacaaaaac aagctgacgc ta                     162

<210> SEQ ID NO 252
<211> LENGTH: 172
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 252
gctgcgagcc acggacttaa ataattgagc cttaaagaag aaattcttta agtggatgct    60
ctcaaactca gggaaaccta aatctagtta tagacaaggc aatcctgagc caagccgaag  120
tagtaattag taagttaaca aaacaaaaac aagctgacgc tagtatgagt at          172

<210> SEQ ID NO 253
<211> LENGTH: 182
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

```
<400> SEQUENCE: 253
gctgcgagcc acggacttaa ataattgagc cttaaagaag aaattcttta agtggatgct    60
ctcaaactca gggaaaccta aatctagtta tagacaaggc aatcctgagc caagccgaag   120
tagtaattag taagttaaca aaacaaaaac aagctgacgc tagtatgagt atagcttcac   180
ac                                                                  182

<210> SEQ ID NO 254
<211> LENGTH: 192
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 254
gctgcgagcc acggacttaa ataattgagc cttaaagaag aaattcttta agtggatgct    60
ctcaaactca gggaaaccta aatctagtta tagacaaggc aatcctgagc caagccgaag   120
tagtaattag taagttaaca aaacaaaaac aagctgacgc tagtatgagt atagcttcac   180
actcaggtga gg                                                       192

<210> SEQ ID NO 255
<211> LENGTH: 202
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 255
gctgcgagcc acggacttaa ataattgagc cttaaagaag aaattcttta agtggatgct    60
ctcaaactca gggaaaccta aatctagtta tagacaaggc aatcctgagc caagccgaag   120
tagtaattag taagttaaca aaacaaaaac aagctgacgc tagtatgagt atagcttcac   180
actcaggtga ggcatcattc gg                                            202

<210> SEQ ID NO 256
<211> LENGTH: 162
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 256
gctgcgagcc acggacttaa ataattgagc cttaaagaag aaattcttta agtggatgct    60
ctcaaactca gggaaaccta aatctagtta tagacaaggc aatcctgagc caagccgaag   120
tagtaattag taagttaaca aaacaaaaac aagctcgcac cg                      162

<210> SEQ ID NO 257
<211> LENGTH: 172
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 257
```

```
gctgcgagcc acggacttaa ataattgagc cttaaagaag aaattcttta agtggatgct    60
ctcaaactca gggaaaccta aatctagtta tagacaaggc aatcctgagc caagccgaag   120
tagtaattag taagttaaca aaacaaaaac aagctcgcac tgggtcggag cg           172
```

<210> SEQ ID NO 258
<211> LENGTH: 182
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 258

```
gctgcgagcc acggacttaa ataattgagc cttaaagaag aaattcttta agtggatgct    60
ctcaaactca gggaaaccta aatctagtta tagacaaggc aatcctgagc caagccgaag   120
tagtaattag taagttaaca acacaaacac aagtcatata ctgagtataa gtataatttc   180
ag                                                                  182
```

<210> SEQ ID NO 259
<211> LENGTH: 182
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 259

```
gctgcgagcc acggacttaa ataattgagc cttaaagaag aaattcttta agtggatgct    60
ctcaaactca gggaaaccta aatctagtta tagacaaggc aatcctgagc caagccgaag   120
tagtaattag taagttaaca acacaaacac aagtcatata ctgagtataa gtataatttc   180
ag                                                                  182
```

<210> SEQ ID NO 260
<211> LENGTH: 182
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 260

```
gctgcgagcc acggacttaa ataattgagc cttaaagaag aaattcttta agtggatgct    60
ctcaaactca gggaaaccta aatctagtta tagacaaggc aatcctgagc caagccgaag   120
tagtaattag taagttaaca acacaaacac aagtcatata ctgagtataa gtataatttc   180
ag                                                                  182
```

<210> SEQ ID NO 261
<211> LENGTH: 182
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 261
gctgcgagcc acggacttaa ataattgagc cttaaagaag aaattcttta agtggatgct        60
ctcaaactca gggaaaccta aatctagtta tagacaaggc aatcctgagc caagccgaag       120
tagtaattag taagttaaca acacaaacac aagtcatata ctgagtataa gtataatttc       180
ag                                                                     182

<210> SEQ ID NO 262
<211> LENGTH: 182
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 262
gctgcgagcc acggacttaa ataattgagc cttaaagaag aaattcttta agtggatgct        60
ctcaaactca gggaaaccta aatctagtta tagacaaggc aatcctgagc caagccgaag       120
tagtaattag taagttaaca acacaaacac aagtaactta gagagtataa gtataatttc       180
ag                                                                     182

<210> SEQ ID NO 263
<211> LENGTH: 182
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 263
gctgcgagcc acggacttaa ataattgagc cttaaagaag aaattcttta agtggatgct        60
ctcaaactca gggaaaccta aatctagtta tagacaaggc aatcctgagc caagccgaag       120
tagtaattag taagttaaca acacaaacac aagtaactta gatgtaacac acataatttc       180
ag                                                                     182

<210> SEQ ID NO 264
<211> LENGTH: 182
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 264
gctgcgagcc acggacttaa ataattgagc cttaaagaag aaattcttta agtggatgct        60
ctcaaactca gggaaaccta aatctagtta tagacaaggc aatcctgagc caagccgaag       120
tagtaattag taagttaaca acacaaacac aagtaactta gatgtaacac acaccgatca       180
ac                                                                     182

<210> SEQ ID NO 265
<211> LENGTH: 182
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 265

```
ctgtttaatc acggacttaa ataattgagc cttaaagaag aaattcttta agtggatgct    60
ctcaaactca gggaaaccta aatctagtta tagacaaggc aatcctgagc caagccgaag   120
tagtaattag taagttaaca acacaaacac aagtcatata ctgagtataa gtataatttc   180
ag                                                                  182
```

<210> SEQ ID NO 266
<211> LENGTH: 192
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 266

```
cgtaatttat attgtgaatc acggacttaa ataattgagc cttaaagaag aaattcttta    60
agtggatgct ctcaaactca gggaaaccta aatctagtta tagacaaggc aatcctgagc   120
caagccgaag tagtaattag taagttaaca acacaaacac aagtcatata ctgagtataa   180
gtataatttc ag                                                       192
```

<210> SEQ ID NO 267
<211> LENGTH: 182
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 267

```
gctatgatcc acggacttaa ataattgagc cttaaagaag aaattcttta agtggatgct    60
ctcaaactca gggaaaccta aatctagtta tagacaaggc aatcctgagc caagccgaag   120
tagtaattag taagttaaca acacaaacac aagtcatata ctgagtataa gtataatttc   180
ag                                                                  182
```

<210> SEQ ID NO 268
<211> LENGTH: 192
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 268

```
cggatattat gctgcgatcc acggacttaa ataattgagc cttaaagaag aaattcttta    60
agtggatgct ctcaaactca gggaaaccta aatctagtta tagacaaggc aatcctgagc   120
caagccgaag tagtaattag taagttaaca acacaaacac aagtcatata ctgagtataa   180
gtataatttc ag                                                       192
```

<210> SEQ ID NO 269
<211> LENGTH: 192
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

```
<400> SEQUENCE: 269
cggtaggcgc gctgcgagcc acggacttaa ataattgagc cttaaagaag aaattctttta    60 agtggatgct ctcaaactca gggaaaccta aatctagtta tagacaaggc aatcctgagc   120
caagccgaag tagtaattag taagttaaca acacaaacac aagtcatata ctgagtataa   180
gtataatttc ag                                                       192

<210> SEQ ID NO 270
<211> LENGTH: 215
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 270
gcgctaacgt cgacgccggc aaacggtagg cgcgctgcga gccacggact taaataattg    60
agccttaaag aagaaattct ttaagtggat gctctcaaac tcagggaaac ctaaatctag   120
ttatagacaa ggcaatcctg agccaagccg aagtagtaat tagtaagtta acaacacaaa   180
cacaagtcat atactgagta taagtataat ttcag                              215

<210> SEQ ID NO 271
<211> LENGTH: 215
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 271
gcatgtcact tgtatcctcg aaacggatat tatgctgcga tccacggact taaataattg    60
agccttaaag aagaaattct ttaagtggat gctctcaaac tcagggaaac ctaaatctag   120
ttatagacaa ggcaatcctg agccaagccg aagtagtaat tagtaagtta acaacacaaa   180
cacaagtcat atactgagta taagtataat ttcag                              215

<210> SEQ ID NO 272
<211> LENGTH: 215
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 272
gttagagtta tcatttatcg aaacgtaatt tagattgtga atcacggact taaataattg    60
agccttaaag aagaaattct ttaagtggat gctctcaaac tcagggaaac ctaaatctag   120
ttatagacaa ggcaatcctg agccaagccg aagtagtaat tagtaagtta acaacacaaa   180
cacaagtcat atactgagta taagtataat ttcag                              215

<210> SEQ ID NO 273
<211> LENGTH: 152
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
```

<400> SEQUENCE: 273

```
gctgcgagcc acggacttaa ataattgagc cttaaagaag aaattcttta agtggatgct    60
ctcaaactca gggaaaccta aatctagtta tagacaaggc aatcctgagc caagccgaag    120
tagtaattag taagttaaca acacaaacac aa                                  152
```

<210> SEQ ID NO 274
<211> LENGTH: 157
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 274

```
gctgcgagcc acggacttaa ataattgagc cttaaagaag aaattcttta agtggatgct    60
ctcaaactca gggaaaccta aatctagtta tagacaaggc aatcctgagc caagccgaag    120
tagtaattag taagttaaca aaacaaaaac aagcccg                             157
```

<210> SEQ ID NO 275
<211> LENGTH: 182
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 275

```
gctgcgagcc acggacttaa ataattgagc cttaaagaag aaattcttta agtggatgct    60
ctcaaactca gggaaaccta aatctagtta tagacaaggc aatcctgagc caagccgaag    120
tagtaattag taagttaaca aaacaaaaac aagctcgcac tggccggaag ctcgtcggag    180
cg                                                                   182
```

<210> SEQ ID NO 276
<211> LENGTH: 251
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 276

```
gctgcgagcc acggacttaa ataattgagc cttaaagaag aaattcttta agtggatgct    60
ctcaaactca gggaaaccta aatctagtta tagacaaggc aatcctgagc caagccgaag    120
tagtaattag taagttaaca atagatgact tacaactaat cggaaggtgc agagactcga    180
cgggagctac cctaacgtca agacgagggt aaagagagag tccaattctc aaagccaata    240
cacaaacaca a                                                         251
```

<210> SEQ ID NO 277
<211> LENGTH: 261
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 277

```
gctgcgagcc acggacttaa ataattgagc cttaaagaag aaattcttta agtggatgct    60
ctcaaactca gggaaaccta aatctagtta tagacaaggc aatcctgagc caagccgaag   120
tagtaattag taagttaaca atagatgact tacaactaat cggaaggtgc agagactcga   180
cgggagctac cctaacgtca agacgagggt aaagagagag tccaattctc aaagccaata   240
cacaaacaca acttatatac t                                             261
```

<210> SEQ ID NO 278
<211> LENGTH: 271
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 278

```
gctgcgagcc acggacttaa ataattgagc cttaaagaag aaattcttta agtggatgct    60
ctcaaactca gggaaaccta aatctagtta tagacaaggc aatcctgagc caagccgaag   120
tagtaattag taagttaaca atagatgact tacaactaat cggaaggtgc agagactcga   180
cgggagctac cctaacgtca agacgagggt aaagagagag tccaattctc aaagccaata   240
cacaaacaca agagtataag tataatttca g                                  271
```

<210> SEQ ID NO 279
<211> LENGTH: 281
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 279

```
gctgcgagcc acggacttaa ataattgagc cttaaagaag aaattcttta agtggatgct    60
ctcaaactca gggaaaccta aatctagtta tagacaaggc aatcctgagc caagccgaag   120
tagtaattag taagttaaca atagatgact tacaactaat cggaaggtgc agagactcga   180
cgggagctac cctaacgtca agacgagggt aaagagagag tccaattctc aaagccaata   240
cacaaacaca agtcatatac tgagtataag tataatttca g                       281
```

<210> SEQ ID NO 280
<211> LENGTH: 261
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 280

```
gctgcgagcc acggacttaa ataattgagc cttaaagaag aaattcttta agtggatgct    60
ctcaaactca gggaaaccta aatctagtta tagacaaggc aatcctgagc caagccgaag   120
tagtaattag taagttaaca atagatgact tacaactaat cggaaggtgc agagactcga   180
cgggagctac cctaacgtca agacgagggt aaagagagag tccaattctc aaagccaata   240
aacaaaaaca agctgacgct a                                             261
```

<210> SEQ ID NO 281
<211> LENGTH: 271
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 281

```
gctgcgagcc acggacttaa ataattgagc cttaaagaag aaattcttta agtggatgct    60
ctcaaactca gggaaaccta aatctagtta tagacaaggc aatcctgagc caagccgaag   120
tagtaattag taagttaaca atagatgact tacaactaat cggaaggtgc agagactcga   180
cgggagctac cctaacgtca agacgagggt aaagagagag tccaattctc aaagccaata   240
aacaaaaaca agctgacgct agtatgagta t                                  271
```

<210> SEQ ID NO 282
<211> LENGTH: 281
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 282

```
gctgcgagcc acggacttaa ataattgagc cttaaagaag aaattcttta agtggatgct    60
ctcaaactca gggaaaccta aatctagtta tagacaaggc aatcctgagc caagccgaag   120
tagtaattag taagttaaca atagatgact tacaactaat cggaaggtgc agagactcga   180
cgggagctac cctaacgtca agacgagggt aaagagagag tccaattctc aaagccaata   240
aacaaaaaca agctgacgct agtatgagta tagcttcaca c                       281
```

<210> SEQ ID NO 283
<211> LENGTH: 261
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 283

```
gctgcgagcc acggacttaa ataattgagc cttaaagaag aaattcttta agtggatgct    60
ctcaaactca gggaaaccta aatctagtta tagacaaggc aatcctgagc caagccgaag   120
tagtaattag taagttaaca atagatgact tacaactaat cggaaggtgc agagactcga   180
cgggagctac cctaacgtca agacgagggt aaagagagag tccaattctc aaagccaata   240
aacaaaaaca agctcgcacc g                                             261
```

<210> SEQ ID NO 284
<211> LENGTH: 271
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 284

```
gctgcgagcc acggacttaa ataattgagc cttaaagaag aaattcttta agtggatgct    60
```

-continued

```
ctcaaactca gggaaaccta aatctagtta tagacaaggc aatcctgagc caagccgaag      120
tagtaattag taagttaaca atagatgact tacaactaat cggaaggtgc agagactcga      180
cgggagctac cctaacgtca agacgagggt aaagagagag tccaattctc aaagccaata     240
aacaaaaaca agctcgcact gggtcggagc g                                    271
```

<210> SEQ ID NO 285
<211> LENGTH: 281
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 285

```
gctgcgagcc acggacttaa ataattgagc cttaaagaag aaattcttta agtggatgct       60
ctcaaactca gggaaaccta aatctagtta tagacaaggc aatcctgagc caagccgaag      120
tagtaattag taagttaaca atagatgact tacaactaat cggaaggtgc agagactcga      180
cgggagctac cctaacgtca agacgagggt aaagagagag tccaattctc aaagccaata     240
aacaaaaaca agctcgcact ggccggaagc tcgtcggagc g                         281
```

<210> SEQ ID NO 286
<211> LENGTH: 210
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 286

```
gctgcgagcc acggacttaa ataattgagc cttaaagaag aaattcttta agtggatgct       60
ctcaaactca gggaaaccta aatctagtta tagacaaggc aatcctgagc caagccgaag      120
tagtaattag taagttaaca atagatgact tacaactaat cggaaggtgc agagactcga      180
cgggagctac cctaacgtcc acaaacacaa                                       210
```

<210> SEQ ID NO 287
<211> LENGTH: 220
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 287

```
gctgcgagcc acggacttaa ataattgagc cttaaagaag aaattcttta agtggatgct       60
ctcaaactca gggaaaccta aatctagtta tagacaaggc aatcctgagc caagccgaag      120
tagtaattag taagttaaca atagatgact tacaactaat cggaaggtgc agagactcga      180
cgggagctac cctaacgtcc acaaacacaa cttatatact                            220
```

<210> SEQ ID NO 288
<211> LENGTH: 230
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 288

| gctgcgagcc acggacttaa ataattgagc cttaaagaag aaattcttta agtggatgct | 60 |
| ctcaaactca gggaaaccta aatctagtta tagacaaggc aatcctgagc caagccgaag | 120 |
| tagtaattag taagttaaca atagatgact tacaactaat cggaaggtgc agagactcga | 180 |
| cgggagctac cctaacgtcc acaaacacaa gagtataagt ataatttcag | 230 |

<210> SEQ ID NO 289
<211> LENGTH: 240
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 289

| gctgcgagcc acggacttaa ataattgagc cttaaagaag aaattcttta agtggatgct | 60 |
| ctcaaactca gggaaaccta aatctagtta tagacaaggc aatcctgagc caagccgaag | 120 |
| tagtaattag taagttaaca atagatgact tacaactaat cggaaggtgc agagactcga | 180 |
| cgggagctac cctaacgtcc acaaacacaa gtcatatact gagtataagt ataatttcag | 240 |

<210> SEQ ID NO 290
<211> LENGTH: 220
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 290

| gctgcgagcc acggacttaa ataattgagc cttaaagaag aaattcttta agtggatgct | 60 |
| ctcaaactca gggaaaccta aatctagtta tagacaaggc aatcctgagc caagccgaag | 120 |
| tagtaattag taagttaaca atagatgact tacaactaat cggaaggtgc agagactcga | 180 |
| cgggagctac cctaacgtca acaaaaacaa gctgacgcta | 220 |

<210> SEQ ID NO 291
<211> LENGTH: 230
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 291

| gctgcgagcc acggacttaa ataattgagc cttaaagaag aaattcttta agtggatgct | 60 |
| ctcaaactca gggaaaccta aatctagtta tagacaaggc aatcctgagc caagccgaag | 120 |
| tagtaattag taagttaaca atagatgact tacaactaat cggaaggtgc agagactcga | 180 |
| cgggagctac cctaacgtca acaaaaacaa gctgacgcta gtatgagtat | 230 |

<210> SEQ ID NO 292
<211> LENGTH: 240
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic polynucleotide"

<400> SEQUENCE: 292

```
gctgcgagcc acggacttaa ataattgagc cttaaagaag aaattcttta agtggatgct    60
ctcaaactca gggaaaccta atctagtta tagacaaggc aatcctgagc caagccgaag    120
tagtaattag taagttaaca atagatgact tacaactaat cggaaggtgc agagactcga    180
cgggagctac cctaacgtca acaaaaacaa gctgacgcta gtatgagtat agcttcacac    240
```

<210> SEQ ID NO 293
<211> LENGTH: 220
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 293

```
gctgcgagcc acggacttaa ataattgagc cttaaagaag aaattcttta agtggatgct    60
ctcaaactca gggaaaccta atctagtta tagacaaggc aatcctgagc caagccgaag    120
tagtaattag taagttaaca atagatgact tacaactaat cggaaggtgc agagactcga    180
cgggagctac cctaacgtca acaaaaacaa gctcgcaccg                          220
```

<210> SEQ ID NO 294
<211> LENGTH: 230
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 294

```
gctgcgagcc acggacttaa ataattgagc cttaaagaag aaattcttta agtggatgct    60
ctcaaactca gggaaaccta atctagtta tagacaaggc aatcctgagc caagccgaag    120
tagtaattag taagttaaca atagatgact tacaactaat cggaaggtgc agagactcga    180
cgggagctac cctaacgtca acaaaaacaa gctcgcactg ggtcggagcg               230
```

<210> SEQ ID NO 295
<211> LENGTH: 240
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 295

```
gctgcgagcc acggacttaa ataattgagc cttaaagaag aaattcttta agtggatgct    60
ctcaaactca gggaaaccta atctagtta tagacaaggc aatcctgagc caagccgaag    120
tagtaattag taagttaaca atagatgact tacaactaat cggaaggtgc agagactcga    180
cgggagctac cctaacgtca acaaaaacaa gctcgcactg gccggaagct cgtcggagcg   240
```

<210> SEQ ID NO 296
<211> LENGTH: 172
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 296
acggacttaa ataattgagc cttaaagaag aaattcttta agtggatgct ctcaaactca    60
gggaaaccta atctagtta tagacaaggc aatcctgagc caagccgaag tagtaattag    120
taagttaaca acacaaacac aagtcatata ctgagtataa gtataatttc ag           172

<210> SEQ ID NO 297
<211> LENGTH: 271
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 297
acggacttaa ataattgagc cttaaagaag aaattcttta agtggatgct ctcaaactca    60
gggaaaccta atctagtta tagacaaggc aatcctgagc caagccgaag tagtaattag    120
taagttaaca atagatgact tacaactaat cggaaggtgc agagactcga cgggagctac    180
cctaacgtca agacgagggt aaagagagag tccaattctc aaagccaata cacaaacaca    240
agtcatatac tgagtataag tataatttca g                                  271

<210> SEQ ID NO 298
<211> LENGTH: 281
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 298
ctgtttaatc acggacttaa ataattgagc cttaaagaag aaattcttta agtggatgct    60
ctcaaactca gggaaaccta atctagtta tagacaaggc aatcctgagc caagccgaag    120
tagtaattag taagttaaca atagatgact tacaactaat cggaaggtgc agagactcga    180
cgggagctac cctaacgtca agacgagggt aaagagagag tccaattctc aaagccaata    240
cacaaacaca agtcatatac tgagtataag tataatttca g                       281

<210> SEQ ID NO 299
<211> LENGTH: 291
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 299
cgtaatttat attgtgaatc acggacttaa ataattgagc cttaaagaag aaattcttta    60
agtggatgct ctcaaactca gggaaaccta atctagtta tagacaaggc aatcctgagc    120
caagccgaag tagtaattag taagttaaca atagatgact tacaactaat cggaaggtgc    180
agagactcga cgggagctac cctaacgtca agacgagggt aaagagagag tccaattctc    240
aaagccaata cacaaacaca agtcatatac tgagtataag tataatttca g            291

<210> SEQ ID NO 300

```
<211> LENGTH: 281
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 300
gctatgatcc acggacttaa ataattgagc cttaaagaag aaattcttta agtggatgct     60
ctcaaactca gggaaaccta aatctagtta tagacaaggc aatcctgagc caagccgaag    120
tagtaattag taagttaaca atagatgact tacaactaat cggaaggtgc agagactcga    180
cgggagctac cctaacgtca agacgagggt aaagagagag tccaattctc aaagccaata    240
cacaaacaca agtcatatac tgagtataag tataatttca g                        281

<210> SEQ ID NO 301
<211> LENGTH: 291
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 301
cggatattat gctgcgatcc acggacttaa ataattgagc cttaaagaag aaattcttta     60
agtggatgct ctcaaactca gggaaaccta aatctagtta tagacaaggc aatcctgagc    120
caagccgaag tagtaattag taagttaaca atagatgact tacaactaat cggaaggtgc    180
agagactcga cgggagctac cctaacgtca agacgagggt aaagagagag tccaattctc    240
aaagccaata cacaaacaca agtcatatac tgagtataag tataatttca g             291

<210> SEQ ID NO 302
<211> LENGTH: 291
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 302
cggtaggcgc gctgcgagcc acggacttaa ataattgagc cttaaagaag aaattcttta     60
agtggatgct ctcaaactca gggaaaccta aatctagtta tagacaaggc aatcctgagc    120
caagccgaag tagtaattag taagttaaca atagatgact tacaactaat cggaaggtgc    180
agagactcga cgggagctac cctaacgtca agacgagggt aaagagagag tccaattctc    240
aaagccaata cacaaacaca agtcatatac tgagtataag tataatttca g             291

<210> SEQ ID NO 303
<211> LENGTH: 230
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 303
acggacttaa ataattgagc cttaaagaag aaattcttta agtggatgct ctcaaactca     60
gggaaaccta aatctagtta tagacaaggc aatcctgagc caagccgaag tagtaattag    120
```
taagttaaca atagatgact tacaactaat cggaaggtgc agagactcga cgggagctac    180
cctaacgtcc acaaacacaa gtcatatact gagtataagt ataatttcag              230

<210> SEQ ID NO 304
<211> LENGTH: 240
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 304
ctgtttaatc acggacttaa ataattgagc cttaaagaag aaattcttta agtggatgct     60
ctcaaactca gggaaaccta aatctagtta tagacaaggc aatcctgagc caagccgaag    120
tagtaattag taagttaaca atagatgact tacaactaat cggaaggtgc agagactcga    180
cgggagctac cctaacgtcc acaaacacaa gtcatatact gagtataagt ataatttcag    240

<210> SEQ ID NO 305
<211> LENGTH: 250
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 305
cgtaatttat attgtgaatc acggacttaa ataattgagc cttaaagaag aaattcttta     60
agtggatgct ctcaaactca gggaaaccta aatctagtta tagacaaggc aatcctgagc    120
caagccgaag tagtaattag taagttaaca atagatgact tacaactaat cggaaggtgc    180
agagactcga cgggagctac cctaacgtcc acaaacacaa gtcatatact gagtataagt    240
ataatttcag                                                          250

<210> SEQ ID NO 306
<211> LENGTH: 240
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 306
gctatgatcc acggacttaa ataattgagc cttaaagaag aaattcttta agtggatgct     60
ctcaaactca gggaaaccta aatctagtta tagacaaggc aatcctgagc caagccgaag    120
tagtaattag taagttaaca atagatgact tacaactaat cggaaggtgc agagactcga    180
cgggagctac cctaacgtcc acaaacacaa gtcatatact gagtataagt ataatttcag    240

<210> SEQ ID NO 307
<211> LENGTH: 250
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 307

```
cggatattat gctgcgatcc acggacttaa ataattgagc cttaaagaag aaattcttta    60
agtggatgct ctcaaactca gggaaaccta aatctagtta tagacaaggc aatcctgagc   120
caagccgaag tagtaattag taagttaaca atagatgact tacaactaat cggaaggtgc   180
agagactcga cgggagctac cctaacgtcc acaaacacaa gtcatatact gagtataagt   240
ataatttcag                                                         250

<210> SEQ ID NO 308
<211> LENGTH: 250
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 308
cggtaggcgc gctgcgagcc acggacttaa ataattgagc cttaaagaag aaattcttta    60
agtggatgct ctcaaactca gggaaaccta aatctagtta tagacaaggc aatcctgagc   120
caagccgaag tagtaattag taagttaaca atagatgact tacaactaat cggaaggtgc   180
agagactcga cgggagctac cctaacgtcc acaaacacaa gtcatatact gagtataagt   240
ataatttcag                                                         250

<210> SEQ ID NO 309
<211> LENGTH: 1137
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 309
atgctgctgc tggtcacatc tctgctgctg tgcgagctgc cccatcctgc ctttctgctg    60
atccccgaca tccagatgac ccagaccaca agcagcctgt ctgccagcct gggcgataga   120
gtgaccatca gctgtagagc cagccaggac atcagcaagt acctgaactg gtatcagcaa   180
aagcccgacg gcaccgtgaa gctgctgatc taccacacca gcagactgca cagcggcgtg   240
ccaagcagat ttctggcag cggctctggc accgactaca gcctgacaat cagcaacctg   300
gaacaagagg atatcgctac ctacttctgc cagcaaggca cacccctgcc ttacaccttt   360
ggcggaggca ccaagctgga aatcaccggc tctacaagcg gcagcggcaa acctggatct   420
ggcgagggat ctaccaaggg cgaagtgaaa ctgcaagagt ctggccctgg actggtggcc   480
ccatctcagt ctctgagcgt gacctgtaca gtcagcggag tgtccctgcc tgattacggc   540
gtgtcctgga tcagacagcc tcctcggaaa ggcctggaat ggctgggagt gatctggggc   600
agcgagacaa cctactacaa cagcgccctg aagtcccggc tgaccatcat caaggacaac   660
tccaagagcc aggtgttcct gaagatgaac agcctgcaga ccgacgacac cgccatctac   720
tattgcgcca agcactacta ctacggcggc agctacgcca tggattattg gggccagggc   780
accagcgtga ccgtttcttc tgccgccgct atcgaagtga tgtaccctcc tccttacctg   840
gacaacgaga agtccaacgg caccatcatc cacgtgaagg gcaagcacct gtgtccttct   900
ccactgttcc ccggacctag caagcctttc tgggtgctcg ttgttgtggg cggcgtgctg   960
gcctgttaca gcctgctggt taccgtggcc ttcatcatct tttgggtcaa gagaggccga  1020
aagaaacttc tttatatatt caagcagccc tttatgcgac ccgttcagac tacccaagag  1080
```
gaagatggat gcagttgccg ctttccagaa gaggaggagg gcgggtgcga actgtaa      1137

<210> SEQ ID NO 310
<211> LENGTH: 1134
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 310

```
atgctgctgc tggtcacatc tctgctgctg tgcgagctgc ccatcctgc ctttctgctg       60 atccccgaca tccagatgac ccagaccaca agcagcctgt ctgccagcct gggcgataga      120
gtgaccatca gctgtagagc cagccaggac atcagcaagt acctgaactg gtatcagcaa      180
aagcccgacg gcaccgtgaa gctgctgatc taccacacca gcagactgca cagcggcgtg      240
ccaagcagat tttctggcag cggctctggc accgactaca gcctgacaat cagcaacctg      300
gaacaagagg atatcgctac ctacttctgc cagcaaggca cacccctgcc ttacacctttt     360 ggcggaggca ccaagctgga aatcaccggc tctacaagcg gcagcggcaa acctggatct      420
ggcgagggat ctaccaaggg cgaagtgaaa ctgcaagagt ctggccctgg actggtggcc      480
ccatctcagt ctctgagcgt gacctgtaca gtcagcggag tgtccctgcc tgattacggc      540
gtgtcctgga tcagacagcc tcctcggaaa ggcctggaat ggctgggagt gatctggggc      600
agcgagacaa cctactacaa cagcgccctg aagtcccggc tgaccatcat caaggacaac      660
tccaagagcc aggtgttcct gaagatgaac agcctgcaga ccgacgacac cgccatctac      720
tattgcgcca agcactacta ctacggcggc agctacgcca tggattattg ggccagggc      780 accagcgtga ccgtttcttc tgccgccgct atcgaagtga tgtaccctcc tccttacctg      840
gacaacgaga gtccaacgg caccatcatc acgtgaagg gcaagcacct gtgtccttct        900
ccactgttcc ccggacctag caagcctttc tgggtgctcg ttgttgttgg cggcgtgctg      960
gcctgttaca gcctgctggt taccgtggcc ttcatcatct ttgggtccg aagcaagcgg      1020 agccggctgc tgcactccga ctacatgaac atgaccccta acggcccggg accaaccaga     1080
aagcactacc agcctacgc tcctcctaga gacttcgccg cctaccggtc ctaa            1134
```

<210> SEQ ID NO 311
<211> LENGTH: 1470
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 311

```
atgctgctgc tggtcacatc tctgctgctg tgcgagctgc ccatcctgc ctttctgctg       60 atccccgaca tccagatgac ccagaccaca agcagcctgt ctgccagcct gggcgataga      120
gtgaccatca gctgtagagc cagccaggac atcagcaagt acctgaactg gtatcagcaa      180
aagcccgacg gcaccgtgaa gctgctgatc taccacacca gcagactgca cagcggcgtg      240
ccaagcagat tttctggcag cggctctggc accgactaca gcctgacaat cagcaacctg      300
gaacaagagg atatcgctac ctacttctgc cagcaaggca cacccctgcc ttacaccttt     360
ggcggaggca ccaagctgga aatcaccggc tctacaagcg gcagcggcaa acctggatct      420
```

```
ggcgagggat ctaccaaggg cgaagtgaaa ctgcaagagt ctggccctgg actggtggcc      480
ccatctcagt ctctgagcgt gacctgtaca gtcagcggag tgtccctgcc tgattacggc      540
gtgtcctgga tcagacagcc tcctcggaaa ggcctggaat ggctgggagt gatctggggc      600
agcgagacaa cctactacaa cagcgccctg aagtcccggc tgaccatcat caaggacaac      660
tccaagagcc aggtgttcct gaagatgaac agcctgcaga ccgacgacac cgccatctac      720
tattgcgcca agcactacta ctacggcggc agctacgcca tggattattg gggccagggc      780
accagcgtga ccgtttcttc tgccgccgct atcgaagtga tgtaccctcc tccttacctg      840
gacaacgaga agtccaacgg caccatcatc cacgtgaagg gcaagcacct gtgtccttct      900
ccactgttcc ccggacctag caagcctttc tgggtgctcg ttgttgttgg cggcgtgctg      960
gcctgttaca gcctgctggt taccgtggcc ttcatcatct tttgggtccg aagcaagcgg      1020
agccggctgc tgcactccga ctacatgaac atgacccctc gacggcccgg accaaccaga     1080
aagcactacc agcctacgc tcctcctaga gacttcgccg cctaccggtc cagagtgaag      1140
ttcagcagat ccgccgatgc tcccgcctat cagcagggcc aaaaccagct gtacaacgag      1200
ctgaacctgg ggagaagaga agagtacgac gtgctggaca gcggagagg cagagatcct      1260 gaaatgggcg gcaagcccag acggaagaat cctcaagagg gcctgtataa tgagctgcag      1320
aaagacaaga tggccgaggc ctacagcgag atcggaatga agggcgagcg cagaagaggc      1380
aagggacacg atggactgta ccagggactg agcaccgcca ccaaggatac ctatgacgcc      1440
ctgcacatgc aggccctgcc tccaagataa                                       1470

<210> SEQ ID NO 312
<211> LENGTH: 1347
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 312
atgctgctgc tggtcacatc tctgctgctg tgcgagctgc cccatcctgc ctttctgctg       60
atccccgaca tccagatgac ccagaccaca agcagcctgt ctgccagcct gggcgataga      120
gtgaccatca gctgtagagc cagccaggac atcagcaagt acctgaactg gtatcagcaa      180
aagcccgacg gcaccgtgaa gctgctgatc taccacacca gcagactgca cagcggcgtg      240
ccaagcagat tttctggcag cggctctggc accgactaca gcctgacaat cagcaacctg      300
gaacaagagg atatcgctac ctacttctgc cagcaaggca cacccctgcc ttacaccttt      360 ggcgaggca ccaagctgga aatcaccggc tctacaagcg gcagcggcaa acctggatct      420
ggcgagggat ctaccaaggg cgaagtgaaa ctgcaagagt ctggccctgg actggtggcc      480
ccatctcagt ctctgagcgt gacctgtaca gtcagcggag tgtccctgcc tgattacggc      540
gtgtcctgga tcagacagcc tcctcggaaa ggcctggaat ggctgggagt gatctggggc      600
agcgagacaa cctactacaa cagcgccctg aagtcccggc tgaccatcat caaggacaac      660
tccaagagcc aggtgttcct gaagatgaac agcctgcaga ccgacgacac cgccatctac      720
tattgcgcca agcactacta ctacggcggc agctacgcca tggattattg gggccagggc      780
accagcgtga ccgtttcttc tgccgccgct atcgaagtga tgtaccctcc tccttacctg      840
gacaacgaga agtccaacgg caccatcatc cacgtgaagg gcaagcacct gtgtccttct      900
ccactgttcc ccggacctag caagcctttc tgggtgctcg ttgttgttgg cggcgtgctg      960
```

```
gcctgttaca gcctgctggt taccgtggcc ttcatcatct tttgggtcag agtgaagttc    1020
agcagatccg ccgatgctcc cgcctatcag cagggccaaa accagctgta caacgagctg    1080
aacctgggga gaagagaaga gtacgacgtg ctggacaagc ggagaggcag agatcctgaa    1140
atgggcggca agcccagacg gaagaatcct caagagggcc tgtataatga gctgcagaaa    1200
gacaagatgg ccgaggccta cagcgagatc ggaatgaagg gcgagcgcag aagaggcaag    1260
ggacacgatg gactgtacca gggactgagc accgccacca aggatacctg tgacgccctg    1320
cacatgcagg ccctgcctcc aagataa                                        1347
```

<210> SEQ ID NO 313
<211> LENGTH: 1461
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 313

```
atggctctcc cggtcacagc ccttctcctg cccctggcac tcttgctgca tgcggcacga      60
cccgacatcc agatgaccca gaccacaagc agcctgtctg ccagcctggg cgatagagtg     120
accatcagct gtagagccag ccaggacatc agcaagtacc tgaactggta tcagcaaaag     180
cccgacggca ccgtgaagct gctgatctac cacaccagca gactgcacag cggcgtgcca     240
agcagatttt ctggcagcgg ctctggcacc gactacagcc tgacaatcag caacctggaa     300
caagaggata tcgctaccta cttctgccag caaggcaaca ccctgcctta cacctttggc     360
ggaggcacca agctggaaat caccggtgga ggtggttctg gcggaggggg atctggtgga     420
ggcggttcag aagtgaaact gcaagagtct ggccctggac tggtggcccc atctcagtct     480
ctgagcgtga cctgtacagt cagcggagtg tccctgcctg attacggcgt gtcctggatc     540
agacagcctc ctcggaaagg cctggaatgg ctgggagtga tctggggcag cgagacaacc     600
tactacaaca gcgccctgaa gtcccggctg accatcatca aggacaactc caagagccag     660
gtgttcctga agatgaacag cctgcagacc gacgacaccg ccatctacta ttgcgccaag     720
cactactact acggcggcag ctacgccatg gattattggg gccagggcac cagcgtgacc     780
gtttcttcta ccacaacgcc cgccccgcga ccgcctactc ccgctcccac aattgcatca     840 caaccectgt ctttgagacc cgaagcttgt cgaccagctg ccggtggcgc ggttcacacg     900
cgggggctcg atttcgcctg tgatatatat atatgggccc cattggctgg aacatgcgga     960
gtattgcttc tgagcctggt gattaccctc tactgtaaga gaggccggaa gaaacttctt    1020
tatatattca gcagcccctt tatgcgaccc gttcagacta cccaagagga agatggatgc    1080
agttgccgct ttccagaaga ggaggagggc gggtgcgaac tgagagtgaa gttcagcaga    1140
tccgccgatg ctcccgccta tcagcagggc caaaaccagc tgtacaacga gctgaacctg    1200
gggagaagag aagagtacga cgtgctggac aagcggagag cagagatcc tgaaatgggc    1260 ggcaagccca cggaagaa tcctcaagag ggcctgtata atgagctgca gaaagacaag    1320
atggccgagg cctacagcga gatcggaatg aagggcgagc gcagaagagg caaggacac    1380 gatggactgt accagggact gagcaccgcc accaaggata cctatgacgc cctgcacatg    1440
caggccctgc ctccaagata a                                               1461
```

<210> SEQ ID NO 314

<211> LENGTH: 1461
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 314

| | | | | | |
|---|---|---|---|---|---|
| atggctctcc | cggtcacagc | ccttctcctg | ccctggcac | tcttgctgca | tgcggcacga | 60 |
| cccgacatcc | agatgaccca | gaccacaagc | agcctgtctg | ccagcctggg | cgatagagtg | 120 |
| accatcagct | gtagagccag | ccaggacatc | agcaagtacc | tgaactggta | tcagcaaaag | 180 |
| cccgacggca | ccgtgaagct | gctgatctac | cacaccagca | gactgcacag | cggcgtgcca | 240 |
| agcagatttt | ctggcagcgg | ctctggcacc | gactacagcc | tgacaatcag | caacctggaa | 300 |
| caagaggata | tcgctaccta | cttctgccag | caaggcaaca | ccctgcctta | cacctttggc | 360 |
| ggaggcacca | agctggaaat | caccggtgga | ggtggttctg | gcggaggggg | atctggtgga | 420 |
| ggcggttcag | aagtgaaact | gcaagagtct | ggccctggac | tggtggcccc | atctcagtct | 480 |
| ctgagcgtga | cctgtacagt | cagcggagtg | tccctgcctg | attacggcgt | gtcctggatc | 540 |
| agacagcctc | ctcggaaagg | cctggaatgg | ctggagtga | tctggggcag | cgagacaacc | 600 |
| tactacaaca | gcgccctgaa | gtcccggctg | accatcatca | aggacaactc | caagagccag | 660 |
| gtgttcctga | agatgaacag | cctgcagacc | gacgacaccg | ccatctacta | ttgcgccaag | 720 |
| cactactact | acggcggcag | ctacgccatg | gattattggg | gccagggcac | cagcgtgacc | 780 |
| gtttcttcta | ccacaacgcc | cgccccgcga | ccgcctactc | ccgctcccac | aattgcatca | 840 |
| caaccctgt | ctttgagacc | cgaagcttgt | cgaccagctg | ccggtggcgc | ggttcacacg | 900 |
| cgggggctcg | atttcgcctg | tgatatatat | atatgggccc | cattggctgg | aacatgcgga | 960 |
| gtattgcttc | tgagcctggt | gattaccctc | tactgtaaga | gaggccggaa | gaaacttctt | 1020 |
| tatatattca | gcagcccctt | tatgcgaccc | gttcagacta | cccaagagga | gatggatgc | 1080 |
| agttgccgct | ttccagaaga | ggaggagggc | gggtgcgaac | tgagagtgaa | gttcagcaga | 1140 |
| tccgccgatg | ctcccgccta | taagcagggc | caaaaccagc | tgtacaacga | gctgaacctg | 1200 |
| gggagaagag | aagagtacga | cgtgctggac | aagcggagag | gcagagatcc | tgaaatgggc | 1260 |
| ggcaagccca | cggaagaa | tcctcaagag | gcctgtata | atgagctgca | gaaagacaag | 1320 |
| atggccgagg | cctacagcga | gatcggaatg | aagggcgagc | gcagaagagg | caaggacac | 1380 |
| gatggactgt | accagggact | gagcaccgcc | accaaggata | cctatgacgc | cctgcacatg | 1440 |
| caggccctgc | ctccaagata | a | | | | 1461 |

<210> SEQ ID NO 315
<211> LENGTH: 1452
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 315

| | | | | | |
|---|---|---|---|---|---|
| atgctgctgc | tggtcacatc | tctgctgctg | tgcgagctgc | cccatcctgc | ctttctgctg | 60 |
| atcccccagg | ttcaactcca | gcagtctggt | cccggcctcg | ttaaaccaag | ccagactttg | 120 |
| tctcttacct | gtgctatcag | tggcgatagc | gtgtctagta | attcagccgc | atggaactgg | 180 |
| atccgacaat | caccgagtag | gggacttgaa | tggctgggta | gaacctatta | ccggtccaaa | 240 |

```
tggtacaatg actatgcagt gtctgtaaaa agcaggatca cgatcaaccc tgatacgtct    300
aaaaaccagt tttctctgca acttaatagt gtgacccctg aagacaccgc tgtgtattac    360
tgtgcacggg aggttaccgg tgatcttgaa gatgcttttg atatatgggg ccaaggtacg    420
atggtcacgg tgtctagtgg gggaggcggc agcgacatac agatgacgca gagcccatcc    480
agtctctccg cgtctgttgg tgacagagtg actattacat gtagggcgtc tcagaccatt    540
tggtcttacc tcaattggta tcaacagcga ccaggcaaag caccgaactt gctcatttac    600
gctgccagct cactccaaag tggtgtgccg tccagattta gtggtagggg cagtggcact    660
gatttcactc tgactatttc aagtcttcaa gctgaggatt ttgccacata ctactgccag    720
caaagttact caatacctca gacttttgga caggggacaa aattggagat aaatccgga    780 accacaacgc ccgccccgcg accgcctact cccgctccca caattgcatc acaacccctg    840
tctttgagac ccgaagcttg tcgaccagct gccggtggcg cggttcacac gcggggctc    900 gatttcgcct gtgatatata tatatgggcc ccattggctg aacatgcgg agtattgctt    960 ctgagcctgg tgattaccct ctactgtaag agaggccgga agaaacttct ttatatattc   1020
aagcagccct ttatgcgacc cgttcagact acccaagagg aagatggatg cagttgccgc   1080
tttccagaag aggaggaggg cgggtgcgaa ctgagagtga agttcagcag atccgccgat   1140
gctcccgcct ataagcaggg ccaaaaccag ctgtacaacg agctgaacct ggggagaaga   1200
gaagagtacg acgtgctgga caagcggaga ggcagagatc ctgaaatggg cggcaagccc   1260
agacggaaga atcctcaaga gggcctgtat aatgagctgc agaaagacaa gatggccgag   1320
gcctacagcg agatcggaat gaagggcgag cgcagaagag gcaagggaca cgatggactg   1380
taccagggac tgagcaccgc caccaaggat acctatgacg ccctgcacat gcaggccctg   1440
cctccaagat aa                                                       1452

<210> SEQ ID NO 316
<211> LENGTH: 2202
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 316
atgctgctgc tggtcacatc tctgctgctg tgcgagctgc cccatcctgc ctttctgctg     60
atccccgaca tccagatgac ccagaccaca agcagcctgt ctgccagcct gggcgataga    120
gtgaccatca gctgtagagc cagccaggac atcagcaagt acctgaactg gtatcagcaa    180
aagcccgacg gcaccgtgaa gctgctgatc taccacacca gcagactgca cagcggcgtg    240
ccaagcagat ttctggcag cggctctggc accgactaca gcctgacaat cagcaacctg    300
gaacaagagg atatcgctac ctacttctgc cagcaaggca cacccctgcc ttacaccttt    360
ggcggaggca ccaagctgga aatcaccggc ggcggaggat cccaggttca actccagcag    420
tctggtcccg gcctcgttaa accaagccag actttgtctc ttacctgtgc tatcagtggc    480
gatagcgtgt ctagtaattc agccgcatgg aactggatcc gacaatcacc gagtagggga    540
cttgaatggc tgggtagaac ctattaccgg tccaaatggt acaatgacta tgcagtgtct    600
gtaaaaagca ggatcacgat caaccсctgat acgtctaaaa accagttttc tctgcaactt    660
aatagtgtga cccctgaaga caccgctgtg tattactgtg cacgggaggt taccggtgat    720
```

```
cttgaagatg ctttttgatat atggggccaa ggtacgatgg tcacggtgtc tagtggctct    780
acaagcggca gcggcaaacc tggatctggc gagggatcta ccaagggcga catacagatg    840
acgcagagcc catccagtct ctccgcgtct gttggtgaca gagtgactat tacatgtagg    900
gcgtctcaga ccatttggtc ttacctcaat tggtatcaac agcgaccagg caaagcaccg    960
aacttgctca tttacgctgc cagctcactc caaagtggtg tgccgtccag atttagtggt   1020
aggggcagtg gcactgattt cactctgact atttcaagtc ttcaagctga ggattttgcc   1080
acatactact gccagcaaag ttactcaata cctcagactt ttggacaggg gacaaaattg   1140
gagattaaag ggggaggcgg cagcgaagtg aaactgcaag agtctggccc tggactggtg   1200
gccccatctc agtctctgag cgtgacctgt acagtcagcg gagtgtccct gcctgattac   1260
ggcgtgtcct ggatcagaca gcctcctcgg aaaggcctgg aatggctggg agtgatctgg   1320
ggcagcgaga caacctacta caacagcgcc ctgaagtccc ggctgaccat catcaaggac   1380
aactccaaga gccaggtgtt cctgaagatg aacagcctgc agaccgacga caccgccatc   1440
tactattgcg ccaagcacta ctactacggc ggcagctacg ccatggatta ttggggccag   1500
ggcaccagcg tgaccgtttc ttcttccgga accacaacgc ccgccccgcg accgcctact   1560
cccgctccca caattgcatc acaaccccctg tctttgagac ccgaagcttg tcgaccagct   1620
gccggtggcg cggttcacac gcgggggctc gatttcgcct gtgatatata tatgtgggcc   1680
ccattggctg gaacatgcgg agtattgctt ctgagcctgg tgattaccct ctactgtaag   1740
agaggccgga gaaacttct ttatatattc aagcagccct ttatgcgacc cgttcagact   1800
acccaagagg aagatggatg cagttgccgc tttccagaag aggaggaggg cggtgcgaa   1860
ctgagagtga agttcagcag atccgccgat gctcccgcct ataagcaggg ccaaaaccag   1920
ctgtacaacg agctgaacct ggggagaaga gaagagtacg acgtgctgga caagcggaga   1980
ggcagagatc ctgaaatggg cggcaagccc agacggaaga tcctcaaga gggcctgtat   2040
aatgagctgc agaaagacaa gatggccgag gcctacagcg agatcggaat gaagggcgag   2100
cgcagaagag gcaagggaca cgatggactg taccagggac tgagcaccgc caccaaggat   2160
acctatgacg ccctgcacat gcaggccctg cctccaagat aa                      2202
```

<210> SEQ ID NO 317
<211> LENGTH: 2262
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 317

```
atgctgctgc tggtcacatc tctgctgctg tgcgagctgc ccatcctgc ctttctgctg     60
atccccagg ttcaactcca gcagtctggt cccggcctcg ttaaaccaag ccagactttg    120
tctcttacct gtgctatcag tggcgatagc gtgtctagta attcagccgc atggaactgg   180
atccgacaat caccgagtag gggacttgaa tggctgggta gaacctatta ccggtccaaa   240
tggtacaatg actatgcagt gtctgtaaaa agcaggatca cgatcaaccc tgatacgtct   300
aaaaaccagt tttctctgca acttaatagt gtgaccctg aagacaccgc tgtgtattac   360
tgtgcacggg aggttaccgg tgatcttgaa gatgcttttg atatatgggg ccaaggtacg   420
atggtcacgg tgtctagtgg gggagcggc agcgacatac agatgacgca gagcccatcc   480
agtctctccg cgtctgttgg tgacagagtg actattacat gtagggcgtc tcagaccatt   540
```

```
tggtcttacc tcaattggta tcaacagcga ccaggcaaag caccgaactt gctcatttac      600
gctgccagct cactccaaag tggtgtgccg tccagattta gtggtagggg cagtggcact      660
gatttcactc tgactatttc aagtcttcaa gctgaggatt ttgccacata ctactgccag      720
caaagttact caatacctca gacttttgga caggggacaa aattggagat taaaggggga      780
ggcggatccg gcggtggtgg ctccggcggt ggtggttctg gaggcggcgg aagcggtggg      840
ggtggtagcg acatccagat gacccagacc acaagcagcc tgtctgccag cctgggcgat      900
agagtgacca tcagctgtag agccagccag gacatcagca agtacctgaa ctggtatcag      960
caaaagcccg acggcaccgt gaagctgctg atctaccaca ccagcagact gcacagcggc     1020
gtgccaagca gattttctgg cagcggctct ggcaccgact acagcctgac aatcagcaac     1080
ctggaacaag aggatatcgc tacctacttc tgccagcaag caacacccct gccttacacc     1140
tttggcggag gcaccaagct ggaaatcacc ggctctacaa gcggcagcgg caaacctgga     1200
tctggcgagg gatctaccaa gggcgaagtg aaactgcaag agtctggccc tggactggtg     1260
gccccatctc agtctctgag cgtgacctgt acagtcagcg gagtgtccct gcctgattac     1320
ggcgtgtcct ggatcagaca gcctcctcgg aaaggcctgg aatggctggg agtgatctgg     1380
ggcagcgaga caacctacta caacagcgcc ctgaagtccc ggctgaccat catcaaggac     1440
aactccaaga gccaggtgtt cctgaagatg aacagcctgc agaccgacga caccgccatc     1500
tactattgcg ccaagcacta ctactacggc ggcagctacg ccatggatta ttggggccag     1560
ggcaccagcg tgaccgtttc ttcttccgga accacaacgc ccgccccgcg accgcctact     1620
cccgctccca caattgcatc acaacccctg tctttgagac ccgaagcttg tcgaccagct     1680
gccggtggcg cggttcacac gcgggggctc gatttcgcct gtgatatata tatatgggcc     1740
ccattggctg gaacatgcgg agtattgctt ctgagcctgg tgattaccct ctactgtaag     1800
agaggccgga gaaacttctc ttatatattc aagcagccct ttatgcgacc cgttcagact     1860
acccaagagg aagatggatg cagttgccgc tttccagaag aggaggaggg cgggtgcgaa     1920
ctgagagtga agttcagcag atccgccgat gctcccgcct ataagcaggg ccaaaaccag     1980
ctgtacaacg agctgaacct ggggagaaga gaagagtacg acgtgctgga caagcggaga     2040
ggcagagatc ctgaaatggg cggcaagccc agacggaaga atcctcaaga gggcctgtat     2100
aatgagctgc agaaagacaa gatggccgag gcctacagcg agatcggaat gaagggcgag     2160
cgcagaagag gcaagggaca cgatggactg taccagggac tgagcaccgc caccaaggat     2220
acctatgacg ccctgcacat gcaggccctg cctccaagat aa                        2262
```

<210> SEQ ID NO 318
<211> LENGTH: 42
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 318

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 319
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 319

```
Arg Val Lys Phe Ser Arg Ser Ala Asp Ala Pro Ala Tyr Lys Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110
```

<210> SEQ ID NO 320
<211> LENGTH: 241
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 320

```
Gln Val Gln Leu Val Gln Ser Gly Ala Glu Val Lys Pro Gly Ala
1               5                   10                  15

Ser Val Lys Val Ser Cys Lys Ala Ser Gly Tyr Thr Phe Thr Asp Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Ser Gly Trp Asp Phe Asp Tyr Trp Gly Gln Gly Thr Leu Val Thr
            100                 105                 110

Val Ser Ser Gly Gly Gly Gly Ser Gly Gly Gly Gly Ser Gly Gly Gly
        115                 120                 125

Gly Ser Gly Gly Gly Gly Ser Asp Ile Val Met Thr Gln Ser Pro Ser
    130                 135                 140

Ser Leu Ser Ala Ser Val Gly Asp Arg Val Thr Ile Thr Cys Arg Ala
145                 150                 155                 160

Ser Gln Ser Ile Arg Tyr Tyr Leu Ser Trp Tyr Gln Gln Lys Pro Gly
                165                 170                 175
```

```
Lys Ala Pro Lys Leu Leu Ile Tyr Thr Ala Ser Ile Leu Gln Asn Gly
            180                 185                 190

Val Pro Ser Arg Phe Ser Gly Ser Gly Ser Gly Thr Asp Phe Thr Leu
            195                 200                 205

Thr Ile Ser Ser Leu Gln Pro Glu Asp Phe Ala Thr Tyr Tyr Cys Leu
            210                 215                 220

Gln Thr Tyr Thr Thr Pro Asp Phe Gly Pro Gly Thr Lys Val Glu Ile
225                 230                 235                 240

Lys

<210> SEQ ID NO 321
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 321

Glu Val Lys Leu Gln Glu Ser Gly Pro Gly Leu Val Ala Pro Ser Gln
1               5                   10                  15

Ser Leu Ser Val Thr Cys Thr Val Ser Gly Val Ser Leu Pro Asp Tyr
            20                  25                  30

Gly Val Ser Trp Ile Arg Gln Pro Pro Arg Lys Gly Leu Glu Trp Leu
        35                  40                  45

Gly Val Ile Trp Gly Ser Glu Thr Thr Tyr Tyr Asn Ser Ala Leu Lys
    50                  55                  60

Ser Arg Leu Thr Ile Ile Lys Asp Asn Ser Lys Ser Gln Val Phe Leu
65                  70                  75                  80

Lys Met Asn Ser Leu Gln Thr Asp Asp Thr Ala Ile Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Ser Val Thr Val Ser Ser
        115                 120

<210> SEQ ID NO 322
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 322

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95
```

Thr Phe Gly Gly Gly Thr Lys Leu Glu Ile Thr
                100                 105

<210> SEQ ID NO 323
<211> LENGTH: 493
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 323

Met Ala Leu Pro Val Thr Ala Leu Leu Leu Pro Leu Ala Leu Leu Leu
1               5                   10                  15

His Ala Ala Arg Pro Asp Ile Val Leu Thr Gln Ser Pro Ala Ser Leu
            20                  25                  30

Ala Val Ser Leu Gly Glu Arg Ala Thr Ile Asn Cys Arg Ala Ser Glu
        35                  40                  45

Ser Val Ser Val Ile Gly Ala His Leu Ile His Trp Tyr Gln Gln Lys
    50                  55                  60

Pro Gly Gln Pro Pro Lys Leu Leu Ile Tyr Leu Ala Ser Asn Leu Glu
65                  70                  75                  80

Thr Gly Val Pro Ala Arg Phe Ser Gly Ser Gly Ser Gly Thr Asp Phe
                85                  90                  95

Thr Leu Thr Ile Ser Ser Leu Gln Ala Glu Asp Ala Ala Ile Tyr Tyr
            100                 105                 110

Cys Leu Gln Ser Arg Ile Phe Pro Arg Thr Phe Gly Gln Gly Thr Lys
        115                 120                 125

Leu Glu Ile Lys Gly Ser Thr Ser Gly Ser Gly Lys Pro Gly Ser Gly
    130                 135                 140

Glu Gly Ser Thr Lys Gly Gln Val Gln Leu Val Gln Ser Gly Ser Glu
145                 150                 155                 160

Leu Lys Lys Pro Gly Ala Ser Val Lys Val Ser Cys Lys Ala Ser Gly
                165                 170                 175

Tyr Thr Phe Thr Asp Tyr Ser Ile Asn Trp Val Arg Gln Ala Pro Gly
            180                 185                 190

Gln Gly Leu Glu Trp Met Gly Trp Ile Asn Thr Glu Thr Arg Glu Pro
        195                 200                 205

Ala Tyr Ala Tyr Asp Phe Arg Gly Arg Phe Val Phe Ser Leu Asp Thr
    210                 215                 220

Ser Val Ser Thr Ala Tyr Leu Gln Ile Ser Ser Leu Lys Ala Glu Asp
225                 230                 235                 240

Thr Ala Val Tyr Tyr Cys Ala Arg Asp Tyr Ser Tyr Ala Met Asp Tyr
                245                 250                 255

Trp Gly Gln Gly Thr Leu Val Thr Val Ser Ser Ala Ala Ala Thr Thr
            260                 265                 270

Thr Pro Ala Pro Arg Pro Pro Thr Pro Ala Pro Thr Ile Ala Ser Gln
        275                 280                 285

Pro Leu Ser Leu Arg Pro Glu Ala Cys Arg Pro Ala Ala Gly Gly Ala
    290                 295                 300

Val His Thr Arg Gly Leu Asp Phe Ala Cys Asp Ile Tyr Ile Trp Ala
305                 310                 315                 320

Pro Leu Ala Gly Thr Cys Gly Val Leu Leu Leu Ser Leu Val Ile Thr
                325                 330                 335

```
Leu Tyr Cys Lys Arg Gly Arg Lys Leu Leu Tyr Ile Phe Lys Gln
            340                 345                 350

Pro Phe Met Arg Pro Val Gln Thr Thr Gln Glu Glu Asp Gly Cys Ser
        355                 360                 365

Cys Arg Phe Pro Glu Glu Glu Gly Gly Cys Glu Leu Arg Val Lys
370                 375                 380

Phe Ser Arg Ser Ala Asp Ala Pro Ala Tyr Gln Gln Gly Gln Asn Gln
385                 390                 395                 400

Leu Tyr Asn Glu Leu Asn Leu Gly Arg Arg Glu Glu Tyr Asp Val Leu
            405                 410                 415

Asp Lys Arg Arg Gly Arg Asp Pro Glu Met Gly Gly Lys Pro Arg Arg
        420                 425                 430

Lys Asn Pro Gln Glu Gly Leu Tyr Asn Glu Leu Gln Lys Asp Lys Met
            435                 440                 445

Ala Glu Ala Tyr Ser Glu Ile Gly Met Lys Gly Glu Arg Arg Arg Gly
        450                 455                 460

Lys Gly His Asp Gly Leu Tyr Gln Gly Leu Ser Thr Ala Thr Lys Asp
465                 470                 475                 480

Thr Tyr Asp Ala Leu His Met Gln Ala Leu Pro Pro Arg
            485                 490

<210> SEQ ID NO 324
<211> LENGTH: 207
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 324

Lys Asn Gln Val Glu Gln Ser Pro Gln Ser Leu Ile Ile Leu Glu Gly
1               5                   10                  15

Lys Asn Cys Thr Leu Gln Cys Asn Tyr Thr Val Ser Pro Phe Ser Asn
            20                  25                  30

Leu Arg Trp Tyr Lys Gln Asp Thr Gly Arg Gly Pro Val Ser Leu Thr
        35                  40                  45

Ile Met Thr Phe Ser Glu Asn Thr Lys Ser Asn Gly Arg Tyr Thr Ala
    50                  55                  60

Thr Leu Asp Ala Asp Thr Lys Gln Ser Ser Leu His Ile Thr Ala Ser
65                  70                  75                  80

Gln Leu Ser Asp Ser Ala Ser Tyr Ile Cys Val Val Asn His Ser Gly
            85                  90                  95

Gly Ser Tyr Ile Pro Thr Phe Gly Arg Gly Thr Ser Leu Ile Val His
        100                 105                 110

Pro Tyr Ile Gln Lys Pro Asp Pro Ala Val Tyr Gln Leu Arg Asp Ser
    115                 120                 125

Lys Ser Ser Asp Lys Ser Val Cys Leu Phe Thr Asp Phe Asp Ser Gln
130                 135                 140

Thr Asn Val Ser Gln Ser Lys Asp Ser Asp Val Tyr Ile Thr Asp Lys
145                 150                 155                 160

Thr Val Leu Asp Met Arg Ser Met Asp Phe Lys Ser Asn Ser Ala Val
            165                 170                 175

Ala Trp Ser Asn Lys Ser Asp Phe Ala Cys Ala Asn Ala Phe Asn Asn
        180                 185                 190

Ser Ile Ile Pro Glu Asp Thr Phe Phe Pro Ser Pro Glu Ser Ser
```

```
                195                 200                 205

<210> SEQ ID NO 325
<211> LENGTH: 246
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 325

Asp Val Lys Val Thr Gln Ser Ser Arg Tyr Leu Val Lys Arg Thr Gly
1               5                   10                  15

Glu Lys Val Phe Leu Glu Cys Val Gln Asp Met Asp His Glu Asn Met
            20                  25                  30

Phe Trp Tyr Arg Gln Asp Pro Gly Leu Gly Leu Arg Leu Ile Tyr Phe
        35                  40                  45

Ser Tyr Asp Val Lys Met Lys Glu Lys Gly Asp Ile Pro Glu Gly Tyr
50                  55                  60

Ser Val Ser Arg Glu Lys Lys Glu Arg Phe Ser Leu Ile Leu Glu Ser
65                  70                  75                  80

Ala Ser Thr Asn Gln Thr Ser Met Tyr Leu Cys Ala Ser Ser Phe Leu
                85                  90                  95

Met Thr Ser Gly Asp Pro Tyr Glu Gln Tyr Phe Gly Pro Gly Thr Arg
            100                 105                 110

Leu Thr Val Thr Glu Asp Leu Lys Asn Val Phe Pro Pro Glu Val Ala
        115                 120                 125

Val Phe Glu Pro Ser Glu Ala Glu Ile Ser His Thr Gln Lys Ala Thr
130                 135                 140

Leu Val Cys Leu Ala Thr Gly Phe Tyr Pro Asp His Val Glu Leu Ser
145                 150                 155                 160

Trp Trp Val Asn Gly Lys Glu Val His Ser Gly Val Ser Thr Asp Pro
                165                 170                 175

Gln Pro Leu Lys Glu Gln Pro Ala Leu Asn Asp Ser Arg Tyr Cys Leu
            180                 185                 190

Ser Ser Arg Leu Arg Val Ser Ala Thr Phe Trp Gln Asn Pro Arg Asn
        195                 200                 205

His Phe Arg Cys Gln Val Gln Phe Tyr Gly Leu Ser Glu Asn Asp Glu
210                 215                 220

Trp Thr Gln Asp Arg Ala Lys Pro Val Thr Gln Ile Val Ser Ala Glu
225                 230                 235                 240

Ala Trp Gly Arg Ala Asp
                245

<210> SEQ ID NO 326
<211> LENGTH: 115
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 326

Met Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
            20                  25                  30
```

```
Leu Gln Trp Phe Arg Gln Asp Pro Gly Lys Gly Leu Thr Ser Leu Leu
            35                  40                  45

Leu Ile Gln Ser Ser Gln Arg Glu Gln Thr Ser Gly Arg Leu Asn Ala
 50                  55                  60

Ser Leu Asp Lys Ser Ser Gly Arg Ser Thr Leu Tyr Ile Ala Ala Ser
 65                  70                  75                  80

Gln Pro Gly Asp Ser Ala Thr Tyr Leu Cys Ala Val Arg Pro Thr Ser
                 85                  90                  95

Gly Gly Ser Tyr Ile Pro Thr Phe Gly Arg Gly Thr Ser Leu Ile Val
                100                 105                 110

His Pro Tyr
        115
```

<210> SEQ ID NO 327
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 327

```
Met Gly Val Thr Gln Thr Pro Lys Phe Gln Val Leu Lys Thr Gly Gln
 1               5                  10                  15

Ser Met Thr Leu Gln Cys Ala Gln Asp Met Asn His Glu Tyr Met Ser
                 20                  25                  30

Trp Tyr Arg Gln Asp Pro Gly Met Gly Leu Arg Leu Ile His Tyr Ser
            35                  40                  45

Val Gly Ala Gly Ile Thr Asp Gln Gly Glu Val Pro Asn Gly Tyr Asn
 50                  55                  60

Val Ser Arg Ser Thr Thr Glu Asp Phe Pro Leu Arg Leu Leu Ser Ala
 65                  70                  75                  80

Ala Pro Ser Gln Thr Ser Val Tyr Phe Cys Ala Ser Ser Tyr Val Gly
                 85                  90                  95

Asn Thr Gly Glu Leu Phe Phe Gly Glu Gly Ser Arg Leu Thr Val Leu
                100                 105                 110
```

<210> SEQ ID NO 328
<211> LENGTH: 166
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 328

```
Ala Pro Pro Arg Leu Ile Cys Asp Ser Arg Val Leu Glu Arg Tyr Leu
 1               5                  10                  15

Leu Glu Ala Lys Glu Ala Glu Asn Ile Thr Thr Gly Cys Ala Glu His
                 20                  25                  30

Cys Ser Leu Asn Glu Asn Ile Thr Val Pro Asp Thr Lys Val Asn Phe
            35                  40                  45

Tyr Ala Trp Lys Arg Met Glu Val Gly Gln Gln Ala Val Glu Val Trp
 50                  55                  60

Gln Gly Leu Ala Leu Leu Ser Glu Ala Val Leu Arg Gly Gln Ala Leu
 65                  70                  75                  80
```

```
Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165
```

<210> SEQ ID NO 329
<211> LENGTH: 452
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 329

```
Met Ser Thr Ala Val Leu Glu Asn Pro Gly Leu Gly Arg Lys Leu Ser
1               5                   10                  15

Asp Phe Gly Gln Glu Thr Ser Tyr Ile Glu Asp Asn Cys Asn Gln Asn
            20                  25                  30

Gly Ala Ile Ser Leu Ile Phe Ser Leu Lys Glu Glu Val Gly Ala Leu
        35                  40                  45

Ala Lys Val Leu Arg Leu Phe Glu Glu Asn Asp Val Asn Leu Thr His
    50                  55                  60

Ile Glu Ser Arg Pro Ser Arg Leu Lys Lys Asp Glu Tyr Glu Phe Phe
65                  70                  75                  80

Thr His Leu Asp Lys Arg Ser Leu Pro Ala Leu Thr Asn Ile Ile Lys
                85                  90                  95

Ile Leu Arg His Asp Ile Gly Ala Thr Val His Glu Leu Ser Arg Asp
            100                 105                 110

Lys Lys Lys Asp Thr Val Pro Trp Phe Pro Arg Thr Ile Gln Glu Leu
        115                 120                 125

Asp Arg Phe Ala Asn Gln Ile Leu Ser Tyr Gly Ala Glu Leu Asp Ala
    130                 135                 140

Asp His Pro Gly Phe Lys Asp Pro Val Tyr Arg Ala Arg Arg Lys Gln
145                 150                 155                 160

Phe Ala Asp Ile Ala Tyr Asn Tyr Arg His Gly Gln Pro Ile Pro Arg
                165                 170                 175

Val Glu Tyr Met Glu Glu Glu Lys Lys Thr Trp Gly Thr Val Phe Lys
            180                 185                 190

Thr Leu Lys Ser Leu Tyr Lys Thr His Ala Cys Tyr Glu Tyr Asn His
        195                 200                 205

Ile Phe Pro Leu Leu Glu Lys Tyr Cys Gly Phe His Glu Asp Asn Ile
    210                 215                 220

Pro Gln Leu Glu Asp Val Ser Gln Phe Leu Gln Thr Cys Thr Gly Phe
225                 230                 235                 240

Arg Leu Arg Pro Val Ala Gly Leu Leu Ser Ser Arg Asp Phe Leu Gly
                245                 250                 255

Gly Leu Ala Phe Arg Val Phe His Cys Thr Gln Tyr Ile Arg His Gly
```

```
                260                 265                 270
Ser Lys Pro Met Tyr Thr Pro Glu Pro Asp Ile Cys His Glu Leu Leu
        275                 280                 285

Gly His Val Pro Leu Phe Ser Asp Arg Ser Phe Ala Gln Phe Ser Gln
    290                 295                 300

Glu Ile Gly Leu Ala Ser Leu Gly Ala Pro Asp Glu Tyr Ile Glu Lys
305                 310                 315                 320

Leu Ala Thr Ile Tyr Trp Phe Thr Val Glu Phe Gly Leu Cys Lys Gln
                325                 330                 335

Gly Asp Ser Ile Lys Ala Tyr Gly Ala Gly Leu Leu Ser Ser Phe Gly
            340                 345                 350

Glu Leu Gln Tyr Cys Leu Ser Glu Lys Pro Lys Leu Leu Pro Leu Glu
        355                 360                 365

Leu Glu Lys Thr Ala Ile Gln Asn Tyr Thr Val Thr Glu Phe Gln Pro
370                 375                 380

Leu Tyr Tyr Val Ala Glu Ser Phe Asn Asp Ala Lys Glu Lys Val Arg
385                 390                 395                 400

Asn Phe Ala Ala Thr Ile Pro Arg Pro Phe Ser Val Arg Tyr Asp Pro
                405                 410                 415

Tyr Thr Gln Arg Ile Glu Val Leu Asp Asn Thr Gln Gln Leu Lys Ile
            420                 425                 430

Leu Ala Asp Ser Ile Asn Ser Glu Ile Gly Leu Cys Ser Ala Leu
        435                 440                 445

Gln Lys Ile Lys
    450

<210> SEQ ID NO 330
<211> LENGTH: 1462
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 330

Leu Ser Val Lys Ala Gln Thr Ala His Ile Val Leu Glu Asp Gly Thr
1               5                   10                  15

Lys Met Lys Gly Tyr Ser Phe Gly His Pro Ser Ser Val Ala Gly Glu
            20                  25                  30

Val Val Phe Asn Thr Gly Leu Gly Gly Tyr Pro Glu Ala Ile Thr Asp
        35                  40                  45

Pro Ala Tyr Lys Gly Gln Ile Leu Thr Met Ala Asn Pro Ile Ile Gly
    50                  55                  60

Asn Gly Gly Ala Pro Asp Thr Thr Ala Leu Asp Glu Leu Gly Leu Ser
65                  70                  75                  80

Lys Tyr Leu Glu Ser Asn Gly Ile Lys Val Ser Gly Leu Leu Val Leu
                85                  90                  95

Asp Tyr Ser Lys Asp Tyr Asn His Trp Leu Ala Thr Lys Ser Leu Gly
            100                 105                 110

Gln Trp Leu Gln Glu Lys Val Pro Ala Ile Tyr Gly Val Asp Thr
        115                 120                 125

Arg Met Leu Thr Lys Ile Ile Arg Asp Lys Gly Thr Met Leu Gly Lys
    130                 135                 140

Ile Glu Phe Glu Gly Gln Pro Val Asp Phe Val Asp Pro Asn Lys Gln
145                 150                 155                 160
```

-continued

Asn Leu Ile Ala Glu Val Ser Thr Lys Asp Val Lys Val Tyr Gly Lys
                165                 170                 175

Gly Asn Pro Thr Lys Val Val Ala Val Asp Cys Gly Ile Lys Asn Asn
            180                 185                 190

Val Ile Arg Leu Leu Val Lys Arg Gly Ala Glu Val His Leu Val Pro
        195                 200                 205

Trp Asn His Asp Phe Thr Lys Met Glu Tyr Asp Gly Ile Leu Ile Ala
    210                 215                 220

Gly Gly Pro Gly Asn Pro Ala Leu Ala Glu Pro Leu Ile Gln Asn Val
225                 230                 235                 240

Arg Lys Ile Leu Glu Ser Asp Arg Lys Glu Pro Leu Phe Gly Ile Ser
                245                 250                 255

Thr Gly Asn Leu Ile Thr Gly Leu Ala Ala Gly Ala Lys Thr Tyr Lys
            260                 265                 270

Met Ser Met Ala Asn Arg Gly Gln Asn Gln Pro Val Leu Asn Ile Thr
        275                 280                 285

Asn Lys Gln Ala Phe Ile Thr Ala Gln Asn His Gly Tyr Ala Leu Asp
    290                 295                 300

Asn Thr Leu Pro Ala Gly Trp Lys Pro Leu Phe Val Asn Val Asn Asp
305                 310                 315                 320

Gln Thr Asn Glu Gly Ile Met His Glu Ser Lys Pro Phe Phe Ala Val
                325                 330                 335

Gln Phe His Pro Glu Val Thr Pro Gly Pro Ile Asp Thr Glu Tyr Leu
            340                 345                 350

Phe Asp Ser Phe Phe Ser Leu Ile Lys Lys Gly Lys Ala Thr Thr Ile
        355                 360                 365

Thr Ser Val Leu Pro Lys Pro Ala Leu Val Ala Ser Arg Val Glu Val
    370                 375                 380

Ser Lys Val Leu Ile Leu Gly Ser Gly Gly Leu Ser Ile Gly Gln Ala
385                 390                 395                 400

Gly Glu Phe Asp Tyr Ser Gly Ser Gln Ala Val Lys Ala Met Lys Glu
                405                 410                 415

Glu Asn Val Lys Thr Val Leu Met Asn Pro Asn Ile Ala Ser Val Gln
            420                 425                 430

Thr Asn Glu Val Gly Leu Lys Gln Ala Asp Thr Val Tyr Phe Leu Pro
        435                 440                 445

Ile Thr Pro Gln Phe Val Thr Glu Val Ile Lys Ala Glu Gln Pro Asp
    450                 455                 460

Gly Leu Ile Leu Gly Met Gly Gly Gln Thr Ala Leu Asn Cys Gly Val
465                 470                 475                 480

Glu Leu Phe Lys Arg Gly Val Leu Lys Glu Tyr Gly Val Lys Val Leu
                485                 490                 495

Gly Thr Ser Val Glu Ser Ile Met Ala Thr Glu Asp Arg Gln Leu Phe
            500                 505                 510

Ser Asp Lys Leu Asn Glu Ile Asn Glu Lys Ile Ala Pro Ser Phe Ala
        515                 520                 525

Val Glu Ser Ile Glu Asp Ala Leu Lys Ala Asp Thr Ile Gly Tyr
    530                 535                 540

Pro Val Met Ile Arg Ser Ala Tyr Ala Leu Gly Gly Leu Gly Ser Gly
545                 550                 555                 560

Ile Cys Pro Asn Arg Glu Thr Leu Met Asp Leu Ser Thr Lys Ala Phe
                565                 570                 575

```
Ala Met Thr Asn Gln Ile Leu Val Glu Lys Ser Val Thr Gly Trp Lys
            580                 585                 590

Glu Ile Glu Tyr Glu Val Val Arg Asp Ala Asp Asn Cys Val Thr
        595                 600                 605

Val Cys Asn Met Glu Asn Val Asp Ala Met Gly Val His Thr Gly Asp
610                 615                 620

Ser Val Val Ala Pro Ala Gln Thr Leu Ser Asn Ala Glu Phe Gln
625                 630                 635                 640

Met Leu Arg Arg Thr Ser Ile Asn Val Arg His Leu Gly Ile Val
                645                 650                 655

Gly Glu Cys Asn Ile Gln Phe Ala Leu His Pro Thr Ser Met Glu Tyr
                660                 665                 670

Cys Ile Ile Glu Val Asn Ala Arg Leu Ser Arg Ser Ser Ala Leu Ala
            675                 680                 685

Ser Lys Ala Thr Gly Tyr Pro Leu Ala Phe Ile Ala Ala Lys Ile Ala
690                 695                 700

Leu Gly Ile Pro Leu Pro Glu Ile Lys Asn Val Val Ser Gly Lys Thr
705                 710                 715                 720

Ser Ala Cys Phe Glu Pro Ser Leu Asp Tyr Met Val Thr Lys Ile Pro
                725                 730                 735

Arg Trp Asp Leu Asp Arg Phe His Gly Thr Ser Ser Arg Ile Gly Ser
                740                 745                 750

Ser Met Lys Ser Val Gly Glu Val Met Ala Ile Gly Arg Thr Phe Glu
            755                 760                 765

Glu Ser Phe Gln Lys Ala Leu Arg Met Cys His Pro Ser Ile Glu Gly
770                 775                 780

Phe Thr Pro Arg Leu Pro Met Asn Lys Glu Trp Pro Ser Asn Leu Asp
785                 790                 795                 800

Leu Arg Lys Glu Leu Ser Glu Pro Ser Ser Thr Arg Ile Tyr Ala Ile
                805                 810                 815

Ala Lys Ala Ile Asp Asp Asn Met Ser Leu Asp Glu Ile Glu Lys Leu
                820                 825                 830

Thr Tyr Ile Asp Lys Trp Phe Leu Tyr Lys Met Arg Asp Ile Leu Asn
        835                 840                 845

Met Glu Lys Thr Leu Lys Gly Leu Asn Ser Glu Ser Met Thr Glu Glu
850                 855                 860

Thr Leu Lys Arg Ala Lys Glu Ile Gly Phe Ser Asp Lys Gln Ile Ser
865                 870                 875                 880

Lys Cys Leu Gly Leu Thr Glu Ala Gln Thr Arg Glu Leu Arg Leu Lys
                885                 890                 895

Lys Asn Ile His Pro Trp Val Lys Gln Ile Asp Thr Leu Ala Ala Glu
                900                 905                 910

Tyr Pro Ser Val Thr Asn Tyr Leu Tyr Val Thr Tyr Asn Gly Gln Glu
        915                 920                 925

His Asp Val Asn Phe Asp Asp His Gly Met Met Val Leu Gly Cys Gly
        930                 935                 940

Pro Tyr His Ile Gly Ser Ser Val Glu Phe Asp Trp Cys Ala Val Ser
945                 950                 955                 960

Ser Ile Arg Thr Leu Arg Gln Leu Gly Lys Lys Thr Val Val Val Asn
                965                 970                 975

Cys Asn Pro Glu Thr Val Ser Thr Asp Phe Asp Glu Cys Asp Lys Leu
                980                 985                 990

Tyr Phe Glu Glu Leu Ser Leu Glu  Arg Ile Leu Asp Ile  Tyr His Gln
```

```
            995                 1000                1005
Glu Ala Cys Gly Gly Cys Ile Ile Ser Val Gly Gly Gln Ile Pro
        1010                1015                1020

Asn Asn Leu Ala Val Pro Leu Tyr Lys Asn Gly Val Lys Ile Met
        1025                1030                1035

Gly Thr Ser Pro Leu Gln Ile Asp Arg Ala Glu Asp Arg Ser Ile
        1040                1045                1050

Phe Ser Ala Val Leu Asp Glu Leu Lys Val Ala Gln Ala Pro Trp
        1055                1060                1065

Lys Ala Val Asn Thr Leu Asn Glu Ala Leu Glu Phe Ala Lys Ser
        1070                1075                1080

Val Asp Tyr Pro Cys Leu Leu Arg Pro Ser Tyr Val Leu Ser Gly
        1085                1090                1095

Ser Ala Met Asn Val Val Phe Ser Glu Asp Glu Met Lys Lys Phe
        1100                1105                1110

Leu Glu Glu Ala Thr Arg Val Ser Gln Glu His Pro Val Val Leu
        1115                1120                1125

Thr Lys Phe Val Glu Gly Ala Arg Glu Val Glu Met Asp Ala Val
        1130                1135                1140

Gly Lys Asp Gly Arg Val Ile Ser His Ala Ile Ser Glu His Val
        1145                1150                1155

Glu Asp Ala Gly Val His Ser Gly Asp Ala Thr Leu Met Leu Pro
        1160                1165                1170

Thr Gln Thr Ile Ser Gln Gly Ala Ile Glu Lys Val Lys Asp Ala
        1175                1180                1185

Thr Arg Lys Ile Ala Lys Ala Phe Ala Ile Ser Gly Pro Phe Asn
        1190                1195                1200

Val Gln Phe Leu Val Lys Gly Asn Asp Val Leu Val Ile Glu Cys
        1205                1210                1215

Asn Leu Arg Ala Ser Arg Ser Phe Pro Phe Val Ser Lys Thr Leu
        1220                1225                1230

Gly Val Asp Phe Ile Asp Val Ala Thr Lys Val Met Ile Gly Glu
        1235                1240                1245

Asn Val Asp Glu Lys His Leu Pro Thr Leu Asp His Pro Ile Ile
        1250                1255                1260

Pro Ala Asp Tyr Val Ala Ile Lys Ala Pro Met Phe Ser Trp Pro
        1265                1270                1275

Arg Leu Arg Asp Ala Asp Pro Ile Leu Arg Cys Glu Met Ala Ser
        1280                1285                1290

Thr Gly Glu Val Ala Cys Phe Gly Glu Gly Ile His Thr Ala Phe
        1295                1300                1305

Leu Lys Ala Met Leu Ser Thr Gly Phe Lys Ile Pro Gln Lys Gly
        1310                1315                1320

Ile Leu Ile Gly Ile Gln Gln Ser Phe Arg Pro Arg Phe Leu Gly
        1325                1330                1335

Val Ala Glu Gln Leu His Asn Glu Gly Phe Lys Leu Phe Ala Thr
        1340                1345                1350

Glu Ala Thr Ser Asp Trp Leu Asn Ala Asn Asn Val Pro Ala Thr
        1355                1360                1365

Pro Val Ala Trp Pro Ser Gln Glu Gly Gln Asn Pro Ser Leu Ser
        1370                1375                1380

Ser Ile Arg Lys Leu Ile Arg Asp Gly Ser Ile Asp Leu Val Ile
        1385                1390                1395
```

```
Asn Leu Pro Asn Asn Thr Lys Phe Val His Asp Asn Tyr Val
    1400            1405                1410

Ile Arg Arg Thr Ala Val Asp Ser Gly Ile Pro Leu Leu Thr Asn
    1415                1420                1425

Phe Gln Val Thr Lys Leu Phe Ala Glu Ala Val Gln Lys Ser Arg
    1430                1435                1440

Lys Val Asp Ser Lys Ser Leu Phe His Tyr Arg Gln Tyr Ser Ala
    1445                1450                1455

Gly Lys Ala Ala
    1460

<210> SEQ ID NO 331
<211> LENGTH: 1053
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 331

Met Lys Arg Asn Tyr Ile Leu Gly Leu Asp Ile Gly Ile Thr Ser
1               5                   10                  15

Gly Tyr Gly Ile Ile Asp Tyr Glu Thr Arg Asp Val Ile Asp Ala Gly
                20                  25                  30

Val Arg Leu Phe Lys Glu Ala Asn Val Glu Asn Asn Glu Gly Arg Arg
                35                  40                  45

Ser Lys Arg Gly Ala Arg Arg Leu Lys Arg Arg Arg His Arg Ile
50                  55                  60

Gln Arg Val Lys Lys Leu Leu Phe Asp Tyr Asn Leu Leu Thr Asp His
65                  70                  75                  80

Ser Glu Leu Ser Gly Ile Asn Pro Tyr Glu Ala Arg Val Lys Gly Leu
                85                  90                  95

Ser Gln Lys Leu Ser Glu Glu Glu Phe Ser Ala Ala Leu Leu His Leu
                100                 105                 110

Ala Lys Arg Arg Gly Val His Asn Val Asn Glu Val Glu Glu Asp Thr
            115                 120                 125

Gly Asn Glu Leu Ser Thr Lys Glu Gln Ile Ser Arg Asn Ser Lys Ala
130                 135                 140

Leu Glu Glu Lys Tyr Val Ala Glu Leu Gln Leu Glu Arg Leu Lys Lys
145                 150                 155                 160

Asp Gly Glu Val Arg Gly Ser Ile Asn Arg Phe Lys Thr Ser Asp Tyr
                165                 170                 175

Val Lys Glu Ala Lys Gln Leu Leu Lys Val Gln Lys Ala Tyr His Gln
                180                 185                 190

Leu Asp Gln Ser Phe Ile Asp Thr Tyr Ile Asp Leu Leu Glu Thr Arg
            195                 200                 205

Arg Thr Tyr Tyr Glu Gly Pro Gly Glu Gly Ser Pro Phe Gly Trp Lys
210                 215                 220

Asp Ile Lys Glu Trp Tyr Glu Met Leu Met Gly His Cys Thr Tyr Phe
225                 230                 235                 240

Pro Glu Glu Leu Arg Ser Val Lys Tyr Ala Tyr Asn Ala Asp Leu Tyr
                245                 250                 255

Asn Ala Leu Asn Asp Leu Asn Asn Leu Val Ile Thr Arg Asp Glu Asn
                260                 265                 270
```

```
Glu Lys Leu Glu Tyr Tyr Glu Lys Phe Gln Ile Ile Glu Asn Val Phe
            275                 280                 285
Lys Gln Lys Lys Lys Pro Thr Leu Lys Gln Ile Ala Lys Glu Ile Leu
    290                 295                 300
Val Asn Glu Glu Asp Ile Lys Gly Tyr Arg Val Thr Ser Thr Gly Lys
305                 310                 315                 320
Pro Glu Phe Thr Asn Leu Lys Val Tyr His Asp Ile Lys Asp Ile Thr
                325                 330                 335
Ala Arg Lys Glu Ile Ile Glu Asn Ala Glu Leu Leu Asp Gln Ile Ala
            340                 345                 350
Lys Ile Leu Thr Ile Tyr Gln Ser Ser Glu Asp Ile Gln Glu Glu Leu
            355                 360                 365
Thr Asn Leu Asn Ser Glu Leu Thr Gln Glu Glu Ile Glu Gln Ile Ser
370                 375                 380
Asn Leu Lys Gly Tyr Thr Gly Thr His Asn Leu Ser Leu Lys Ala Ile
385                 390                 395                 400
Asn Leu Ile Leu Asp Glu Leu Trp His Thr Asn Asp Asn Gln Ile Ala
                405                 410                 415
Ile Phe Asn Arg Leu Lys Leu Val Pro Lys Lys Val Asp Leu Ser Gln
            420                 425                 430
Gln Lys Glu Ile Pro Thr Thr Leu Val Asp Asp Phe Ile Leu Ser Pro
            435                 440                 445
Val Val Lys Arg Ser Phe Ile Gln Ser Ile Lys Val Ile Asn Ala Ile
    450                 455                 460
Ile Lys Lys Tyr Gly Leu Pro Asn Asp Ile Ile Glu Leu Ala Arg
465                 470                 475                 480
Glu Lys Asn Ser Lys Asp Ala Gln Lys Met Ile Asn Glu Met Gln Lys
                485                 490                 495
Arg Asn Arg Gln Thr Asn Glu Arg Ile Glu Glu Ile Ile Arg Thr Thr
            500                 505                 510
Gly Lys Glu Asn Ala Lys Tyr Leu Ile Glu Lys Ile Lys Leu His Asp
            515                 520                 525
Met Gln Glu Gly Lys Cys Leu Tyr Ser Leu Glu Ala Ile Pro Leu Glu
            530                 535                 540
Asp Leu Leu Asn Asn Pro Phe Asn Tyr Glu Val Asp His Ile Ile Pro
545                 550                 555                 560
Arg Ser Val Ser Phe Asp Asn Ser Phe Asn Asn Lys Val Leu Val Lys
                565                 570                 575
Gln Glu Glu Asn Ser Lys Lys Gly Asn Arg Thr Pro Phe Gln Tyr Leu
            580                 585                 590
Ser Ser Ser Asp Ser Lys Ile Ser Tyr Glu Thr Phe Lys Lys His Ile
            595                 600                 605
Leu Asn Leu Ala Lys Gly Lys Gly Arg Ile Ser Lys Thr Lys Lys Glu
    610                 615                 620
Tyr Leu Leu Glu Glu Arg Asp Ile Asn Arg Phe Ser Val Gln Lys Asp
625                 630                 635                 640
Phe Ile Asn Arg Asn Leu Val Asp Thr Arg Tyr Ala Thr Arg Gly Leu
                645                 650                 655
Met Asn Leu Leu Arg Ser Tyr Phe Arg Val Asn Asn Leu Asp Val Lys
            660                 665                 670
Val Lys Ser Ile Asn Gly Gly Phe Thr Ser Phe Leu Arg Arg Lys Trp
            675                 680                 685
Lys Phe Lys Lys Glu Arg Asn Lys Gly Tyr Lys His His Ala Glu Asp
```

```
            690                 695                 700
Ala Leu Ile Ile Ala Asn Ala Asp Phe Ile Phe Lys Glu Trp Lys Lys
705                 710                 715                 720

Leu Asp Lys Ala Lys Lys Val Met Glu Asn Gln Met Phe Glu Glu Lys
                725                 730                 735

Gln Ala Glu Ser Met Pro Glu Ile Glu Thr Gln Glu Glu Tyr Lys Glu
            740                 745                 750

Ile Phe Ile Thr Pro His Gln Ile Lys His Ile Lys Asp Phe Lys Asp
                755                 760                 765

Tyr Lys Tyr Ser His Arg Val Asp Lys Lys Pro Asn Arg Glu Leu Ile
            770                 775                 780

Asn Asp Thr Leu Tyr Ser Thr Arg Lys Asp Asp Lys Gly Asn Thr Leu
785                 790                 795                 800

Ile Val Asn Asn Leu Asn Gly Leu Tyr Asp Lys Asp Asn Asp Lys Leu
                805                 810                 815

Lys Lys Leu Ile Asn Lys Ser Pro Glu Lys Leu Leu Met Tyr His His
                820                 825                 830

Asp Pro Gln Thr Tyr Gln Lys Leu Lys Leu Ile Met Glu Gln Tyr Gly
            835                 840                 845

Asp Glu Lys Asn Pro Leu Tyr Lys Tyr Tyr Glu Glu Thr Gly Asn Tyr
850                 855                 860

Leu Thr Lys Tyr Ser Lys Lys Asp Asn Gly Pro Val Ile Lys Lys Ile
865                 870                 875                 880

Lys Tyr Tyr Gly Asn Lys Leu Asn Ala His Leu Asp Ile Thr Asp Asp
                885                 890                 895

Tyr Pro Asn Ser Arg Asn Lys Val Val Lys Leu Ser Leu Lys Pro Tyr
            900                 905                 910

Arg Phe Asp Val Tyr Leu Asp Asn Gly Val Tyr Lys Phe Val Thr Val
            915                 920                 925

Lys Asn Leu Asp Val Ile Lys Lys Glu Asn Tyr Tyr Glu Val Asn Ser
930                 935                 940

Lys Cys Tyr Glu Glu Ala Lys Lys Leu Lys Lys Ile Ser Asn Gln Ala
945                 950                 955                 960

Glu Phe Ile Ala Ser Phe Tyr Asn Asn Asp Leu Ile Lys Ile Asn Gly
                965                 970                 975

Glu Leu Tyr Arg Val Ile Gly Val Asn Asn Asp Leu Leu Asn Arg Ile
            980                 985                 990

Glu Val Asn Met Ile Asp Ile Thr Tyr Arg Glu Tyr Leu Glu Asn Met
            995                 1000                1005

Asn Asp Lys Arg Pro Pro Arg Ile Ile Lys Thr Ile Ala Ser Lys
    1010                1015                1020

Thr Gln Ser Ile Lys Lys Tyr Ser Thr Asp Ile Leu Gly Asn Leu
    1025                1030                1035

Tyr Glu Val Lys Ser Lys Lys His Pro Gln Ile Ile Lys Lys Gly
    1040                1045                1050

<210> SEQ ID NO 332
<211> LENGTH: 1353
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 332
```

-continued

```
Ala Ala Gly Gly Ile Leu His Leu Glu Leu Val Ala Val Gly Pro
1               5                   10                  15

Asp Val Phe Gln Ala His Gln Glu Asp Thr Glu Arg Tyr Val Leu Thr
            20                  25                  30

Asn Leu Asn Ile Gly Ala Glu Leu Leu Arg Asp Pro Ser Leu Gly Ala
            35                  40                  45

Gln Phe Arg Val His Leu Val Lys Met Val Ile Leu Thr Glu Pro Glu
    50                  55                  60

Gly Ala Pro Asn Ile Thr Ala Asn Leu Thr Ser Ser Leu Leu Ser Val
65                  70                  75                  80

Cys Gly Trp Ser Gln Thr Ile Asn Pro Glu Asp Thr Asp Pro Gly
                85                  90                  95

His Ala Asp Leu Val Leu Tyr Ile Thr Arg Phe Asp Leu Glu Leu Pro
            100                 105                 110

Asp Gly Asn Arg Gln Val Arg Gly Val Thr Gln Leu Gly Gly Ala Cys
        115                 120                 125

Ser Pro Thr Trp Ser Cys Leu Ile Thr Glu Asp Thr Gly Phe Asp Leu
    130                 135                 140

Gly Val Thr Ile Ala His Glu Ile Gly His Ser Phe Gly Leu Glu His
145                 150                 155                 160

Asp Gly Ala Pro Gly Ser Gly Cys Gly Pro Ser Gly His Val Met Ala
                165                 170                 175

Ser Asp Gly Ala Ala Pro Arg Ala Gly Leu Ala Trp Ser Pro Cys Ser
            180                 185                 190

Arg Arg Gln Leu Leu Ser Leu Leu Ser Ala Gly Arg Ala Arg Cys Val
        195                 200                 205

Trp Asp Pro Arg Pro Gln Pro Gly Ser Ala Gly His Pro Pro Asp
210                 215                 220

Ala Gln Pro Gly Leu Tyr Tyr Ser Ala Asn Glu Gln Cys Arg Val Ala
225                 230                 235                 240

Phe Gly Pro Lys Ala Val Ala Cys Thr Phe Ala Arg Glu His Leu Asp
                245                 250                 255

Met Cys Gln Ala Leu Ser Cys His Thr Asp Pro Leu Asp Gln Ser Ser
            260                 265                 270

Cys Ser Arg Leu Leu Val Pro Leu Leu Asp Gly Thr Glu Cys Gly Val
        275                 280                 285

Glu Lys Trp Cys Ser Lys Gly Arg Cys Arg Ser Leu Val Glu Leu Thr
    290                 295                 300

Pro Ile Ala Ala Val His Gly Arg Trp Ser Ser Trp Gly Pro Arg Ser
305                 310                 315                 320

Pro Cys Ser Arg Ser Cys Gly Gly Val Val Thr Arg Arg Arg Gln
                325                 330                 335

Cys Asn Asn Pro Arg Pro Ala Phe Gly Gly Arg Ala Cys Val Gly Ala
            340                 345                 350

Asp Leu Gln Ala Glu Met Cys Asn Thr Gln Ala Cys Glu Lys Thr Gln
        355                 360                 365

Leu Glu Phe Met Ser Gln Gln Cys Ala Arg Thr Asp Gly Gln Pro Leu
    370                 375                 380

Arg Ser Ser Pro Gly Gly Ala Ser Phe Tyr His Trp Gly Ala Ala Val
385                 390                 395                 400

Pro His Ser Gln Gly Asp Ala Leu Cys Arg His Met Cys Arg Ala Ile
                405                 410                 415
```

-continued

Gly Glu Ser Phe Ile Met Lys Arg Gly Asp Ser Phe Leu Asp Gly Thr
                420                 425                 430

Arg Cys Met Pro Ser Gly Pro Arg Glu Asp Gly Thr Leu Ser Leu Cys
            435                 440                 445

Val Ser Gly Ser Cys Arg Thr Phe Gly Cys Asp Gly Arg Met Asp Ser
        450                 455                 460

Gln Gln Val Trp Asp Arg Cys Gln Val Cys Gly Gly Asp Asn Ser Thr
465                 470                 475                 480

Cys Ser Pro Arg Lys Gly Ser Phe Thr Ala Gly Arg Ala Arg Glu Tyr
                485                 490                 495

Val Thr Phe Leu Thr Val Thr Pro Asn Leu Thr Ser Val Tyr Ile Ala
            500                 505                 510

Asn His Arg Pro Leu Phe Thr His Leu Ala Val Arg Ile Gly Gly Arg
        515                 520                 525

Tyr Val Val Ala Gly Lys Met Ser Ile Ser Pro Asn Thr Thr Tyr Pro
530                 535                 540

Ser Leu Leu Glu Asp Gly Arg Val Glu Tyr Arg Val Ala Leu Thr Glu
545                 550                 555                 560

Asp Arg Leu Pro Arg Leu Glu Glu Ile Arg Ile Trp Gly Pro Leu Gln
                565                 570                 575

Glu Asp Ala Asp Ile Gln Val Tyr Arg Arg Tyr Gly Glu Glu Tyr Gly
            580                 585                 590

Asn Leu Thr Arg Pro Asp Ile Thr Phe Thr Tyr Phe Gln Pro Lys Pro
        595                 600                 605

Arg Gln Ala Trp Val Trp Ala Ala Val Arg Gly Pro Cys Ser Val Ser
610                 615                 620

Cys Gly Ala Gly Leu Arg Trp Val Asn Tyr Ser Cys Leu Asp Gln Ala
625                 630                 635                 640

Arg Lys Glu Leu Val Glu Thr Val Gln Cys Gln Gly Ser Gln Gln Pro
                645                 650                 655

Pro Ala Trp Pro Glu Ala Cys Val Leu Glu Pro Cys Pro Pro Tyr Trp
            660                 665                 670

Ala Val Gly Asp Phe Gly Pro Cys Ser Ala Ser Cys Gly Gly Gly Leu
        675                 680                 685

Arg Glu Arg Pro Val Arg Cys Val Glu Ala Gln Gly Ser Leu Leu Lys
690                 695                 700

Thr Leu Pro Pro Ala Arg Cys Arg Ala Gly Ala Gln Gln Pro Ala Val
705                 710                 715                 720

Ala Leu Glu Thr Cys Asn Pro Gln Pro Cys Pro Ala Arg Trp Glu Val
                725                 730                 735

Ser Glu Pro Ser Ser Cys Thr Ser Ala Gly Gly Ala Gly Leu Ala Leu
            740                 745                 750

Glu Asn Glu Thr Cys Val Pro Gly Ala Asp Gly Leu Glu Ala Pro Val
        755                 760                 765

Thr Glu Gly Pro Gly Ser Val Asp Glu Lys Leu Pro Ala Pro Glu Pro
770                 775                 780

Cys Val Gly Met Ser Cys Pro Pro Gly Trp Gly His Leu Asp Ala Thr
785                 790                 795                 800

Ser Ala Gly Glu Lys Ala Pro Ser Pro Trp Gly Ser Ile Arg Thr Gly
                805                 810                 815

Ala Gln Ala Ala His Val Trp Thr Pro Ala Ala Gly Ser Cys Ser Val
            820                 825                 830

Ser Cys Gly Arg Gly Leu Met Glu Leu Arg Phe Leu Cys Met Asp Ser

-continued

```
            835                 840                 845
Ala Leu Arg Val Pro Val Gln Glu Glu Leu Cys Gly Leu Ala Ser Lys
850                 855                 860

Pro Gly Ser Arg Arg Glu Val Cys Gln Ala Val Pro Cys Pro Ala Arg
865                 870                 875                 880

Trp Gln Tyr Lys Leu Ala Ala Cys Ser Val Ser Cys Gly Arg Gly Val
                885                 890                 895

Val Arg Arg Ile Leu Tyr Cys Ala Arg Ala His Gly Asp Asp Gly
            900                 905                 910

Glu Glu Ile Leu Leu Asp Thr Gln Cys Gln Gly Leu Pro Arg Pro Glu
            915                 920                 925

Pro Gln Glu Ala Cys Ser Leu Glu Pro Cys Pro Pro Arg Trp Lys Val
930                 935                 940

Met Ser Leu Gly Pro Cys Ser Ala Ser Cys Gly Leu Gly Thr Ala Arg
945                 950                 955                 960

Arg Ser Val Ala Cys Val Gln Leu Asp Gln Gly Gln Asp Val Glu Val
                965                 970                 975

Asp Glu Ala Ala Cys Ala Ala Leu Val Arg Pro Glu Ala Ser Val Pro
            980                 985                 990

Cys Leu Ile Ala Asp Cys Thr Tyr Arg Trp His Val Gly Thr Trp Met
            995                 1000                1005

Glu Cys Ser Val Ser Cys Gly Asp Gly Ile Gln Arg Arg Arg Asp
1010                1015                1020

Thr Cys Leu Gly Pro Gln Ala Gln Ala Pro Val Pro Ala Asp Phe
1025                1030                1035

Cys Gln His Leu Pro Lys Pro Val Thr Val Arg Gly Cys Trp Ala
1040                1045                1050

Gly Pro Cys Val Gly Gln Gly Thr Pro Ser Leu Val Pro His Glu
1055                1060                1065

Glu Ala Ala Ala Pro Gly Arg Thr Thr Ala Thr Pro Ala Gly Ala
1070                1075                1080

Ser Leu Glu Trp Ser Gln Ala Arg Gly Leu Leu Phe Ser Pro Ala
1085                1090                1095

Pro Gln Pro Arg Arg Leu Leu Pro Gly Pro Gln Glu Asn Ser Val
1100                1105                1110

Gln Ser Ser Ala Cys Gly Arg Gln His Leu Glu Pro Thr Gly Thr
1115                1120                1125

Ile Asp Met Arg Gly Pro Gly Gln Ala Asp Cys Ala Val Ala Ile
1130                1135                1140

Gly Arg Pro Leu Gly Glu Val Val Thr Leu Arg Val Leu Glu Ser
1145                1150                1155

Ser Leu Asn Cys Ser Ala Gly Asp Met Leu Leu Leu Trp Gly Arg
1160                1165                1170

Leu Thr Trp Arg Lys Met Cys Arg Lys Leu Leu Asp Met Thr Phe
1175                1180                1185

Ser Ser Lys Thr Asn Thr Leu Val Val Arg Gln Arg Cys Gly Arg
1190                1195                1200

Pro Gly Gly Gly Val Leu Leu Arg Tyr Gly Ser Gln Leu Ala Pro
1205                1210                1215

Glu Thr Phe Tyr Arg Glu Cys Asp Met Gln Leu Phe Gly Pro Trp
1220                1225                1230

Gly Glu Ile Val Ser Pro Ser Leu Ser Pro Ala Thr Ser Asn Ala
1235                1240                1245
```

```
Gly Gly Cys Arg Leu Phe Ile Asn Val Ala Pro His Ala Arg Ile
    1250                1255                1260

Ala Ile His Ala Leu Ala Thr Asn Met Gly Ala Gly Thr Glu Gly
    1265                1270                1275

Ala Asn Ala Ser Tyr Ile Leu Ile Arg Asp Thr His Ser Leu Arg
    1280                1285                1290

Thr Thr Ala Phe His Gly Gln Gln Val Leu Tyr Trp Glu Ser Glu
    1295                1300                1305

Ser Ser Gln Ala Glu Met Glu Phe Ser Glu Gly Phe Leu Lys Ala
    1310                1315                1320

Gln Ala Ser Leu Arg Gly Gln Tyr Trp Thr Leu Gln Ser Trp Val
    1325                1330                1335

Pro Glu Met Gln Asp Pro Gln Ser Trp Lys Gly Lys Glu Gly Thr
    1340                1345                1350

<210> SEQ ID NO 333
<211> LENGTH: 431
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 333

Met Pro Asn Pro Arg Pro Gly Lys Pro Ser Ala Pro Ser Leu Ala Leu
1               5                   10                  15

Gly Pro Ser Pro Gly Ala Ser Pro Ser Trp Arg Ala Ala Pro Lys Ala
                20                  25                  30

Ser Asp Leu Leu Gly Ala Arg Gly Pro Gly Gly Thr Phe Gln Gly Arg
            35                  40                  45

Asp Leu Arg Gly Gly Ala His Ala Ser Ser Ser Leu Asn Pro Met
        50                  55                  60

Pro Pro Ser Gln Leu Gln Leu Pro Thr Leu Pro Leu Val Met Val Ala
65                  70                  75                  80

Pro Ser Gly Ala Arg Leu Gly Pro Leu Pro His Leu Gln Ala Leu Leu
                85                  90                  95

Gln Asp Arg Pro His Phe Met His Gln Leu Ser Thr Val Asp Ala His
            100                 105                 110

Ala Arg Thr Pro Val Leu Gln Val His Pro Leu Glu Ser Pro Ala Met
        115                 120                 125

Ile Ser Leu Thr Pro Pro Thr Thr Ala Thr Gly Val Phe Ser Leu Lys
130                 135                 140

Ala Arg Pro Gly Leu Pro Pro Gly Ile Asn Val Ala Ser Leu Glu Trp
145                 150                 155                 160

Val Ser Arg Glu Pro Ala Leu Leu Cys Thr Phe Pro Asn Pro Ser Ala
                165                 170                 175

Pro Arg Lys Asp Ser Thr Leu Ser Ala Val Pro Gln Ser Ser Tyr Pro
            180                 185                 190

Leu Leu Ala Asn Gly Val Cys Lys Trp Pro Gly Cys Glu Lys Val Phe
        195                 200                 205

Glu Glu Pro Glu Asp Phe Leu Lys His Cys Gln Ala Asp His Leu Leu
    210                 215                 220

Asp Glu Lys Gly Arg Ala Gln Cys Leu Leu Gln Arg Glu Met Val Gln
225                 230                 235                 240
```

Ser Leu Glu Gln Gln Leu Val Leu Glu Lys Glu Lys Leu Ser Ala Met
            245                 250                 255

Gln Ala His Leu Ala Gly Lys Met Ala Leu Thr Lys Ala Ser Ser Val
            260                 265                 270

Ala Ser Ser Asp Lys Gly Ser Cys Cys Ile Val Ala Ala Gly Ser Gln
            275                 280                 285

Gly Pro Val Pro Ala Trp Ser Gly Pro Arg Glu Ala Pro Asp Ser
290                 295                 300

Leu Phe Ala Val Arg Arg His Leu Trp Gly Ser His Gly Asn Ser Thr
305                 310                 315                 320

Phe Pro Glu Phe Leu His Asn Met Asp Tyr Phe Lys Phe His Asn Met
            325                 330                 335

Arg Pro Pro Phe Thr Tyr Ala Thr Leu Ile Arg Trp Ala Ile Leu Glu
            340                 345                 350

Ala Pro Glu Lys Gln Arg Thr Leu Asn Glu Ile Tyr His Trp Phe Thr
            355                 360                 365

Arg Met Phe Ala Phe Phe Arg Asn His Pro Ala Thr Trp Lys Asn Ala
            370                 375                 380

Ile Arg His Asn Leu Ser Leu His Lys Cys Phe Val Arg Val Glu Ser
385                 390                 395                 400

Glu Lys Gly Ala Val Trp Thr Val Asp Glu Leu Glu Phe Arg Lys Lys
            405                 410                 415

Arg Ser Gln Arg Pro Ser Arg Cys Ser Asn Pro Thr Pro Gly Pro
            420                 425                 430

<210> SEQ ID NO 334
<211> LENGTH: 160
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 334

Ser Pro Gly Gln Gly Thr Gln Ser Glu Asn Ser Cys Thr His Phe Pro
1               5                   10                  15

Gly Asn Leu Pro Asn Met Leu Arg Asp Leu Arg Asp Ala Phe Ser Arg
            20                  25                  30

Val Lys Thr Phe Phe Gln Met Lys Asp Gln Leu Asp Asn Leu Leu Leu
            35                  40                  45

Lys Glu Ser Leu Leu Glu Asp Phe Lys Gly Tyr Leu Gly Cys Gln Ala
50                  55                  60

Leu Ser Glu Met Ile Gln Phe Tyr Leu Glu Glu Val Met Pro Gln Ala
65                  70                  75                  80

Glu Asn Gln Asp Pro Asp Ile Lys Ala His Val Asn Ser Leu Gly Glu
            85                  90                  95

Asn Leu Lys Thr Leu Arg Leu Arg Leu Arg Arg Cys His Arg Phe Leu
            100                 105                 110

Pro Cys Glu Asn Lys Ser Lys Ala Val Glu Gln Val Lys Asn Ala Phe
            115                 120                 125

Asn Lys Leu Gln Glu Lys Gly Ile Tyr Lys Ala Met Ser Glu Phe Asp
            130                 135                 140

Ile Phe Ile Asn Tyr Ile Glu Ala Tyr Met Thr Met Lys Ile Arg Asn
145                 150                 155                 160

```
<210> SEQ ID NO 335
<211> LENGTH: 133
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 335

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
    130

<210> SEQ ID NO 336
<211> LENGTH: 37
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 336
gagacgtttt cttgggtcta ccgtttaata ttgcgtc                            37
```